(12) United States Patent
Brown et al.

(10) Patent No.: US 8,278,450 B2
(45) Date of Patent: Oct. 2, 2012

(54) KINASE INHIBITORS

(75) Inventors: Jason W. Brown, San Diego, CA (US); Qing Dong, San Diego, CA (US); Bheema R. Paraselli, San Diego, CA (US); Nicholas Scorah, San Diego, CA (US); Jeffrey A. Stafford, San Diego, CA (US); Michael B. Wallace, San Diego, CA (US); Hasanthi Wijesekera, Brookwater (AU)

(73) Assignee: Takeda Pharmaceutical Company Limited, Osaka (JP)

( * ) Notice: Subject to any disclaimer, the term of this patent is extended or adjusted under 35 U.S.C. 154(b) by 1043 days.

(21) Appl. No.: 12/103,882

(22) Filed: Apr. 16, 2008

(65) Prior Publication Data

US 2012/0095233 A1   Apr. 19, 2012

Related U.S. Application Data

(60) Provisional application No. 60/912,629, filed on Apr. 18, 2007.

(51) Int. Cl.
*C07D 471/00* (2006.01)
*C07D 209/88* (2006.01)

(52) U.S. Cl. .......................................... 546/86; 548/444

(58) Field of Classification Search ........................ None
See application file for complete search history.

(56) References Cited

U.S. PATENT DOCUMENTS

| | | | |
|---|---|---|---|
| 4,260,776 A | 4/1981 | Harnisch |
| 5,491,147 A | 2/1996 | Boyd |
| 5,739,144 A | 4/1998 | Warrellow |
| 5,859,034 A | 1/1999 | Warrellow |
| 5,962,312 A | 10/1999 | Plowman |
| 5,972,676 A | 10/1999 | Plowman |
| 6,143,480 A | 11/2000 | Obayashi et al. |
| 6,207,401 B1 | 3/2001 | Plowman |
| 6,265,411 B1 | 7/2001 | Thomas et al. |
| 6,294,532 B1 | 9/2001 | Thomas et al. |
| 6,352,858 B1 | 3/2002 | Cowsert |
| 6,455,559 B1 | 9/2002 | Pevarello |
| 6,528,509 B1 | 3/2003 | Hale |
| 6,555,329 B2 | 4/2003 | Jenuwein et al. |
| 6,593,357 B1 | 7/2003 | Green |
| 6,610,677 B2 | 8/2003 | Davies |
| 6,613,776 B2 | 9/2003 | Knegtel |
| 6,638,926 B2 | 10/2003 | Davies |
| 6,653,300 B2 | 11/2003 | Bebbington |
| 6,653,301 B2 | 11/2003 | Bebbington |
| 6,656,939 B2 | 12/2003 | Bebbington |
| 6,660,731 B2 | 12/2003 | Bebbington |
| 6,664,247 B2 | 12/2003 | Bebbington |
| 6,696,452 B2 | 2/2004 | Davies |
| 6,699,865 B2 | 3/2004 | Hale |
| 6,706,491 B1 | 3/2004 | Chang |
| 6,716,575 B2 | 4/2004 | Plowman |
| 6,727,251 B2 | 4/2004 | Bebbington |
| 6,743,791 B2 | 6/2004 | Cao |
| 6,762,179 B2 | 7/2004 | Cochran et al. |
| 6,770,643 B2 | 8/2004 | Cox |
| 6,784,195 B2 | 8/2004 | Hale |
| 6,787,545 B1 | 9/2004 | Ohtani et al. |
| 6,806,272 B2 | 10/2004 | Bauer |
| 6,831,091 B2 | 12/2004 | Gant |
| 6,841,579 B1 | 1/2005 | Plowman |
| 6,846,928 B2 | 1/2005 | Bebbington |
| 6,849,653 B2 | 2/2005 | Clare |
| 6,858,638 B2 | 2/2005 | Damour |
| 6,861,422 B2 | 3/2005 | Hoffmann |
| 6,872,533 B2 | 3/2005 | Toland |
| 6,890,927 B2 | 5/2005 | Bogle |
| 6,897,207 B2 | 5/2005 | Cox |
| 6,916,798 B2 | 7/2005 | Green |
| 6,919,338 B2 | 7/2005 | Mortlock |
| 6,949,580 B2 | 9/2005 | Hale et al. |
| 6,956,052 B2 | 10/2005 | Bergmanis et al. |
| 6,982,265 B1 | 1/2006 | Hunt et al. |
| 6,989,385 B2 | 1/2006 | Bebbington et al. |
| 6,989,451 B2 | 1/2006 | Zhang et al. |

(Continued)

FOREIGN PATENT DOCUMENTS

CA    2517020    8/2005

(Continued)

OTHER PUBLICATIONS

Cecil Textbook of Medicine, edited by Bennet, J.C. and Plum F., 20th edition, vol. 1, 1998, pp. 1004-1010. Fabbro et al. Pharmacology & Therapeutics vol. 93, p. 79-98, 2002.
Mass, R. D. Int. J. Radiation Oncology Bio. Phys. vol. 58 (3): p. 932-40, 2004.
U.S. Appl. No. 12/708,304, filed Feb. 18, 2010, Qing Dong, et al.
U.S. Appl. No. 12/706,837, filed Jun. 18, 2009, Qing Dong, et al.
U.S. Appl. No. 12/444,957, filed Apr. 9, 2009, Qing Dong, et al.
F. Zaragoza Dorward "Side Reactions in Organic Synthesis" 2005, iley: VCH, Weinheim p. IX of Preface.
Bhatti, Inayat A. et al. "Prolysis of 1-substituted pyrazoles and chloroform at 550 C: formation of a-carbaline from 1-benzylpyrazoles" Journal of Chemical Society, Perkin Transactions 1: Organic and Bio-Organic Chemistry, (24), 3581-3586 Coden: JCPRB4; ISSN: 0300-922X, 1997, XP002417212 p. 3583; examples 24-27.

(Continued)

*Primary Examiner* — Janet Andres
*Assistant Examiner* — Timothy R Rozof
(74) *Attorney, Agent, or Firm* — Mitchell R. Brustein; C. Amy Smith; David M. Stemerick

(57) ABSTRACT

Compounds are provided for use with kinases that comprise a compound selected from the group consisting of:

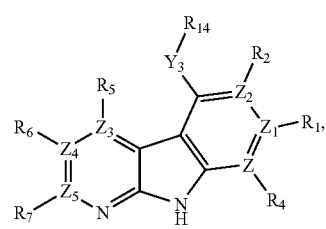

wherein the variables are as defined herein. Also provided are pharmaceutical compositions, kits and articles of manufacture comprising such compounds; methods and intermediates useful for making the compounds; and methods of using said compounds.

3 Claims, 1 Drawing Sheet

U.S. PATENT DOCUMENTS

| | | |
|---|---|---|
| 7,008,948 B2 | 3/2006 | Bebbington |
| 7,038,045 B2 | 5/2006 | Guzi et al. |
| 7,056,944 B2 | 6/2006 | Hale et al. |
| 7,081,461 B1 | 7/2006 | Mortlock et al. |
| 7,087,603 B2 | 8/2006 | Bebbington et al. |
| 7,091,213 B2 | 8/2006 | Metcalf, III et al. |
| 7,091,343 B2 | 8/2006 | Bebbington et al. |
| 7,098,330 B2 | 8/2006 | Bebbington et al. |
| 7,105,669 B1 | 9/2006 | Mortlock et al. |
| 7,115,739 B2 | 10/2006 | Bebbington et al. |
| 7,151,113 B2 | 12/2006 | Dyckman et al. |
| 7,157,476 B2 | 1/2007 | Come et al. |
| 2002/0151573 A1 | 10/2002 | Gant |
| 2002/0151574 A1 | 10/2002 | Hale |
| 2003/0004161 A1 | 1/2003 | Bebbington |
| 2003/0004164 A1 | 1/2003 | Bebbington |
| 2003/0022885 A1 | 1/2003 | Bebbington |
| 2003/0036543 A1 | 2/2003 | Bebbington |
| 2003/0040536 A1 | 2/2003 | Hale |
| 2003/0055044 A1 | 3/2003 | Davies |
| 2003/0055068 A1 | 3/2003 | Bebbington |
| 2003/0064981 A1 | 4/2003 | Knegtel |
| 2003/0064982 A1 | 4/2003 | Davies |
| 2003/0073687 A1 | 4/2003 | Bebbington |
| 2003/0073692 A1 | 4/2003 | Pulici |
| 2003/0078166 A1 | 4/2003 | Davies |
| 2003/0078275 A1 | 4/2003 | Bebbington |
| 2003/0083327 A1 | 5/2003 | Davies |
| 2003/0092714 A1 | 5/2003 | Cao |
| 2003/0105090 A1 | 6/2003 | Bebbington |
| 2003/0105129 A1 | 6/2003 | Mortlock |
| 2003/0109550 A1 | 6/2003 | Clare |
| 2003/0109697 A1 | 6/2003 | Shepard |
| 2003/0114432 A1 | 6/2003 | Clare |
| 2003/0119856 A1 | 6/2003 | Cochran |
| 2003/0125361 A1 | 7/2003 | Clare |
| 2003/0171357 A1 | 9/2003 | Fancelli |
| 2003/0171359 A1 | 9/2003 | Dahmann |
| 2003/0187002 A1 | 10/2003 | Mortlock |
| 2003/0187007 A1 | 10/2003 | Cao |
| 2003/0208067 A1 | 11/2003 | Cao |
| 2003/0225073 A1 | 12/2003 | Bebbington |
| 2003/0225151 A1 | 12/2003 | Hale |
| 2004/0002496 A1 | 1/2004 | Bebbington |
| 2004/0009974 A1 | 1/2004 | Bebbington |
| 2004/0009981 A1 | 1/2004 | Bebbington |
| 2004/0009983 A1 | 1/2004 | Cox |
| 2004/0010027 A1 | 1/2004 | Casuscelli |
| 2004/0019046 A1 | 1/2004 | Pevarello |
| 2004/0024040 A1 | 2/2004 | Green |
| 2004/0029157 A1 | 2/2004 | Tatsuka |
| 2004/0029857 A1 | 2/2004 | Hale |
| 2004/0029885 A1 | 2/2004 | Bauer |
| 2004/0048849 A1 | 3/2004 | Prevost et al. |
| 2004/0049032 A1 | 3/2004 | Charrier |
| 2004/0053931 A1 | 3/2004 | Cox |
| 2004/0054179 A1 | 3/2004 | Yura et al. |
| 2004/0063715 A1 | 4/2004 | Paruch et al. |
| 2004/0082631 A1 | 4/2004 | Hale |
| 2004/0097501 A1 | 5/2004 | Bebbington |
| 2004/0097531 A1 | 5/2004 | Ledeboer |
| 2004/0102360 A1 | 5/2004 | Barnett |
| 2004/0102506 A1 | 5/2004 | Hale |
| 2004/0106615 A1 | 6/2004 | Cochran |
| 2004/0106667 A1 | 6/2004 | Damour |
| 2004/0110741 A1 | 6/2004 | Bergmanis |
| 2004/0116454 A1 | 6/2004 | Davies |
| 2004/0147524 A1 | 7/2004 | Bauer |
| 2004/0157893 A1 | 8/2004 | Bebbington |
| 2004/0167121 A1 | 8/2004 | Aronov |
| 2004/0167124 A1 | 8/2004 | Chen |
| 2004/0167141 A1 | 8/2004 | Bebbington |
| 2004/0176380 A1 | 9/2004 | Hoffmann |
| 2004/0180881 A1 | 9/2004 | Berta |
| 2004/0198737 A1 | 10/2004 | Cox |
| 2004/0214814 A1 | 10/2004 | Bebbington |
| 2004/0220200 A1 | 11/2004 | Maltais |
| 2004/0224944 A1 | 11/2004 | Bebbington |
| 2004/0229875 A1 | 11/2004 | Cao |
| 2004/0235867 A1 | 11/2004 | Bilodeau |
| 2004/0235919 A1 | 11/2004 | Pevarello |
| 2004/0242559 A1 | 12/2004 | Ugolini |
| 2004/0242613 A1 | 12/2004 | Cardozo |
| 2004/0248853 A1 | 12/2004 | Dyckman |
| 2004/0254177 A1 | 12/2004 | Amici |
| 2004/0265852 A1 | 12/2004 | Plowman |
| 2005/0002938 A1 | 1/2005 | Plowman |
| 2005/0004110 A1 | 1/2005 | Bebbington |
| 2005/0004152 A1 | 1/2005 | Cochran |
| 2005/0004176 A1 | 1/2005 | Dyckman |
| 2005/0009876 A1 | 1/2005 | Bhagwat |
| 2005/0014760 A1 | 1/2005 | Hoffmann |
| 2005/0014761 A1 | 1/2005 | Hoffmann |
| 2005/0020583 A1 | 1/2005 | Pulici |
| 2005/0026984 A1 | 2/2005 | Bigot |
| 2005/0026991 A1 | 2/2005 | Cholody |
| 2005/0032839 A1 | 2/2005 | Fancelli |
| 2005/0032869 A1 | 2/2005 | Berta |
| 2005/0038023 A1 | 2/2005 | Bebbington |
| 2005/0043323 A1 | 2/2005 | Vanotti |
| 2005/0043346 A1 | 2/2005 | Vanotti |
| 2005/0059657 A1 | 3/2005 | Cavicchioli |
| 2005/0059722 A1 | 3/2005 | Damour |
| 2005/0065169 A1 | 3/2005 | Wang |
| 2005/0065171 A1 | 3/2005 | Shakespeare |
| 2005/0070561 A1 | 3/2005 | Jung |
| 2005/0085490 A1 | 4/2005 | Wang |
| 2005/0085531 A1 | 4/2005 | Hodge |
| 2005/0090498 A1 | 4/2005 | Samizu et al. |
| 2005/0107386 A1 | 5/2005 | Narla |
| 2005/0113460 A1 | 5/2005 | Glick |
| 2005/0124640 A1 | 6/2005 | Cardozo |
| 2005/0125852 A1 | 6/2005 | Caenepeel |
| 2005/0130977 A1 | 6/2005 | Lindsley |
| 2005/0137171 A1 | 6/2005 | Cherrier |
| 2005/0137199 A1 | 6/2005 | Jin |
| 2005/0137201 A1 | 6/2005 | Aronov |
| 2005/0143402 A1 | 6/2005 | Cheetham |
| 2005/0170442 A1 | 8/2005 | Kupcho |
| 2006/0004014 A1 | 1/2006 | Hoffmann et al. |
| 2006/0014751 A1 | 1/2006 | Hoffmann et al. |
| 2006/0046990 A1 | 3/2006 | Stadtmueller et al. |
| 2006/0047118 A1 | 3/2006 | Stadtmueller et al. |
| 2006/0148800 A1 | 7/2006 | Stadtmueller et al. |
| 2007/0004684 A1 | 1/2007 | Sennhenn et al. |
| 2007/0093488 A1 | 4/2007 | Deprets et al. |
| 2007/0117816 A1 | 5/2007 | Brown et al. |
| 2007/0161626 A1 | 7/2007 | Halley et al. |
| 2008/0139606 A1 | 6/2008 | Tabart et al. |
| 2008/0146542 A1 | 6/2008 | Barberis et al. |
| 2009/0030034 A1 | 1/2009 | Badorc et al. |
| 2009/0156557 A1 | 6/2009 | Qing et al. |
| 2009/0233924 A1 | 9/2009 | Ple et al. |

FOREIGN PATENT DOCUMENTS

| | | |
|---|---|---|
| DE | 28 44 606 | 4/1980 |
| EP | 1134221 A1 | 9/2001 |
| EP | 1209158 A1 | 5/2002 |
| EP | 1367058 A1 | 12/2003 |
| FR | 1 242 962 | 10/1960 |
| FR | 1242962 | 10/1960 |
| FR | 2818278 | 6/2002 |
| FR | 2876377 | 4/2006 |
| GB | 828 847 | 2/1960 |
| GB | 1268773 | 3/1972 |
| WO | WO 97/42187 | 11/1997 |
| WO | WO 98/18782 A1 | 5/1998 |
| WO | WO 98/28281 A1 | 7/1998 |
| WO | WO 98/41512 A1 | 9/1998 |
| WO | WO 99/10349 | 3/1999 |
| WO | WO 99/37788 | 7/1999 |
| WO | WO 01/07466 | 2/2001 |
| WO | WO 01/21594 A1 | 3/2001 |
| WO | WO 01/21595 A1 | 3/2001 |
| WO | WO 01/21596 A1 | 3/2001 |
| WO | WO 01/21597 A1 | 3/2001 |
| WO | WO 01/25220 A1 | 4/2001 |

| | | |
|---|---|---|
| WO | WO 01/32653 A1 | 5/2001 |
| WO | WO 01/47922 A2 | 7/2001 |
| WO | WO 01/47922 A3 | 7/2001 |
| WO | WO 01/55116 A2 | 8/2001 |
| WO | WO 01/55116 A3 | 8/2001 |
| WO | WO 01/56993 A2 | 8/2001 |
| WO | WO 01/56993 A3 | 8/2001 |
| WO | WO 01/57022 A2 | 8/2001 |
| WO | WO 01/57022 A3 | 8/2001 |
| WO | WO 01/98299 A1 | 12/2001 |
| WO | WO 02/00649 A1 | 1/2002 |
| WO | WO 02/06280 A2 | 1/2002 |
| WO | WO 02/12242 A2 | 2/2002 |
| WO | WO 02/22601 A1 | 3/2002 |
| WO | WO 02/22602 A2 | 3/2002 |
| WO | WO 02/22602 A3 | 3/2002 |
| WO | WO 02/22603 A1 | 3/2002 |
| WO | WO 02/22604 A1 | 3/2002 |
| WO | WO 02/22605 A1 | 3/2002 |
| WO | WO 02/22606 A1 | 3/2002 |
| WO | WO 02/22607 A1 | 3/2002 |
| WO | WO 02/22608 A1 | 3/2002 |
| WO | WO 02/48114 A1 | 6/2002 |
| WO | WO 02/50065 A2 | 6/2002 |
| WO | WO 02/50065 A3 | 6/2002 |
| WO | WO 02/50066 A2 | 6/2002 |
| WO | WO 02/50066 A3 | 6/2002 |
| WO | WO 02/057259 A2 | 7/2002 |
| WO | WO 02/057259 A3 | 7/2002 |
| WO | WO 02/059111 A2 | 8/2002 |
| WO | WO 02/059111 A3 | 8/2002 |
| WO | WO 02/059112 A2 | 8/2002 |
| WO | WO 02/059112 A3 | 8/2002 |
| WO | WO 02/062789 A1 | 8/2002 |
| WO | WO 02/062804 A1 | 8/2002 |
| WO | WO 02/064586 A2 | 8/2002 |
| WO | WO 02/064586 A3 | 8/2002 |
| WO | WO 02/066461 A1 | 8/2002 |
| WO | WO 02/068415 A1 | 9/2002 |
| WO | WO 02/079192 | 10/2002 |
| WO | WO 02/083654 A1 | 10/2002 |
| WO | WO 02/094809 A1 | 11/2002 |
| WO | WO 02/096867 A2 | 12/2002 |
| WO | WO 02/096867 A3 | 12/2002 |
| WO | WO 02/096905 A1 | 12/2002 |
| WO | WO 03/000688 A1 | 1/2003 |
| WO | WO 03/000695 A1 | 1/2003 |
| WO | WO 03/000833 | 1/2003 |
| WO | WO 03/008365 A2 | 1/2003 |
| WO | WO 03/009852 | 2/2003 |
| WO | WO 03/011287 A1 | 2/2003 |
| WO | WO 03/012046 A2 | 2/2003 |
| WO | WO 03/012046 A3 | 2/2003 |
| WO | WO 03/020276 A1 | 3/2003 |
| WO | WO 03/028720 A1 | 4/2003 |
| WO | WO 03/031606 A2 | 4/2003 |
| WO | WO 03/031606 A3 | 4/2003 |
| WO | WO 03/035625 A1 | 5/2003 |
| WO | WO 03/037886 | 5/2003 |
| WO | WO 03/051358 A1 | 6/2003 |
| WO | WO 03/053330 A2 | 7/2003 |
| WO | WO 03/055491 A1 | 7/2003 |
| WO | WO 03/064383 | 8/2003 |
| WO | WO 03/077921 A1 | 9/2003 |
| WO | WO 03/078402 A1 | 9/2003 |
| WO | WO 03/078423 | 9/2003 |
| WO | WO 03/078426 A1 | 9/2003 |
| WO | WO 03/078427 A1 | 9/2003 |
| WO | WO 03/082853 A1 | 10/2003 |
| WO | WO 03/087395 A2 | 10/2003 |
| WO | WO 03/087395 A3 | 10/2003 |
| WO | WO 03/091246 A1 | 11/2003 |
| WO | WO 03/092607 A2 | 11/2003 |
| WO | WO 03/092607 A3 | 11/2003 |
| WO | WO 03/097610 A1 | 11/2003 |
| WO | WO 03/106417 A1 | 12/2003 |
| WO | WO 03/106500 A1 | 12/2003 |
| WO | WO 03/107002 A1 | 12/2003 |
| WO | WO 03/107002 A1 | 12/2003 |
| WO | WO 2004/000833 A1 | 12/2003 |
| WO | WO 2004/005283 A1 | 1/2004 |
| WO | WO 2004/006838 A2 | 1/2004 |
| WO | WO 2004/006838 A3 | 1/2004 |
| WO | WO 2004/007504 A1 | 1/2004 |
| WO | WO 2004/013144 A1 | 2/2004 |
| WO | WO 2004/013146 A1 | 2/2004 |
| WO | WO 2004/014374 A1 | 2/2004 |
| WO | WO2004/016597 | 2/2004 |
| WO | WO2004/016612 | 2/2004 |
| WO | WO2004/016613 | 2/2004 |
| WO | WO 2004/037814 A1 | 5/2004 |
| WO | WO 2004/043953 A1 | 5/2004 |
| WO | WO 2004/055019 A1 | 7/2004 |
| WO | WO 2004/056812 A1 | 7/2004 |
| WO | WO 2004/056827 A2 | 7/2004 |
| WO | WO 2004/058752 A1 | 7/2004 |
| WO | WO 2004/058781 A1 | 7/2004 |
| WO | WO 2004/058782 A1 | 7/2004 |
| WO | WO 2004/066919 A2 | 8/2004 |
| WO | WO 2004/067516 A1 | 8/2004 |
| WO | WO 2004/070062 A2 | 8/2004 |
| WO | WO 2004/071390 A2 | 8/2004 |
| WO | WO 2004/071507 A1 | 8/2004 |
| WO | WO 2004/076454 A1 | 9/2004 |
| WO | WO 2004/080457 A1 | 9/2004 |
| WO | WO 2004/083203 A1 | 9/2004 |
| WO | WO 2004/087056 A2 | 10/2004 |
| WO | WO 2004/087056 A3 | 10/2004 |
| WO | WO 2004/087707 A1 | 10/2004 |
| WO | WO 2004/090106 A2 | 10/2004 |
| WO | WO 2004/094410 A1 | 11/2004 |
| WO | WO 2004/096129 A2 | 11/2004 |
| WO | WO 2004/096130 A1 | 11/2004 |
| WO | WO 2004/096131 A2 | 11/2004 |
| WO | WO 2004/096135 A2 | 11/2004 |
| WO | WO 2004/098518 A2 | 11/2004 |
| WO | WO 2004/098528 A2 | 11/2004 |
| WO | WO 2004/099156 A1 | 11/2004 |
| WO | WO 2004/104007 A1 | 12/2004 |
| WO | WO 2004/105764 A1 | 12/2004 |
| WO | WO2004/112719 | 12/2004 |
| WO | WO 2004/113324 A1 | 12/2004 |
| WO | WO 2005/002552 A2 | 1/2005 |
| WO | WO 2005/002571 A1 | 1/2005 |
| WO | WO 2005/002576 A2 | 1/2005 |
| WO | WO 2005/004988 A2 | 1/2005 |
| WO | WO 2005/004988 A3 | 1/2005 |
| WO | WO 2005/005414 A2 | 1/2005 |
| WO | WO 2005/005414 A3 | 1/2005 |
| WO | WO 2005/005427 A1 | 1/2005 |
| WO | WO 2005/005438 A1 | 1/2005 |
| WO | WO 2005/007641 A1 | 1/2005 |
| WO | WO 2005/009348 A2 | 2/2005 |
| WO | WO 2005/009987 A1 | 2/2005 |
| WO | WO 2005/011675 A1 | 2/2005 |
| WO | WO 2005/012262 A1 | 2/2005 |
| WO | WO 2005/012280 A1 | 2/2005 |
| WO | WO 2005/012298 A1 | 2/2005 |
| WO | WO 2005/012304 A2 | 2/2005 |
| WO | WO2005/012307 A1 | 2/2005 |
| WO | WO 2005/016252 A1 | 2/2005 |
| WO | WO 2005/019190 A2 | 3/2005 |
| WO | WO 2005/026150 A1 | 3/2005 |
| WO | WO 2005/026155 A1 | 3/2005 |
| WO | WO 2005/026156 A1 | 3/2005 |
| WO | WO 2005/026157 A1 | 3/2005 |
| WO | WO 2005/027907 A1 | 3/2005 |
| WO | WO 2005/028475 A2 | 3/2005 |
| WO | WO 2005/033102 | 4/2005 |
| WO | WO 2005/034840 A2 | 4/2005 |
| WO | WO 2005/035527 A1 | 4/2005 |
| WO | WO 2005/037797 A1 | 4/2005 |
| WO | WO 2005/037825 A2 | 4/2005 |
| WO | WO 2005/037843 A1 | 4/2005 |
| WO | WO 2005/040133 A1 | 5/2005 |
| WO | WO 2005/040159 A1 | 5/2005 |
| WO | WO 2005/040368 | 5/2005 |
| WO | WO 2005/042525 A1 | 5/2005 |

| | | |
|---|---|---|
| WO | WO 2005/044270 A1 | 5/2005 |
| WO | WO 2005/047266 A1 | 5/2005 |
| WO | WO 2005/049033 A1 | 6/2005 |
| WO | WO 2005/051308 | 6/2005 |
| WO | WO 2005/051942 | 6/2005 |
| WO | WO 2005/058923 A1 | 6/2005 |
| WO | WO 2005/063746 A1 | 7/2005 |
| WO | WO 2005/063747 A1 | 7/2005 |
| WO | WO 2005/068473 A1 | 7/2005 |
| WO | WO 2005/070930 A2 | 8/2005 |
| WO | WO 2005/071419 A2 | 8/2005 |
| WO | WO 2005/074922 A1 | 8/2005 |
| WO | WO 2005/075468 A2 | 8/2005 |
| WO | WO 2005/082457 A2 | 9/2005 |
| WO | WO 2005/082908 A1 | 9/2005 |
| WO | WO 2005/094830 A1 | 10/2005 |
| WO | WO 2005/095400 A1 | 10/2005 |
| WO | WO 2005/097758 A1 | 10/2005 |
| WO | WO 2005/097787 A2 | 10/2005 |
| WO | WO 2005/105777 A1 | 11/2005 |
| WO | WO 2005/105788 A1 | 11/2005 |
| WO | WO 2005/111039 A2 | 11/2005 |
| WO | WO 2005/113494 A2 | 12/2005 |
| WO | WO 2005/113507 A1 | 12/2005 |
| WO | WO 2005/113515 A1 | 12/2005 |
| WO | WO 2005/113550 A1 | 12/2005 |
| WO | WO 2005/113550 A1 | 12/2005 |
| WO | WO 2005/116028 A2 | 12/2005 |
| WO | WO 2005/117909 A2 | 12/2005 |
| WO | WO 2005/117943 A2 | 12/2005 |
| WO | WO 2005/117980 A1 | 12/2005 |
| WO | WO 2005/118544 A2 | 12/2005 |
| WO | WO 2005/118587 A1 | 12/2005 |
| WO | WO 2005/120509 A1 | 12/2005 |
| WO | WO 2005/123672 | 12/2005 |
| WO | WO 2005/123672 A2 | 12/2005 |
| WO | WO 2005/123696 A1 | 12/2005 |
| WO | WO 2005/123736 A1 | 12/2005 |
| WO | WO 2006/000589 A1 | 1/2006 |
| WO | WO 2006/002236 A1 | 1/2006 |
| WO | WO 2006/002367 A1 | 1/2006 |
| WO | WO 2006/003276 A1 | 1/2006 |
| WO | WO 2006/003378 A1 | 1/2006 |
| WO | WO 2006/003440 A1 | 1/2006 |
| WO | WO 2006/005941 A1 | 1/2006 |
| WO | WO 2006/005955 A1 | 1/2006 |
| WO | WO 2006/007496 A2 | 1/2006 |
| WO | WO 2006/007501 A2 | 1/2006 |
| WO | WO 2006/008028 A1 | 1/2006 |
| WO | WO 2006/008523 A1 | 1/2006 |
| WO | WO 2006/008545 A2 | 1/2006 |
| WO | WO 2006/012624 A2 | 2/2006 |
| WO | WO 2006/014482 A1 | 2/2006 |
| WO | WO 2006/015123 A1 | 2/2006 |
| WO | WO 2006/015312 A2 | 2/2006 |
| WO | WO 2006/017054 A2 | 2/2006 |
| WO | WO 2006/017443 A2 | 2/2006 |
| WO | WO 2006/017549 A2 | 2/2006 |
| WO | WO 2006/018628 A1 | 2/2006 |
| WO | WO 2006/020767 A2 | 2/2006 |
| WO | WO 2006/021544 A1 | 3/2006 |
| WO | WO 2006/021547 A1 | 3/2006 |
| WO | WO 2006/021548 A1 | 3/2006 |
| WO | WO 2006/023083 A1 | 3/2006 |
| WO | WO 2006/023440 A2 | 3/2006 |
| WO | WO 2006/023931 A2 | 3/2006 |
| WO | WO 2006/024836 A1 | 3/2006 |
| WO | WO 2006/024841 A2 | 3/2006 |
| WO | WO 2006/024858 A1 | 3/2006 |
| WO | WO 2006/026500 A1 | 3/2006 |
| WO | WO2006/026501 | 3/2006 |
| WO | WO 2006/026597 A2 | 3/2006 |
| WO | WO 2006/031348 A2 | 3/2006 |
| WO | WO2006/032518 | 3/2006 |
| WO | WO 2006/036266 A1 | 4/2006 |
| WO | WO 2006/036395 A2 | 4/2006 |
| WO | WO 2006/036883 A2 | 4/2006 |
| WO | WO 2006/036941 A2 | 4/2006 |
| WO | WO 2006/037032 A2 | 4/2006 |
| WO | WO 2006/040451 A2 | 4/2006 |
| WO | WO 2006/040520 A1 | 4/2006 |
| WO | WO 2006/040568 A1 | 4/2006 |
| WO | WO 2006/041773 A2 | 4/2006 |
| WO | WO2006/044687 | 4/2006 |
| WO | WO2006/046735 | 5/2006 |
| WO | WO2006/050076 | 5/2006 |
| WO | WO2006/052936 | 5/2006 |
| WO | WO2006/055561 | 5/2006 |
| WO | WO2006/055831 | 5/2006 |
| WO | WO2006/058074 | 6/2006 |
| WO | WO2006/067391 | 6/2006 |
| WO | WO2006/067557 | 6/2006 |
| WO | WO2006/070192 | 7/2006 |
| WO | WO2006/070195 | 7/2006 |
| WO | WO2006/070198 | 7/2006 |
| WO | WO2006/075152 | 7/2006 |
| WO | WO 2006/092510 A1 | 9/2006 |
| WO | WO 2006/092573 A1 | 9/2006 |
| WO | WO 2006/092574 A1 | 9/2006 |
| WO | WO2006/114520 | 11/2006 |
| WO | WO2006/117549 | 11/2006 |
| WO | WO2006/117552 | 11/2006 |
| WO | WO2006/117570 | 11/2006 |
| WO | WO2006/124863 | 11/2006 |
| WO | WO2006/130673 | 12/2006 |
| WO | WO 2006/131552 A1 | 12/2006 |
| WO | WO2006/131835 | 12/2006 |
| WO | WO 2007/044779 | 4/2007 |
| WO | WO 2007/117816 | 5/2007 |
| WO | WO 2008/016184 | 2/2008 |
| WO | WO 2008/045834 | 4/2008 |
| WO | WO 2008/054956 | 5/2008 |

OTHER PUBLICATIONS

Database Registry ACS; Oct. 20, 2000; XP002368779, retrieved from STN, Database accession No. 297763-91-8/RN abstract.
Database Caplus, Chemical Abstracts Service, Columbus, Ohio, US: XP002368789 retrieved from STN, Database accession No. 135:332604/DN abstract RN369597.42-2,-43-3 & JP 2001 294772 A, Oct. 23, 2001.
Database HCAPLUS ACS; XP002368787, retrieved from STN, Database accession No. 57:76580/DN abstract RN95936-94-0 & Sabata, B.K. et al.: Journal of Scientific and Industrial Research, Section B: Physical Sciences, vol. 21B, 1962, pp. 227-229.
Database HCAPLUS ACS; XP002368788 retrieved from STN, Database accession No. 91:176650/DN abstract RN71811-83-1 & Vavrova, Jaroslava et al.: Collection of Czechoslovak Chemical Communications, vol. 44, 1979, pp. 1413-1422.
Database Registry ACS; Apr. 10, 2001; XP002368782, retrieved from STN, Database accession No. 330683-80-2/RN abstract.
Database Registry ACS; Feb. 8, 2001; XP002368783, retrieved from STN, Database accession No. 320741-28-4/RN abstract.
Database Registry ACS; Jan. 11, 2001; XP002368784, retrieved from STN, Database accession No. 313549-01-8/RN abstract.
Database Registry ACS; Jan. 11, 2001; XP002368785, retrieved from STN, Database accession No. 313522-23-5/RN abstract.
Database Registry ACS; Jan. 4, 2001; XP002368786, retrieved from STN, Database accession No. 312755-54-7/RN abstract.
Database Registry ACS; Mar. 18, 2002; XP002368781, retrieved from STN, Database accession No. 401622-65-9/RN abstract.
Database Registry ACS; Oct. 9 2000; XP002368780, retrieved from STN, Database accession No. 293763-18-5/RN abstract.
Drobnic-Kosorok, M. et al., "Transformations of Some Substituted Methylene Heterocycles with Some Nucleophiles (1)", Journal of Heterocyclic Chemistry, vol. 13, 1976, pp. 1279-1282, XP008060243.
Kurasawa, Y. et al., "A Facile Synthesis of Novel Heterocycle-Conjugated Quinoxalines", Heterocycles vol. 22, No. 5, 1984, pp. 1189-1193, XP008059222 ISSN: 0385-5414.
Kurasawa, Y. et al., "A New Synthesis of 1,5-Dihydropyridazino[3,4-b] quinoxalines and 2-(Pyrazol-4-yl) quinoxalines", J. Heterocyclic Chemistry, vol. 33, 1996, pp. 757-762, XP008060252.
Li Sun et al.: Identification of substituted 3-(4, 5, 6, 7-tetrahydro-1H-indol-2-yl)met hylene)-1, 3-dihydroindol-2-ones as growth factor receptor inhibitors for VEGF-R2 (Flk-1/KDR), FGF-R1 and PDGF-Rbeta tyroine kinases, Journal of Medicinal Chemistry, American Chemical Society, Washington, US, vol. 43, Jun. 23, 2000, pp. 2655-2663, XP002222716.

Li Sun et al.: Synthesis and biological evaluation of 3-substituted indolin-2-ones: a novel class of tyrosine kinase inhibitors that exhibit selectivity toward particular receptor tyrosine kinases. Journal of Medicinal and Pharmaceutical Chemistry, American Chemistry Society, Easton, US, vol. 41, No. 14, 1998, pp. 2588-2603, XP002184621.

Mehta, Lina K. et al. The Eliminatin of an Alkoxy Group in the Photo-Graebe-Ullmann Convention of 1-(2,5-Dialkoxyphenyl)triazolopyridines into Carbolines, and the Preparation of a-,u-and x-Carboine Quinones, Date: 1993. J. Chem. Soc. Perkin Trans. 1 1261-67 (1993).

P. Brunt, G. Guerra: Enolizable cylic ketones. I. Reaction with activated heteroaromatic N-oxides, Annali Di Chimica, vol. 57, No. 6, 1967, pp. 688-697, XP009048877 Rome p. 691, reaction scheme middle of page, last compound.

Non-Final Office Action dated Feb. 16, 2012, issued in U.S. Appl. No. 12/708,304, filed Feb. 18, 2010.

Response as filed on May 10, 2012, to Non-Final Office Action dated Feb. 16, 2012, issued in U.S. Appl. No. 12/708,304, filed Feb. 18, 2010.

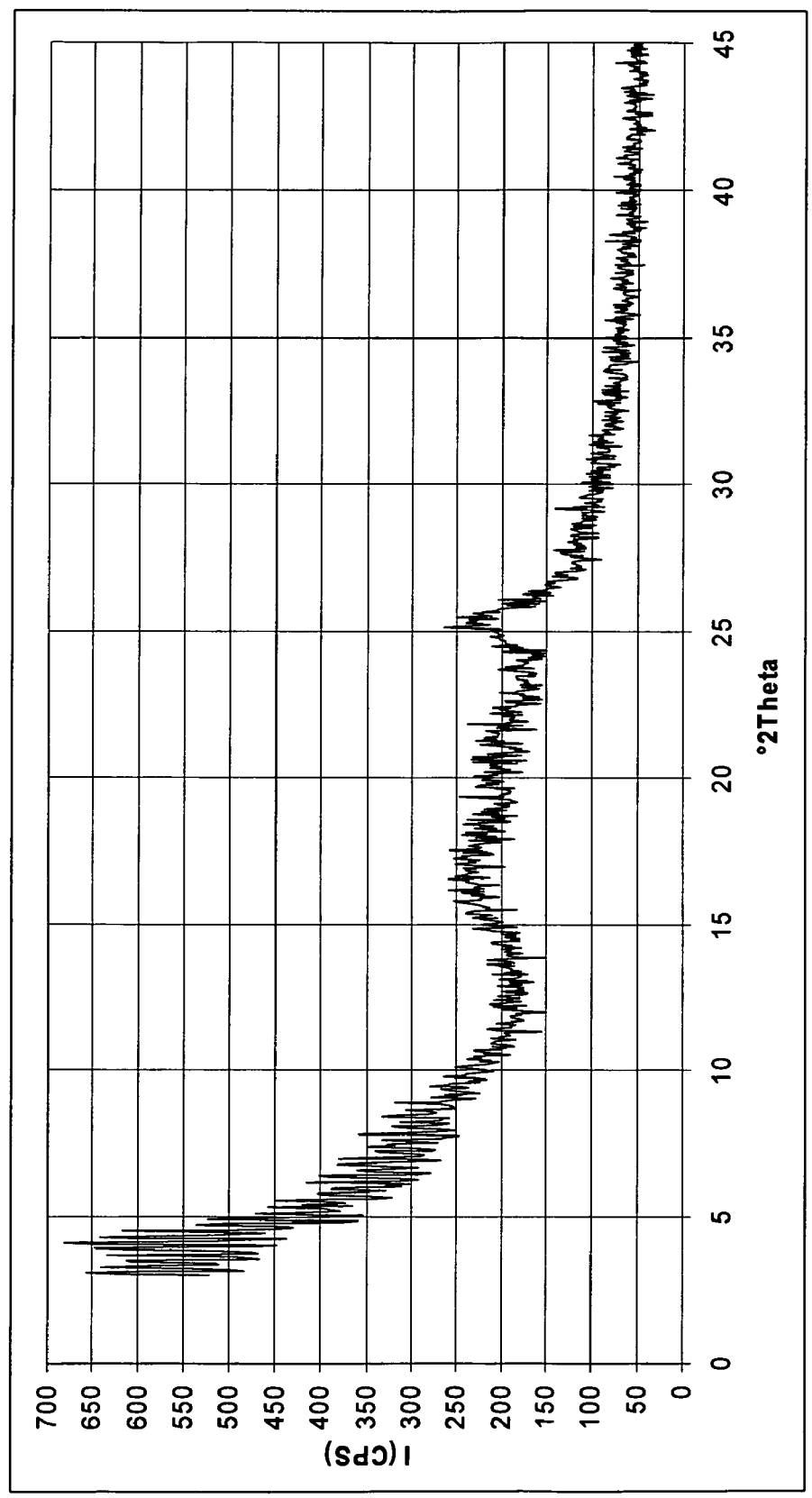

KINASE INHIBITORS

RELATED APPLICATION

This application claims the benefit of U.S. Provisional Application No. 60/912,629 filed Apr. 18, 2007, which is incorporated herein by reference.

FIELD OF THE INVENTION

The present invention relates to compounds that may be used to inhibit kinases as well as compositions of matter, kits and articles of manufacture comprising these compounds. The present invention also relates to methods for inhibiting kinases as well as treatment methods using compounds according to the present invention. In addition, the present invention relates to methods of making the compounds of the present invention, as well as intermediates useful in such methods. In particular, the present invention relates to Aurora kinase inhibitors; compositions of matter, kits and articles of manufacture comprising these compounds; methods for inhibiting Aurora kinase; and methods of making Aurora kinase inhibitors.

BACKGROUND OF THE INVENTION

The present invention relates to inhibitors of enzymes that catalyze phosphoryl transfer and/or that bind ATP/GTP nucleotides, compositions comprising the inhibitors, kits and articles of manufacture comprising the inhibitors and compositions, methods of making the inhibitors and compositions, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) starting with 2.7.-.- (See, Bairoch A., The ENZYME database in Nucleic Acids Res. 28:204-305 (2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K.; Hunter, T., FASEB J. 9:576-596 (1995); Kinghton et al., Science, 253:407-414 (1991); Hiles et al., Cell 70:419-429 (1992); Kunz et al., Cell, 73:585-596 (1993); Garcia-Bustos et al., EMBO J., 13:2352-2361 (1994)). Lipid kinases (e.g. PI3K) constitute a separate group of kinases with structural similarity to protein kinases.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferatives disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Cancer results from the deregulation of the normal processes that control cell division, differentiation and apoptotic cell death. Protein kinases play a critical role in this regulatory process. A partial non-limiting list of such kinases includes ab1, Aurora-A, Aurora-B, Aurora-C, ATK, bcr-abl, Blk, Brk, Btk, c-Kit, c-Met, c-Src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In mammalian biology, such protein kinases comprise mitogen activated protein kinase (MAPK) signaling pathways. MAPK signaling pathways are inappropriately activated by a variety of common disease-associated mechanisms such as mutation of ras genes and deregulation of growth factor receptors (Magnuson et al., Seminars in Cancer Biology 5:247-252 (1994)). Therefore the inhibition of protein kinases is an object of the present invention.

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B and Aurora-C have been found to be overexpressed (See, Bischoff et al., EMBO J., 17:3052-3065 (1998); Schumacher et al., J. Cell Biol. 143:1635-1646 (1998); Kimura et al., J. Biol. Chem., 272:13766-13771 (1997)).

There is a continued need to find new therapeutic agents to treat human diseases. The protein kinases, specifically but not limited to Aurora-A, Aurora-B and Aurora-C are especially attractive targets for the discovery of new therapeutics due to their important role in cancer, diabetes, Alzheimer's disease and other diseases.

SUMMARY OF THE INVENTION

The present invention relates to compounds that have activity for inhibiting kinases. The present invention also provides compositions, articles of manufacture and kits comprising these compounds.

In one embodiment, a pharmaceutical composition is provided that comprises a kinase inhibitor according to the present invention as an active ingredient. Pharmaceutical compositions according to the invention may optionally comprise 0.001%-100% of one or more kinase inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with kinases.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit kinases. In particular, the compounds, compositions, kits and articles of manufacture are used to inhibit an Aurora kinase.

In another embodiment, the compounds, compositions, kits and articles of manufacture are used to treat a disease state for which kinases possess activity that contributes to the pathology and/or symptomology of the disease state.

In another embodiment, a compound is administered to a subject wherein kinases activity within the subject is altered, preferably reduced.

In another embodiment, a prodrug of a compound is administered to a subject that is converted to the compound in vivo where it inhibits kinases.

In another embodiment, a method of inhibiting kinases is provided that comprises contacting kinases with a compound according to the present invention.

In another embodiment, a method of inhibiting kinases is provided that comprises causing a compound according to the present invention to be present in a subject in order to inhibit kinases in vivo.

In another embodiment, a method of inhibiting kinases is provided that comprises administering a first compound to a subject that is converted in vivo to a second compound wherein the second compound inhibits kinases in vivo. It is noted that the compounds of the present invention may be the first or second compounds.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by kinases, or which is known to be treated by kinase inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by kinases, or which is known to be treated by kinase inhibitors.

In another embodiment, a method is provided for treating a disease state for which kinases possess activity that contributes to the pathology and/or symptomology of the disease state, the method comprising: causing a compound according to the present invention to be present in a subject in a therapeutically effective amount for the disease state.

In another embodiment, a method is provided for treating a disease state for which kinases possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which kinases possesses activity that contributes to the pathology and/or symptomology of the disease state, the method comprising: administering a compound according to the present invention to a subject such that the compound is present in the subject in a therapeutically effective amount for the disease state.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting kinases and thus may themselves be prodrugs for another compound. Such prodrugs of another compound may or may not themselves independently have kinase inhibitory activity.

BRIEF DESCRIPTION OF THE FIGURES

FIG. 1 is a characteristic XRPD spectrum of an amorphous form of Compound 88.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $(C_{3-8})$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR═CR'— or —CR═CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a $(C_{2-20})$alkenyl, a $(C_{2-15})$alkenyl, a $(C_{2-10})$alkenyl, a $(C_{2-5})$ alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR═CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with an oxygen (See "oxaalkyl"), a carbonyl group (See "oxoalkyl"), a sulfur (See "thioalkyl"), or a nitrogen (See "azaalkyl"). $(C_X)$ alkyl and $(C_{X-Y})$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$ alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$ alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$ alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$ alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH═CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkenylene," either alone or represented along with another radical, can be a $(C_2)$ alkynylene, a $(C_3)$ alkynylene or a $(C_4)$ alkynylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $C_{1-6}$ alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a $(C_{1-20})$alkylidene, a $(C_{1-15})$alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a (C$_{1-10}$)azaalkyl refers to a chain comprising between 1 and 10 carbons and one or more nitrogen atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$ bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR' where R and R' are each independently hydrogen or further substituents.

"Carbocycle" means a ring consisting of carbon atoms.

"Carbocyclic ketone derivative" means a carbocyclic derivative wherein the ring contains a —CO— moiety.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)— and/or —C(=O)R, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$ cycloalkyl and $(C_{X-Y})$ cycloalkyl are typically used where X and Y indicate the number of carbon atoms in the ring assembly. For example, $(C_{3-10})$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent saturated or partially unsaturated, monocyclic, bicyclic or polycyclic ring assembly. ($C_X$) cycloalkylene and ($C_{X-Y}$) cycloalkylene are typically used where X and Y indicate the number of carbon atoms in the ring assembly. In particular embodiments, "cycloalkylene," either alone or represented along with another radical, can be a ($C_{3-14}$)cycloalkylene, a ($C_{3-10}$)cycloalkylene, a ($C_{3-7}$)cycloalkylene, a ($C_{8-10}$)cycloalkylene or a ($C_{5-7}$)cycloalkylene. Alternatively, "cycloalkylene," either alone or represented along with another radical, can be a ($C_5$)cycloalkylene, a ($C_6$)cycloalkylene, a ($C_7$)cycloalkylene, a ($C_8$)cycloalkylene, a ($C_9$)cycloalkylene or a ($C_{10}$)cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this application. Halo-substituted alkyl includes haloalkyl, dihaloalkyl, trihaloalkyl, perhaloalkyl and the like (e.g., halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —N—NR—, —N$^+$(O$^-$)=, —O—, —S— or —S(O)$_2$—, wherein R is hydrogen or a further substituent.

"Heteroalkyl" means alkyl, as defined in this application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$)alkyl, a hetero($C_{1-5}$)alkyl, a hetero($C_{1-3}$)alkyl or a hetero($C_{1-2}$)alkyl. Alternatively, "heteroalkyl," either alone or represented along with another radical, can be a hetero($C_1$)alkyl, a hetero($C_2$)alkyl or a hetero($C_3$)alkyl.

"Heterobicycloalkyl" means bicycloalkyl, as defined in this application,
provided that one or more of the atoms within the ring is a heteroatom. For example hetero($C_{9-12}$)bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterocycloalkylene" means cycloalkylene, as defined in this application,
provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$) cycloalkylene, hetero($C_8$)cycloalkylene or a hetero($C_9$)cycloalkylene.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heterobicycloaryl" means bicycloaryl, as defined in this application, provided that one or more of the atoms within the ring is a heteroatom. For example, hetero($C_{4-12}$)bicycloaryl as used in this application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this application, provided that one or more of the atoms forming the ring is a heteroatom selected, independently from N, O, or S, Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl, tetrazolyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Hydroxy" means the radical —OH.

"$IC_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Iminoketone derivative" means a derivative comprising the moiety —C(NR)—, wherein R is a hydrogen or a further substituent.

"Isomers" mean compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Linker providing X atom separation" and "moiety providing X atom separation" between two other moieties mean that the chain of atoms directly linking the two other moieties is X atoms in length. When X is given as a range (e.g., $X_1$—$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-$(L)_X$-R' where each L is independently selected from the group consisting of CR"R''', NR'''', O, S, CO, CS, C=NR''''', SO, $SO_2$, and the like, where any two or more of R", R''', R'''' and R can be taken together to form a substituted or unsubstituted ring.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa ($C_{1-10}$) alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent. The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have kinase inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" mean a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" includes humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [$(CH_3)_3C$—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)CO$—), Arg (arginine), Asn (asparagine), Asp (aspartic acid), Cys (cysteine), Glu (glutamic acid), His (histidine), Ile (isoleucine), Leu (leucine; $(CH_3)_2CHCH_2CH(NH_2)CO$—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C$—OCO—], and the like. Suitable peptide residues include peptide residues comprising two to five, and optionally two to three, of the aforesaid amino acid residues. Examples of such peptide residues include, but are not limited to, residues of such peptides as Ala-Ala [$CH_3CH(NH_2)CO$—$NHCH(CH_3)CO$—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C$—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, $(C_{1-10})$alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$— and/or —$SO_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio$(C_{1-10})$ alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomotology of the disease, (2) inhibiting the disease in an animal that is experiencing or displaying the pathology or symptomotology of the diseased (i.e., arresting further development of the pathology and/or symptomotology), or (3) ameliorating the disease in an animal that is experiencing or displaying the pathology or symptomotology of the diseased (i.e., reversing the pathology and/or symptomotology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $(C_1)$ alkyl comprises methyl (i.e., —$CH_3$) as well as —CRR"R where R, R', and R" may each independently be hydrogen or a further substituent where the atom attached to the carbon is a heteroatom or cyano. Hence, $CF_3$, $CH_2OH$ and $CH_2CN$, for example, are all $(C_1)$ alkyls. Similarly, terms such as alkylamino and the like comprise dialkylamino and the like.

"Crystalline", as the term is used herein, refers to a material that contains a specific compound, which may be hydrated and/or solvated, and has sufficient crystalline content to exhibit a discernable diffraction pattern by XRPD or other diffraction techniques. Often, a crystalline material that is obtained by direct crystallization of a compound dissolved in a solution or interconversion of crystals obtained under different crystallization conditions, will have crystals that contain the solvent used in the crystallization, termed a crystalline solvate. Also, the specific solvent system and physical embodiment in which the crystallization is performed, collectively termed crystallization conditions, may result in the crystalline material having physical and chemical properties that are unique to the crystallization conditions, generally due to the orientation of the chemical moieties of the compound with respect to each other within the crystal and/or the predominance of a specific polymorphic form of the compound in the crystalline material.

Depending upon the polymorphic form(s) of the compound that are present in a composition, various amounts of the compound in an amorphous solid state may also be present, either as a side product of the initial crystallization, and/or a product of degradation of the crystals comprising the crystalline material. Thus, crystalline, as the term is used herein, contemplates that the composition may include amorphous content; the presence of the crystalline material among the amorphous material being detectably among other methods by the composition having a discernable diffraction pattern.

The amorphous content of a crystalline material may be increased by grinding or pulverizing the material, which is evidenced by broadening of diffraction and other spectral lines relative to the crystalline material prior to grinding. Sufficient grinding and/or pulverizing may broaden the lines relative to the crystalline material prior to grinding to the extent that the XRPD or other crystal specific spectrum may become undiscernable, making the material substantially amorphous or quasi-amorphous.

Continued grinding would be expected to increase the amorphous content and further broaden the XRPD pattern with the limit of the XRPD pattern being so broadened that it can no longer be discerned above noise. When the XRPD pattern is broadened to the limit of being indiscernible, the material may be considered to no longer be a crystalline material, and instead be wholly amorphous. For material having increased amorphous content and wholly amorphous material, no peaks should be observed that would indicate grinding produces another form.

"Amorphous", as the term is used herein, refers to a composition comprising a compound that contains too little crystalline content of the compound to yield a discernable pattern by XRPD or other diffraction techniques. Glassy materials are a type of amorphous material. Amorphous materials do not have a true crystal lattice, and are consequently glassy rather than true solids, technically resembling very viscous non-crystalline liquids. Rather than being true solids, glasses may better be described as quasi-solid amorphous material. Thus, an amorphous material refers to a quasi-solid, glassy material.

"Broad" or "broadened", as the term is used herein to describe spectral lines, including XRPD, NMR and IR spectroscopy, and Raman spectroscopy lines, is a relative term that relates to the line width of a baseline spectrum. The baseline spectrum is often that of an unmanipulated crystalline form of a specific compound as obtained directly from a given set of physical and chemical conditions, including solvent composition and properties such as temperature and pressure. For example, broadened can be used to describe the spectral lines of a XRPD spectrum of ground or pulverized material comprising a crystalline compound relative to the material prior to grinding. In materials where the constituent molecules, ions or atoms, as solvated or hydrated, are not tumbling rapidly, line broadening is indicative of increased randomness in the orientation of the chemical moieties of the compound, thus indicative of an increased amorphous content. When comparisons are made between crystalline materials obtained via different crystallization conditions, broader spectral lines indicate that the material producing the relatively broader spectral lines has a higher level of amorphous material.

"About" as the term is used herein, refers to an estimate that the actual value falls within ±5% of the value cited.

Kinase Inhibitors

In one embodiment, kinase inhibitors of the present invention comprise the formula:

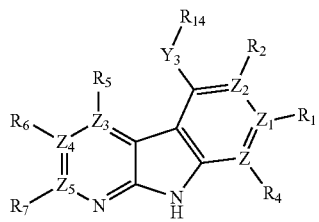

or a polymorph, solvate, ester, tautomer, enantiomer, pharmaceutically acceptable salt or prodrug thereof, wherein $Z$, $Z_1$, $Z_2$, $Z_3$, $Z_4$ and $Z_5$ are each independently selected from the group consisting of C and N;

$R_1$ is —$Y_1$—$R_{12}$, or $R_1$ is absent when $Z_1$ is N;

$R_2$ is —$Y_2$—$R_{13}$, or $R_2$ is absent when $Z_2$ is N, or $R_1$ and $R_2$ are taken together to form a ring;

$Y_1$, $Y_2$ and $Y_3$ are each independently absent or a linker providing 1 or 2 atom separation between $R_{12}$, $R_{13}$ or $R_{14}$ and the ring to which $Y_1$, $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a ring; and $R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In one variation of the above embodiment, —$Y_3$—$R_{14}$ is not H when $Z$, $Z_1$, $Z_2$, $Z_3$ and $Z_5$ are all C; $R_5$ is a substituted amino group; and $R_2$ is methoxy or $R_7$ is methyl or amino. In another variation of the above embodiment and variation, $R_{14}$ is not 3-chlorophenyl when $R_1$, $R_5$, $R_6$ and $R_7$ are each H; Z and $Z_2$ are each N; $R_2$ and $R_4$ are absent; $Z_1$, $Z_3$, $Z_4$ and $Z_5$ are all C; and $Y_3$ is NH.

In another embodiment, kinase inhibitors of the present invention comprise the formula:

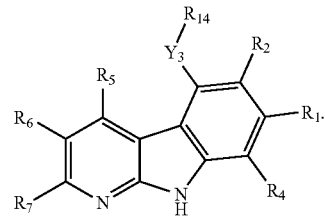

In still another embodiment, kinase inhibitors of the present invention comprise the formula:

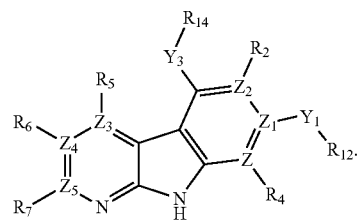

In yet another embodiment, kinase inhibitors of the present invention comprise the formula:

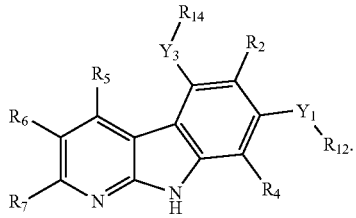

In a further embodiment, kinase inhibitors of the present invention comprise the formula:

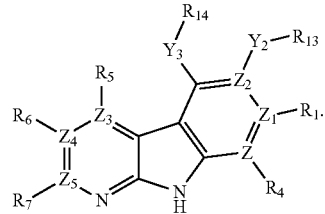

In still a further embodiment, kinase inhibitors of the present invention comprise the formula:

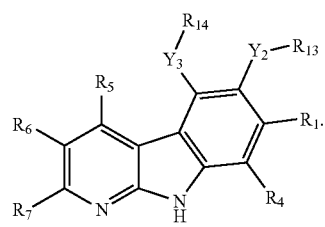

In yet a further embodiment, kinase inhibitors of the present invention comprise the formula:

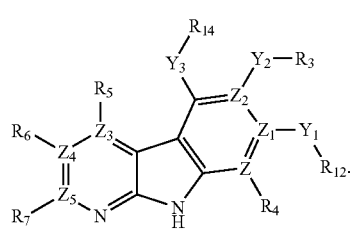

In one variation of the above embodiment, —$Y_1$—$R_{12}$ is absent when $Z_1$ is N and —$Y_2$—$R_{13}$ is absent when $Z_2$ is N.

In another embodiment, kinase inhibitors of the present invention comprise the formula:

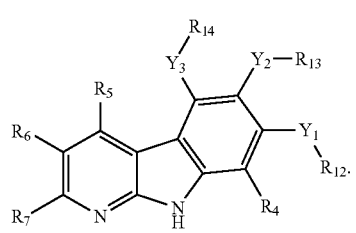

In still another embodiment, kinase inhibitors of the present invention comprise the formula:

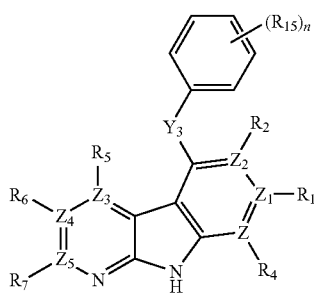

or a polymorph, solvate, ester, tautomer, enantiomer, pharmaceutically acceptable salt or prodrug thereof, wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two $R_{15}$ are taken together to form a ring.

In one variation of the above embodiment, $R_{15}$ is not 3-chloro when n is 1; $R_1$, $R_5$, $R_6$ and $R_7$ are each H; Z and $Z_2$ are each N; $R_2$ and $R_4$ are absent; $Z_1$, $Z_3$, $Z_4$ and $Z_5$ are all C; and $Y_3$ is NH.

In yet another embodiment, kinase inhibitors of the present invention comprise the formula:

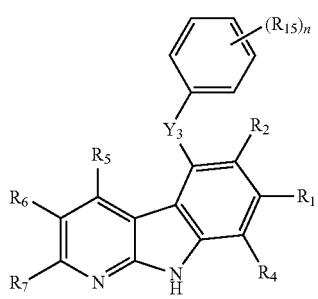

or a polymorph, solvate, ester, tautomer, enantiomer, pharmaceutically acceptable salt or prodrug thereof, wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In a further embodiment, kinase inhibitors of the present invention comprise the formula:

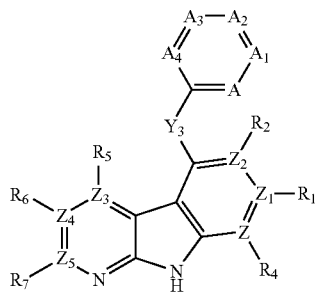

or a polymorph, solvate, ester, tautomer, enantiomer, pharmaceutically acceptable salt or prodrug thereof, wherein $A, A_1, A_2, A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In one variation of the above embodiment, $A_1$ is not CCl when $A, A_2, A_3$ and $A_4$ are each CH; $R_1, R_5, R_6$ and $R_7$ are each H; Z and $Z_2$ are each N; $R_2$ and $R_4$ are absent; $Z_1, Z_3, Z_4$ and $Z_5$ are all C; and $Y_3$ is NH.

In still a further embodiment, kinase inhibitors of the present invention comprise the formula:

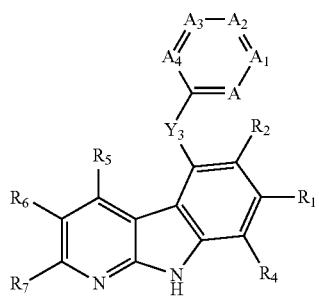

or a polymorph, solvate, ester, tautomer, enantiomer, pharmaceutically acceptable salt or prodrug thereof, wherein $A, A_1, A_2, A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In yet a further embodiment, kinase inhibitors of the present invention comprise the formula:

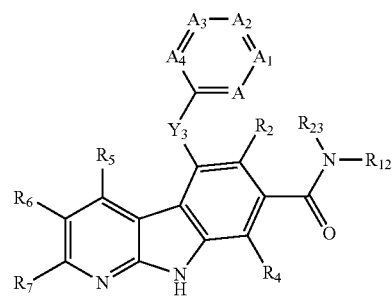

or a polymorph, solvate, ester, tautomer, enantiomer, pharmaceutically acceptable salt or prodrug thereof, wherein $A, A_1, A_2, A_3$ and $A_4$ are each independently selected from the group consisting of $CR_{25}$ and N;

$R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In another embodiment, kinase inhibitors of the present invention comprise the formula:

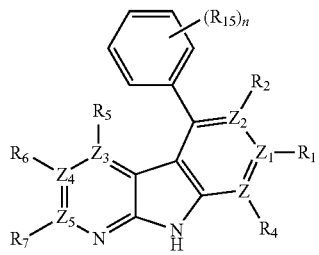

or a polymorph, solvate, ester, tautomer, enantiomer, pharmaceutically acceptable salt or prodrug thereof, wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In still another embodiment, kinase inhibitors of the present invention comprise the formula:

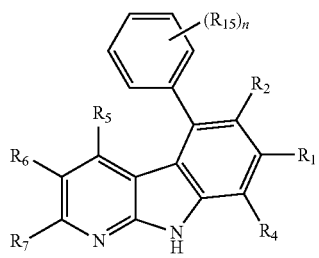

or a polymorph, solvate, ester, tautomer, enantiomer, pharmaceutically acceptable salt or prodrug thereof, wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In yet another embodiment, kinase inhibitors of the present invention comprise the formula:

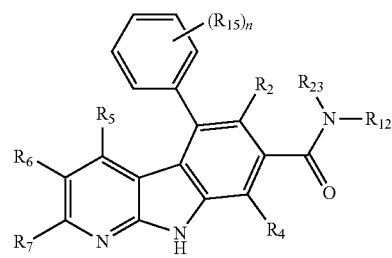

or a polymorph, solvate, ester, tautomer, enantiomer, pharmaceutically acceptable salt or prodrug thereof, wherein n is selected from the group consisting of 0, 1, 2, 3, 4 and 5;

$R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring.

In a further embodiment, kinase inhibitors of the present invention comprise the formula:

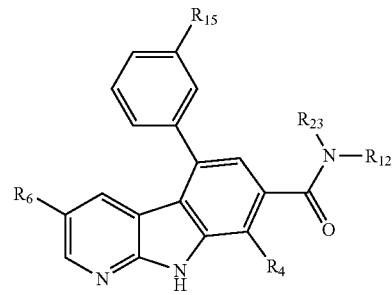

or a polymorph, solvate, ester, tautomer, enantiomer, pharmaceutically acceptable salt or prodrug thereof, wherein $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{23}$ is selected from the group consisting of hydrogen, carbonyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted, or $R_{23}$ and $R_{12}$ are taken together to form a ring.

In still a further embodiment, kinase inhibitors of the present invention comprise the formula:

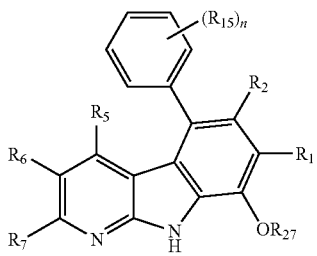

or a polymorph, solvate, ester, tautomer, enantiomer, pharmaceutically acceptable salt or prodrug thereof, wherein n is selected from the group consisting of 0, 1, 2, 3, 4 and 5;

$R_{15}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two $R_{15}$ are taken together to form a ring; and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In yet a further embodiment, kinase inhibitors of the present invention comprise the formula:

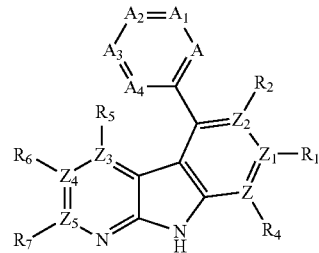

or a polymorph, solvate, ester, tautomer, enantiomer, pharmaceutically acceptable salt or prodrug thereof, wherein A, $A_1$, $A_2$, $A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two $R_{25}$ are taken together to form a ring.

In another embodiment, kinase inhibitors of the present invention comprise the formula:

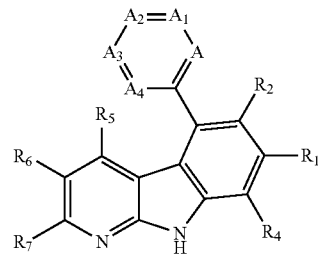

or a polymorph, solvate, ester, tautomer, enantiomer, pharmaceutically acceptable salt or prodrug thereof, wherein A, $A_1$, $A_2$, $A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, (C₉₋₁₂)bicycloaryl and hetero(C₄₋₁₂)bicycloaryl, each substituted or unsubstituted, or any two R₂₅ are taken together to form a ring.

In still another embodiment, kinase inhibitors of the present invention comprise the formula:

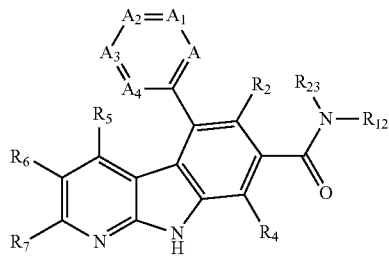

or a polymorph, solvate, ester, tautomer, enantiomer, pharmaceutically acceptable salt or prodrug thereof, wherein A, A₁, A₂, A₃ and A₄ are each independently selected from the group consisting of CR₂₅ and N;

R₂₃ is selected from the group consisting of hydrogen, carbonyl, (C₁₋₁₀)alkyl, halo(C₁₋₁₀)alkyl, carbonyl(C₁₋₃) alkyl, thiocarbonyl(C₁₋₃)alkyl, sulfonyl(C₁₋₃)alkyl, sulfinyl(C₁₋₃)alkyl, amino(C₁₋₁₀)alkyl, imino(C₁₋₃) alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅) alkyl, (C₃₋₁₂)cycloalkyl, hetero(C₃₋₁₂)cycloalkyl, aryl and heteroaryl, each substituted or unsubstituted, or R₂₃ and R₁₂ are taken together to form a ring; and R₂₅ is selected from the group consisting of hydrogen, halo, nitro, cyano, thio, oxy, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo (C₁₋₁₀)alkyl, carbonyl(C₁₋₃)alkyl, thiocarbonyl(C₁₋₃) alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅) alkyl, hetero(C₃₋₁₂)cycloalkyl(C₁₋₅)alkyl, aryl(C₁₋₁₀) alkyl, heteroaryl(C₁₋₅)alkyl, (C₉₋₁₂)bicycloaryl(C₁₋₅) alkyl, hetero(C₈₋₁₂)bicycloaryl(C₁₋₅)alkyl, (C₃₋₁₂) cycloalkyl, hetero(C₃₋₁₂)cycloalkyl, (C₉₋₁₂) bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or any two R₂₅ are taken together to form a ring.

In yet another embodiment, kinase inhibitors of the present invention comprise the formula:

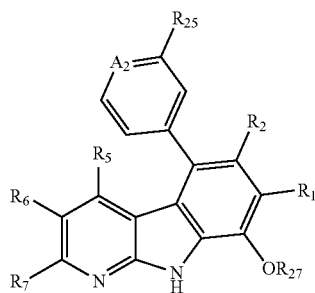

or a polymorph, solvate, ester, tautomer, enantiomer, pharmaceutically acceptable salt or prodrug thereof, wherein A₂ is selected from the group consisting of CR₂₅ and N;

R₂₅ is selected from the group consisting of hydrogen, halo, nitro, cyano, thio, oxy, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo (C₁₋₁₀)alkyl, carbonyl(C₁₋₃)alkyl, thiocarbonyl(C₁₋₃) alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅) alkyl, hetero(C₃₋₁₂)cycloalkyl(C₁₋₅)alkyl, aryl(C₁₋₁₀) alkyl, heteroaryl(C₁₋₅)alkyl, (C₉₋₁₂)bicycloaryl(C₁₋₅) alkyl, hetero(C₈₋₁₂)bicycloaryl(C₁₋₅)alkyl, (C₃₋₁₂) cycloalkyl, hetero(C₃₋₁₂)cycloalkyl, (C₉₋₁₂) bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or any two R₂₅ are taken together to form a ring; and R₂₇ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, aminocarbonyl, amino, (C₁₋₁₀) alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, (C₁₋₁₀)azaalkyl, (C₁₋₁₀)oxaalkyl, (C₁₋₁₀)oxoalkyl, imino(C₁₋₁₀)alkyl, (C₃₋₁₂)cycloalkyl(C₁₋₅)alkyl, hetero(C₃₋₁₂)cycloalkyl (C₁₋₁₀)alkyl, aryl(C₁₋₁₀)alkyl, hetero(C₁₋₁₀)aryl(C₁₋₅) alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂) cycloalkyl, hetero(C₃₋₁₂)cycloalkyl, (C₉₋₁₂) bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂) bicycloaryl, each substituted or unsubstituted.

In a further embodiment, kinase inhibitors of the present invention comprise the formula:

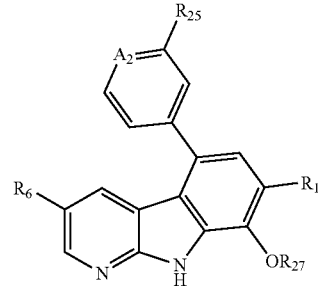

or a polymorph, solvate, ester, tautomer, enantiomer, pharmaceutically acceptable salt or prodrug thereof, wherein A₂ is selected from the group consisting of CR₂₅ and N;

R₂₅ is selected from the group consisting of hydrogen, halo, nitro, cyano, thio, oxy, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo (C₁₋₁₀)alkyl, carbonyl(C₁₋₃)alkyl, thiocarbonyl(C₁₋₃) alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅) alkyl, hetero(C₃₋₁₂)cycloalkyl(C₁₋₅)alkyl, aryl(C₁₋₁₀) alkyl, heteroaryl(C₁₋₅)alkyl, (C₉₋₁₂)bicycloaryl(C₁₋₅) alkyl, hetero(C₈₋₁₂)bicycloaryl(C₁₋₅)alkyl, (C₃₋₁₂) cycloalkyl, hetero(C₃₋₁₂)cycloalkyl, (C₉₋₁₂) bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or any two $R_{25}$ are taken together to form a ring; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further embodiment, kinase inhibitors of the present invention comprise the formula:

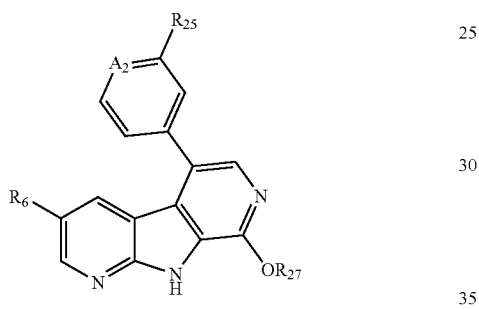

or a polymorph, solvate, ester, tautomer, enantiomer, pharmaceutically acceptable salt or prodrug thereof, wherein $A_2$ is selected from the group consisting of $CR_{25}$ and N;

$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet a further embodiment, kinase inhibitors of the present invention comprise the formula:

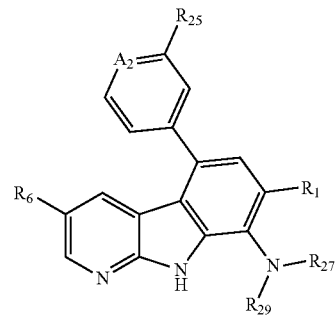

or a polymorph, solvate, ester, tautomer, enantiomer, pharmaceutically acceptable salt or prodrug thereof, wherein $A_2$ is selected from the group consisting of $CR_{25}$ and N;

$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring; and $R_{27}$ and $R_{29}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{27}$ and $R_{29}$ are taken together to form a substituted or unsubstituted ring.

In another embodiment, kinase inhibitors of the present invention comprise the formula:

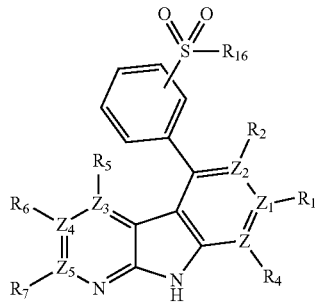

or a polymorph, solvate, ester, tautomer, enantiomer, pharmaceutically acceptable salt or prodrug thereof, wherein $R_{16}$ is selected from the group consisting of amino, $(C_{1-10})$alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In still another embodiment, kinase inhibitors of the present invention comprise the formula:

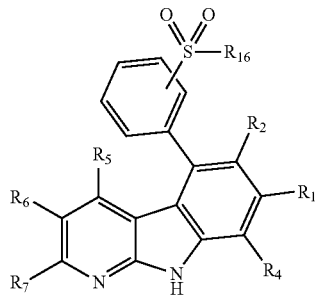

or a polymorph, solvate, ester, tautomer, enantiomer, pharmaceutically acceptable salt or prodrug thereof, wherein $R_{16}$ is selected from the group consisting of amino, $(C_{1-10})$alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In yet another embodiment, kinase inhibitors of the present invention comprise the formula:

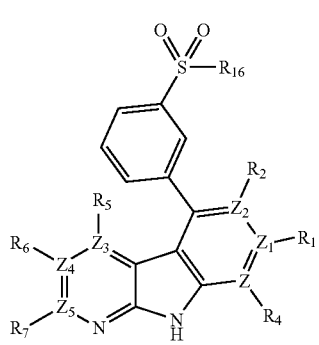

or a polymorph, solvate, ester, tautomer, enantiomer, pharmaceutically acceptable salt or prodrug thereof, wherein $R_{16}$ is selected from the group consisting of amino, $(C_{1-10})$alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In a further embodiment, kinase inhibitors of the present invention comprise the formula:

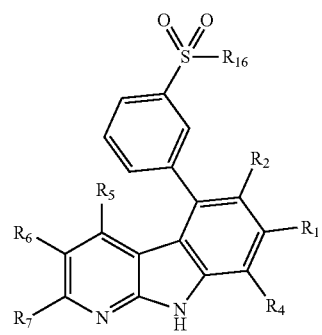

or a polymorph, solvate, ester, tautomer, enantiomer, pharmaceutically acceptable salt or prodrug thereof, wherein $R_{16}$ is selected from the group consisting of amino, $(C_{1-10})$alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In still a further embodiment, kinase inhibitors of the present invention comprise the formula:

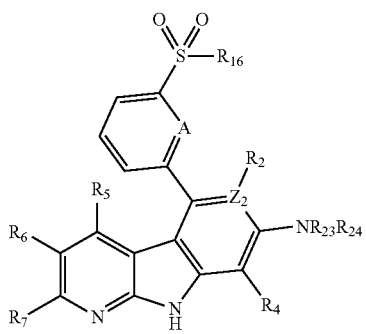

or a polymorph, solvate, ester, tautomer, enantiomer, pharmaceutically acceptable salt or prodrug thereof, wherein A is selected from the group consisting of $CR_{25}$ and N;

$R_{16}$ is selected from the group consisting of amino, $(C_{1-10})$alkylamino, $(C_{1-10})$alkyl, halo$(C_{1-10})$alkyl, hydroxy ($C_{1-5}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted;

$R_{23}$ and $R_{24}$ are each independently selected from the group consisting of hydrogen, carbonyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted, or $R_{23}$ and $R_{24}$ are taken together to form a ring; and $R_{25}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In yet a further embodiment, kinase inhibitors of the present invention comprise the formula:

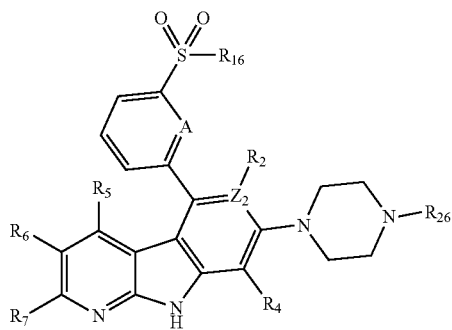

or a polymorph, solvate, ester, tautomer, enantiomer, pharmaceutically acceptable salt or prodrug thereof, wherein A is selected from the group consisting of $CR_{25}$ and N;

$R_{16}$ is selected from the group consisting of amino, ($C_{1-10}$)alkylamino, ($C_{1-10}$)alkyl, halo($C_{1-10}$)alkyl, hydroxy($C_{1-5}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted;

$R_{25}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{26}$ is selected from the group consisting of hydrogen, carbonyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted.

In another embodiment, kinase inhibitors of the present invention comprise the formula:

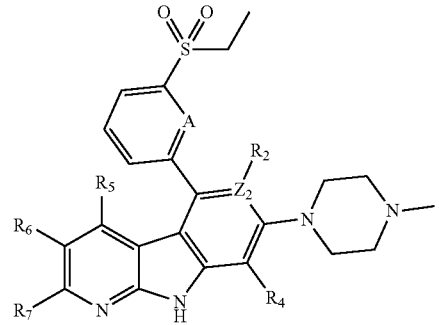

or a polymorph, solvate, ester, tautomer, enantiomer, pharmaceutically acceptable salt or prodrug thereof, wherein A is selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In still another embodiment, kinase inhibitors of the present invention comprise the formula:

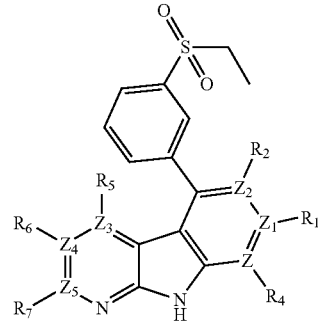

or a polymorph, solvate, ester, tautomer, enantiomer, pharmaceutically acceptable salt or prodrug thereof.

In yet another embodiment, kinase inhibitors of the present invention comprise the formula:

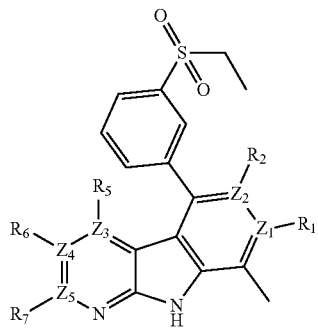

or a polymorph, solvate, ester, tautomer, enantiomer, pharmaceutically acceptable salt or prodrug thereof.

In a further embodiment, kinase inhibitors of the present invention comprise the formula:

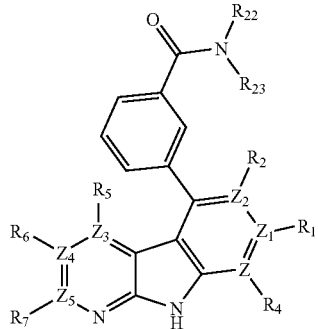

or a polymorph, solvate, ester, tautomer, enantiomer, pharmaceutically acceptable salt or prodrug thereof, wherein $R_{22}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ is selected from the group consisting of hydrogen, carbonyl, $(C_{1-10})$alkyl, halo$(C_{1-10})$alkyl, carbonyl$(C_{1-3})$ alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$ alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$ alkyl, $(C_{3-12})$cycloalkyl, hetero$(C_{3-12})$cycloalkyl, aryl and heteroaryl, each substituted or unsubstituted, or $R_{23}$ and $R_{22}$ are taken together to form a ring.

In yet a further embodiment, kinase inhibitors of the present invention comprise the formula:

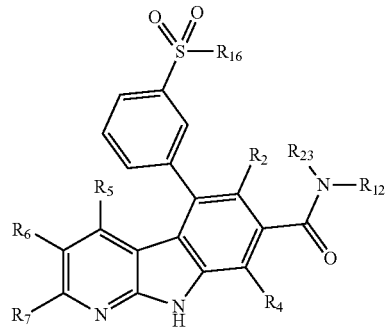

or a polymorph, solvate, ester, tautomer, enantiomer, pharmaceutically acceptable salt or prodrug thereof, wherein $R_2$ is —$Y_2$—$R_{13}$;

$Y_2$ is absent or a linker providing 1 or 2 atom separation between $R_{13}$ and the ring to which $Y_2$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, $(C_{1-5})$alkylamino, $(C_{1-5})$alkyl, halo $(C_{1-5})$alkyl, carbonyl$(C_{1-3})$alkyl, sulfonyl$(C_{1-3})$alkyl, amino $(C_{1-5})$alkyl, aryl$(C_{1-5})$alkyl, heteroaryl$(C_{1-5})$ alkyl, $(C_{3-6})$cycloalkyl and hetero$(C_{3-6})$cycloalkyl, each substituted or unsubstituted;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_7$ is selected from the group consisting of hydrogen, halo, hydroxy, alkoxy, amino and $(C_{1-5})$alkyl, each substituted or unsubstituted;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring;

$R_{16}$ is selected from the group consisting of amino, $(C_{1-10})$ alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino (C$_{1-10}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted; and R$_{23}$ is selected from the group consisting of hydrogen, carbonyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted, or R$_{23}$ and R$_{12}$ are taken together to form a substituted or unsubstituted ring.

In still another embodiment, kinase inhibitors of the present invention comprise the formula:

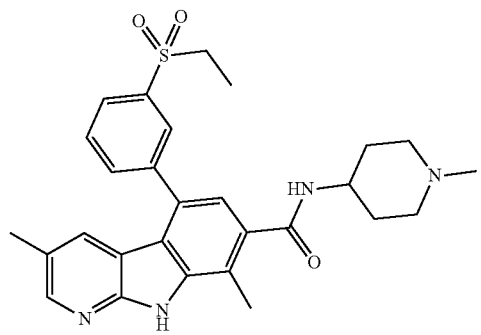

or a polymorph, solvate, ester, tautomer, enantiomer, pharmaceutically acceptable salt or prodrug thereof.

In a further embodiment, kinase inhibitors of the present invention comprise the formula:

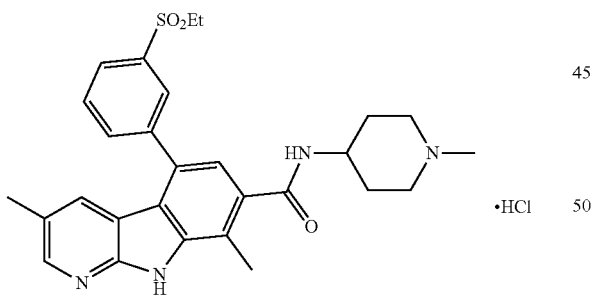

or a polymorph, solvate, ester, tautomer, enantiomer, pharmaceutically acceptable salt or prodrug thereof, wherein at least a portion of the compound is present as Amorphous Form, characterized by physical properties which comprise one or more of the following:

(a) may be formed by lyophilizing a solution of Compound 88 in ACN and water;

(b) has an XRPD spectrum characterized by a diffuse halo with no discernable peaks; and/or (c) shows 7.6 wt % Cl⁻ present using ion chromatography.

In yet another embodiment, kinase inhibitors of the present invention comprise the formula:

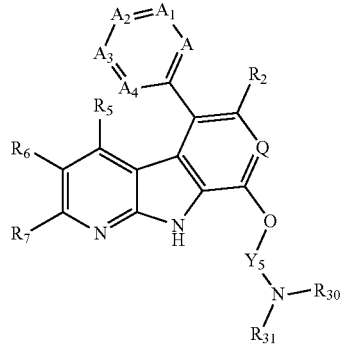

or a polymorph, solvate, ester, tautomer, enantiomer, pharmaceutically acceptable salt or prodrug thereof, wherein
Q is selected from the group consisting of CRi and N;
A, A$_1$, A$_2$, A$_3$ and A$_4$ are each independently selected from the group consisting of CR$_{25}$ and N;
R$_1$ is —Y$_1$—R$_{12}$;
R$_2$ is —Y$_2$—R$_{13}$;
Y$_1$ and Y$_2$ are each independently absent or a linker providing 1 or 2 atom separation between R$_{12}$ or R$_{13}$ and the ring to which Y$_1$ or Y$_2$ is attached, wherein the atoms of the linker providing the separation are selected from the group consisting of carbon, oxygen, nitrogen, and sulfur;
Y$_5$ is absent or a linker providing 1, 2, 3, 4, 5, 6, 7 or 8 atom separation between the O and the N to which Y$_5$ is attached, wherein the atoms of the linker providing the separation are selected from the group consisting of carbon, oxygen, nitrogen, and sulfur;
R$_5$ and R$_6$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted;
R$_7$ is selected from the group consisting of hydrogen, halo, hydroxy, alkoxy, amino and (C$_{1-5}$)alkyl, each substituted or unsubstituted;
R$_{12}$ and R$_{13}$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{12}$ and R$_{13}$ are taken together to form a substituted or unsubstituted ring;

$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a substituted or unsubstituted ring; and $R_{30}$ and $R_{31}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring.

In a further embodiment, kinase inhibitors of the present invention comprise the formula:

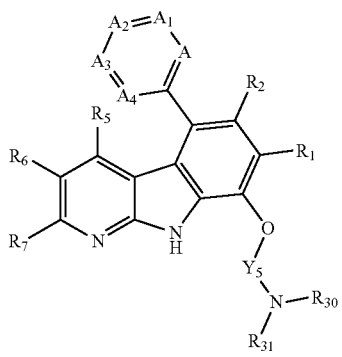

or a polymorph, solvate, ester, tautomer, enantiomer, pharmaceutically acceptable salt or prodrug thereof, wherein A, $A_1$, $A_2$, $A_3$ and $A_4$ are each independently selected from the group consisting of $CR_{25}$ and N;

$R_1$ is —$Y_1$—$R_{12}$;

$R_2$ is —$Y_2$—$R_{13}$;

$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

$Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_7$ is selected from the group consisting of hydrogen, halo, hydroxy, alkoxy, amino and $(C_{1-5})$alkyl, each substituted or unsubstituted;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring;

$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a substituted or unsubstituted ring; and $R_{30}$ and $R_{31}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$ bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring.

In still a further embodiment, kinase inhibitors of the present invention comprise the formula:

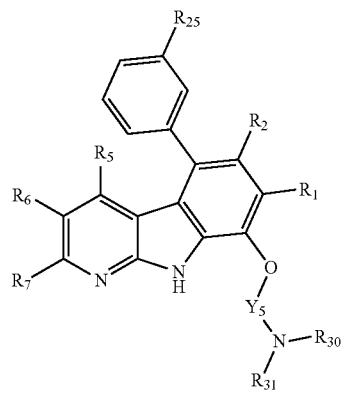

or a polymorph, solvate, ester, tautomer, enantiomer, pharmaceutically acceptable salt or prodrug thereof.

In yet a further embodiment, kinase inhibitors of the present invention comprise the formula:

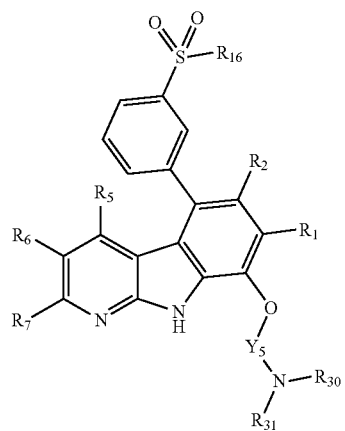

or a polymorph, solvate, ester, tautomer, enantiomer, pharmaceutically acceptable salt or prodrug thereof, wherein $R_{16}$ is selected from the group consisting of amino, ($C_{1-10}$) alkylamino, ($C_{1-10}$)alkyl, halo($C_{1-10}$)alkyl, hydroxy ($C_{1-5}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted.

In another embodiment, kinase inhibitors of the present invention comprise the formula:

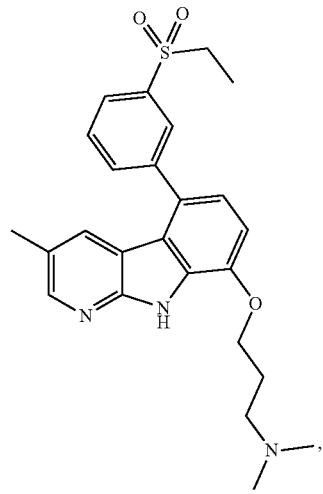

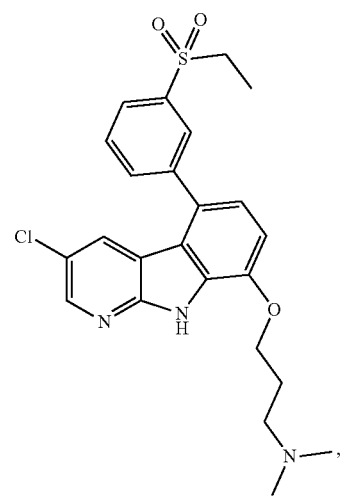

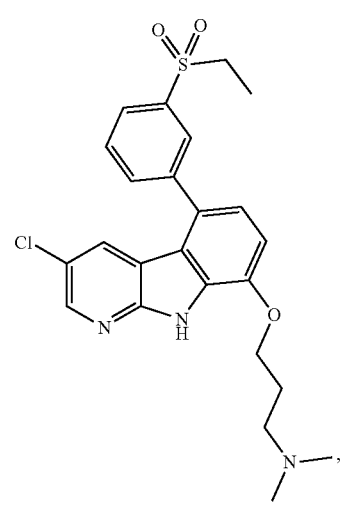

-continued

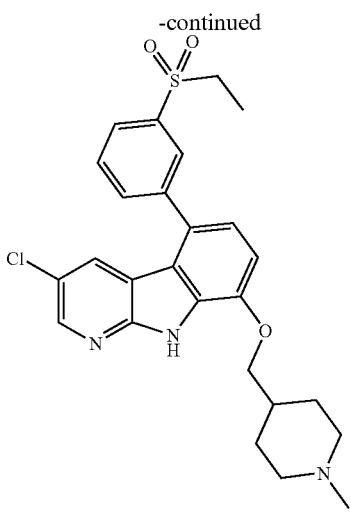

and

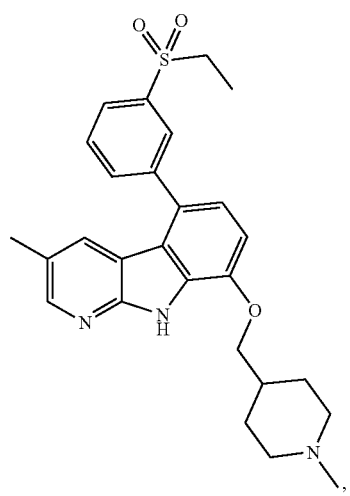

or a polymorph, solvate, ester, tautomer, enantiomer, pharmaceutically acceptable salt or prodrug thereof.

In another of its aspects, the present invention relates to processes for preparing compounds of the present invention. In one embodiment, the process comprises:

reacting a compound comprising the formula

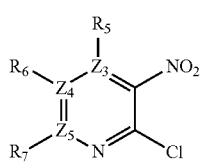

with a compound comprising the formula

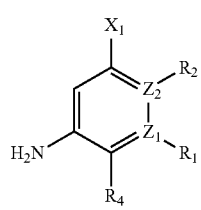

under conditions that form a first reaction product comprising the formula

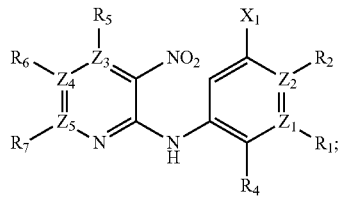

treating the first reaction product under conditions that form a second reaction product comprising the formula

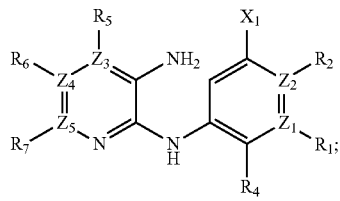

treating the second reaction product under conditions that form a third reaction product comprising the formula

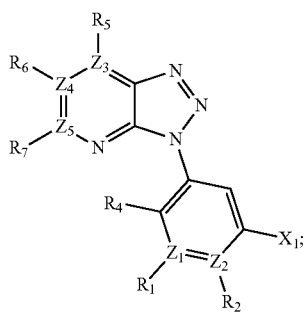

treating the third reaction product under conditions that form a fourth reaction product comprising the formula

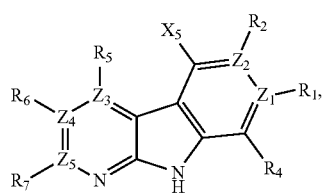

wherein
$Z_1$, $Z_2$, $Z_3$, $Z_4$ and $Z_5$ are each independently selected from the group consisting of C and N;
$R_1$ is —$Y_1$—$R_{12}$, or $R_1$ is absent when $Z_1$ is N;
$R_2$ is —$Y_2$—$R_{13}$, or $R_2$ is absent when $Z_2$ is N, or $R_1$ and $R_2$ are taken together to form a ring;
$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

R$_4$ is selected from the group consisting of hydrogen, halo, nitro, cyano, thio, oxy, hydroxy, carbonyloxy, alkoxy, carbonyl, amino, (C$_{1-5}$)alkylamino, (C$_{1-5}$)alkyl, halo (C$_{1-5}$)alkyl, carbonyl(C$_{1-3}$)alkyl, sulfonyl(C$_{1-3}$)alkyl, amino (C$_{1-5}$)alkyl, aryl(C$_{1-5}$)alkyl, heteroaryl(C$_{1-5}$) alkyl, (C$_{3-6}$)cycloalkyl and hetero(C$_{3-6}$)cycloalkyl, each substituted or unsubstituted, with the proviso that R$_4$ is absent when the atom to which it is bound is N;

R$_5$ and R$_6$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that each of R$_5$ and R$_6$ is absent when the atom to which it is bound is N;

R$_7$ is selected from the group consisting of hydrogen, halo, hydroxy, alkoxy, amino and (C$_{1-5}$)alkyl, each substituted or unsubstituted, with the proviso that R$_7$ is absent when the atom to which it is bound is N;

R$_{12}$ and R$_{13}$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{12}$ and R$_{13}$ are taken together to form a ring; and X$_1$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, (C$_{1-10}$)azaalkyl, (C$_{1-10}$) oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted.

In one variation of the above embodiment, the process further comprises:

treating the fourth reaction product under conditions that form a compound comprising the formula

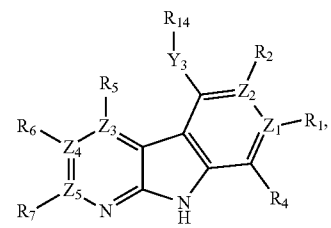

wherein

Y$_3$ is absent or a linker providing 1 or 2 atom separation between R$_{14}$ and the ring to which Y$_3$ is attached, wherein the atoms of the linker providing the separation are selected from the group consisting of carbon, oxygen, nitrogen, and sulfur; and R$_{14}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted.

In another embodiment, the process comprises:

reacting a compound comprising the formula

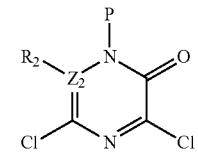

with a compound comprising the formula

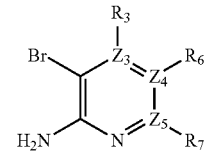

under conditions that form a first reaction product comprising the formula

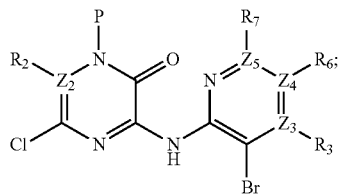

reacting the first reaction product with ethynyltrimethylsilane under conditions that form a second reaction product comprising the formula

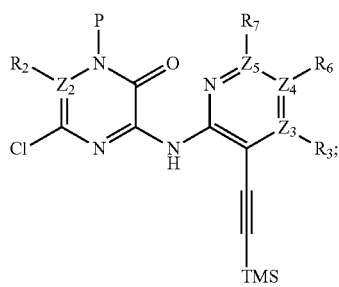

treating the second reaction product under conditions that form a third reaction product comprising the formula

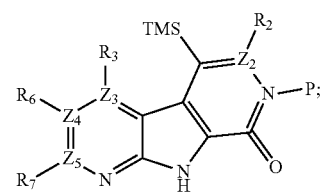

treating the third reaction product under conditions that form a fourth reaction product comprising the formula

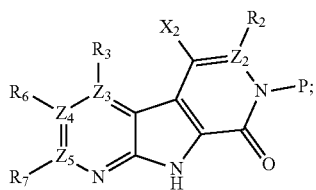

treating the fourth reaction product under conditions that form a fifth reaction product comprising the formula

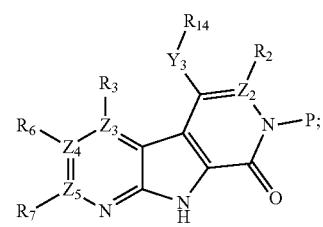

treating the fifth reaction product under conditions that form a sixth reaction product comprising the formula

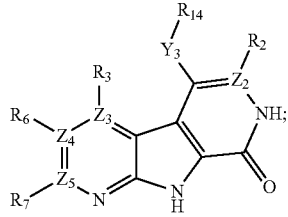

treating the sixth reaction product under conditions that form a seventh reaction product comprising the formula

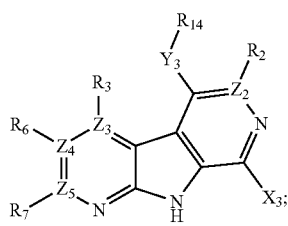

and treating the seventh reaction product under conditions that form a compound comprising the formula

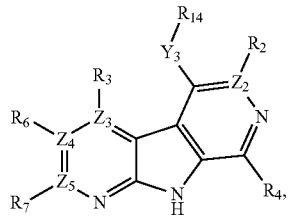

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that each of $R_5$ and $R_6$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_{14}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

P is a protecting group; and $X_2$ and $X_3$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$ alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted.

In still another embodiment, the process comprises:
reacting a compound comprising the formula

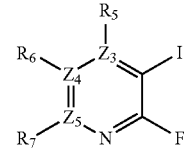

with a compound comprising the formula

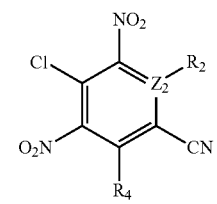

under conditions that form a first reaction product comprising the formula

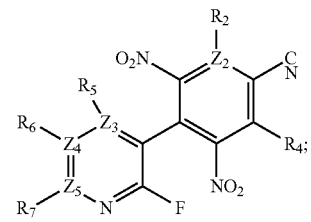

treating the first reaction product under conditions that form a second reaction product comprising the formula

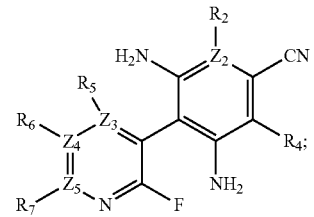

treating the second reaction product under conditions that form a third reaction product comprising the formula

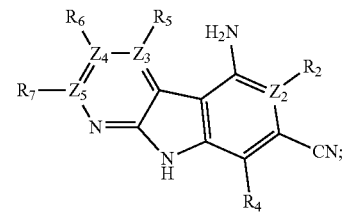

treating the third reaction product under conditions that form a fourth reaction product comprising the formula

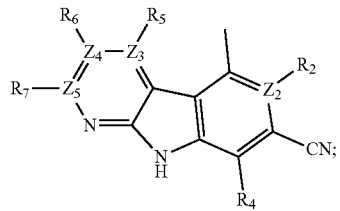

treating the fourth reaction product under conditions that form a fifth reaction product comprising the formula

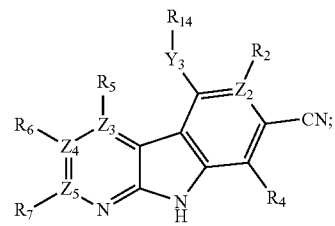

and
treating the fifth reaction product under conditions that form a compound comprising the formula

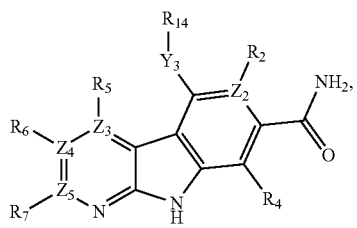

wherein
$Z_2$, $Z_3$, $Z_4$ and $Z_5$ are each independently selected from the group consisting of C and N;
$R_2$ is —$Y_2$-$R_{13}$, or $R_2$ is absent when $Z_2$ is N;
$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;
$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo ($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$) alkyl, ($C_{3-6}$)cycloalkyl and hetero($C_{3-6}$)cycloalkyl, each substituted or unsubstituted, with the proviso that $R_4$ is absent when the atom to which it is bound is N;
$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;
$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;
$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and
$R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In yet another embodiment, the process comprises:
reacting a compound comprising the formula

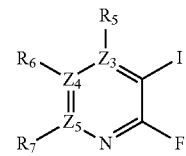

with a compound comprising the formula

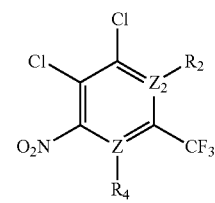

under conditions that form a first reaction product comprising the formula

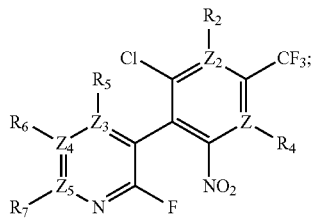

treating the first reaction product under conditions that form a second reaction product comprising the formula

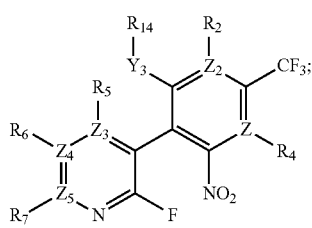

treating the second reaction product under conditions that form a third reaction product comprising the formula

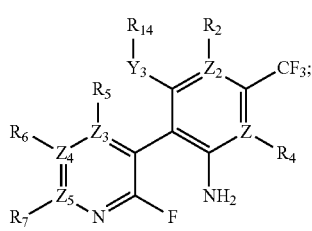

treating the third reaction product under conditions that form a fourth reaction product comprising the formula

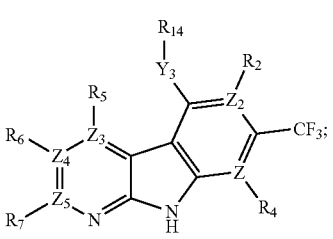

treating the fourth reaction product under conditions that form a fifth reaction product comprising the formula

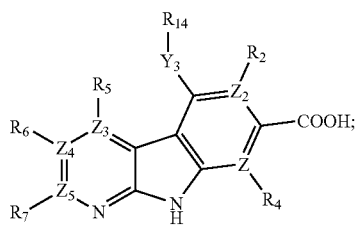

and reacting the fifth reaction product with a compound comprising the formula $HNR_{23}R_{24}$ under conditions that form a compound comprising the formula

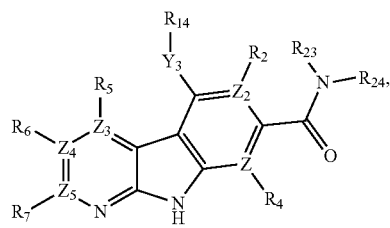

wherein

Z, $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo ($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$) alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

R$_{14}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted; and R$_{23}$ and R$_{24}$ are each independently selected from the group consisting of hydrogen, carbonyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted, or R$_{23}$ and R$_{24}$ are taken together to form a ring.

In another embodiment, the process comprises:

reacting a compound comprising the formula

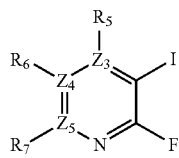

with a compound comprising the formula

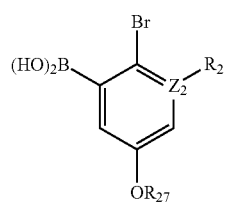

under conditions that form a first reaction product comprising the formula

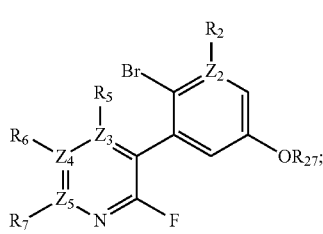

treating the first reaction product under conditions that form a second reaction product comprising the formula

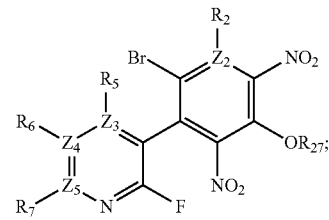

treating the second reaction product under conditions that form a third reaction product comprising the formula

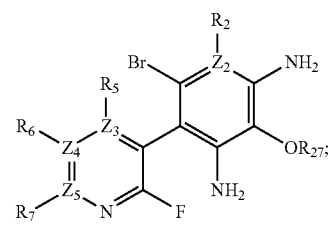

treating the third reaction product under conditions that form a fourth reaction product comprising the formula

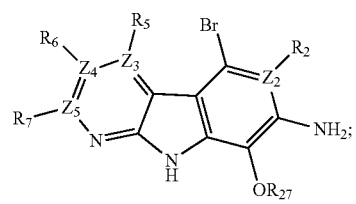

and treating the fourth reaction product under conditions that form a fifth reaction product comprising the formula

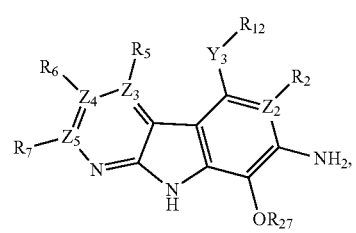

wherein

Z$_2$, Z$_3$, Z$_4$ and Z$_5$ are each independently selected from the group consisting of C and N;

R$_2$ is —Y$_2$—R$_{13}$, or R$_2$ is absent when Z$_2$ is N;

Y$_2$ and Y$_3$ are each independently absent or a linker providing 1 or 2 atom separation between R$_{13}$ or R$_{14}$ and the ring to which Y$_2$ or Y$_3$ is attached, wherein the atoms of the linker providing the separation are selected from the group consisting of carbon, oxygen, nitrogen, and sulfur;

R$_5$ and R$_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and $(C_{1-5})$alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$ alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted.

In one variation of the above embodiment, the process further comprises treating the fifth reaction product under conditions that form a compound comprising the formula

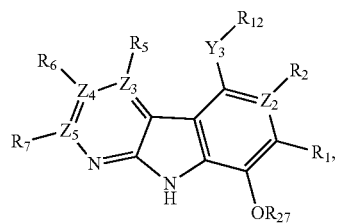

wherein
$R_1$ is —$Y_1$-$R_{12}$;

$Y_1$ is absent or a linker providing 1 or 2 atom separation between $R_{12}$ and the ring to which $Y_1$ is attached, wherein the atoms of the linker providing the separation are selected from the group consisting of carbon, oxygen, nitrogen, and sulfur; and $R_{12}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In still another embodiment, the process comprises:

reacting a compound comprising the formula

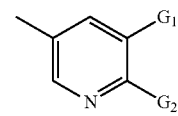

with a compound comprising the formula

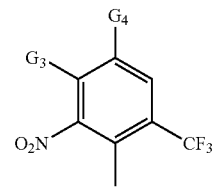

under conditions that form a first reaction product comprising the formula

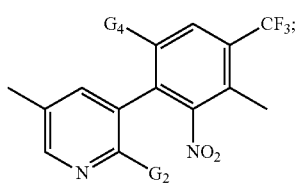

reacting the first reaction product with a compound comprising the formula

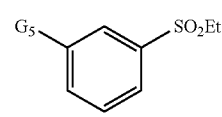

under conditions that form a second reaction product comprising the formula

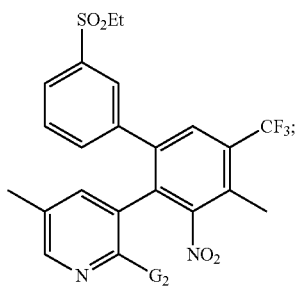

treating the second reaction product under conditions that form a third reaction product comprising the formula

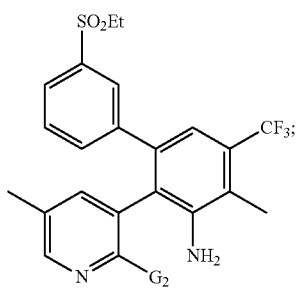

treating the third reaction product under conditions that form a fourth reaction product comprising the formula

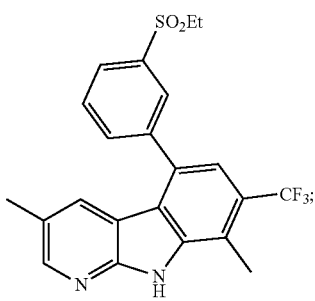

treating the fourth reaction product under conditions that form a fifth reaction product comprising the formula

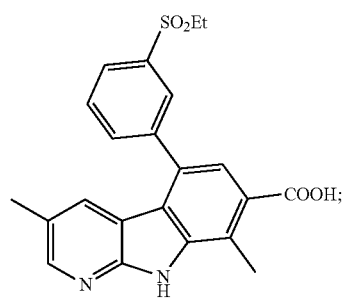

and reacting the fifth reaction product with a compound comprising the formula

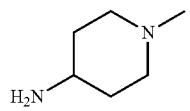

under conditions that form a sixth reaction product comprising the formula

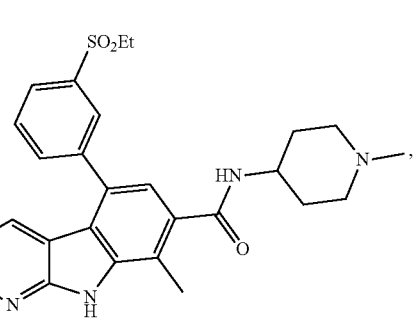

wherein $G_1$, $G_2$, $G_3$, $G_4$ and $G_5$ are each independently a leaving group.

In yet another embodiment, the process comprises:

reacting a compound comprising the formula

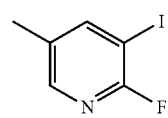

with a compound comprising the formula

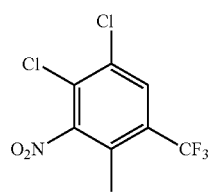

under conditions that form a first reaction product comprising the formula

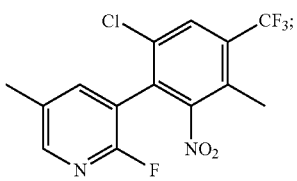

reacting the first reaction product with a compound comprising the formula

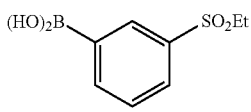

under conditions that form a second reaction product comprising the formula

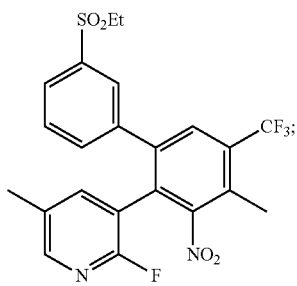

treating the second reaction product under conditions that form a third reaction product comprising the formula

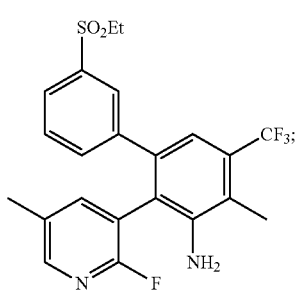

treating the third reaction product under conditions that form a fourth reaction product comprising the formula

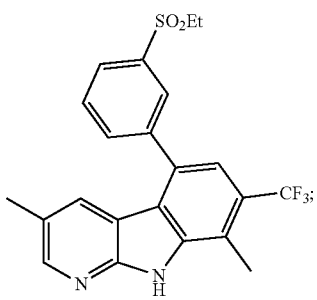

treating the fourth reaction product under conditions that form a fifth reaction product comprising the formula

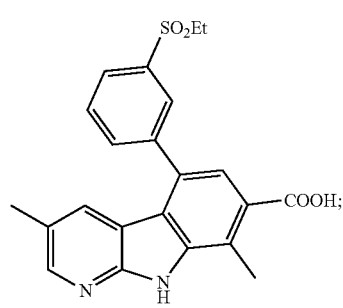

and reacting the fifth reaction product with a compound comprising the formula

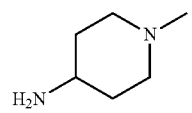

under conditions that form a sixth reaction product comprising the formula

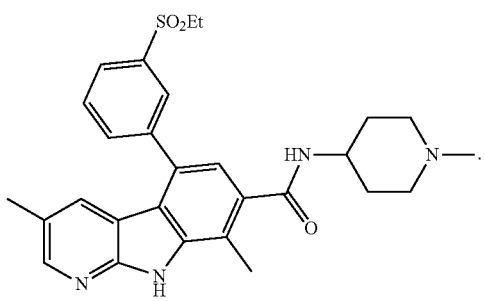

In a further embodiment, the process comprises:

reacting a compound comprising the formula

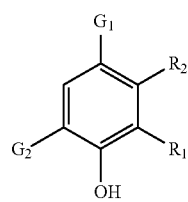

with a compound comprising the formula

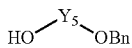

under conditions that form a first reaction product comprising the formula

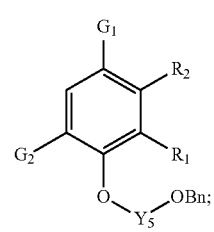

reacting the first reaction product with a compound comprising the formula

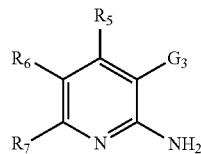

under conditions that form a second reaction product comprising the formula

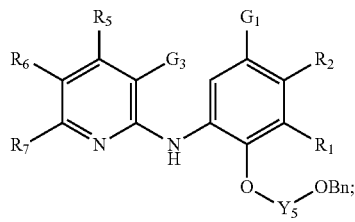

treating the second reaction product under conditions that form a third reaction product comprising the formula

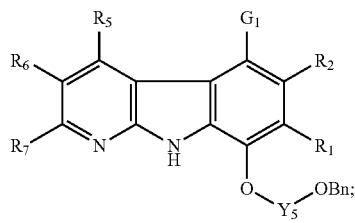

treating the third reaction product under conditions that form a fourth reaction product comprising the formula

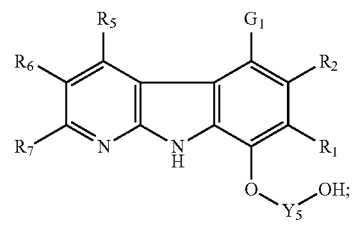

reacting the fourth reaction product with a compound comprising the formula

under conditions that form a fifth reaction product comprising the formula

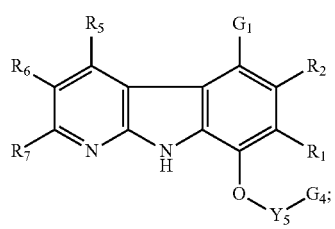

reacting the fifth reaction product with a compound comprising the formula

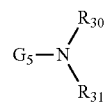

under conditions that form a sixth reaction product comprising the formula

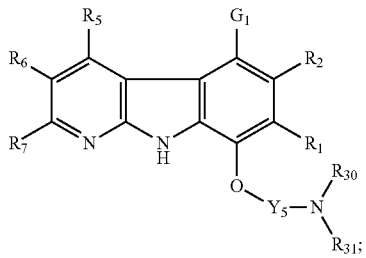

and reacting the sixth reaction product with a compound comprising the formula

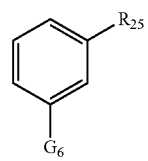

under conditions that form a seventh reaction product comprising the formula

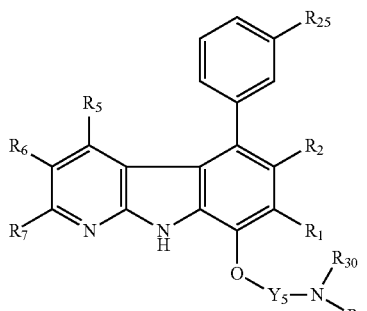

wherein $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;

$R_1$ is —$Y_1$-$R_{12}$;
$R_2$ is —$Y_2$-$R_{13}$;
$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;
$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
$R_7$ is selected from the group consisting of hydrogen, halo, hydroxy, alkoxy, amino and $(C_{1-5})$alkyl, each substituted or unsubstituted;
$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring;
$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a substituted or unsubstituted ring;
$R_{30}$ and $R_{31}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring; and $X_4$, $G_1$, $G_2$, $G_3$, $G_4$, $G_5$ and $G_6$ are each independently a leaving group.

In still a further embodiment, the process comprises:

reacting a compound comprising the formula

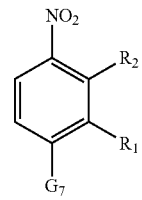

with a compound comprising the formula

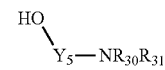

under conditions that form a first reaction product comprising the formula

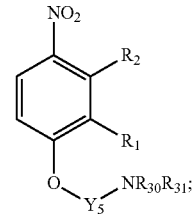

reacting the first reaction product with a compound comprising the formula

under conditions that form a second reaction product comprising the formula

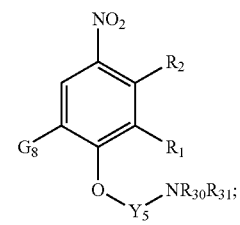

reacting the second reaction product with a compound comprising the formula

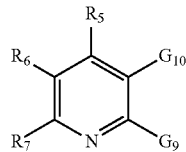

under conditions that form a third reaction product comprising the formula

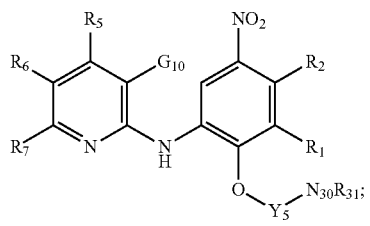

treating the third reaction product under conditions that form a fourth reaction product comprising the formula

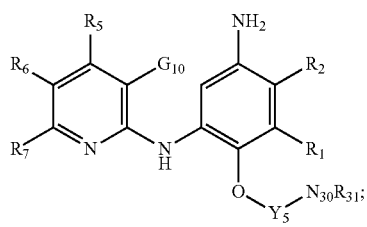

treating the fourth reaction product under conditions that form a fifth reaction product comprising the formula

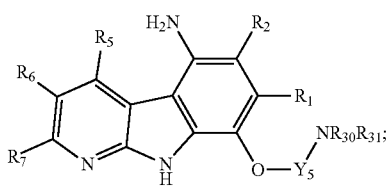

reacting the fifth reaction product with a compound comprising the formula

under conditions that form a sixth reaction product comprising the formula

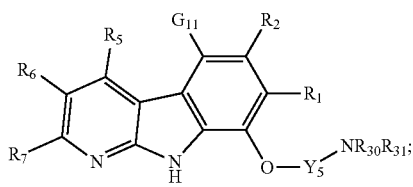

and reacting the sixth reaction product with a compound comprising the formula

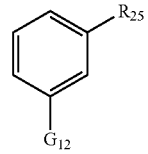

under conditions that form a seventh reaction product comprising the formula

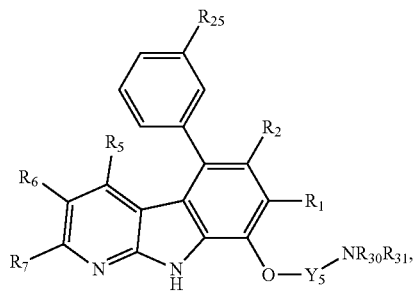

wherein $Y_5$ is absent or a linker providing 1, 2, 3, 4, 5, 6, 7 or 8 atom separation between the and the N to which $Y_5$ is attached, wherein the atoms of the linker providing the separation are selected from the group consisting of carbon, oxygen, nitrogen, and sulfur;

$R_1$ is —$Y_1$-$R_{12}$;

$R_2$ is —$Y_2$—$R_{13}$;

$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bi-cycloalkyl, aryl, heteroaryl, $(C_{9-12})$bicycloaryl and hetero$(C_{4-12})$bicycloaryl, each substituted or unsubstituted;

R$_7$ is selected from the group consisting of hydrogen, halo, hydroxy, alkoxy, amino and (C$_{1-5}$)alkyl, each substituted or unsubstituted;

R$_{12}$ and R$_{13}$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{12}$ and R$_{13}$ are taken together to form a substituted or unsubstituted ring;

R$_{25}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted;

R$_{30}$ and R$_{31}$ are each independently selected from the group consisting of hydrogen, oxy, hydroxy, carbonyloxy, (C$_{1-10}$)alkoxy, (C$_{4-12}$)aryloxy, hetero(C$_{1-10}$)aryloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{30}$ and R$_{31}$ are taken together to form a substituted or unsubstituted ring, or R$_{30}$ and Y$_5$ are taken together to form a substituted or unsubstituted ring; and X$_5$, X$_6$, G$_7$, G$_8$, G$_9$, G$_{10}$, G$_{11}$ and G$_{12}$ are each independently a leaving group.

In still another of its aspects, the present invention relates to compounds useful in preparing compounds of the present invention. In one embodiment, such compounds comprise a formula

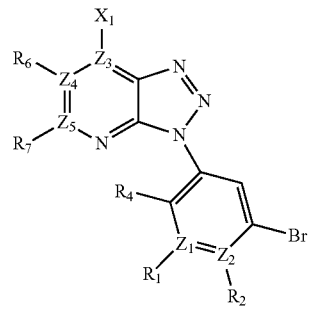

wherein

X$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbony(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted.

Z$_1$, Z$_2$, Z$_3$, Z$_4$ and Z$_5$ are each independently selected from the group consisting of C and N;

R$_1$ is —Y$_1$—R$_{12}$, or R$_1$ is absent when Z$_1$ is N;

R$_2$ is —Y$_2$-R$_{13}$, or R$_2$ is absent when Z$_2$ is N, or R$_1$ and R$_2$ are taken together to form a ring;

Y$_1$ and Y$_2$ are each independently absent or a linker providing 1 or 2 atom separation between R$_{12}$ or R$_{13}$ and the ring to which Y$_1$ or Y$_2$ is attached, wherein the atoms of the linker providing the separation are selected from the group consisting of carbon, oxygen, nitrogen, and sulfur;

R$_4$ is selected from the group consisting of hydrogen, halo, nitro, cyano, thio, oxy, hydroxy, carbonyloxy, alkoxy, carbonyl, amino, (C$_{1-5}$)alkylamino, (C$_{1-5}$)alkyl, halo (C$_{1-5}$)alkyl, carbonyl(C$_{1-3}$)alkyl, sulfonyl(C$_{1-3}$)alkyl, amino (C$_{1-5}$)alkyl, aryl(C$_{1-5}$)alkyl, heteroaryl(C$_{1-5}$)alkyl, (C$_{3-6}$)cycloalkyl and hetero(C$_{3-6}$)cycloalkyl, each substituted or unsubstituted, with the proviso that R$_4$ is absent when the atom to which it is bound is N;

R$_6$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)

bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N; and $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a ring.

In another embodiment, such compounds comprise a formula

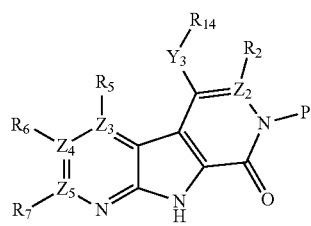

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and P is a protecting group.

In still another embodiment, such compounds comprise a formula

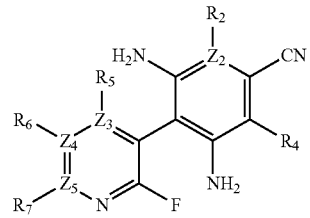

wherein $Z_2$, $Z_3$, $Z_4$ and $Z_5$ are each independently selected from the group consisting of C and N;

$R_2$ is —$Y_2$-$R_{13}$, or $R_2$ is absent when $Z_2$ is N;

$Y_2$ is absent or a linker providing 1 or 2 atom separation between $R_{13}$ and the ring to which $Y_2$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N; and $R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In yet another embodiment, such compounds comprise a formula

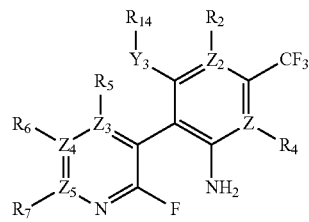

wherein

Z, $Z_2$, $Z_3$, $Z_4$ and $Z_5$ are each independently selected from the group consisting of C and N;

$R_2$ is —$Y_2$-$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo ($C_{1-5}$)alkyl, carbonyl($C_{1-3}$)alkyl, sulfonyl($C_{1-3}$)alkyl, amino ($C_{1-5}$)alkyl, aryl($C_{1-5}$)alkyl, heteroaryl($C_{1-5}$) alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In another embodiment, such compounds comprise a formula

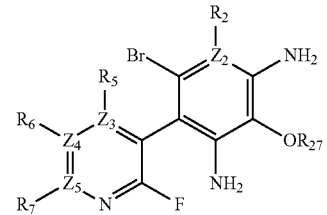

wherein $Z_2$, $Z_3$, $Z_4$ and $Z_5$ are each independently selected from the group consisting of C and N;

$R_2$ is —$Y_2$-$R_{13}$, or $R_2$ is absent when $Z_2$ is N;

$Y_2$ is absent or a linker providing 1 or 2 atom separation between $R_{13}$ and the ring to which $Y_2$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that each of R$_5$ and R$_6$ is absent when the atom to which it is bound is N;

R$_7$ is selected from the group consisting of hydrogen, halo, hydroxy, alkoxy, amino and (C$_{1-5}$)alkyl, each substituted or unsubstituted, with the proviso that R$_7$ is absent when the atom to which it is bound is N;

R$_{13}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted; and R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$) alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl (C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted.

In still another embodiment, such compounds comprise a formula

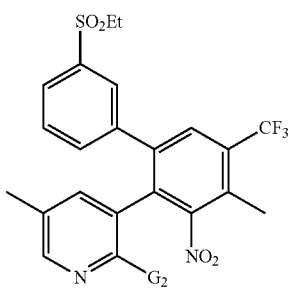

wherein

G$_2$ is a leaving group.

In yet another embodiment, such compounds comprise a formula

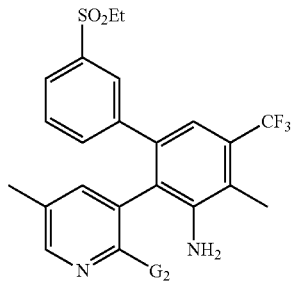

wherein

G$_2$ is a leaving group.

In a further embodiment, such compounds comprise a formula

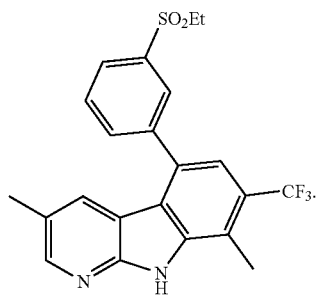

In still a further embodiment, such compounds comprise a formula

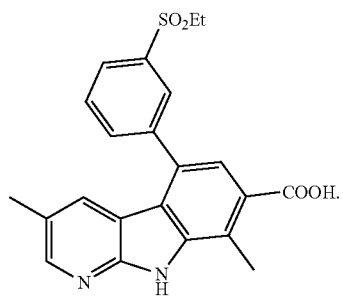

In yet a further embodiment, such compounds comprise a formula

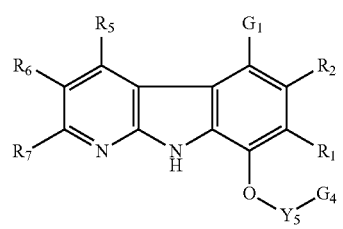

wherein
- $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;
- $R_1$ is $-Y_1-R_{12}$;
- $R_2$ is $-Y_2-R_{13}$;
- $Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;
- $R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
- $R_7$ is selected from the group consisting of hydrogen, halo, hydroxy, alkoxy, amino and $(C_{1-5})$alkyl, each substituted or unsubstituted;
- $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring; and
- $G_1$ and $G_4$ are each independently a leaving group.

In another embodiment, such compounds comprise a formula

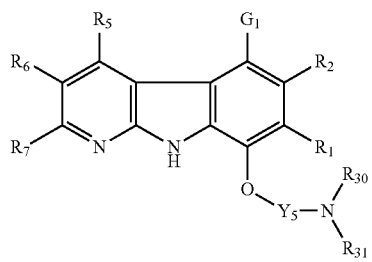

wherein
- $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;
- $R_1$ is $-Y_1-R_{12}$;
- $R_2$ is $-Y_2-R_{13}$;
- $Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;
- $R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
- $R_7$ is selected from the group consisting of hydrogen, halo, hydroxy, alkoxy, amino and $(C_{1-5})$alkyl, each substituted or unsubstituted;
- $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring;
- $R_{30}$ and $R_{31}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring; and
- $G_1$ is a leaving group.

In still another embodiment, such compounds comprise a formula

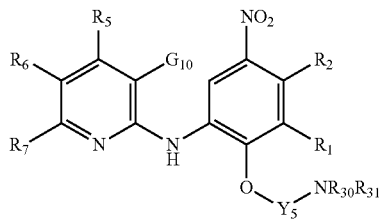

wherein
- $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;
- $R_1$ is —$Y_1$—$R_{12}$;
- $R_2$ is —$Y_2$—$R_{13}$;
- $Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;
- $R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;
- $R_7$ is selected from the group consisting of hydrogen, halo, hydroxy, alkoxy, amino and ($C_{1-5}$)alkyl, each substituted or unsubstituted;
- $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a substituted or unsubstituted ring;
- $R_{30}$ and $R_{31}$ are each independently selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring; and
- $G_{10}$ is a leaving group.

In yet another embodiment, such compounds comprise a formula

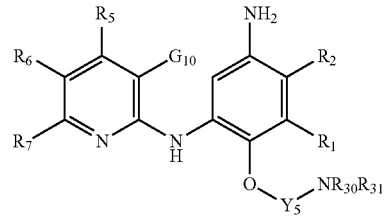

wherein
- $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;
- $R_1$ is —$Y_1$—$R_{12}$;
- $R_2$ is —$Y_2$—$R_{13}$;
- $Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;
- $R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;
- $R_7$ is selected from the group consisting of hydrogen, halo, hydroxy, alkoxy, amino and ($C_{1-5}$)alkyl, each substituted or unsubstituted;
- $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)

cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a substituted or unsubstituted ring;

$R_{30}$ and $R_{31}$ are each independently selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{3-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring; and $G_{10}$ is a leaving group.

In a further embodiment, such compounds comprise a formula

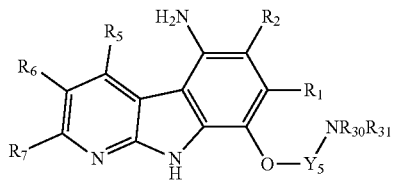

wherein $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;

$R_1$ is —$Y_1$-$R_{12}$;

$R_2$ is —$Y_2$-$R_{13}$;

$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_7$ is selected from the group consisting of hydrogen, halo, hydroxy, alkoxy, amino and ($C_{1-5}$)alkyl, each substituted or unsubstituted;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a substituted or unsubstituted ring;

$R_{30}$ and $R_{31}$ are each independently selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring.

In still a further embodiment, such compounds comprise a formula

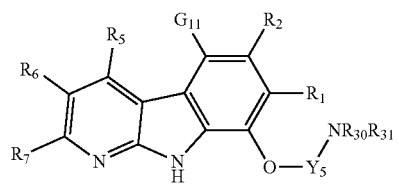

wherein $Y_5$ is absent or a linker providing 1, 2, 3, 4, 5, 6, 7 or 8 atom separation between the O and the N to which $Y_5$ is attached, wherein the atoms of the linker providing the separation are selected from the group consisting of carbon, oxygen, nitrogen, and sulfur;

$R_1$ is —$Y_1$-$R_{12}$;

$R_2$ is —$Y_2$—$R_{13}$;

$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_7$ is selected from the group consisting of hydrogen, halo, hydroxy, alkoxy, amino and $(C_{1-5})$alkyl, each substituted or unsubstituted;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a substituted or unsubstituted ring;

$R_{30}$ and $R_{31}$ are each independently selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, or $R_{30}$ and $R_{31}$ are taken together to form a substituted or unsubstituted ring, or $R_{30}$ and $Y_5$ are taken together to form a substituted or unsubstituted ring; and $G_{11}$ is a leaving group.

In one variation of the compounds and processes of each of the above embodiments and variations, A is $CR_{25}$. In another variation of the compounds and processes of each of the above embodiments and variations, $A_1$ is $CR_{25}$. In still another variation of the compounds and processes of each of the above embodiments and variations, $A_2$ is $CR_{25}$. In yet another variation of the compounds and processes of each of the above embodiments and variations, $A_3$ is $CR_{25}$. In a further variation of the compounds and processes of each of the above embodiments and variations, $A_4$ is $CR_{25}$.

In another variation of the compounds and processes of each of the above embodiments and variations, $Y_1$ is selected from the group consisting of —$CH_2$—, —NH—, —O— and —S—.

In still another variation of the compounds and processes of each of the above embodiments and variations, $Y_1$ is selected from the group consisting of —O—, —$(CR_{19}R_{20})_m$—, —$NR_{21}$—, —S— and —S—$CH_2$—; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl$(C_{1-5})$ alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{19}$ and $R_{12}$ are taken together to form a substituted or unsubstituted ring; and $R_{21}$ is selected from the group consisting of hydrogen, carbonyloxy, alkoxy, aryloxy, heteroaryloxy, carbonyl, oxycarbonyl, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$ alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{21}$ and $R_{12}$ are taken together to form a substituted or unsubstituted ring.

In yet another variation of the compounds and processes of each of the above embodiments and variations, $Y_1$ is —C(O)—$NR_{23}$—; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino$(C_{1-3})$ alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{3-12})$ cycloalkyl, hetero$(C_{3-12})$cycloalkyl, aryl and heteroaryl, each substituted or unsubstituted, or $R_{23}$ and $R_{12}$ are taken together to form a substituted or unsubstituted ring.

In a further variation of the compounds and processes of each of the above embodiments and variations, $Y_1$ is —C(O)—O—.

In still a further variation of the compounds and processes of each of the above embodiments and variations, $Y_1$ is —$NR_{23}$—C(O)—; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$ alkyl, sulfinyl$(C_{1-3})$alkyl, amino$(C_{1-10})$alkyl, imino$(C_{1-3})$ alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{3-12})$ cycloalkyl, hetero$(C_{3-12})$cycloalkyl, aryl and heteroaryl, each substituted or unsubstituted, or $R_{23}$ and $R_{12}$ are taken together to form a ring.

In yet a further variation of the compounds and processes of each of the above embodiments and variations, $Y_2$ is selected from the group consisting of —$CH_2$—, —NH—, —O— and —S—.

In another variation of the compounds and processes of each of the above embodiments and variations, $Y_2$ is selected from the group consisting of —O—, —$(CR_{19}R_{20})_m$—, —$NR_2'$-, —S— and —S—$CH_2$—; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{1-8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{19}$ and $R_{13}$ are taken together to form a substituted or unsubstituted ring; and $R_{21}$ is selected from the group consisting of hydrogen, carbonyloxy, alkoxy, aryloxy, heteroaryloxy, carbonyl, oxycarbonyl, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{1-8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{21}$ and $R_{13}$ are taken together to form a substituted or unsubstituted ring.

In still another variation of the compounds and processes of each of the above embodiments and variations, $Y_3$ is selected from the group consisting of —CH$_2$—, —NH—, —O— and —S—.

In yet another variation of the compounds and processes of each of the above embodiments and variations, $Y_3$ is selected from the group consisting of —O—, —(CR$_{19}$R$_{20}$)$_m$—, —NR$_{21}$—, —S— and —S—CH$_2$—; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{21}$ is selected from the group consisting of hydrogen, carbonyloxy, alkoxy, aryloxy, heteroaryloxy, carbonyl, oxycarbonyl, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of the compounds and processes of each of the above embodiments and variations, $Y_3$ is absent.

In still a further variation of the compounds and processes of each of the above embodiments and variations, —Y$_3$—R$_{14}$ is selected from the group consisting of aryl, heteroaryl, $(C_{9-12})$bicycloaryl and hetero$(C_{4-12})$bicycloaryl, each substituted or unsubstituted.

In yet a further variation of the compounds and processes of each of the above embodiments and variations, Z is N. In another variation of the compounds and processes of each of the above embodiments and variations, $Z_1$ is N. In still another variation of the compounds and processes of each of the above embodiments and variations, $Z_2$ is N. In yet another variation of the compounds and processes of each of the above embodiments and variations, $Z_3$ is N. In a further variation of the compounds and processes of each of the above embodiments and variations, $Z_4$ is N. In still a further variation of the compounds and processes of each of the above embodiments and variations, $Z_5$ is N. In yet a further variation of the compounds and processes of each of the above embodiments and variations, Z, $Z_2$, $Z_3$, $Z_4$ and $Z_5$ are each C. In another variation of the compounds and processes of each of the above embodiments and variations, Z, $Z_1$, $Z_2$, $Z_3$, $Z_4$ and $Z_5$ are each C.

In still another variation of the compounds and processes of each of the above embodiments and variations, $R_1$ is selected from the group consisting of hydrogen, halo, amino, alkoxy, carbonyloxy, aminocarbonyl, sulfonyl, carbonylamino, sulfonylamino, $(C_{1-10})$alkyl, hetero$(C_{3-12})$cycloalkyl and aryl, each substituted or unsubstituted. In yet another variation of the compounds and processes of each of the above embodiments and variations, $R_1$ is a substituted or unsubstituted piperadinyl. In a further variation of the compounds and processes of each of the above embodiments and variations, $R_1$ is a substituted or unsubstituted 1-methyl(piperadin-4-yl).

In still a further variation of the compounds and processes of each of the above embodiments and variations, $R_2$ is selected from the group consisting of hydrogen, halo, amino, alkoxy, $(C_{1-10})$alkyl, hetero$(C_{3-12})$cycloalkyl and aryl, each substituted or unsubstituted. In yet a further variation of the compounds and processes of each of the above embodiments and variations, $R_2$ is hydrogen.

In another variation of the compounds and processes of each of the above embodiments and variations, $R_4$ is selected from the group consisting of hydrogen, halo and substituted or unsubstituted $(C_{1-5})$alkyl. In still another variation of the compounds and processes of each of the above embodiments and variations, $R_4$ is methyl. In yet another variation of the compounds and processes of each of the above embodiments and variations, $R_4$ is trifluoromethyl. In a further variation of the compounds and processes of each of the above embodiments and variations, $R_4$ is a substituted or unsubstituted oxaalkyl. In still a further variation of the compounds and processes of each of the above embodiments and variations, $R_4$ is a substituted or unsubstituted alkoxy. In yet a further variation of the compounds and processes of each of the above embodiments and variations, $R_4$ is a substituted or unsubstituted aryloxy.

In another variation of the compounds and processes of each of the above embodiments and variations, $R_4$ is —Y$_4$—R$_{27}$; $Y_4$ is absent or a linker providing 1 or 2 atom separation between $R_{27}$ and the ring to which $Y_4$ is attached; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In one variation, $Y_4$ is selected from the group consisting of —$CH_2$—, —NH—, —O— and —S—. In another variation, $Y_4$ is absent.

In still another variation of the compounds and processes of each of the above embodiments and variations, $R_4$ is —$OR_{27}$ and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In yet another variation of the compounds and processes of each of the above embodiments and variations, $R_4$ is —$SR_{27}$ and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In a further variation of the compounds and processes of each of the above embodiments and variations, $R_4$ is —$NR_{28}R_{27}$; $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{28}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In one variation, $R_{28}$ is selected from the group consisting of hydrogen and a substituted or unsubstituted ($C_{1-5}$)alkyl.

In still a further variation of the compounds and processes of each of the above embodiments and variations, $R_5$ is selected from the group consisting of hydrogen, halo and substituted or unsubstituted ($C_{1-5}$)alkyl. In yet a further variation of the compounds and processes of each of the above embodiments and variations, $R_5$ is hydrogen. In another variation of the compounds and processes of each of the above embodiments and variations, $R_5$ is halo. In still another variation of the compounds and processes of each of the above embodiments and variations, $R_5$ is a substituted or unsubstituted ($C_{1-5}$)alkyl.

In another variation of the compounds and processes of each of the above embodiments and variations, $R_6$ is selected from the group consisting of hydrogen, halo, amino, carbonyl, alkoxy and ($C_{1-5}$)alkyl, each substituted or unsubstituted. In a further variation of the compounds and processes of each of the above embodiments and variations, $R_6$ is a substituted or unsubstituted ($C_{1-5}$)alkyl. In still another variation of the compounds and processes of each of the above embodiments and variations, $R_6$ is halo. In yet another variation of the compounds and processes of each of the above embodiments and variations, $R_6$ is selected from the group consisting of methyl, ethyl, isopropyl and cyclopropyl, each substituted or unsubstituted.

In a further variation of the compounds and processes of each of the above embodiments and variations, $R_7$ is selected from the group consisting of hydrogen, hydroxy, amino and ($C_{1-5}$)alkyl, each substituted or unsubstituted. In still a further variation of the compounds and processes of each of the above embodiments and variations, $R_7$ is hydrogen.

In yet a further variation of the compounds and processes of each of the above embodiments and variations, $R_{12}$ is selected from the group consisting of hydrogen, halo, amino, alkoxy, carbonyloxy, aminocarbonyl, sulfonyl, carbonylamino, sulfonylamino, ($C_{1-10}$)alkyl, hetero($C_{3-12}$)cycloalkyl and aryl, each substituted or unsubstituted.

In another variation of the compounds and processes of each of the above embodiments and variations, $R_{13}$ is selected from the group consisting of hydrogen, halo, amino, alkoxy, carbonyloxy, aminocarbonyl, sulfonyl, carbonylamino, sulfonylamino, ($C_{1-10}$)alkyl, hetero($C_{3-12}$)cycloalkyl and aryl, each substituted or unsubstituted.

In still another variation of the compounds and processes of each of the above embodiments and variations, $R_{14}$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted. In yet another variation of the compounds and processes of each of the above embodiments and variations, $R_{14}$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted. In a further variation of the compounds and processes of each of the above embodiments and variations, $R_{14}$ is selected from the group consisting of aryl and heteroaryl, each substituted with a substituent selected from the group consisting of halo, carbonyl, $(C_{1-5})$alkyl, alkoxy, aminocarbonyl, amino and sulfonyl, each substituted or unsubstituted.

In still a further variation of the compounds and processes of each of the above embodiments and variations, $R_{15}$ is selected from the group consisting of $(C_{1-10})$alkyl, —OR$_{22}$, —C(O)—R$_{22}$, —NR$_{23}$—C(O)—R$_{22}$, —C(O)—NR$_{23}$-R$_{22}$, —SO$_2$—R$_{22}$, —NR$_{23}$—SO$_2$—R$_{22}$ and —SO$_2$—NR$_{23}$R$_{24}$; $R_{22}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ and $R_{24}$ are each independently selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{24}$ are taken together to form a ring.

In yet a further variation of the compounds and processes of each of the above embodiments and variations, $R_{16}$ is —NR$_{23}$—C(O)—R$_{22}$; $R_{22}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{24}$ are taken together to form a ring.

In another variation of the compounds and processes of each of the above embodiments and variations, $R_{22}$ is a substituted or unsubstituted $(C_{3-6})$cycloalkyl. In still another variation of the compounds and processes of each of the above embodiments and variations, $R_{22}$ is a substituted or unsubstituted cyclopropyl.

In yet another variation of the compounds and processes of each of the above embodiments and variations, $R_{23}$ and $R_{24}$ are taken together to form a carbocyclic or heterocyclic $(C_{5-10})$ ring. In a further variation of the compounds and processes of each of the above embodiments and variations, $R_{23}$ and $R_{24}$ are taken together to form a substituted or unsubstituted piperazine.

In still a further variation of the compounds and processes of each of the above embodiments and variations, $R_{23}$ is hydrogen.

In yet a further variation of the compounds and processes of each of the above embodiments and variations, $R_{25}$ is hydrogen.

In another variation of the compounds and processes of each of the above embodiments and variations, $R_{27}$ is a substituted or unsubstituted heterocycloalkyl$(C_{1-3})$alkyl. In still another variation of the compounds and processes of each of the above embodiments and variations, $R_{27}$ is a substituted or unsubstituted piperadinyl$(C_{1-3})$alkyl. In yet another variation of the compounds and processes of each of the above embodiments and variations, $R_{27}$ is a substituted or unsubstituted 1-methyl(piperadin-4-yl)$(C_{1-3})$alkyl. In a further variation of the compounds and processes of each of the above embodiments and variations, $R_{27}$ is a substituted or unsubstituted 1-methyl(piperadin-4-yl)methyl. In still a further variation of the compounds and processes of each of the above embodiments and variations, $R_{27}$ is a substituted or unsubstituted amino$(C_{1-5})$alkyl. In yet a further variation of the compounds and processes of each of the above embodiments and variations, $R_{27}$ is a substituted or unsubstituted dimethylaminopropyl.

In another variation of the compounds and processes of each of the above embodiments and variations, $R_{30}$ is a substituted or unsubstituted $(C_{1-5})$alkyl. In still another variation of the compounds and processes of each of the above embodiments and variations, $R_{30}$ is methyl.

In still another variation of the compounds and processes of each of the above embodiments and variations, $R_{31}$ is a substituted or unsubstituted $(C_{1-5})$alkyl. In another variation of the compounds and processes of each of the above embodiments and variations, $R_{31}$ is methyl.

In another variation of the compounds and processes of each of the above embodiments and variations, P is selected from the group consisting of benzyl and p-methoxybenzyl.

In still another variation of the compounds and processes of each of the above embodiments and variations, $G_1$ is halo. In yet another variation of the compounds and processes of each of the above embodiments and variations, $G_2$ is halo. In still another variation of the compounds and processes of each of the above embodiments and variations, $G_3$ is halo. In yet another variation of the compounds and processes of each of the above embodiments and variations, $G_4$ is halo. In a further variation of the compounds and processes of each of the above embodiments and variations, $G_5$ is —B(OH)$_2$.

In yet another variation of the compounds and processes of each of the above embodiments and variations, $Y_5$ is a substituted or unsubstituted $(C_{1-5})$alkylene. In a further variation of the compounds and processes of each of the above embodiments and variations, $Y_5$ is ethyl. In still a further variation of the compounds and processes of each of the above embodiments and variations, $Y_5$ is propyl.

Particular examples of compounds according to the present invention include, but are not limited to:

5-bromo-9H-pyrido[2,3-b]indole;
5-bromo-8-methyl-9H-pyrido[2,3-b]indole;
5-bromo-3,8-dimethyl-9H-pyrido[2,3-b]indole;
5-phenyl-9H-pyrido[2,3-b]indole;
5-(3-(methylsulfonyl)phenyl)-9H-pyrido[2,3-b]indole;
5-(3-(ethylsulfonyl)phenyl)-9H-pyrido[2,3-b]indole;
N-(3-(9H-pyrido[2,3-b]indol-5-yl)phenyl)ethanesulfonamide;
5-m-tolyl-9H-pyrido[2,3-b]indole;
N-cyclopropyl-3-(9H-pyrido[2,3-b]indol-5-yl)benzenesulfonamide;
5-(3-methoxyphenyl)-9H-pyrido[2,3-b]indole;
5-(3,8-dimethyl-9H-pyrido[2,3-b]indol-5-yl)-2-methoxy-N-methylbenzenesulfonamide;
3-(3,8-dimethyl-9H-pyrido[2,3-b]indol-5-yl)-N-methylbenzenesulfonamide;
3-(3,8-dimethyl-9H-pyrido[2,3-b]indol-5-yl)-N,N-dimethylbenzenesulfonamide;
5-(3-(ethylsulfonyl)phenyl)-8-methyl-9H-pyrido[2,3-b]indole;
5-(3-(ethylsulfonyl)phenyl)-3,8-dimethyl-9H-pyrido[2,3-b]indole;
N-(3-(3,8-dimethyl-9H-pyrido[2,3-b]indol-5-yl)phenyl)propionamide;
N-cyclopropyl-3-(3,8-dimethyl-9H-pyrido[2,3-b]indol-5-yl)benzamide;
N-(4-(9H-pyrido[2,3-b]indol-5-ylthio)phenyl)acetamide;
5-(benzylthio)-9H-pyrido[2,3-b]indole;
5-(phenylthio)-9H-pyrido[2,3-b]indole;
5-(benzylthio)-8-methyl-9H-pyrido[2,3-b]indole;
5-(benzylthio)-3,8-dimethyl-9H-pyrido[2,3-b]indole;
7-Benzyl-5-(3-ethanesulfonyl-phenyl)-3-methyl-7,9-dihydro-dipyrido[2,3-b; 4',3'-d]pyrrol-8-one;
8-Chloro-5-(3-ethanesulfonyl-phenyl)-3-methyl-9H-dipyrido[2,3-b; 4',3'-d]pyrrole;
N'-[5-(3-Ethanesulfonyl-phenyl)-3-methyl-9H-dipyrido[2,3-b; 4',3'-d]pyrrol-8-yl]-N,N-dimethyl-ropane-1,3-diamine;
N'-[5-(3-Ethanesulfonyl-phenyl)-3-methyl-9H-dipyrido[2,3-b; 4',3'-d]pyrrol-8-yl]-N,N-dimethyl-ethane-1,2-diamine;
[5-(3-Ethanesulfonyl-phenyl)-3-methyl-9H-dipyrido[2,3-b; 4',3'-d]pyrrol-8-yl]-(3-morpholin-4-yl-propyl)-amine;
[5-(3-Ethanesulfonyl-phenyl)-3-methyl-9H-dipyrido[2,3-b; 4',3'-d]pyrrol-8-yl]-(1-methyl-piperidin-4-yl)-amine;
2-[5-(3-Ethanesulfonyl-phenyl)-3-methyl-9H-dipyrido[2,3-b; 4',3'-d]pyrrol-8-ylamino]-ethanol;
[5-(3-Ethanesulfonyl-phenyl)-3-methyl-9H-dipyrido[2,3-b; 4',3'-d]pyrrol-8-yl]-(1-methyl-piperidin-4-ylmethyl)-amine;
5-(3-Ethanesulfonyl-phenyl)-3,8-dimethyl-9H-dipyrido[2,3-b; 4',3'-d]pyrrole;
5-(3-Ethanesulfonyl-phenyl)-8-ethyl-3-methyl-9H-dipyrido[2,3-b; 4',3'-d]pyrrole;
5-(3-Ethanesulfonyl-phenyl)-3-methyl-9H-dipyrido[2,3-b; 4',3'-d]pyrrole-8-carbonitrile;
5-(3-Ethanesulfonyl-phenyl)-3-methyl-9H-dipyrido[2,3-b; 4',3'-d]pyrrole-8-carboxylic acid amide;
5-(3-Ethanesulfonyl-phenyl)-8-ethoxy-3-methyl-9H-dipyrido[2,3-b; 4',3'-d]pyrrole;
{3-[5-(3-Ethanesulfonyl-phenyl)-3-methyl-9H-dipyrido[2,3-b; 4',3'-d]pyrrol-8-yloxy]-propyl}-dimethyl-amine;
2-[5-(3-Ethanesulfonyl-phenyl)-3-methyl-9H-dipyrido[2,3-b; 4',3'-d]pyrrol-8-yloxy]-ethanol;
5-(3-Ethanesulfonyl-phenyl)-3-methyl-8-(1-methyl-piperidin-4-ylmethoxy)-9H-dipyrido[2,3-b; 4',3'-d]pyrrole;
3-[5-(3-Ethanesulfonyl-phenyl)-3-methyl-9H-dipyrido[2,3-b; 4',3'-d]pyrrol-8-yloxy]-propan-1-ol;
(R)-2-[5-(3-Ethanesulfonyl-phenyl)-3-methyl-9H-dipyrido[2,3-b; 4',3'-d]pyrrol-8-yloxymethyl]-propane-1,3-diol;
(S)-2-[5-(3-Ethanesulfonyl-phenyl)-3-methyl-9H-dipyrido[2,3-b; 4',3'-d]pyrrol-8-yloxymethyl]-propane-1,3-diol;
1-[5-(3-Ethanesulfonyl-phenyl)-3-methyl-9H-dipyrido[2,3-b; 4',3'-d]pyrrol-8-yloxy]-2-methyl-propan-2-ol;
5-(3-Ethanesulfonyl-phenyl)-3-methyl-8-phenoxy-9H-dipyrido[2,3-b; 4',3'-d]pyrrole;
5-(3-Ethanesulfonyl-phenyl)-3-methyl-8-(thiazol-5-ylmethoxy)-9H-dipyrido[2,3-b; 4',3'-d]pyrrole;
5-(3-Ethanesulfonyl-phenyl)-8-(1-ethyl-piperidin-4-ylmethoxy)-3-methyl-9H-dipyrido[2,3-b; 4',3'-d]pyrrole;
(S)-1-[5-(3-Ethanesulfonyl-phenyl)-3-methyl-9H-dipyrido[2,3-b; 4',3'-d]pyrrol-8-yloxy]-propan-2-ol;
(R)-1-[5-(3-Ethanesulfonyl-phenyl)-3-methyl-9H-dipyrido[2,3-b; 4',3'-d]pyrrol-8-yloxy]-propan-2-ol;
L-Valine-2-[5-(3-ethanesulfonyl-phenyl)-3-methyl-9H-dipyrido[2,3-b; 4',3'-d]pyrrol-8-yloxy]-ethyl ester;
L-Alanine-(R)-2-[5-(3-ethanesulfonyl-phenyl)-3-methyl-9H-dipyrido[2,3-b; 4',3'-d]pyrrol-8-yloxy]-1-methyl-ethyl ester;
3-(3-Bromo-5-chloro-pyridin-2-ylamino)-5-chloro-1-(4-methoxy-benzyl)-1H-pyrazin-2-one;
3,8-Dichloro-5-(3-ethanesulfonyl-phenyl)-9H-dipyrido[2,3-b; 4',3'-d]pyrrole;
3-Chloro-5-(3-ethanesulfonyl-phenyl)-8-(1-methyl-piperidin-4-ylmethoxy)-9H-dipyrido[2,3-b; 4',3'-d]pyrrole;
(R)-1-[3-Chloro-5-(3-ethanesulfonyl-phenyl)-9H-dipyrido[2,3-b; 4',3'-d]pyrrol-8-yloxy]-propan-2-ol;
2-[5-(3-Ethanesulfonyl-phenyl)-3-methyl-9H-dipyrido[2,3-b; 4',3'-d]pyrrol-8-yl]methyl amine;
2-[5-(3-Ethanesulfonyl-phenyl)-3-methyl-9H-dipyrido[2,3-b; 4',3'-d]pyrrol-8-yl]methanethiol;
2-[5-(3-Ethanesulfonyl-phenyl)-3-methyl-9H-dipyrido[2,3-b; 4',3'-d]pyrrol-8-yl]ethanethiol;
8-Chloro-5-[3-(cyclopropylcarboxamide)phenyl]-3-methyl-9H-dipyrido[2,3-b; 4',3'-d]pyrrole;
2-[5-(3-cyclopropylcarbonylamino-phenyl)-3-methyl-9H-dipyrido[2,3-b; 4',3'-d]pyrrol-8-yl]ethanethiol;
9-(3-Ethanesulfonyl-phenyl)-5H-pyrazino[2,3-b]indole;
5-(3-(ethylsulfonyl)phenyl)-3,8-dimethyl-7-(trifluoromethyl)-9H-pyrido[2,3-b]indole acetate;
5-(3-(ethylsulfonyl)phenyl)-3,8-dimethyl-9H-pyrido[2,3-b]indole-7-carboxylic acid;
N-(2-(dimethylamino)ethyl)-5-(3-(ethylsulfonyl)phenyl)-3,8-dimethyl-9H-pyrido[2,3-b]indole-7-carboxamide;
N-(2-(methylamino)ethyl)-5-(3-(ethylsulfonyl)phenyl)-3,8-dimethyl-9H-pyrido[2,3-b]indole-7-carboxamide;
N-(2-(methoxy)ethyl)-5-(3-(ethylsulfonyl)phenyl)-3,8-dimethyl-9H-pyrido[2,3-b]indole-7-carboxamide;
N-(2-(dimethylamino)ethyl)-N-methyl-5-(3-(ethylsulfonyl)phenyl)-3,8-dimethyl-9H-pyrido[2,3-b]indole-7-carboxamide;
N,N-dimethyl-5-(3-(ethylsulfonyl)phenyl)-3,8-dimethyl-9H-pyrido[2,3-b]indole-7-methylcarboxamide;
5-(3-(ethylsulfonyl)phenyl)-3,8-dimethyl-9H-pyrido[2,3-b]indole-7-yl)(4-methylpiperazin-1-yl)methanone;
5-(3-(ethylsulfonyl)phenyl)-3,8-dimethyl-N-(2-piperazin-1-yl)ethyl)-9H-pyrido[2,3-b]indole-7-carboxamide;
5-(3-(ethylsulfonyl)phenyl)-3,8-dimethyl-N-(3-(4-methylpiperazin-1-yl)propyl)-9H-pyrido[2,3-b]indole-7-carboxamide;

5-(3-(ethylsulfonyl)phenyl)-3,8-dimethyl-9H-pyrido[2,3-b]indole-7-yl)(morpholino)methanone;

azetidin-1-yl(5-(3-(ethylsulfonyl)phenyl)-3,8-dimethyl-9H-pyrido[2,3-b]indol-7-yl)methanone;

(5-(3-(ethylsulfonyl)phenyl)-3,8-dimethyl-9H-pyrido[2,3-b]indol-7-yl)(thaiazolidin-3-yl)methanone;

(R)-5-(3-(ethylsulfonyl)phenyl)-N-(2-hydroxypropyl)-3,8-dimethyl-9H-pyrido[2,3-b]indole-7-carboxamide;

(S)-5-(3-(ethylsulfonyl)phenyl)-N-(2-hydroxypropyl)-3,8-dimethyl-9H-pyrido[2,3-b]indole-7-carboxamide;

5-(3-(ethylsulfonyl)phenyl)-N-(2-hydroxyethyl)-3,8-dimethyl-9H-pyrido[2,3-b]indole-7-carboxamide;

N-(2,3-dihydroxypropyl)-5-(3-(ethylsulfonyl)phenyl)-3,8-dimethyl-9H-pyrido[2,3-b]indole-7-carboxamide;

5-(3-(ethylsulfonyl)phenyl)-N-(2-hydroxy-2-methylpropyl)-3,8-dimethyl-9H-pyrido[2,3-b]indole-7-carboxamide;

5-(3-(ethylsulfonyl)phenyl)-N-(1-isopropylpiperidin-4-yl)-3,8-dimethyl-9H-pyrido[2,3-b]indole-7-carboxamide;

N-(1-ethylpiperidin-4-yl)-5-(3-(ethylsulfonyl)phenyl)-3,8-dimethyl-9H-pyrido[2,3-b]indole-7-carboxamide;

5-(3-(ethylsulfonyl)phenyl)-3,8-dimethyl-N-thiazol-2-yl)-9H-pyrido[2,3-b]indole-7-carboxamide;

5-(3-(ethylsulfonyl)phenyl)-3,8-dimethyl-N-(2-(2,2,2-trifluoroethoxy)ethyl-9H-pyrido[2,3-b]indole-7-carboxamide;

5-(3-(ethylsulfonyl)phenyl)-3,8-dimethyl-N-(piperidin-3-yl)-9H-pyrido[2,3-b]indole-7-carboxamide;

5-(3-(ethylsulfonyl)phenyl)-3,8-dimethyl-N-(piperidin-4-yl)-9H-pyrid o[2,3-b]indole-7-carboxamide;

5-(3-(ethylsulfonyl)phenyl)-3,8-dimethyl-N-(piperidin-3-yl)-9H-pyrido[2,3-b]indole-7-carboxamide;

5-(3-(ethylsulfonyl)phenyl)-N-(2-(2-hydroxyethoxy)ethyl-3,8-dimethyl-9H-pyrido[2,3-b]indole-7-carboxamide;

5-(3-(cyclopropanecarboxamido)phenyl)-N-(2-(dimethylamino)ethyl)-3,8-dimethyl-9H-pyrido[2,3-b]indole-7-carboxamide;

5-(3-(ethylsulfonyl)phenyl)-3,8-dimethyl-N-(1-methylpiperidin-4-yl)-9H-pyrido[2,3-b]indole-7-carboxamide;

5-(3-(ethylsulfonyl)phenyl)-3,8-dimethyl-N-((1-methylpiperidin-4-yl)methyl)-9H-pyrido[2,3-b]indole-7-carboxamide;

N-(3-(dimethylamino)propyl)-5-(3-(ethylsulfonyl)phenyl)-3,8-dimethyl-9H-pyrido[2,3-b]indole-7-carboxamide;

5-(3-(ethylsulfonyl)phenyl)-3,8-dimethyl-N-(2-(pyrrolidin-1-yl)ethyl)-9H-pyrido[2,3-b]indole-7-carboxamide;

(S)-5-(3-(ethylsulfonyl)phenyl)-3,8-dimethyl-N-(1-methylpiperidin-3-yl)-9H-pyrido[2,3-b]indole-7-carboxamide;

(R)-5-(3-(ethylsulfonyl)phenyl)-3,8-dimethyl-N-(1-methylpiperidin-3-yl)-9H-pyrido[2,3-b]indole-7-carboxamide;

5-chloro-3,8-dimethyl-N-(1-methylpiperidin-4-yl)-9H-pyrido[2,3-b]indole-7-carboxamide;

5-(3-(cyclopropanecarboxamido)phenyl)-3,8-dimethyl-N-(1-methyl-piperidin-4-yl)-9H-pyrido[2,3-b]indole-7-carboxamide;

5-chloro-N-(2-(dimethylamino)ethyl)-3,8-dimethyl-9H-pyrido[2,3-b]indole-7-carboxamide;

5-(3-(cyclopropylcarbamoyl)phenyl)-N-(2-(dimethylamino)ethyl)-3,8-dimethyl-9H-pyrido[2,3-b]indole-7-carboxamide;

5-Amino-3-methyl-9H-pyrido[2,3-b]indole-7-carbonitrile;

5-Iodo-3-methyl-9H-pyrido[2,3-b]indole-7-carbonitrile;

5-(3-Ethanesulfonyl-phenyl)-3-methyl-9H-pyrido[2,3-b]indole-7-carbonitrile;

5-(3-Ethanesulfonyl-phenyl)-3-methyl-9H-pyrido[2,3-b]indole-7-carboxylic acid amide;

5-Amino-3-methyl-9H-pyrido[2,3-b]indole-7-carboxylic acid methyl ester;

5-Iodo-3-methyl-9H-pyrido[2,3-b]indole-7-carboxylic acid methyl ester;

5-(3-Ethanesulfonyl-phenyl)-3-methyl-9H-pyrido[2,3-b]indole-7-carboxylic acid methyl ester;

[5-(3-Ethanesulfonyl-phenyl)-3-methyl-9H-pyrido[2,3-b]indol-7-yl]-methanol;

[5-(3-Ethanesulfonyl-phenyl)-3-methyl-9H-pyrido[2,3-b]indol-7-ylmethyl]-dimethyl-amine;

5-(3-Ethanesulfonyl-phenyl)-3-methyl-7-morpholin-4-ylmethyl-9H-pyrido[2,3-b]indole;

5-(3-Ethanesulfonyl-phenyl)-3-methyl-7-(4-methyl-piperazin-1-ylmethyl)-9H-pyrido[2,3-b]indole;

5-(3-Ethanesulfonyl-phenyl)-3-methyl-7-pyrrolidin-1-ylmethyl-9H-pyrido[2,3-b]indole;

[5-(3-Ethanesulfonyl-phenyl)-3-methyl-9H-pyrido[2,3-b]indol-7-ylmethyl]-ethyl-amine;

5-(3-Ethanesulfonyl-phenyl)-3-methyl-9H-pyrido[2,3-b]indole-7-carboxylic acid;

[5-(3-Ethanesulfonyl-phenyl)-3-methyl-9H-pyrido[2,3-b]indol-7-yl]-(4-methyl-piperazin-1-yl)-methanone;

5-(3-Ethanesulfonyl-phenyl)-3-methyl-9H-pyrido[2,3-b]indole-7-carboxylic acid (2-dimethylamino-ethyl)-amide;

5-(3-Ethanesulfonyl-phenyl)-3-methyl-9H-pyrido[2,3-b]indole-7-carboxylic acid (3-dimethylamino-propyl)-amide;

5-(3-Ethanesulfonyl-phenyl)-3-methyl-7-(2H-tetrazol-5-yl)-9H-pyrido[2,3-b]indole;

(3-Dimethylamino-pyrrolidin-1-yl)-[5-(3-ethanesulfonyl-phenyl)-3-methyl-9H-pyrido[2,3-b]indol-7-yl]-methanone;

N-ethyl-5-(3-(ethylsulfonyl)phenyl)-3-methyl-9H-pyrido[2,3-b]indole-7-carboxamide;

6-Bromo-5-(3-ethanesulfonyl-phenyl)-3-methyl-9H-pyrido[2,3-b]indole-7-carboxylic acid methyl ester;

8-Bromo-5-(3-ethanesulfonyl-phenyl)-3-methyl-9H-pyrido[2,3-b]indole-7-carboxylic acid methyl ester;

6-Chloro-5-(3-ethanesulfonyl-phenyl)-3-methyl-9H-pyrido[2,3-b]indole-7-carboxylic acid methyl ester;

8-Chloro-5-(3-ethanesulfonyl-phenyl)-3-methyl-9H-pyrido[2,3-b]indole-7-carboxylic acid methyl ester;

5-(benzylthio)-3-methyl-9H-pyrido[2,3-b]indole-7-carboxylic acid;

5-(benzylthio)-N-(2-(dimethylamino)ethyl)-3-methyl-9H-pyrido[2,3-b]indole-7-carboxamide;

5-(3-(N-ethylsulfamoyl)phenyl)-8-methoxy-3-methyl-N-(1-methylpiperidin-4-yl)-9H-pyrido[2,3-b]indole-7-carboxamide;

5-(3-(cyclopropylsulfonyl)phenyl)-3,8-dimethyl-N-(1-methylpiperidin-4-yl)-9H-pyrido[2,3-b]indole-7-carboxamide;

5-choloro-8-methoxy-9H-pyrido[2,3-b]indole;

5-(3-(ethylsulfonyl)phenyl-8-methoxy-3-methyl-9H-pyrido[2,3-b]indole;

5-(3-(ethylsulfonyl)phenyl)-3-methyl-9H-pyrido[2,3-b]indol-8-ol;

8-methoxy-3-methyl-5-(3-(pyrrolidin-1-ylsulfonyl)phenyl)-9H-pyrido[2,3-b]indole;

(R)-8-methoxy-3-methyl-5-(3-(pyrrolidin-3-ylsulfonyl)phenyl)-9H-pyrido[2,3-b]indole;

N-cyclopropyl-4-(8-methoxy-3-methyl-9H-pyrido[2,3-b]indol-5-yl)picolinamide;

N-(3-(8-methoxy-3-methyl-9H-pyrido[2,3-b]indol-5-yl)phenyl)acetamide;

N-(3-(8-methoxy-3-methyl-9H-pyrido[2,3-b]indol-5-yl)phenyl)cyclopropanecarboxamide;
N-cyclopropyl-3-(8-methoxy-3-methyl-9H-pyrido[2,3-b]indol-5-yl)benzamide;
N,N-diethyl-3-(8-methoxy-3-methyl-9H-pyrido[2,3-b]indol-5-yl)benzamide;
5-(benzo[d][1,3]dioxol-5-yl)-8-methoxy-3-methyl-9H-pyrido[2,3-b]indole;
6-(8-methoxy-3-methyl-9H-pyrido[2,3-b]indol-5-yl)-4H-chromen-4-one;
N-(2-hydroxyethyl)-3-(8-methoxy-3-methyl-9H-pyrido[2,3-b]indol-5-yl)benzamide;
(3-(8-methoxy-3-methyl-9H-pyrido[2,3-b]indol-5-yl)phenyl)(pyrrolidin-1-yl)methanone;
N-ethyl-3-(8-methoxy-3-methyl-9H-pyrido[2,3-b]indol-5-yl)benzenesulfonamide;
8-ethoxy-5-(3-(ethylsulfonyl)phenyl)-3-methyl-9H-pyrido[2,3-b]indole;
8-(difluoromethoxy)-5-(3-(ethylsulfonyl)phenyl)-3-methyl-9H-pyrido[2,3-b]indole;
5-(3-(ethylsulfonyl)phenyl)-3-methyl-8-(2,2,2-trifluoroethoxy)-9H-pyrido[2,3-b]indole;
5-(3-(ethylsulfonyl)phenyl)-3-methyl-8-((1-methylpiperidin-4-yl)methoxy)-9H-pyrido[2,3-b]indole;
N-cyclopropyl-3-(3-methyl-8-((1-methylpiperidin-4-yl)methoxy)-9H-pyrido[2,3-b]indol-5-yl)benzamide;
5-(3-(cyclopropylsulfonyl)phenyl)-3-methyl-8-((1-methylpiperidin-4-yl)methoxy)-9H-pyrido[2,3-b]indole;
N-methyl-3-(3-methyl-8-((1-methylpiperidin-4-yl)methoxy)-9H-pyrido[2,3-b]indol-5-yl)benzenesulfonamide;
N,N-dimethyl-3-(3-methyl-8-((1-methylpiperidin-4-yl)methoxy)-9H-pyrido[2,3-b]indol-5-yl)benzenesulfonamide;
N-(3-(3-methyl-8-((1-methylpiperidin-4-yl)methoxy)-9H-pyrido[2,3-b]indol-5-yl)phenyl)cyclopropanecarboxamide;
5-(3-(ethylthio)phenyl)-3-methyl-8-((1-methylpiperidin-4-yl)methoxy)-9H-pyrido[2,3-b]indole;
5-(3-ethoxyphenyl)-3-methyl-8-((1-methylpiperidin-4-yl)methoxy)-9H-pyrido[2,3-b]indole;
5-(3-(ethylsulfonyl)phenyl)-3-methyl-8-(piperidin-4-ylmethoxy)-9H-pyrido[2,3-b]indole;
(S)-5-(3-(ethylsulfonyl)phenyl)-3-methyl-8-((1-methylpyrrolidin-3-yl)methoxy)-9H-pyrido[2,3-b]indole;
(R)-5-(3-(ethylsulfonyl)phenyl)-3-methyl-8-((1-methylpyrrolidin-3-yl)methoxy)-9H-pyrido[2,3-b]indole;
(S)-5-(3-(ethylsulfonyl)phenyl)-3-methyl-8-((1-methylpyrrolidin-2-yl)methoxy)-9H-pyrido[2,3-b]indole;
(S)-5-(3-(ethylsulfonyl)phenyl)-3-methyl-8-(pyrrolidin-3-ylmethoxy)-9H-pyrido[2,3-b]indole;
(R)-5-(3-(ethylsulfonyl)phenyl)-3-methyl-8-(pyrrolidin-3-ylmethoxy)-9H-pyrido[2,3-b]indole;
3-(5-chloro-3-methyl-9H-pyrido[2,3-b]indol-8-yloxy)-N,N-dimethylpropan-1-amine;
N-(3-(8-(3-(dimethylamino)propoxy)-3-methyl-9H-pyrido[2,3-b]indol-5-yl)phenyl)cyclopropanecarboxamide;
N-cyclopropyl-3-(8-(3-(dimethylamino)propoxy)-3-methyl-9H-pyrido[2,3-b]indol-5-yl)benzamide;
3-(8-(3-(dimethylamino)propoxy)-3-methyl-9H-pyrido[2,3-b]indol-5-yl)-N-methylbenzenesulfonamide;
3-(8-(3-(dimethylamino)propoxy)-3-methyl-9H-pyrido[2,3-b]indol-5-yl)-N—N-dimethylbenzenesulfonamide;
3-chloro-5-(3-(ethylsulfonyl)phenyl)-8-((1-methylpiperidin-4-yl)methoxy)-9H-pyrido[2,3-b]indole;
3-chloro-5-(3-(ethylsulfonyl)phenyl)-8-(piperidin-4-ylmethoxy)-9H-pyrido[2,3-b]indole;
5-(3-(ethylsulfonyl)phenyl)-8-((1-methylpiperidin-4-yl)methoxy)-3-(trifluoromethyl)-9H-pyrido[2,3-b]indole;
5-(3-(ethylsulfonyl)phenyl)-8-((1-methylpiperidin-4-yl)methoxy)-9H-pyrido[2,3-b]indole-3-carbonitrile;
2-(5-(3-(ethylsulfonyl)phenyl)-7-fluoro-3-methyl-9H-pyrido[2,3-b]indol-8-yloxy)-N,N-dimethylethanamine;
3-(3-chloro-5-(3-(ethylsulfonyl)phenyl)-7-fluoro-9H-pyrido[2,3-b]indol-8-yloxy)-N,N-dimethylpropan-1-amine;
3-(5-(3-(ethylsulfonyl)phenyl)-3-methyl-9H-pyrido[2,3-b]indol-8-yloxy)-N,N-dimethylpropan-1-amine;
2-(5-(3-(ethylsulfonyl)phenyl)-3-methyl-9H-pyrido[2,3-b]indol-8-yloxy)-N,N-dimethylethanamine;
5-(3-(ethylsulfonyl)phenyl)-8-(2-methoxyethoxy)-3-methyl-9H-pyrido[2,3-b]indole;
2-(5-(3-(ethylsulfonyl)phenyl)-3-methyl-9H-pyrido[2,3-b]indol-8-yloxy)acetonitrile;
3-(5-(3-(ethylsulfonyl)phenyl)-3-methyl-9H-pyrido[2,3-b]indol-8-yloxy)propanenitrile;
(R)-8-(1-tert-butyldiphenylsilyloxy)propan-2-yloxy)-(5-(3-(ethylsulfonyl)phenyl)-3-methyl-9H-pyrido[2,3-b]indole;
(R)-2-(5-(3-(ethylsulfonyl)phenyl)-3-methyl-9H-pyrido[2,3-b]indol-8-yloxy)propan-1-ol;
(S)-2-(5-(3-(ethylsulfonyl)phenyl)-3-methyl-9H-pyrido[2,3-b]indol-8-yloxy)propan-1-ol;
1-(5-(3-(ethylsulfonyl)phenyl)-3-methyl-9H-pyrido[2,3-b]indol-8-yloxy)propan-2-ol;
(S)-4-(5-(3-(ethylsulfonyl)phenyl)-3-methyl-9H-pyrido[2,3-b]indol-8-yloxy)-2-methylpentan-2-ol;
2-(5-(3-(ethylsulfonyl)phenyl)-3-methyl-9H-pyrido[2,3-b]indol-8-yloxy)ethanol;
3-(5-(3-(ethylsulfonyl)phenyl)-3-methyl-9H-pyrido[2,3-b]indol-8-yloxy)propan-1-ol;
3-(3-chloro-5-(3-(ethylsulfonyl)phenyl)-8-methoxy-9H-pyrido[2,3-b]indol-8-ol;
(3-chloro-5-(3-(ethylsulfonyl)phenyl)-9H-pyrido[2,3-b]indol-8-ol;
3-(3-chloro-5-(3-(ethylsulfonyl)phenyl)-9H-pyrido[2,3-b]indol-8-yloxy)-N,N-dimethylpropan-1-amine;
2-(3-chloro-5-(3-(ethylsulfonyl)phenyl)-9H-pyrido[2,3-b]indol-8-yloxy)-N,N-diethylethanamine;
2-(3-chloro-5-(3-(ethylsulfonyl)phenyl)-9H-pyrido[2,3-b]indol-8-yloxy)-N,N-dimethylethanamine;
3-chloro-5-(3-(ethylsulfonyl)phenyl)-8-(2-(pyrrolidin-1-yl)ethoxy)-9H-pyrido[2,3-b]indole;
3-chloro-5-(3-(ethylsulfonyl)phenyl)-8-(2-(4-methylpiperazin-1-yl)ethoxy)-9H-pyrido[2,3-b]indole;
2-(3-chloro-5-(3-(ethylsulfonyl)phenyl)-9H-pyrido[2,3-b]indol-8-yloxy)ethanol;
3-(3-chloro-5-(3-(ethylsulfonyl)phenyl)-9H-pyrido[2,3-b]indol-8-yloxy)propan-1-ol;
(S)-2-(5-(3-(ethylsulfonyl)phenyl)-3-methyl-9H-pyrido[2,3-b]indol-8-yloxy)ethyl 2-aminopropanoate;
(S)-3-(5-(3-(ethylsulfonyl)phenyl)-3-methyl-9H-pyrido[2,3-b]indol-8-yloxy)propyl 2-aminopropanoate;
(S)-3-(3-chloro-5-(3-(ethylsulfonyl)phenyl)-9H-pyrido[2,3-b]indol-8-yloxy)propyl 2-aminopropanoate;
(R)-8-((2,2-dimethyl-1,3-dioxolan-4-yl)methoxy-5-(3-ethylsulfonyl)phenyl)-3-methyl-9H-pyrido[2,3-b]indole;
(S)-3-(5-(3-(ethylsulfonyl)phenyl)-3-methyl-9H-pyrido[2,3-b]indol-8-yloxy)propane-1,2-diol;
(R)-3-(5-(3-(ethylsulfonyl)phenyl)-3-methyl-9H-pyrido[2,3-b]indol-8-yloxy)propane-1,2-diol;
(R)-1-(dimethylamino)-3-(5-(3-(ethylsulfonyl)phenyl)-3-methyl-9H-pyrido[2,3-b]indol-8-yloxy)propan-2-ol;
(R)-1-(5-(3-(ethylsulfonyl)phenyl)-3-methyl-9H-pyrido[2,3-b]indol-8-yloxy)propan-2-ol;

(S)-1-(5-(3-(ethylsulfonyl)phenyl)-3-methyl-9H-pyrido[2,3-b]indol-8-yloxy)propan-2-ol;
5-bromo-8-methoxy-3-methyl-9H-pyrido[2,3-b]indol-7-amine;
(5-(3-(ethylsulfonyl)phenyl)-8-methoxy-3-methyl-9H-pyrido[2,3-b]indol-7-amine;
N-(3-(7-amino-8-methoxy-3-methyl-9H-pyrido[2,3-b]indol-5-yl)phenyl)-cyclopropanecarboxamide;
3-(dimethylamino)-N-(5-(3-(ethylsulfonyl)phenyl)-8-methoxy-3-methyl-9H-pyrido[2,3-b]indol-7-yl)propanamide;
N-(5-(3-(ethylsulfonyl)phenyl)-8-methoxy-3-methyl-9H-pyrido[2,3-b]indol-7-yl)-cyclopropanecarboxamide;
1-acetyl-N-(5-(3-(ethylsulfonyl)phenyl)-8-methoxy-3-methyl-9H-pyrido[2,3-b]indol-7-yl)piperidine-4-carboxamide;
3-(7-amino-8-methoxy-3-methyl-9H-pyrido[2,3-b]indol-5-yl)-N-cyclopropylbenzamide;
3-(7-(cyclopropanecarboxamido)-8-methoxy-3-methyl-9H-pyrido[2,3-b]indol-5-yl)-N-cyclopropylbenzamide;
7-chloro-5-(3-(ethylsulfonyl)phenyl)-8-methoxy-3-methyl-9H-pyrido[2,3-b]indole;
7-chloro-5-(3-(ethylsulfonyl)phenyl)-3-methyl-9H-pyrido[2,3-b]indol-8-ol;
3-(7-chloro-5-(3-(ethylsulfonyl)phenyl)-3-methyl-9H-pyrido[2,3-b]indol-8-yloxy)propan-1-ol;
N-(5-(3-(ethylsulfonyl)phenyl)-8-methoxy-3-methyl-9H-pyrido[2,3-b]indol-7-yl)-N-methylcyclopropanecarboxamide;
3-(dimethylamino)-N-(5-(3-(ethylsulfonyl)phenyl)-8-methoxy-3-methyl-9H-pyrido[2,3-b]indol-7-yl)-N-methylpropanamide;
5-(3-(cyclopropylcarbamoyl)phenyl)-3,8-dimethyl-N-(1-methylpiperidin-4-yl)-9H-pyrido[2,3-b]indole-7-carboxamide;
4-(2-(3-chloro-5-(3-(ethylsulfonyl)phenyl)-9H-pyrido[2,3-b]indol-8-yloxy)ethyl)morpholine;
3-(3-chloro-5-(3-(ethylsulfonyl)phenyl)-9H-pyrido[2,3-b]indol-8-yloxy)propanenitrile;
3-chloro-5-(3-(ethylsulfonyl)phenyl)-8-(1-methylpiperidin-4-yloxy)-9H-pyrido[2,3-b]indole;
3-(5-(3-(ethylsulfonyl)phenyl)-3-(trifluoromethyl)-9H-pyrido[2,3-b]indol-8-yloxy)-N,N-dimethylpropan-1-amine;
(3-(8-methoxy-3-methyl-9H-pyrido[2,3-b]indol-5-yl)phenyl)(morpholino)methanone;
N-methoxy-3-(8-methoxy-3-methyl-9H-pyrido[2,3-b]indol-5-yl)benzamide;
5-(3-Ethanesulfonyl-phenyl)-8-(cyclopropylmethoxy)-3-methyl-9H-dipyrido[2,3-b; 4',3'-d]pyrrole;
N-(2-(diethylamino)ethyl)-5-(3-(ethylsulfonyl)phenyl)-3,8-dimethyl-9H-pyrido[2,3-b]indole-7-carboxamide; and
5-(3-(ethylsulfonyl)phenyl)-3,8-dimethyl-N-(3-morpholinopropyl)-9H-pyrido[2,3-b]indole-7-carboxamide.

Particular examples of compounds according to the present invention also include, but are not limited to:
5-(3-(ethylsulfonyl)phenyl)-3,8-dimethyl-N-(1-methylpiperidin-4-yl)-9H-pyrido[2,3-b]indole-7-carboxamide HCl salt;
5-(3-(ethylsulfonyl)phenyl)-3-methyl-8-((1-methylpiperidin-4-yl)methoxy)-9H-pyrido[2,3-b]indole HCl salt;
3-chloro-5-(3-(ethylsulfonyl)phenyl)-8-((1-methylpiperidin-4-yl)methoxy)-9H-pyrido[2,3-b]indole HCl salt;
3-(5-(3-(ethylsulfonyl)phenyl)-3-methyl-9H-pyrido[2,3-b]indol-8-yloxy)-N,N-dimethylpropan-1-amine HCl salt;
3-(3-chloro-5-(3-(ethylsulfonyl)phenyl)-9H-pyrido[2,3-b]indol-8-yloxy)-N,N-dimethylpropan-1-amine HCl salt; and
N-cyclopropyl-3-(3-methyl-8-((1-methylpiperidin-4-yl)methoxy)-9H-pyrido[2,3-b]indol-5-yl)benzamide HCl salt.

In addition, particular examples of compounds according to the present invention include, but are not limited to:
N-(2-(methylamino)ethyl)-5-(3-(ethylsulfonyl)phenyl)-3,8-dimethyl-9H-pyrido[2,3-b]indole-7-carboxamide;
N-(2-(methoxy)ethyl)-5-(3-(ethylsulfonyl)phenyl)-3,8-dimethyl-9H-pyrido[2,3-b]indole-7-carboxamide;
N-(2-(dimethylamino)ethyl)-N-methyl-5-(3-(ethylsulfonyl)phenyl)-3,8-dimethyl-9H-pyrido[2,3-b]indole-7-carboxamide;
N,N-dimethyl-5-(3-(ethylsulfonyl)phenyl)-3,8-dimethyl-9H-pyrido[2,3-b]indole-7-methylcarboxamide;
5-(3-(ethylsulfonyl)phenyl)-3,8-dimethyl-9H-pyrido[2,3-b]indole-7-yl)(4-methylpiperazin-1-yl)methanone;
5-(3-(ethylsulfonyl)phenyl)-3,8-dimethyl-N-(2-piperazin-1-yl)ethyl)-9H-pyrido[2,3-b]indole-7-carboxamide;
5-(3-(ethylsulfonyl)phenyl)-3,8-dimethyl-N-(3-(4-methylpiperazin-1-yl)propyl)-9H-pyrido[2,3-b]indole-7-carboxamide;
5-(3-(ethylsulfonyl)phenyl)-3,8-dimethyl-9H-pyrido[2,3-b]indole-7-yl)(morpholino)methanone;
azetidin-1-yl(5-(3-(ethylsulfonyl)phenyl)-3,8-dimethyl-9H-pyrido[2,3-b]indol-7-yl)methanone;
(5-(3-(ethylsulfonyl)phenyl)-3,8-dimethyl-9H-pyrido[2,3-b]indol-7-yl)(thaiazolidin-3-yl)methanone;
(R)-5-(3-(ethylsulfonyl)phenyl)-N-(2-hydroxypropyl)-3,8-dimethyl-9H-pyrido[2,3-b]indole-7-carboxamide;
(S)-5-(3-(ethylsulfonyl)phenyl)-N-(2-hydroxypropyl)-3,8-dimethyl-9H-pyrido[2,3-b]indole-7-carboxamide;
5-(3-(ethylsulfonyl)phenyl)-N-(2-hydroxyethyl)-3,8-dimethyl-9H-pyrido[2,3-b]indole-7-carboxamide;
N-(2,3-dihydroxypropyl)-5-(3-(ethylsulfonyl)phenyl)-3,8-dimethyl-9H-pyrido[2,3-b]indole-7-carboxamide;
5-(3-(ethylsulfonyl)phenyl)-N-(2-hydroxy-2-methylpropyl)-3,8-dimethyl-9H-pyrido[2,3-b]indole-7-carboxamide;
5-(3-(ethylsulfonyl)phenyl)-N-(1-isopropylpiperidin-4-yl)-3,8-dimethyl-9H-pyrido[2,3-b]indole-7-carboxamide;
N-(1-ethylpiperidin-4-yl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-thiazol-2-yl)-9H-pyrido[2,3-b]indole-7-carboxamide;
5-(3-(ethylsulfonyl)phenyl)-3,8-dimethyl-N-(2-(2,2,2-trifluoroethoxy)ethyl-9H-pyrido[2,3-b]indole-7-carboxamide;
5-(3-(ethylsulfonyl)phenyl)-3,8-dimethyl-N-(piperidin-3-yl)-9H-pyrido[2,3-b]indole-7-carboxamide;
5-(3-(ethylsulfonyl)phenyl)-3,8-dimethyl-N-(piperidin-4-yl)-9H-pyrid o[2,3-b]indole-7-carboxamide;
5-(3-(ethylsulfonyl)phenyl)-3,8-dimethyl-N-(piperidin-3-yl)-9H-pyrido[2,3-b]indole-7-carboxamide;
5-(3-(ethylsulfonyl)phenyl)-N-(2-(2-hydroxyethoxy)ethyl-3,8-dimethyl-9H-pyrido[2,3-b]indole-7-carboxamide;
5-(3-(cyclopropanecarboxamido)phenyl)-N-(2-(dimethylamino)ethyl)-3,8-dimethyl-9H-pyrido[2,3-b]indole-7-carboxamide;
N-(2-(dimethylamino)ethyl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-((1-methylpiperidin-4-yl)methyl)-9H-pyrido[2,3-b]indole-7-carboxamide;
N-(3-(dimethylamino)propyl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-(2-(pyrrolidin-1-yl)ethyl)-9H-pyrido[2,3-b]indole-7-carboxamide;

(S)-5-(3-(ethylsulfonyl)phenyl)-3,8-dimethyl-N-(1-methylpiperidin-3-yl)-9H-pyrido[2,3-b]indole-7-carboxamide;
(R)-5-(3-(ethylsulfonyl)phenyl)-3,8-dimethyl-N-(1-methylpiperidin-3-yl)-9H-pyrido[2,3-b]indole-7-carboxamide;
5-(3-(cyclopropanecarboxamido)phenyl)-3,8-dimethyl-N-(1-methyl-piperidin-4-yl)-9H-pyrido[2,3-b]indole-7-carboxamide;
5-(3-(cyclopropylcarbamoyl)phenyl)-N-(2-(dimethylamino)ethyl)-3,8-dimethyl-9H-pyrido[2,3-b]indole-7-carboxamide;
5-(3-Ethanesulfonyl-phenyl)-3-methyl-9H-pyrido[2,3-b]indole-7-carboxylic acid amide;
[5-(3-Ethanesulfonyl-phenyl)-3-methyl-9H-pyrido[2,3-b]indol-7-yl]-(4-methyl-piperazin-1-yl)-methanone;
5-(3-Ethanesulfonyl-phenyl)-3-methyl-9H-pyrido[2,3-b]indole-7-carboxylic acid (2-dimethylamino-ethyl)-amide;
5-(3-Ethanesulfonyl-phenyl)-3-methyl-9H-pyrido[2,3-b]indole-7-carboxylic acid (3-dimethylamino-propyl)-amide;
(3-Dimethylamino-pyrrolidin-1-yl)-[5-(3-ethanesulfonyl-phenyl)-3-methyl-9H-pyrido[2,3-b]indol-7-yl]-methanone;
N-ethyl-5-(3-(ethylsulfonyl)phenyl)-3-methyl-9H-pyrido[2,3-b]indole-7-carboxamide;
5-(benzylthio)-N-(2-(dimethylamino)ethyl)-3-methyl-9H-pyrido[2,3-b]indole-7-carboxamide;
5-(3-(N-ethylsulfamoyl)phenyl)-8-methoxy-3-methyl-N-(1-methylpiperidin-4-yl)-9H-pyrido[2,3-b]indole-7-carboxamide;
5-(3-(cyclopropylsulfonyl)phenyl)-3,8-dimethyl-N-(1-methylpiperidin-4-yl)-9H-pyrido[2,3-b]indole-7-carboxamide;
5-(3-(cyclopropylcarbamoyl)phenyl)-3,8-dimethyl-N-(1-methylpiperidin-4-yl)-9H-pyrido[2,3-b]indole-7-carboxamide;
N-(2-(diethylamino)ethyl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-(3-morpholinopropyl)-9H-pyrido[2,3-b]indole-7-carboxamide;
5-(3-(cyclopropylcarbamoyl)phenyl)-3,8-dimethyl-N-(1-methylpiperidin-4-yl)-9H-pyrido[2,3-b]indole-7-carboxamide;
5-(3-(ethylsulfonyl)phenyl)-8-methyl-N-(1-methylpiperidin-4-yl)-9H-pyrido[2,3-b]indole-7-carboxamide;
5-(3-(cyclopropylsulfonyl)phenyl)-8-methyl-N-(1-methylpiperidin-4-yl)-9H-pyrido[2,3-b]indole-7-carboxamide;
5-(3-(cyclopropylsulfonyl)phenyl)-3-fluoro-8-methyl-N-(1-methylpiperidin-4-yl)-9H-pyrido[2,3-b]indole-7-carboxamide;
3-chloro-5-(3-(cyclopropylsulfonyl)phenyl)-8-methyl-N-(1-methylpiperidin-4-yl)-9H-pyrido[2,3-b]indole-7-carboxamide;
5-(3-(ethylsulfonyl)phenyl)-N-(1-(2-hydroxyethyl)piperidin-4-yl)-3,8-dimethyl-9H-pyrido[2,3-b]indole-7-carboxamide;
2-(4-(5-(3-(ethylsulfonyl)phenyl)-3,8-dimethyl-9H-pyrido[2,3-b]indole-7-carboxamido)piperidin-1-yl)ethyl dihydrogen phosphate;
3-chloro-5-(3-(ethylsulfonyl)phenyl)-N-(1-(2-hydroxyethyl)piperidin-4-yl)-8-methyl-9H-pyrido[2,3-b]indole-7-carboxamide;
2-(4-(3-chloro-5-(3-(ethylsulfonyl)phenyl)-8-methyl-9H-pyrido[2,3-b]indole-7-carboxamido)piperidin-1-yl)ethyl dihydrogen phosphate;
5-(3-(cyclopropylsulfonyl)phenyl)-N-(1-(2-hydroxyethyl)piperidin-4-yl)-3,8-dimethyl-9H-pyrido[2,3-b]indole-7-carboxamide;
2-(4-(5-(3-(cyclopropylsulfonyl)phenyl)-3,8-dimethyl-9H-pyrido[2,3-b]indole-7-carboxamido)piperidin-1-yl)ethyl dihydrogen phosphate;
3-chloro-5-(3-(cyclopropylsulfonyl)phenyl)-N-(1-(2-hydroxyethyl)piperidin-4-yl)-8-methyl-9H-pyrido[2,3-b]indole-7-carboxamide;
2-(4-(3-chloro-5-(3-(cyclopropylsulfonyl)phenyl)-8-methyl-9H-pyrido[2,3-b]indole-7-carboxamido)piperidin-1-yl)ethyl dihydrogen phosphate;
5-(3-(ethylsulfonyl)phenyl)-N-(2-((2-hydroxyethyl)(methyl)amino)ethyl)-3,8-dimethyl-9H-pyrido[2,3-b]indole-7-carboxamide;
2-((2-(5-(3-(ethylsulfonyl)phenyl)-3,8-dimethyl-9H-pyrido[2,3-b]indole-7-carboxamido)ethyl)(methyl)amino)ethyl dihydrogen phosphate;
3-chloro-5-(3-(ethylsulfonyl)phenyl)-N-(2-((2-hydroxyethyl)(methyl)amino)ethyl)-8-methyl-9H-pyrido[2,3-b]indole-7-carboxamide;
2-((2-(3-chloro-5-(3-(ethylsulfonyl)phenyl)-8-methyl-9H-pyrido[2,3-b]indole-7-carboxamido)ethyl)(methyl)amino)ethyl dihydrogen phosphate;
5-(3-(cyclopropylsulfonyl)phenyl)-N-(2-((2-hydroxyethyl)(methyl)amino)ethyl)-3,8-dimethyl-9H-pyrido[2,3-b]indole-7-carboxamide;
2-((2-(5-(3-(cyclopropylsulfonyl)phenyl)-3,8-dimethyl-9H-pyrido[2,3-b]indole-7-carboxamido)ethyl)(methyl)amino)ethyl dihydrogen phosphate;
3-chloro-5-(3-(cyclopropylsulfonyl)phenyl)-N-(2-((2-hydroxyethyl)(methyl)amino)ethyl)-8-methyl-9H-pyrido[2,3-b]indole-7-carboxamide;
2-((2-(3-chloro-5-(3-(cyclopropylsulfonyl)phenyl)-8-methyl-9H-pyrido[2,3-b]indole-7-carboxamido)ethyl)(methyl)amino)ethyl dihydrogen phosphate;
N-(3-(ethyl(2-hydroxyethyl)amino)propyl)-5-(3-(ethylsulfonyl)phenyl)-3,8-dimethyl-9H-pyrido[2,3-b]indole-7-carboxamide;
2-(ethyl(3-(5-(3-(ethylsulfonyl)phenyl)-3,8-dimethyl-9H-pyrido[2,3-b]indole-7-carboxamido)propyl)amino)ethyl dihydrogen phosphate;
5-(3-(ethylsulfonyl)phenyl)-N-(3-((2-hydroxyethyl)(methyl)amino)propyl)-3,8-dimethyl-9H-pyrido[2,3-b]indole-7-carboxamide;
2-((3-(5-(3-(ethylsulfonyl)phenyl)-3,8-dimethyl-9H-pyrido[2,3-b]indole-7-carboxamido)propyl)(methyl)amino)ethyl dihydrogen phosphate;
5-(3-(ethylsulfonyl)phenyl)-N-((1r,4r)-hydroxycyclohexyl)-3,8-dimethyl-9H-pyrido[2,3-b]indole-7-carboxamide;
5-(3-(ethylsulfonyl)phenyl)-N-((1s,4s)-4-hydroxycyclohexyl)-3,8-dimethyl-9H-pyrido[2,3-b]indole-7-carboxamide;
5-(3-(ethylsulfonyl)phenyl)-N-(4-(hydroxymethyl)cyclohexyl)-3,8-dimethyl-9H-pyrido[2,3-b]indole-7-carboxamide;
5-(3-(ethylsulfonyl)phenyl)-N-(4-(2-hydroxyethyl)cyclohexyl)-3,8-dimethyl-9H-pyrido[2,3-b]indole-7-carboxamide;
(5-(3-(ethylsulfonyl)phenyl)-3,8-dimethyl-9H-pyrido[2,3-b]indol-7-yl)(4-(hydroxymethyl)piperidin-1-yl)methanone;
(5-(3-(ethylsulfonyl)phenyl)-3,8-dimethyl-9H-pyrido[2,3-b]indol-7-yl)(4-(2-hydroxyethyl)piperidin-1-yl)methanone;
(5-(3-(ethylsulfonyl)phenyl)-3,8-dimethyl-9H-pyrido[2,3-b]indol-7-yl)(4-hydroxypiperidin-1-yl)methanone;

(5-(3-(ethylsulfonyl)phenyl)-3,8-dimethyl-9H-pyrido[2,3-b]
   indol-7-yl)(2-(hydroxymethyl)pyrrolidin-1-yl)metha-
   none;
(5-(3-(ethylsulfonyl)phenyl)-3,8-dimethyl-9H-pyrido[2,3-b]
   indol-7-yl)(2-(hydroxymethyl)morpholino)methanone;
5-(3-(ethylsulfonyl)phenyl)-N-(3-hydroxypropyl)-3,8-dim-
   ethyl-9H-pyrido[2,3-b]indole-7-carboxamide;
(R)-5-(3-(ethylsulfonyl)phenyl)-N-(3-hydroxybutyl)-3,8-
   dimethyl-9H-pyrido[2,3-b]indole-7-carboxamide;
(S)-5-(3-(ethylsulfonyl)phenyl)-N-(3-hydroxybutyl)-3,8-
   dimethyl-9H-pyrido[2,3-b]indole-7-carboxamide;
5-(3-(ethylsulfonyl)phenyl)-N-(3-hydroxy-3-methylbutyl)-
   3,8-dimethyl-9H-pyrido[2,3-b]indole-7-carboxamide;
(S)—N-(3-(dimethylamino)-2-hydroxypropyl)-5-(3-(ethyl-
   sulfonyl)phenyl)-3,8-dimethyl-9H-pyrido[2,3-b]indole-
   7-carboxamide;
(S)—N-(2-(dimethylamino)-3-hydroxypropyl)-5-(3-(ethyl-
   sulfonyl)phenyl)-3,8-dimethyl-9H-pyrido[2,3-b]indole-
   7-carboxamide;
N-(3-(ethyl(2-hydroxyethyl)amino)propyl)-5-(3-(ethylsul-
   fonyl)phenyl)-3,8-dimethyl-9H-pyrido[2,3-b]indole-7-
   carboxamide;
5-(3-(ethylsulfonyl)phenyl)-N-(3-((2-hydroxyethyl)(me-
   thyl)amino)propyl)-3,8-dimethyl-9H-pyrido[2,3-b]in-
   dole-7-carboxamide;
N-(2-(ethyl(2-hydroxyethyl)amino)ethyl)-5-(3-(ethylsulfo-
   nyl)phenyl)-3,8-dimethyl-9H-pyrido[2,3-b]indole-7-car-
   boxamide; and
5-(3-(ethylsulfonyl)phenyl)-N-(2-((2-hydroxyethyl)(me-
   thyl)amino)ethyl)-3,8-dimethyl-9H-pyrido[2,3-b]indole-
   7-carboxamide.
In addition, particular examples of compounds according
to the present invention include, but are not limited to:
5-phenyl-9H-pyrido[2,3-b]indole;
3-(3,8-dimethyl-9H-pyrido[2,3-b]indol-5-yl)-N-methylben-
   zenesulfonamide; 5
5-(3-(ethylsulfonyl)phenyl)-3,8-dimethyl-9H-pyrido[2,3-b]
   indole;
8-chloro-5-[3-(ethylsulfonyl)phenyl]-3-methyl-9H-pyrido
   [4',3':4,5]pyrrolo[2,3-b]pyridine;
N'-[5-(3-Ethanesulfonyl-phenyl)-3-methyl-9H-dipyrido[2,
   3-b;   4',3'-d]pyrrol-8-yl]-N,N-dimethyl-propane-1,3-di-
   amine;
5-(3-Ethanesulfonyl-phenyl)-8-ethoxy-3-methyl-9H-dipy-
   rido[2,3-b; 4',3'-d]pyrrole;
3-[5-(3-Ethanesulfonyl-phenyl)-3-methyl-9H-dipyrido[2,3-
   b; 4',3'-d]pyrrol-8-yloxy]-propan-1-ol;
(S)-1-[5-(3-Ethanesulfonyl-phenyl)-3-methyl-9H-dipyrido
   [2,3-b; 4',3'-d]pyrrol-8-yloxy]-propan-2-ol;
5-(3-Ethanesulfonyl-phenyl)-3-methyl-9H-pyrido[2,3-b]in-
   dole-7-carboxylic acid;
5-(3-(ethylsulfonyl)phenyl-8-methoxy-3-methyl-9H-pyrido
   [2,3-b]indole;
5-(3-(ethylsulfonyl)phenyl)-3-methyl-9H-pyrido[2,3-b]in-
   dol-8-ol;
N-(3-(8-methoxy-3-methyl-9H-pyrido[2,3-b]indol-5-yl)
   phenyl)cyclopropanecarboxamide;
N-ethyl-3-(8-methoxy-3-methyl-9H-pyrido[2,3-b]indol-5-
   yl)benzenesulfonamide;
8-ethoxy-5-(3-(ethylsulfonyl)phenyl)-3-methyl-9H-pyrido
   [2,3-b]indole;
5-(3-(ethylsulfonyl)phenyl)-3-methyl-8-(2,2,2-trifluoroet-
   hoxy)-9H-pyrido[2,3-b]indole;
3-(5-(3-(ethylsulfonyl)phenyl)-3-methyl-9H-pyrido[2,3-b]
   indol-8-yloxy)propan-1-ol; and
(R)-3-(5-(3-(ethylsulfonyl)phenyl)-3-methyl-9H-pyrido[2,
   3-b]indol-8-yloxy)propane-1,2-diol.

In addition, particular examples of compounds according
to the present invention include, but are not limited to:
5-(3-(ethylsulfonyl)phenyl)-3,8-dimethyl-N-(1-methylpip-
   eridin-4-yl)-9H-pyrido[2,3-b]indole-7-carboxamide;
N-(2-(methoxy)ethyl)-5-(3-(ethylsulfonyl)phenyl)-3,8-dim-
   ethyl-9H-pyrido[2,3-b]indole-7-carboxamide;
5-(3-(ethylsulfonyl)phenyl)-3,8-dimethyl-N-(3-(4-meth-
   ylpiperazin-1-yl)propyl)-9H-pyrido[2,3-b]indole-7-car-
   boxamide;
(S)-5-(3-(ethylsulfonyl)phenyl)-N-(2-hydroxypropyl)-3,8-
   dimethyl-9H-pyrido[2,3-b]indole-7-carboxamide;
5-(3-(ethylsulfonyl)phenyl)-N-(2-hydroxyethyl)-3,8-dim-
   ethyl-9H-pyrido[2,3-b]indole-7-carboxamide;
N-(1-ethylpiperidin-4-yl)-5-(3-(ethylsulfonyl)phenyl)-3,8-
   dimethyl-9H-pyrido[2,3-b]indole-7-carboxamide;
5-(3-(cyclopropanecarboxamido)phenyl)-N-(2-(dimethy-
   lamino)ethyl)-3,8-dimethyl-9H-pyrido[2,3-b]indole-7-
   carboxamide;
N-(2-(dimethylamino)ethyl)-5-(3-(ethylsulfonyl)phenyl)-3,
   8-dimethyl-9H-pyrido[2,3-b]indole-7-carboxamide;
5-(3-(ethylsulfonyl)phenyl)-3,8-dimethyl-N-((1-methylpip-
   eridin-4-yl)methyl)-9H-pyrido[2,3-b]indole-7-carboxam-
   ide;
(S)-5-(3-(ethylsulfonyl)phenyl)-3,8-dimethyl-N-(1-meth-
   ylpiperidin-3-yl)-9H-pyrido[2,3-b]indole-7-carboxam-
   ide;
5-(3-(cyclopropanecarboxamido)phenyl)-3,8-dimethyl-N-
   (1-methyl-piperidin-4-yl)-9H-pyrido[2,3-b]indole-7-car-
   boxamide;
5-(3-Ethanesulfonyl-phenyl)-3-methyl-9H-pyrido[2,3-b]in-
   dole-7-carboxylic acid amide;
5-(3-Ethanesulfonyl-phenyl)-3-methyl-9H-pyrido[2,3-b]in-
   dole-7-carboxylic acid (2-dimethylamino-ethyl)-amide;
5-(3-(N-ethylsulfamoyl)phenyl)-8-methoxy-3-methyl-N-(1-
   methylpiperidin-4-yl)-9H-pyrido[2,3-b]indole-7-car-
   boxamide; and
5-(3-(cyclopropylsulfonyl)phenyl)-3,8-dimethyl-N-(1-me-
   thylpiperidin-4-yl)-9H-pyrido[2,3-b]indole-7-carboxam-
   ide.

In addition, particular examples of compounds according
to the present invention include, but are not limited to:
{3-[5-(3-Ethanesulfonyl-phenyl)-3-methyl-9H-dipyrido[2,
   3-b; 4',3'-d]pyrrol-8-yloxy]-propyl}-dimethyl-amine;
5-(3-Ethanesulfonyl-phenyl)-3-methyl-8-(1-methyl-piperi-
   din-4-ylmethoxy)-9H-dipyrido[2,3-b; 4',3'-d]pyrrole;
5-(3-Ethanesulfonyl-phenyl)-8-(1-ethyl-piperidin-4-yl-
   methoxy)-3-methyl-9H-dipyrido[2,3-b; 4',3'-d]pyrrole;
L-Valine-2-[5-(3-ethanesulfonyl-phenyl)-3-methyl-9H-
   dipyrido[2,3-b; 4',3'-d]pyrrol-8-yloxy]-ethyl ester;
L-Alanine-(R)-2-[5-(3-ethanesulfonyl-phenyl)-3-methyl-
   9H-dipyrido[2,3-b;   4',3'-d]pyrrol-8-yloxy]-1-methyl-
   ethyl ester;
3-Chloro-5-(3-ethanesulfonyl-phenyl)-8-(1-methyl-piperi-
   din-4-ylmethoxy)-9H-dipyrido[2,3-b; 4',3'-d]pyrrole;
5-(3-(ethylsulfonyl)phenyl)-3-methyl-8-((1-methylpiperi-
   din-4-yl)methoxy)-9H-pyrido[2,3-b]indole;
N-cyclopropyl-3-(3-methyl-8-((1-methylpiperidin-4-yl)
   methoxy)-9H-pyrido[2,3-b]indol-5-yl)benzamide;
5-(3-(cyclopropylsulfonyl)phenyl)-3-methyl-8-((1-meth-
   ylpiperidin-4-yl)methoxy)-9H-pyrido[2,3-b]indole;
N-methyl-3-(3-methyl-8-((1-methylpiperidin-4-yl)meth-
   oxy)-9H-pyrido[2,3-b]indole-5-yl)benzenesulfonamide;
N,N-dimethyl-3-(3-methyl-8-((1-methylpiperidin-4-yl)
   methoxy)-9H-pyrido[2,3-b]indol-5-yl)benzenesulfona-
   mide;

N-(3-(3-methyl-8-((1-methylpiperidin-4-yl)methoxy)-9H-pyrido[2,3-b]indol-5-yl)phenyl)cyclopropanecarboxamide;
5-(3-(ethylthio)phenyl)-3-methyl-8-((1-methylpiperidin-4-yl)methoxy)-9H-pyrido[2,3-b]indole;
5-(3-ethoxyphenyl)-3-methyl-8-((1-methylpiperidin-4-yl)methoxy)-9H-pyrido[2,3-b]indole;
5-(3-(ethylsulfonyl)phenyl)-3-methyl-8-(piperidin-4-ylmethoxy)-9H-pyrido[2,3-b]indole;
(S)-5-(3-(ethylsulfonyl)phenyl)-3-methyl-8-((1-methylpyrrolidin-3-yl)methoxy)-9H-pyrido[2,3-b]indole;
(R)-5-(3-(ethylsulfonyl)phenyl)-3-methyl-8-((1-methylpyrrolidin-3-yl)methoxy)-9H-pyrido[2,3-b]indole;
(S)-5-(3-(ethylsulfonyl)phenyl)-3-methyl-8-((1-methylpyrrolidin-2-yl)methoxy)-9H-pyrido[2,3-b]indole;
(S)-5-(3-(ethylsulfonyl)phenyl)-3-methyl-8-(pyrrolidin-3-ylmethoxy)-9H-pyrido[2,3-b]indole;
(R)-5-(3-(ethylsulfonyl)phenyl)-3-methyl-8-(pyrrolidin-3-ylmethoxy)-9H-pyrido[2,3-b]indole;
3-(5-(3-(cyclopropylsulfonyl)phenyl)-3-methyl-9H-pyrido[2,3-b]indol-8-yloxy)-N,N-dimethylpropan-1-amine;
N-(3-(8-(3-(dimethylamino)propoxy)-3-methyl-9H-pyrido[2,3-b]indol-5-yl)phenyl)cyclopropanecarboxamide;
3-chloro-5-(3-(ethylsulfonyl)phenyl)-8-((1-methylpiperidin-4-yl)methoxy)-9H-pyrido[2,3-b]indole;
3-chloro-5-(3-(ethylsulfonyl)phenyl)-8-(piperidin-4-ylmethoxy)-9H-pyrido[2,3-b]indole;
5-(3-(ethylsulfonyl)phenyl)-8-((1-methylpiperidin-4-yl)methoxy)-3-(trifluoromethyl)-9H-pyrido[2,3-b]indole;
5-(3-(ethylsulfonyl)phenyl)-8-((1-methylpiperidin-4-yl)methoxy)-9H-pyrido[2,3-b]indole-3-carbonitrile;
2-(5-(3-(ethylsulfonyl)phenyl)-7-fluoro-3-methyl-9H-pyrido[2,3-b]indol-8-yloxy)-N,N-dimethylethanamine;
3-(3-chloro-5-(3-(ethylsulfonyl)phenyl)-7-fluoro-9H-pyrido[2,3-b]indol-8-yloxy)-N,N-dimethylpropan-1-amine;
3-(5-(3-(ethylsulfonyl)phenyl)-3-methyl-9H-pyrido[2,3-b]indol-8-yloxy)-N,N-dimethylpropan-1-amine;
2-(5-(3-(ethylsulfonyl)phenyl)-3-methyl-9H-pyrido[2,3-b]indol-8-yloxy)-N,N-dimethylethanamine;
3-(3-chloro-5-(3-(ethylsulfonyl)phenyl)-9H-pyrido[2,3-b]indol-8-yloxy)-N,N-dimethylpropan-1-amine;
2-(3-chloro-5-(3-(ethylsulfonyl)phenyl)-9H-pyrido[2,3-b]indol-8-yloxy)-N,N-diethylethanamine;
2-(3-chloro-5-(3-(ethylsulfonyl)phenyl)-9H-pyrido[2,3-b]indol-8-yloxy)-N,N-dimethylethanamine;
3-chloro-5-(3-(ethylsulfonyl)phenyl)-8-(2-(pyrrolidin-1-yl)ethoxy)-9H-pyrido[2,3-b]indole;
3-chloro-5-(3-(ethylsulfonyl)phenyl)-8-(2-(4-methylpiperazin-1-yl)ethoxy)-9H-pyrido[2,3-b]indole;
(S)-2-(5-(3-(ethylsulfonyl)phenyl)-3-methyl-9H-pyrido[2,3-b]indol-8-yloxy)ethyl 2-aminopropanoate;
(S)-3-(5-(3-(ethylsulfonyl)phenyl)-3-methyl-9H-pyrido[2,3-b]indol-8-yloxy)propyl 2-aminopropanoate;
(R)-1-(dimethylamino)-3-(5-(3-(ethylsulfonyl)phenyl)-3-methyl-9H-pyrido[2,3-b]indol-8-yloxy)propan-2-ol;
4-(2-(3-chloro-5-(3-(ethylsulfonyl)phenyl)-9H-pyrido[2,3-b]indol-8-yloxy)ethyl)morpholine;
3-chloro-5-(3-(ethylsulfonyl)phenyl)-8-(1-methylpiperidin-4-yloxy)-9H-pyrido[2,3-b]indole;
3-(5-(3-(ethylsulfonyl)phenyl)-3-(trifluoromethyl)-9H-pyrido[2,3-b]indol-8-yloxy)-N,N-dimethylpropan-1-amine;
2-((3-(5-(3-(cyclopropylsulfonyl)phenyl)-3-methyl-9H-pyrido[2,3-b]indol-8-yloxy)propyl)(ethyl)amino)ethanol;
di-tert-butyl-2-((3-(5-(3-(cyclopropylsulfonyl)phenyl)-3-methyl-9H-pyrido[2,3-b]indol-8-yloxy)propyl)(ethyl)amino)ethyl phosphate;
2-((3-(5-(3-(cyclopropylsulfonyl)phenyl)-3-methyl-9H-pyrido[2,3-b]indol-8-yloxy)propyl)(ethyl)amino)ethyl dihydrogen phosphate;
N-cyclopropyl-3-(8-(3-(ethyl(2-hydroxyethyl)amino)propoxy)-3-methyl-9H-pyrido[2,3-b]indol-5-yl)benzamide;
di-tert-butyl-2-((3-(5-(3-(cyclopropylcarbamoyl)phenyl)-3-methyl-9H-pyrido[2,3-b]indol-8-yloxy)propyl)(ethyl)amino)ethyl phosphate;
2-((3-(5-(3-(cyclopropylcarbamoyl)phenyl)-3-methyl-9H-pyrido[2,3-b]indol-8-yloxy)propyl)(ethyl)amino)ethyl dihydrogen phosphate;
2-((3-(4-chloro-6-methyl-9H-carbazol-1-yloxy)propyl)(ethyl)amino)-ethanol;
di-tert-butyl 2-(ethyl(3-(5-(3-(ethylsulfonyl)phenyl)-3-methyl-9H-pyrido[2,3-b]indol-8-yloxy)propyl)amino)ethyl phosphate;
2-(ethyl(3-(5-(3-(ethylsulfonyl)phenyl)-3-methyl-9H-pyrido[2,3-b]indol-8-yloxy)propyl)amino)ethyl dihydrogen phosphate;
3-(3-chloro-8-((1-methylpiperidin-4-yl)methoxy)-9H-pyrido[2,3-b]indol-5-yl)-N-cyclopropylbenzamide;
3-chloro-5-(3-(cyclopropylsulfonyl)phenyl)-8-((1-methylpiperidin-4-yl)methoxy)-9H-pyrido[2,3-b]indole;
5-(3-(ethylsulfonyl)phenyl)-3-fluoro-8-((1-methylpiperidin-4-yl)methoxy)-9H-pyrido[2,3-b]indole;
2-((3-(3-chloro-5-(3-(ethylsulfonyl)phenyl)-9H-pyrido[2,3-b]indol-8-yloxy)propyl)(ethyl)amino)ethanol;
2-((3-(3-chloro-5-(3-(ethylsulfonyl)phenyl)-9H-pyrido[2,3-b]indol-8-yloxy)propyl)(ethyl)amino)ethyl dihydrogen phosphate;
3-(8-(3-(dimethylamino)propoxy)-3-methyl-9H-pyrido[2,3-b]indol-5-yl)-N-ethylbenzenesulfonamide;
3-(8-(3-(dimethylamino)propoxy)-3-methyl-9H-pyrido[2,3-b]indol-5-yl)-N,N-dimethylbenzenesulfonamide;
(S)-3-(3-chloro-5-(3-(ethylsulfonyl)phenyl)-9H-pyrido[2,3-b]indol-8-yloxy)propyl 2-aminopropanoate;
2-((3-(3-chloro-5-(3-(cyclopropylsulfonyl)phenyl)-9H-pyrido[2,3-b]indol-8-yloxy)propyl)(ethyl)amino)ethanol;
2-((3-(3-chloro-5-(3-(cyclopropylsulfonyl)phenyl)-9H-pyrido[2,3-b]indol-8-yloxy)propyl)(ethyl)amino)ethyl dihydrogen phosphate;
1-(3-(5-(3-(cyclopropylsulfonyl)phenyl)-3-methyl-9H-pyrido[2,3-b]indol-8-yloxy)propyl)piperidin-4-ol;
8-(3-(1H-imidazol-1-yl)propoxy)-3-chloro-5-(3-(ethylsulfonyl)phenyl)-9H-pyrido[2,3-b]indole;
2-((3-(5-(3-(ethylsulfonyl)phenyl)-3-methyl-9H-pyrido[2,3-b]indol-8-yloxy)propyl)(methyl)amino)ethanol;
di-tert-butyl 2-((3-(5-(3-(ethylsulfonyl)phenyl)-3-methyl-9H-pyrido[2,3-b]indol-8-yloxy)propyl)(methyl)amino)ethyl phosphate;
2-((3-(5-(3-(ethylsulfonyl)phenyl)-3-methyl-9H-pyrido[2,3-b]indol-8-yloxy)propyl)(methyl)amino)ethyl dihydrogen phosphate, dihydrochloride;
2-((3-(5-(3-(ethylsulfonyl)phenyl)-3-methyl-9H-pyrido[2,3-b]indol-8-yloxy)propyl)(methyl)amino)ethyl dihydrogen phosphate;
(S)-1-(5-(3-(cyclopropylsulfonyl)phenyl)-3-methyl-9H-pyrido[2,3-b]indol-8-yloxy)-3-(dimethylamino)propan-2-ol;
(S)-1-(5-(3-(cyclopropylsulfonyl)phenyl)-3-methyl-9H-pyrido[2,3-b]indol-8-yloxy)-3-(dimethylamino)propan-2-yl dihydrogen phosphate;
(R)-1-(5-(3-(cyclopropylsulfonyl)phenyl)-3-methyl-9H-pyrido[2,3-b]indol-8-yloxy)-3-(dimethylamino)propan-2-yl dihydrogen phosphate;

3-chloro-N-(3-methyl-4-(4-methylpiperazin-1-yl)phenyl)-8-((1-methylpiperidin-4-yl)methoxy)-9H-pyrido[2,3-b]indol-5-amine;

5-(3-(cyclopropylsulfonyl)phenyl)-8-((1-methylpiperidin-4-yl)methoxy)-9H-pyrido[2,3-b]indole;

2-((2-(5-(3-(cyclopropylsulfonyl)phenyl)-3-methyl-9H-pyrido[2,3-b]indol-8-yloxy)ethyl)(ethyl)amino)ethanol;

2-((2-(3-chloro-5-(3-(cyclopropylsulfonyl)phenyl)-9H-pyrido[2,3-b]indol-8-yloxy)ethyl)(methyl)amino)ethanol;

2-((2-(5-(3-(cyclopropylsulfonyl)phenyl)-9H-pyrido[2,3-b]indol-8-yloxy)ethyl)(methyl)amino)ethanol;

2-((2-(5-(3-(cyclopropylsulfonyl)phenyl)-3-methyl-9H-pyrido[2,3-b]indol-8-yloxy)ethyl)(methyl)amino)ethanol;

1-(2-(5-(3-(cyclopropylsulfonyl)phenyl)-3-methyl-9H-pyrido[2,3-b]indol-8-yloxy)ethyl)piperidin-4-ol;

2-((2-(3-chloro-5-(3-(cyclopropylsulfonyl)phenyl)-9H-pyrido[2,3-b]indol-8-yloxy)ethyl)(ethyl)amino)ethanol;

2-((2-(5-(3-(cyclopropylsulfonyl)phenyl)-9H-pyrido[2,3-b]indol-8-yloxy)ethyl)(ethyl)amino)ethanol;

1-(2-(3-chloro-5-(3-(cyclopropylsulfonyl)phenyl)-9H-pyrido[2,3-b]indol-8-yloxy)ethyl)piperidin-4-ol;

1-(2-(5-(3-(cyclopropylsulfonyl)phenyl)-9H-pyrido[2,3-b]indol-8-yloxy)ethyl)piperidin-4-ol;

1-(2-(5-(3-(ethylsulfonyl)phenyl)-9H-pyrido[2,3-b]indol-8-yloxy)ethyl)piperidin-4-ol;

1-(2-(5-(3-(ethylsulfonyl)phenyl)-3-methyl-9H-pyrido[2,3-b]indol-8-yloxy)ethyl)piperidin-4-ol;

1-(2-(3-chloro-5-(3-(ethylsulfonyl)phenyl)-9H-pyrido[2,3-b]indol-8-yloxy)ethyl)piperidin-4-ol;

N-cyclopropyl-3-(8-(3-(dimethylamino)propoxy)-3-methyl-9H-pyrido[2,3-b]indol-5-yl)benzamide;

3-(8-(3-(dimethylamino)propoxy)-3-methyl-9H-pyrido[2,3-b]indol-5-yl)-N-methylbenzenesulfonamide;

8-(2-(1H-imidazol-1-yl)ethoxy)-5-(3-(ethylsulfonyl)phenyl)-3-methyl-9H-pyrido[2,3-b]indole;

8-(2-(1H-imidazol-1-yl)ethoxy)-3-chloro-5-(3-(ethylsulfonyl)phenyl)-9H-pyrido[2,3-b]indole;

(1-(3-(5-(3-(ethylsulfonyl)phenyl)-3-methyl-9H-pyrido[2,3-b]indol-8-yloxy)propyl)-1H-imidazol-4-yl)methanol;

(1-(3-(5-(3-(ethylsulfonyl)phenyl)-3-methyl-9H-pyrido[2,3-b]indol-8-yloxy)propyl)-1H-imidazol-4-yl)methyl dihydrogen phosphate;

8-(3-(4H-1,2,4-triazol-4-yl)propoxy)-5-(3-(ethylsulfonyl)phenyl)-3-methyl-9H-pyrido[2,3-b]indole;

8-(3-(1H-1,2,3-triazol-1-yl)propoxy)-5-(3-(ethylsulfonyl)phenyl)-3-methyl-9H-pyrido[2,3-b]indole;

(1-(3-(3-chloro-5-(3-(ethylsulfonyl)phenyl)-9H-pyrido[2,3-b]indol-8-yloxy)propyl)-1H-imidazol-4-yl)methanol;

(1-(3-(3-chloro-5-(3-(ethylsulfonyl)phenyl)-9H-pyrido[2,3-b]indol-8-yloxy)propyl)-1H-imidazol-4-yl)methyl dihydrogen phosphate;

8-(3-(4H-1,2,4-triazol-4-yl)propoxy)-3-chloro-5-(3-(ethylsulfonyl)phenyl)-9H-pyrido[2,3-b]indole;

8-(3-(1H-1,2,3-triazol-1-yl)propoxy)-3-chloro-5-(3-(ethylsulfonyl)phenyl)-9H-pyrido[2,3-b]indole;

(1-(3-(5-(3-(cyclopropylsulfonyl)phenyl)-3-methyl-9H-pyrido[2,3-b]indol-8-yloxy)propyl)-1H-imidazol-4-yl)methanol;

(1-(3-(5-(3-(cyclopropylsulfonyl)phenyl)-3-methyl-9H-pyrido[2,3-b]indol-8-yloxy)propyl)-1H-imidazol-4-yl)methyl dihydrogen phosphate;

8-(3-(4H-1,2,4-triazol-4-yl)propoxy)-5-(3-(cyclopropylsulfonyl)phenyl)-3-methyl-9H-pyrido[2,3-b]indole;

8-(3-(1H-1,2,3-triazol-1-yl)propoxy)-5-(3-(cyclopropylsulfonyl)phenyl)-3-methyl-9H-pyrido[2,3-b]indole;

(1-(3-(3-chloro-5-(3-(cyclopropylsulfonyl)phenyl)-9H-pyrido[2,3-b]indol-8-yloxy)propyl)-1H-imidazol-4-yl)methanol;

(1-(3-(3-chloro-5-(3-(cyclopropylsulfonyl)phenyl)-9H-pyrido[2,3-b]indol-8-yloxy)propyl)-1H-imidazol-4-yl)methyl dihydrogen phosphate;

8-(3-(4H-1,2,4-triazol-4-yl)propoxy)-3-chloro-5-(3-(cyclopropylsulfonyl)phenyl)-9H-pyrido[2,3-b]indole;

8-(3-(1H-1,2,3-triazol-1-yl)propoxy)-3-chloro-5-(3-(cyclopropylsulfonyl)phenyl)-9H-pyrido[2,3-b]indole;

2-((2,2-difluoroethyl)(3-(5-(3-(ethylsulfonyl)phenyl)-3-methyl-9H-pyrido[2,3-b]indol-8-yloxy)propyl)amino)ethanol;

2-((2,2-difluoroethyl)(3-(5-(3-(ethylsulfonyl)phenyl)-3-methyl-9H-pyrido[2,3-b]indol-8-yloxy)propyl)amino)ethyl dihydrogen phosphate;

2-((3-(3-chloro-5-(3-(ethylsulfonyl)phenyl)-9H-pyrido[2,3-b]indol-8-yloxy)propyl)(2,2-difluoroethyl)amino)ethanol;

2-((3-(3-chloro-5-(3-(ethylsulfonyl)phenyl)-9H-pyrido[2,3-b]indol-8-yloxy)propyl)(2,2-difluoroethyl)amino)ethyl dihydrogen phosphate;

2-((3-(5-(3-(cyclopropylsulfonyl)phenyl)-3-methyl-9H-pyrido[2,3-b]indol-8-yloxy)propyl)(2,2-difluoroethyl)amino)ethanol;

2-((3-(5-(3-(cyclopropylsulfonyl)phenyl)-3-methyl-9H-pyrido[2,3-b]indol-8-yloxy)propyl)(2,2-difluoroethyl)amino)ethyl dihydrogen phosphate;

2-((3-(3-chloro-5-(3-(cyclopropylsulfonyl)phenyl)-9H-pyrido[2,3-b]indol-8-yloxy)propyl)(2,2-difluoroethyl)amino)ethanol;

2-((3-(3-chloro-5-(3-(cyclopropylsulfonyl)phenyl)-9H-pyrido[2,3-b]indol-8-yloxy)propyl)(2,2-difluoroethyl)amino)ethyl dihydrogen phosphate;

2-((3-(5-(3-(ethylsulfonyl)phenyl)-3-methyl-9H-pyrido[2,3-b]indol-8-yloxy)propyl)(2,2,2-trifluoroethyl)amino)ethanol;

2-((3-(5-(3-(ethylsulfonyl)phenyl)-3-methyl-9H-pyrido[2,3-b]indol-8-yloxy)propyl)(2,2,2-trifluoroethyl)amino)ethyl dihydrogen phosphate;

2-((3-(3-chloro-5-(3-(ethylsulfonyl)phenyl)-9H-pyrido[2,3-b]indol-8-yloxy)propyl)(2,2,2-trifluoroethyl)amino)ethanol;

2-((3-(3-chloro-5-(3-(ethylsulfonyl)phenyl)-9H-pyrido[2,3-b]indol-8-yloxy)propyl)(2,2,2-trifluoroethyl)amino)ethyl dihydrogen phosphate;

2-((3-(5-(3-(cyclopropylsulfonyl)phenyl)-3-methyl-9H-pyrido[2,3-b]indol-8-yloxy)propyl)(2,2,2-trifluoroethyl)amino)ethanol;

2-((3-(5-(3-(cyclopropylsulfonyl)phenyl)-3-methyl-9H-pyrido[2,3-b]indol-8-yloxy)propyl)(2,2,2-trifluoroethyl)amino)ethyl dihydrogen phosphate;

2-((3-(3-chloro-5-(3-(cyclopropylsulfonyl)phenyl)-9H-pyrido[2,3-b]indol-8-yloxy)propyl)(2,2,2-trifluoroethyl)amino)ethanol;

2-((3-(3-chloro-5-(3-(cyclopropylsulfonyl)phenyl)-9H-pyrido[2,3-b]indol-8-yloxy)propyl)(2,2,2-trifluoroethyl)amino)ethyl dihydrogen phosphate;

2-(ethyl(3-(5-(3-(ethylsulfonyl)phenyl)-3-methyl-9H-pyrido[2,3-b]indol-8-yloxy)propyl)amino)-2,2-difluoroethanol;

2-(ethyl(3-(5-(3-(ethylsulfonyl)phenyl)-3-methyl-9H-pyrido[2,3-b]indol-8-yloxy)propyl)amino)-2,2-difluoroethyl dihydrogen phosphate;

2-((3-(3-chloro-5-(3-(ethylsulfonyl)phenyl)-9H-pyrido[2,3-b]indol-8-yloxy)propyl)(ethyl)amino)-2,2-difluoroethanol;

2-((3-(3-chloro-5-(3-(ethylsulfonyl)phenyl)-9H-pyrido[2,3-b]indol-8-yloxy)propyl)(ethyl)amino)-2,2-difluoroethyl dihydrogen phosphate;
2-((3-(5-(3-(cyclopropylsulfonyl)phenyl)-3-methyl-9H-pyrido[2,3-b]indol-8-yloxy)propyl)(ethyl)amino)-2,2-difluoroethanol;
2-((3-(5-(3-(cyclopropylsulfonyl)phenyl)-3-methyl-9H-pyrido[2,3-b]indol-8-yloxy)propyl)(ethyl)amino)-2,2-difluoroethyl dihydrogen phosphate;
2-((3-(3-chloro-5-(3-(cyclopropylsulfonyl)phenyl)-9H-pyrido[2,3-b]indol-8-yloxy)propyl)(ethyl)amino)-2,2-difluoroethanol;
2-((3-(3-chloro-5-(3-(cyclopropylsulfonyl)phenyl)-9H-pyrido[2,3-b]indol-8-yloxy)propyl)(ethyl)amino)-2,2-difluoroethyl dihydrogen phosphate;
2-(ethyl(3-(5-(3-(ethylsulfonyl)phenyl)-3-methyl-9H-pyrido[2,3-b]indol-8-yloxy)-1,1-difluoropropyl)amino)ethanol;
2-(ethyl(3-(5-(3-(ethylsulfonyl)phenyl)-3-methyl-9H-pyrido[2,3-b]indol-8-yloxy)-1,1-difluoropropyl)amino)ethyl dihydrogen phosphate;
2-((3-(3-chloro-5-(3-(ethylsulfonyl)phenyl)-9H-pyrido[2,3-b]indol-8-yloxy)-1,1-difluoropropyl)(ethyl)amino)ethanol;
2-((3-(3-chloro-5-(3-(ethylsulfonyl)phenyl)-9H-pyrido[2,3-b]indol-8-yloxy)-1,1-difluoropropyl)(ethyl)amino)ethyl dihydrogen phosphate;
2-((3-(5-(3-(cyclopropylsulfonyl)phenyl)-3-methyl-9H-pyrido[2,3-b]indol-8-yloxy)-1,1-difluoropropyl)(ethyl)amino)ethanol;
2-((3-(5-(3-(cyclopropylsulfonyl)phenyl)-3-methyl-9H-pyrido[2,3-b]indol-8-yloxy)-1,1-difluoropropyl)(ethyl)amino)ethyl dihydrogen phosphate;
2-((3-(3-chloro-5-(3-(cyclopropylsulfonyl)phenyl)-9H-pyrido[2,3-b]indol-8-yloxy)-1,1-difluoropropyl)(ethyl)amino)ethanol;
2-((3-(3-chloro-5-(3-(cyclopropylsulfonyl)phenyl)-9H-pyrido[2,3-b]indol-8-yloxy)-1,1-difluoropropyl)(ethyl)amino)ethyl dihydrogen phosphate;
2-(ethyl(3-(5-(3-(ethylsulfonyl)phenyl)-3-methyl-9H-pyrido[2,3-b]indol-8-yloxy)-3,3-difluoropropyl)amino)ethanol;
2-(ethyl(3-(5-(3-(ethylsulfonyl)phenyl)-3-methyl-9H-pyrido[2,3-b]indol-8-yloxy)-3,3-difluoropropyl)amino)ethyl dihydrogen phosphate;
2-((3-(3-chloro-5-(3-(ethylsulfonyl)phenyl)-9H-pyrido[2,3-b]indol-8-yloxy)-3,3-difluoropropyl)(ethyl)amino)ethanol;
2-((3-(3-chloro-5-(3-(ethylsulfonyl)phenyl)-9H-pyrido[2,3-b]indol-8-yloxy)-3,3-difluoropropyl)(ethyl)amino)ethyl dihydrogen phosphate;
2-((3-(5-(3-(cyclopropylsulfonyl)phenyl)-3-methyl-9H-pyrido[2,3-b]indol-8-yloxy)-3,3-difluoropropyl)(ethyl)amino)ethanol;
2-((3-(5-(3-(cyclopropylsulfonyl)phenyl)-3-methyl-9H-pyrido[2,3-b]indol-8-yloxy)-3,3-difluoropropyl)(ethyl)amino)ethyl dihydrogen phosphate;
2-((3-(3-chloro-5-(3-(cyclopropylsulfonyl)phenyl)-9H-pyrido[2,3-b]indol-8-yloxy)-3,3-difluoropropyl)(ethyl)amino)ethanol; and
2-((3-(3-chloro-5-(3-(cyclopropylsulfonyl)phenyl)-9H-pyrido[2,3-b]indol-8-yloxy)-3,3-difluoropropyl)(ethyl)amino)ethyl dihydrogen phosphate.

Particular examples of compounds according to the present invention also include, but are not limited to:
{3-[5-(3-Ethanesulfonyl-phenyl)-3-methyl-9H-dipyrido[2,3-b; 4',3'-d]pyrrol-8-yloxy]-propyl}-dimethyl-amine;
5-(3-Ethanesulfonyl-phenyl)-3-methyl-8-(1-methyl-piperidin-4-ylmethoxy)-9H-dipyrido[2,3-b; 4',3'-d]pyrrole;
3-Chloro-5-(3-ethanesulfonyl-phenyl)-8-(1-methyl-piperidin-4-ylmethoxy)-9H-dipyrido[2,3-b; 4',3'-d]pyrrole;
5-(3-(ethylsulfonyl)phenyl)-3-methyl-8-((1-methylpiperidin-4-yl)methoxy)-9H-pyrido[2,3-b]indole;
N-cyclopropyl-3-(3-methyl-8-((1-methylpiperidin-4-yl)methoxy)-9H-pyrido[2,3-b]indol-5-yl)benzamide;
5-(3-(cyclopropylsulfonyl)phenyl)-3-methyl-8-((1-methylpiperidin-4-yl)methoxy)-9H-pyrido[2,3-b]indole;
N-(3-(3-methyl-8-((1-methylpiperidin-4-yl)methoxy)-9H-pyrido[2,3-b]indol-5-yl)phenyl)cyclopropanecarboxamide;
5-(3-(ethylsulfonyl)phenyl)-3-methyl-8-(piperidin-4-ylmethoxy)-9H-pyrido[2,3-b]indole;
3-(5-(3-(cyclopropylsulfonyl)phenyl)-3-methyl-9H-pyrido[2,3-b]indol-8-yloxy)-N,N-dimethylpropan-1-amine;
N-(3-(8-(3-(dimethylamino)propoxy)-3-methyl-9H-pyrido[2,3-b]indol-5-yl)phenyl)cyclopropanecarboxamide;
3-chloro-5-(3-(ethylsulfonyl)phenyl)-8-((1-methylpiperidin-4-yl)methoxy)-9H-pyrido[2,3-b]indole;
3-chloro-5-(3-(ethylsulfonyl)phenyl)-8-(piperidin-4-ylmethoxy)-9H-pyrido[2,3-b]indole;
3-(5-(3-(ethylsulfonyl)phenyl)-3-methyl-9H-pyrido[2,3-b]indol-8-yloxy)-N,N-dimethylpropan-1-amine;
3-(3-chloro-5-(3-(ethylsulfonyl)phenyl)-9H-pyrido[2,3-b]indol-8-yloxy)-N,N-dimethylpropan-1-amine;
(R)-1-(dimethylamino)-3-(5-(3-(ethylsulfonyl)phenyl)-3-methyl-9H-pyrido[2,3-b]indol-8-yloxy)propan-2-ol;
2-((3-(5-(3-(cyclopropylsulfonyl)phenyl)-3-methyl-9H-pyrido[2,3-b]indol-8-yloxy)propyl)(ethyl)amino)ethanol;
di-tert-butyl-2-((3-(5-(3-(cyclopropylsulfonyl)phenyl)-3-methyl-9H-pyrido[2,3-b]indol-8-yloxy)propyl)(ethyl)amino)ethyl phosphate;
2-((3-(5-(3-(cyclopropylsulfonyl)phenyl)-3-methyl-9H-pyrido[2,3-b]indol-8-yloxy)propyl)(ethyl)amino)ethyl dihydrogen phosphate;
3-(3-chloro-8-((1-methylpiperidin-4-yl)methoxy)-9H-pyrido[2,3-b]indol-5-yl)-N-cyclopropylbenzamide;
3-chloro-5-(3-(cyclopropylsulfonyl)phenyl)-8-((1-methylpiperidin-4-yl)methoxy)-9H-pyrido[2,3-b]indole;
3-(8-(3-(dimethylamino)propoxy)-3-methyl-9H-pyrido[2,3-b]indol-5-yl)-N-ethylbenzenesulfonamide;
2-((3-(3-chloro-5-(3-(cyclopropylsulfonyl)phenyl)-9H-pyrido[2,3-b]indol-8-yloxy)propyl)(ethyl)amino)ethyl dihydrogen phosphate;
2-((3-(5-(3-(ethylsulfonyl)phenyl)-3-methyl-9H-pyrido[2,3-b]indol-8-yloxy)propyl)(methyl)amino)ethyl dihydrogen phosphate;
(S)-1-(5-(3-(cyclopropylsulfonyl)phenyl)-3-methyl-9H-pyrido[2,3-b]indol-8-yloxy)-3-(dimethylamino)propan-2-ol;
(S)-1-(5-(3-(cyclopropylsulfonyl)phenyl)-3-methyl-9H-pyrido[2,3-b]indol-8-yloxy)-3-(dimethylamino)propan-2-yl dihydrogen phosphate; and
(R)-1-(5-(3-(cyclopropylsulfonyl)phenyl)-3-methyl-9H-pyrido[2,3-b]indol-8-yloxy)-3-(dimethylamino)propan-2-yl dihydrogen phosphate.

In addition, particular examples of compounds according to the present invention include, but are not limited to:
3-chloro-5-(3-(ethylsulfonyl)phenyl)-8-methoxy-9H-pyrido[2,3-b]indole; and
3-chloro-5-(3-(ethylsulfonyl)phenyl)-9H-pyrido[2,3-b]indol-8-ol.

Further particular examples of compounds according to the present invention include, but are not limited to:
5-bromo-9H-pyrido[2,3-b]indole;

5-phenyl-9H-pyrido[2,3-b]indole;
5-bromo-8-methyl-9H-pyrido[2,3-b]indole;
5-bromo-3,8-dimethyl-9H-pyrido[2,3-b]indole;
5-(3-(methylsulfonyl)phenyl)-9H-pyrido[2,3-b]indole;
5-(3-(ethylsulfonyl)phenyl)-9H-pyrido[2,3-b]indole;
N-(3-(9H-pyrido[2,3-b]indol-5-yl)phenyl)ethanesulfonamide;
5-m-tolyl-9H-pyrido[2,3-b]indole;
N-cyclopropyl-3-(9H-pyrido[2,3-b]indol-5-yl)benzenesulfonamide;
5-(3-methoxyphenyl)-9H-pyrido[2,3-b]indole;
5-(3,8-dimethyl-9H-pyrido[2,3-b]indol-5-yl)-2-methoxy-N-methylbenzenesulfonamide;
3-(3,8-dimethyl-9H-pyrido[2,3-b]indol-5-yl)-N-methylbenzenesulfonamide;
3-(3,8-dimethyl-9H-pyrido[2,3-b]indol-5-yl)-N,N-dimethylbenzenesulfonamide;
5-(3-(ethylsulfonyl)phenyl)-8-methyl-9H-pyrido[2,3-b]indole;
5-(3-(ethylsulfonyl)phenyl)-3,8-dimethyl-9H-pyrido[2,3-b]indole;
N-(3-(3,8-dimethyl-9H-pyrido[2,3-b]indol-5-yl)phenyl)propionamide;
N-cyclopropyl-3-(3,8-dimethyl-9H-pyrido[2,3-b]indol-5-yl)benzamide;
N-(4-(9H-pyrido[2,3-b]indol-5-ylthio)phenyl)acetamide;
5-(benzylthio)-9H-pyrido[2,3-b]indole;
5-(phenylthio)-9H-pyrido[2,3-b]indole;
5-(benzylthio)-8-methyl-9H-pyrido[2,3-b]indole;
5-(benzylthio)-3,8-dimethyl-9H-pyrido[2,3-b]indole;
8-Chloro-5-(3-ethanesulfonyl-phenyl)-3-methyl-9H-dipyrido[2,3-b; 4',3'-d]pyrrole;
8-chloro-5-[3-(ethylsulfonyl)phenyl]-3-methyl-9H-pyrido[4',3':4,5]pyrrolo[2,3-b]pyridine;
N'-[5-(3-Ethanesulfonyl-phenyl)-3-methyl-9H-dipyrido[2,3-b; 4',3'-d]pyrrol-8-yl]-N,N-dimethyl-propane-1,3-diamine;
N'-[5-(3-Ethanesulfonyl-phenyl)-3-methyl-9H-dipyrido[2,3-b; 4',3'-d]pyrrol-8-yl]-N,N-dimethyl-ethane-1,2-diamine;
[5-(3-Ethanesulfonyl-phenyl)-3-methyl-9H-dipyrido[2,3-b; 4',3'-d]pyrrol-8-yl]-(3-morpholin-4-yl-propyl)-amine;
[5-(3-Ethanesulfonyl-phenyl)-3-methyl-9H-dipyrido[2,3-b; 4',3'-d]pyrrol-8-yl]-(1-methyl-piperidin-4-yl)-amine;
2-[5-(3-Ethanesulfonyl-phenyl)-3-methyl-9H-dipyrido[2,3-b; 4',3'-d]pyrrol-8-ylamino]-ethanol;
[5-(3-Ethanesulfonyl-phenyl)-3-methyl-9H-dipyrido[2,3-b; 4',3'-d]pyrrol-8-yl]-(1-methyl-piperidin-4-ylmethyl)-amine;
5-(3-Ethanesulfonyl-phenyl)-3,8-dimethyl-9H-dipyrido[2,3-b; 4',3'-d]pyrrole;
5-(3-Ethanesulfonyl-phenyl)-8-ethyl-3-methyl-9H-dipyrido[2,3-b; 4',3'-d]pyrrole;
5-(3-Ethanesulfonyl-phenyl)-3-methyl-9H-dipyrido[2,3-b; 4',3'-d]pyrrole-8-carbonitrile;
5-(3-Ethanesulfonyl-phenyl)-3-methyl-9H-dipyrido[2,3-b; 4',3'-d]pyrrole-8-carboxylic acid amide;
5-(3-Ethanesulfonyl-phenyl)-8-ethoxy-3-methyl-9H-dipyrido[2,3-b; 4',3'-d]pyrrole;
2-[5-(3-Ethanesulfonyl-phenyl)-3-methyl-9H-dipyrido[2,3-b; 4',3'-d]pyrrol-8-yloxy]-ethanol;
3-[5-(3-Ethanesulfonyl-phenyl)-3-methyl-9H-dipyrido[2,3-b; 4',3'-d]pyrrol-8-yloxy]-propan-1-ol;
(R)-2-[5-(3-Ethanesulfonyl-phenyl)-3-methyl-9H-dipyrido[2,3-b; 4',3'-d]pyrrol-8-yloxymethyl]-propane-1,3-diol;
(S)-2-[5-(3-Ethanesulfonyl-phenyl)-3-methyl-9H-dipyrido[2,3-b; 4',3'-d]pyrrol-8-yloxymethyl]-propane-1,3-diol;
1-[5-(3-Ethanesulfonyl-phenyl)-3-methyl-9H-dipyrido[2,3-b; 4',3'-d]pyrrol-8-yloxy]-2-methyl-propan-2-ol;
5-(3-Ethanesulfonyl-phenyl)-3-methyl-8-phenoxy-9H-dipyrido[2,3-b; 4',3'-d]pyrrole;
5-(3-Ethanesulfonyl-phenyl)-3-methyl-8-(thiazol-5-ylmethoxy)-9H-dipyrido[2,3-b; 4',3'-d]pyrrole;
(S)-1-[5-(3-Ethanesulfonyl-phenyl)-3-methyl-9H-dipyrido[2,3-b; 4',3'-d]pyrrol-8-yloxy]-propan-2-ol;
(R)-1-[5-(3-Ethanesulfonyl-phenyl)-3-methyl-9H-dipyrido[2,3-b; 4',3'-d]pyrrol-8-yloxy]-propan-2-ol;
3-(3-Bromo-5-chloro-pyridin-2-ylamino)-5-chloro-1-(4-methoxy-benzyl)-1H-pyrazin-2-one;
5-Chloro-3-(5-chloro-3-trimethylsilanylethynyl-pyridin-2-ylamino)-1-(4-methoxy-benzyl)-1H-pyrazin-2-one;
3,8-Dichloro-5-(3-ethanesulfonyl-phenyl)-9H-dipyrido[2,3-b; 4',3'-d]pyrrole;
(R)-1-[3-Chloro-5-(3-ethanesulfonyl-phenyl)-9H-dipyrido[2,3-b; 4',3'-d]pyrrol-8-yloxy]-propan-2-ol;
2-[5-(3-Ethanesulfonyl-phenyl)-3-methyl-9H-dipyrido[2,3-b; 4',3'-d]pyrrol-8-yl]methyl amine;
2-[5-(3-Ethanesulfonyl-phenyl)-3-methyl-9H-dipyrido[2,3-b; 4',3'-d]pyrrol-8-yl]methanethiol;
2-[5-(3-Ethanesulfonyl-phenyl)-3-methyl-9H-dipyrido[2,3-b; 4',3'-d]pyrrol-8-yl]ethanethiol;
5-[3-(cyclopropylcarboxamide)phenyl]-7-(4-methoxybenzyl)-3-methyl-7,9-dihydro-8H-pyrido[4',3':4,5]pyrrolo[2,3-b]pyridin-8-one;
8-Chloro-5-[3-(cyclopropylcarboxamide)phenyl]-3-methyl-9H-dipyrido[2,3-b; 4',3'-d]pyrrole;
2-[5-(3-cyclopropylcarbonylamino-phenyl)-3-methyl-9H-dipyrido[2,3-b; 4',3'-d]pyrrol-8-yl]ethanethiol;
9-(3-Ethanesulfonyl-phenyl)-5H-pyrazino[2,3-b]indole;
5-(3-(ethylsulfonyl)phenyl)-3,8-dimethyl-7-(trifluoromethyl)-9H-pyrido[2,3-b]indole acetate;
5-(3-(ethylsulfonyl)phenyl)-3,8-dimethyl-9H-pyrido[2,3-b]indole-7-carboxylic acid;
5-(3-(cyclopropanecarboxamido)phenyl)-N-(2-(dimethylamino)ethyl)-3,8-dimethyl-9H-pyrido[2,3-b]indole-7-carboxamide;
5-chloro-3,8-dimethyl-N-(1-methylpiperidin-4-yl)-9H-pyrido[2,3-b]indole-7-carboxamide;
5-(3-(cyclopropanecarboxamido)phenyl)-3,8-dimethyl-N-(1-methyl-piperidin-4-yl)-9H-pyrido[2,3-b]indole-7-carboxamide;
5-chloro-N-(2-(dimethylamino)ethyl)-3,8-dimethyl-9H-pyrido[2,3-b]indole-7-carboxamide;
5-(3-(cyclopropylcarbamoyl)phenyl)-N-(2-(dimethylamino)ethyl)-3,8-dimethyl-9H-pyrido[2,3-b]indole-7-carboxamide;
5-(3-Ethanesulfonyl-phenyl)-3-methyl-9H-pyrido[2,3-b]indole-7-carbonitrile;
5-(3-Ethanesulfonyl-phenyl)-3-methyl-9H-pyrido[2,3-b]indole-7-carboxylic acid methyl ester;
[5-(3-Ethanesulfonyl-phenyl)-3-methyl-9H-pyrido[2,3-b]indol-7-yl]-methanol;
[5-(3-Ethanesulfonyl-phenyl)-3-methyl-9H-pyrido[2,3-b]indol-7-ylmethyl]-dimethyl-amine;
5-(3-Ethanesulfonyl-phenyl)-3-methyl-7-morpholin-4-ylmethyl-9H-pyrido[2,3-b]indole;
5-(3-Ethanesulfonyl-phenyl)-3-methyl-7-(4-methyl-piperazin-1-ylmethyl)-9H-pyrido[2,3-b]indole;
5-(3-Ethanesulfonyl-phenyl)-3-methyl-7-pyrrolidin-1-ylmethyl-9H-pyrido[2,3-b]indole;
[5-(3-Ethanesulfonyl-phenyl)-3-methyl-9H-pyrido[2,3-b]indol-7-ylmethyl]-ethyl-amine;
5-(3-Ethanesulfonyl-phenyl)-3-methyl-9H-pyrido[2,3-b]indole-7-carboxylic acid;

5-(3-Ethanesulfonyl-phenyl)-3-methyl-7-(2H-tetrazol-5-yl)-9H-pyrido[2,3-b]indole;

6-Bromo-5-(3-ethanesulfonyl-phenyl)-3-methyl-9H-pyrido[2,3-b]indole-7-carboxylic acid methyl ester;

8-Bromo-5-(3-ethanesulfonyl-phenyl)-3-methyl-9H-pyrido[2,3-b]indole-7-carboxylic acid methyl ester;

6-Chloro-5-(3-ethanesulfonyl-phenyl)-3-methyl-9H-pyrido[2,3-b]indole-7-carboxylic acid methyl ester;

8-Chloro-5-(3-ethanesulfonyl-phenyl)-3-methyl-9H-pyrido[2,3-b]indole-7-carboxylic acid methyl ester;

5-(benzylthio)-3-methyl-9H-pyrido[2,3-b]indole-7-carboxylic acid;

5-(benzylthio)-N-(2-(dimethylamino)ethyl)-3-methyl-9H-pyrido[2,3-b]indole-7-carboxamide;

5-(3-(ethylsulfonyl)phenyl-8-methoxy-3-methyl-9H-pyrido[2,3-b]indole;

5-(3-(ethylsulfonyl)phenyl)-3-methyl-9H-pyrido[2,3-b]indol-8-ol;

8-methoxy-3-methyl-5-(3-(pyrrolidin-1-ylsulfonyl)phenyl)-9H-pyrido[2,3-b]indole;

(R)-8-methoxy-3-methyl-5-(3-(pyrrolidin-3-ylsulfonyl)phenyl)-9H-pyrido[2,3-b]indole;

N-cyclopropyl-4-(8-methoxy-3-methyl-9H-pyrido[2,3-b]indol-5-yl)picolinamide;

N-(3-(8-methoxy-3-methyl-9H-pyrido[2,3-b]indol-5-yl)phenyl)acetamide;

N-(3-(8-methoxy-3-methyl-9H-pyrido[2,3-b]indol-5-yl)phenyl)cyclopropanecarboxamide;

N-cyclopropyl-3-(8-methoxy-3-methyl-9H-pyrido[2,3-b]indol-5-yl)benzamide;

N,N-diethyl-3-(8-methoxy-3-methyl-9H-pyrido[2,3-b]indol-5-yl)benzamide;

5-(benzo[d][1,3]dioxol-5-yl)-8-methoxy-3-methyl-9H-pyrido[2,3-b]indole;

6-(8-methoxy-3-methyl-9H-pyrido[2,3-b]indol-5-yl)-4H-chromen-4-one;

N-(2-hydroxyethyl)-3-(8-methoxy-3-methyl-9H-pyrido[2,3-b]indol-5-yl)benzamide;

(3-(8-methoxy-3-methyl-9H-pyrido[2,3-b]indol-5-yl)phenyl)(pyrrolidin-1-yl)methanone;

N-ethyl-3-(8-methoxy-3-methyl-9H-pyrido[2,3-b]indol-5-yl)benzenesulfonamide;

8-ethoxy-5-(3-(ethylsulfonyl)phenyl)-3-methyl-9H-pyrido[2,3-b]indole;

8-(difluoromethoxy)-5-(3-(ethylsulfonyl)phenyl)-3-methyl-9H-pyrido[2,3-b]indole;

5-(3-(ethylsulfonyl)phenyl)-3-methyl-8-(2,2,2-trifluoroethoxy)-9H-pyrido[2,3-b]indole;

5-(3-(ethylsulfonyl)phenyl)-8-(2-methoxyethoxy)-3-methyl-9H-pyrido[2,3-b]indole;

2-(5-(3-(ethylsulfonyl)phenyl)-3-methyl-9H-pyrido[2,3-b]indol-8-yloxy)acetonitrile;

3-(5-(3-(ethylsulfonyl)phenyl)-3-methyl-9H-pyrido[2,3-b]indol-8-yloxy)propanenitrile;

(R)-8-(1-tert-butyldiphenylsilyloxy)propan-2-yloxy)-(5-(3-(ethylsulfonyl)phenyl)-3-methyl-9H-pyrido[2,3-b]indole;

(R)-2-(5-(3-(ethylsulfonyl)phenyl)-3-methyl-9H-pyrido[2,3-b]indol-8-yloxy)propan-1-ol;

(S)-2-(5-(3-(ethylsulfonyl)phenyl)-3-methyl-9H-pyrido[2,3-b]indol-8-yloxy)propan-1-ol;

1-(5-(3-(ethylsulfonyl)phenyl)-3-methyl-9H-pyrido[2,3-b]indol-8-yloxy)propan-2-ol;

(S)-4-(5-(3-(ethylsulfonyl)phenyl)-3-methyl-9H-pyrido[2,3-b]indol-8-yloxy)-2-methylpentan-2-ol;

2-(5-(3-(ethylsulfonyl)phenyl)-3-methyl-9H-pyrido[2,3-b]indol-8-yloxy)ethanol;

3-(5-(3-(ethylsulfonyl)phenyl)-3-methyl-9H-pyrido[2,3-b]indol-8-yloxy)propan-1-ol;

3-(3-chloro-5-(3-(ethylsulfonyl)phenyl)-8-methoxy-9H-pyrido[2,3-b]indol-8-ol;

(3-chloro-5-(3-(ethylsulfonyl)phenyl)-9H-pyrido[2,3-b]indol-8-ol;

2-(3-chloro-5-(3-(ethylsulfonyl)phenyl)-9H-pyrido[2,3-b]indol-8-yloxy)ethanol;

5-(3-(cyclopropylcarbamoyl)phenyl)-3,8-dimethyl-N-(1-methylpiperidin-4-yl)-9H-pyrido[2,3-b]indole-7-carboxamide;

(R)-8-((2,2-dimethyl-1,3-dioxolan-4-yl)methoxy-5-(3-ethylsulfonyl)phenyl)-3-methyl-9H-pyrido[2,3-b]indole;

(S)-3-(5-(3-(ethylsulfonyl)phenyl)-3-methyl-9H-pyrido[2,3-b]indol-8-yloxy)propane-1,2-diol;

(R)-3-(5-(3-(ethylsulfonyl)phenyl)-3-methyl-9H-pyrido[2,3-b]indol-8-yloxy)propane-1,2-diol;

(R)-1-(5-(3-(ethylsulfonyl)phenyl)-3-methyl-9H-pyrido[2,3-b]indol-8-yloxy)propan-2-ol;

(S)-1-(5-(3-(ethylsulfonyl)phenyl)-3-methyl-9H-pyrido[2,3-b]indol-8-yloxy)propan-2-ol;

(5-(3-(ethylsulfonyl)phenyl)-8-methoxy-3-methyl-9H-pyrido[2,3-b]indol-7-amine;

3-(dimethylamino)-N-(5-(3-(ethylsulfonyl)phenyl)-8-methoxy-3-methyl-9H-pyrido[2,3-b]indol-7-yl)propanamide;

N-(3-(7-amino-8-methoxy-3-methyl-9H-pyrido[2,3-b]indol-5-yl)phenyl)-cyclopropanecarboxamide;

N-(5-(3-(ethylsulfonyl)phenyl)-8-methoxy-3-methyl-9H-pyrido[2,3-b]indol-7-yl)-cyclopropanecarboxamide;

1-acetyl-N-(5-(3-(ethylsulfonyl)phenyl)-8-methoxy-3-methyl-9H-pyrido[2,3-b]indol-7-yl)piperidine-4-carboxamide;

3-(7-amino-8-methoxy-3-methyl-9H-pyrido[2,3-b]indol-5-yl)-N-cyclopropylbenzamide;

3-(7-(cyclopropanecarboxamido)-8-methoxy-3-methyl-9H-pyrido[2,3-b]indol-5-yl)-N-cyclopropylbenzamide;

7-chloro-5-(3-(ethylsulfonyl)phenyl)-8-methoxy-3-methyl-9H-pyrido[2,3-b]indol;

7-chloro-5-(3-(ethylsulfonyl)phenyl)-3-methyl-9H-pyrido[2,3-b]indol-8-ol;

3-(7-chloro-5-(3-(ethylsulfonyl)phenyl)-3-methyl-9H-pyrido[2,3-b]indol-8-yloxy)propan-1-ol;

tert-butyl 7-(tert-butoxycarbonyl(methyl)amino)-5-(3-(ethylsulfonyl)phenyl)-8-methoxy-3-methyl-9H-pyrido[2,3-b]indole-9-carboxylate;

5-(3-(ethylsulfonyl)phenyl)-8-methoxy-N,3-dimethyl-9H-pyrido[2,3-b]indol-7-amine;

N-(5-(3-(ethylsulfonyl)phenyl)-8-methoxy-3-methyl-9H-pyrido[2,3-b]indol-7-yl)-N-methylcyclopropanecarboxamide;

3-(dimethylamino)-N-(5-(3-(ethylsulfonyl)phenyl)-8-methoxy-3-methyl-9H-pyrido[2,3-b]indol-7-yl)-N-methylpropanamide;

3-(3-chloro-5-(3-(ethylsulfonyl)phenyl)-9H-pyrido[2,3-b]indol-8-yloxy)propanenitrile;

(3-(8-methoxy-3-methyl-9H-pyrido[2,3-b]indol-5-yl)phenyl)(morpholino)methanone;

N-methoxy-3-(8-methoxy-3-methyl-9H-pyrido[2,3-b]indol-5-yl)benzamide;

5-(3-Ethanesulfonyl-phenyl)-8-(cyclopropylmethoxy)-3-methyl-9H-dipyrido[2,3-b; 4',3'-d]pyrrole;

8-(3-(benzyloxy)propoxy)-3-chloro-5-(3-(ethylsulfonyl)phenyl)-9H-pyrido[2,3-b]indole;

3-(3-chloro-5-(3-(ethylsulfonyl)phenyl)-9H-pyrido[2,3-b]indol-8-yloxy)propan-1-ol;

3-chloro-5-(3-(ethylsulfonyl)phenyl)-8-(3-iodopropoxy)-9H-pyrido[2,3-b]indole;

8-(3-(1H-imidazol-1-yl)propoxy)-3-chloro-5-(3-(ethylsulfonyl)phenyl)-9H-pyrido[2,3-b]indole; and 5-(3-(cyclopropylcarbamoyl)phenyl)-3,8-dimethyl-N-(1-methylpiperidin-4-yl)-9H-pyrido[2,3-b]indole-7-carboxamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as a hydrogen.

In one particular variation, the compound is in the form of a salt selected from the group consisting of a hydrochloric acid salt, a trifluoroacetic acid salt, a toluenesulfonic acid salt, a benzenesulfonic acid salt, a methanesulfonic acid salt, a succinic acid salt, a tartaric acid salt, a citric acid salt, a fumaric acid salt, a sulfuric acid salt, a phosphoric acid salt, a benzoic acid salt, a bis-hydrogen chloride salt, a bis-trifluoroacetic acid salt, a tosylate salt, a hemi-fumarate salt, a lactic acid salt, a malic acid salt, a hippuric acid salt and a hydrobromic acid salt.

In another particular variation, the compound is in the form of a salt selected from the group consisting of a hydrochloric acid salt, a toluenesulfonic acid salt, a hemi-fumarate salt, and a hippuric acid salt. In still another particular variation, the compound is in the form of a hydrochloric acid salt. In one particular variation, the hydrochloric acid salt is formed in acetonitrile. In yet another particular variation, the compound is in the form of a hemi-fumarate salt. In one particular variation, the hemi-fumarate salt is formed in methanol.

It is further noted that the compounds of the present invention may optionally be solely or predominantly in the enol tautomer in its active state. It is further noted that the compound may be present in a mixture of stereoisomers, or the compound may comprise a single stereoisomer.

The invention also provides pharmaceutical compositions comprising, as an active ingredient, a compound according to any one of the above embodiments and variations. In addition, the composition may be a solid or liquid formulation adapted for oral administration. In a further variation, the pharmaceutical composition may be a tablet. In yet another variation, the pharmaceutical composition may be a liquid formulation adapted for parenteral administration.

In one embodiment, there is provided the pharmaceutical composition comprising a compound according to any one of the above embodiments and variations wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another embodiment, there is provided the pharmaceutical composition comprising:
a compound having the formula

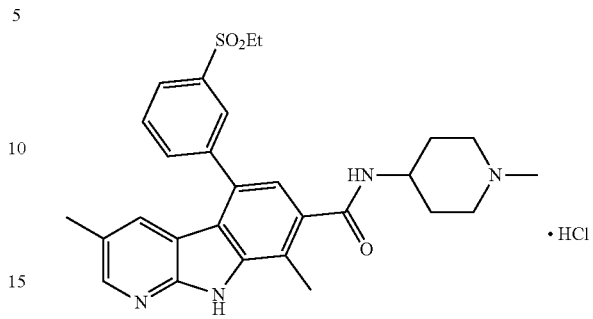

wherein at least a portion of the compound is present as Amorphous Form, characterized by physical properties which comprise one or more of the following:
(a) may be formed by lyophilizing a solution of Compound 88 in ACN and water;
(b) has an XRPD spectrum characterized by a diffuse halo with no discernable peaks; and/or
(c) shows 7.6 wt % Cl⁻ present using ion chromatography.

In still another embodiment, there is provided the pharmaceutical composition comprising:
a compound having the formula

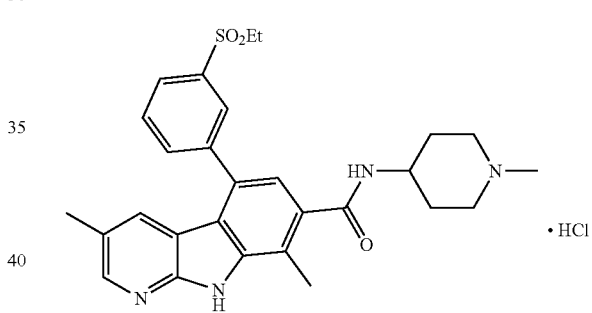

wherein at least a portion of the compound is present as Amorphous Form characterized by physical properties which comprise one or more of the following:
(a) may be formed by lyophilizing a solution of Compound 88 in ACN and water;
(b) has an XRPD spectrum characterized by a diffuse halo with no discernable peaks; and/or
(c) shows 7.6 wt % Cl⁻ present using ion chromatography; and
one or more pharmaceutical carriers.

In one variation of the above embodiments, between 0.1% and 100% of the compound (by weight) is present in the composition as Amorphous Form. In a further variation of the above embodiments, between 0.1% and 99% of the compound (by weight) is present in the composition as Amorphous Form. In still another variation of the above embodiments, greater than 0.1% of the compound (by weight) is present in the composition as Amorphous Form. In yet another variation of the above embodiments, greater than 1% of the compound (by weight) is present in the composition as Amorphous Form. In another variation of the above embodiments, greater than 5% of the compound (by weight) is present in the composition as Amorphous Form. In still another variation of the above embodiments, greater than 10% of the compound (by weight) is present in the composition as Amorphous Form. In yet another variation of the above embodiments, greater than 50% of the compound (by weight) is present in the composition as Amorphous Form. In a further variation of the above embodiments, greater than 75% of the compound (by weight) is present in the composition as Amorphous Form. In still a further variation of the above embodiments, greater than 90% of C the compound (by weight) is present in the composition as Amorphous Form. In yet a further variation of the above embodiments, greater than 99% of the compound (by weight) is present in the composition as Amorphous Form. In another variation of the above embodiments, greater than 99% of the compound (by weight) is present in the composition as Amorphous Form.

In a further variation of the above embodiments and variations, the composition is a pill or capsule adapted for oral administration. In still a further variation of the above embodiments and variations, the composition is in an oral dosage form selected from the group consisting of pills, tablets, capsules, emulsions, suspensions, microsuspensions, wafers, sprinkles, chewing gum, powders, lyophilized powders, granules, and troches. In yet a further variation of the above embodiments and variations, the composition is in a parenteral dosage form selected from the group consisting of suspensions, microsuspensions, emulsions, solid forms suitable for suspension or emulsification prior to injection, and implantable devices. In another variation of the above embodiments and variations, the composition is adapted for topical or transdermal administration. In still another variation of the above embodiments and variations, the composition is in a topical or transdermal dosage form selected from the group consisting of suspensions, microsuspensions, emulsions, creams, gels, ointments, lotions, tinctures, pastes, powders, foams, aerosols, irrigations, sprays, suppositories, bandages, and dermal patches. In still another variation of the above embodiments and variations, the composition is in a pulmonary dosage form selected from the group consisting of powders, aerosols, suspensions, microsuspensions, and emulsions.

In yet another variation of the above embodiments and variations, the polymorphic form of the compound is at least partially preserved for a period of time following administration.

The invention also provides a kit comprising a compound or composition according to any one of the above embodiments and variations, and instructions which comprise one or more forms of information selected from the group consisting of indicating a disease state for which the compound is to be administered, storage information for the compound, dosing information and instructions regarding how to administer the compound. In one variation, the kit comprises the compound or composition in a multiple dose form.

In another embodiment, the present invention provides an article of manufacture comprising a compound or composition according to any one of the above embodiments and variations, and packaging materials. In one variation, the packaging material comprises a container for housing the compound or composition. The container optionally comprises a label indicating a disease state for which the compound or composition is to be administered, storage information, dosing information and/or instructions regarding how to administer the compound or composition. In regard to the above embodiments and variations, the article of manufacture optionally comprises the compound or composition in a multiple dose form.

In another embodiment, the present invention provides a therapeutic method comprising administering a compound or composition according to any one of the above embodiments and variations to a subject.

In yet another embodiment, the present invention provides a method of inhibiting a kinase comprising contacting a kinase with a compound or composition according to any one of the above embodiments and variations.

In still another embodiment, there is provided a method of inhibiting kinase comprising causing a compound or composition according to any one of the above embodiments and variations to be present in a subject in order to inhibit kinase in vivo.

In yet another of its aspects, there is provided a method of treating a disease state for which a kinase possesses activity that contributes to the pathology and/or symptomology of the disease state, the method comprising administering a compound of any one of the above embodiments and variations to a subject, wherein the compound is present in the subject in a therapeutically effective amount for the disease state.

The present invention also provides a method of inhibiting a kinase comprising administering a first compound to a subject that is converted in vivo to a second compound wherein the second compound inhibits kinase in vivo, the second compound being a compound according to any one of the above embodiments and variations.

In yet another embodiment, there is provided a method of preventing or treating a disease state for which a kinase possesses activity that contributes to the pathology and/or symptomology of the disease state comprising causing a compound or composition according to any one of the above embodiments and variations to be present in a subject in a therapeutically effective amount for the disease state.

The present invention also provides a method of preventing or treating a disease state for which a kinase possesses activity that contributes to the pathology and/or symptomology of the disease state comprising administering a first compound to a subject that is converted in vivo to a second compound according to any one of the above embodiments and variations wherein the second compound is present in a subject in a therapeutically effective amount for the disease state.

In addition, there is provided a method of preventing or treating a disease state for which a kinase possesses activity that contributes to the pathology and/or symptomology of the disease state comprising administering a compound or composition according to any one of the above embodiments and variations, wherein the compound or composition is present in the subject in a therapeutically effective amount for the disease state.

In each of the above embodiments and variations, the kinase is optionally an Aurora kinase. In particular variations of each of the above embodiments and variations, the kinase is an Aurora-B kinase.

In another embodiment, there is provided a method for treating cancer comprising administering a therapeutically effective amount of a compound or composition of the present invention to a mammalian species in need thereof. In one embodiment, the cancer is selected from the group consisting of squamous cell carcinoma, astrocytoma, Kaposi's sarcoma, glioblastoma, non small-cell lung cancer, bladder cancer, head and neck cancer, melanoma, ovarian cancer, prostate cancer, breast cancer, small-cell lung cancer, glioma, colorectal cancer, genitourinary cancer, gastrointestinal cancer, thyroid cancer, skin cancer, kidney cancer, rectal cancer, colonic cancer, cervical cancer, mesothelioma, pancreatic cancer, liver cancer, uterus cancer, cerebral tumor cancer, urinary bladder cancer and blood cancers including multiple myeloma. In particular embodiments, the compound or method is useful for inhibiting growth of cancer, for suppressing metastasis of cancer, for suppressing apoptosis and the like.

In another embodiment, there is provided a method for treating inflammation, inflammatory bowel disease, psoriasis, or transplant rejection, comprising administration to a mammalian species in need thereof of a therapeutically effective amount of a compound or composition according to the present invention.

In another embodiment, there is provided a method for preventing or treating amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication, comprising administration to a mammalian species in need thereof of a therapeutically effective amount of a compound or composition according to any one of the above embodiments.

In yet another embodiment, there is provided a method for preventing or treating mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment and androgenetic alopecia, comprising administering to a mammal, including man in need of such prevention and/or treatment, a therapeutically effective amount of a compound or composition according to any one of the above embodiments.

In a further embodiment, there is provided a method for preventing or treating dementia related diseases, Alzheimer's Disease and conditions associated with kinases, comprising administration to a mammalian species in need thereof of a therapeutically effective amount of a compound or composition according to any one of the above embodiments. In one particular variation, the dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica.

In another embodiment, there is provided a method for treating arthritis comprising administration to a mammalian species in need thereof of a therapeutically effective amount of a compound or composition according to any one of the above embodiment.

In still another embodiment, there is provided a compound according to any one of the above embodiments and variations for use as a medicament.

In yet another embodiment, there is provided a compound according to any one of the above embodiments and variations for use in the manufacture of a medicament for inhibiting a kinase.

In a further embodiment, there is provided a compound according to any one of the above embodiments and variations for use in the manufacture of a medicament for treating a disease state for which a kinase possesses activity that contributes to the pathology and/or symptomology of the disease state.

In still a further embodiment, there is provided a compound according to any one of the above embodiments and variations for use in the manufacture of a medicament for treating cancer, inflammation, inflammatory bowel disease, psoriasis, transplant rejection, amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss, contraception, mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment, cognitive impairment, androgenetic alopecia, dementia related diseases, and Alzheimer's Disease.

Salts, Hydrates, and Prodrugs of Kinase Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, Protecting *Groups in Organic Synthesis*, 3$^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Composition Comprising Kinase Inhibitors

A wide variety of compositions and administration methods may be used in conjunction with the kinase inhibitors of the present invention. Such compositions may include, in addition to the kinase inhibitors of the present invention, conventional pharmaceutical excipients, and other conventional, pharmaceutically inactive agents. Additionally, the compositions may include active agents in addition to the kinase inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising kinase inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The kinase inhibitors and compositions comprising them may be administered or coadministered in any conventional dosage form. Co-administration in the context of this invention is intended to mean the administration of more than one therapeutic agent, one of which includes a kinase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When kinase inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding kinase inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more kinase inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a kinase inhibitor of the present invention to reduce kinases activity in vivo, thereby treating the disease state of the subject.

Dosage forms or compositions may optionally comprise one or more kinase inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more kinase inhibitors, optionally 0.1-95%, and optionally 1-95%.

In one variation, the composition comprises at least 0.1%, 0.25%, 0.5%, 1%, 5%, 10%, 25%, 50%, 75%, 80%, 85%, 90%, 95%, 97%, or 99% (by weight) of one or more kinase inhibitors according to the present invention. In particular variations, greater than 0.1%, 1%, 5%, 10%, 25%, 50%, 75%, 80%, 85%, 90%, 95%, 97% or 99% (by weight) of one or more kinase inhibitors according to the present invention is present in the composition as a single crystalline or amorphous form. The composition may optionally be a pharmaceutical composition. The pharmaceutical composition may optionally further include one or more pharmaceutical carriers.

Salts, preferably sodium salts, of the kinase inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, kinase inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The kinase inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising kinase inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the kinase inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a kinase inhibitor in the parenteral formulation may be adjusted so that an injection administers a pharmaceutically effective amount sufficient to produce the desired pharmacological effect. The exact concentration of a kinase inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the kinase inhibitor to the treated tissue(s). The kinase inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The kinase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The kinase inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a kinase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the kinase inhibitor.

Topical Administration

The kinase inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The kinase inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The kinase inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the kinase inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of the Present Invention | 1% |
| Microcrystalline Cellulose | 73% |
| Stearic Acid | 25% |
| Colloidal Silica | 1%. |

Kits Comprising Kinase Inhibitors

The invention is also directed to kits and other articles of manufacture for treating diseases associated with kinases. It is noted that diseases are intended to cover all conditions for which the kinases possesses activity that contributes to the pathology and/or symptomology of the condition.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

The invention also provided are kits and other articles of manufacture comprising a composition that comprises one or more compounds of the present invention, wherein the one or more compounds of the present invention are present as a single crystalline or amorphous form. In one variation, the composition comprises at least 0.1%, 0.25%, 0.5%, 1%, 5%, 10%, 25%, 50%, 75%, 80%, 85%, 90%, 95%, 97%, or 99% of the one or more compounds of the present invention where greater than 0.1%, 1%, 5%, 10%, 25%, 50%, 75%, 80%, 85%, 90%, 95%, 97% or 99% of the one or more compounds of the present invention (by weight) is present in the composition as a single crystalline or amorphous form. The composition in the kits and articles of manufacture may optionally be a pharmaceutical composition. The pharmaceutical composition may optionally further include one or more pharmaceutical carriers. In regard to each of the above embodiments including a pharmaceutical composition, the pharmaceutical composition may optionally be formulated such that a portion of the one or more compounds of the present invention is present as a single crystalline or amorphous form for a period of time subsequent to administration of the pharmaceutical formulation to a human.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as kinase inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, about 10 to 200 mg, about 100 to 500 mg, about 150 to 450 mg, about 200 to 400 mg, or about 200 to 300 mg. It will be appreciated that the daily dose can be given in a single administration or in multiple (e.g., 2 or 3) portions a day.

Combination Therapies

A wide variety therapeutic agents may have a therapeutic additive or synergistic effect with kinase inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. For example, such therapeutic agents may additively or synergistically combine with the kinase inhibitors to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with kinase inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a kinase inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a kinase inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a kinase inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a kinase inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a kinase inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a kinase inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with kinase inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a kinase inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a kinase inhibitor to reduce chemotherapy-induced myelopoietic toxicity.

Other immuno-modulating agents other than cytokines may also be used in conjunction with a kinase inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including kinase inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma. Combination therapy including kinase inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a kinase inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2

(IL-2), granulocyte-macrophage colony-stimulating factor (GM-CSF) and cytoxan, a chemotherapeutic agent which is believe to reduce tumor-induced suppression when given in low doses.

EXAMPLES

1. Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, 3$^{rd}$ edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
Et$_2$O (diethyl ether); EDCI (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
Et (ethyl); tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid.

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosure of all documents cited throughout this application are incorporated herein by reference.

2. Synthetic Schemes for Kinase Inhibitors of the Present Invention

Kinase inhibitors according to the present invention may be synthesized according to the reaction scheme shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Experimental Methods

General synthetic routes for producing compounds of the present invention are shown in Schemes 1-8.

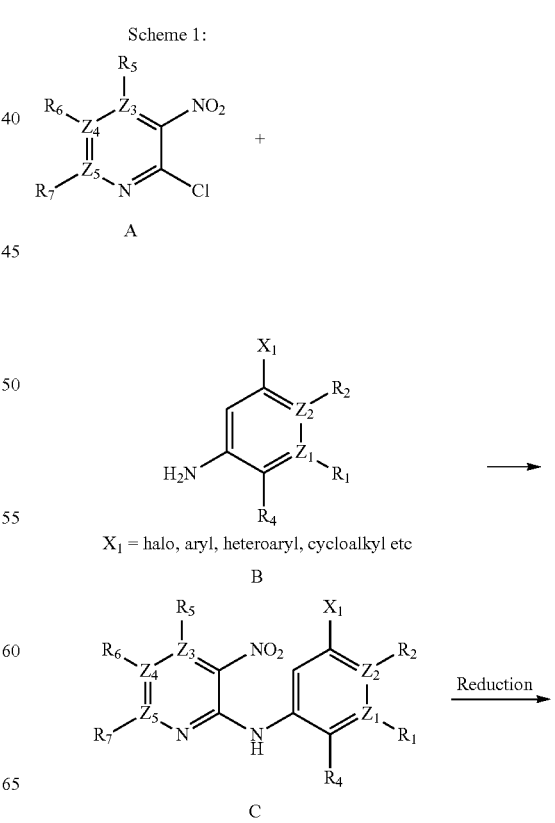

-continued

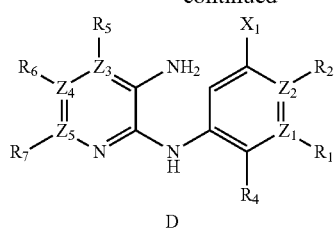

D

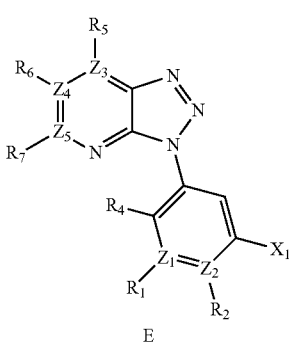

E

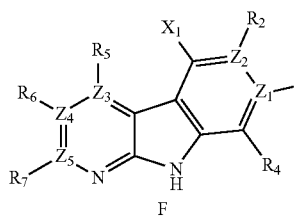

F  If X₁ is halo →

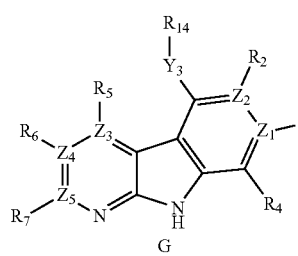

G

Referring to Scheme 1, Compound A and Compound B are mixed and treated under a variety of conditions to form Compound C. For example, the mixture of Compound A and Compound B can be subjected to microwave irradiation, either neat or in an appropriate solvent, at temperatures ranging from 80° C. to 200° C. The nitro group in Compound C is reduced by, for example, catalytic hydrogenation or metal reductions (e.g., with SnCl₂) to form Compound D. Compound D is converted to Compound E using NaNO₂ under suitable conditions (e.g., in AcOH). Compound E is treated with an acid (e.g., o-phosphoric acid) or under flash vacuum at 150° C. to 350° C. to obtain Compound F. If X₁ in Compound F is halo, Compound F can be further converted to Compound G either by treating with alcohol, amine, thiol or by Suzuki type coupling.

Scheme 2:

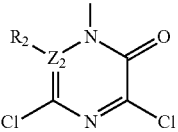

P = protecting group such as benzyl, PMB etc.
H

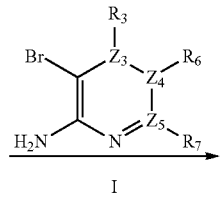

I

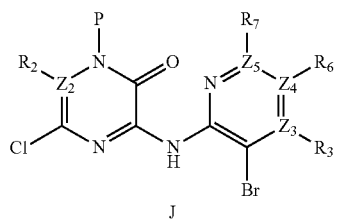

J

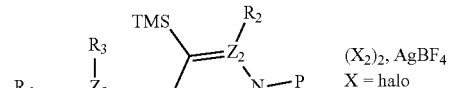

K  Diels-Alder 100 - 200° C. →

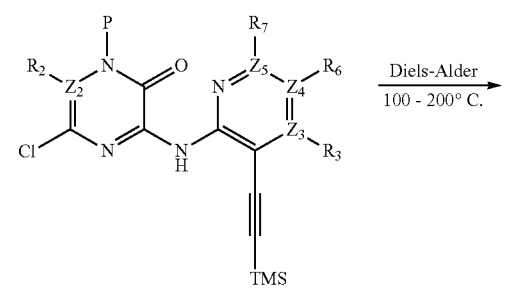

L  (X₂)₂, AgBF₄  X = halo →

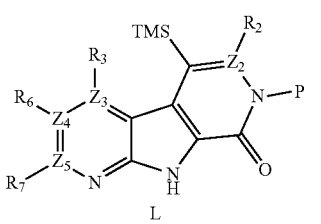

M

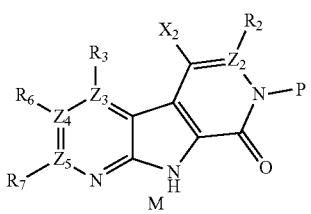

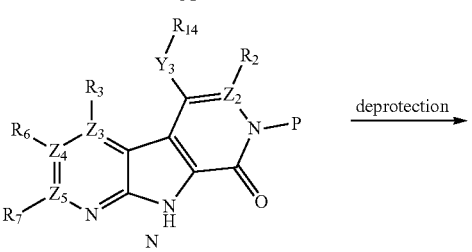

N  deprotection →

-continued

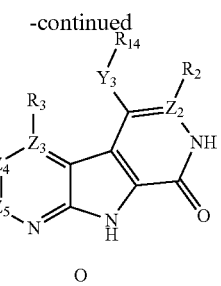

O

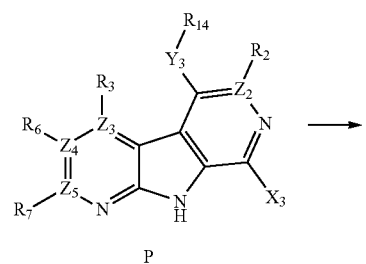

P

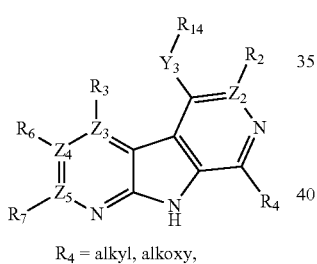

R₄ = alkyl, alkoxy,
amino, thioalkyl,
aryloxy, cycloalkyloxy,
heteroaryloxy etc

Q

Referring to Scheme 2, Compound H is reacted with Compound I using Sonogashira type coupling to give Compound J. Compound J is reacted with ethynyltrimethylsilane under suitable conditions (e.g., Pd mediated in the presence or absence of a base) to provide Compound K. Compound K is transformed to Compound L under Diels-Alder reaction conditions (e.g., heating to a temperature between 100° C. and 200° C.). The TMS group in Compound L is converted to a halo group to yield Compound M. Compound M is further converted to Compound N either by treating with alcohol, amine or thiol, or by Suzuki type coupling. Deprotection of Compound N provides Compound O. Compound O is treated with POX₃ to obtain Compound P. Compound P is further converted to Compound Q either by treating with alcohol, amine or thiol, or by Suzuki type coupling.

Scheme 3:

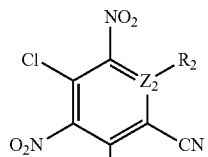

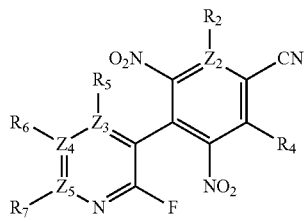

R

S
Ullmann coupling

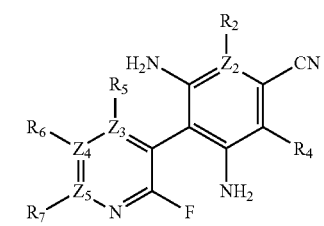

T

Reduction

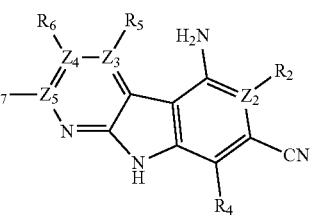

U

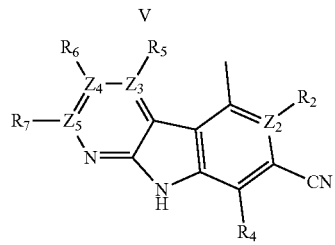

V

Sandmeyer

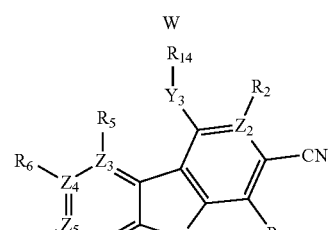

W

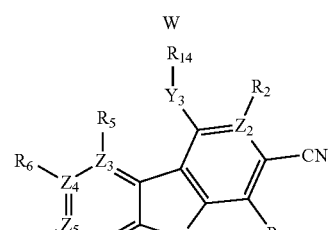

X

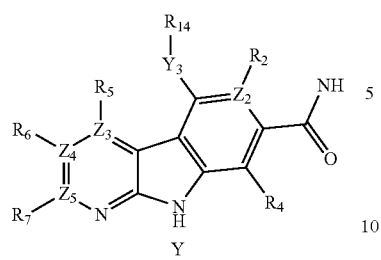

Y

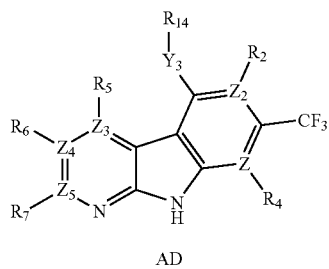

AD

Referring to Scheme 3, Ullmann coupling of Compound R with Compound S provides Compound T. The nitro group in Compound T is reduced (e.g., by catalytic hydrogenation or metal reductions such as with Fe) to form Compound U. Compound U is cyclized to form Compound V. Compound V subjected to Sandmeyer reaction conditions to provide Compound W. Compound W is further converted to Compound X either by treating with alcohol, amine or thiol, or by Suzuki type coupling. The cyano group of Compound X is hydrolyzed by treating Compound X with a base (e.g., KOH) to obtain Compound Y.

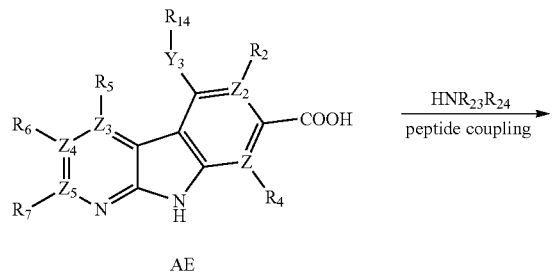

AE

AF $R_{23}$ and $R_{24}$ = H, alkyl, cycloalkyl, heterocyclylalkyl etc

Scheme 4:

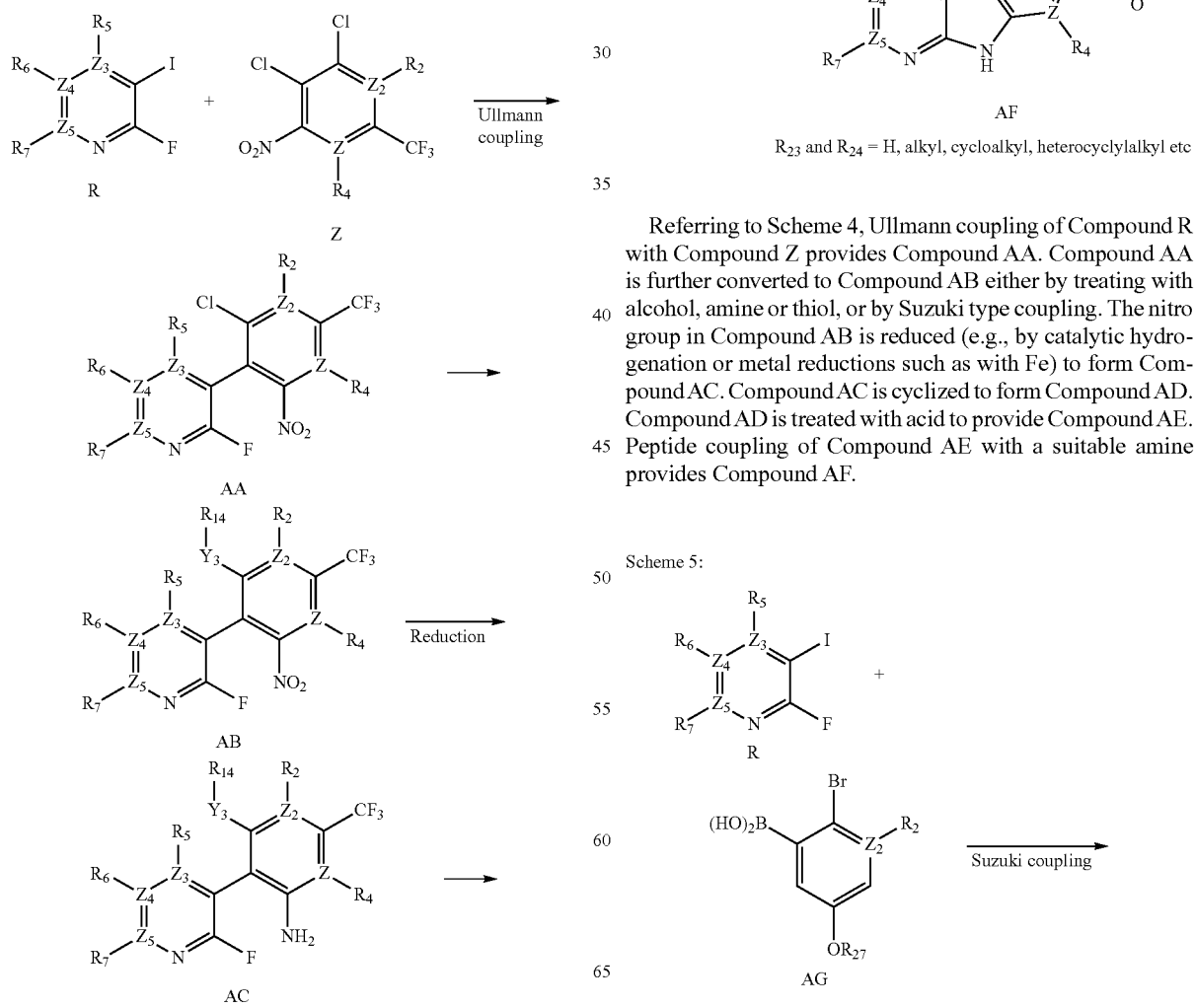

Referring to Scheme 4, Ullmann coupling of Compound R with Compound Z provides Compound AA. Compound AA is further converted to Compound AB either by treating with alcohol, amine or thiol, or by Suzuki type coupling. The nitro group in Compound AB is reduced (e.g., by catalytic hydrogenation or metal reductions such as with Fe) to form Compound AC. Compound AC is cyclized to form Compound AD. Compound AD is treated with acid to provide Compound AE. Peptide coupling of Compound AE with a suitable amine provides Compound AF.

Scheme 5:

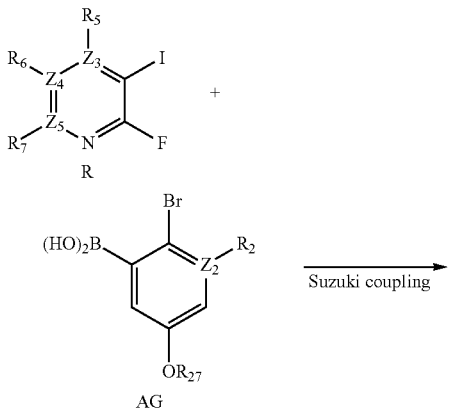

AG converted to Compound AL either by treating with alcohol, amine or thiol, or by Suzuki type coupling. Compound AI can be converted to the corresponding halo derivative (Compound AM with $R_1$=halo) by Sandmeyers reaction or to the corresponding amides (Compound AM with $R_1$=NHCOR$_{28}$) by peptide coupling with suitable acids.

Scheme 6:

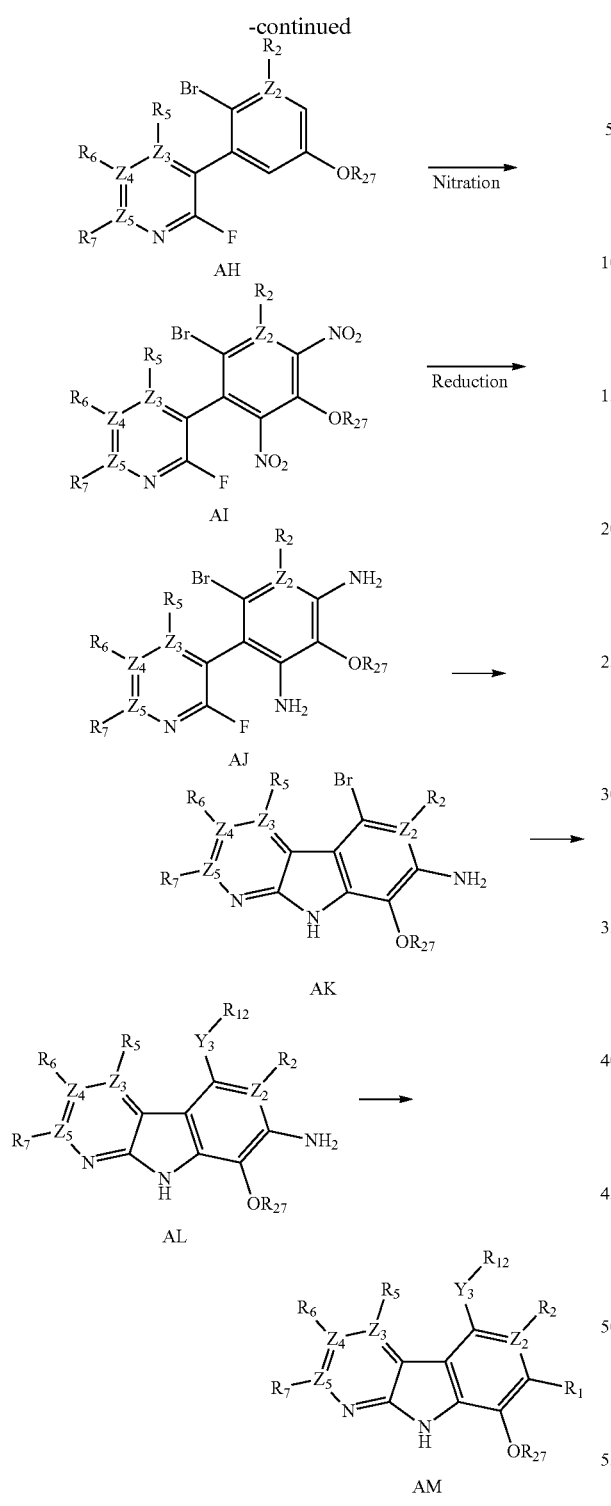

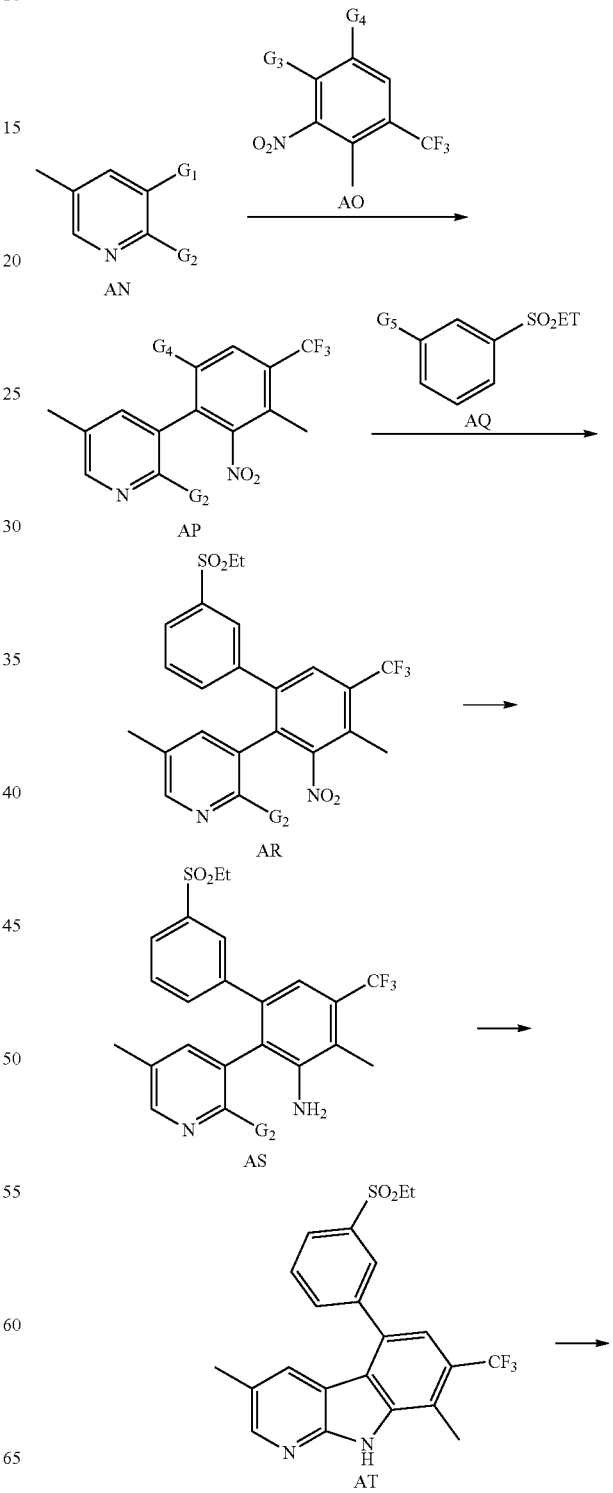

Referring to Scheme 5, Suzuki type coupling of Compound R with a boronic acid (Compound AG) under Pd mediated conditions (e.g., Pd(PPh$_3$)$_4$ in presence of base such as Na$_2$CO$_3$ in a suitable solvent at temperatures ranging from 50° C. to 200° C.) provides Compound AH. Compound AH is subjected to nitration conditions (e.g., HNO$_3$/H$_2$SO$_4$) to obtain Compound AI. The nitro groups in Compound AI are reduced (e.g., by catalytic hydrogenation or metal reductions such as with Fe) to form Compound AJ. Compound AJ is cyclized to form Compound AK. Compound AK is further

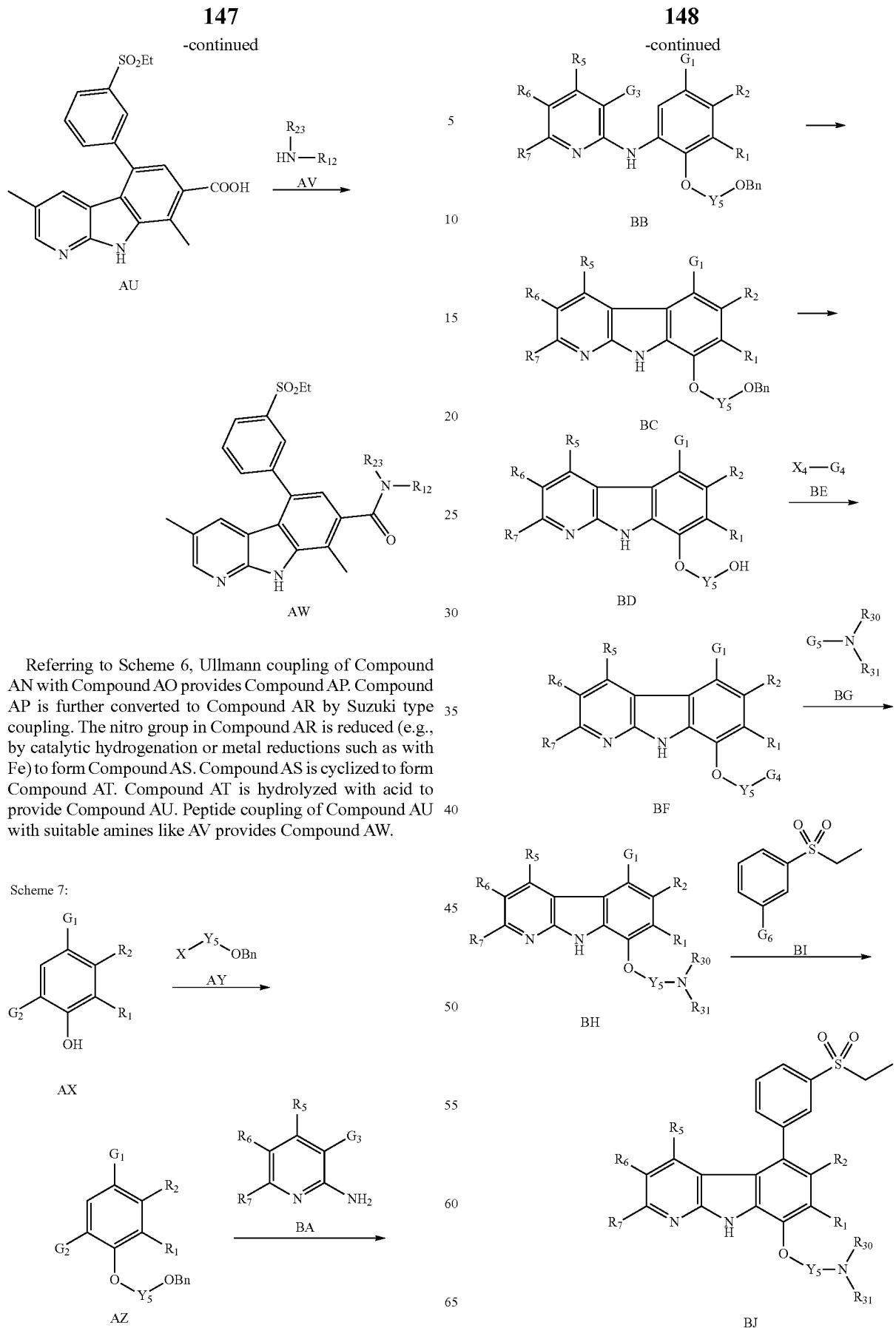

Referring to Scheme 6, Ullmann coupling of Compound AN with Compound AO provides Compound AP. Compound AP is further converted to Compound AR by Suzuki type coupling. The nitro group in Compound AR is reduced (e.g., by catalytic hydrogenation or metal reductions such as with Fe) to form Compound AS. Compound AS is cyclized to form Compound AT. Compound AT is hydrolyzed with acid to provide Compound AU. Peptide coupling of Compound AU with suitable amines like AV provides Compound AW.

Scheme 7:

Referring to Scheme 7, Compound AX is alkylated either by Mitsunobu reaction or base mediated nucleophilic substitution reaction with different alkyl halides to provide Compound AZ. Buchwald reaction of aromatic amine BA with Compound AZ forms Compound BB. Intramolecular Heck reaction is carried out on Compound BB to provide Compound BC. By functional group manipulation on Compound BC the protected hydroxyl group is converted to a suitable leaving group in Compound BF via Compound BD. Direct displacement of the leaving group in Compound BF by a suitable amine BG provides Compound BH. Suzuki type coupling reaction between Compound BH and Compound BI can be performed to form Compound BJ.

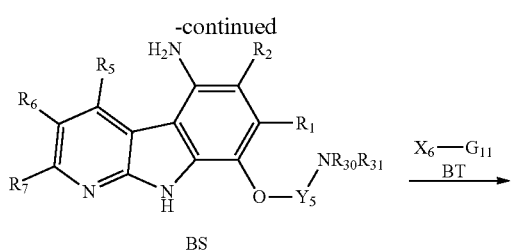

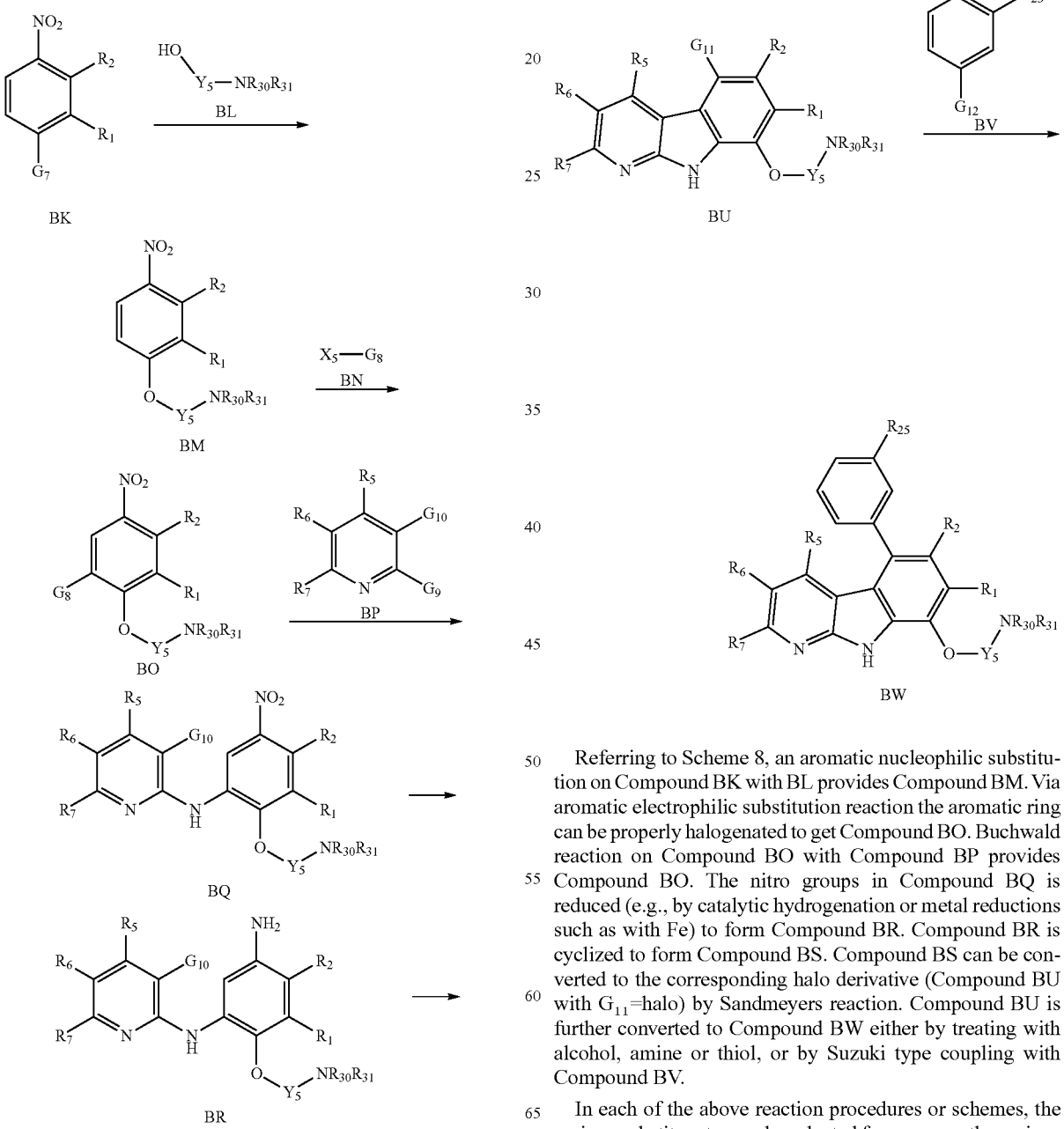

Referring to Scheme 8, an aromatic nucleophilic substitution on Compound BK with BL provides Compound BM. Via aromatic electrophilic substitution reaction the aromatic ring can be properly halogenated to get Compound BO. Buchwald reaction on Compound BO with Compound BP provides Compound BQ. The nitro groups in Compound BQ is reduced (e.g., by catalytic hydrogenation or metal reductions such as with Fe) to form Compound BR. Compound BR is cyclized to form Compound BS. Compound BS can be converted to the corresponding halo derivative (Compound BU with $G_{11}$=halo) by Sandmeyers reaction. Compound BU is further converted to Compound BW either by treating with alcohol, amine or thiol, or by Suzuki type coupling with Compound BV.

In each of the above reaction procedures or schemes, the various substituents may be selected from among the various substituents otherwise taught herein.

Descriptions of the syntheses of particular compounds according to the present invention based on the above reaction scheme are set forth herein.

3. Examples of Kinase Inhibitors

The present invention is further exemplified, but not limited by, the following examples that describe the synthesis of particular compounds according to the invention.

Compound 1

N-(3-bromophenyl)-3-nitropyridin-2-amine

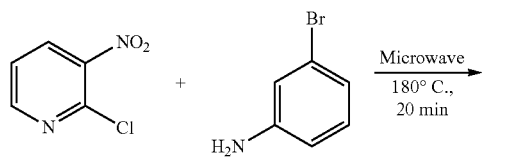

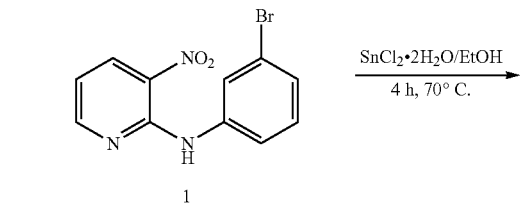

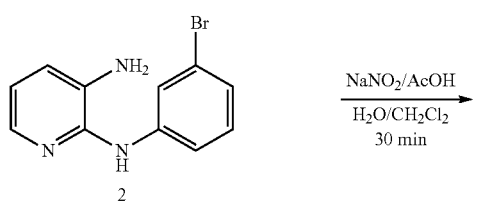

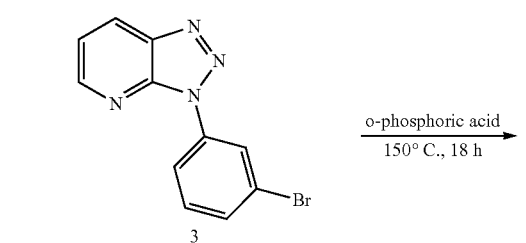

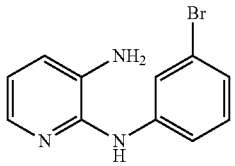

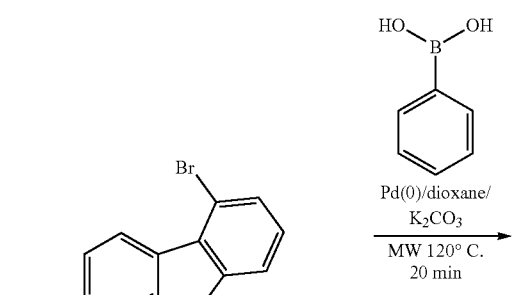

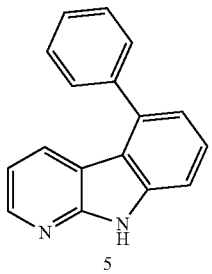

2-Chloro-3-nitropyridine (2.0 g, 12.6 mmol, 1 eq) was reacted with 5-bromoaniline (4.12 ml, 37.8 mmol, 3 eq) for 20 minutes at 180° C. in a microwave reactor. The product was isolated by column chromatography to provide the title compound as a red solid (4.9 g). [M+H] calc'd for $C_{11}H_8BrN_3O_2$, 293; found 293.

Compound 2

N2-(3-bromophenyl)pyridine-2,3-diamine

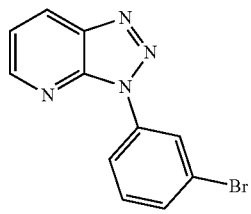

Compound 1 (4.9 g, 16.6 mmol) was dissolved in ethanol (20 ml). Tin (II) Chloride dihydrate (7.5 g, 33.3 mmol) was added and the solution stirred at 70° C. for 4 hours to provide the title compound. The product was confirmed by LC-MS. Addition of excess triethylamine caused a solid to form. The solid was filtered and the solution evaporated to leave an off white solid. The solid as recrystallized from ethanol to provide the title compound (3.8 g, 86%). [M+H] calc'd for $C_{11}H_{10}BrN_3$, 265; found 265.

Compound 3

3-(3-bromophenyl)-3H-[1,2,3]triazolo[4,5-b]pyridine

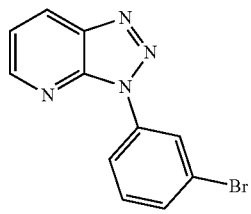

Compound 2 (3.8 g, 14.4 mmol) was dissolved in a mixture of acetic acid (4 mL), water (4 mL) and methylene chloride (4 mL). The mixture was cooled to 0° C., then sodium nitrate (1.29 g, 18.7 mmol) was slowly added. Upon completion of the addition of sodium nitrate, the mixture was brought to room temperature and stirred for 20 minutes. The intended product was confirmed by LC-MS. The reaction mixture was diluted with methylene chloride (30 mL) and washed with water (3×30 mL). The organic layer was dried over magnesium sulfate and then evaporated to provide the title compound (2.9 g, 73%). [M+H] calc'd for $C_{11}H_7BrN_4$, 274; found, 274.

Compound 4

5-bromo-9H-pyrido[2,3-b]indole

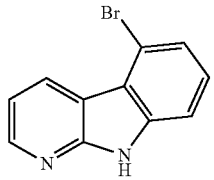

Compound 3 (2.8 g, 10.2 mmol) was dissolved in orthophosphoric acid (40 mL). The mixture was heated to 150° C. for 18 hours, and the intended product confirmed by LC-MS. The mixture was cooled to 0° C. and neutralized with aqueous NaOH. The crude product was extracted with methylene chloride and purified by Preparative HPLC to provide Compound 4 (180 mg, 9%). $^1$H NMR (400 MHz, CD$_3$OD) δ 9.16 (d, J=7.8 Hz 1H) 8.48 (s, 1H) 7.62 (d, J=7.8 Hz 1H) 7.52 (d, J=6.8 Hz 1H) 7.44 (m, 2H). [M+H] calc'd for $C_{17}H_{12}N2$, 245; found 245.

Compound 5

5-phenyl-9H-pyrido[2,3-b]indole

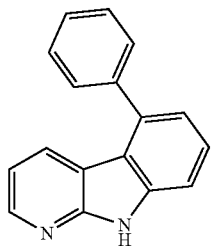

Compound 4 (20 mg, 0.081 mmol) was mixed with phenylboronic acid (20 mg, 0.16 mmol) and Pd(PPh$_3$)$_4$ (19 mg, 0.016 mmol) in a solution comprising dioxane (3 mL) and a saturated K$_2$CO$_3$ solution (1 mL). The mixture was heated in a microwave reactor at 150° C. for 20 minutes. Purification by HPLC afforded the title compound as a tan solid (4 mg, 22%). $^1$H NMR (400 MHz, CD$_3$OD) δ 8.39 (s, 1H) 8.10 (d, J=7.84 Hz, 1H) 7.67 (m, 2H) 7.60 (m, 5H) 7.27 (m, 2H). [M+H] calc'd for $C_{17}H_{12}N2$, 245; found 245.

Compound 6

5-bromo-8-methyl-9H-pyrido[2,3-b]indole

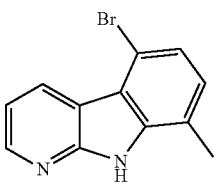

The title compound was synthesized using an analogous procedure to that described in the preparation of Compound 4 except that 5-bromo-2-methylaniline was used as the starting material. $^1$H NMR (400 MHz, CD$_3$OD) δ 9.16 (d, J=7.8 Hz 1H) 8.48 (s, 1H) 7.62 (d, J=7.8 Hz 1H) 7.52 (d, J=6.8 Hz 1H) 7.44 (m, 2H) 2.27 (s, 3H). [M+H] calc'd for $C_{17}H_{12}N2$, 257; found 257.

Compound 7

5-bromo-3,8-dimethyl-9H-pyrido[2,3-b]indole

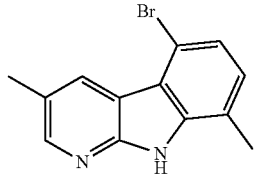

The title compound was synthesized using an analogous procedure to that described in the preparation of Compound 4. $^1$H NMR (400 MHz, DMSO-d$_6$) δ ppm 2.48 (s, 3H) 2.52 (s, 3H) 7.18 (d, J=7.83 Hz, 1H) 7.31 (d, J=7.83 Hz, 1H) 8.37 (d, J=2.02 Hz, 1H) 8.65 (d, J=1.77 Hz, 1H) 12.01 (s, 1H). [M+H] calc'd for $C_{13}H_{11}BrN_2$ 275, 277; found, 275.2, 277.2.

Compound 8

5-(3-(methylsulfonyl)phenyl)-9H-pyrido[2,3-b]indole

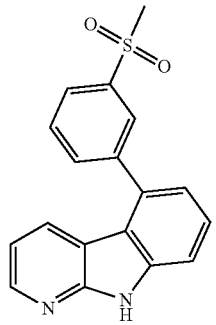

The title compound was synthesized using an analogous procedure to that described in the preparation of Compound 5 using 3-methylsulfonylphenylboronic acid. Yield=27%. $^1$H NMR (400 MHz, DMSO) δ 8.40 (d, J=0.076 Hz, 1H) 8.15 (s, 1H) 8.08 (d, J=8.56 Hz, 1H) 8.02 (d, J=7.6 Hz, 1H) 7.87 (t, 1H) 7.68 (d, J=6.04, 1H) 7.59 (m, 2 H) 7.19 (d, J=8.6 Hz, 1H) 7.03 (m, 1H) 3.32 (s, 3H). [M+H] calc'd for $C_{18}H_{14}N_2O_2S$, 323; found, 323.

Compound 9

5-(3-(ethylsulfonyl)phenyl)-9H-pyrido[2,3-b]indole

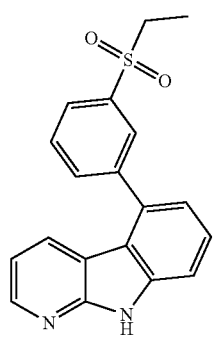

The title compound was synthesized using an analogous procedure to that described in the preparation of Compound 5 using 3-ethylsulfonylphenylboronic acid. Yield=48%. $^1$H NMR (400 MHz, CD$_3$OD) δ 8.46 (s, 1H) 8.15 (s, 1H) 8.09 (t, 2H) 8.02 (d, J=7.84 Hz, 1H) 7.88 (t, 1H) 7.74 (m, 2H) 7.35 (m, 2H) 3.30 (s, 2H) 1.28 (m, 3H). [M+H] calc'd for $C_{19}H_{16}N_2O_2S$, 337; found 337.

Compound 10

N-(3-(9H-pyrido[2,3-b]indol-5-yl)phenyl)ethanesulfonamide

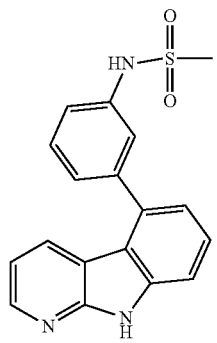

The title compound was synthesized using an analogous procedure to that described in the preparation of Compound 5 using 3-(methanesulfonylamino) phenylboronic acid. Yield=63%. $^1$H NMR (400 MHz, CD$_3$OD) δ 8.42 (s, 1H) 8.28 (d, J=7.6 Hz 1H) 7.70 (d, J=4.04 Hz 2H) 7.57 (t, 1H) 7.52 (s, 1H) 7.41 (m, 1H) 7.32 (d, J=7.32 Hz 1H) 7.24 (d, J=8.6 Hz, 1H) 7.31 (t, 1H) 2.93 (s, 3H). [M+H] calc'd for $C_{18}H_{15}N_3O_2S$, 338; found 338.

Compound 11

5-m-tolyl-9H-pyrido[2,3-b]indole

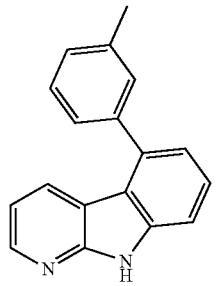

The title compound was synthesized using an analogous procedure to that described in the preparation of Compound 5 using m-tolylboronic acid. Yield=18%. $^1$H NMR (400 MHz, CD$_3$OD) δ 8.35 (s, 1H) 8.01 (d, J=7.84 Hz 1H) 7.62 (d, J=4.8 Hz 2H) 7.45 (t, 1H) 7.39 (m, 3H) 7.21 (t, 1H) 7.16 (m, 1H) 3.30 (m, 3H). [M+H] calc'd for $C_{18}H_{14}N_2$ 259; found 259.

Compound 12

N-cyclopropyl-3-(9H-pyrido[2,3-b]indol-5-yl)benzenesulfonamide

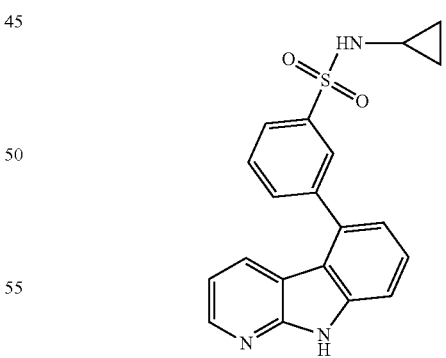

The title compound was synthesized using an analogous procedure to that described in the preparation of Compound 5 using 3-(N-cyclopropylsulfamoyl)phenylboronic acid. Yield=19%. $^1$H NMR (400 MHz, CD$_3$OD) δ 8.38 (s, 1H) 8.12 (s, 1H) 8.06 (d, J=7.84 Hz 1H) 7.97 (d, J=8.6 Hz 1H) 7.90 (m, 1H) 7.81 (t, 1H) 7.68 (m, 2H) 7.28 (d, J=6.32 Hz 1H) 7.18 (t, 1H) 2.26 (m, 1H) 1.28 (s, 2H) 0.53 (m, 2H). [M+H] calc'd for C$_{20}$H$_{17}$N$_3$O$_2$S 364; found 364.

Compound 13

5-(3-methoxyphenyl)-9H-pyrido[2,3-b]indole

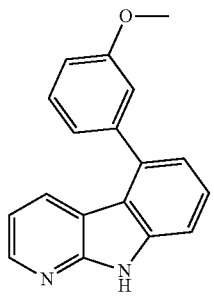

The title compound was synthesized using an analogous procedure to that described in the preparation of Compound 5 using 3-methoxyphenylboronic acid. Yield=42%. $^1$H NMR (400 MHz, CD$_3$OD) δ 8.02 (d, J=7.08 1H) 7.60 (m, 2H) 7.48 (t, 1H) 7.22 (m, 1H) 7.17 (d, J=8.08 Hz 2H) 7.12 (m, 1H) 7.10 (d, J=9.08 Hz 1H) 3.85 (s, 3 H). [M+H] calc'd for C$_{18}$H$_{14}$N$_2$O 275; found, 275.

Compound 14

5-(3,8-dimethyl-9H-pyrido[2,3-b]indol-5-yl)-2-methoxy-N-methylbenzenesulfonamide

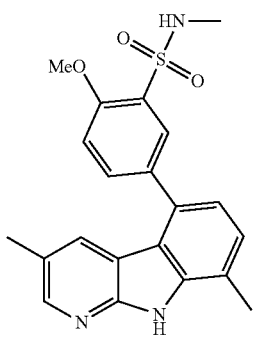

The title compound was synthesized using an analogous procedure to that described in the preparation of Compound 5. $^1$H NMR (400 MHz, DMSO-d$_6$) δ ppm 2.27 (s, 3H) 2.53 (d, J=5.05 Hz, 3H) 2.59 (s, 3H) 4.01 (s, 3H) 7.00 (d, J=7.33 Hz, 1H) 7.18 (q, J=5.05 Hz, 1H) 7.32 (d, J=7.58 Hz, 1H) 7.43 (d, J=8.59 Hz, 1H) 7.58 (d, J=1.52 Hz, 1H) 7.82 (dd, J=8.34, 2.27 Hz, 1H) 7.92 (d, J=2.27 Hz, 1H) 8.27 (d, J=2.02 Hz, 1H) 11.91 (s, 1H). [M+H] calc'd for C$_{21}$H$_{21}$N$_3$O$_3$S 396; found, 396.3.

Compound 15

3-(3,8-dimethyl-9H-pyrido[2,3-b]indol-5-yl)-N-methylbenzenesulfonamide

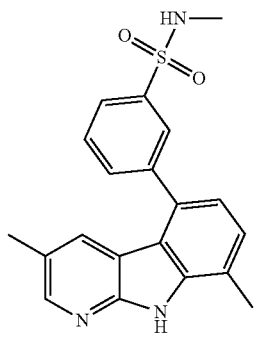

The title compound was synthesized using an analogous procedure to that described in the preparation of Compound 5. $^1$H NMR (400 MHz, DMSO-d$_6$) δ ppm 2.26 (s, 3H) 2.48 (s, 3H) 2.61 (s, 3H) 7.06 (d, J=7.33 Hz, 1H) 7.36 (d, J=6.82 Hz, 1H) 7.51 (d, J=2.02 Hz, 1H) 7.60 (q, J=5.05 Hz, 1H) 7.82 (d, J=7.58 Hz, 1H) 7.86-7.93 (m, 2H) 8.00 (t, J=1.52 Hz, 1H) 8.27 (d, J=2.02 Hz, 1H) 11.96 (s, 1H). [M+H] calc'd for C$_{20}$H$_{19}$N$_3$O$_2$S 366; found, 366.3.

Compound 16

3-(3,8-dimethyl-9H-pyrido[2,3-b]indol-5-yl)-N,N-dimethylbenzenesulfonamide

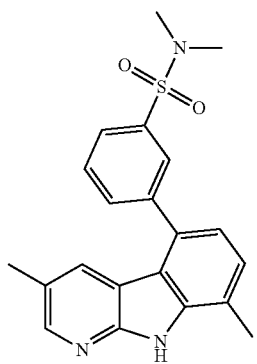

The title compound was synthesized using an analogous procedure to that described in the preparation of Compound 5. $^1$H NMR (400 MHz, DMSO-d$_6$) δ ppm 2.27 (s, 3H) 2.62 (s, 3H) 2.70 (s, 6H) 7.08 (d, J=7.58 Hz, 1H) 7.38 (d, J=7.33 Hz, 1H) 7.51 (s, 1H) 7.86-7.96 (m, 4H) 8.31 (br. s., 1H) 12.11 (s, 1H). [M+H] calc'd for $C_{21}H_{21}N_3O_2S$ 380; found, 380.3.

Compound 17

5-(3-(ethylsulfonyl)phenyl)-8-methyl-9H-pyrido[2,3-b]indole

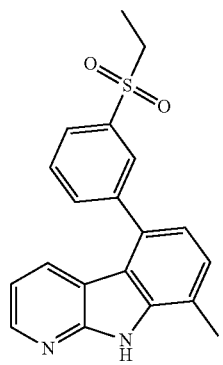

The title compound was synthesized using an analogous procedure to that described in the preparation of Compound 5. Yield=51%. $^1$H NMR (400 MHz, CD$_3$OD) δ 8.41 (s, 1H) 8.13 (s, 1H) 8.08 (d, J=8.08 Hz 1H) 7.99 (t, 2H) 7.86 (t, 1H) 7.52 (d, J=8.08 Hz 1H) 7.23 (m, 2H) 2.70 (s, 3H) 1.28 (m, 3H). [M+H] calc'd for $C_{20}H_{18}N_2O_2S$ 351; found, 351.

Compound 18

5-(3-(ethylsulfonyl)phenyl)-3,8-dimethyl-9H-pyrido[2,3-b]indole

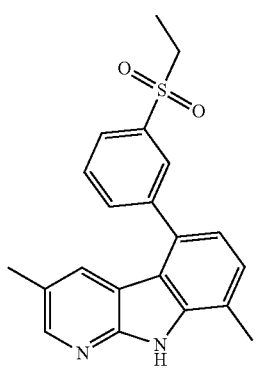

The title compound was synthesized using an analogous procedure to that described in the preparation of Compound 5. $^1$H NMR (400 MHz, CD$_3$OD) δ 8.27 (s, 1H) 8.17 (t, J=3.83 Hz, 1H) 8.07 (d, J=7.83 Hz 1H) 7.98 (d, J=8.08 Hz, 1H) 7.92 (s, 1H) 7.86 (t, J=7.71 Hz, 1H) 7.51 (d, J=8.59 Hz, 1H) 7.23 (d, J=7.58 Hz, 1H) 2.68 (s, 3H) 2.38 (s, 3H) 1.28 (t, J=7.33 Hz, 3H). [M+H] calc'd for $C_{21}H_{20}N_2O_2S$; found, 364.

Compound 19

N-(3-(3,8-dimethyl-9H-pyrido[2,3-b]indol-5-yl)phenyl)propionamide

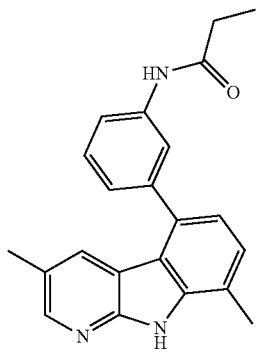

The title compound was synthesized using an analogous procedure to that described in the preparation of Compound 5. $^1$H NMR (400 MHz, CD$_3$OD) δ ppm 1.20 (t, J=7.58 Hz, 3H) 1.93 (s, 2H) 2.41 (s, 3H) 2.68 (s, 3H) 7.21 (d, J=7.58 Hz, 1H) 7.31 (dt, J=7.07, 1.64 Hz, 1H) 7.50 (d, J=8.84 Hz, 1H) 7.47 (s, 1H) 7.54 (dd, J=3.41, 1.64 Hz, 2 H) 7.97 (t, J=1.64 Hz, 1H) 8.29 (br. s., 1H) [M+H] calc'd for $C_{22}H_{21}N_3O$, 344; found, 344.

Compound 20

N-cyclopropyl-3-(3,8-dimethyl-9H-pyrido[2,3-b]indol-5-yl)benzamide

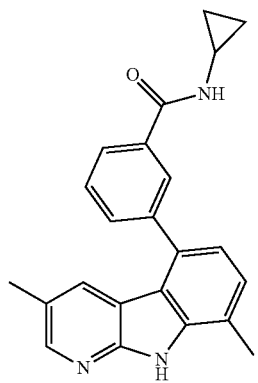

The title compound was synthesized using an analogous procedure to that described in the preparation of Compound 5. $^1$H NMR (400 MHz, CD$_3$OD) δ ppm 0.65 (dd, J=3.79, 2.02 Hz, 2H) 0.82 (dd, J=7.20, 2.15 Hz, 2H) 1.93 (s, 1H) 2.37 (s, 3H) 2.68 (s, 3H) 2.88 (td, J=7.20, 4.04 Hz, 1H) 7.22 (d, J=7.58 Hz, 1H) 7.50 (dd, J=7.58, 0.76 Hz, 1H) 7.53-7.59 (m, 1H) 7.66 (t, J=7.71 Hz, 1H) 7.77 (dt, J=7.64, 1.48 Hz, 1H) 7.91 (d, J=0.76 Hz, 1H) 7.95 (dt, J=7.64, 0.98 Hz, 1H) 8.05 (t, J=1.77 Hz, 1H) 8.24 (br. s., 1 H) [M+H] calc'd for $C_{23}H_{21}N_3O$, 355; found, 355.

Compound 21

N-(4-(9H-pyrido[2,3-b]indol-5-ylthio)phenyl)acetamide

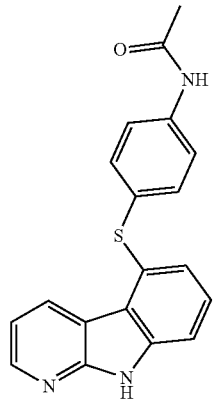

The title compound was synthesized by mixing Compound 4 (25 mg, 0.10 mmol, 4-mercapto-N-methylbenzamide (21 μl, 0.20 mmol), $CS_2CO_3$ (33 mg, 0.10 mmol) and [1,1'-Bis(diphenylphosphino)-ferrocene]dichloropalladium(II) (7 mg, 0.01 mmol) in DMF and heating at 170° C. for 20 minutes in a microwave reactor. The product was purified by HPLC (Yield=42%). $^1$H NMR (400 MHz, $CD_3OD$) δ 8.97 (d, J=7.84 1H) 8.41 (d, J=5.56 Hz 1H) 7.55 (m, 3H) 7.50 (t, 1H) 7.40 (q, 1H) 7.36 (d, J=8.84 Hz 2H) 7.12 (d, J=7.36 Hz 1H) 2.11 (s, 3H). [M+H] calc'd for $C_{19}H_{15}N_3OS$ 334; found, 334.

Compound 22

5-(benzylthio)-9H-pyrido[2,3-b]indole

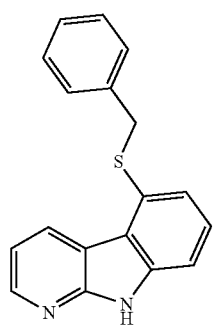

The title compound was synthesized using an analogous procedure to that described in the preparation of Compound 21. Yield=39%. $^1$H NMR (400 MHz, $CD_3OD$) δ 8.40 (s, 1H) 8.15 (s, 1H) 8.10 (d, J=7.84 Hz 1H) 8.01 (d, J=8.56 Hz 2H) 7.87 (t, 1H) 7.71 (t, 2H) 7.32 (d, J=8.36 Hz 1H) 7.24 (q, 1H) 1.28 (t, 2H). [M+H] calc'd for $C_{18}H_{14}N_2S$ 291; found, 291.

Compound 23

5-(phenylthio)-9H-pyrido[2,3-b]indole

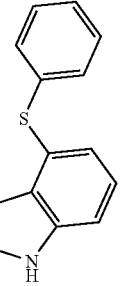

The title compound was synthesized using an analogous procedure to that described in the preparation of Compound 21. Yield=18%. $^1$H NMR (400 MHz, $CD_3OD$) δ 8.66 (d, J=7.84 Hz 1H) 8.33 (s, 1H) 7.56 (d, J=8.32 Hz 1H) 7.45 (t, 1H) 7.25 (m, 3 H) 7.21 (d, J=7.93 Hz 2H) 7.14 (q, 1H) 1.30 (t, 2H). [M+H] calc'd for $C_{17}H_{12}N_2S$ 277; found, 277.

Compound 24

5-(benzylthio)-8-methyl-9H-pyrido[2,3-b]indole

The title compound was synthesized using an analogous procedure to that described in the preparation of Compound 21. Yield=14%. $^1$H NMR (400 MHz, $CD_3OD$) δ 8.88 (d, J=7.84 Hz 1H) 8.34 (s, 1H) 7.74 (s, 1H) 7.19 (m, 6H) 7.11 (d, J=7.56 Hz 1 H) 6.89 (s, 1H) 2.28 (s, 3H). [M+H] calc'd for $C_{19}H_{16}N_2S$ 305; found, 305.

Compound 25

5-(benzylthio)-3,8-dimethyl-9H-pyrido[2,3-b]indole

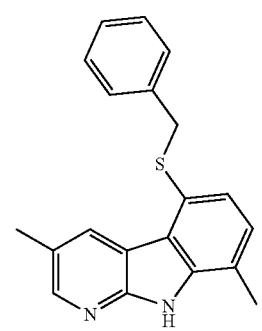

The title compound was synthesized using an analogous procedure to that described in the preparation of Compound 21. $^1$H NMR (400 MHz, MeOD) δ ppm 2.54 (s, 4H) 2.59 (s, 3H) 4.27 (s, 2H) 7.18 (dd, J=7.45, 1.39 Hz, 1H) 7.16-7.19 (m, 1H) 7.21 (dd, J=6.19, 1.39 Hz, 2H) 7.25 (d, J=9.09 Hz, 1H) 7.24 (s, 1H) 7.87 (s, 1H) 8.22 (br. s., 1H) 8.91 (d, J=1.52 Hz, 1H). [M+H] calc'd for $C_{20}H_{18}N_2S$, 319; found, 319.

Compound 26

1-Benzyl-3-(3-bromo-5-methyl-pyridin-2-ylamino)-5-chloro-1H-pyrazin-2-one

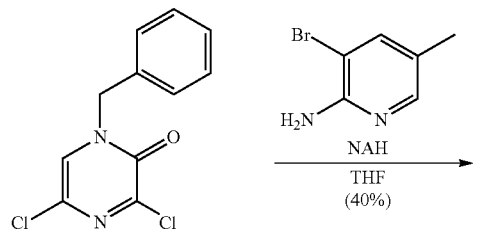

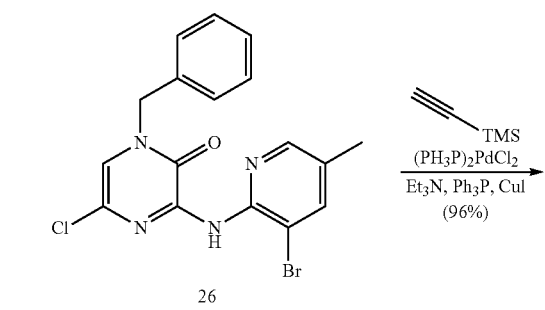

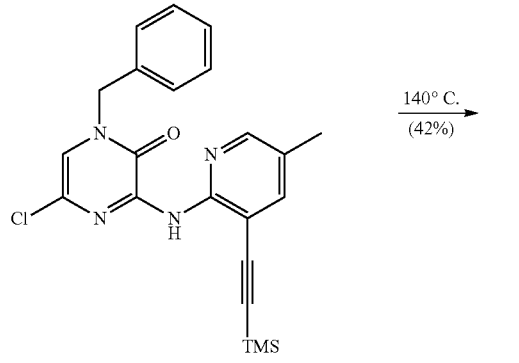

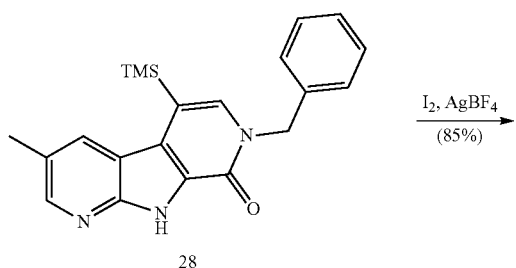

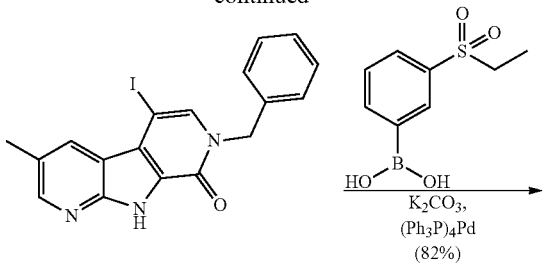

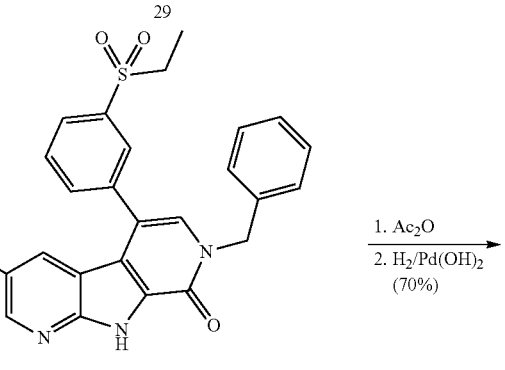

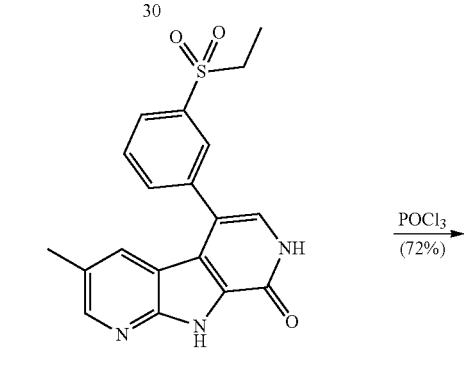

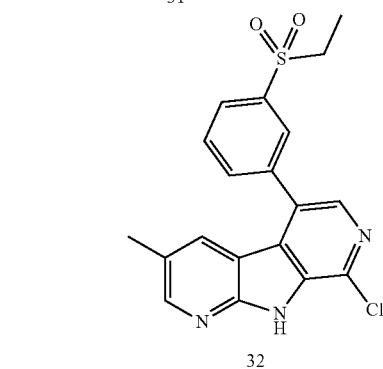

2-Amino-3-bromo-5-methyl-pyridine (1.0 g, 5.35 mmol) was added to a solution of sodium hydride (60%, 321 mg, 8.0 mmol) in dry THF (20 mL) at r.t. under nitrogen. After 30 minutes, 1-benzyl-3,5-dichloro-2(1H)-pyrazinone (see Vekemans, et. al., *J. Heterocyclic Chem.*, 20, (1983), 919-923) (1.36 g, 5.35 mmol) was added, and the reaction stirred at 72° C. for 4 h. The solution was concentrated in vacuo and the residue was dissolved in $CH_2Cl_2$. Organics were washed with $H_2O$ and brine, dried ($MgSO_4$), and concentrated. Purification by silica gel chromatography (2:1:1 hexanes/EtOAc/$CH_2Cl_2$) provided the title compound as a pale yellow solid (860 mg, 40%). $^1$H NMR (400 MHz, DMSO-$d_6$): δ 9.51 (s, 1H), 8.27 (s, 1H), 8.00 (s, 1H), 7.43 (s, 1H), 7.29-7.39 (m, 5H), 5.07 (s, 2H), 2.29 (s, 3H). MS (ES) [m+H] calc'd for C₁₇H₁₄BrClN₄O, 405, 407; found 405, 407.

Compound 27

1-Benzyl-5-chloro-3-(5-methyl-3-trimethylsilanyl-ethynyl-pyridin-2-ylamino)-1H-pyrazin-2-one

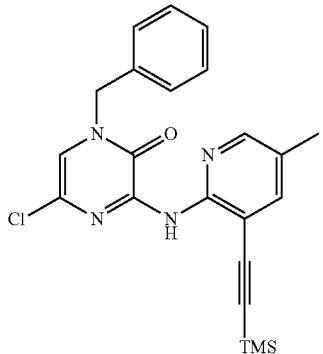

Compound 26 (2.0 g, 4.9 mmol), triphenylphosphine (52 mg, 0.2 mmol), dichlorobis(triphenylphosphine)palladium (II) (173 mg, 0.25 mmol), triethylamine (1.03 mL, 7.4 mmol), and TMS-acetylene (1.05 mL, 7.4 mmol) were combined in THF (20 mL) at r.t. under nitrogen. After stirring 10 min, copper iodide (40 mg) was added, and the reaction stirred for 8 h. The reaction was diluted with EtOAc, washed with brine, dried (MgSO₄), and concentrated in vacuo. Purification by silica gel chromatography (2:1:2 hexanes/EtOAc/CH₂Cl₂) provided the title compound as a pale yellow solid (2.0 g, 96%). MS (ES) [m+H] calc'd for C₂₁H₂₃ClN₄OSi, 423, 425; found 423, 425.

Compound 28

7-Benzyl-3-methyl-5-trimethylsilanyl-7,9-dihydro-dipyrido[2,3-b; 4',3'-d]pyrrol-8-one

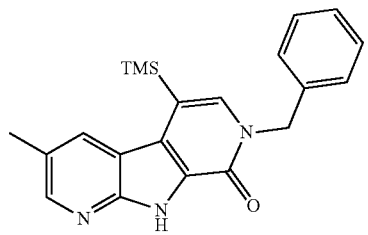

Compound 27 (3.5 g, 8.29 mmol) was dissolved in bromobenzene (150 mL). The solution was heated at 140° C. under N₂ for 7 hours. The solution was evaporated and the residue was purified by flash chromatography (3% MeOH/CH₂Cl₂) to provide the title compound as a tan solid (2.5 g, 83%). ¹H NMR (400 MHz, CDCl₃): δ 8.22 (s, 1H), 7.27-7.39 (m, 6H), 5.40 (s, 2H), 2.57 (s, 3H). MS (ES) [m+H] calc'd for C₂₁H₂₃N₃OSi, 362; found 362.

Compound 29

7-Benzyl-5-iodo-3-methyl-7,9-dihydro-dipyrido[2,3-b; 4',3'-d]pyrrol-8-one

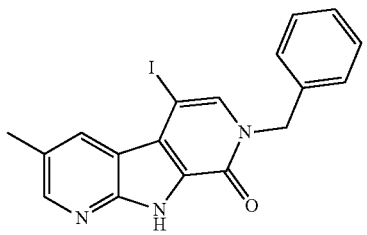

Compound 28 (2.5 g, 6.93 mmol) dissolved in dry ethanol (200 mL) and stirred under nitrogen at 0° C. Silver tetrafluoroborate (1.45 g, 7.45 mmol) was added, and the solution stirred for 10 minutes. Iodine (1.85 g, 7.3 mmol) was added, and the reaction stirred 1 h as a precipitate began to form. After evaporation of the solvent, the solid was taken up in CH₂Cl₂ and washed with water, which caused an insoluble precipitate to form. The solid was collected by filtration and washed with ethyl acetate to provide the title compound (2.5 g, 87%). ¹H NMR (400 MHz, DMSO-d₆): δ 12.74 (s, 1H), 8.69 (s, 1H), 8.42 (s, 1H), 7.90 (s, 1H), 7.25-7.36 (m, 5H), 5.26 (s, 2H), 2.46 (s, 3H). MS (ES) [m+H] calc'd for C₁₈H₁₄IN₃O, 416; found 416.

Compound 30

7-Benzyl-5-(3-ethanesulfonyl-phenyl)-3-methyl-7,9-dihydro-dipyrido[2,3-b; 4',3'-d]pyrrol-8-one

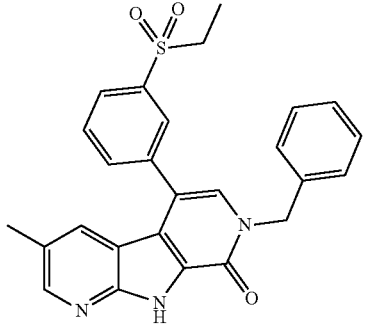

Compound 29 (2.82 g, 6.79 mmol), 3-ethansulfonylboronic acid (1.59 g, 7.46 mmol), and saturated potassium carbonate solution (2 mL) were combined in dioxane (8 mL) in a flask purged with nitrogen. Tetrakis(triphenylphosphine)palladium(0) (1.57 g, 1.36 mmol) was added, and the reaction stirred at 150° C. in the microwave for 20 min. The solution was filtered, and the solid was washed with water and then DCM to provide the title compound as an off-white solid (1.7 g, 55%). ¹H NMR (400 MHz, DMSO-d₆): δ 12.73 (s, 1H), 8.36 (s, 1H), 8.09 (s, 1H), 7.92-7.99 (m, 2H), 7.83 (t, 1H, J=7.6 Hz), 7.68 (s, 1H), 7.54 (s, 1H), 7.23-7.40 (m, 5H), 5.34

(s, 2H), 3.39 (q, 2H, J=7.2 Hz), 2.27 (s, 3H), 1.15 (t, 3H, J=7.2 Hz). MS (ES) [m+H] calc'd for $C_{26}H_{23}N_3O_3S$, 458; found 458.

Compound 31

5-(3-Ethanesulfonyl-phenyl)-3-methyl-7,9-dihydro-dipyrido[2,3-b; 4',3'-d]pyrrol-8-one

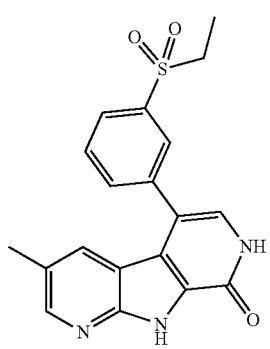

Compound 30 (24 mg, 0.053 mmol) was stirred in acetic anhydride (2 mL) under reflux overnight. Solvent was removed in vacuo, and the residue was subjected to hydrogenation with 20% palladium hydroxide on carbon (25 mg) in acetic acid (5 mL) under an atmosphere of hydrogen at 36° C. for 4 h. The reaction was filtered through Celite and concentrated in vacuo. Purification by prep HPLC provided the title compound as a white solid (4.6 mg, 24%). $^1$H NMR (400 MHz, MeOD-$d_4$/CDCl$_3$): δ 8.41 (br s, 1H), 8.12 (s, 1H), 8.02 (d, 1H, J=8.0 Hz), 7.92 (d, 1H, J=8.0 Hz), 7.80 (t, 1H, J=8.0 Hz), 7.67 (s, 1H), 7.30 (br s, 1H), 7.14 (s, 1H), 3.25 (q, 2H, J=7.2 Hz), 2.35 (s, 3H), 1.31 (t, 3H, J=7.2 Hz). MS (ES) [m+H] calc'd for $C_{19}H_{17}N_3O_3S$, 368; found 368.

Compound 32

8-Chloro-5-(3-ethanesulfonyl-phenyl)-3-methyl-9H-dipyrido[2,3-b; 4',3'-d]pyrrole

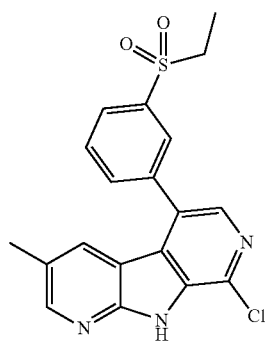

Compound 31 (50 mg, 0.136 mmol) was stirred in POCl$_3$ (2 mL) with dimethylaniline (0.1 mL) at 108° C. under nitrogen for 16 h. The solution was concentrated and the residue dissolved in CH$_2$Cl$_2$. Ice and saturated NaHCO$_3$ solution were added, and organics were extracted twice with CH$_2$Cl$_2$, dried (MgSO$_4$), and concentrated in vacuo. Purification by silica gel chromatography (3% MeOH/CH$_2$Cl$_2$) provided the title compound as a pale yellow solid (36 mg, 69%). $^1$H NMR (400 MHz, MeOD-$d_4$/CDCl$_3$): δ 8.46 (s, 1H), 8.22 (s, 1H), 8.14 (s, 1H), 8.11 (d, 1H, J=8.0 Hz), 8.01 (d, 1H, J=8.0 Hz), 7.89 (t, 1H, J=8.0 Hz), 7.84 (s, 1H), 7.76 (s, 1H), 3.28 (q, 2H, J=7.2 Hz), 2.38 (s, 3H), 1.31 (t, 3H, J=7.2 Hz). MS (ES) [m+H] calc'd for $C_{19}H_{16}ClN_3O_2S$, 386, 388; found 386, 388.

Alternatively, Compound 32 was synthesized from Compound 33 as follows.

Compound 33

2-(4-methoxybenzylamino) acetonitrile-HCl

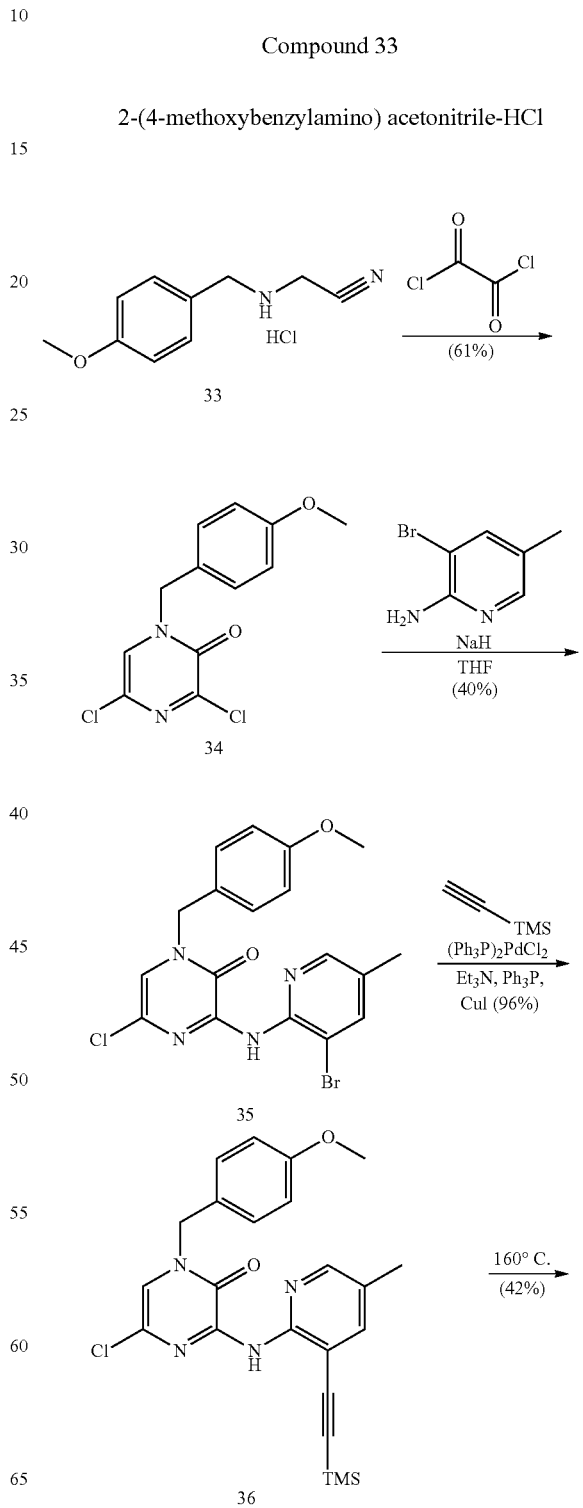

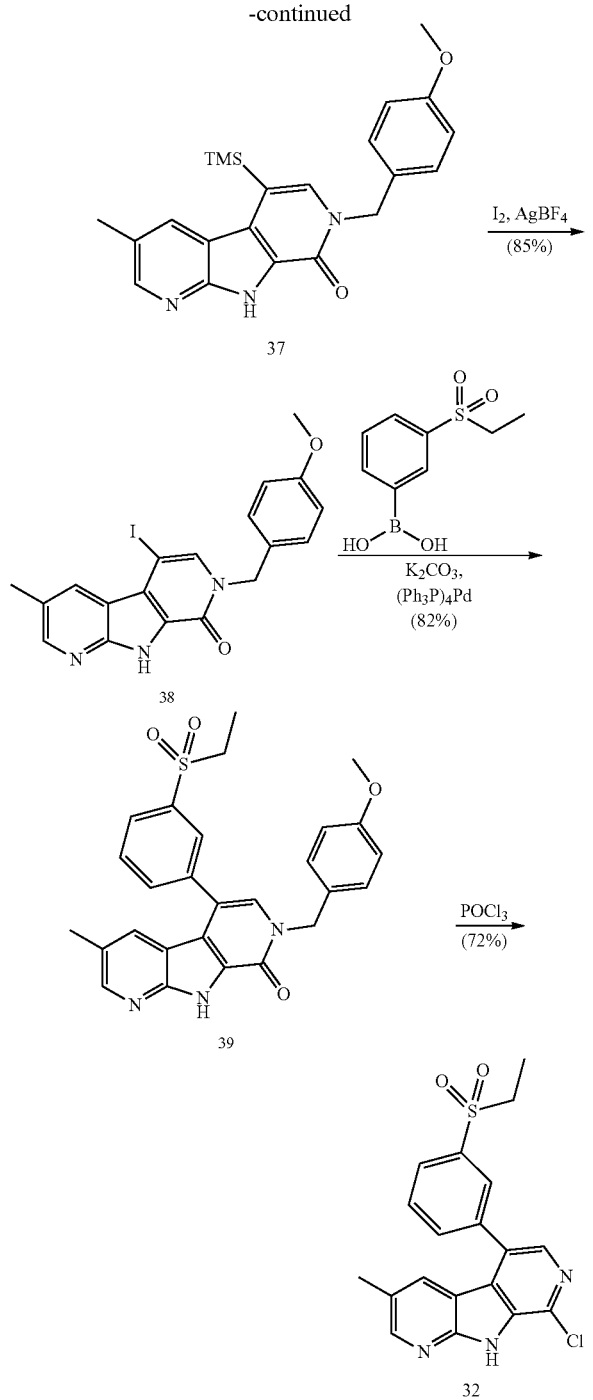

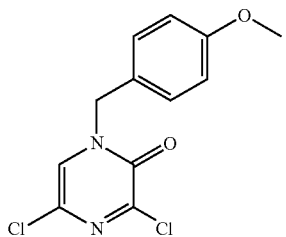

In an appropriate round bottom flask, 4-methoxyybenzylamine (50.57 g, 368.66 mmol) was first suspended in anhydrous THF (800 mL), treated with triethylamine (39.05 g, 385.89 mmol) and cooled in an ice/water bath. Bromoacetonitrile (41.33 g, 344.54 mmol) was added last and the reaction mixture was slowly warmed to ambient temperature, under N₂. After 3 h, the reaction was concentrated in vacuo, diluted with ethyl acetate (500 mL) and transferred to a 1 L separatory funnel containing 400 mL of water. After separating the two layers, the aqueous layer was washed with additional ethyl acetate (2×100 mL). The combined organic layers were washed with brine (2×300 mL), dried (MgSO₄), filtered and concentrated in vacuo to afford a cloudy white solid. Chromatography on silica gel with ethyl acetate/hexanes (2/3) afforded clear oil (46.4 g, 76%) which was confirmed by ¹H-NMR and analytical LCMS. After suspending the clear oil in diethyl ether, 1.4 eqv of 4N HCl/dioxane (92.1 mL, 368.63 mmol) was added and the mixture was concentrated in vacuo affording a white solid that was carried on as is without further purification. ¹H NMR (400 MHz, DMSO-d₆) δ ppm 2.94 (t, J=6.06 Hz, 1 H) 3.54 (d, J=7.07 Hz, 2H) 3.67 (d, J=5.56 Hz, 2H) 3.73 (s, 3H) 6.88 (d, J=8.59 Hz, 2 H) 7.23 (d, J=8.59 Hz, 2H). ESI-MS: m/z 177.3 (M+H)⁺.

Compound 34

3,5-dichloro-1-(4-methoxybenzyl)pyrazin-2(1H)-one

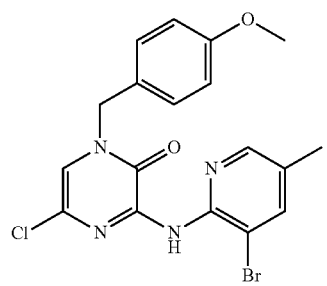

To the 1 L round bottom flask containing 2-(4-methoxybenzylamino)acetonitrile-HCl (55.6 g, 261.43 mmol), under N₂, was added chlorobenzene (414 mL) followed by oxalyl chloride (99.54 g, 784.27 mmol). After stirring at ambient temperature for 30 minutes, triethylamine-HCl (179.9 g, 1307.13 mmol) was added and mixture was allowed to stir overnight at ambient temperature. The reaction mixture was concentrated in vacuo, and the crude was taken up with DCM (700 mL) and transferred to a 2 L reparatory funnel. The organic layer was then washed with water (2×600 mL) and brine (2×500 mL). After drying (MgSO₄), the organic layer was filtered and concentrated to a clear, brown oil. Chromatography on silica gel with ethyl acetate/DCM (3/97) afforded a light yellow crystalline solid (63.1 g, 84.6%). The desired product was verified by ¹H-NMR and analytical LCMS. ¹H NMR (400 MHz, DMSO-d₆) δ ppm 3.73 (s, 3H) 5.02 (s, 2H) 6.92 (d, J=8.59 Hz, 2H) 7.36 (d, J=8.59 Hz, 2H) 8.24 (s, 1H). ESI-MS: m/z 307.2 (M+Na)⁺.

Compound 35

3-(3-bromo-5-methylpyridin-2-ylamino)-5-chloro-1-(4-methoxybenzyl)pyrazin-2(1H)-one An oven dried, 2 L, three necked round bottom flask was charged with NaH (60% dispersion in oil, 11.9 g, 298.11 mmol), suspended in anhydrous tetrahydrofuran (500 mL) and cooled in an ice bath. To the cooled mixture, was added the solution of 2-amino-3-bromo-5-methylpyridine (39.4 g, 210.433 mmol, 150 mL of anhydrous THF). The ice bath was removed and the reaction was allowed to warm to room temperature over a 1 h period. Via addition funnel, the solution of 3,5-dichloro-1-(4-methoxybenzyl)pyrazin-2(1H)-one (50.0 g, 175.36 mmol, 150 mL anhydrous tetrahydrofuran) was added in a rapid, drop-wise fashion, attached a reflux condenser and stirred in an oil bath heated at 72° C. (exothermic reaction occurred upon heating). After 3 h, the flask was removed from the oil bath, cooled to room temperature, quenched with isopropanol (15 mL) and BHT (0.075 g), and concentrated in vacuo to a dark crude. Chromatography on silica gel plug with ethyl acetate/DCM (3/97) afforded the desired product as a light tan solid. The mix fractions were combined, concentrated and the desired product was purified by recrystallization in ethyl acetate/diethyl ether and isolated by vacuum filtration. The two solid pools were combined (43 g, 56% yield) and verified by $^1$H-NMR and analytical LCMS. $^1$H NMR (400 MHz, DMSO-$d_6$) δ ppm 2.30 (s, 3H) 3.74 (s, 3H) 5.00 (s, 2H) 6.93 (d, J=8.84 Hz, 2H) 7.39 (s, 2H) 7.42 (s, 1H) 8.01 (s, 1H) 8.28 (s, 1H) 9.50 (s, 1H). ESI-MS: m/z 437.2 (M+H)$^+$.

Compound 36

5-chloro-1-(4-methoxybenzyl)-3-(5-methyl-3-((trimethylsilyl)ethynyl)pyridin-2-ylamino)pyrazin-2(1H)-one

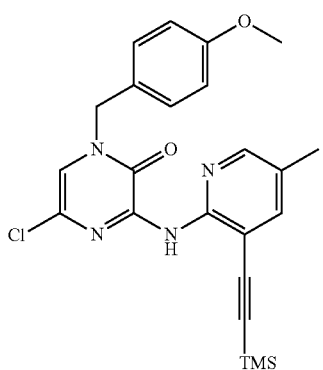

In a 1 L round bottom combined 3-(3-bromo-5-methylpyridin-2-ylamino)-5-chloro-1-(4-methoxybenzyl)pyrazin-2(1H)-one (51.90 g, 119.12 mmol), triphenylphosphine (1.56 g, 5.96 mmol), (Ph$_3$P)PdCl$_2$ (4.18 g, 5.96 mmol) and suspended in anhydrous THF (450 mL). Triethylamine (18.08 g, 178.68 mmol) and trimethylsilyl acetylene (35.10 g, 357.36 mmol) were added next and mixture was stirred at ambient temperature, under N$_2$ for 10 minutes. Copper iodide (catalytic) was added last and reaction was stirred at ambient temperature. Reaction was monitored by analytical LCMS at one hour intervals and CuI was added until reaction is complete. The completed reaction was concentrated in vacuo, taken up with ethyl acetate (700 mL) and brine (300 mL) and filtered off undissolved solids before taking on to extraction. The organic layer was washed with additional brine (4×300 mL), dried with MgSO$_4$, filtered and concentrated in vacuo. Chromatography on silica gel plug with ethyl acetate/hexanes (1/9), two attempts, afforded the desired product (43.36 g, 81% yield). $^1$H NMR (400 MHz, DMSO-$d_6$) δ ppm 0.11 (s, 9H) 2.26 (s, 3H) 3.73 (s, 3H) 5.00 (s, 2H) 6.91 (d, J=8.59 Hz, 2H) 7.38 (d, J=8.59 Hz, 2H) 7.45 (s, 1H) 7.74 (d, J=2.27 Hz, 1H) 8.25 (d, J=2.27 Hz, 1H) 9.51 (s, 1H). ESI-MS: m/z 453.3 (M+H)$^+$.

Compound 37

7-(4-methoxybenzyl)-3-methyl-5-trimethylsilyl-7,9-dihydro-8H-pyrido[4',3':4,5]pyrrolo[2,3-b]pyridin-8-one

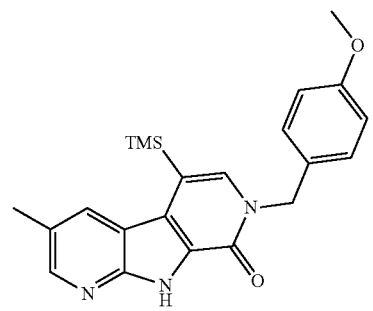

In a 2 L round bottom flask, 5-chloro-1-(4-methoxybenzyl)-3-(5-methyl-3-((trimethylsilyl)ethynyl)pyridin-2-ylamino)pyrazin-2(1H)-one (35.2 g, 77.85 mmol) was taken up with anhydrous toluene (880 mL), attached a reflux condenser and transferred to an oil bath that was heated to 130° C. The reaction was stirred in the oil bath for 94 h and concentrated in vacuo to afford a brown solid. The crude was suspended in ethyl acetate (200 mL) and heated to a mild boil. The solids were collected by filtration, washed with additional ethyl acetate, diethyl ether and dried in vacuo to provide the title compound as a pale yellow powder (27.4 g, 89%). $^1$H NMR (400 MHz, CHLOROFORM-d) δ ppm 0.43 (s, 9H) 2.56 (s, 3H) 3.80 (s, 3H) 5.30 (s, 2H) 6.89 (d, J=8.59 Hz, 2H) 7.11 (s, 1H) 7.35 (d, J=8.84 Hz, 2H) 8.22 (s, 1H) 8.52 (d, J=1.52 Hz, 1H). ESI-MS: m/z 392.4 (M+H)$^+$.

Compound 38

5-iodo-7-(4-methoxybenzyl)-3-methyl-7,9-dihydro-8H-pyrido[4',3':4,5]pyrrolo[2,3-b]pyridin-8-one.

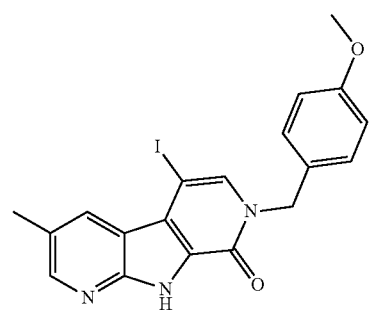

In a 2 L round bottom flask, 7-(4-methoxybenzyl)-3-methyl-5-trimethylsilyl-7,9-dihydro-8H-pyrrolo[4',3':4,5]pyrrolo[2,3-b]pyridin-8-one (18.6 g, 47.505 mmol) was suspended in ethanol (1 L) and DCM (150 mL), then cooled in an ice bath. To the cooled mixture was added silver tetrafluoroborate (AgBF$_4$, 10.17 g, 52.3 mmol) and after 15 minutes of stirring, iodine (18.08 g, 71.3 mmol) was added. The reaction was stirred at 0° C. for one hour followed by five hours at ambient temperature. The crude yellow solid was collected by filtration, suspended in 10% wt Na$_2$S$_2$O$_3$ (700 mL) and stirred for 1 h. The solid was collected by filtration and again washed with 10% wt Na$_2$S$_2$O$_3$. The product (light yellow solid) was collected by filtration, washed with water and diethyl ether and dried under high vacuum. The material was taken forward without further purification. $^1$H NMR (400 MHz, CHLOROFORM-d) δ ppm 2.59 (s, 3H) 3.81 (s, 3H) 5.26 (s, 2H) 6.90 (d, J=8.84 Hz, 2H) 7.34 (d, J=8.59 Hz, 2H) 7.44 (s, 1H) 8.51 (s, 1H) 8.92 (s, 1H). ESI-MS: m/z 446.2 (M+H)$^+$.

Compound 39

5-[3-(ethylsulfonyl)phenyl]-7-(4-methoxybenzyl)-3-methyl-7,9-dihydro-8H-pyrido[4',3':4,5]pyrrolo[2,3-b]pyridin-8-one

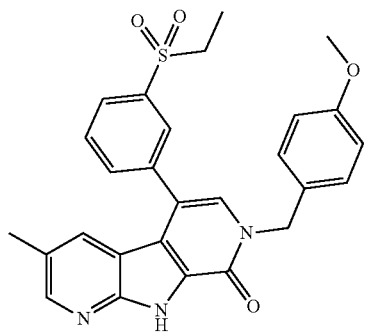

In an appropriate microwave reaction vessel was placed, 5-iodo-7-(4-methoxybenzyl)-3-methyl-7,9-dihydro-8H-pyrido[4',3':4,5]pyrrolo[2,3-b]pyridin-8-one (8.0 g, 17.967 mmol), 3-(ethylsulfonyl)phenyl boronic acid (4.62 g, 21.6 mmol), and Tetrakis(triphenylphosphine)Pd(0) (6.23 g, 5.4 mmol). The solids were then suspended in a dioxane/saturated K$_2$CO$_3$ solution (40.0 mL, 4/1) and the mixture was heated in a large scale CEM microwave for 20 minutes at 150° C. The reaction mixture was diluted with DCM (400 mL), then filtered off undissolved solids. The organic layer was washed with brine (300 mL), dried with MgSO$_4$, filtered and concentrated in vacuo affording an orange solid. The crude solid was washed with a hot ethyl acetate/hexanes solution (400 mL, 1/1) followed by a hot ethanol/DCM solution (400 mL, 4/1). The product was isolated by filtration, washed with ether and dried under vacuum affording an off-white solid. (6.83 g, 78%) $^1$H NMR (400 MHz, CHLOROFORM-d) δ ppm 1.36 (t, J=7.45 Hz, 3H) 2.44 (s, 3H) 3.20 (q, J=7.33 Hz, 2H) 3.80 (s, 3H) 5.37 (s, 2H) 6.90 (d, J=8.59 Hz, 2H) 7.16 (s, 1H) 7.37 (d, J=8.59 Hz, 3H) 7.75 (t, J=7.71 Hz, 1H) 7.78-7.87 (m, 2H) 8.03 (d, J=7.58 Hz, 1H) 8.12 (s, 1H) 8.43 (s, 1H). ESI-MS: m/z 488.3 (M+H)$^+$.

Compound 40

8-chloro-5-[3-(ethylsulfonyl)phenyl]-3-methyl-9H-pyrido[4',3':4,5]pyrrolo[2,3-b]pyridine

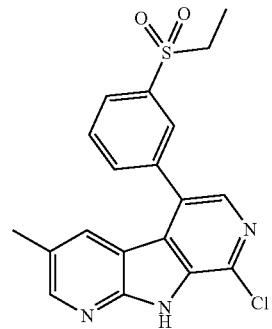

A 500 mL round bottom flask equipped with an N$_2$ inlet and reflux condenser was charged with 5-[3-(ethylsulfonyl)phenyl]-7-(4-methoxybenzyl)-3-methyl-7,9-dihydro-8H-pyrido[4',3':4,5]pyrrolo[2,3-b]pyridin-8-one (19.3 g, 39.6 mmol), tetramethylammonium chloride (4.77 g, 43.542 mmol), and POCl$_3$ (249.5 g, 1626.9 mmol) at room temperature, transferred to an oil bath and heated at 100° C. The reaction was monitored by HPLC, and determined to be complete after 2 h. The mixture was allowed to cool to ambient temperature. A separate 3 neck, 3 L flask was fitted with a cold thermometer, and two addition funnels. To this flask was added a solution of 33% by weight aqueous K$_3$PO$_4$ (1500 mL), cooled in a dry ice/acetone bath, followed by the drop-wise addition of the aryl chloride suspension. The internal temperature was kept between 5 to 20° C. and the pH was carefully monitored and maintained at 11.5 during the quench using a slow addition of 10M KOH when necessary. The suspension was allowed to stir for 10 min at 5° C. after the addition was complete, and at ambient temperature for 2 h. The crude product was extracted from the aqueous layer with DCM (5×500 mL), dried with MgSO$_4$, filtered and concentrated in vacuo to a total volume of about 500 mL. The solution was allowed to sit at ambient temperature overnight. The precipitate was collected by filtration, washed with additional DCM and dried, affording a light grey solid (9.79 g) which was confirmed by analytical LCMS and $^1$H-NMR as the free base. The DCM mother liquor was concentrated and taken up with a methanol/DCM mixture (300 mL, 15/85). To the light green solution was slowly added 30 mL 4N HCl in dioxane and the mixture were stirred for one hour at ambient temperature. 1200 mL of MTBE was slowly added and the resultant suspension was filtered. Chromatography on silica gel plug with methanol/DCM (3/97) afforded a yellow solid. The solid was washed with warm methanol (30 mL) and the resulting product was collected by filtration and washed with diethyl ether, affording an additional 1.7 g of the product as a free base. (9.79+1.7=11.49 g, 75% yield). $^1$H NMR (400 MHz, DMSO-d$_6$) δ ppm 1.18 (t, J=7.33 Hz, 3H) 2.32 (s, 3H) 3.44 (q, J=7.33 Hz, 2H) 7.70 (d, J=1.26 Hz, 1H) 7.93 (t, J=7.71 Hz, 1H) 8.04-8.15

(m, 2H) 8.21 (d, J=10.61 Hz, 2H) 8.53 (d, J=1.52 Hz, 1H) 12.78 (br. s., 1H). ESI-MS: m/z 386.3 (M+H)+.

Compound 41

N'[5-(3-Ethanesulfonyl-phenyl)-3-methyl-9H-dipyrido[2,3-b; 4',3'-d]pyrrol-8-yl]-N,N-dimethyl-propane-1,3-diamine

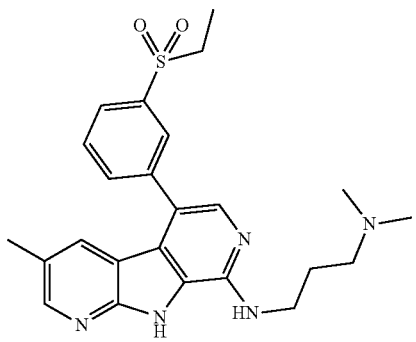

Compound 40 (16 mg, 0.041 mmol) was heated with 3-dimethylamino-1-propylamine (1 mL) at 206° C. in the microwave for 30 min. Purification by prep-HPLC provided the title compound as a pale yellow solid (10.2 mg, 55%). ¹H NMR (400 MHz, MeOD-d₄): δ 8.65 (br s, 1H), 8.17 (s, 1H), 8.12 (d, 1H, J=7.6 Hz), 7.98 (d, 1H, J=7.6 Hz), 7.91 (t, 1H, J=7.6 Hz), 7.67 (s, 1H), 7.66 (s, 1H), 3.80 (t, 2H, J=6.8 Hz), 3.28-3.43 (m, 4H), 2.96 (s, 6H), 2.29-2.38 (m, 5H), 1.28 (t, 3H, J=7.2 Hz). MS (ES) [m+H] calc'd for C₂₄H₂₉N₅O₂S, 452; found 452.

Compound 42

N'-[5-(3-Ethanesulfonyl-phenyl)-3-methyl-9H-dipyrido[2,3-b; 4',3'-d]pyrrol-8-yl]-N,N-dimethyl-ethane-1,2-diamine

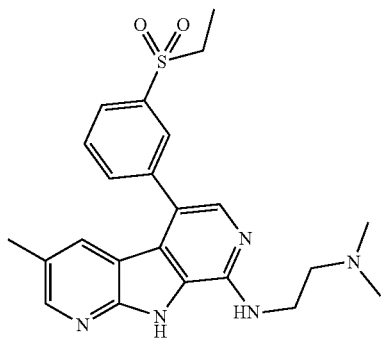

The title compound was prepared in 77% yield using N,N-dimethylethylenediamine in the procedure outlined for the preparation of Compound 41. ¹H NMR (400 MHz, MeOD-d₄): δ 8.53 (br s, 1H), 8.15 (s, 1H), 8.12 (d, 1H, J=7.6 Hz), 7.97 (d, 1H, J=7.6 Hz), 7.88 (t, 1H, J=7.6 Hz), 7.73 (s, 1H), 7.72 (s, 1H), 4.11 (t, 2H, J=5.6 Hz), 3.66 (t, 2H, J=5.6 Hz), 3.32 (q, 2H, J=7.2 Hz), 3.06 (s, 6H), 2.37 (s, 3H), 1.29 (t, 3H, J=7.6 Hz). MS (ES) [m+H] calc'd for C₂₃H₂₇N₅O₂S, 438; found 438.

Compound 43

[5-(3-Ethanesulfonyl-phenyl)-3-methyl-9H-dipyrido[2,3-b; 4',3'-d]pyrrol-8-yl]-(3-morpholin-4-yl-propyl)-amine

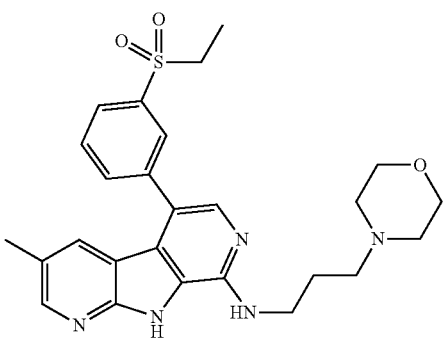

The title compound was prepared in 81% yield using 1-(3-aminopropyl)-morpholine in the procedure outlined for the preparation of Compound 41. ¹H NMR (400 MHz, MeOD-d₄): δ 8.52 (s, 1H), 8.18 (s, 1H), 8.14 (d, 1H, J=7.6 Hz), 7.99 (d, 1H, J=7.6 Hz), 7.90 (t, 1H, J=7.6 Hz), 7.66 (s, 1H), 7.65 (s, 1H), 3.82-4.03 (m, 4H), 3.81 (t, 2H, J=6.4 Hz), 3.20-3.55 (m, 8H), 2.32-2.40 (m, 5H), 1.29 (t, 3H, J=7.2 Hz). MS (ES) [m+H] calc'd for C₂₆H₃₁N₅O₃S, 494; found 494.

Compound 44

[5-(3-Ethanesulfonyl-phenyl)-3-methyl-9H-dipyrido[2,3-b; 4',3'-d]pyrrol-8-yl]-(1-methyl-piperidin-4-yl)-amine

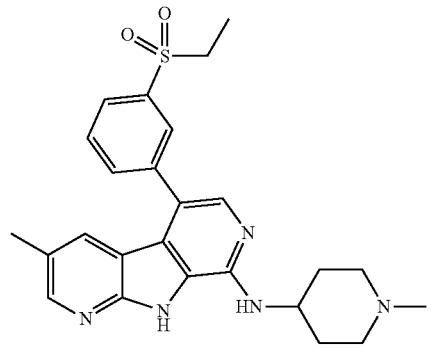

The title compound was prepared in 31% yield using 4-amino-1-methyl-piperidine in the procedure outlined for the preparation of Compound 41. ¹H NMR (400 MHz, MeOD-d₄): δ 8.53 (br s, 1H), 8.19 (s, 1H), 8.13 (d, 1H, J=7.6 Hz), 8.01 (d, 1H, J=7.6 Hz), 7.90 (t, 1H, J=7.6 Hz), 7.72 (s, 1H), 7.67 (s, 1H), 4.23-4.31 (m, 1H), 3.69-3.77 (m, 2H), 3.20-3.38 (m, 4H), 2.97 (s, 3H), 2.46-2.54 (m, 2H), 2.36 (s, 3H), 2.01-2.15 (m, 2H), 1.29 (t, 3H, J=7.2 Hz). MS (ES) [m+H] calc'd for C25H29N5O2S, 464; found 464.

Compound 45

2-[5-(3-Ethanesulfonyl-phenyl)-3-methyl-9H-dipyrido[2,3-b; 4',3'-d]pyrrol-8-ylamino]-ethanol

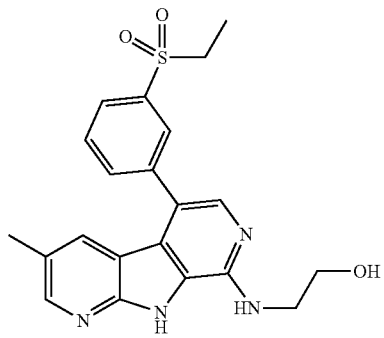

The title compound was prepared in 88% yield using ethanolamine in the procedure outlined for the preparation of Compound 41. ¹H NMR (400 MHz, MeOD-d4): δ 8.51 (s, 1H), 8.20 (s, 1H), 8.13 (d, 1H, J=7.6 Hz), 8.00 (d, 1H, J=7.6 Hz), 7.90 (t, 1H, J=7.6 Hz), 7.64 (s, 1H), 7.63 (s, 1H), 3.99 (t, 2H, J=4.8 Hz), 3.82 (t, 2H, J=4.8 Hz), 3.33 (q, 2H, J=7.2 Hz), 2.35 (s, 3H), 1.29 (t, 3H, J=7.2 Hz). MS (ES) [m+H] calc'd for C21H22N4O3S, 411; found 411.

Compound 46

[5-(3-Ethanesulfonyl-phenyl)-3-methyl-9H-dipyrido[2,3-b; 4',3'-d]pyrrol-8-yl]-(1-methyl-piperidin-4-ylmethyl)-amine

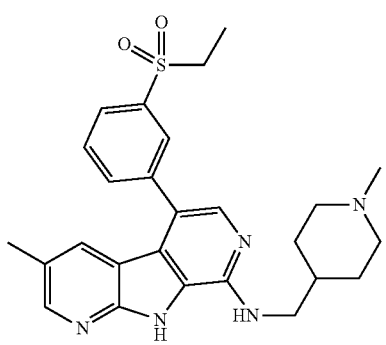

The title compound was prepared in 55% yield using 4-aminomethyl-1-methyl-piperidine in the procedure outlined for the preparation of Compound 41. ¹H NMR (400 MHz, MeOD-d4): δ 8.55 (s, 1H), 8.22 (s, 1H), 8.16 (d, 1H, J=7.6 Hz), 8.03 (d, 1H, J=7.6 Hz), 7.94 (t, 1H, J=7.6 Hz), 7.69 (s, 1H), 7.68 (s, 1H), 3.60-3.70 (m, 4H), 3.33 (q, 2H, J=7.2 Hz), 3.03-3.12 (m, 2H), 2.92 (s, 3H), 2.39 (s, 3H), 2.21-2.30 (m, 3H), 1.69-1.79 (m, 2H), 1.31 (t, 3H, J=7.2 Hz). MS (ES) [m+H] calc'd for C26H31N5O2S, 478; found 478.

Compound 47

5-(3-Ethanesulfonyl-phenyl)-3,8-dimethyl-9H-dipyrido[2,3-b; 4',3'-d]pyrrole

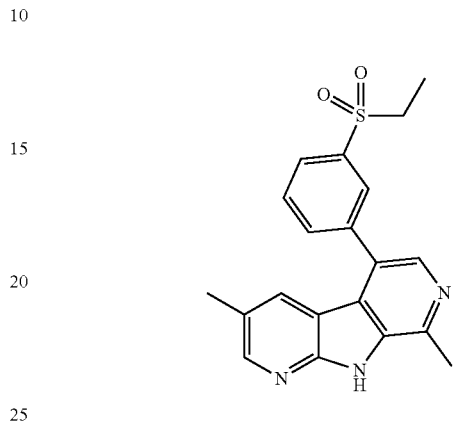

Trimethylaluminum (2.0 M, 70 μL, 0.14 mmol) was added to a solution of Compound 40 (9.0 mg, 0.023 mmol) and tetrakis(triphenylphosphine)palladium (0) (13.3 mg, 0.012 mmol) in dioxane (1 mL) under nitrogen in sealed tube. The reaction was heated at 120° C. in the microwave for 20 min and then concentrated in vacuo. Purification by prep-HPLC provided the title compound as a pale yellow solid (8.2 mg, 96%). ¹H NMR (400 MHz, MeOD-d4): δ 8.68 (s, 1H), 8.43 (s, 1H), 8.32 (s, 1H), 8.21 (d, 1H, J=7.6 Hz), 8.11 (d, 1H, J=7.6 Hz), 7.97 (t, 1H, J=7.6 Hz), 7.81 (s, 1H), 3.34 (q, 2H, J=7.2 Hz), 3.14 (s, 3H), 2.39 (s, 3H), 1.29 (t, 3H, J=7.2 Hz). MS (ES) [m+H] calc'd for C20H19N3O2S, 366; found 366.

Compound 48

5-(3-Ethanesulfonyl-phenyl)-8-ethyl-3-methyl-9H-dipyrido[2,3-b; 4',3'-d]pyrrole

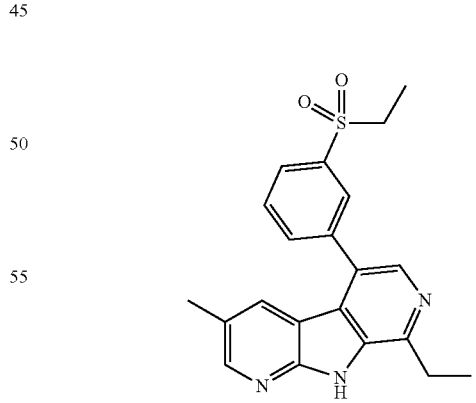

The title compound was prepared in 68% yield using triethylaluminum in the procedure outlined for the preparation of Compound 47. ¹H NMR (400 MHz, MeOD-d4): δ 8.69 (s, 1H), 8.42 (s, 1H), 8.31 (s, 1H), 8.21 (d, 1H, J=7.6 Hz), 8.12 (d, 1H, J=7.6 Hz), 7.98 (t, 1H, J=7.6 Hz), 7.80 (s, 1H), 3.51 (q, 2H, J=7.6 Hz), 3.33 (q, 2H, J=7.2 Hz), 2.39 (s, 3H), 1.57 (t, 3H, J=7.6 Hz), 1.29 (t, 3H, J=7.2 Hz). MS (ES) [m+H] calc'd for $C_{21}H_{21}N_3O_2S$, 380; found 380.

Compound 49

5-(3-Ethanesulfonyl-phenyl)-3-methyl-9H-dipyrido[2,3-b; 4',3'-d]pyrrole-8-carbonitrile

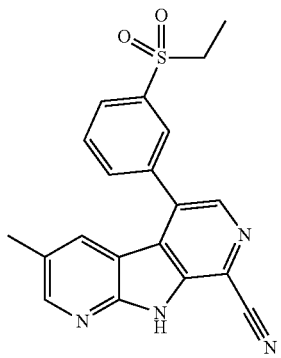

Zinc cyanide (5.0 mg, 0.037 mmol) was added to a solution of Compound 40 (12.0 mg, 0.031 mmol) and tetrakis(triphenylphosphine)palladium(0) (11 mg, 0.009 mmol) in DMF (1 mL) under nitrogen in sealed tube. The reaction was heated at 160° C. in the microwave for 30 min and then concentrated in vacuo. Purification by prep-HPLC provided the title compound as a pale yellow solid (10 mg, 86%). $^1$H NMR (400 MHz, MeOD-$d_4$): δ 8.76 (br s, 1H), 8.48 (s, 1H), 8.26 (s, 1H), 8.16 (d, 1H, J=7.6 Hz), 8.02 (d, 1H, J=7.6 Hz), 7.91 (t, 1H, J=7.6 Hz), 7.81 (s, 1H), 3.29 (q, 2H, J=7.2 Hz), 2.40 (s, 3H), 1.35 (t, 3H, J=7.2 Hz). MS (ES) [m+H] calc'd for $C_{20}H_{16}N_4O_2S$, 377; found 377.

Compound 50

5-(3-Ethanesulfonyl-phenyl)-3-methyl-9H-dipyrido[2,3-b; 4',3'-d]pyrrole-8-carboxylic acid amide

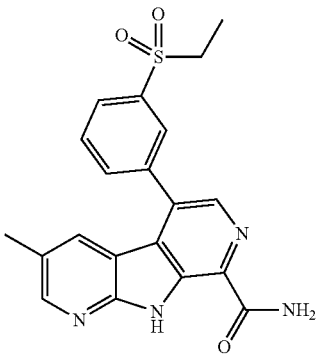

To a stirred solution of Compound 49 (10 mg, 0.027 mmol) in THF (1 mL) was added a solution of KOH (25 mg, 0.44 mmol) and 30% $H_2O_2$ (0.5 mL). The reaction was stirred for 3 h at r.t. Purification by prep-HPLC provided the title compound as an off-white solid (8.2 mg, 77%). $^1$H NMR (400 MHz, MeOD-$d_4$): δ 8.49 (br s, 1H), 8.41 (s, 1H), 8.26 (s, 1H), 8.15 (d, 1H, J=7.6 Hz), 8.06 (d, 1H, J=7.6 Hz), 7.92 (t, 1H, J=7.6 Hz), 7.85 (s, 1H), 3.32 (q, 2H, J=7.2 Hz), 2.39 (s, 3H), 1.31 (t, 3H, J=7.6 Hz). MS (ES) [m+H] calc'd for $C_{20}H_{18}N_4O_3S$, 395; found 395.

Compound 51

5-(3-Ethanesulfonyl-phenyl)-8-ethoxy-3-methyl-9H-dipyrido[2,3-b; 4',3'-d]pyrrole

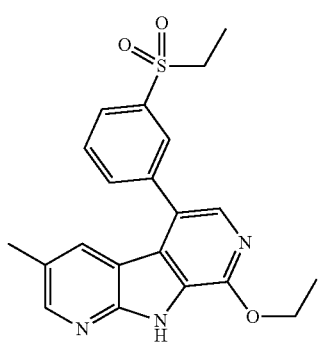

Compound 40 (4 mg, 0.01 mmol) was heated in a solution of sodium ethoxide in ethanol (21 wt. %, 0.5 mL) at 200° C. in the microwave for 30 min. Purification by prep-HPLC provided the title compound as a pale yellow solid (3.2 mg, 78%). $^1$H NMR (400 MHz, MeOD-$d_4$): δ 8.47 (br s, 1H), 8.18 (s, 1H), 8.03 (d, 1H, J=7.6 Hz), 7.96 (d, 1H, J=7.6 Hz), 7.81-7.89 (m, 3H), 4.63 (q, 2H, J=7.2 Hz), 3.26 (q, 2H, J=7.2 Hz), 2.38 (s, 3H), 1.56 (t, 3H, J=7.6 Hz), 1.32 (t, 3H, J=7.6 Hz). MS (ES) [m+H] calc'd for $C_{21}H_{21}N_3O_3S$, 396; found 396.

Compound 52

{3-[5-(3-Ethanesulfonyl-phenyl)-3-methyl-9H-dipyrido[2,3-b; 4',3'-d]pyrrol-8-yloxy]-propyl}-dimethylamine

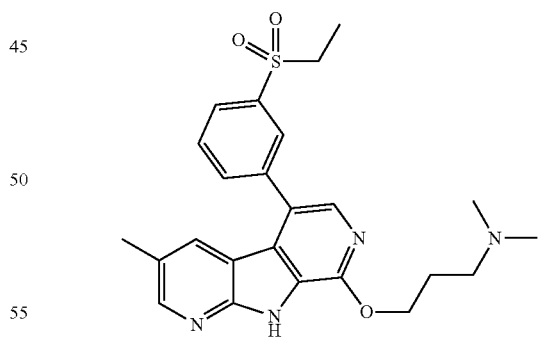

3-Dimethylamino-1-propanol (100 mL, 0.84 mmol) was added to a solution of sodium hydride (60%, 34 mg, 0.84 mmol) in dry dioxane (1 mL) under nitrogen. After stirring for 20 min, Compound 40 (30 mg, 0.11 mmol) was added, and the reaction stirred at 180° C. in the microwave for 1 h. The solution was concentrated and purified by prep-HPLC to provide the title compound as a pale yellow solid (30 mg, 69%). $^1$H NMR (400 MHz, MeOD-$d_4$): δ 8.42 (br s, 1H), 8.24 (s, 1H), 8.10 (d, 1H, J=7.6 Hz), 8.03 (d, 1H, J=7.6 Hz), 7.90 (t, 1H, J=7.6 Hz), 7.89 (s, 1H), 7.82 (s, 1H), 4.75 (t, 2H, J=5.6

Hz), 3.46-3.54 (m, 2H), 3.34 (q, 2H, J=7.2 Hz), 3.01 (s, 6H), 2.38-2.46 (m, 2H), 2.38 (s, 3H), 1.32 (t, 3H, J=7.6 Hz). MS (ES) [m+H] calc'd for $C_{24}H_{28}N_4O_3S$, 453; found 453.

Compound 53

2-[5-(3-Ethanesulfonyl-phenyl)-3-methyl-9H-dipyrido[2,3-b; 4',3'-d]pyrrol-8-yloxy]-ethanol

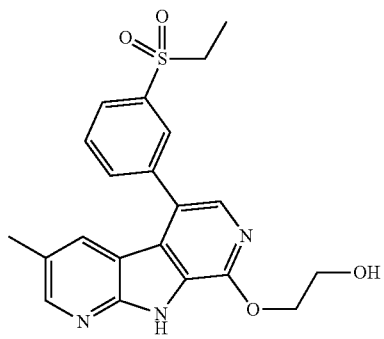

The title compound was prepared in 18% yield using ethylene glycol in the procedure outlined for the preparation of Compound 52. $^1$H NMR (400 MHz, MeOD-d$_4$): δ 8.47 (br s, 1H), 8.19 (s, 1H), 8.02-8.09 (m, 2H), 7.97 (d, 1H, J=7.6 Hz), 7.94 (s, 1H), 7.88 (t, 1H, J=7.6 Hz), 4.68 (t, 2H, J=4.8 Hz), 4.05 (t, 2H, J=4.8 Hz), 3.31 (q, 2H, J=7.2 Hz), 2.41 (s, 3H), 1.29 (t, 3H, J=7.6 Hz). MS (ES) [m+H] calc'd for $C_{21}H_{21}N_3O_4S$, 412; found 412.

Compound 54

5-(3-Ethanesulfonyl-phenyl)-3-methyl-8-(1-methyl-piperidin-4-ylmethoxy)-9H-dipyrido[2,3-b; 4',3'-d]pyrrole

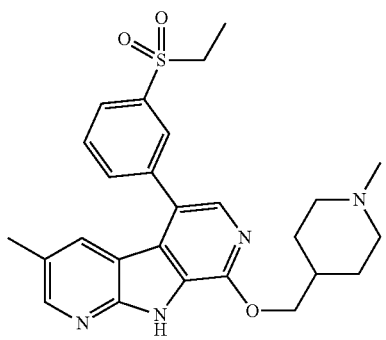

The title compound was prepared in 78% yield using 1-methyl-piperidine-3-methanol in the procedure outlined for the preparation of Compound 52. $^1$H NMR (400 MHz, MeOD-d$_4$): δ 8.42 (br s, 1H), 8.20 (s, 1H), 8.06 (d, 1H, J=7.6 Hz), 7.99 (d, 1H, J=7.6 Hz), 7.81-7.89 (m, 3H), 4.51 (d, 2H, J=6.4 Hz), 3.57-3.63 (m, 2H), 3.32 (q, 2H, J=7.2 Hz), 3.02-3.13 (m, 2H), 2.90 (s, 3H), 2.36 (s, 3H), 2.24-2.32 (m, 3H), 1.61-1.73 (m, 2H), 1.29 (t, 3H, J=7.2 Hz). MS (ES) [m+H] calc'd for $C_{26}H_{30}N_4O_3S$, 479; found 479.

Compound 55

3-[5-(3-Ethanesulfonyl-phenyl)-3-methyl-9H-dipyrido[2,3-b; 4',3'-d]pyrrol-8-yloxy]-propan-1-ol

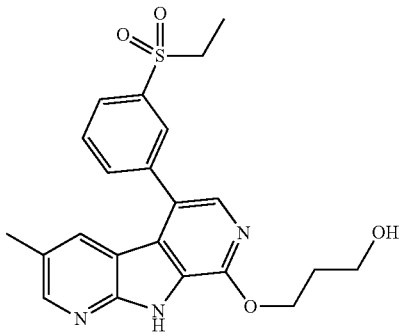

The title compound was prepared in 30% yield using 1,3-propanediol in the procedure outlined for the preparation of Compound 52. $^1$H NMR (400 MHz, MeOD-d$_4$): δ 8.52 (br s, 1H), 8.23 (s, 1H), 8.09 (d, 1H, J=7.6 Hz), 7.96-8.03 (m, 2H), 7.93 (s, 1H), 7.89 (t, 1H, J=7.6 Hz), 4.75 (t, 2H, J=6.4 Hz), 3.88 (t, 2H, J=6.4 Hz), 3.34 (q, 2H, J=7.2 Hz), 2.41 (s, 3H), 2.16-2.22 (m, 2H), 1.32 (t, 3H, J=7.2 Hz). MS (ES) [m+H] calc'd for $C_{22}H_{23}N_3O_4S$, 426; found 426.

Compound 56

(R)-2-[5-(3-Ethanesulfonyl-phenyl)-3-methyl-9H-dipyrido[2,3-b; 4',3'-d]pyrrol-8-yloxymethyl]-propane-1,3-diol

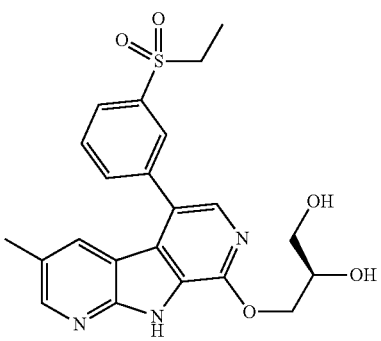

The title compound was prepared in 68% yield using (S)-2,2-dimethyl-1,3-dioxolane-4-methanol in the procedure outlined for the preparation of Compound 52, followed by deprotection in TFA/H$_2$O/THF (1:1:5) for 3 h. $^1$H NMR (400 MHz, DMSO-d$_6$): δ 12.37 (s, 1H), 8.42 (s, 1H), 8.14 (s, 1H), 7.96-8.04 (m, 2H), 7.80-7.88 (m, 2H), 7.69 (s, 1H), 4.40-4.90 (m, 4H), 3.91-3.99 (m, 1H), 3.52-3.60 (m, 2H), 3.55 (q, 2H, J=7.2 Hz), 2.29 (s, 3H), 1.18 (t, 3H, J=7.2 Hz). MS (ES) [m+H] calc'd for $C_{22}H_{23}N_3O_5S$, 442; found 442.

Compound 57

(S)-2-[5-(3-Ethanesulfonyl-phenyl)-3-methyl-9H-dipyrido[2,3-b; 4',3'-d]pyrrol-8-yloxymethyl]-propane-1,3-diol

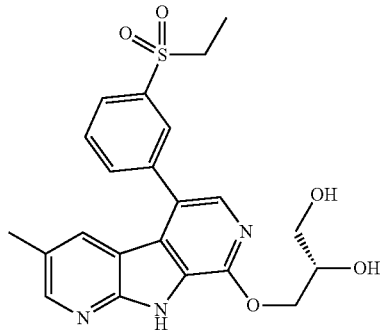

The title compound was prepared in 65% yield using (R)-2,2-dimethyl-1,3-dioxolane-4-methanol in the procedure outlined for the preparation of Compound 52, followed by deprotection in TFA/H$_2$O/THF (1:1:5) for 3 h. $^1$H NMR (400 MHz, DMSO-d$_6$): δ 12.37 (s, 1H), 8.42 (s, 1H), 8.14 (s, 1H), 7.96-8.04 (m, 2H), 7.80-7.88 (m, 2H), 7.69 (s, 1H), 4.40-4.90 (m, 4H), 3.91-3.99 (m, 1H), 3.52-3.60 (m, 2H), 3.55 (q, 2H, J=7.2 Hz), 2.29 (s, 3H), 1.18 (t, 3H, J=7.2 Hz). MS (ES) [m+H] calc'd for $C_{22}H_{23}N_3O_5S$, 442; found 442.

Compound 58

1-[5-(3-Ethanesulfonyl-phenyl)-3-methyl-9H-dipyrido[2,3-b; 4',3'-d]pyrrol-8-yloxy]-2-methyl-propan-2-ol

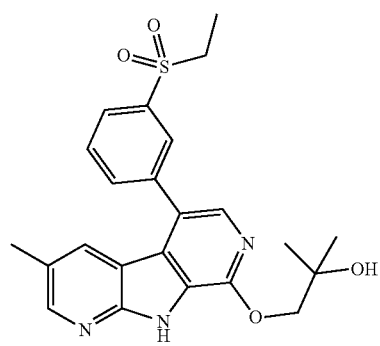

The title compound was prepared in 16% yield using 2-benzyloxy-2-methyl-1-propanol (see Fleming, et. al., Can. J. Chem., 52, (1974), 888-892) in the procedure outlined for the preparation of compound 52, followed by benzyl deprotection by hydrogenation at 1 atm with 10% Pd/C in MeOH for 1 h. $^1$H NMR (400 MHz, DMSO-d$_6$): δ 12.40 (s, 1H), 8.45 (s, 1H), 8.15 (s, 1H), 7.98-8.05 (m, 2H), 7.82-7.89 (m, 2H), 7.71 (s, 1H), 4.27 (s, 2H), 3.40 (q, 2H, J=7.2 Hz), 2.31 (s, 3H), 1.30 (s, 6H), 1.17 (t, 3H, J=7.2 Hz). MS (ES) [m+H] calc'd for $C_{23}H_{25}N_3O_4S$, 440; found 440.

Compound 59

5-(3-Ethanesulfonyl-phenyl)-3-methyl-8-phenoxy-9H-dipyrido[2,3-b; 4',3'-d]pyrrole

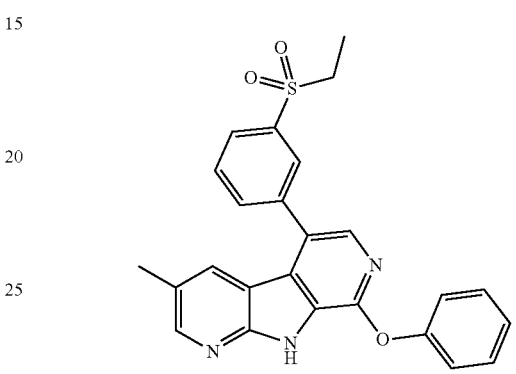

The title compound was prepared in 30% yield using phenol in the procedure outlined for the preparation of Compound 52. $^1$H NMR (400 MHz, MeOD-d$_4$): δ 8.40 (br s, 1H), 8.18 (s, 1H), 8.03 (d, 1H, J=7.6 Hz), 7.92 (d, 1H, J=7.6 Hz), 7.77-7.85 (m, 3H), 7.40-7.48 (m, 2H), 7.21-7.29 (m, 3H), 3.21 (q, 2H, J=7.2 Hz), 2.38 (s, 3H), 1.31 (t, 3H, J=7.2 Hz). MS (ES) [m+H] calc'd for $C_{25}H_{21}N_3O_3S$, 444; found 444.

Compound 60

5-(3-Ethanesulfonyl-phenyl)-3-methyl-8-(thiazol-5-ylmethoxy)-9H-dipyrido[2,3-b; 4',3'-d]pyrrole

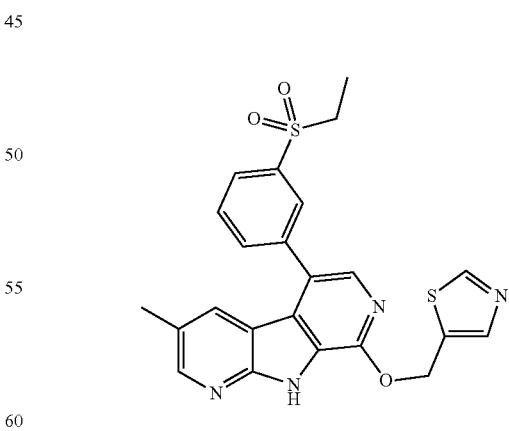

The title compound was prepared in 20% yield using thiazole-5-methanol in the procedure outlined for the preparation of Compound 52. $^1$H NMR (400 MHz, MeOD-d$_4$): δ 8.98 (br s, 1H), 8.34 (br s, 1H), 8.19 (s, 1H), 7.96-8.07 (m, 3H), 7.90 (s, 1H), 7.80-7.87 (m, 2H), 5.91 (s, 2H), 3.26 (q, 2H, J=7.2

Hz), 2.35 (s, 3H), 1.32 (t, 3H, J=7.2 Hz). MS (ES) [m+H] calc'd for $C_{23}H_{20}N_4O_3S_2$, 465; found 465.

Compound 61

5-(3-Ethanesulfonyl-phenyl)-8-(1-ethyl-piperidin-4-ylmethoxy)-3-methyl-9H-dipyrido[2,3-b; 4',3'-d]pyrrole

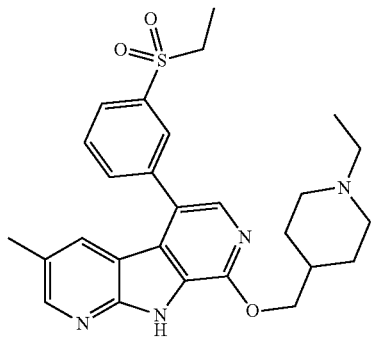

The title compound was prepared in 24% yield using 1-ethyl-piperidine-3-methanol in the procedure outlined for the preparation of Compound 52. $^1$H NMR (400 MHz, MeOD-d$_4$): δ 8.49 (br s, 1H), 8.20 (s, 1H), 8.03-8.10 (m, 2H), 7.99 (d, 1H, J=7.6 Hz), 7.95 (s, 1H), 7.89 (t, 1H, J=7.6 Hz), 4.56 (d, 2H, J=6.4 Hz), 3.65-3.73 (m, 2H), 3.21-3.36 (m, 4H), 3.02-3.12 (m, 2H), 2.43 (s, 3H), 2.24-2.40 (m, 3H), 1.80-1.90 (m, 2H), 1.43 (t, 3H, J=7.2 Hz), 1.31 (t, 3H, J=7.2 Hz). MS (ES) [m+H] calc'd for $C_{27}H_{32}N_4O_3S$, 493; found 493.

Compound 62

(S)-1-[5-(3-Ethanesulfonyl-phenyl)-3-methyl-9H-dipyrido[2,3-b; 4',3'-d]pyrrol-8-yloxy]-propan-2-ol

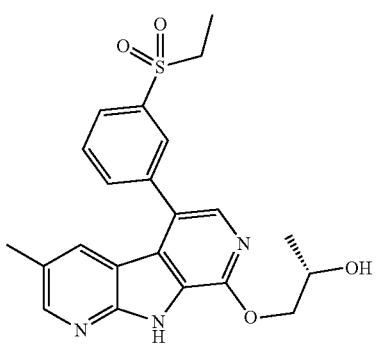

The title compound was prepared in 13% yield using (S)-2-benzyloxy-1-propanol (see Mislow, et. al., *J. Am. Chem. Soc.*, 82, (1960), 5512-5513) in the procedure outlined for the preparation of Compound 52, followed by benzyl deprotection by hydrogenation at 1 atm with 10% Pd/C in MeOH for 1 h. $^1$H NMR (400 MHz, MeOD-d$_4$): δ 8.43 (br s, 1H), 8.21 (s, 1H), 8.09 (d, 1H, J=7.6 Hz), 8.02 (d, 1H, J=7.6 Hz), 7.82-7.90 (m, 3H), 4.29-4.59 (m, 3H), 3.36 (q, 2H, J=7.6 Hz), 2.39 (s, 3H), 1.38 (d, 3H, J=6.4 Hz), 1.30 (t, 3H, J=7.6 Hz). MS (ES) [m+H] calc'd for $C_{22}H_{23}N_3O_4S$, 426; found 426.

Compound 63

(R)-1-[5-(3-Ethanesulfonyl-phenyl)-3-methyl-9H-dipyrido[2,3-b; 4',3'-d]pyrrol-8-yloxy]-propan-2-ol

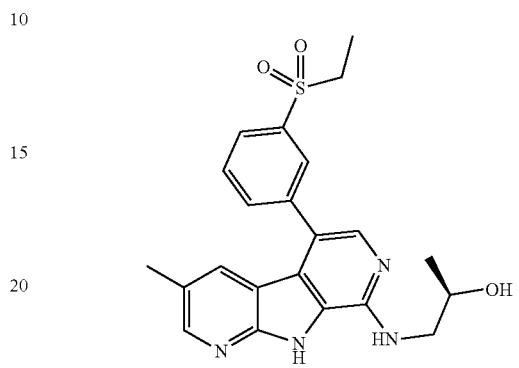

The title compound was prepared in 56% yield using (S)-2-benzyloxy-1-propanol (see Mulzer, et. al., *Tetrahedron Lett.*, 24, (1983), 2843-2846) in the procedure outlined for the preparation of Compound 52, followed by benzyl deprotection by hydrogenation at 1 atm with 10% Pd/C in MeOH for 1 h. $^1$H NMR (400 MHz, DMSO-d$_6$): δ 12.40 (s, 1H), 8.44 (s, 1H), 8.16 (s, 1H), 8.00-8.07 (m, 2H), 7.85-7.92 (m, 2H), 7.71 (s, 1H), 4.30-4.40 (m, 2H), 4.08-4.15 (m, 1H), 3.43 (q, 2H, J=7.2 Hz), 2.31 (s, 3H), 1.26 (d, 3H, J=6.4 Hz), 1.18 (t, 3H, J=7.2 Hz). MS (ES) [m+H] calc'd for $C_{22}H_{23}N_3O_4S$, 426; found 426.

Compound 64

L-Valine-2-[5-(3-ethanesulfonyl-phenyl)-3-methyl-9H-dipyrido[2,3-b; 4',3'-d]pyrrol-8-yloxy]-ethyl ester

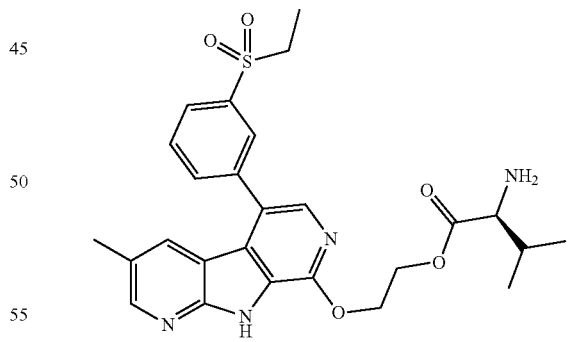

BOC-L-valine (51 mg, 0.23 mmol) and compound 53 (80 mg, 0.19 mmol) were stirred in CH$_2$Cl$_2$ (6 mL) at r.t. DIEA (51 µL, 0.29 mmol) and HATU (110 mg, 0.29 mmol) were added, and the reaction stirred for 6 h. Organics were washed with 0.1 N HCl and brine, dried (Na$_2$SO$_4$) and concentrated in vacuo. The residue was stirred in 33% TFA/CH$_2$Cl$_2$ (3 mL) for 1 h, concentrated, and purified by prep-HPLC to provide the title compound as a pale yellow powder (68 mg, 68%). $^1$H NMR (400 MHz, MeOD-d$_4$): δ 8.40 (br s, 1H), 8.19 (s, 1H), 8.06 (d, 1H, J=7.6 Hz), 7.97 (d, 1H, J=7.6 Hz), 7.81-7.88 (m, 3H), 4.69-4.96 (m, 4H), 3.97 (d, 1H, J=4.8 Hz), 3.33 (q, 2H, J=7.2 Hz), 2.35 (s, 3H), 2.20-2.30 (m, 1H), 1.29 (t, 3H, J=7.2 Hz), 0.93-1.02 (m, 6H). MS (ES) [m+H] calc'd for $C_{26}H_{30}N_4O_5S$, 511; found 511.

Compound 65

L-Alanine-(R)-2-[5-(3-ethanesulfonyl-phenyl)-3-methyl-9H-dipyrido[2,3-b; 4',3'-d]pyrrol-8-yloxy]-1-methyl-ethyl ester

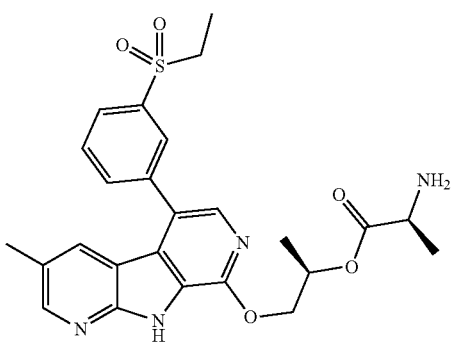

The title compound was prepared in 79% yield using BOC-L-alanine and Compound 63 in the procedure outlined for the preparation of compound 64. $^1$H NMR (400 MHz, MeOD-d$_4$): δ 8.46 (br s, 1H), 8.19 (s, 1H), 8.05 (d, 1H, J=7.6 Hz), 7.98 (d, 1H, J=7.6 Hz), 7.79-7.88 (m, 3H), 5.51-5.59 (m, 1H), 4.60-4.85 (m, 2H), 4.12 (q, 1H, J=7.2 Hz), 3.33 (q, 2H, J=7.2 Hz), 2.34 (s, 3H), 1.55 (d, 3H, J=7.2 Hz), 1.51 (d, 3H, J=6.4 Hz), 1.29 (t, 3H, J=7.2 Hz). MS (ES) [m+H] calc'd for $C_{25}H_{28}N_4O_5S$, 497; found 497.

Compound 66

3-(3-Bromo-5-chloro-pyridin-2-ylamino)-5-chloro-1-(4-methoxy-benzyl)-1H-pyrazin-2-one

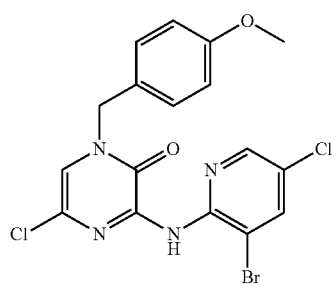

The title compound was prepared in 58% yield from 2-amino-3-bromo-5-chloropyridine and 3,5-dichloro-1-(4-methoxy-benzyl)-1H-pyrazin-2-one in a manner analogous to that for the preparation of Compound 26. $^1$H NMR (400 MHz, DMSO-d$_6$): δ 9.58 (s, 1H), 8.51 (d, 1H, J=2.4 Hz), 8.40 (d, 1H, J=2.4 Hz), 7.51 (s, 1H), 7.36 (d, 2H, J=8.8 Hz), 6.92 (d, 2H, J=8.8 Hz), 5.00 (s, 2H), 3.73 (s, 3H). MS (ES) [m+H] calc'd for $C_{17}H_{13}BrCl_2N_4O_2$, 455, 457, 459; found 455, 457, 459.

Compound 67

5-Chloro-3-(5-chloro-3-trimethylsilanylethynyl-pyridin-2-ylamino)-1-(4-methoxy-benzyl)-1H-pyrazin-2-one

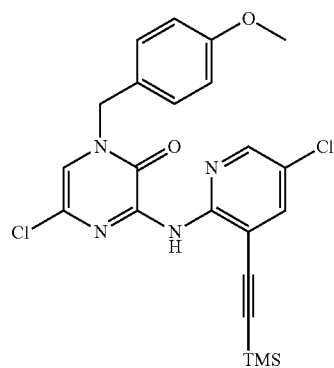

The title compound was prepared in 89% yield from compound 66 according to the procedure outline for the preparation of Compound 27. $^1$H NMR (400 MHz, DMSO-d$_6$): δ 9.68 (s, 1H), 8.46 (d, 1H, J=2.8 Hz), 8.07 (d, 1H, J=2.8 Hz), 7.54 (s, 1H), 7.37 (d, 2H, J=8.8 Hz), 6.90 (d, 2H, J=8.8 Hz), 5.00 (s, 2H), 3.72 (s, 3H), 0.16 (s, 9H). MS (ES) [m+H] calc'd for $C_{22}H_{22}Cl_2N_4O_2Si$, 473, 475; found 473, 475.

Compound 68

3-Chloro-7-(4-methoxy-benzyl)-5-trimethylsilanyl-7,9-dihydro-dipyrido[2,3-b; 4',3'-d]pyrrol-8-one

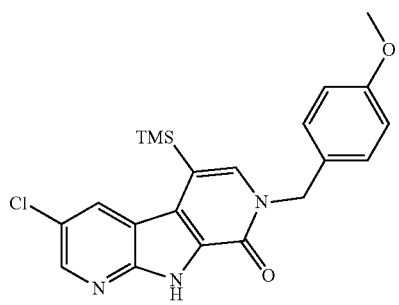

Compound 67 (5.8 g, 12.3 mmol) and DIEA (3.2 mL, 18.4 mmol) were dissolved in toluene (600 mL), and the solution was heated at reflux under N$_2$ for four days. The solution was concentrated and purified by flash chromatography (30% EtOAc/CH$_2$Cl$_2$) to provide the title compound as a tan solid (4.4 g, 87%). $^1$H NMR (400 MHz, DMSO-d$_6$): δ 12.98 (s, 1H), 8.54 (d, 1H, J=2.4 Hz), 8.20 (d, 1H, J=2.4 Hz), 7.37 (s, 1H), 7.32 (d, 2H, J=8.8 Hz), 6.90 (d, 2H, J=8.8 Hz), 5.25 (s, 2H), 3.71 (s, 3H), 0.39 (s, 9H). MS (ES) [m+H] calc'd for $C_{21}H_{22}ClN_3O_2Si$, 412, 414; found 412, 414.

Compound 69

3-Chloro-5-iodo-7-(4-methoxy-benzyl)-7,9-dihydro-dipyrido[2,3-b; 4',3'-d]pyrrol-8-one

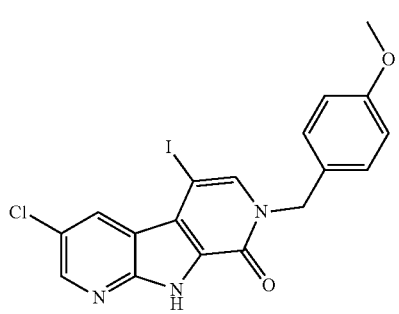

The title compound was prepared in quantitative yield from compound 68 according to the procedure outline for the preparation of Compound 29. $^1$H NMR (400 MHz, DMSO-$d_6$): δ 13.12 (s, 1H), 8.84 (d, 1H, J=2.4 Hz), 8.59 (d, 1H, J=2.4 Hz), 7.94 (s, 1H), 7.34 (d, 2H, J=8.8 Hz), 6.89 (d, 2H, J=8.8 Hz), 5.19 (s, 2H), 3.71 (s, 3H). MS (ES) [m+H] calc'd for $C_{18}H_{13}Cl_1N_3O_2$, 466, 468; found 466, 468.

Compound 70

3-Chloro-5-(3-ethanesulfonyl-phenyl)-7-(4-methoxy-benzyl)-7,9-dihydro-dipyrido[2,3-b; 4',3'-d]pyrrol-8-one

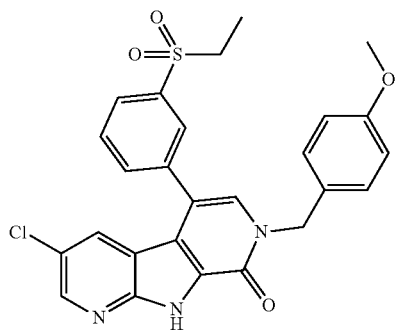

The title compound was prepared in 48% yield from compound 69 according to the procedure outline for the preparation of Compound 30. $^1$H NMR (400 MHz, DMSO-$d_6$): δ 13.12 (s, 1H), 8.52 (d, 1H, J=2.4 Hz), 8.06 (d, 1H, J=2.4 Hz), 7.80-7.99 (m, 3H), 7.73 (s, 1H), 7.65 (s, 1H), 7.39 (d, 2H, J=8.8 Hz), 6.89 (d, 2H, J=8.8 Hz), 5.27 (s, 2H), 3.70 (s, 3H), 3.39 (q, 2H, J=7.2 Hz), 1.15 (t, 3H, J=7.2 Hz). MS (ES) [m+H] calc'd for $C_{26}H_{22}ClN_3O_4S$, 508, 510; found 508, 510.

Compound 71

3,8-Dichloro-5-(3-ethanesulfonyl-phenyl)-9H-dipyrido[2,3-b; 4',3'-d]pyrrole

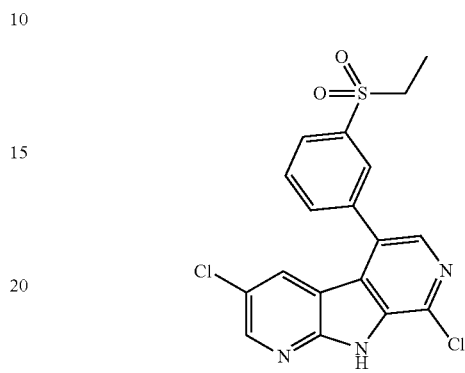

Phosphorous oxychloride (8 mL) was added to a mixture of compound 70 (1.05 g, 2.07 mmol) and ammonium chloride (380 mg, 2.28 mmol), and the reaction was heated at 108° C. for 4 h. The reaction was concentrated in vacuo and quenched with ice. The precipitated was collected by filtration and washed with $H_2O$ and cold MeOH to provide the title compound as a pale yellow solid (660 mg, 79%). $^1$H NMR (400 MHz, DMSO-$d_6$): δ 13.12 (s, 1H), 8.69 (d, 1H, J=2.4 Hz), 8.25 (s, 1H), 8.20 (d, 1H, J=2.4 Hz), 8.04-8.10 (m, 2H), 7.93 (t, 1H, J=7.6 Hz), 7.80 (s, 1H), 3.42 (q, 2H, J=7.2 Hz), 1.17 (t, 3H, J=7.2 Hz). MS (ES) [m+H] calc'd for $C_{18}H_{13}Cl_2N_3O_2S$, 406, 408; found 406, 408.

Compound 72

3-Chloro-5-(3-ethanesulfonyl-phenyl)-8-(1-methyl-piperidin-4-ylmethoxy)-9H-dipyrido[2,3-b; 4',3'-d]pyrrole

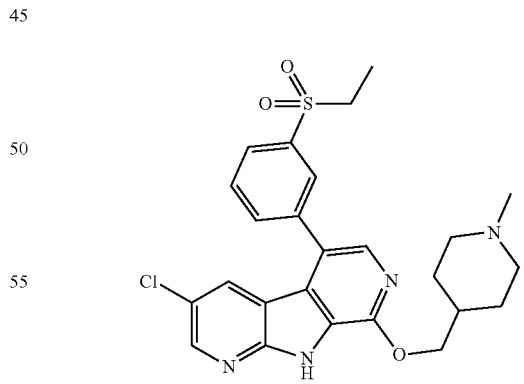

The title compound was prepared in 14% yield using compound 71 and 1-methyl-piperidine-3-methanol in the procedure outlined for the preparation of Compound 52. $^1$H NMR (400 MHz, MeOD-$d_4$): δ 8.49 (s, 1H), 8.17 (d, 1H, J=1.6 Hz), 8.08 (d, 1H, J=7.6 Hz), 7.99 (d, 1H, J=7.6 Hz), 7.82-7.90 (m, 2H), 7.80 (s, 1H), 4.52 (d, 2H, J=6.0 Hz), 3.56-3.62 (m, 2H), 3.33 (q, 2H, J=7.2 Hz), 3.02-3.11 (m, 2H), 2.90 (s, 3H), 2.25-2.33 (m, 3H), 1.60-1.72 (m, 2H), 1.31 (t, 3H, J=7.2 Hz). MS (ES) [m+H] calc'd for $C_{25}H_{27}ClN_4O_3S$, 499, 501; found 499, 501.

Compound 73

(R)-1-[3-Chloro-5-(3-ethanesulfonyl-phenyl)-9H-dipyrido[2,3-b; 4',3'-d]pyrrol-8-yloxy]-propan-2-ol

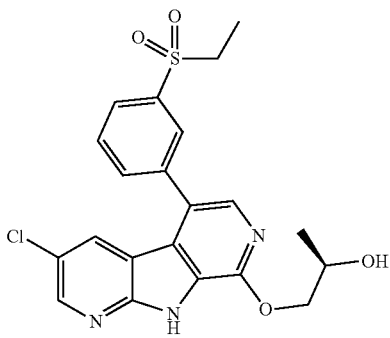

The title compound was prepared in 15% yield using (S)-2-benzyloxy-1-propanol (see Mulzer, et. al., *Tetrahedron Lett.*, 24, (1983), 2843-2846) and Compound 71 in the procedure outlined for the preparation of compound 52, followed by benzyl deprotection by hydrogenation at 1 atm with 10% Pd/C in MeOH for 1 h. $^1$H NMR (400 MHz, MeOD-d$_4$): δ 8.49 (s, 1H), 8.17 (s, 1H), 8.06 (d, 1H, J=7.6 Hz), 7.97 (d, 1H, J=7.6 Hz), 7.80-7.89 (m, 3H), 4.30-4.59 (m, 3H), 3.32 (q, 2H, J=7.2 Hz), 1.32-1.40 (m, 6H). MS (ES) [m+H] calc'd for $C_{21}H_{20}ClN_3O_4S$, 446, 448; found 446, 448.

Compound 74

2-[5-(3-Ethanesulfonyl-phenyl)-3-methyl-9H-dipyrido[2,3-b; 4',3'-d]pyrrol-8-yl]methyl amine

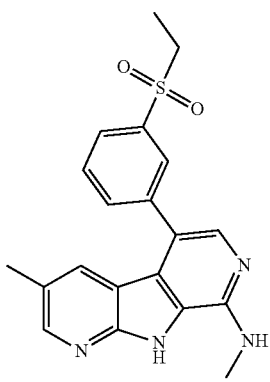

The title compound was prepared using methyl amine in the procedure outlined for the preparation of Compound 41. $^1$H NMR (400 MHz, CD$_3$OD) δ ppm 1.30 (s, 3H) 2.37 (s, 3H) 7.64 (s, 1H) 7.66 (dd, J=2.02, 0.76 Hz, 1H) 7.91 (t, J=7.71 Hz, 1H) 8.01-8.04 (m, J=7.71, 1.14, 0.88, 0.88 Hz, 1H) 8.15 (ddd, J=7.89, 1.83, 1.14 Hz, 1H) 8.22 (t, J=1.64 Hz, 1H) 8.53 (s, 1H) [M+H] calc'd for $C_{20}H_{20}N_4O_2S$, 381; found, 381.

Compound 75

2-[5-(3-Ethanesulfonyl-phenyl)-3-methyl-9H-dipyrido[2,3-b; 4',3'-d]pyrrol-8-yl]methanethiol

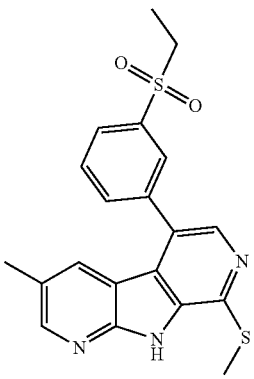

The title compound was prepared using methanethiol in the procedure outlined for the preparation of Compound 41. $^1$H NMR (400 MHz, CD$_3$OD) δ ppm 1.28-1.31 (m, 3H) 2.38 (s, 3H) 2.85 (s, 3H) 7.82 (s, 1H) 7.92 (t, J=7.45 Hz, 1H) 8.05-8.08 (m, J=7.71, 1.14, 0.88, 0.88 Hz, 1H) 8.14 (ddd, J=7.64, 1.20, 1.01 Hz, 1H) 8.27 (dd, J=3.66, 0.63 Hz, 1H) 8.30 (s, 1H) 8.49 (s, 1H) [M+H] calc'd for $C_{20}H_{19}N_3O_2S_2$, 398; found, 398.

Compound 76

2-[5-(3-Ethanesulfonyl-phenyl)-3-methyl-9H-dipyrido[2,3-b; 4',3'-d]pyrrol-8-yl]ethanethiol

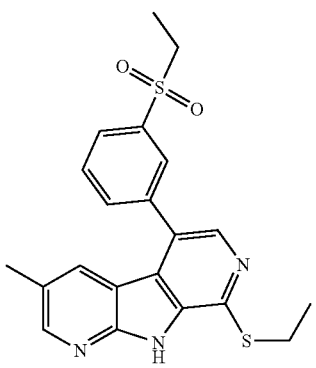

The title compound was prepared using ethanethiol in the procedure outlined for the preparation of Compound 41. $^1$H NMR (400 MHz, CD$_3$OD) δ ppm 1.30 (t, J=7.33 Hz, 3H) 1.45 (t, J=7.33 Hz, 3H) 1.93 (s, 3H) 2.37 (s, 2H) 3.44 (d, J=7.33 Hz, 2H) 7.82 (s, 1 H) 7.92 (t, J=7.71 Hz, 1H) 8.07 (dt, J=7.77, 1.42 Hz, 1H) 8.13 (dt, J=7.83, 1.52 Hz, 1H) 8.27 (t, J=1.77 Hz, 1H)

8.31 (s, 1H) 8.50 (br. s., 1H) [M+H] calc'd for C$_{21}$H$_{21}$N$_3$O$_2$S$_2$, 412; found, 412.

Compound 77

5-[3-(cyclopropylcarboxamide)phenyl]-7-(4-methoxybenzyl)-3-methyl-7,9-dihydro-8H-pyrido[4',3':4,5]pyrrolo[2,3-b]pyridin-8-one

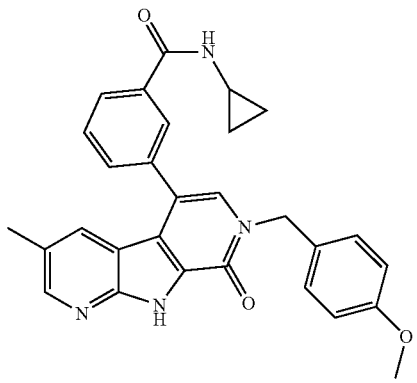

The title compound was prepared using the similar procedure outlined for the preparation of Compound 39. $^1$H NMR (400 MHz, CHLOROFORM-d) δ ppm 0.63 (ddd, J=3.79, 1.77, 1.52 Hz, 2H) 0.81 (dd, J=7.33, 2.02 Hz, 2H) 2.31 (s, 2H) 2.66 (s, 3H) 3.76 (s, 3H) 5.34 (s, 2H) 6.89 (d, J=8.84 Hz, 2H) 7.35 (d, J=8.84 Hz, 2H) 7.40 (s, 1H) 7.64 (d, J=7.83 Hz, 1H) 7.60 (t, J=2.02 Hz, 1H) 7.75 (d, J=2.78 Hz, 1H) 7.92 (dd, J=7.96, 1.14 Hz, 1H) 8.00 (t, J=1.64 Hz, 1H) 8.34 (d, J=2.02 Hz, 1H) [M+H] calc'd for C$_{29}$H$_{26}$N$_4$O$_3$, 479; found, 479.

Compound 78

8-Chloro-5-[3-(cyclopropylcarboxamide)phenyl]-3-methyl-9H-dipyrido[2,3-b; 4',3'-d]pyrrole

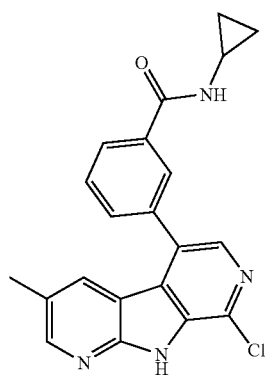

The title compound was prepared from Compound 77 using the similar procedure outlined for the preparation of compound 40. [M+H] calc'd for C$_{21}$H$_{17}$ClN$_4$O, 377.1; found, 377.2.

Compound 79

2-[5-(3-cyclopropylcarbonylamino-phenyl)-3-methyl-9H-dipyrido[2,3-b; 4',3'-d]pyrrol-8-yl]ethanethiol

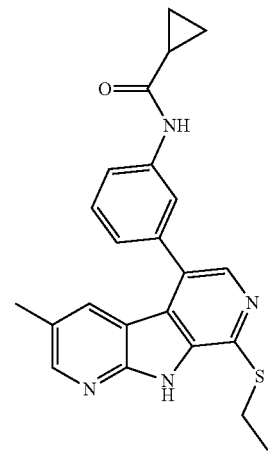

The title compound was prepared using ethanethiol in the procedure outlined for the preparation of Compound 41. $^1$H NMR (400 MHz, CD$_3$OD) δ ppm 0.88 (d, J=7.83 Hz, 2H) 0.97 (t, J=2.40 Hz, 2H) 1.44 (t, J=7.33 Hz, 3H) 2.38 (s, 3H) 3.41 (d, J=7.33 Hz, 2H) 7.39 (d, J=7.83 Hz, 1H) 7.56 (t, J=7.83 Hz, 1H) 7.66 (d, J=8.84 Hz, 1H) 7.85 (s, 1H) 8.26 (s, 1H) 8.48 (br. s., 1H) 10.26 (s, 1H) [M+H] calc'd for C$_{23}$H$_{22}$N$_4$OS, 403; found, 403.

Compound 80

1-Acetyl-4-bromo-1,2-dihydro-indol-3-one

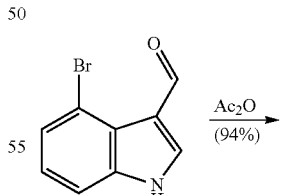

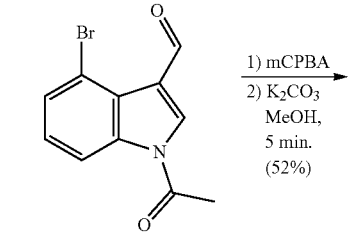

-continued

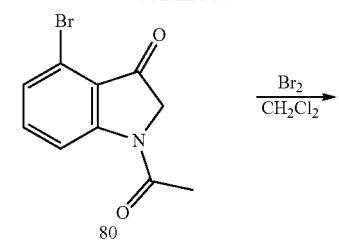

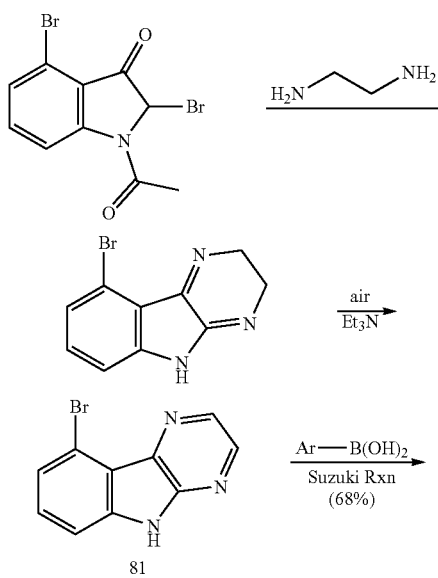

(55%), 3 steps)

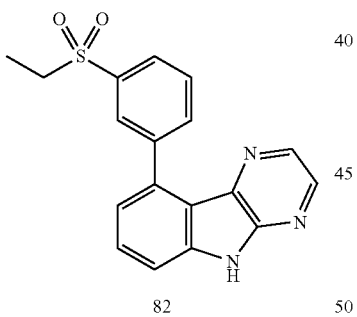

82

4-Bromo-1H-indole-3-carbaldehyde (4.0 g, 17.8 mmol) was stirred in acetic anhydride (20 mL) at reflux for 4 h. The reaction was cooled and concentrated in vacuo. Cold MeOH was added to precipitate a white solid, which was collected by filtration to provide the title compound (3.5 g, 74%). MS (ES) [m+H] calc'd for $C_{11}H_8BrNO_2$, 266, 268; found 266, 268.

1-Acetyl-4-bromo-1H-indole-3-carbaldehyde (3.5 g, 13.2 mmol) was dissolved in $CH_2Cl_2$ (50 mL). 3-Chloroperbenzoic acid (3.9 g, 15.8 mmol) was added, and the reaction stirred 16 h at r.t. The solution was washed with sat. $NaHCO_3$ and brine, dried ($MgSO_4$), and concentrated. The residue was stirred with $K_2CO_3$ (100 mg) in MeOH (50 mL) for 2 min. The solution was concentrated and purified by silica gel chromatography (100% $CH_2Cl_2$) to provide the title compound as a faintly blue solid (880 mg, 26%). MS (ES) [m+H] calc'd for $C_{10}H_8BrNO_2$, 254, 256; found 254, 256.

Compound 81

9-Bromo-5H-pyrazino[2,3-b]indole

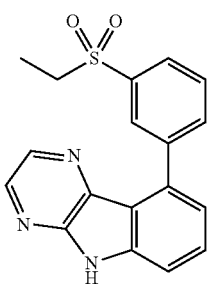

1-Acetyl-4-bromo-1,2-dihydro-indol-3-one (460 mg, 1.81 mmol) was dissolved in $CH_2Cl_2$ (8 mL). Bromine (111 μL, 2.2 mmol) was added slowly, and the reaction stirred for 20 min and then was concentrated in vacuo. The residue was dissolved in THF (8 mL). Ethylenediamine (244 μL, 3.6 mmol) was added, and the reaction stirred for 16 h at r.t. Triethylamine (2 mL) and MeOH (4 mL) were added, and the reaction stirred while left open to air for 24 h. The solution was concentrated in vacuo and purified by silica gel chromatography (8% MeOH/$CH_2Cl_2$) to provide the title compound as a red solid (248 mg, 55%). MS (ES) [m+H] calc'd for $C_{10}H_6BrN_3$, 248, 250; found 248, 250.

Compound 82

9-(3-Ethanesulfonyl-phenyl)-5H-pyrazino[2,3-b]indole

Compound 81 (50 mg, 0.2 mmol), 3-ethanesulfonyl-phenylboronic acid (65 mg, 0.3 mmol), tetrakis(triphenylphosphine)palladium (0) (116 mg, 0.1 mmol), and potassium carbonate (83 mg, 0.6 mmol), were combined in dioxane (2 mL) and $H_2O$ (0.2 mL) in a sealed tube under nitrogen. The reaction was heated at 150° C. in the microwave for 20 min and then concentrated in vacuo. Purification by silica gel chromatography (5% MeOH/$CH_2Cl_2$) provided the title compound as a light orange solid (46 mg, 68%). $^1$H NMR (400 MHz, $CD_3OD$) δ 8.42 (t, 1H, J=2.8 Hz), 8.31 (d, 1H, J=2.8 Hz), 8.24 (d, 1H, J=2.8 Hz), 8.06 (d, 1H, J=7.6 Hz), 7.96 (d, 1H, J=7.6 Hz), 7.60-7.75 (m, 3H), 7.31 (dd, 1H, J=7.2, 1.2 Hz), 3.33 (q, 2H, J=7.2 Hz), 1.37 (t, 3H, J=7.2 Hz). MS (ES) [m+H] calc'd for C₁₈H₁₅N₃O₂S, 338; found 338.

Compound 83

3-(6-chloro-3-methyl-2-nitro-4-(trifluoromethyl)phenyl)-2-fluoro-5-methylpyridine

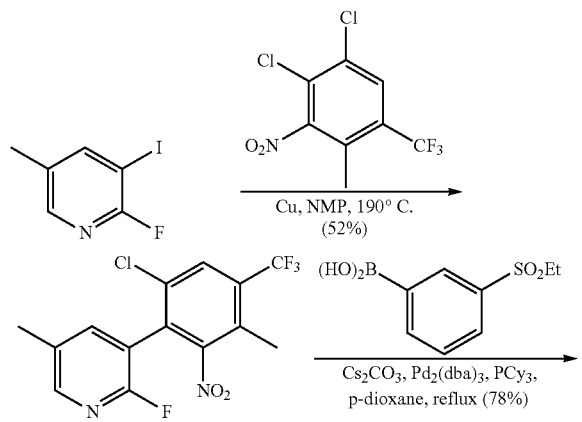

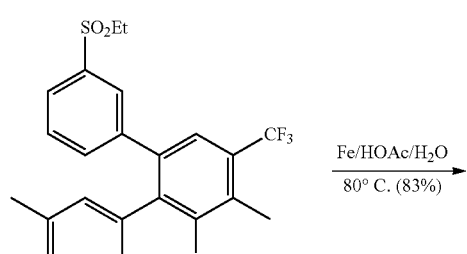

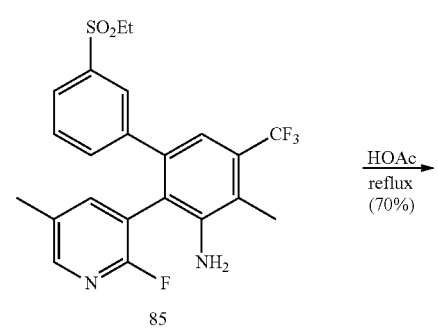

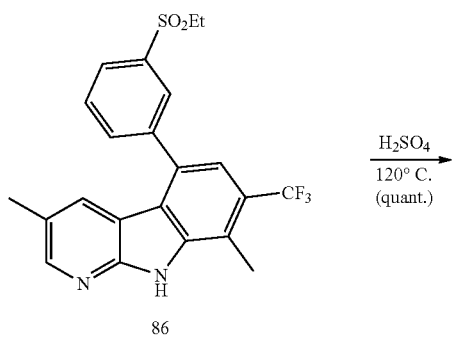

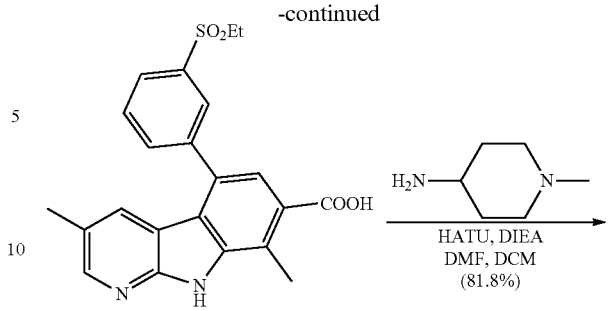

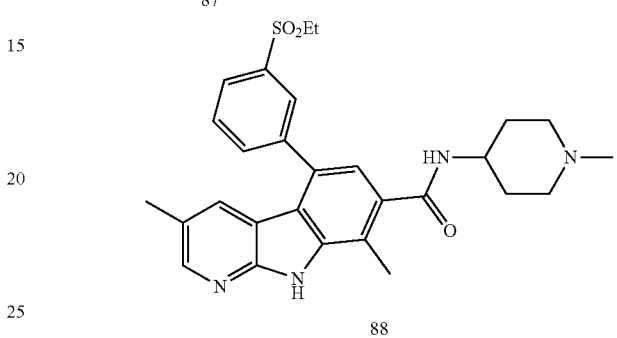

2-Fluoro-3-iodo-5-picoline (15.0 g, 63 mmol) was added drop wise during 2 h as a solution in NMP (20 mL) to a stirred suspension of 3,4-dichloropro-2-nitro-6-(trifluoromethyl)-toluene (52.1 g, 190 mmol) and copper (12.1 g, 190 mmol) in NMP (115 mL) at 190° C. After completion of the reaction (2.5 h), the mixture was cooled to room temperature, filtered, rinsed with NMP (3×5 mL) followed by EtOAc (1×100 mL). The filtrate was diluted with EtOAc (400 mL) affording a turbid solution. The organic layer was partitioned with sat. NaHCO₃ (150 mL) affording a suspension/emulsion. H₂O (50 mL) and MeOH (50 mL) were added to aid solubility. The aqueous layer was washed with EtOAc (5×150 mL). The organic layers were combined, dried (MgSO₄), and concentrated in vacuo. The crude product was purified by silica gel chromatography (98:2 Toluene:EtOAc) to provide the title compound as a tan solid (11.4 g, 52%). ¹H NMR (400 MHz, DMSO-d₆): δ 8.34 (s, 1H), 8.26 (s, 1H), 7.86-7.89 (m, 1H), 2.4 (s, 3H), 2.34 (s, 3H). MS (ES) [m+H] calc'd for C₁₄H₉ClF₄N₂O₂, 349; found 349.2.

Compound 84

3-(3'-(ethylsulfonyl)-4-methyl-3-nitro-5-(trifluoromethyl)biphenyl-2-yl)-2-fluoro-5-methylpyridine

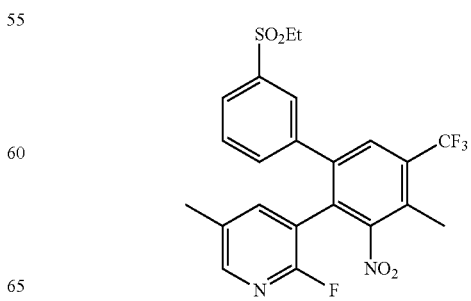

A mixture of Compound 83 (6.0 g, 17.2 mmol), 3-ethylsulfonylphenylboronic acid (4.79 g, 22.4 mmol), bis(dibenzylideneacetone)Pd(0) (1.48 g, 2.6 mmol), tricyclohexylphosphine (1.45 g, 5.2 mmol), Cs$_2$CO$_3$ (14.0 g, 43 mmol), and dioxane (60 mL) was heated at reflux for 4.5 hr. After completion the reaction was cooled to room temperature, filtered, rinsed with dioxane, and concentrated in vacuo. The resulting oil was reconstituted in EtOAc (75 mL) washed with H$_2$O (1×30 mL) and brine (1×30 mL), dried (MgSO$_4$), and concentrated in vacuo. The crude product was purified by silica gel chromatography (4:1 hexanes/EtOAc) to provide the title compound as a tan solid (6.5 g, 78%). $^1$H NMR (400 MHz, DMSO-d$_6$): δ 8.15 (s, 1H), 8.04 (s, 1H), 7.90-7.93 (m, 1H), 7.80-7.82 (m, 1H), 7.60-7.70 (m, 3H), 3.1-3.2 (m, 2H), 2.49 (s, 3H), 2.25 (s, 3H), 0.85 (t, 3H). MS (ES) [m+H] calc'd for C$_{22}$H$_{18}$F$_4$N$_2$O$_4$S, 483; found 483.3.

Compound 85

3'-(ethylsulfonyl)-2-(2-fluoro-5-methylpyridin-3-yl)-4-methyl-5-(trifluoromethyl)biphenyl-3-amine

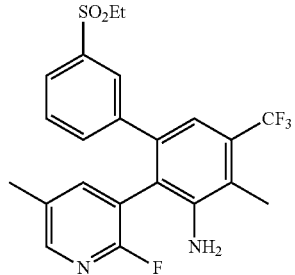

A mixture of Compound 84 (6.4 g, 13.3 mmol), iron (3.7 g, 66.3 mmol), HOAc, (32 mL), and H$_2$O (11 mL) was heated at 80° C. for 2 h. After completion the reaction was concentrated in vacuo. The residue was reconstituted in dichloromethane (100 mL), filtered, and rinsed with dichloromethane (3×30 mL). The organic phase was washed with sat. NaHCO$_3$ (1×100 mL) and brine (1×50 mL), dried (MgSO$_4$), filtered, and concentrated in vacuo. The crude product was purified by silica gel chromatography (1:1 hexanes/EtOAc) to provide the title compound as a tan solid (5.0 g, 83%). $^1$H NMR (400 MHz, DMSO-d$_6$): δ 7.93 (s, 1H), 7.67-7.7.71 (m, 2H), 7.53 (t, 1H), 7.46-7.48 (m, 1H), 7.42 (s, 1H), 6.93 (s, 1H), 5.09 (s, 2H), 3.11 (q, 2H), 2.27 (s, 3H), 2.21 (s, 3H), 0.85 (t, 3H). MS (ES) [m+H] calc'd for C$_{22}$H$_{20}$F$_4$N$_2$O$_2$S, 453; found 453.3.

Compound 86

5-(3-(ethylsulfonyl)phenyl)-3,8-dimethyl-7-(trifluoromethyl)-9H-pyrido[2,3-b]indole acetate

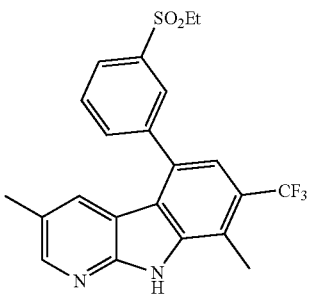

Compound 85 (4.9 g, 10.8 mmol) was dissolved in HOAc (35 mL) and heated at reflux for 3 h. The reaction mixture was cooled to room temperature affording a crystalline product. The resulting suspension was filtered, rinsed with HOAc (3×5 mL) followed by H$_2$O (3×10 mL) and the solids dried in vacuo to provide the title compound as a white solid (3.73 g, 70%). NMR analysis confirmed that the product was isolated as the mono-acetate salt. $^1$H NMR (400 MHz, DMSO-d$_6$): δ 12.35 (s, 1H), 12.0 (s, 1H), 8.39 (s, 1H), 8.15 (s, 1H), 8.04-8.09 (m, 2H), 7.90 (t, 1H), 7.51 (s, 1H), 7.42 (s, 1H), 3.43 (q, 2H), 2.76 (s, 3H), 2.28 (s, 3H), 1.91 (s, 3H), 1.18 (t, 3H). MS (ES) [m+H] calc'd for C$_{22}$H$_{19}$F$_3$N$_2$O$_2$S, 433; found 433.3.

Compound 87

5-(3-(ethylsulfonyl)phenyl)-3,8-dimethyl-9H-pyrido[2,3-b]indole-7-carboxylic acid

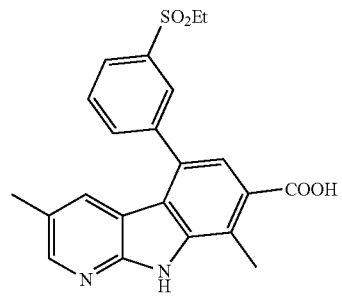

Compound 86 (3.6 g, 7.3 mmol) was dissolved in concentrated H$_2$SO$_4$ (30 mL) and heated at 120° C. for 30 min. The reaction was cooled to room temperature and poured over ice affording a white precipitate. The resulting suspension was filtered, rinsed with H$_2$O (3×30 mL) followed by IPA (3×10 mL) and dried in vacuo to provide the title compound as a white solid (3.2 g, quant.). $^1$H NMR (400 MHz, DMSO-d$_6$): δ 12.20 (s, 1H), 8.36 (s, 1H), 8.12 (s, 1H), 8.02-8.07 (m, 2H), 7.89 (t, 1H), 7.61 (s, 1H), 7.54 (s, 1H), 3.43 (q, 2H), 2.85 (s, 3H), 2.28 (s, 3H), 1.18 (t, 3H). MS (ES) [m+H] calc'd for C$_{22}$H$_{20}$N$_2$O$_4$S, 409; found 409.3.

Compound 88

5-(3-(ethylsulfonyl)phenyl)-3,8-dimethyl-N-(1-methylpiperidin-4-yl)-9H-pyrido[2,3-b]indole-7-carboxamide

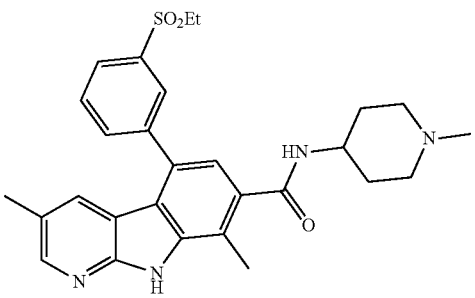

A mixture of Compound 87 (11.3 g, 27.6 mmol), 1-methylpiperidin-4-amine (9.47 g, 82.9 mmol), HATU (13.66 g, 35.9 mmol), DIEA (17.88 g, 138 mmol), DMF (250 mL), and DCM (250 mL) was stirred at room temperature for 30 minutes. The resulting suspension was filtered, rinsed with DMF (10 mL×4) and concentrated in vacuo. The residue was dissolved in DMSO (77 mL), filtered, and the filtrate was purified by preparative HPLC (ACN/H$_2$O with TFA). Following HPLC purification, the pure fractions were combined, basified with sodium bicarbonate and concentrated in vacuo to half volume. The resulting suspension was filtered, rinsed with H$_2$O (200 mL×5) and dried in vacuo to provide Compound 88 as a white solid (11.41 g, 81.8%).

The hydrochloride salt of Compound 88 was prepared as follows. To a stirred suspension of Compound 88 (8.7 g) in ACN (175 mL) and H$_2$O (175 mL) was added 1N HCl (18.1 mL, 1.05 eq) affording a yellow solution. After 15 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide hydrochloride as a yellow solid (9.02 g, 96.7%). The above process provided 543-(ethylsulfonyl)phenyl)-3,8-dimethyl-N-(1-methylpiperidin-4-yl)-9H-pyrido[2,3-b]indole-7-carboxamide hydrochloride as an amorphous material ("Amorphous Form"), which may be characterized as having one or more of the following physical characteristics (it being noted that a composition need not necessarily exhibit all of these characteristics in order to indicate the presence of Amorphous Form):
  (a) may be formed by lyophilizing a solution of Compound 88 in ACN, water, and HCl;
  (b) has an XRPD spectrum characterized by a diffuse halo with no discernable peaks; and/or
  (c) shows 7.6 wt % Cl$^-$ present using ion chromatography.

The crystalline hydrochloride salt of Compound 88 was prepared as follows. To a stirred suspension of Compound 88 (0.55 g) in IPA (2.5 mL) and H$_2$O (2.5 mL) was added 12.1N HCl (1.05-1.10 eq) affording a yellow solution. After stirring for 45 minutes, crystallization occurred and additional IPA (15 mL) was added at room temperature. The resulting suspension was allowed to stir overnight. The solids were isolated by filtration and dried in vacuo at 60° C. to provide 5-(3-(ethylsulfonyl)phenyl)-3,8-dimethyl-N-(1-methylpiperidin-4-yl)-9H-pyrido[2,3-b]indole-7-carboxamide hydrochloride as a tan to gold colored solid (0.51 g, 87%).

The dihydrochloride salt of Compound 88 was prepared as follows. To a stirred suspension of Compound 88 (101 mg) in ACN (2.5 mL) and H$_2$O (2.5 mL) was added 12.1N HCl (0.42 mL, 2.1 eq) affording a yellow solution. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide dihydrochloride as a yellow solid (0.108 g).

The benzenesulfate salt of Compound 88 was prepared as follows. To a stirred suspension of Compound 88 (98 mg) in ACN (2.5 mL) and H$_2$O (2.5 mL) was added benzenesulfonic acid (32 mg, 1.05 eq) to give a slightly cloudy solution that was warmed to assist solubility. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide benzenesulfonate (118 mg).

The methanesulfonate salt of Compound 88 was prepared as follows. To a stirred suspension of Compound 88 (101 mg) in ACN (2.5 mL) and H$_2$O (2.5 mL) was added methanesulfonic acid (0.014 mL, 1.05 eq) affording a clear solution. After 5 minutes, the solution was frozen on dry ice/acetone and lyophilized to provide 543-(ethylsulfonyl)phenyl)-3,8-dimethyl-N-(1-methylpiperidin-4-yl)-9H-pyrido[2,3-b]indole-7-carboxamide methane sulfonate (116 mg).

The succinate salt of Compound 88 was prepared as follows. To a stirred suspension of Compound 88 (100 mg) in ACN (2.5 mL) and H$_2$O (2.5 mL) was added succinic acid (25 mg, 1.05 eq) to give a clear solution. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide succinate (119 mg).

The tartrate salt of Compound 88 was prepared as follows. To a stirred suspension of Compound 88 (108 mg) in ACN (2.5 mL) and H$_2$O (2.5 mL) was added L-tartaric acid (34 mg, 1.05 eq) affording a clear solution. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide tartrate (137 mg).

The citrate salt of Compound 88 was as follows. To a stirred suspension of Compound 88 (104 mg) in ACN (2.5 mL) and H$_2$O (2.5 mL) was added citric acid (42 mg, 1.05 eq) affording a clear solution. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide citrate (142 mg).

The fumarate salt of Compound 88 was prepared as follows. To a stirred suspension of Compound 88 (104 mg) in ACN (2.5 mL) and H$_2$O (2.5 mL) was added fumaric acid (25 mg, 1.05 eq) affording a very slightly cloudy solution. After 5 minutes, the solution was frozen on dry ice/acetone and lyophilized to provide 543-(ethylsulfonyl)phenyl)-3,8-dimethyl-N-(1-methylpiperidin-4-yl)-9H-pyrido[2,3-b]indole-7-carboxamide fumarate (123 mg).

The sulfate salt of Compound 88 was prepared as follows. To a stirred suspension of Compound 88 (107 mg) in ACN (2.5 mL) and H$_2$O (2.5 mL) was added sulfuric acid (0.012 mL, 1.05 eq) affording a yellow solution. After 5 minutes, the solution was frozen on dry ice/acetone and lyophilized to provide 543-(ethylsulfonyl)phenyl)-3,8-dimethyl-N-(1-methylpiperidin-4-yl)-9H-pyrido[2,3-b]indole-7-carboxamide sulfate (125 mg).

The phosphate salt of Compound 88 was prepared as follows. To a stirred suspension of Compound 88 (104 mg) in ACN (2.5 mL) and H$_2$O (2.5 mL) was added phosphoric acid (0.015 mL, 1.05 eq) affording a slightly cloudy solution that was warmed to assist solubility. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide phosphate (122 mg).

The benzoate salt of Compound 88 was prepared as follows. To a stirred suspension of Compound 88 (100 mg) in ACN (2.5 mL) and H$_2$O (2.5 mL) was added benzoic acid (25 mg, 1.05 eq) affording a clear solution containing a very small amount of suspended benzoic acid crystals. After 5 minutes, the solution was frozen on dry ice/acetone and lyophilized to provide 5-(3-(ethylsulfonyl)phenyl)-3,8-dimethyl-N-(1-methylpiperidin-4-yl)-9H-pyrido[2,3-b]indole-7-carboxamide benzoate (118 mg).

The bis-trifluoroacetic acid salt of Compound 88 was prepared as follows. Following HPLC purification (ACN/H$_2$O with TFA) of crude Compound 88, the pure fractions were combined and lyophilized to provide 5-(3-(ethylsulfonyl) phenyl)-3,8-dimethyl-N-(1-methylpiperidin-4-yl)-9H-pyrido[2,3-b]indole-7-carboxamide bis(2,2,2-trifluoroacetate) as a yellow solid.

The tosylate salt of Compound 88 was prepared as follows. To a stirred suspension of Compound 88 (103 mg) in ACN (2.5 mL) and H₂O (2.5 mL) was added p-toluenesulfonic acid (39 mg, 1.05 eq) affording a clear solution. After 5 minutes, the solution was frozen on dry ice/acetone and lyophilized to provide 5-43-(ethylsulfonyl)phenyl)-3,8-dimethyl-N-(1-methylpiperidin-4-yl)-9H-pyrido[2,3-b]indole-7-carboxamide tosylate (130 mg).

The hemi-fumarate salt of Compound 88 was prepared as follows. To a stirred solution of Compound 88 (360 mg) in MeOH at 58° C. was added 0.5M fumaric acid (0.53 eq) in MeOH. After 15 minutes crystallization occurred and the resulting suspension was cooled to room temperature and allowed to stir for an additional 2 hours. The solids were isolated by filtration and dried in vacuo to provide 5-(3-(ethylsulfonyl)phenyl)-3,8-dimethyl-N-(1-methylpiperidin-4-yl)-9H-pyrido[2,3-b]indole-7-carboxamide hemifumarate as a white crystalline powder (219.24 mg, 50%).

Compound 89

N-(2-(methylamino)ethyl)-5-(3-(ethylsulfonyl)phenyl)-3,8-dimethyl-9H-pyrido[2,3-b]indole-7-carboxamide

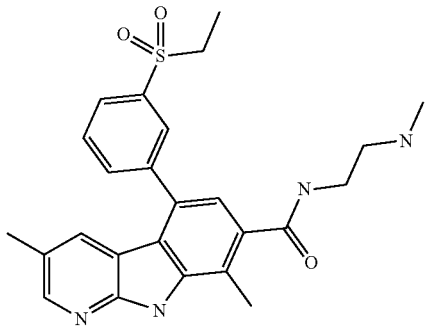

The title compound was synthesized using an analogous procedure to that described in the preparation of Compound 88. ¹H NMR (400 MHz, DMSO-d₆) δ ppm 1.17 (t, J=7.33 Hz, 3H) 2.27 (s, 3H) 2.63 (t, J=5.31 Hz, 3H) 2.67 (s, 3H) 3.12 (ddd, J=11.87, 6.32, 6.06 Hz, 2H) 3.42 (q, J=7.41 Hz, 2H) 3.56 (q, J=6.15 Hz, 2H) 7.28 (s, 1 H) 7.51 (s, 1H) 7.91 (t, J=7.83 Hz, 1H) 8.04 (ddd, J=16.36, 7.77, 1.14 Hz, 2H) 8.12 (s, 1 H) 8.33 (s, 1H) 8.43 (br. s., 1H) 8.57 (t, J=5.68 Hz, 1H) 12.09 (s, 1H) ESI-MS: m/z 465 (m+H)⁺.

Compound 90

N-(2-(methoxy)ethyl)-5-(3-(ethylsulfonyl)phenyl)-3,8-dimethyl-9H-pyrido[2,3-b]indole-7-carboxamide

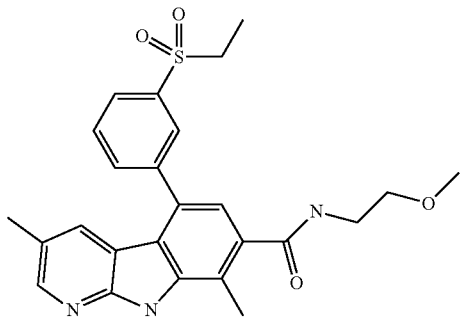

The title compound was synthesized using an analogous procedure to that described in the preparation of Compound 88. ¹H NMR (400 MHz, DMSO-d₆) δ ppm 1.17 (t, J=7.33 Hz, 3H) 2.27 (s, 3H) 2.63 (s, 3H) 3.29 (s, 3H) 3.37-3.51 (m, 6H) 7.12 (s, 1H) 7.53 (d, J=1.26 Hz, 1H) 7.89 (t, J=7.71 Hz, 1H) 7.99-8.06 (m, 2H) 8.12 (s, 1 H) 8.31 (s, 1H) 8.43 (t, J=5.31 Hz, 1H) 12.05 (s, 1H) ESI-MS: m/z 466 (m+H)⁺.

Compound 91

N-(2-(dimethylamino)ethyl)-N-methyl-5-(3-(ethylsulfonyl)phenyl)-3,8-dimethyl-9H-pyrido[2,3-b]indole-7-carboxamide

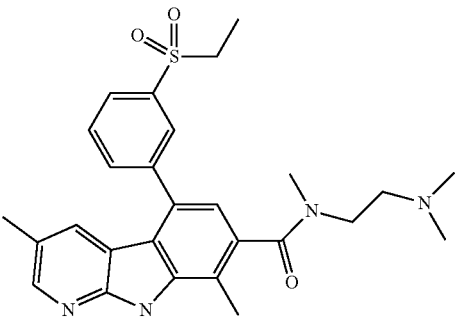

The title compound was synthesized using an analogous procedure to that described in the preparation of Compound 88. ¹H NMR (400 MHz, DMSO-d₆) δ ppm 1.17 (t, J=7.20 Hz, 3H) 2.26 (s, 3H) 2.64 (br. s., 3H) 2.86 (s, 3H) 2.91 (s, 3H) 3.35-3.45 (m, 6H) 7.06 (s, 1H) 7.47 (s, 1H) 7.89 (t, J=7.71 Hz, 1H) 8.00-8.09 (m, 3H) 8.31 (s, 1H) 9.49 (br. s., 1H) 12.11 (s, 1H). ESI-MS: m/z 493 (m+H)⁺.

Compound 92

N,N-dimethyl-5-(3-(ethylsulfonyl)phenyl)-3,8-dimethyl-9H-pyrido[2,3-b]indole-7-methylcarboxamide

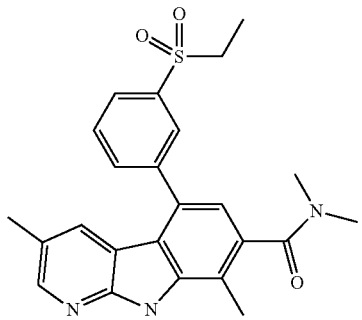

The title compound was synthesized using an analogous procedure to that described in the preparation of Compound 88. ¹H NMR (400 MHz, DMSO-d₆) δ ppm 1.17 (t, J=7.33 Hz, 3H) 2.27 (s, 3H) 2.46 (br. s., 3H) 2.84 (s, 3H) 3.05 (br. s., 3H) 3.33-3.50 (m, 2H) 6.97 (s, 1H) 7.52 (d, J=1.52 Hz, 1H) 7.87 (t, J=7.71 Hz, 1H) 8.02 (t, J=7.33 Hz, 2H) 8.10 (s, 1H) 8.30 (d, J=1.52 Hz, 1H) 12.08 (s, 1H). ESI-MS: m/z 436 (m+H)⁺.

Compound 93

5-(3-(ethylsulfonyl)phenyl)-3,8-dimethyl-9H-pyrido[2,3-b]indole-7-yl)(4-methylpiperazin-1-yl)methanone

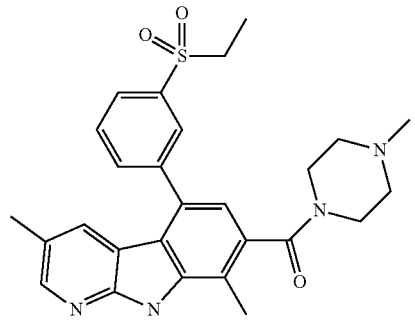

The title compound was synthesized using an analogous procedure to that described in the preparation of Compound 88. $^1$H NMR (400 MHz, DMSO-d$_6$) δ ppm 1.18 (t, J=7.33 Hz, 3H) 2.27 (s, 3H) 2.57 (br. s., 3H) 2.82-2.85 (br, 3H) 3.10-3.68 (m, 9H) 4.77 (m, 1H) 7.10 (br. d., 1H) 7.51 (br. d, J=7.83 Hz, 1H) 7.90 (t, J=7.33 Hz, 1H) 7.99-8.13 (m, 3H) 8.32 (s, 1H) 9.96 (br. s., 1H) 12.15 (s, 1H). ESI-MS: m/z 491 (m+H)$^+$.

Compound 94

5-(3-(ethylsulfonyl)phenyl)-3,8-dimethyl-N-(2-piperazin-1-yl)ethyl)-9H-pyrido[2,3-b]indole-7-carboxamide

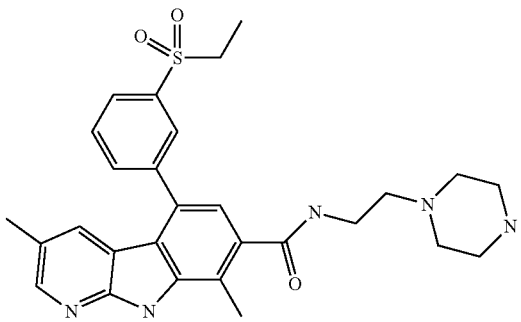

The title compound was synthesized using an analogous procedure to that described in the preparation of Compound 88. $^1$H NMR (400 MHz, DMSO-d$_6$) δ ppm 1.17 (t, J=7.33 Hz, 3H) 2.27 (s, 3H) 2.66 (s, 3H) 3.17-3.45 (m, 12H) 3.59 (q, J=5.64 Hz, 2H) 7.20 (s, 1H) 7.52 (s, 1H) 7.90 (t, J=7.71 Hz, 1H) 8.04 (m, 2H) 8.12 (s, 1H) 8.33 (d, J=2.02 Hz, 1H) 8.56 (t, J=5.68 Hz, 1H) 8.99 (br. s., 1H) 12.10 (s, 1H). ESI-MS: m/z 520 (m+H)$^+$.

Compound 95

5-(3-(ethylsulfonyl)phenyl)-3,8-dimethyl-N-(3-(4-methylpiperazin-1-yl)propyl)-9H-pyrido[2,3-b]indole-7-carboxamide

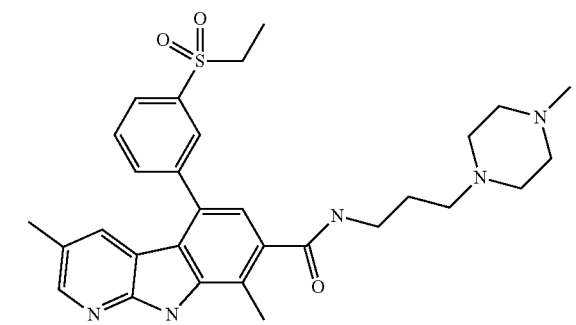

The title compound was synthesized using an analogous procedure to that described in the preparation of Compound 88. $^1$H NMR (400 MHz, DMSO-d$_6$) δ ppm 1.17 (t, J=7.83 Hz, 3H) 1.87 (br. s., 2H) 2.27 (s, 3H) 2.64 (s, 3H) 2.82 (br. s., 3H) 3.03 (br. s., 4H) 3.31-3.49 (m, 8H) 7.15 (s, 1H) 7.52 (s, 1H) 7.90 (t, J=7.71 Hz, 1H) 8.00-8.07 (m, 2H) 8.11 (s, 1H) 8.32 (d, J=2.02 Hz, 1H) 8.49-8.53 (m, 1H) 12.08 (s, 1H) ESI-MS: m/z 548 (m+H)$^+$.

Compound 96

5-(3-(ethylsulfonyl)phenyl)-3,8-dimethyl-9H-pyrido[2,3-b]indole-7-yl)(morpholino)methanone

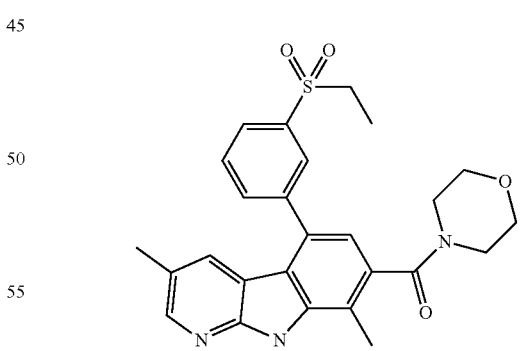

The title compound was synthesized using an analogous procedure to that described in the preparation of Compound 88. $^1$H NMR (400 MHz, DMSO-d$_6$) δ ppm 1.38 (t, J=7.33 Hz, 3H) 2.37 (s, 3H) 2.71 (s, 3H) 3.23 (q, J=7.33 Hz, 2H) 3.39 (m, 2H) 3.64 (d, J=13.14 Hz, 1H) 3.64 (d, J=5.05 Hz, 1H) 3.80-4.01 (m, 4H) 7.04 (s, 1H) 7.62 (s, 1H) 7.78 (t, J=7.71 Hz, 1H) 7.93 (dt, J=7.77, 1.42 Hz, 1H) 8.07 (ddd, J=7.71, 1.64, 1.52

Hz, 1H) 8.24 (t, J=1.64 Hz, 1H) 8.34 (d, J=1.77 Hz, 1H) 10.97 (br. s., 1H) ESI-MS: m/z 478 (m+H)+.

Compound 97 azetidin-1-yl(5-(3-(ethylsulfonyl)phenyl)-3,8-dimethyl-9H-pyrido[2,3-b]indol-7-yl)methanone

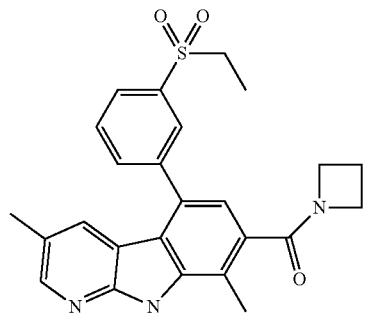

The title compound was synthesized using an analogous procedure to that described in the preparation of Compound 88. $^1$H NMR (400 MHz, DMSO-d$_6$) δ ppm 1.37 (t, J=7.45 Hz, 3H) 2.28-2.41 (m, 5H) 2.75 (s, 3H) 3.23 (q, J=7.58 Hz, 2H) 4.03 (t, J=7.58 Hz, 2H) 4.30 (t, J=7.96 Hz, 2H) 7.12 (s, 1H) 7.61 (s, 1H) 7.77 (t, J=7.96 Hz, 1 H) 7.94 (ddd, J=7.89, 1.45, 1.26 Hz, 1H) 8.06 (dd, J=8.21, 1.39 Hz, 1H) 8.22 (t, J=1.52 Hz, 1H) 8.33 (d, J=1.26 Hz, 1H) 10.25 (br. s., 1H). ESI-MS: m/z 448 (m+H)+.

Compound 98

(5-(3-(ethylsulfonyl)phenyl)-3,8-dimethyl-9H-pyrido[2,3-b]indol-7-yl)(thaiazolidin-3-yl)methanone

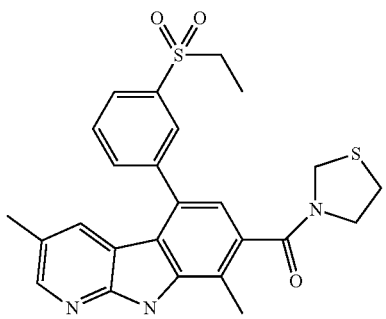

The title compound was synthesized using an analogous procedure to that described in the preparation of Compound 88. $^1$H NMR (400 MHz, DMSO-d$_6$) δ ppm 1.18 (t, J=7.33 Hz, 3H) 2.27 (s, 3H) 2.56 (s, 3H) 2.99 (m, 1H) 3.12 (m, 1H) 3.43-3.51 m, 3H) 3.89 (m, 1H) 4.32 (s, 1H) 4.71 (s, 1H) 7.06 (d, J=3.03 Hz, 1H) 7.52 (br. s., 1H) 7.88 (t, J=7.83 Hz, 1H) 7.98-8.07 (m, 2H) 8.12 (d, J=1.52 Hz, 1H) 8.32 (d, J=1.77 Hz, 1H) 12.11 (br. s., 1H). ESI-MS: m/z 480 (m+H)+.

Compound 99

(R)-5-(3-(ethylsulfonyl)phenyl)-N-(2-hydroxypropyl)-3,8-dimethyl-9H-pyrido[2,3-b]indole-7-carboxamide

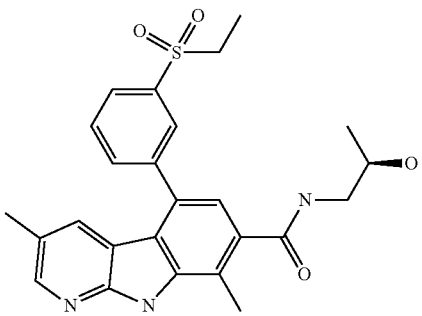

The title compound was synthesized using an analogous procedure to that described in the preparation of Compound 88. $^1$H NMR (400 MHz, DMSO-d$_6$) δ ppm 1.13 (d, J=6.82 Hz, 3H) 1.17 (t, J=7.33 Hz, 3H) 2.26 (s, 3H) 2.62 (s, 3H) 3.30-3.45 (m, 2H) 3.41 (q, J=7.33 Hz, 2H) 4.00-4.06 (m, 1H) 7.12 (s, 1H) 7.51 (d, J=1.26 Hz, 1H) 7.89 (t, J=7.71 Hz, 1H) 7.99-8.05 (m, 2H) 8.11 (m, 2H) 8.30 (s, 1H) 12.04 (s, 1H) ESI-MS: m/z 466 (m+H)+.

Compound 100

(S)-5-(3-(ethylsulfonyl)phenyl)-N-(2-hydroxypropyl)-3,8-dimethyl-9H-pyrido[2,3-b]indole-7-carboxamide

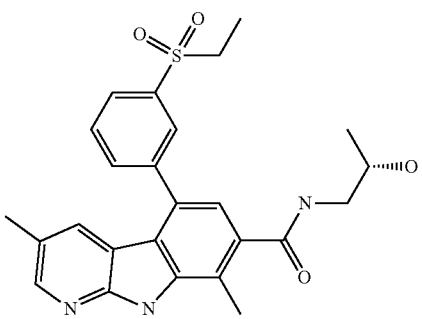

The title compound was synthesized using an analogous procedure to that described in the preparation of Compound 88. $^1$H NMR (400 MHz, DMSO-d$_6$) δ ppm 1.10 (d, J=6.32 Hz, 3H) 1.17 (t, J=7.33 Hz, 3H) 2.27 (s, 3H) 2.64 (s, 3H) 3.22 (t, J=6.06 Hz, 2H) 3.42 (q, J=7.33 Hz, 2H) 3.72-3.88 (m, 1H) 7.17 (s, 1H) 7.55 (d, J=1.52 Hz, 1 H) 7.89 (t, J=7.71 Hz, 1H)

8.03 (m, 2H) 8.13 (t, J=1.64 Hz, 1H) 8.31 (d, J=1.52 Hz, 1 H) 8.34 (t, J=5.94 Hz, 1H) 12.09 (s, 1H). ESI-MS: m/z 466 (m+H)⁺.

Compound 101

5-(3-(ethylsulfonyl)phenyl)-N-(2-hydroxyethyl)-3,8-dimethyl-9H-pyrido[2,3-b]indole-7-carboxamide

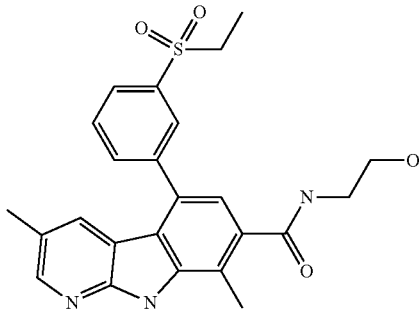

The title compound was synthesized using an analogous procedure to that described in the preparation of Compound 88. ¹H NMR (400 MHz, DMSO-d₆) δ ppm 1.17 (t, J=7.33 Hz, 3H) 2.27 (s, 3H) 2.63 (s, 3H) 3.34 (q, J=6.23 Hz, 2H) 3.42 (q, J=7.33 Hz, 2H) 3.53 (t, J=6.19 Hz, 2H) 7.17 (s, 1H) 7.53 (d, J=1.77 Hz, 1H) 7.89 (t, J=7.71 Hz, 1H) 8.03 (m, 2H) 8.13 (t, J=1.64 Hz, 1H) 8.34 (t, J=5.68 Hz, 1H) 8.31 (d, J=1.52 Hz, 1H) 12.05 (s, 1H). ESI-MS: m/z 452 (m+H)⁺.

Compound 102

N-(2,3-dihydroxypropyl)-5-(3-(ethylsulfonyl)phenyl)-3,8-dimethyl-9H-pyrido[2,3-b]indole-7-carboxamide

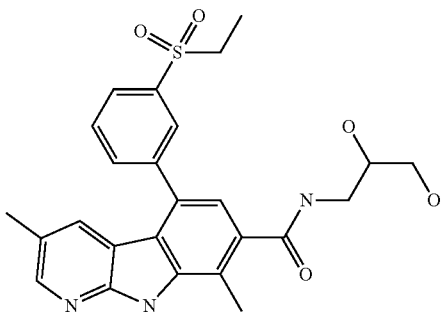

The title compound was synthesized using an analogous procedure to that described in the preparation of Compound 88. ¹H NMR (400 MHz, DMSO-d₆) δ ppm 1.17 (t, J=7.33 Hz, 3H) 2.27 (s, 3H) 2.64 (s, 3H) 3.22 (ddd, J=13.14, 6.44, 6.19 Hz, 1H) 3.35-3.45 (m, 5H) 3.66 (qd, J=5.60, 5.43 Hz, 1H) 7.18 (s, 1H) 7.54 (s, 1H) 7.89 (t, J=7.83 Hz, 1H) 8.03 (m, 2H) 8.13 (s, 1H) 8.29-8.35 (m, 2H) 12.09 (s, 1H). ESI-MS: m/z 482 (m+H)⁺.

Compound 103

5-(3-(ethylsulfonyl)phenyl)-N-(2-hydroxy-2-methyl-propyl)-3,8-dimethyl-9H-pyrido[2,3-b]indole-7-carboxamide

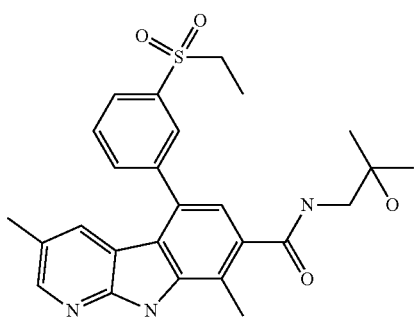

The title compound was synthesized using an analogous procedure to that described in the preparation of Compound 88. ¹H NMR (400 MHz, DMSO-d₆) δ ppm 1.17-1.14 (m, 9H) 2.27 (s, 3H) 2.64 (s, 3H) 3.26 (d, J=6.32 Hz, 2H) 3.41 (q, J=7.33 Hz, 2H) 7.16 (s, 1H) 7.54 (s, 1H) 7.89 (t, J=7.71 Hz, 1H) 8.04 (d, J=7.58 Hz, 2H) 8.13 (t, J=1.64 Hz, 1H) 8.25 (t, J=5.94 Hz, 1H) 8.31 (d, J=1.26 Hz, 1H) 12.07 (s, 1H). ESI-MS: m/z 480 (m+H)⁺.

Compound 104

5-(3-(ethylsulfonyl)phenyl)-N-(1-isopropylpiperidin-4-yl)-3,8-dimethyl-9H-pyrido[2,3-b]indole-7-carboxamide

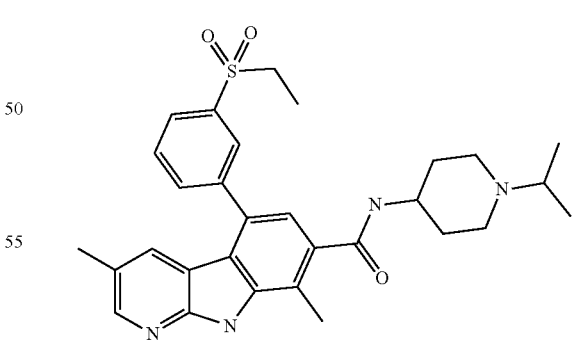

The title compound was synthesized using an analogous procedure to that described in the preparation of Compound 88. ¹H NMR (400 MHz, DMSO-d₆) δ ppm 1.13-1.27 (m, 9H) 1.72-1.84 (m, 2H) 2.05-2.17 (m, 2H) 2.27 (s, 3H) 2.63 (s, 3H) 3.13 (m, 3H) 3.42 (m, 4H) 4.08 (m, 1H) 7.12 (s, 1H) 7.53 (d, J=1.77 Hz, 1H) 7.89 (t, J=7.71 Hz, 1H) 8.04 (m, 2H) 8.09-

8.14 (s, 1H) 8.32 (d, J=1.52 Hz, 1H) 8.55 (d, J=7.58 Hz, 1H) 9.11 (br. s., 1H) 12.11 (s, 1H). ESI-MS: m/z 533 (m+H)+.

Compound 105

N-(1-ethylpiperidin-4-yl)-5-(3-(ethylsulfonyl)phenyl)-3,8-dimethyl-9H-pyrido[2,3-b]indole-7-carboxamide

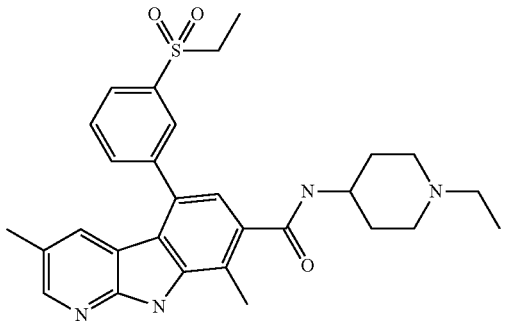

The title compound was synthesized using an analogous procedure to that described in the preparation of Compound 88. $^1$H NMR (400 MHz, DMSO-$d_6$) δ ppm 1.14-1.25 (m, 6H) 1.73 (m, 2H) 2.00-2.12 (m, 2H) 2.27 (s, 3H) 2.63 (s, 3H) 3.00-3.17 (m, 4H) 3.42 (q, J=7.33 Hz, 2H) 3.53 (m, 2H) 7.12 (s, 1H) 7.52 (d, J=1.26 Hz, 1 H) 7.89 (t, J=7.71 Hz, 1H) 7.99-8.07 (m, 2H) 8.11 (s, 1H) 8.31 (s, 1H) 8.53 (d, J=7.58 Hz, 1H) 9.17 (br. s., 1H) 12.08 (s, 1H). ESI-MS: m/z 519 (m+H)+.

Compound 106

5-(3-(ethylsulfonyl)phenyl)-3,8-dimethyl-N-thiazol-2-yl)-9H-pyrido[2,3-b]indole-7-carboxamide

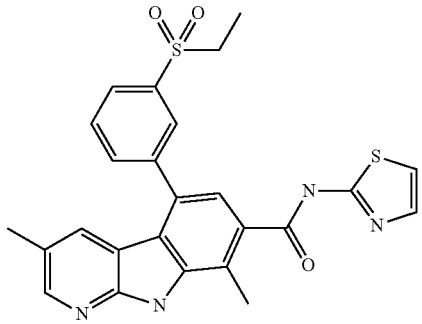

The title compound was synthesized using an analogous procedure to that described in the preparation of Compound 88. $^1$H NMR (400 MHz, DMSO-$d_6$) δ ppm 1.18 (t, J=7.33 Hz, 3H) 2.30 (s, 3H) 2.72 (s, 3H) 3.42 (q, J=7.41 Hz, 2H) 7.30 (d, J=3.54 Hz, 1H) 7.41 (s, 1H) 7.56 (d, J=3.79 Hz, 1H) 7.63 (s, 1H) 7.90 (t, J=7.83 Hz, 1 H) 8.04 (d, J=7.59 Hz, 1H) 8.12 (d, J=7.58 Hz, 1H) 8.21 (s, 1H) 8.36 (s, 1H) 12.25 (s, 1 H) 12.66 (br. s., 1H). ESI-MS: m/z 491 (m+H)+.

Compound 107

5-(3-(ethylsulfonyl)phenyl)-3,8-dimethyl-N-(2-(2,2,2-trifluoroethoxy)ethyl-9H-pyrido[2,3-b]indole-7-carboxamide

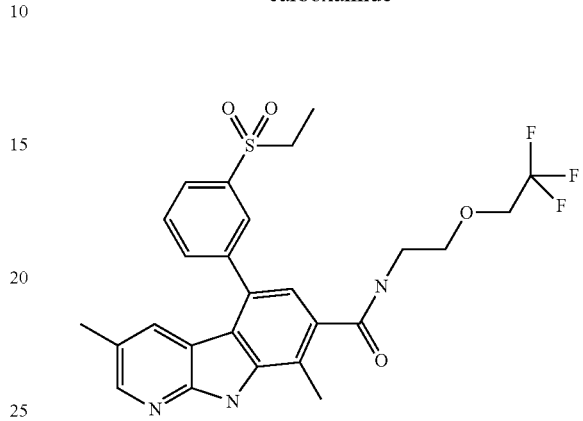

The title compound was synthesized using an analogous procedure to that described in the preparation of Compound 88. $^1$H NMR (400 MHz, DMSO-$d_6$) δ ppm 1.17 (t, J=7.33 Hz, 3H) 2.27 (s, 3H) 2.63 (s, 3H) 3.41 (q, J=7.33 Hz, 2H) 3.47 (q, J=5.56 Hz, 2H) 3.75 (t, J=5.68 Hz, 2H) 4.11 (q, J=9.52 Hz, 2H) 7.14 (s, 1H) 7.56 (s, 1 H) 7.91 (t, J=7.83 Hz, 1H) 7.99-8.06 (m, 2H) 8.12 (s, 1H) 8.32 (s, 1H) 8.49 (t, J=5.68 Hz, 1H) 12.10 (s, 1H). ESI-MS: m/z 534 (m+H)+.

Compound 108

5-(3-(ethylsulfonyl)phenyl)-3,8-dimethyl-N-(piperidin-3-yl)-9H-pyrido[2,3-b]indole-7-carboxamide

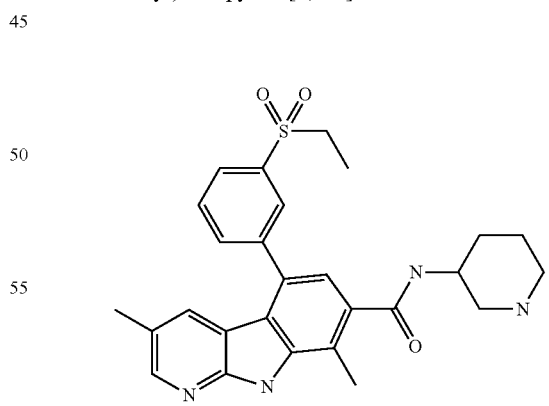

The title compound was synthesized using an analogous procedure to that described in the preparation of Compound 88. $^1$H NMR (400 MHz, DMSO-$d_6$) δ ppm 1.17 (t, J=7.33 Hz, 3H) 1.56-1.69 (m, 2H) 1.96-1.88 (m, 2H) 2.27 (s, 3H) 2.63 (s, 3 H) 2.82 (m, 2H) 3.22 (m, 1H) 3.42 (m, 3H) 4.16 (m, 1H) 7.16 (s, 1H) 7.51 (s, 1H) 7.90 (t, J=7.71 Hz, 1H) 7.99-8.08 (m, 2H) 8.11 (t, J=1.64 Hz, 1H) 8.32 (d, J=2.02 Hz, 1H) 8.51 (d, J=7.58 Hz, 1H) 8.58-8.74 (m, 2H) 12.09 (s, 1H). ESI-MS: m/z 491 (m+H)⁺.

Compound 109

5-(3-(ethylsulfonyl)phenyl)-3,8-dimethyl-N-(piperidin-4-yl)-9H-pyrido[2,3-b]indole-7-carboxamide

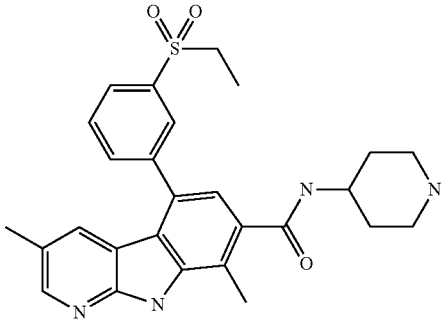

The title compound was synthesized using an analogous procedure to that described in the preparation of Compound 88. ¹H NMR (400 MHz, DMSO-d₆) δ ppm 1.18 (t, J=7.33 Hz, 3H) 1.60-1.77 (m, 2H) 2.05-2.03 (m, 2H) 2.27 (s, 3H) 2.62 (s, 3 H) 3.04 (q, J=9.85 Hz, 2H) 3.33-3.29 (m, 2H) 3.42 (q, J=7.49 Hz, 2H) 4.10 (m, 1H) 7.12 (s, 1H) 7.51 (d, J=1.52 Hz, 1H) 7.89 (t, J=7.71 Hz, 1H) 7.99-8.08 (m, 2H) 8.11 (s, 1H) 8.32 (d, J=1.52 Hz, 1H) 8.34-8.42 (m, 1H) 8.51 (d, J=7.58 Hz, 1H) 8.60-8.66 (m, 1H) 12.08 (s, 1H). ESI-MS: m/z 491 (m+H)⁺.

Compound 110

5-(3-(ethylsulfonyl)phenyl)-3,8-dimethyl-N-(piperidin-3-yl)-9H-pyrido[2,3-b]indole-7-carboxamide

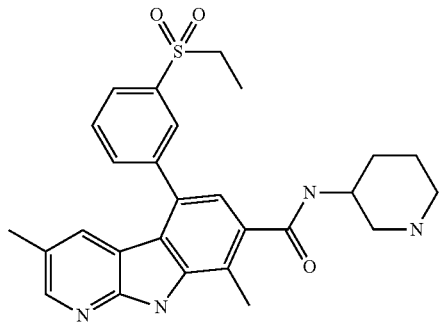

The title compound was synthesized using an analogous procedure to that described in the preparation of Compound 88. ¹H NMR (400 MHz, DMSO-d₆) δ ppm 1.17 (t, J=7.45 Hz, 3H) 1.57-1.69 (m, 2H) 1.83-2.01 (m, 2H) 2.27 (s, 3H) 2.63 (s, 3H) 2.74-2.90 (m, 2H) 3.21 (m, 1H) 3.42 ((m, 3H)) 4.17 (m, 1H) 7.16 (s, 1H) 7.51 (s, 1H) 7.90 (t, J=7.58 Hz, 1H) 8.03 (m, 2H) 8.11 (s, 1H) 8.32 (s, 1H) 8.50 (d, J=7.58 Hz, 1H) 8.58-8.71 (m, 2H) 12.09 (s, 1H). ESI-MS: m/z 491 (m+H)⁺.

Compound 111

5-(3-(ethylsulfonyl)phenyl)-N-(2-(2-hydroxyethoxy)ethyl-3,8-dimethyl-9H-pyrido[2,3-b]indole-7-carboxamide

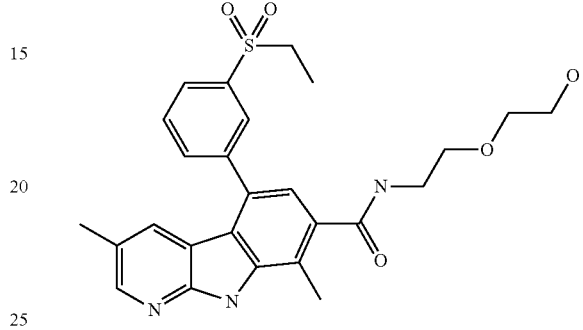

The title compound was synthesized using an analogous procedure to that described in the preparation of Compound 88. ¹H NMR (400 MHz, DMSO-d₆) δ ppm 1.17 (t, J=7.20 Hz, 3H) 2.27 (s, 3H) 2.63 (s, 3H) 3.37-3.58 (m, 11H) 7.14 (s, 1H) 7.55 (s, 1H) 7.88 (t, J=7.83 Hz, 1H) 8.04-8.03 (m, 2H) 8.12 (s, 1H) 8.31 (s, 1H) 8.41 (t, J=5.68 Hz, 1H) 12.08 (s, 1H). ESI-MS: m/z 496 (m+H)⁺.

Compound 112

5-(3-(cyclopropanecarboxamido)phenyl)-N-(2-(dimethylamino)ethyl)-3,8-dimethyl-9H-pyrido[2,3-b]indole-7-carboxamide

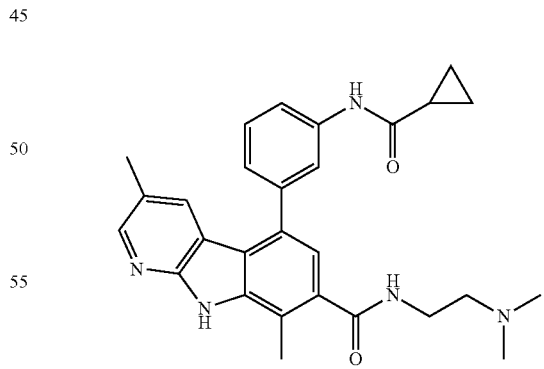

The title compound was synthesized using an analogous procedure to that described in the preparation of Compound 88. ¹H NMR (400 MHz, DMSO-d₆) δ ppm 0.75-0.84 (m, 4H) 1.80 (t, J=4.93 Hz, 1H) 2.27 (s, 3H) 2.64 (s, 3H) 2.87 (d, J=4.55 Hz, 6H) 3.29 (q, J=5.56 Hz, 2H) 3.61 (q, J=5.64 Hz, 2H) 7.16 (s, 1H) 7.27 (d, J=7.33 Hz, 1 H) 7.50 (t, J=7.71 Hz, 1H) 7.63 (d, J=8.34 Hz, 1H) 7.68 (s, 1H) 7.99 (s, 1H) 8.29 (s, 1 H) 8.58 (t, J=5.43 Hz, 1H) 9.39 (br. s., 1H) 10.38 (s, 1H) 11.99 (s, 1H); ESI-MS: m/z calc'd for $C_{28}H_{31}N_5O_2$ 469.25; found 470.4 (M+H)+.

Compound 113

N-(2-(dimethylamino)ethyl)-5-(3-(ethylsulfonyl)phenyl)-3,8-dimethyl-9H-pyrido[2,3-b]indole-7-carboxamide

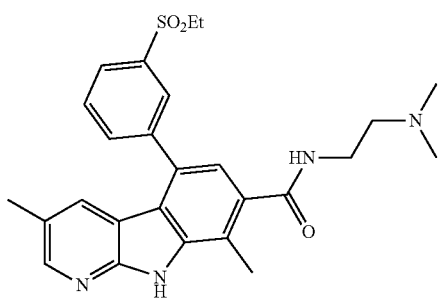

The title compound was synthesized using an analogous procedure to that described in the preparation of Compound 88. $^1$H NMR (400 MHz, DMSO-d$_6$): δ 12.04 (s, 1H), 8.28-8.31 (m, 2H), 8.12 (s, 1H), 8.01-8.05 (m, 2H), 7.89 (t, 1H), 7.52 (s, 1H), 7.12 (s, 1H), 3.43 (q, 2H), 2.63 (s, 3H), 2.27 (s, 3H), 2.20 (s, 6H), 1.17 (t, 3H). MS (ES) [m+H] calc'd for $C_{26}H_{30}N_4O_3S$, 479; found 479.4.

Compound 114

5-(3-(ethylsulfonyl)phenyl)-3,8-dimethyl-N-((1-methylpiperidin-4-yl)methyl)-9H-pyrido[2,3-b]indole-7-carboxamide

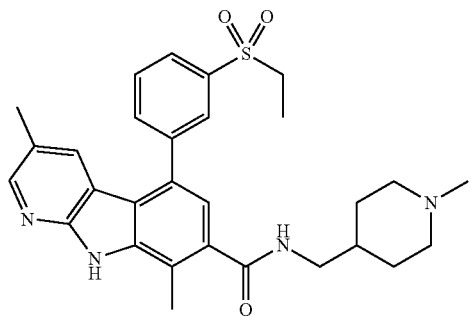

The title compound was synthesized using an analogous procedure to that described in the preparation of Compound 88. $^1$H NMR (400 MHz, DMSO-d$_6$) δ ppm 1.18 (t, J=7.33 Hz, 3H) 1.38 (d, J=10.86 Hz, 2H) 1.78 (br. s., 1H) 1.91 (d, J=13.39 Hz, 2 H) 2.27 (s, 3H) 2.63 (s, 3H) 2.75 (d, J=4.80 Hz, 3H) 2.86-2.97 (m, 2H) 3.20 (t, J=6.19 Hz, 2H) 3.42 (q, J=7.33 Hz, 4H) 7.14 (s, 1H) 7.51 (d, J=1.26 Hz, 1H) 7.89 (t, J=7.71 Hz, 1H) 8.03 (dd, J=10.61, 8.59 Hz, 2H) 8.12 (s, 1H) 8.32 (d, J=1.52 Hz, 1H) 8.50 (q, J=6.06 Hz, 1H) 9.18 (br. s., 1H) 12.08 (s, 1H); ESI-MS: m/z calc'd for $C_{29}H_{34}N_4O_3S$ 518.24; found 519.4 (M+H)+.

Compound 115

N-(3-(dimethylamino)propyl)-5-(3-(ethylsulfonyl)phenyl)-3,8-dimethyl-9H-pyrido[2,3-b]indole-7-carboxamide

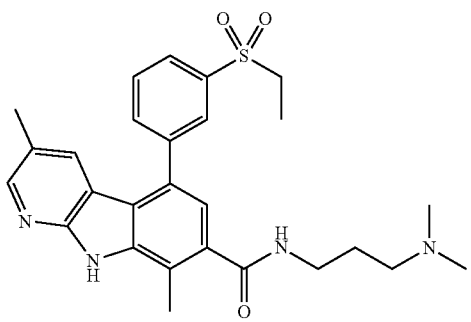

The title compound was synthesized using an analogous procedure to that described in the preparation of Compound 88. $^1$H NMR (400 MHz, DMSO-d$_6$) δ ppm 1.18 (t, J=7.33 Hz, 3H) 1.85-1.95 (m, 1H) 1.91 (d, J=7.83 Hz, 1H) 2.27 (s, 3H) 2.65 (s, 3H) 2.80 (d, J=4.80 Hz, 6H) 3.13 (dt, J=10.36, 5.18 Hz, 2H) 3.34 (q, J=6.32 Hz, 2H) 3.42 (q, J=7.41 Hz, 2H) 7.17 (s, 1H) 7.52 (s, 1H) 7.90 (t, J=7.71 Hz, 1H) 8.04 (t, J=9.09 Hz, 2H) 8.12 (s, 1H) 8.32 (d, J=1.52 Hz, 1H) 8.53 (t, J=5.81 Hz, 1H) 9.35 (br. s., 1H) 12.08 (s, 1H); ESI-MS: m/z calc'd for $C_{27}H_{32}N_4O_3S$ 492.22; found 493.4 (M+H)+.

Compound 116

5-(3-(ethylsulfonyl)phenyl)-3,8-dimethyl-N-(2-(pyrrolidin-1-yl)ethyl)-9H-pyrido[2,3-b]indole-7-carboxamide

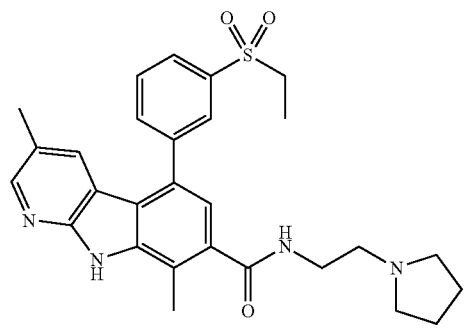

The title compound was synthesized using an analogous procedure to that described in the preparation of Compound 88. $^1$H NMR (400 MHz, DMSO-d$_6$) δ ppm 1.17 (t, J=7.33 Hz, 3H) 1.87 (dd, J=7.20, 4.93 Hz, 2H) 2.03 (t, J=6.82 Hz, 2H) 2.27 (s, 3 H) 3.08 (dd, J=10.48, 7.45 Hz, 2H) 3.36 (q, J=5.89 Hz, 2H) 3.42 (q, J=7.33 Hz, 2H) 3.63 (td, J=12.88, 5.56 Hz, 4H) 7.24 (s, 1H) 7.52 (s, 1H) 7.90 (t, J=7.71 Hz, 1H) 8.04 (dd, J=14.27, 7.71 Hz, 2H) 8.12 (s, 1H) 8.33 (d, J=1.52 Hz, 1H)

8.62 (t, J=5.68 Hz, 1H) 9.53 (br. s., 1H) 12.10 (s, 1H); ESI-MS: m/z calc'd for $C_{28}H_{32}N_4O_3S$ 504.22; found 505.4 (M+H)⁺.

Compound 117

(S)-5-(3-(ethylsulfonyl)phenyl)-3,8-dimethyl-N-(1-methylpiperidin-3-yl)-9H-pyrido[2,3-b]indole-7-carboxamide

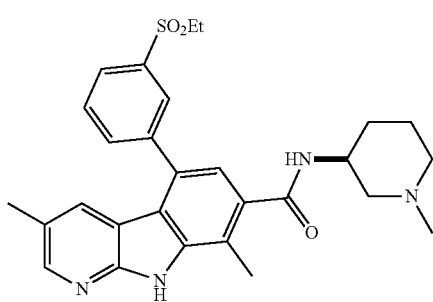

The title compound was synthesized using an analogous procedure to that described in the preparation of Compound 88. ¹H NMR (400 MHz, DMSO-d₆) δ ppm 1.18 (t, J=7.45 Hz, 3H) 1.20-2.0 (m, 6H) 2.27 (s, 3H) 2.62 (s, 3H) 2.70-4.4 (m, 8H) 7.12 (s, 1H) 7.52 (s, 1H) 7.91 (d, J=7.58 Hz, 1H) 8.01 (d, J=8.84 Hz, 1H) 8.06 (d, J=8.84 Hz, 1H) 8.11 (d, J=1.52 Hz, 1H) 8.33 (s, 1H) 8.62 (d, J=7.83 Hz, 1H). [M+H] calc'd for $C_{28}H_{32}N_2O_2S$ 505; found, 505.4.

Compound 118

(R)-5-(3-(ethylsulfonyl)phenyl)-3,8-dimethyl-N-(1-methylpiperidin-3-yl)-9H-pyrido[2,3-b]indole-7-carboxamide

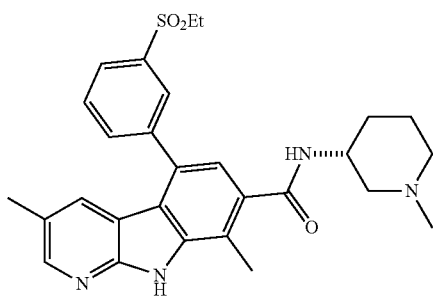

The title compound was synthesized using an analogous procedure to that described in the preparation of Compound 88. ¹H NMR (400 MHz, DMSO-d₆) δ ppm 1.18 (t, J=7.45 Hz, 3H) 1.20-2.0 (m, 6H) 2.27 (s, 3H) 2.62 (s, 3H) 2.70-4.40 (m, 8H) 7.13 (s, 1H) 7.53 (d, J=1.01 Hz, 1H) 7.90 (t, J=7.83 Hz, 1H) 8.04 (dd, J=17.43, 8.34 Hz, 2H) 8.11 (d, J=1.52 Hz, 1H) 8.33 (s, 1H) 8.62 (d, J=7.83 Hz, 1H) 12.11 (s, 1H). [M+H] calc'd for $C_{28}H_{32}N_2O_2S$ 505; found, 505.4.

Compound 119

5-chloro-3,8-dimethyl-N-(1-methylpiperidin-4-yl)-9H-pyrido[2,3-b]indole-7-carboxamide

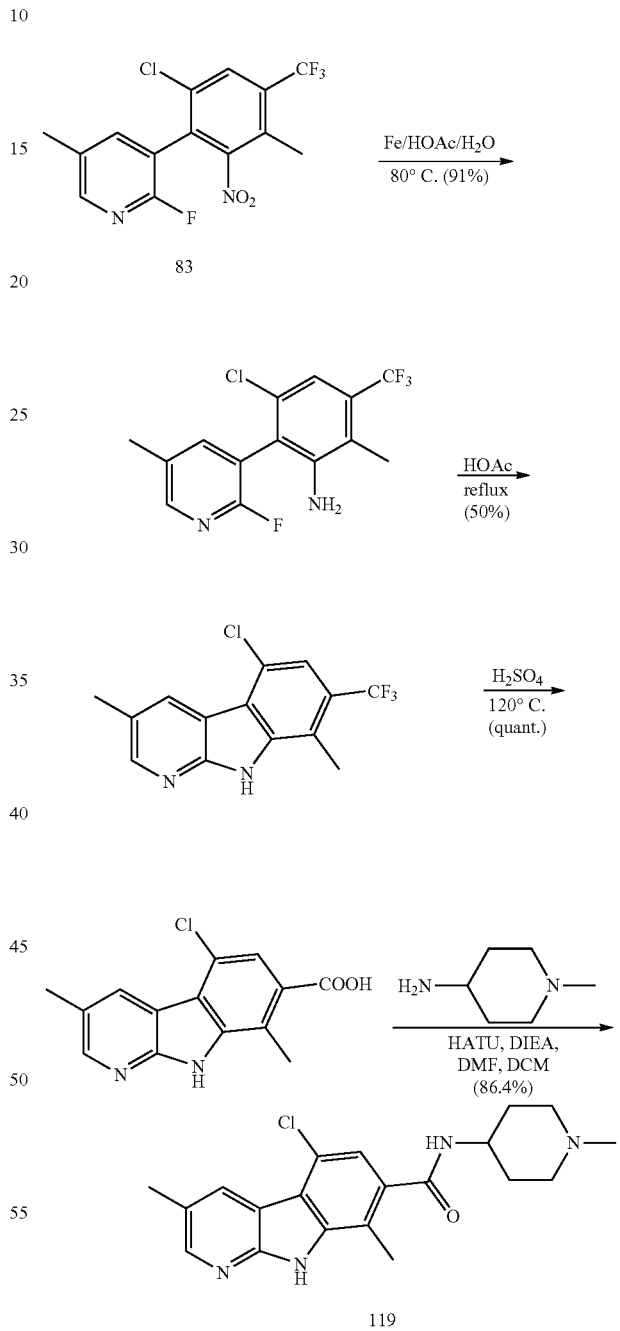

The title compound was synthesized from 5-chloro-3,8-dimethyl-9H-pyrido[2,3-b]indole-7-carboxylic acid and 1-methylpiperidin-4-amine using an analogous procedure to that described in the preparation of Compound 88. ¹H NMR (400 MHz, DMSO-d₆ with TFD) δ ppm 1.70-2.2 (m, 4H) 2.53 (br. s., 3H) 2.58 (s, 3H) 2.74-2.82 (m, 3H) 2.80-4.10 (m, 5H)

7.29 (s, 1H) 8.47 (s, 1H) 8.70 (s, 1H). [M+H] calc'd for C$_{20}$H$_{18}$N$_2$O$_2$S 371; found, 371.4.

Compound 120

5-(3-(cyclopropanecarboxamido)phenyl)-3,8-dimethyl-N-(1-methyl-piperidin-4-yl)-9H-pyrido[2,3-b]indole-7-carboxamide

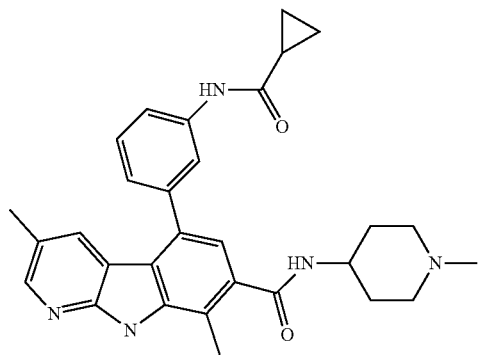

The title compound was synthesized from Compound 119 and 3-(cyclopropanecarboxamido) phenyl boronic acid using an analogous procedure to that described in the preparation of Compound 84. $^1$H NMR (400 MHz, DMSO-d$_6$) δ ppm 0.77-0.82 (m, 4H) 1.53 (qd, J=11.66, 3.41 Hz, 2H) 1.79-1.82 (m, 3H) 1.95 (t, J=10.86 Hz, 2H) 2.15 (s, 3H) 2.27 (s, 3H) 2.59 (s, 3H) 2.74 (d, J=11.12 Hz, 2H) 3.75 (m, 1H) 6.98 (s, 1H) 7.27 (d, J=7.58 Hz, 1H) 7.49 (t, J=7.96 Hz, 1H) 7.69 (d, J=2.02 Hz, 2H) 7.91 (s, 1H) 8.25-8.30 (m, 2H) 10.37 (s, 1H) 11.92 (br. s., 1H); [M+H] calc'd for C$_{30}$H$_{34}$N$_5$O$_2$, 496.3; found, 496.4.

Compound 121

5-chloro-N-(2-(dimethylamino)ethyl)-3,8-dimethyl-9H-pyrido[2,3-b]indole-7-carboxamide

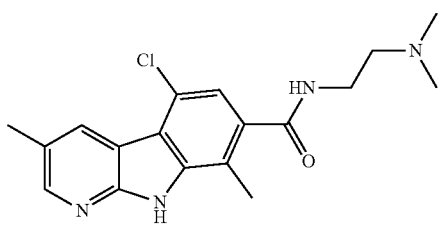

The title compound was synthesized from 5-chloro-3,8-dimethyl-9H-pyrido[2,3-b]indole-7-carboxylic acid and N,N-dimethylethane-1,2-diamine using an analogous procedure to that described in the preparation of Compound 88. $^1$H NMR (400 MHz, DMSO-d$_6$) δ ppm 2.20 (s, 6H) 2.42 (t, J=6.69 Hz, 2H) 2.49 (br. s., 3H) 2.55 (s, 3 H) 3.35 (d, J=6.57 Hz, 2H) 7.18 (s, 1H) 8.31 (t, J=5.56 Hz, 1H) 8.40 (d, J=2.02 Hz, 1H) 8.53 (s, 1H) 12.14 (s, 1H). [M+H] calc'd for C$_{18}$H$_{21}$ClN$_4$O 345; found, 345.4.

Compound 122

5-(3-(cyclopropylcarbamoyl)phenyl)-N-(2-(dimethylamino)ethyl)-3,8-dimethyl-9H-pyrido[2,3-b]indole-7-carboxamide

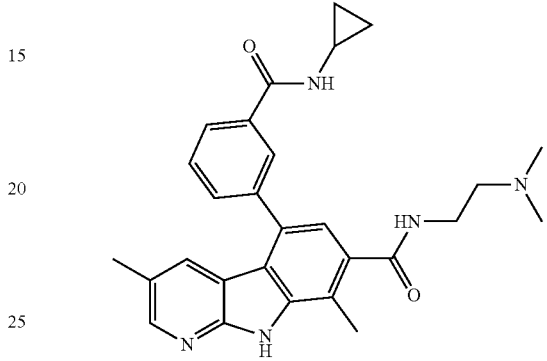

The title compound was synthesized from 5-chloro-N-(2-(dimethylamino)ethyl)-3,8-dimethyl-9H-pyrido[2,3-b]indole-7-carboxamide and 3-(cyclopropylcarbamoyl)phenyl boronic acid using an analogous procedure to that described in the preparation of Compound 84. $^1$H NMR (400 MHz, DMSO-d$_6$) δ ppm 0.57 (dd, J=3.92, 2.40 Hz, 2H) 0.71 (dd, J=6.95, 2.40 Hz, 2H) 1.23 (s, 1H) 2.26 (s, 3H) 2.65 (s, 3H) 2.87 (d, J=5.05 Hz, 6H) 3.29 (q, J=5.98 Hz, 2H) 3.61 (q, J=6.15 Hz, 2H) 7.20 (s, 1H) 7.50 (s, 1H) 7.66 (t, J=7.83 Hz, 1H) 7.77 (d, J=7.83 Hz, 1H) 7.98 (d, J=7.83 Hz, 1H) 8.08 (s, 1H) 8.31 (d, J=1.77 Hz, 1H) 8.57-8.61 (m, 1H) 8.59 (d, J=4.55 Hz, 1H) 12.05 (s, 1H). [M+H] calc'd for C$_{28}$H$_{31}$N$_5$O$_2$ 470; found, 470.4.

Compound 123

4-(2-Fluoro-5-methyl-pyridin-3-yl)-3,5-dinitro-benzonitrile

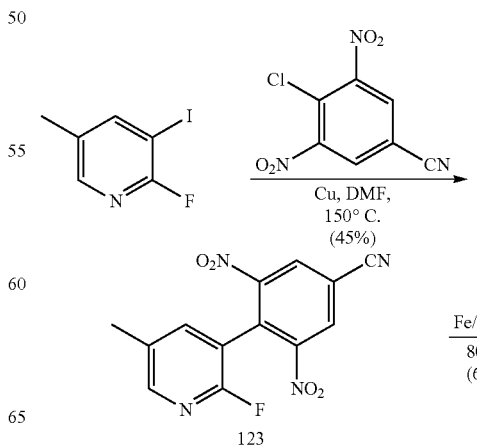

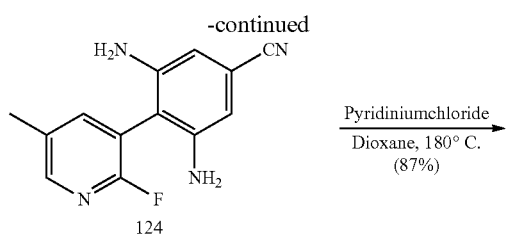

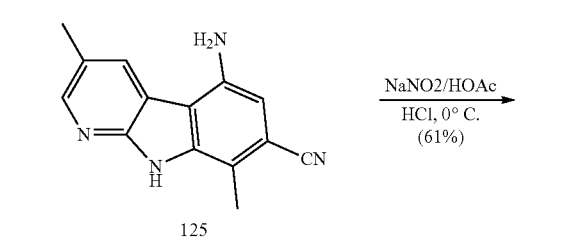

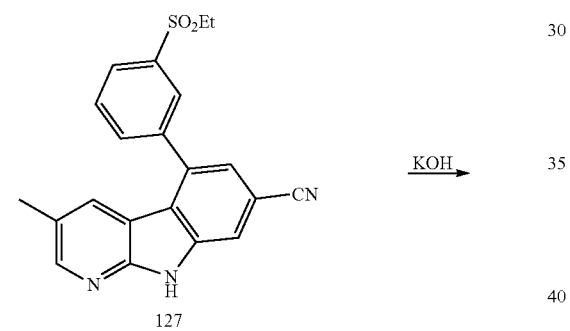

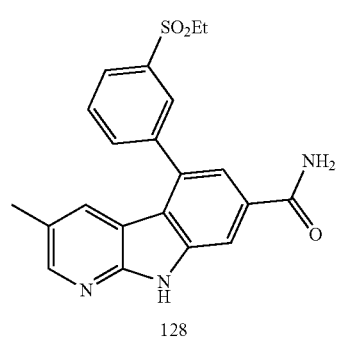

4-Chloro-3,5-dinitro-benzonitrile (200 mg, 0.88 mmol), 2-fluoro-3-iodo-5-picolione (208 mg, 0.88 mmol), and copper (45 μm powder, 168 mg, 2.6 mmol) were combined in DMF (2 mL) in a sealed tube purged with nitrogen. The reaction was heated at 150° C. for 30 min in the microwave. The reaction was diluted with acetone and the solids were removed by filtration. The solution was concentrated in vacuo. The crude product was purified by silica gel chromatography (80% CH$_2$Cl$_2$/hexanes) to provide the title compound as a faintly yellow solid (119 mg, 45%), which was slow to crystallize. $^1$H NMR (400 MHz, CDCl$_3$): δ 8.50 (s, 2H), 8.16 (d, 1H, J=1.2 Hz), 7.42 (dd, 1H, J=8.8, 2.0 Hz), 2.38 (s, 3H). MS (ES) [m+H] calc'd for C$_{13}$H$_7$FN$_4$O$_4$, 303; found 303.

Compound 124

3,5-Diamino-4-(2-fluoro-5-methyl-pyridin-3-yl)-benzonitrile

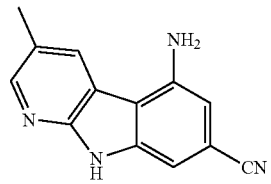

Compound 123 (119 mg, 0.39 mmol) was stirred in HOAc (3 mL) with H$_2$O (0.5 mL) and stirred at 76° C. Iron powder (~325 mesh, 88 mg, 1.56 mmol) was added, and the reaction stirred for 4 h. The solution was concentrated in vacuo, diluted with EtOAc (30 mL), and made basic with sat. NaHCO$_3$. The material was then filtered through Celite, and the organics were separated, dried (MgSO$_4$), and concentrated in vacuo to provide the title compound as a brown oil (148 mg, 66%). MS (ES) [m+H] calc'd for C$_{13}$H$_{11}$FN$_4$, 243; found 243.

Compound 125

5-Amino-3-methyl-9H-pyrido[2,3-b]indole-7-carbonitrile

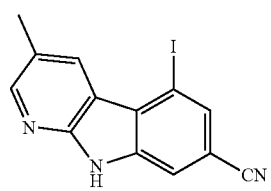

Compound 124 (148 mg, 0.61 mmol) was dissolved in dioxane (2 mL) and pyridinium chloride (80 mg), and the solution was heated at 180° C. in the microwave for 15 minutes. The solution was concentrated in vacuo. Purification by flash chromatography (20% acetone/CH$_2$Cl$_2$) to provide the title compound as an off-white solid (118 mg, 87%). MS (ES) [m+H] calc'd for C$_{13}$H$_{10}$N$_4$, 223; found 223.

Compound 126

5-Iodo-3-methyl-9H-pyrido[2,3-b]indole-7-carbonitrile

Compound 125 (118 mg, 0.53 mmol) was dissolved in HOAc (2 mL) and H$_2$O (1 mL), and the solution stirred at 0° C. Concentrated HCl (120 μL) in H$_2$O (120 mL) was added, and the reaction stirred for 5 min. Sodium nitrite (54 mg, 0.78 mmol) in H$_2$O (120 μL) was added dropwise, and the red solution stirred for 10 min. A solution of iodine (10 mg) and potassium iodide (129 mg, 0.78 mmol) in H$_2$O (300 μL) was added dropwise, and the brown frothy solution stirred for 30 min at 0° C. and then 30 min while warming to r.t. The reaction was diluted with H$_2$O (5 mL) and extracted with CHCl$_3$. Organics were dried (MgSO$_4$) and concentrated in vacuo. Purification by silica gel chromatography provided the title compound as a faintly yellow solid (108 mg, 61%). MS (ES) [m+H] calc'd for C$_{13}$H$_{81}$N$_3$, 334; found 334.

Compound 127

5-(3-Ethanesulfonyl-phenyl)-3-methyl-9H-pyrido[2,3-b]indole-7-carbonitrile

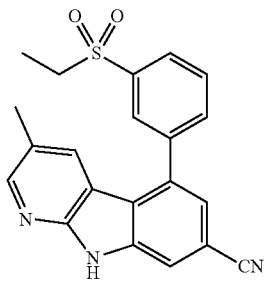

The title compound was prepared in 43% yield from Compound 126 according to the procedure outlined in the preparation of Compound 84. $^1$H NMR (400 MHz, CD$_3$OD) δ 8.34 (s, 1H), 8.21 (s, 1H), 8.13 (d, 1H, J=7.6 Hz), 8.00 (t, 1H, J=7.6 Hz), 7.89-7.98 (m, 2H), 7.59 (s, 1H), 7.49 (s, 1H), 3.35 (q, 2H, J=7.2 Hz), 2.33 (s, 3H), 1.29 (t, 3H, J=7.2 Hz). MS (ES) [m+H] calc'd for C$_{21}$H$_{17}$N$_3$O$_2$S, 376; found 376.

Compound 128

5-(3-Ethanesulfonyl-phenyl)-3-methyl-9H-pyrido[2,3-b]indole-7-carboxylic acid amide

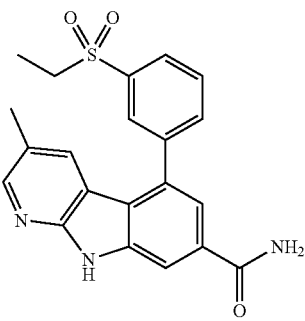

Compound 127 (30 mg, 0.08 mmol) was dissolved in dioxane (2 mL) and stirred at r.t. A solution of potassium hydroxide (25 mg, 0.44 mmol) in 30% H$_2$O$_2$ solution (1 mL) was added, and the reaction stirred for 18 h. The solution was neutralized with 1N HCl and concentrated in vacuo. Purification by silica gel chromatography (5 to 8% MeOH/CH$_2$Cl$_2$ g provided the title compound as a white solid (14.8 mg, 47%). $^1$H NMR (400 MHz, CD$_3$OD) δ 8.28 (s, 1H), 8.22 (s, 1H), 8.12 (s, 1H), 8.10 (d, 1H, J=7.6 Hz), 8.02 (d, 1H, J=7.6 Hz), 7.88 (t, 1H, J=7.6 Hz), 7.68 (s, 1H), 7.62 (s, 1H), 3.34 (q, 2H, J=7.2 Hz), 2.31 (s, 3H), 1.29 (t, 3H, J=7.2 Hz). MS (ES) [m+H] calc'd for C$_{21}$H$_{19}$N$_3$O$_3$S, 394; found 394.

Compound 129

4-(2-Fluoro-5-methyl-pyridin-3-yl)-3,5-dinitro-benzoic acid methyl ester

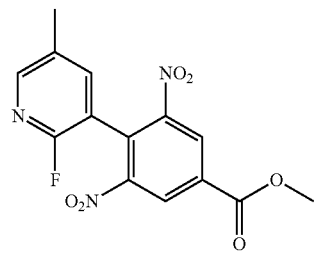

The title compound was prepared from 4-chloro-3,5-dinitro-benzoic acid methyl ester in 94% yield according to the procedure outline for the preparation of Compound 123. MS (ES) [m+H] calc'd for C$_{14}$H$_{10}$FN$_3$O$_6$, 336; found 336.

Compound 130

3,5-Diamino-4-(2-fluoro-5-methyl-pyridin-3-yl)-benzoic acid methyl ester

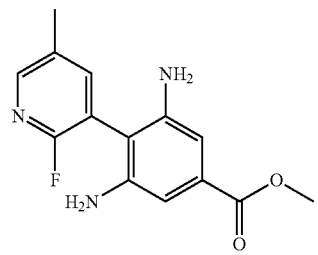

Compound 129 (2.02, 6.03 mmol) was stirred in MeOH (150 mL) with 10% Pd/C (200 mg) under a hydrogen atmosphere for 1.5 h. The reaction was filtered through Celite and concentrated to provide the title compound as a brown solid (1.64 g, 99%). MS (ES) [m+H] calc'd for C$_{14}$H$_{14}$FN$_3$O$_2$, 276; found 276.

Compound 131

5-Amino-3-methyl-9H-pyrido[2,3-b]indole-7-carboxylic acid methyl ester

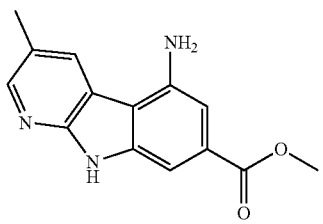

The title compound was prepared in 88% yield from example Compound 130 according to the procedure outlined for the preparation of Compound 125. MS (ES) [m+H] calc'd for $C_{14}H_{13}N_3O_2$, 256; found 256.

Compound 132

5-Iodo-3-methyl-9H-pyrido[2,3-b]indole-7-carboxylic acid methyl ester

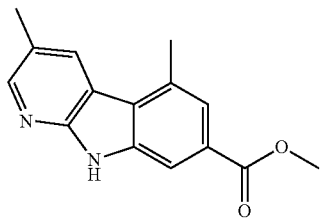

The title compound was prepared in 69% yield from Compound 131 according to the procedure outlined for the preparation of Compound 126. MS (ES) [m+H] calc'd for $C_{14}H_{11}IN_2O_2$, 367; found 367.

Compound 133

5-(3-Ethanesulfonyl-phenyl)-3-methyl-9H-pyrido[2,3-b]indole-7-carboxylic acid methyl ester

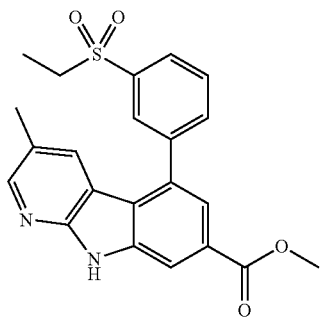

The title compound was prepared in 65% yield from Compound 132 according to the procedure outlined in the preparation of Compound 84. MS (ES) [m+H] calc'd for $C_{22}H_{20}N_2O_4S$, 409; found 409.

Compound 134

[5-(3-Ethanesulfonyl-phenyl)-3-methyl-9H-pyrido[2,3-b]indol-7-yl]-methanol

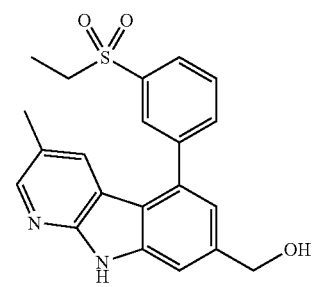

LAH reduction of Compound 133 provided the title compound. $^1$H NMR (400 MHz, MeOD) δ ppm 1.29 (t, J=7.45 Hz, 5H) 2.40 (s, 4H) 7.34 (s, 1H) 7.74 (d, J=0.51 Hz, 1H) 7.90 (t, J=7.83 Hz, 2H) 7.99 (s, 1H) 8.03 (ddd, J=7.71, 1.39, 1.26 Hz, 2H) 8.11 (d, J=7.07 Hz, 1H) 8.22 (t, J=1.52 Hz, 1H) 8.27 (br. s., 1H) [M+H] calc'd for $C_{21}H_{20}N_2O_3S$, 381; found, 381.

Compound 135

[5-(3-Ethanesulfonyl-phenyl)-3-methyl-9H-pyrido[2,3-b]indol-7-ylmethyl]-dimethyl-amine

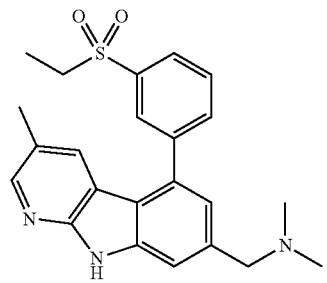

Methanesulfonyl chloride (18 µL, 0.24 mmol) was added to a solution of Compound 134 (46 mg, 0.12 mmol) and diisopropylethylamine (43 µL, 0.25 mmol) in THF (1 mL) at 0° C. After stirring for 3 h, dimethylamine (2M, 1 mL, 2 mmol) was added, and the reaction stirred for 16 h. The solution was concentrated in vacuo and purified by prep-HPLC to provide the title compound as a pale yellow oil (32 mg, 65%). $^1$H NMR (400 MHz, CD$_3$OD) δ 8.36 (br s, 1H), 8.22 (s, 1H), 8.13 (d, 1H, J=7.6 Hz), 8.05 (d, 1H, J=7.6 Hz), 7.88-7.94 (m, 2H), 7.85 (s, 1H), 7.44 (s, 1H), 4.57 (s, 2H), 3.33 (q, 2H, J=7.2 Hz), 2.94 (s, 6H), 2.39 (s, 3H), 1.30 (t, 3H, J=7.2 Hz). MS (ES) [m+H] calc'd for $C_{23}H_{25}N_3O_2S$, 408; found 408.

Compound 136

5-(3-Ethanesulfonyl-phenyl)-3-methyl-7-morpholin-4-ylmethyl-9H-pyrido[2,3-b]indole

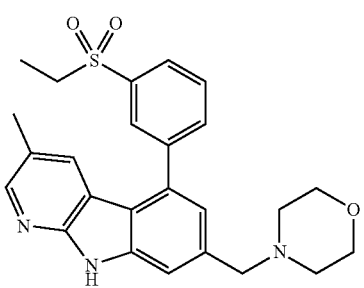

The title compound was prepared from Compound 134 and morpholine according to the procedure outline for the preparation of Compound 135. $^1$H NMR (400 MHz, CD$_3$OD) δ 8.42 (br s, 1H), 8.24 (s, 1H), 8.14 (d, 1H, J=7.6 Hz), 8.03 (d, 1H, J=7.6 Hz), 7.97 (s, 1H), 7.90 (t, 1H, J=7.6 Hz), 7.87 (s, 1H), 7.48 (s, 1H), 4.62 (s, 2H), 4.00-4.09 (m, 2H), 3.71-3.80 (m, 2H), 3.41-3.50 (m, 2H), 3.27-3.32 (m, 4H), 2.39 (s, 3H), 1.29 (t, 3H, J=7.2 Hz). MS (ES) [m+H] calc'd for $C_{25}H_{27}N_3O_3S$, 450; found 450.

Compound 137

5-(3-Ethanesulfonyl-phenyl)-3-methyl-7-(4-methyl-piperazin-1-ylmethyl)-9H-pyrido[2,3-b]indole

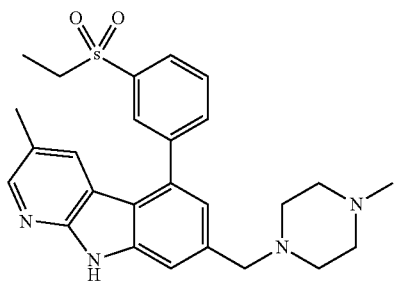

The title compound was prepared from Compound 134 and 1-methylpiperazine according to the procedure outline for the preparation of Compound 135. $^1$H NMR (400 MHz, CD$_3$OD) δ 8.39 (br s, 1H), 8.23 (s, 1H), 8.12 (d, 1H, J=7.6 Hz), 8.05 (s, 1H), 8.03 (d, 1H, J=7.6 Hz), 7.90 (t, 1H, J=7.6 Hz), 7.83 (s, 1H), 7.49 (s, 1H), 4.38 (s, 2H), 3.48-3.56 (m, 2H), 3.26-3.40 (m, 6H), 2.95 (s, 3H), 2.41 (s, 3H), 1.29 (t, 3H, J=7.2 Hz). MS (ES) [m+H] calc'd for $C_{26}H_{30}N_4O_2S$, 463; found 463.

Compound 138

5-(3-Ethanesulfonyl-phenyl)-3-methyl-7-pyrrolidin-1-ylmethyl-9H-pyrido[2,3-b]indole

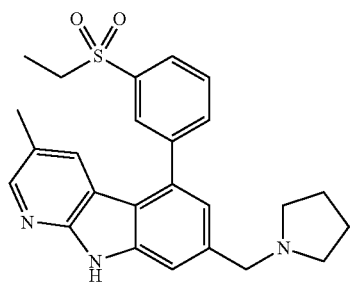

The title compound was prepared from Compound 134 and pyrrolidine according to the procedure outline for the preparation of Compound 135. $^1$H NMR (400 MHz, CD$_3$OD) δ 8.36 (br s, 1H), 8.23 (s, 1H), 8.13 (d, 1H, J=7.6 Hz), 8.04 (d, 1H, J=7.6 Hz), 7.96 (s, 1H), 7.91 (t, 1H, J=7.6 Hz), 7.87 (s, 1H), 7.47 (s, 1H), 4.62 (s, 2H), 3.51-3.60 (m, 2H), 3.20-3.36 (m, 4H), 2.39 (s, 3H), 2.15-2.23 (m, 2H), 1.99-2.07 (m, 2H), 1.29 (t, 3H, J=7.2 Hz). MS (ES) [m+H] calc'd for $C_{25}H_{27}N_3O_2S$, 434; found 434.

Compound 139

[5-(3-Ethanesulfonyl-phenyl)-3-methyl-9H-pyrido[2,3-b]indol-7-ylmethyl]-ethyl-amine

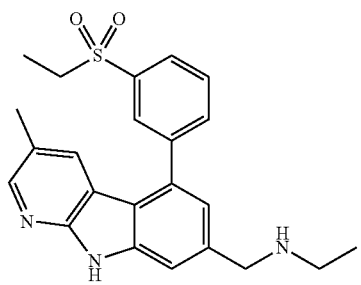

The title compound was prepared from Compound 134 and ethylamine according to the procedure outline for the preparation of Compound 135. $^1$H NMR (400 MHz, CD$_3$OD) δ 8.19 (s, 1H), 8.13 (s, 1H), 8.04 (d, 1H, J=7.6 Hz), 7.97 (d, 1H, J=7.6 Hz), 7.84 (t, 1H, J=7.6 Hz), 7.64 (s, 1H), 7.54 (s, 1H), 7.22 (s, 1H), 4.25 (s, 2H), 3.34 (q, 2H, J=7.2 Hz), 2.99-3.07 (m, 2H), 2.25 (s, 3H), 1.20-1.29 (m, 6H). MS (ES) [m+H] calc'd for $C_{23}H_{25}N_3O_2S$, 408; found 408.

Compound 140

5-(3-Ethanesulfonyl-phenyl)-3-methyl-9H-pyrido[2,3-b]indole-7-carboxylic acid

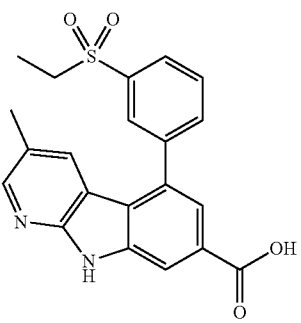

Compound 133 (260 mg, 0.64 mmol) was dissolved 1N NaOH (1 mL) and MeOH (2 mL) at 60° C. for 2 h. The reaction was allowed to cool, and was acidified with 1 N HCl and extracted with CHCl$_3$. Organics were dried (MgSO$_4$) and concentrated to provide the title compound as a white solid (228 mg, 90%). $^1$H NMR (400 MHz, CD$_3$OD) δ 8.34 (br s, 1H), 8.29 (s, 1H), 8.21 (s, 1H), 8.11 (d, 1H, J=7.6 Hz), 8.01 (d, 1H, J=7.6 Hz), 7.90 (t, 1H, J=7.6 Hz), 7.87 (s, 1H), 7.79 (s, 1H), 3.31 (q, 2H, J=7.2 Hz), 2.35 (s, 3H), 1.29 (t, 3H, J=7.2 Hz). MS (ES) [m+H] calc'd for C$_{21}$H$_{18}$N$_2$O$_4$S, 395; found 395.

Compound 141

[5-(3-Ethanesulfonyl-phenyl)-3-methyl-9H-pyrido[2,3-b]indol-7-yl]-(4-methyl-piperazin-1-yl)-methanone

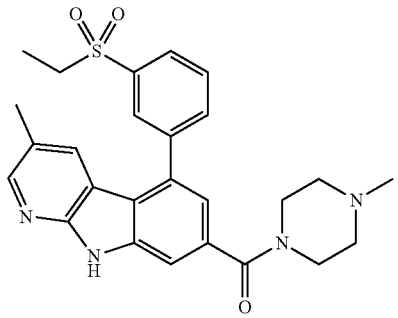

Compound 140 (40 mg, 0.1 mmol) and HOBT (17 mg, 0.11 mmol) were dissolved in CH$_2$Cl$_2$ (2 mL) at r.t. EDC (29 mg, 0.15 mmol) and 1-methylpiperazine (45 mL, 0.4 mmol) were added, and the reaction stirred for 3 h. Organics were washed with brine, dried (Na$_2$SO$_4$), and concentrated in vacuo. Purification by prep-HPLC provided the title compound as a pale yellow solid (32 mg, 67%). $^1$H NMR (400 MHz, CD$_3$OD) δ 8.36 (s, 1H), 8.22 (s, 1H), 8.12 (d, 1H, J=7.6 Hz), 8.03 (d, 1H, J=7.6 Hz), 7.87-7.95 (m, 2H), 7.80 (s, 1H), 7.40 (s, 1H), 3.39-3.62 (m, 4H), 3.31 (q, 2H, J=7.2 Hz), 3.16-3.30 (m, 4H), 2.95 (s, 3H), 2.38 (s, 3H), 1.29 (t, 3H, J=7.2 Hz). MS (ES) [m+H] calc'd for C$_{26}$H$_{28}$N$_4$O$_3$S, 477; found 477.

Compound 142

5-(3-Ethanesulfonyl-phenyl)-3-methyl-9H-pyrido[2,3-b]indole-7-carboxylic acid (2-dimethylamino-ethyl)-amide

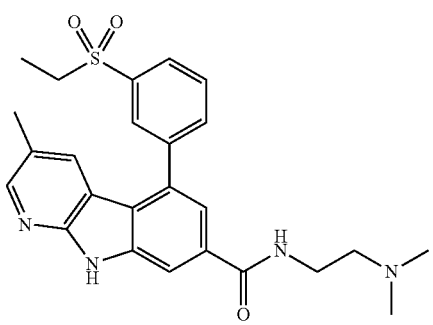

The title compound was prepared in 65% yield according to the procedure outlined for the preparation of Compound 141. $^1$H NMR (400 MHz, CD$_3$OD) δ 8.38 (br s, 1H), 8.23 (s, 1H), 8.20 (s, 1H), 8.12 (d, 1H, J=7.6 Hz), 8.04 (d, 1H, J=7.6 Hz), 7.91 (t, 1H, J=7.6 Hz), 7.84 (s, 1H), 7.75 (s, 1H), 3.80-3.86 (m, 2H), 3.42 (t, 2H, J=5.6 Hz), 3.34 (q, 2H, J=7.2 Hz), 3.01 (s, 6H), 2.38 (s, 3H), 1.30 (t, 3H, J=7.2 Hz). MS (ES) [m+H] calc'd for C$_{25}$H$_{28}$N$_4$O$_3$S, 465; found 465.

Compound 143

5-(3-Ethanesulfonyl-phenyl)-3-methyl-9H-pyrido[2,3-b]indole-7-carboxylic acid (3-dimethylamino-propyl)-amide

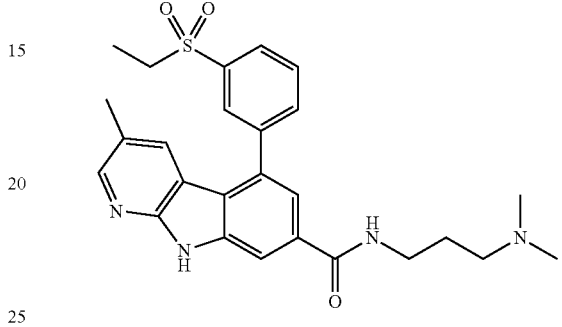

The title compound was prepared in 63% yield according to the procedure outlined for the preparation of Compound 141. $^1$H NMR (400 MHz, CD$_3$OD) δ 8.39 (br s, 1H), 8.24 (s, 1H), 8.19 (s, 1H), 8.13 (d, 1H, J=7.6 Hz), 8.04 (d, 1H, J=7.6 Hz), 7.88-7.96 (m, 2H), 7.78 (s, 1H), 3.56 (t, 2H, J=6.4 Hz), 3.20-3.35 (m, 4H), 2.93 (s, 6H), 2.39 (s, 3H), 2.02-2.11 (m, 2H), 1.30 (t, 3H, J=7.2 Hz). MS (ES) [m+H] calc'd for C$_{26}$H$_{30}$N$_4$O$_3$S, 478; found 478.

Compound 144

5-(3-Ethanesulfonyl-phenyl)-3-methyl-7-(2H-tetrazol-5-yl)-9H-pyrido[2,3-b]indole

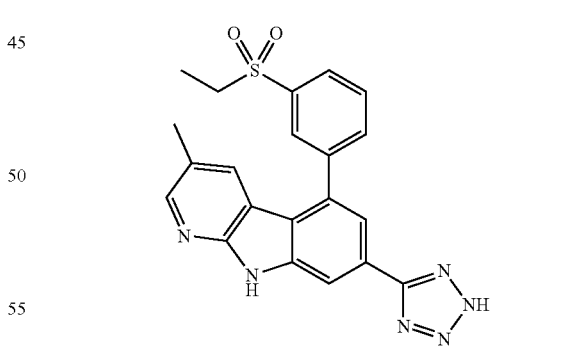

Compound 127 (14 mg, 0.037 mmol), sodium azide (9.7 mg, 0.15 mmol), and ammonium chloride (8.0 mg, 0.15 mmol) were dissolved in DMF (1 mL) and heated at 158° C. in the microwave for 1 h. Purification by prep-HPLC provided the title compound as a white solid (12 mg, 77%). $^1$H NMR (400 MHz, DMSO-d$_6$) δ 12.35 (s, 1H), 8.35 (s, 1H), 8.26 (s, 1H), 8.20 (s, 1H), 8.02-8.11 (m, 2H), 7.94 (t, 1H, J=5.6 Hz), 7.83 (s, 1H), 7.54 (s, 1H), 3.44 (q, 2H, J=7.2 Hz), 2.27 (s, 3H), 1.17 (t, 3H, J=7.2 Hz). MS (ES) [m+H] calc'd for C$_{21}$H$_{18}$N$_6$O$_2$S, 419; found 419.

Compound 145

(3-Dimethylamino-pyrrolidin-1-yl)-[5-(3-ethanesulfonyl-phenyl)-3-methyl-9H-pyrido[2,3-b]indol-7-yl]-methanone

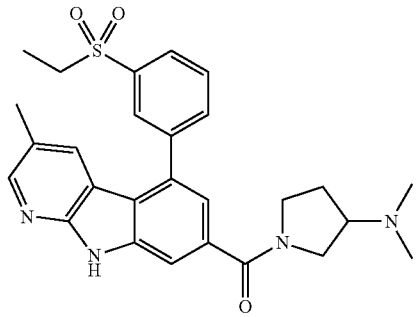

The title compound was prepared in 71% yield according to the procedure outlined for the preparation of Compound 141. $^1$H NMR (400 MHz, CD$_3$OD) δ 8.33 (br s, 1H), 8.21 (s, 1H), 8.11 (d, 1H, J=7.6 Hz), 8.03 (d, 1H, J=7.6 Hz), 7.90 (t, 1H, J=7.6 Hz), 7.81 (s, 1H), 7.76 (s, 1H), 7.40 (s, 1H), 3.71-4.16 (m, 5H), 3.32 (q, 2H, J=7.2 Hz), 2.85-3.05 (m, 6H), 2.45-2.55 (m, 1H), 2.35 (s, 3H), 2.16-2.24 (m, 1H), 1.29 (t, 3H, J=7.2 Hz). MS (ES) [m+H] calc'd for C$_{27}$H$_{30}$N$_4$O$_3$S, 491; found 491.

Compound 146

N-ethyl-5-(3-(ethylsulfonyl)phenyl)-3-methyl-9H-pyrido[2,3-b]indole-7-carboxamide

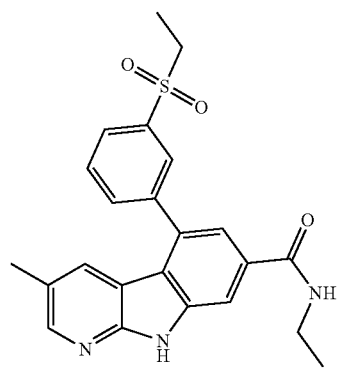

The title compound was synthesized using an analogous procedure to that described in the preparation of Compound 141. $^1$H NMR (400 MHz, MeOD) δ ppm 1.28 (dt, J=10.29, 7.23 Hz, 7H) 2.37 (s, 3H) 3.32-3.36 (m, 2H) 3.48 (q, J=7.33 Hz, 2H) 7.71 (d, J=1.52 Hz, 1H) 7.85 (s, 1H) 7.91 (t, J=7.83 Hz, 1H) 8.06 (ddd, J=7.70, 1.39, 1.26 Hz, 1H) 8.11-8.14 (m, 1H) 8.12 (d, J=1.52 Hz, 1H) 8.24 (t, J=1.77 Hz, 1H) 8.33 (s, 1H) [M+H] calc'd for C$_{23}$H$_{23}$N$_3$O$_3$S, 422; found, 422.

Compound 147

6-Bromo-5-(3-ethanesulfonyl-phenyl)-3-methyl-9H-pyrido[2,3-b]indole-7-carboxylic acid methyl ester

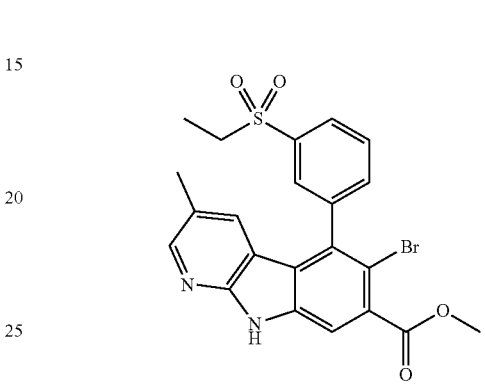

N-Bromosuccinimide (59 mg, 0.33 mmol) was added to a solution of Compound 133 (128 mg, 0.31 mmol) in CH$_2$Cl$_2$ (3 mL) at r.t. The reaction was stirred for 18 h at 30° C. and was then concentrated in vacuo. Purification by prep-HPLC provided the title compound as a white solid (36 mg, 24%). $^1$H NMR (400 MHz, CDCl$_3$) δ 12.28 (br s, 1H), 8.23 (s, 1H), 8.15-8.19 (m, 2H), 7.98 (s, 1H), 7.87 (t, 1H, J=7.6 Hz), 7.72 (d, 1H, J=7.6 Hz), 7.08 (s, 1H), 4.03 (s, 3H), 3.22 (q, 2H, J=7.2 Hz), 2.34 (s, 3H), 1.33 (t, 3H, J=7.2 Hz). MS (ES) [m+H] calc'd for C$_{22}$H$_{19}$BrN$_2$O$_4$S, 487, 489; found 487, 489.

Compound 148

8-Bromo-5-(3-ethanesulfonyl-phenyl)-3-methyl-9H-pyrido[2,3-b]indole-7-carboxylic acid methyl ester

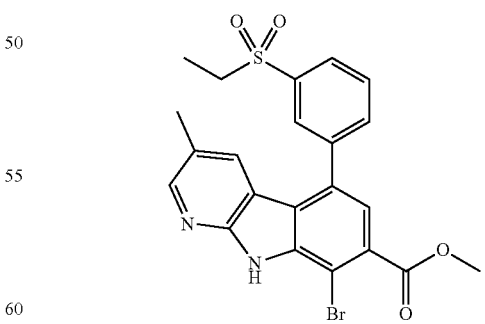

The title compound was isolated in 8% yield during for the preparation of Compound 147. $^1$H NMR (400 MHz, CDCl$_3$) δ 13.32 (br s, 1H), 8.23 (s, 1H), 8.10-8.20 (m, 3H), 7.94 (d, 1H, J=7.6 Hz), 7.79-7.88 (m, 2H), 4.02 (s, 3H), 3.22 (q, 2H, J=7.2 Hz), 2.49 (s, 3H), 1.35 (t, 3H, J=7.2 Hz). MS (ES) [m+H] calc'd for $C_{22}H_{19}BrN_2O_4S$, 487, 489; found 487, 489.

Compound 149

6-Chloro-5-(3-ethanesulfonyl-phenyl)-3-methyl-9H-pyrido[2,3-b]indole-7-carboxylic acid methyl ester

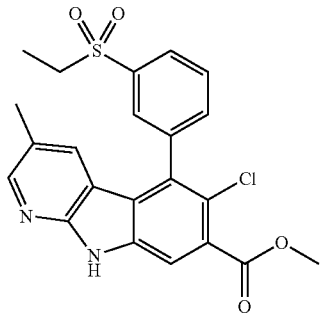

N-Chlorosuccinimide (79 mg, 0.59 mmol) was added to a solution of Compound 133 (220 mg, 0.54 mmol) in $CH_2Cl_2$ (3 mL) and HOAc (1 mL) at r.t. The reaction was stirred for 18 h at 32° C. and was then concentrated in vacuo. Purification by prep-HPLC provided the title compound as a white solid (88 mg, 37%). $^1$H NMR (400 MHz, $CDCl_3$) δ 14.20 (br s, 1H), 8.23 (s, 1H), 8.11-8.19 (m, 2H), 8.00 (s, 1H), 7.87 (t, 1H, J=7.6 Hz), 7.74 (d, 1H, J=7.6 Hz), 7.28 (s, 1H), 4.01 (s, 3H), 3.23 (q, 2H, J=7.2 Hz), 2.37 (s, 3H), 1.34 (t, 3H, J=7.2 Hz). MS (ES) [m+H] calc'd for $C_{22}H_{19}ClN_2O_4S$, 443, 445; found 443, 445.

Compound 150

8-Chloro-5-(3-ethanesulfonyl-phenyl)-3-methyl-9H-pyrido[2,3-b]indole-7-carboxylic acid methyl ester

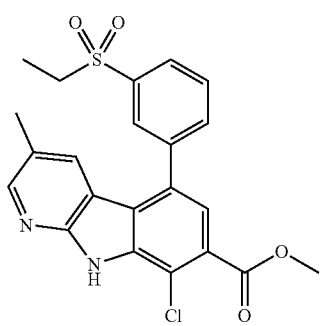

The title compound was isolated in 5% yield during for the preparation of Compound 149. $^1$H NMR (400 MHz, $CDCl_3$) δ 13.70 (br s, 1H), 8.30 (s, 1H), 8.11-8.26 (m, 3H), 7.94 (d, 1H, J=7.6 Hz), 7.80-7.88 (m, 2H), 4.03 (s, 3H), 3.23 (q, 2H, J=7.2 Hz), 2.50 (s, 3H), 1.36 (t, 3H, J=7.2 Hz). MS (ES) [m+H] calc'd for $C_{22}H_{19}ClN_2O_4S$, 443, 445; found 443, 445.

Compound 151

5-(benzylthio)-3-methyl-9H-pyrido[2,3-b]indole-7-carboxylic acid

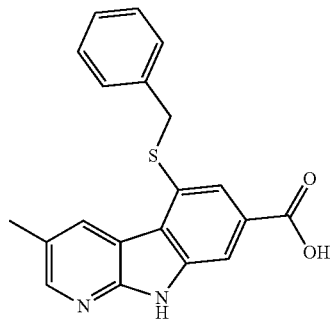

The title compound was synthesized using an analogous procedure to that described in the preparation of Compound 21. $^1$H NMR (400 MHz, MeOD δ ppm 2.52 (s, 3H) 4.39 (s, 2H) 7.15-7.29 (m, 3H) 7.34 (d, J=7.83 Hz, 2H) 7.87 (s, 2H) 7.92 (s, 1H) 8.07 (s, 1H) 8.30 (s, 1H) 8.75 (br. s., 1H) [M+H] calc'd for $C_{20}H_{16}N_2O_2S$, 349; found, 349.

Compound 152

5-(benzylthio)-N-(2-(dimethylamino)ethyl)-3-methyl-9H-pyrido[2,3-b]indole-7-carboxamide

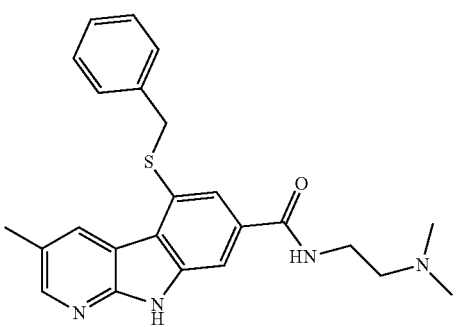

The title compound was synthesized from Compound 151 using an analogous procedure to that described in the preparation of Compound 141. $^1$H NMR (400 MHz, MeOD) δ ppm 2.53 (s, 3H) 3.02 (s, 6H) 3.43 (t, J=5.81 Hz, 2H) 3.82 (t, J=5.81 Hz, 2H) 4.42 (s, 2H) 7.16-7.26 (m, 3H) 7.31 (d, J=7.83

Hz, 2H) 7.82 (d, J=1.26 Hz, 1H) 7.96 (s, 1H) 8.30 (s, 1H) 8.80 (s, 1H) [M+H] calc'd for $C_{24}H_{26}N_4OS$, 419; found, 419.

Compound 153

5-(3-(N-ethylsulfamoyl)phenyl)-8-methoxy-3-methyl-N-(1-methylpiperidin-4-yl)-9H-pyrido[2,3-b]indole-7-carboxamide

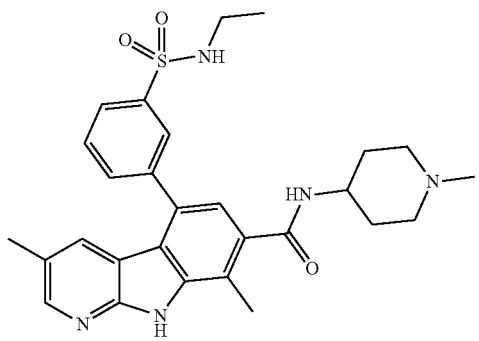

The title compound was synthesized from compound 119 and 3-(N-ethylsulfamoyl)phenylboronic acid using an analogous procedure to that described in the preparation of Compound 84. $^1$H NMR (400 MHz, Methanol-$d_4$) δ 8.28 (s, 1H) 8.13 (s, 1 H) 8.04 (m, 1H) 7.88 (m, 1H) 7.75 (m, 1H) 7.81 (t, J=7.84 Hz, 1H) 7.24 (s, 1H) 4.22 (m, 1H) 3.62 (m, br, 2H) 3.22 (m, 2H) 3.01 (q, J=7.32 Hz, 2H) 2.92 (s, 3H) 2.72 (s, 3 H) 2.36 (m, 5H) 1.93 (m, 2H) 1.11 (t, J=7.32 Hz, 3H). [M+H] calc'd for $C_{28}H_{34}N_5O_3S$, 520; found, 520.

Compound 154

5-(3-(cyclopropylsulfonyl)phenyl)-3,8-dimethyl-N-(1-methylpiperidin-4-yl)-9H-pyrido[2,3-b]indole-7-carboxamide

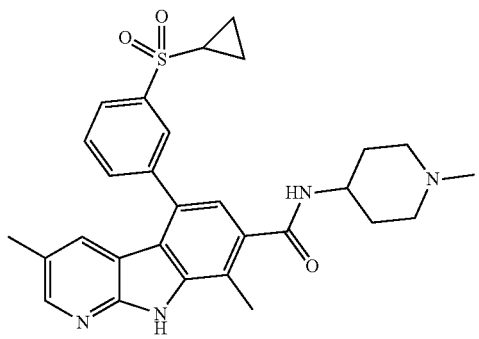

The title compound was synthesized from compound 119 and 3-(cyclopropylsulfonyl)phenylboronic acid using an analogous procedure to that described in the preparation of Compound 84. $^1$H NMR (400 MHz, Methanol-$d_4$) δ 8.32 (s, 1H) 8.19 (s, 1H) 8.11 (m, 1H) 7.99 (m, 1H) 7.89 (m, 2H) 7.3 (s, 1H) 4.22 (m, 1H) 3.74 (m, 1H) 3.65 (m, 2H) 3.22 (m, 2H) 2.93 (s, 3H) 2.72 (s, 3H) 2.36 (m, 5H) 1.93 (m, 2H) 1.28 (m, 2H) 1.14 (m, 2H). [M+H] calc'd for $C_{29}H_{33}N_4O_3S$, 517; found, 517.

Compound 155

3-bromo-N-(5-chloro-2-methoxyphenyl)-5-methylpyridin-amine

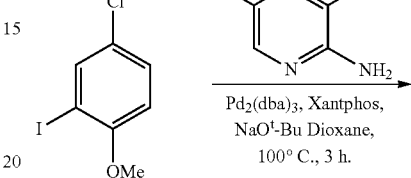

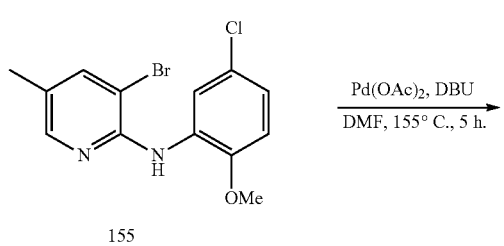

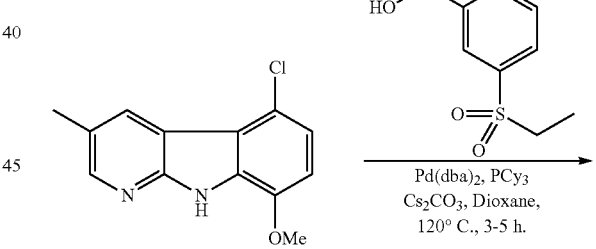

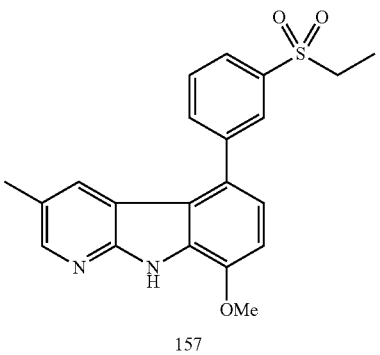

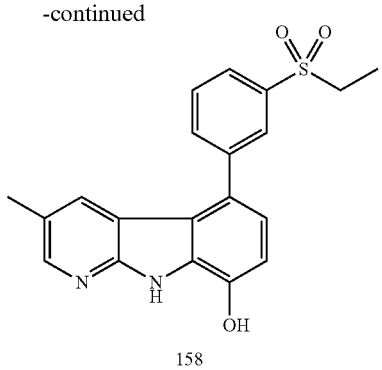

158

In a oven dried 50 mL round bottom flask were sequentially added 4-chloro-2-iodo-1-methoxybenzene (1.13 g, 4.2 mmol), 3-bromo-5-methylpyridin-2-amine (945 mg, 5.05 mmol), Pd$_2$(dba)$_3$ (192 mg, 0.21 mmol), xantphos (146 mg, 0.25 mmol) and Na$^t$BuO (605 mg, 6.3 mmol) at room temperature. The solid materials were kept under vacuum for 5 min. and then refilled with nitrogen. This process was repeated thrice before adding dry, degassed dioxane (10 mL). The heterogeneous mixture was stirred at room temperature for 15 min. and then at 100° C. for 1 h. Finally upon completion of the reaction, it was diluted with ether and filtered through a small pad of silica gel with several washings. All the washings and filtrate concentrated in vacuum and the crude residue was further purified by flash chromatography to provide title compound (1.16 g, 84%). $^1$H NMR (400 MHz, CHLOROFORM-d) δ ppm 2.26 (s, 3H) 3.94 (s, 3H) 6.81 (d, J=8.59 Hz, 1H) 6.93 (dd, J=8.72, 2.65 Hz, 1H) 7.65 (d, J=2.02 Hz, 1H) 7.77 (br. s, 1H) 8.07 (d, J=1.26 Hz, 1H) 8.58 (d, J=2.27 Hz, 1H). [M+H] calc'd for C$_{13}$H$_{13}$ClN$_2$O, 326.98; found 327.2.

Compound 156

5-choloro-8-methoxy-9H-pyrido[2,3-b]indole

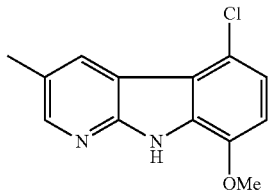

To a stirred solution of Compound 155 (1.0 g, 3.05 mmol) in anhydrous and degassed DMF (10 mL), were added Pd(OAc)$_2$ (69 mg, 0.31 mmol) and DBU (1.37 mL, 9.15 mmol), under nitrogen. After being stirred for 6 h. at 155° C. the reaction was quenched by addition of water (20 mL). The solid precipitates out was filtered and washed thoroughly with water. The residue was dried under vacuum and purified by flash chromatography to furnish the title compound (488 mg, 65%).

Compound 157

5-(3-(ethylsulfonyl)phenyl-8-methoxy-3-methyl-9H-pyrido[2,3-b]indole

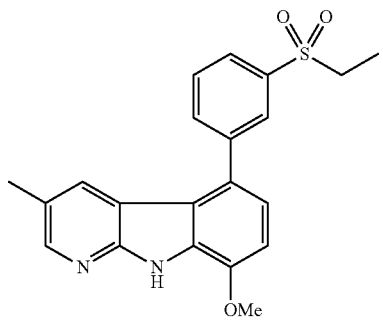

To a stirred solution of Compound 156 (400 mg, 1.62 mmol) and 3-(ethylsulfonyl)phenylboronic acid (694 mg, 3.24 mmol) in anhydrous and degassed dioxane (8 mL), were added Pd(dba)$_2$ (140 mg, 0.24 mmol), PCy$_3$ (0.68 mL, 20% wt solution in toluene, 0.49 mmol) and Cs$_2$CO$_3$ (1.32 g, 4.05 mmol), under nitrogen. After being stirred for 6 h. under reflux (oil bath temperature 125° C.) the reaction was diluted with EtOAc and filtered through a small pad of celite. The residue was washed thoroughly with EtOAc and 10% MeOH in CH$_2$Cl$_2$. All the washings and filtrate were concentrated in vacuum and the crude residue was triturated with ether and then with MeOH. The crude mass was dried under vacuum to give title compound (493 mg, 80%) which was used directly for next step without further purification. $^1$H NMR (400 MHz, DMSO-d$_6$) δ ppm 1.17 (t, J=7.33 Hz, 2H) 2.26 (s, 3H) 3.41 (q, J=7.33 Hz, 2H) 4.02 (s, 3H) 7.06-7.18 (m, 2H) 7.53 (br. s, 1H) 7.85 (t, J=7.71 Hz, 1H) 7.98 (t, J=6.95 Hz, 1H) 8.05-8.10 (m, 1H) 8.26 (d, J=2.02 Hz, 1H) 12.03 (s, 1H). [M+H] calc'd for C$_{21}$H$_{21}$N$_2$O$_3$S, 381.12; found 381.3.

Compound 158

5-(3-(ethylsulfonyl)phenyl)-3-methyl-9H-pyrido[2,3-b]indol-8-ol

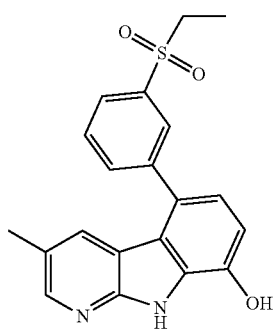

Compound 157 (450 mg, 1.18 mmol) and pyridine hydrochloride (2.73 g, 23.6 mmol) were taken in a sealed tube and heated at 215° C. for 12 h. The black mass was dissolved in water and extracted twice with 5% EtOH in CH$_2$Cl$_2$. The combined organic extracts were concentrated and the residual mass was purified by flash chromatography to provide the title compound (259 mg, 60%). $^1$H NMR (400 MHz, DMSO-d$_6$) δ ppm 1.17 (t, J=7.33 Hz, 3H) 2.25 (s, 3H) 3.40 (q, J=7.49

Hz, 2H) 6.97 (s, 2H) 7.54 (d, J=1.77 Hz, 1 H) 7.83 (t, J=7.71 Hz, 1H) 7.94-7.98 (m, 2H) 8.06 (t, J=1.64 Hz, 1H) 8.24 (d, J=1.77 Hz, 1H) 10.08 (s, 1H) 11.73 (s, 1H). [M+H] calc'd for $C_{20}H_{18}N_2O_3S$ 367; found, 367.1.

Compound 159

8-methoxy-3-methyl-5-(3-(pyrrolidin-1-ylsulfonyl)phenyl)-9H-pyrido[2,3-b]indole

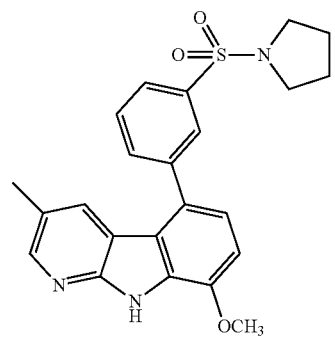

The title compound was synthesized from Compound 156 using an analogous procedure to that outlined in the preparation of Compound 157. $^1$H NMR (400 MHz, DMSO-d$_6$) δ ppm 1.72-1.68 (m, 4H) 2.25 (s, 3H) 3.23-3.19 (m, 4H) 4.02 (s, 3H) 7.07 (d, J=8.4 Hz, 1H) 7.15 (d, J=8.0 Hz, 1H) 7.47 (d, J=1.26 Hz, 1H) 7.83 (d, J=7.58 Hz, 1 H) 7.90-7.94 (m, 3H) 8.26 (d, J=1.77 Hz, 1H) 12.03 (s, 1H); [M+H] calc'd for $C_{23}H_{24}N_3O_3S$, 422.2; found, 422.3.

Compound 160

(R)-8-methoxy-3-methyl-5-(3-(pyrrolidin-3-ylsulfonyl)phenyl)-9H-pyrido[2,3-b]indole

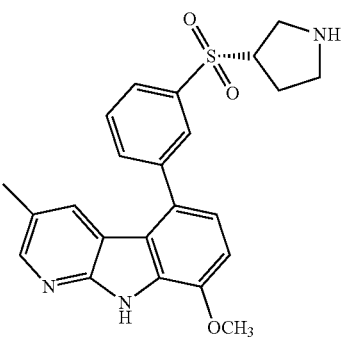

The title compound was synthesized from Compound 156 using an analogous procedure to that outlined in the preparation of Compound 157. $^1$H NMR (400 MHz, DMSO-d$_6$) δ ppm 1.92-2.02 (m, 2H) 2.26 (s, 3H) 2.74-2.87 (m, 2H) 3.03 (dd, J=8.0, 8.1, Hz, 1H) 3.11 (dd, J=5.31, 8.0 Hz, 1H) 3.17 (d, J=5.31 Hz, 1H) 4.02 (s, 3H) 7.09 (d, J=8.1 Hz, 1H) 7.15 (d, J=8.0 Hz, 1H) 7.51 (d, J=1.26 Hz, 1H) 7.85 (t, J=7.71 Hz, 1 H) 7.97 (d, J=7.96 Hz, 1H) 8.01 (d, J=8.0 Hz, 1H) 8.07 (d, J=1.52 Hz, 1H) 8.26 (d, J=1.52 Hz, 1H) 12.04 (s, 1H); [M+H] calc'd for $C_{23}H_{23}N_3O_3S$, 422.2; found, 422.3.

Compound 161

N-cyclopropyl-4-(8-methoxy-3-methyl-9H-pyrido[2,3-b]indol-5-yl)picolinamide

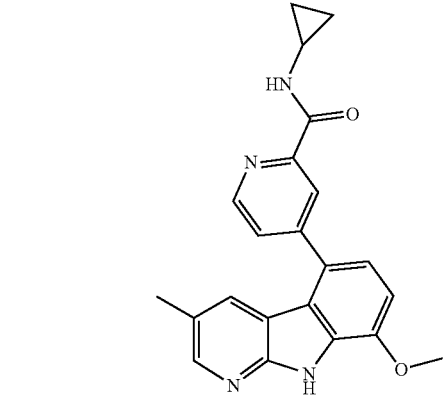

The title compound was synthesized from Compound 156 using an analogous procedure to that outlined in the preparation of Compound 157. $^1$H NMR (400 MHz, MeOD) δ ppm 0.74 (br. s., 2H) 0.88 (d, J=9.35 Hz, 2H) 2.37 (s, 3H) 4.11 (s, 3H) 7.22 (s, 2H) 7.82 (br. s., 1H) 7.94 (s, 1H) 8.26 (br. s., 1H) 8.36 (br. s., 1H) 8.76 (br. s., 1H) [M+H] calc'd for $C_{22}H_{20}N_4O_2$, 373; found, 373.

Compound 162

N-(3-(8-methoxy-3-methyl-9H-pyrido[2,3-b]indol-5-yl)phenyl)acetamide

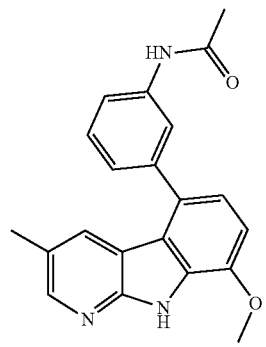

The title compound was synthesized from Compound 156 using an analogous procedure to that outlined in the preparation of Compound 157. $^1$H NMR (400 MHz, Methanol-d$_4$) δ 8.24 (s, 1H) 8.18 (s, 1H) 7.93 (s, 1H) 7.56 (m, 1H) 7.52 (t, J=7.56 Hz, 1 H) 7.34 (m, 1H) 7.22 (d, J=8.08 Hz, 1H) 7.18 (d, J=8.08 Hz, 1H) 4.11 (s, 3H) 2.40 (s, 3H) 2.17 (s, 3H). [M+H] calc'd for $C_{21}H_{20}N_3O_2$, 346; found, 346.

Compound 163

N-(3-(8-methoxy-3-methyl-9H-pyrido[2,3-b]indol-5-yl)phenyl)cyclopropanecarboxamide

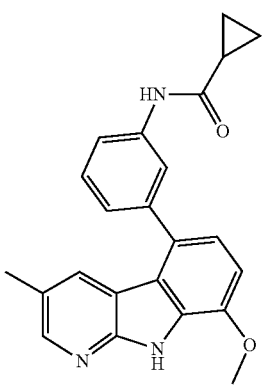

The title compound was synthesized from Compound 156 using an analogous procedure to that outlined in the preparation of Compound 157. $^1$H NMR (400 MHz, Methanol-$d_4$) δ 8.44 (s, 1H) 8.25 (s, 1H) 8.00 (s, 1H) 7.52 (m, 2H) 7.27 (m, 3H) 4.11 (s, 3H) 2.43 (s, 3H) 1.80 (m, 1H) 0.95 (m, 2H) 0.88 (m, 2H). [M+H] calc'd for $C_{23}H_{22}N_3O_2$, 372; found, 372.

Compound 164

N-cyclopropyl-3-(8-methoxy-3-methyl-9H-pyrido[2,3-b]indol-5-yl)benzamide

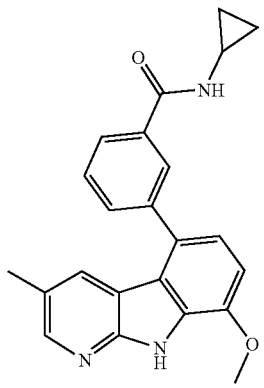

The title compound was synthesized from Compound 156 using an analogous procedure to that outlined in the preparation of Compound 157. $^1$H NMR (400 MHz, Methanol-$d_4$) δ 8.26 (s, 1H) 8.07 (s, 1H) 7.91 (m, 2H) 7.77 (m, 1H) 7.66 (t, J=7.56 Hz, 1H) 7.24 (m, 2H) 4.12 (s, 3H) 2.80 (m, 1H) 2.38 (s, 3H) 0.82 (m, 2H) 0.66 (m, 2H). [M+H] calc'd for $C_{23}H_{22}N_3O_2$, 372; found, 372.

Compound 165

N,N-diethyl-3-(8-methoxy-3-methyl-9H-pyrido[2,3-b]indol-5-yl)benzamide

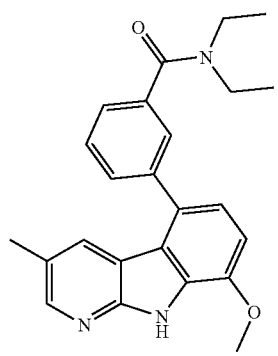

The title compound was synthesized from Compound 156 using an analogous procedure to that outlined in the preparation of Compound 157. $^1$H NMR (400 MHz, Methanol-$d_4$) δ 8.26 (s, 1H) 8.07 (s, 1H) 7.91 (m, 2H) 7.77 (m, 1H) 7.66 (t, J=7.56 Hz, 1H) 7.24 (m, 2H) 4.12 (s, 3H) 3.99 (q, J=7.52 Hz, 4H) 2.38 (s, 3H) 1.35 (t, J=7.52 Hz, 6H). [M+H] calc'd for $C_{24}H_{25}N_3O_2$, 387; found, 387.2

Compound 166

5-(benzo[d][1,3]dioxol-5-yl)-8-methoxy-3-methyl-9H-pyrido[2,3-b]indole

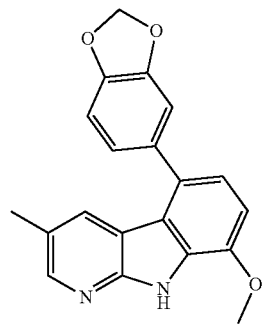

The title compound was synthesized from Compound 156 using an analogous procedure to that outlined in the preparation of Compound 157. $^1$H NMR (400 MHz, Methanol-$d_4$) δ 8.14 (s, 1H) 7.20 (d, J=8.36 Hz, 1H) 7.18 (d, J=8.36 Hz, 1H)

7.04 (m, 4H) 6.10 (s, 2H) 4.11 (s, 3H) 2.42 (s, 3H). [M+H] calc'd for $C_{20}H_{17}N_2O_3$, 333; found, 333.

Compound 167

6-(8-methoxy-3-methyl-9H-pyrido[2,3-b]indol-5-yl)-4H-chromen-4-one

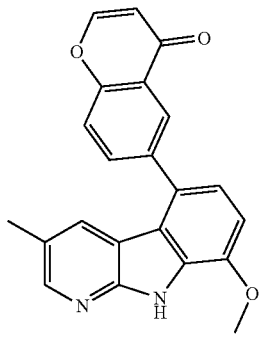

The title compound was synthesized from Compound 156 using an analogous procedure to that outlined in the preparation of Compound 157. $^1$H NMR (400 MHz, Methanol-d$_4$) δ 8.37 (s, 1H) 8.29 (m, 2H) 8.07 (m, 2H) 7.84 (d, J=8.84 Hz, 1H) 7.31 (m, 2H) 6.48 (d, J=5.8 Hz, 1H) 4.15 (s, 3H) 2.40 (s, 3H). [M+H] calc'd for $C_{22}H_{17}N_2O_3$, 357; found, 357.

Compound 168

N-(2-hydroxyethyl)-3-(8-methoxy-3-methyl-9H-pyrido[2,3-b]indol-5-yl)benzamide

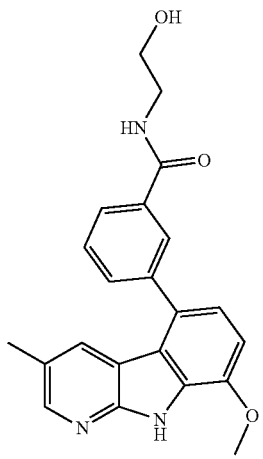

The title compound was synthesized from Compound 156 using an analogous procedure to that outlined in the preparation of Compound 157. $^1$H NMR (400 MHz, Methanol-d$_4$) δ 8.30 (s, 1H) 8.12 (m, 2H) 8.00 (m, 1H) 7.72 (m, 1H) 7.70 (t, J=7.84 Hz, 1H) 7.34 (m, 2H) 4.14 (s, 3H) 3.75 (t, J=5.8 Hz, 2H) 3.56 (t, J=5.8 Hz, 2H) 2.43 (s, 3 H). [M+H] calc'd for $C_{22}H_{22}N_3O_3$, 376; found, 376.

Compound 169

(3-(8-methoxy-3-methyl-9H-pyrido[2,3-b]indol-5-yl)phenyl)(pyrrolidin-1-yl)methanone

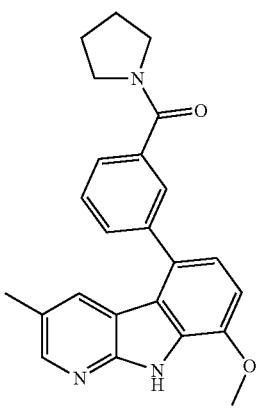

The title compound was synthesized from Compound 156 using an analogous procedure to that outlined in the preparation of Compound 157. $^1$H NMR (400 MHz, Methanol-d$_4$) δ 8.27 (s, 1H) 8.03 (s, 1H) 7.70 (m, 4H) 7.26 (d, J=8.32 Hz, 1H) 7.21 (d, J=8.32 Hz, 1H) 4.12 (s, 3H) 3.64 (t, J=6.84 Hz, 2H) 3.58 (t, J=6.84 Hz, 2H) 2.41 (s, 3H) 1.95 (m, 4H). [M+H] calc'd for $C_{22}H_{22}N_3O_3$, 376; found, 376.

Compound 170

N-ethyl-3-(8-methoxy-3-methyl-9H-pyrido[2,3-b]indol-5-yl)benzenesulfonamide

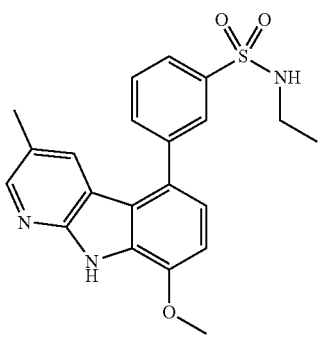

The title compound was synthesized from Compound 156 using an analogous procedure to that outlined in the preparation of Compound 157. $^1$H NMR (400 MHz, DMSO-d$_6$) δ ppm 1.00 (t, J=7.20 Hz, 3H) 2.26 (s, 3H) 2.86 (dd, J=7.33, 5.81 Hz, 2H) 4.02 (s, 3H) 7.07 (d, J=8.08 Hz, 1H) 7.12-7.18 (m, 1H) 7.52 (s, 1H) 7.69 (t, J=5.81 Hz, 1H) 7.79 (d, J=7.58 Hz, 1H) 7.84 (d, J=1.52 Hz, 1H) 7.89 (d, J=7.58 Hz, 1H) 8.00

(d, J=1.77 Hz, 1H) 8.26 (d, J=1.77 Hz, 1H) 12.06 (s, 1H); ESI-MS: m/z calc'd for $C_{21}H_{21}N_3O_3S$ 395.13; found 396.3 $(M+H)^+$.

Compound 171

8-ethoxy-5-(3-(ethylsulfonyl)phenyl)-3-methyl-9H-pyrido[2,3-b]indole

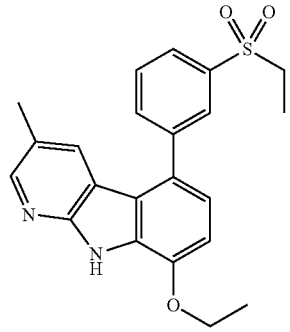

The title compound was synthesized by using an analogous synthetic sequence to that outlined in the preparation of Compound 157. $^1$H NMR (400 MHz, DMSO-$d_6$) δ ppm 1.17 (t, J=7.33 Hz, 3H) 1.48 (t, J=6.95 Hz, 3H) 2.26 (s, 3H) 3.41 (q, J=7.49 Hz, 2 H) 4.31 (q, J=7.24 Hz, 2H) 7.07-7.11 (m, 1H) 7.09 (d, J=6.32 Hz, 1H) 7.12-7.17 (m, 1 H) 7.56 (s, 1H) 7.85 (t, J=7.71 Hz, 1H) 8.00 (d, J=1.26 Hz, 1H) 7.97 (dd, J=3.41, 1.64 Hz, 1H) 8.08 (s, 1H) 8.28 (br. s., 1H) 12.03 (br. s., 1H); ESI-MS: m/z calc'd for $C_{22}H_{22}N_2O_3S$ 394.14; found 395.3 $(M+H)^+$.

Compound 172

8-(difluoromethoxy)-5-(3-(ethylsulfonyl)phenyl)-3-methyl-9H-pyrido[2,3-b]indole

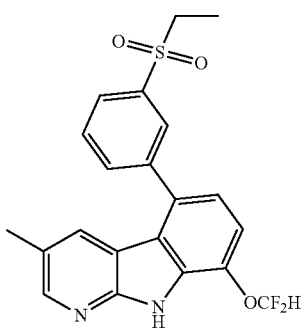

The title compound was synthesized by using an analogous synthetic sequence to that outlined in the preparation of Compound 157. $^1$H NMR (400 MHz, DMSO-$d_6$) δ ppm 1.17 (t, J=7.33 Hz, 3H) 2.27 (s, 3H) 3.42 (q, J=7.33 Hz, 2H) 7.17 (d, J=8.08 Hz, 1 H) 7.40 (t, J=7.36 Hz, 1H) 7.42 (s, 1H) 7.50 (s, 1H) 7.89 (t, J=7.71 Hz, 1H) 8.0-8.1 (m, 2H) 8.11 (t, J=1.77 Hz, 1H) 8.33 (br. s., 1H) 12.36 (s, 1H). [M+H] calc'd for $C_{21}H_{18}F_2N_2O_3S$ 417; found, 417.3.

Compound 173

5-(3-(ethylsulfonyl)phenyl)-3-methyl-8-(2,2,2-trifluoroethoxy)-9H-pyrido[2,3-b]indole

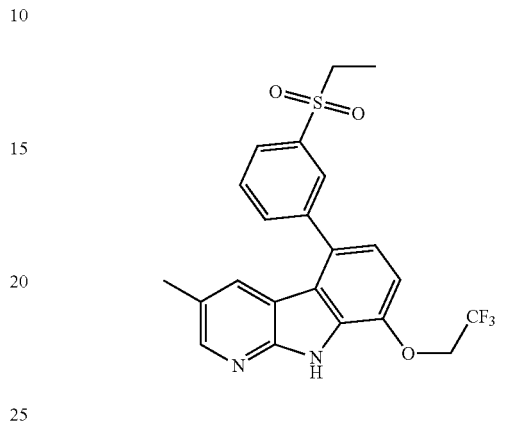

The title compound was synthesized by using an analogous synthetic sequence to that outlined in the preparation of Compound 157. $^1$H NMR (400 MHz, DMSO-$d_6$) δ ppm 1.17 (t, J=7.45 Hz, 3H) 2.27 (s, 3H) 3.42 (q, J=7.33 Hz, 2H) 5.03 (q, J=9.01 Hz, 2 H) 7.13 (d, J=8.34 Hz, 1H) 7.32 (d, J=8.34 Hz, 1H) 7.54 (d, J=1.26 Hz, 1H) 7.87 (t, J=7.71 Hz, 1H) 8.00 (td, J=8.72, 1.26 Hz, 2H) 8.09 (t, J=1.64 Hz, 1H) 8.31 (d, J=1.77 Hz, 1H) 12.23 (s, 1H). [M+H] calc'd for $C_{22}H_{19}F_3N_2O_3S$ 449; found, 449.3.

Compound 174

4-((4-chloro-2-iodophenoxy)methyl)-1-methylpiperidine

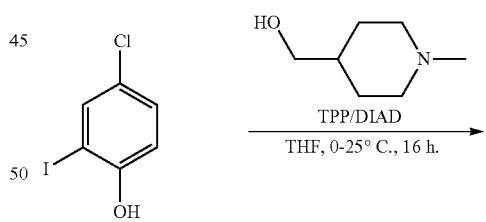

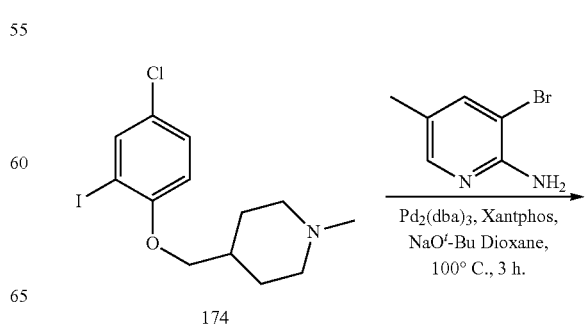

174

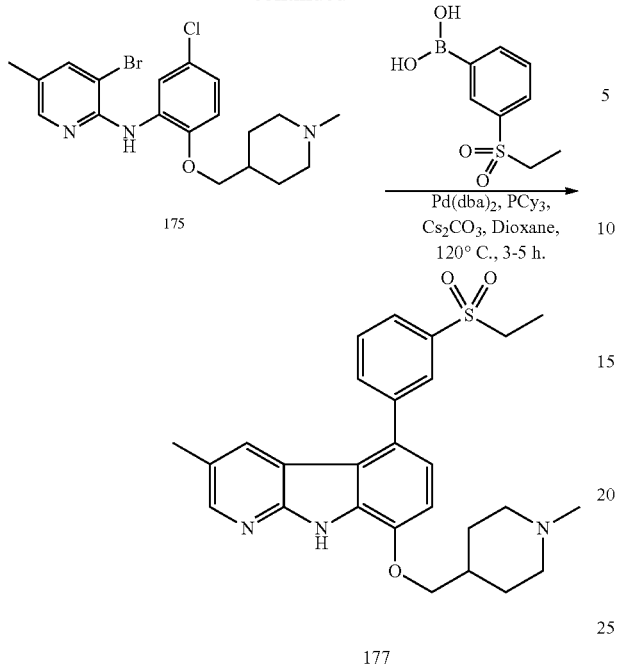

175

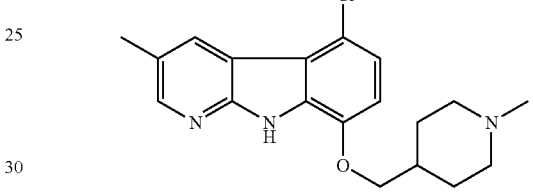

177

To a stirred solution of 4-chloro-2-iodophenol (1.72 g, 6.75 mmol) in anhydrous THF (10.0 mL) were sequentially added (1-methylpiperidin-4-yl)methanol (1.31 g, 10.14 mmol) and triphenyl phosphine (2.66 g, 10.14 mmol). The reaction mixture was cooled to 0° C., and to it diisopropyl-azodicarboxylate (1.96 mL, 10.14 mmol) was added in drop wise manner. After the addition was over, stirring continued for another 0.5 h at 0° C. and then for 12 h at room temperature. Solvents were removed in vacuum and the residue was purified by silica gel column chromatography, providing Compound 172 (1.85 g, 75%). $^1$H NMR (400 MHz, CHLOROFORM-d) δ ppm 1.60-1.63 (m, 2H) 1.63 (br. s., 1H) 1.93-2.00 (m, 3H) 2.19 (t, J=11.24 Hz, 2H) 2.42 (s, 3H) 3.07 (br. d, J=11.62 Hz, 2H) 3.84 (d, J=6.32 Hz, 2H) 6.69 (d, J=8.59 Hz, 1H) 7.25 (dd, J=8.0, 3.6 Hz, 1H) 7.73 (d, J=2.53 Hz, 1H). [M+H] calc'd for $C_{13}H_{18}ClINO$, 366.0; found 366.2.

Compound 175

3-bromo-N-(5-chloro-2-((1-methylpiperidin-4-yl)methoxy)phenyl)-5-methylpyridin-2-amine

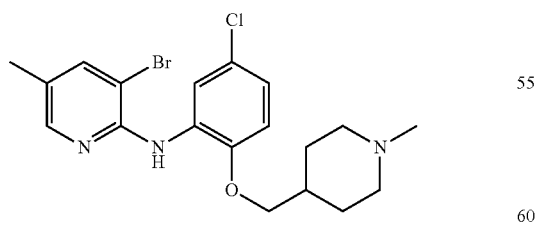

In a oven dried 50 mL round bottom flask were sequentially added Compound 174 (620 mg, 1.69 mmol), 3-bromo-5-methylpyridin-2-amine (381 mg, 2.03 mmol), $Pd_2(dba)_3$ (77 mg, 0.08 mmol), xantphos (59 mg, 0.10 mmol) and Na$^t$BuO (244 mg, 2.53 mmol) at room temperature. The solid materials were kept under vacuum for 5 min. and then refilled with nitrogen. This process was repeated thrice before adding dry, degassed dioxane (8 mL). The heterogeneous mixture was stirred at room temperature for 15 min. and then at 100° C. for 2 h. Finally upon completion of the reaction, it was diluted with EtOAc and filtered through a small pad of silica gel with several washings. All the washings and filtrate concentrated in vacuum and the crude residue was further purified by flash chromatography to provide pure Compound 175 (574 mg, 80%). $^1$H NMR (400 MHz, DMSO-d$_6$) δ ppm 1.53 (br. m, 2H) 2.06 (br. m, 3H) 2.23 (s, 3H) 2.77 (s, 3H) 3.00 (br. m, 2H) 3.48 (br. d, J=12.8 Hz, 2H) 4.03 (br. s., 2H) 6.94-7.01 (m, 1H) 7.08 (d, J=8.84 Hz, 1H) 7.86 (s, 1H) 7.93 (d, J=1.52 Hz, 1H) 8.14 (s, 1H) 8.61 (d, J=2.53 Hz, 1 H) 9.07 (br. s., 1H). [M+H] calc'd for $C_{19}H_{24}BrClN_3O$, 424.07; found 424.2.

Compound 176

5-chloro-3-methyl-8-((1-methylpiperidin-4-yl)methoxy)-9H-pyrido[2,3-b]indole

To a stirred solution of Compound 175 (450 mg, 1.06 mmol) in anhydrous and degassed DMF (3 mL), were added Pd(OAc)$_2$ (59 mg, 0.26 mmol) and DBU (0.48 mL, 3.18 mmol), under nitrogen. After being stirred for 6 h. at 155° C. the reaction was quenched by addition of water (5 mL). The solid precipitates out was filtered and washed thoroughly with water. The residue was dried under vacuum and purified by flash chromatography to furnish Compound 176 (237 mg, 65%). $^1$H NMR (400 MHz, DMSO-d$_6$) δ ppm 1.44 (br. m., 2H) 1.85-1.98 (m, 5H) 2.33 (br. d, J=2.02 Hz, 2H) 2.43 (s, 3H) 2.97 (s, 3H) 4.02 (d, J=6.57 Hz, 2H) 7.02 (d, J=8.59 Hz, 1H) 7.14 (d, J=8.34 Hz, 1H) 8.36 (s, 1H), 8.49 (s, 1H). [M+H] calc'd for $C_{19}H_{23}ClN_3O$, 344.15; found 344.2.

Compound 177

5-(3-(ethylsulfonyl)phenyl)-3-methyl-8-((1-methylpiperidin-4-yl)methoxy)-9H-pyrido[2,3-b]indole To a stirred solution of Compound 176 (170 mg, 0.49 mmol) and 3-(ethylsulfonyl)phenylboronic acid (265 mg, 1.24 mmol) in anhydrous and degassed dioxane (5 mL), were added Pd(dba)$_2$ (70 mg, 0.12 mmol), PCy$_3$ (0.34 mL, 20% wt solution in toluene, 0.24 mmol) and Cs$_2$CO$_3$ (479 mg, 1.47 mmol), under nitrogen. After being stirred for 6 h. under reflux (oil bath temperature 125° C.) the reaction was diluted with EtOAc and filtered through a small pad of celite. The residue was washed thoroughly with EtOAc and 10% MeOH in CH$_2$Cl$_2$. All the washings and filtrate were concentrated in vacuum and the crude residue was triturated with ether and then with MeOH and then purified through preparative HPLC to give Compound 177 as a yellow solid (176 mg, 75%). $^1$H NMR (400 MHz, DMSO-d$_6$) δ ppm 1.20 (t, J=7.34 Hz, 3H) 1.50-1.61 (m, 2 H) 2.13-2.20 (m, 1H) 2.23-2.31 (m, 5H) 2.82 (s, 3H) 2.98-3.09 (m, 2H) 3.39 (q, J=7.34 Hz, 2H) 3.54 (d, J=10.60 Hz, 2H) 4.12 (d, J=6.52 Hz, 2H) 7.06-7.17 (m, 2H) 7.53 (s, 1H) 7.85 (t, J=7.74 Hz, 1H) 7.96 (d, J=7.66 Hz, 1H) 8.00 (d, J=7.66 Hz, 1H) 8.06 (s, 1H) 8.28 (d, J=1.47 Hz, 1H) 11.83 (br. s., 1H), [M+H] calc'd for C$_{27}$H$_{32}$N$_3$O$_3$S, 478.2; found, 478.4; [M+H+TFA] calc'd for C$_{29}$H$_{33}$N$_3$O$_5$F$_3$S, 592.2; found, 592.4.

The hydrogen chloride salt of compound 177 was prepared by using an analogous procedure outlined in the preparation of the HCl salt of compound 88.

The bis-trifluoroacetic acid salt of compound 177 was prepared by using an analogous procedure outlined in the preparation of the TFA salt of compound 88.

Compound 178

N-cyclopropyl-3-(3-methyl-8-((1-methylpiperidin-4-yl)methoxy)-9H-pyrido[2,3-b]indol-5-yl)benzamide

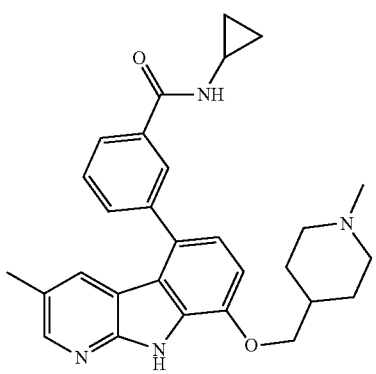

The title compound was synthesized using an analogous procedure to that outlined in the preparation of Compound 177. $^1$H NMR (400 MHz, Methanol-d$_4$) δ 8.28 (s, 1H) 8.07 (s, 1H) 7.92 (m, 3H) 7.79 (m, 1H) 7.67 (t, J=7.56 Hz, 1H) 7.25 (d, J=8.36 Hz, 1H) 7.21 (d, J=8.36 Hz, 1H) 4.24 (d, J=6.08 Hz, 2H) 3.65 (br, m, 2H) 3.14 (m, 2H) 2.94 (m, 4H) 2.38 (m, 6H) 1.75 (m, 2H) 0.83 (m, 2H) 0.66 (m, 2H). [M+H] calc'd for C$_{29}$H$_{33}$N$_4$O$_2$, 469; found, 469.

Compound 179

5-(3-(cyclopropylsulfonyl)phenyl)-3-methyl-8-((1-methylpiperidin-4-yl)methoxy)-9H-pyrido[2,3-b]indole

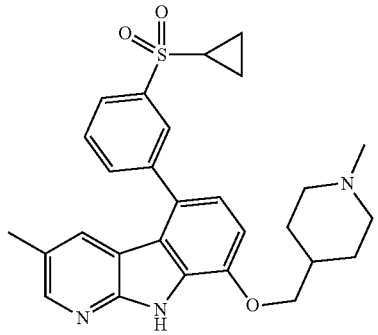

The title compound was synthesized using an analogous procedure to that outlined in the preparation of Compound 177. $^1$H NMR (400 MHz, Methanol-d$_4$) δ 8.28 (s, 1H) 8.18 (s, 1H) 8.05 (m, 2H) 7.93 (m, 1H) 7.85 (t, J=7.56 Hz, 1H) 7.27 (m, 2H) 4.21 (d, J=5.8 Hz, 2H) 3.65 (br, m, 2H) 3.14 (m, 2H) 2.94 (s, 3H) 2.85 (m, 1H) 2.40 (m, 6H) 1.75 (m, 2H) 1.29 (m, 2H) 1.14 (m, 2H). [M+H] calc'd for C$_{28}$H$_{32}$N$_3$O$_3$S, 490; found, 490.

Compound 180

N-methyl-3-(3-methyl-8-((1-methylpiperidin-4-yl)methoxy)-9H-pyrido[2,3-b]indole-5-yl)benzenesulfonamide

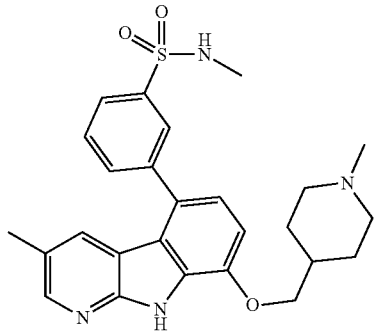

The title compound was synthesized using an analogous procedure to that outlined in the preparation of Compound 177. $^1$H NMR (400 MHz, Methanol-d$_4$) δ 8.28 (s, 1H) 8.18 (s, 1H) 8.05 (m, 2H) 7.93 (m, 1H) 7.85 (t, J=7.56 Hz, 1H) 7.27 (m, 2H) 4.21 (d, J=5.8 Hz, 2H) 3.65 (br, m, 2H) 3.14 (m, 2H)

2.94 (s, 3H) 2.85 (m, 1H) 2.47 (d, J=6.2 Hz, 3H) 1.75 (m, 2H) 1.29 (m, 2H) 1.14 (m, 2H). [M+H] calc'd for $C_{26}H_{30}N_4O_3S$, 479; found, 479.2.

Compound 181

N,N-dimethyl-3-(3-methyl-8-((1-methylpiperidin-4-yl)methoxy)-9H-pyrido[2,3-b]indole-5-yl)benzenesulfonamide

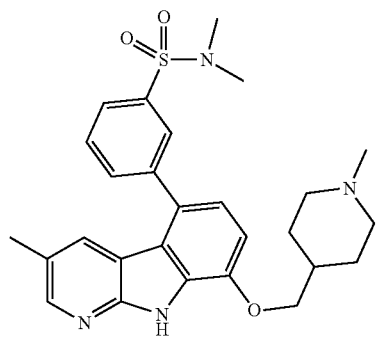

The title compound was synthesized using an analogous procedure to that outlined in the preparation of Compound 177. $^1$H NMR (400 MHz, Methanol-d$_4$) δ 8.28 (s, 1H) 8.18 (s, 1H) 8.05 (m, 2H) 7.93 (m, 1H) 7.85 (t, J=7.56 Hz, 1H) 7.27 (m, 2H) 4.21 (d, J=5.8 Hz, 2H) 3.65 (br m, 2H) 3.14 (m, 2H) 2.94 (s, 3H) 2.85 (m, 1H) 2.66 (s, 3H) 1.75 (m, 2H) 1.29 (m, 2H) 1.14 (m, 2H). [M+H] calc'd for $C_{27}H_{32}N_4O_3S$, 493; found, 493.2

Compound 182

N-(3-(3-methyl-8-((1-methylpiperidin-4-yl)methoxy)-9H-pyrido[2,3-b]indol-5-yl)phenyl)cyclopropanecarboxamide

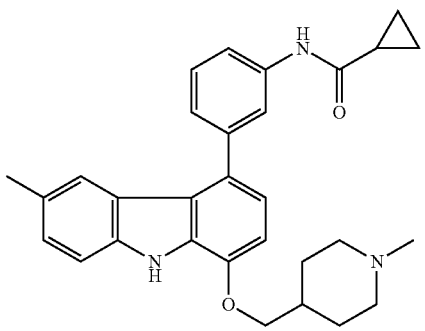

The title compound was synthesized using an analogous procedure to that outlined in the preparation of Compound 177. $^1$H NMR (400 MHz, DMSO-d$_6$) δ ppm 0.78-0.80 (m, 4H) 1.45-1.55 (m, 2H) 1.75-1.84 (m, 1H) 2.09-2.18 (m, 1H) 2.27 (s, 3H) 2.54 (s, 3H) 2.80 (d, J=4.80 Hz, 2H) 2.96-3.08 (m, 2H) 3.53 (d, J=11.37 Hz, 2H) 4.08 (d, J=6.82 Hz, 2H) 6.98 (d, J=8.08 Hz, 1H) 7.09 (d, J=8.34 Hz, 1H) 7.22 (d, J=7.83 Hz, 1H) 7.46 (t, J=7.83 Hz, 1H) 7.61 (d, J=8.08 Hz, 1H) 7.72 (d, J=1.26 Hz, 1H) 7.91 (s, 1H) 8.25 (d, J=1.77 Hz, 1H) 9.23 (br. s., 1H) 10.33 (s, 1H) 11.89 (s, 1H); [M+H] calc'd for $C_{29}H_{33}N_4O_2$, 469.3; found, 469.5; [M+H+ TFA] calc'd for $C_{31}H_{34}N_4O_4F_3$, 583.3; found, 583.5.

Compound 183

5-(3-(ethylthio)phenyl)-3-methyl-8-((1-methylpiperidin-4-yl)methoxy)-9H-pyrido[2,3-b]indole The title compound was synthesized using an analogous procedure to that outlined in the preparation of Compound 177. $^1$H NMR (400 MHz, DMSO-d$_6$) δ ppm 1.28 (t, J=7.20 Hz, 3H) 1.48-1.56 (m, 2H) 2.09-2.20 (m, 1H) 2.25 (br. s., 2H) 2.27 (s, 3H) 2.80 (d, J=4.55 Hz, 3H) 3.03 (q, J=7.16 Hz, 4H) 3.53 (d, J=11.37 Hz, 2H) 4.08 (d, J=6.82 Hz, 2H) 7.00 (d, J=8.08 Hz, 1H) 7.10 (d, J=8.34 Hz, 1H) 7.36-7.52 (m, 4H) 7.59 (s, 1H) 8.27 (s, 1H) 9.41 (br. s., 1H) 11.95 (s, 1H); [M+H] calc'd for $C_{27}H_{32}N_3OS$, 446.2; found, 446.4; [M+H+TFA] calc'd for $C_{29}H_{33}N_3O_3F_3S$, 560.2; found, 560.4.

Compound 184

5-(3-ethoxyphenyl)-3-methyl-8-((1-methylpiperidin-4-yl)methoxy)-9H-pyrido[2,3-b]indole The title compound was synthesized using an analogous procedure to that outlined in the preparation of Compound 177. $^1$H NMR (400 MHz, DMSO-d$_6$) δ ppm 1.35 (t, J=6.95 Hz, 3H) 1.44-1.56 (m, 2H) 2.10-2.18 (m, 1H) 2.25 (br. s., 5H) 2.80 (d, J=4.80 Hz, 3H) 2.97-3.07 (m, 2H) 3.52 (d, J=11.62 Hz, 2H) 4.06-4.09 (m, 4H) 6.98-7.14 (m, 5H) 7.44 (t, J=7.71 Hz, 1H) 7.64 (s, 1H) 8.25 (s, 1H) 9.28 (br. s., 1H) 11.87 (s, 1H); [M+H] calc'd for $C_{27}H_{32}N_3O_2$, 430.2; found, 430.5; [M+H+TFA] calc'd for $C_{29}H_{33}N_3O_4F_3$, 544.2; found, 544.4.

Compound 185

5-(3-(ethylsulfonyl)phenyl)-3-methyl-8-(piperidin-4-ylmethoxy)-9H-pyrido[2,3-b]indole

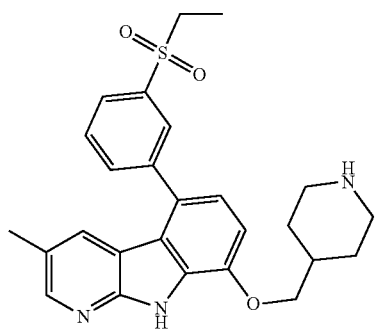

The title compound was synthesized by using an analogous synthetic sequence to that outlined in the preparation of Compound 177. ¹H NMR (400 MHz, MeOD) δ ppm 1.29 (t, J=7.33 Hz, 3H) 1.71 (d, J=11.37 Hz, 2H) 2.27-2.40 (m, 6H) 3.11 (t, J=12.25 Hz, 2H) 3.51 (d, J=12.88 Hz, 2H) 4.20 (br. s., 2H) 7.28 (br. s., 2H) 7.86 (t, J=7.70 Hz, 1H) 7.92-8.00 (m, 1H) 8.00-8.08 (m, 2H) 8.18 (br. s., 1H) 8.29 (br. s., 1H) [M+H] calc'd for $C_{26}H_{29}N_3O_3S$, 464; found, 464.

Compound 186

(S)-5-(3-(ethylsulfonyl)phenyl)-3-methyl-8-((1-methylpyrrolidin-3-yl)methoxy)-9H-pyrido[2,3-b]indole

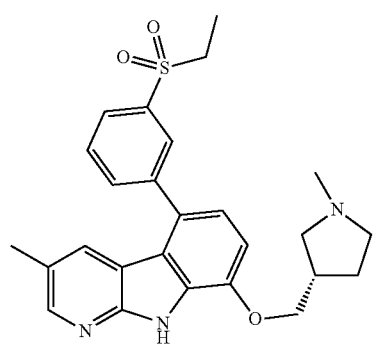

The title compound was synthesized by using an analogous synthetic sequence to that outlined in the preparation of Compound 177. ¹H NMR (400 MHz, Methanol-d₄) δ 8.31 (s, br, 1H) 8.19 (s, 1H) 8.06 (m, 1H) 8.00 (m, 1H) 7.89 (m, 2H) 7.27 (m, 2H) 4.38 (m, 2H) 3.91 (m, 2H) 3.50 (m, 1H) 3.35 (t, J=7.32 Hz, 2H) 3.19 (m, 1H) 3.07 (s, 3H) 2.6-2.25 (m, 6H) 1.31 (t, J=7.32 Hz, 3H). [M+H] calc'd for $C_{26}H_{30}N_3O_3S$, 464; found, 464.

Compound 187

(R)-5-(3-(ethylsulfonyl)phenyl)-3-methyl-8-((1-methylpyrrolidin-3-yl)methoxy)-9H-pyrido[2,3-b]indole

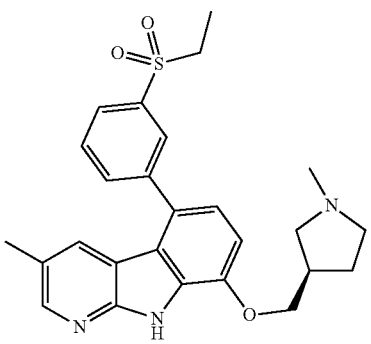

The title compound was synthesized by using an analogous synthetic sequence to that outlined in the preparation of Compound 177. ¹H NMR (400 MHz, Methanol-d₄) δ 8.31 (s, br, 1H) 8.19 (s, 1H) 8.06 (m, 1H) 8.00 (m, 1H) 7.89 (m, 2H) 7.27 (m, 2H) 4.38 (m, 2H) 3.91 (m, 2H) 3.50 (m, 1H) 3.35 (t, J=7.32 Hz, 2H) 3.19 (m, 1H) 3.07 (s, 3H) 2.6-2.25 (m, 6H) 1.31 (t, J=7.32 Hz, 3H). [M+H] calc'd for $C_{26}H_{30}N_3O_3S$, 464; found, 464.

Compound 188

(S)-5-(3-(ethylsulfonyl)phenyl)-3-methyl-8-((1-methylpyrrolidin-2-yl)methoxy)-9H-pyrido[2,3-b]indole

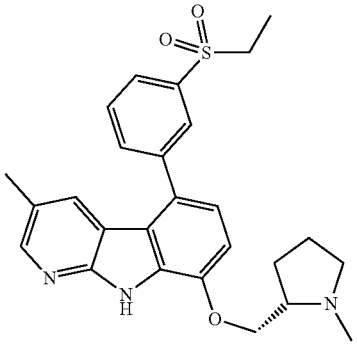

The title compound was synthesized by using an analogous synthetic sequence to that outlined in the preparation of Compound 177. ¹H NMR (400 MHz, DMSO-d₆) δ ppm 1.17 (t, J=7.33 Hz, 3H) 1.71-1.77 (m, 4H) 2.12 (m, 1H) 2.26 (s, 3H) 2.45 (s, 3H) 2.78 (br. s., 1H) 3.03 (m, 1H) 3.41 (q, J=7.33 Hz, 2H) 4.07 (dd, J=9.60, 6.32 Hz, 1H) 4.28 (dd, J=9.85, 5.05 Hz, 1H) 7.06 (d, J=8.01 Hz, 1H) 7.16 (d, J=8.08 Hz, 1H) 7.54 (s, 1H) 7.84 (t, J=7.71 Hz, 1H) 7.98 (t, J=7.58 Hz, 2H) 8.08 (s, Compound 189

(S)-5-(3-(ethylsulfonyl)phenyl)-3-methyl-8-(pyrrolidin-3-ylmethoxy)-9H-pyrido[2,3-b]indole

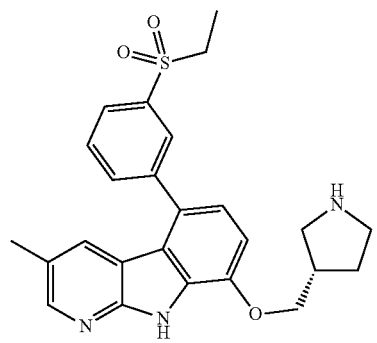

The title compound was synthesized by using an analogous synthetic sequence to that outlined in the preparation of Compound 177. $^1$H NMR (400 MHz, Methanol-$d_4$) δ 8.29-8.21 (m, 2H) 8.07 (m, 1H) 8.00-7.92 (m, 2H) 7.86 (m, 1H) 7.27 (m, 2H) 4.50-4.12 (m, 4H) 3.70-3.48 (m, 1H) 3.35 (t, J=7.32 Hz, 2H) 3.19 (m, 1H) 2.58 (m, 3H) 2.37 (s, 3H) 1.31 (t, J=7.32 Hz, 3H). [M+H] calc'd for $C_{25}H_{28}N_3O_3S$, 450; found, 450.

Compound 190

(R)-5-(3-(ethylsulfonyl)phenyl)-3-methyl-8-(pyrrolidin-3-ylmethoxy)-9H-pyrido[2,3-b]indole

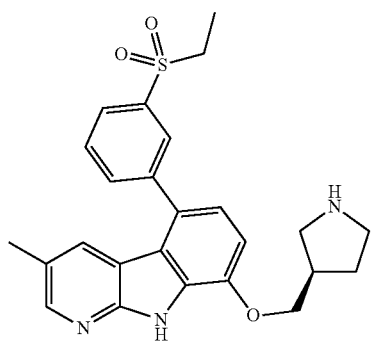

The title compound was synthesized by using an analogous synthetic sequence to that outlined in the preparation of Compound 177. $^1$H NMR (400 MHz, Methanol-$d_4$) δ 8.29-8.21 (m, 2H) 8.07 (m, 1H) 8.00-7.92 (m, 2H) 7.86 (m, 1H) 7.27 (m, 2H) 4.50-4.12 (m, 4H) 3.70-3.48 (m, 1H) 3.35 (t, J=7.32 Hz, 2H) 3.19 (m, 1H) 2.58 (m, 3H) 2.37 (s, 3H) 1.31 (t, J=7.32 Hz, 3H). [M+H] calc'd for $C_{25}H_{28}N_3O_3S$, 450; found, 450.

Compound 191

3-(4-chloro-2-iodophenoxy)-N,N-dimethylpropan-1-amine

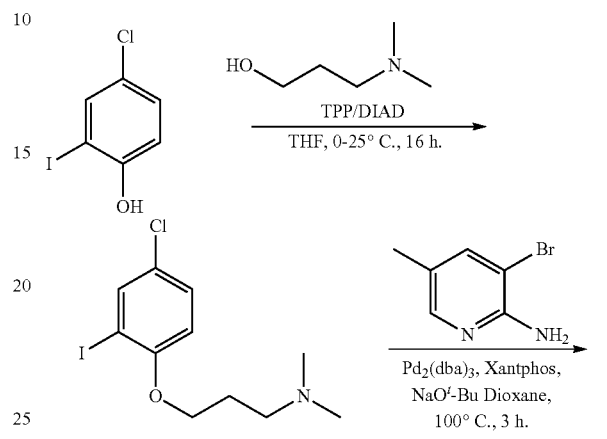

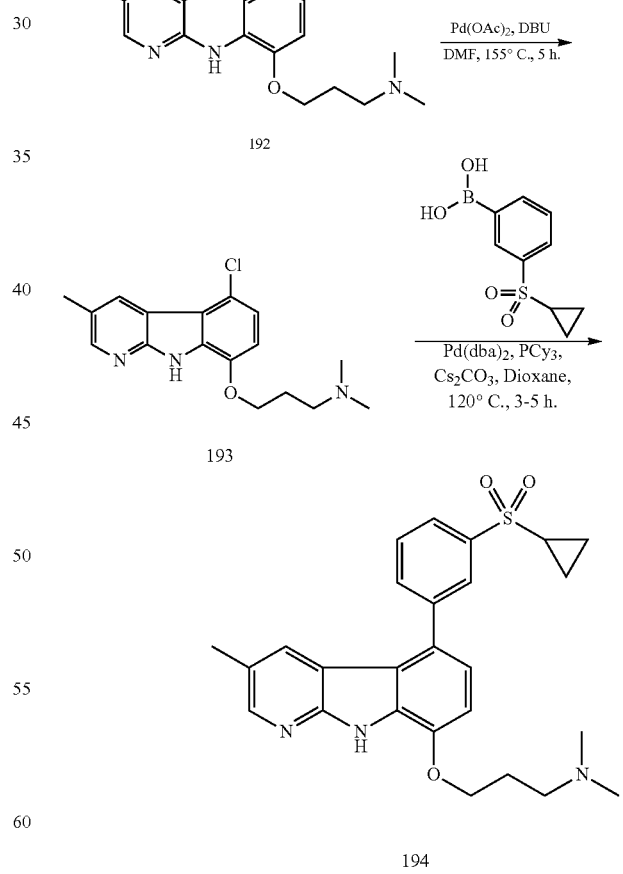

The title compound was synthesized using 4-chloro-2-iodophenol and 3-(dimethylamino)propan-1-ol, in an analogous procedure to that outlined in the preparation of Compound 174. $^1$H NMR (400 MHz, CDCl$_3$) δ ppm 1.99-2.15 (m, 2H) 2.38 (s, 6H) 2.67 (t, J=7.33 Hz, 2H) 4.07 (t, J=6.06 Hz, 2H) 6.73 (d, J=8.84 Hz, 1H) 7.25 (d, J=2.53 Hz, 1H) 7.74 (d, J=2.53 Hz, 1H). [M+H] calc'd for $C_{11}H_{16}Cl_1NO$, 339.99; found, 340.2.

Compound 192

3-bromo-N-(5-chloro-2-(3-(dimethylamino)propoxy)phenyl)-5-methylpyridin-2-amine

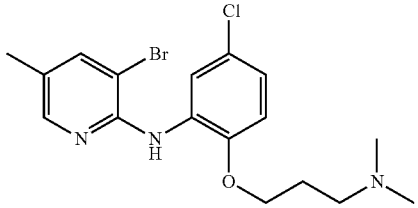

The title compound was synthesized by using an analogous synthetic method as outlined in the preparation of Compound 175. $^1$H NMR (400 MHz, DMSO-d$_6$) δ ppm 2.18 (m, 2H) 2.23 (s, 3H) 2.80 (s, 6H) 3.19-3.28 (m, 2H) 4.18 (t, J=5.81 Hz, 2H) 6.96-7.02 (m, 1H) 7.04-7.09 (m, 1H) 7.82 (s, 1H) 7.93 (d, J=1.26 Hz, 1H) 8.13 (s, 1H) 8.56 (d, J=2.78 Hz, 1H). [M+H] calc'd for $C_{17}H_{22}BrClN_3O$, 398.06; found, 398.2.

Compound 193

3-(5-chloro-3-methyl-9H-pyrido[2,3-b]indol-8-yloxy)-N,N-dimethylpropan-1-amine

The title compound was synthesized by using an analogous synthetic sequence to that outlined in the preparation of Compound 176. $^1$H NMR (400 MHz, DMSO-d$_6$) δ ppm 1.91-1.99 (m, 2H), 2.21 (s, 6H), 2.47 (S, 3H), 2.52-2.56 (m, 2H), 4.19 (t, J=3.6 Hz, 2H), 7.03 (d, J=8.1 Hz, 1H), 7.14 (d, J=7.84 Hz, 1H), 8.36 (s, 1H), 8.49 (d, J=1.8 Hz, 1H), 12.25 (s, 1H); [M+H] calc'd for $C_{17}H_{21}ClN_3O$, 318.13; found, 318.2.

Compound 194

3-(5-(3-(cyclopropylsulfonyl)phenyl)-3-methyl-9H-pyrido[2,3-b]indol-8-yloxy)-N,N-dimethylpropan-1-amine

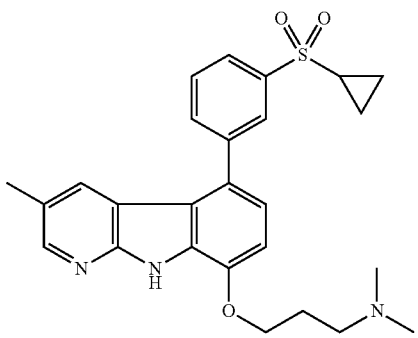

The title compound was synthesized from Compound 191 using an analogous procedure to that outlined in the preparation of Compound 177. $^1$H NMR (400 MHz, DMSO-d$_6$) δ ppm 1.28 (m, 4H) 2.21-2.24 (m, 2H) 2.26 (m, 5H) 2.47 (s, 3H) 3.32 (q, J=7.2 Hz, 2H) 3.47-3.52 (m, 2H) 4.29 (t, J=5.43 Hz, 2H) 7.05 (d, J=8.08 Hz, 1H) 7.13 (d, J=8.08 Hz, 1H) 7.54 (s, 1H) 7.62 (t, J=7.71 Hz, 1H) 7.72 (d, J=7.58 Hz, 1H) 7.93 (d, J=7.83 Hz, 1H) 8.03 (s, 1H) 8.28 (s, 1H) 8.55 (d, J=4.04 Hz, 1H) 9.60 (br. s., 1H) 11.93 (s, 1H); [M+H] calc'd for $C_{26}H_{29}N_3O_3S$, 464.6; found, 464.6.

Compound 195

N-(3-(8-(3-(dimethylamino)propoxy)-3-methyl-9H-pyrido[2,3-b]indol-5-yl)phenyl)cyclopropanecarboxamide

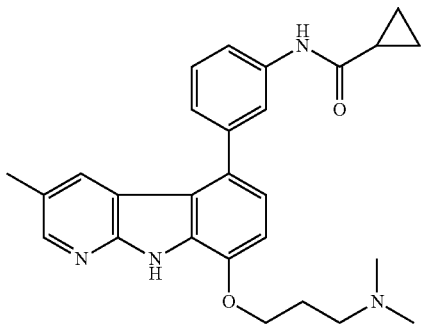

The title compound was synthesized from Compound 193 using an analogous procedure to that outlined in the preparation of Compound 177. $^1$H NMR (400 MHz, DMSO-d$_6$) δ ppm 0.75-0.81 (m, 4H) 1.80 (m, 1H) 2.22 (dd, J=9.98, 5.43 Hz, 2H) 2.27 (s, 3H) 2.88 (s, 3H) 2.89 (s, 3H) 3.46-3.51 (m, 2H) 4.28 (t, J=5.56 Hz, 2H) 6.99 (d, J=8.08 Hz, 1H) 7.10 (d, J=8.08 Hz, 1H) 7.23 (d, J=7.83 Hz, 1H) 7.46 (t, J=7.83 Hz, 1 H) 7.61 (d, J=9.09 Hz, 1H) 7.74 (d, J=1.26 Hz, 1H) 7.92 (s, 1H) 8.27 (d, J=1.52 Hz, 1 H) 9.63 (br. s., 1H) 10.34 (s, 1H) 11.90 (s, 1H); [M+H] calc'd for $C_{27}H_{31}N_4O_2$, 443.2; found, 443.3.

Compound 196

3'-(ethylsulfonyl)biphenyl-4-ol

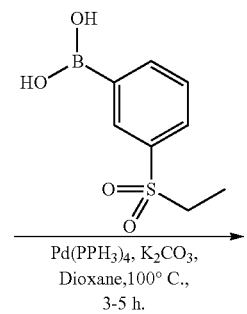

-continued

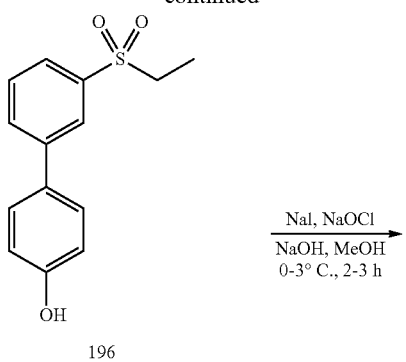
196

Nal, NaOCl
―――――――→
NaOH, MeOH
0-3° C., 2-3 h

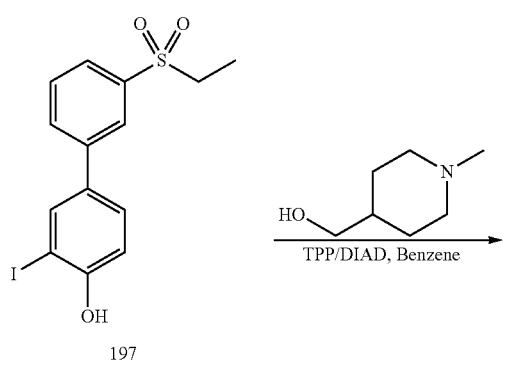
197

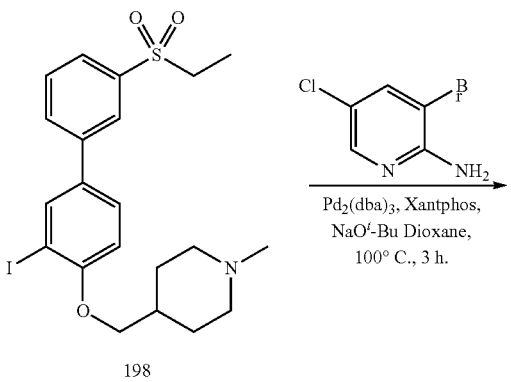
198

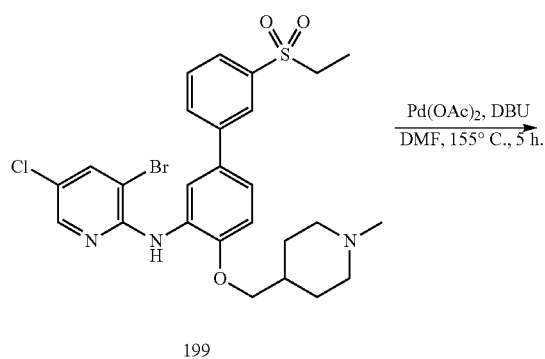
199

-continued

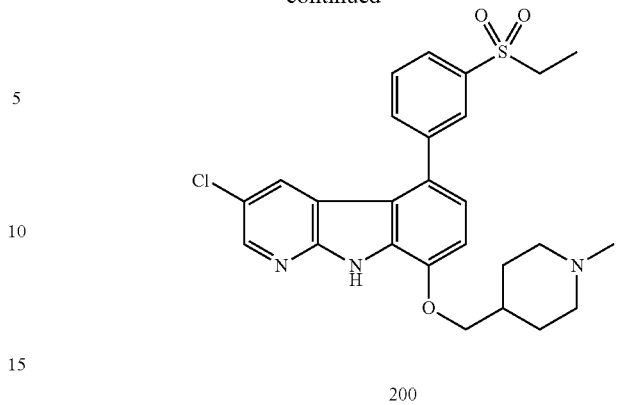
200

4-Bromophenol (10.0 g, 57.8 mmol), 3-(ethylsulfonyl) phenylboronic acid (13.6 g, 63.6 mmol) and Pd(PPh$_3$)$_4$ (3.3 g, 0.05 mmol) were taken in a mixture of dioxane and saturated aqueous potassium carbonate solution (3:1, 280 mL) and heated at 100° C. for 5 h. After disappearance of starting material (as monitored by TLC), dioxane was removed in vacuum and the organic matter was extracted with EtOAc. Organic extract was washed with brine and dried over Na$_2$SO$_4$, concentrated and purified by flash chromatography to yield compound 196 (12.8 g, 85%).

Compound 197

3'-(ethylsulfonyl)-3-iodobiphenyl-4-ol

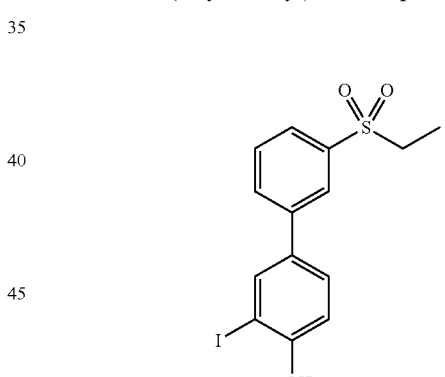

Compound 196 (11.1 g, 42.3 mmol) was dissolve in MeOH (150 mL) and to it were sequentially added NO (6.98 g, 46.5 mmol) and NaOH (1.95 g, 48.6 mmol). The mixture was cooled to 0° C. and aqueous NaOCl (23.2 mL, 13% solution in water; 23.2 mL was diluted to 100 mL before addition) was added dropwise over a period of 2.5 h. at 0° C. to 5° C. The resulting slurry was further stirred for 1 h. and finally quenched with 10% aqueous Na$_2$SO$_3$ solution. With 5% aqueous HCl the pH of the solution was adjusted to 7. MeOH was partially removed in vacuum, and the remaining aqueous layer was extracted with EtOAc. Organic layer was washed with brine, dried (Na$_2$SO$_4$), concentrated and the solid was triturated with ether. The white residue was dried to provide compound 197 (11.4 g, 70%). $^1$H NMR (400 MHz, DMSO-d$_6$) δ ppm 1.12 (t, J=7.45 Hz, 3H) 6.99 (d, J=8.34 Hz, 1H) 7.62 (dd, J=8.59, 2.27 Hz, 1H) 7.69 (t, J=7.83 Hz, 1H) 7.80 (br. d, J=8.08 Hz, 1H) 7.97 (d, J=7.83 Hz, 1H) 8.01-8.03 (m, 1H)

8.07 (d, J=2.27 Hz, 1H) 10.65 (s, 1H). [M+H] calc'd for C$_{14}$H$_{15}$IO$_3$S, 388.96; found, 389.0.

Compound 198

4-((3'-(ethylsulfonyl)-3-iodobiphenyl-4-yloxy)methyl)-1-methylpiperidine

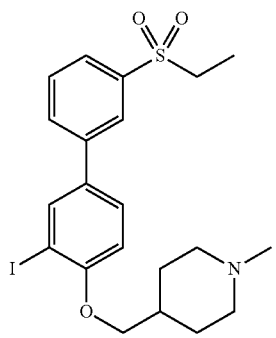

To a stirred solution of compound 197 (1.06 g, 2.73 mmol) in anhydrous benzene (8.0 mL) were sequentially added (1-methylpiperidin-4-yl)methanol (529 mg, 4.09 mmol) and triphenyl phosphine (1.07 g, 4.09 mmol.). The reaction mixture was cooled to 0° C., and to it diisopropyl-azodicarboxylate (0.79 mL, 4.09 mmol) was added in drop wise manner. After the addition was over, stirring continued for another 0.5 h at 0° C. and then for 12 h at room temperature. Solvents were removed in vacuum and the residue was purified by silica gel column chromatography, providing compound 198 (982 mg, 72%). $^1$H NMR (400 MHz, DMSO-d$_6$) δ ppm 1.13 (t, J=7.33 Hz, 3H) 1.42 (qd, J=11.87, 3.54 Hz, 1H) 1.77-1.90 (m, 4H) 2.17 (s, 2H) 2.81 (d, J=11.12 Hz, 2H) 3.40 (q, J=7.33 Hz, 2H) 3.96 (d, J=5.81 Hz, 2H) 7.10 (d, J=8.0 Hz, 1H) 7.71 (t, J=7.71 Hz, 1H) 7.75 (dd, J=8.59, 2.27 Hz, 1H) 7.82 (d, J=7.83 Hz, 1H) 8.01 (d, J=7.58 Hz, 1H) 8.05 (br. m, 1 H) 8.16 (d, J=3.9 Hz, 1H). [M+H] calc'd for C$_{21}$H$_{27}$INO$_3$S, 500.07; found, 500.2.

Compound 199

3-bromo-5-chloro-N-(3'-(ethylsulfonyl)-4-((1-methylpiperidin-4-yl)methoxy)biphenyl-3-yl)pyridin-2-amine

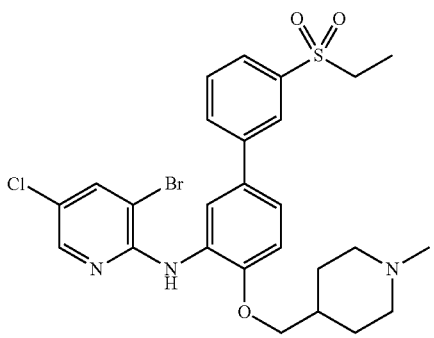

In a oven dried 50 mL round bottom flask were sequentially added compound 198 (1.18 g, 2.36 mmol), compound 3-bromo-5-chloropyridin-2-amine (589 mg, 2.83 mmol), Pd$_2$(dba)$_3$ (108 mg, 0.12 mmol), xantphos (208 mg, 0.36 mmol) and Na$^t$BuO (340 mg, 3.51 mmol) at room temperature. The solid materials were kept under vacuum for 5 min. and then refilled with nitrogen. This process was repeated thrice before adding dry, degassed dioxane (10 mL). The heterogeneous mixture was stirred at room temperature for 15 min. and then at 100° C. for 2 h. Finally upon completion of the reaction, it was diluted with EtOAc and filtered through a small pad of silica gel with several washings. All the washings and filtrate concentrated in vacuum and the crude residue was further purified by flash chromatography to provide pure compound 199 (956 mg, 70%). $^1$H NMR (400 MHz, DMSO-d$_6$) δ ppm 1.14 (t, J=7.33 Hz, 3H) 1.42-1.57 (m, 2H) 1.92 (d, J=13.89 Hz, 2H) 1.98 (br. m, 3H) 2.60 (s., 3H) 2.67 (br.m, 2H) 3.38 (q, J=7.58 Hz, 2H) 4.06 (d, J=6.06 Hz, 2H) 7.22 (d, J=8.59 Hz, 1H) 7.43 (dd, J=8.59, 2.27 Hz, 1H) 7.74 (t, J=7.71 Hz, 1H) 7.84 (d, J=7.83 Hz, 1H) 7.99 (d, J=7.58 Hz, 1H) 8.04 (t, J=1.64 Hz, 1H) 8.05 (s, 1H) 8.25 (s, 1H) 8.63 (d, J=2.53 Hz, 1H). [M+H] calc'd for C$_{26}$H$_{30}$BrClN$_3$O$_3$S, 578.08; found, 578.2.

Compound 200

3-chloro-5-(3-(ethylsulfonyl)phenyl)-8-((1-methylpiperidin-4-yl)methoxy)-9H-pyrido[2,3-b]indole

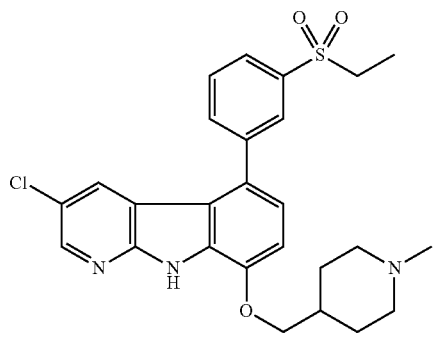

To a stirred solution of compound 199 (1.13 g, 1.95 mmol) in anhydrous and degassed DMF (8 mL), were added Pd(OAc)$_2$ (44 mg, 0.19 mmol) and DBU (0.88 mL, 5.86 mmol), under nitrogen. After being stirred for 6 h. at 155° C. the reaction was quenched by addition of water (10 mL). The solid precipitates out was filtered and washed thoroughly with water. The residue was dried under vacuum and purified by preparative HPLC to furnish compound 200 (388 mg, 40%). $^1$H NMR (400 MHz, DMSO-d$_6$) δ ppm 1.17 (t, J=7.33 Hz, 3H) 1.41 (qd, J=11.62, 3.03 Hz, 2H) 1.86-1.96 (m, 5H) 2.19 (s, 3 H) 2.84 (br. d, J=10.86 Hz, 2H) 3.41 (q, J=7.49 Hz, 2H) 4.09 (d, J=6.32 Hz, 2H) 7.11-7.21 (m, 2H) 7.62 (d, J=2.53 Hz, 1H) 7.87 (t, J=7.71 Hz, 1H) 8.00 (t, J=7.83 Hz, 2H) 8.05 (s, 1H) 8.45 (d, J=2.53 Hz, 1H) 12.45 (s, 1H); [M+H] calc'd for C$_{26}$H$_{29}$ClN$_3$O$_3$S, 498.2; found, 498.2; [M+H+TFA] calc'd for C$_{28}$H$_{30}$ClN$_3$O$_5$F$_3$S, 612.2; found, 612.1.

The hydrogen chloride salt of compound 200 was prepared by using an analogous procedure outlined in the preparation of the HCl salt of compound 88.

The bis-trifluoroacetic acid salt of compound 200 was prepared by using an analogous procedure outlined in the preparation of the TFA salt of compound 88.

Compound 201

3-chloro-5-(3-(ethylsulfonyl)phenyl)-8-(piperidin-4-ylmethoxy)-9H-pyrido[2,3-b]indole

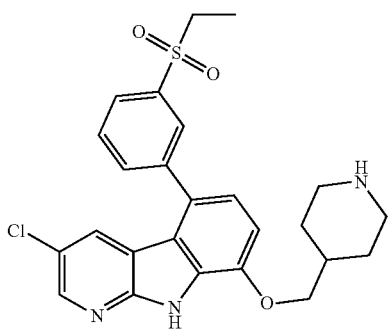

The title compound was synthesized by using an analogous synthetic sequence to that outlined in the preparation of Compound 200. ¹H NMR (400 MHz, MeOD) δ ppm 1.32 (t, J=7.33 Hz, 3H) 1.60-1.72 (m, 5H) 2.31 (d, J=13.89 Hz, 2H) 3.11 (td, J=12.82, 2.40 Hz, 2H) 3.51 (d, J=12.63 Hz, 2H) 4.19 (d, J=6.57 Hz, 2H) 7.11-7.15 (m, 1H) 7.16-7.20 (m, 1H) 7.64 (d, J=2.27 Hz, 1H) 7.85 (t, J=7.71 Hz, 1H) 7.95 (ddd, J=7.71, 1.39, 1.26 Hz, 1H) 8.05 (ddd, J=8.08, 1.52, 1.26 Hz, 1H) 8.13 (t, J=1.52 Hz, 1H) 8.31 (s, 1H).

Compound 202

5-(3-(ethylsulfonyl)phenyl)-8-((1-methylpiperidin-4-yl)methoxy)-3-(trifluoromethyl)-9H-pyrido[2,3-b]indole

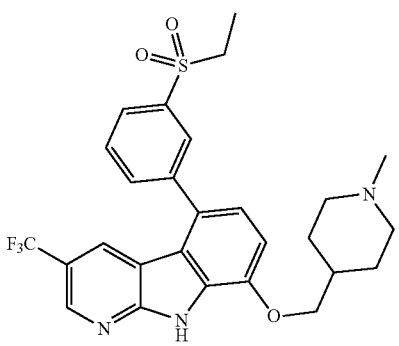

The title compound was synthesized by using an analogous synthetic sequence to that outlined in the preparation of Compound 200. ¹H NMR (400 MHz, Methanol-d₄) δ 8.72 (s, 1H) 8.15 (s, 1H) 8.10 (m, 1H) 7.99 (m, 1H) 7.93 (s, 1H) 7.88 (t, J=7.6 Hz, 1H) 7.28 (d, J=8.08 Hz, 1H) 7.23 (d, J=8.08 Hz, 1H) 4.24 (d, J=6.32 Hz, 2H) 3.65 (br, m, 2H) 3.43 (q, J=7.32 Hz, 2H) 3.14 (br, m, 2H) 2.95 (s, 3H) 2.38 (br, m, 3H) 1.68 (m, br, 2H) 1.31 (t, J=7.32 Hz, 3H). [M+H] calc'd for C₂₇H₂₉F₃N₃O₃S, 532; found, 532.

Compound 203

5-(3-(ethylsulfonyl)phenyl)-8-((1-methylpiperidin-4-yl)methoxy)-9H-pyrido[2,3-b]indole-3-carbonitrile

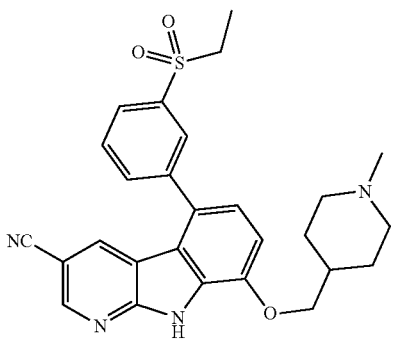

The title compound was synthesized by using an analogous synthetic sequence to that outlined in the preparation of Compound 200. ¹H NMR (400 MHz, Methanol-d₄) δ 8.63 (s, 1H) 8.22 (s, 1H) 8.09 (m, 1H) 7.98 (m, 1H) 7.94 (m, 2H) 7.89 (t, J=7.84 Hz, 1 H) 7.26 (d, J=8.08 Hz, 1H) 7.23 (d, J=8.08 Hz, 1H) 4.24 (d, J=6.28 Hz, 2H) 3.65 (m, br, 2H) 3.38 (q, J=7.32 Hz, 2H) 3.15 (br, m, 2H) 2.95 (s, 3H) 2.42 (br, m, 3H) 1.72 (br, m, 2H) 1.31 (t, J=7.32 Hz, 3H). [M+H] calc'd for C₂₇H₂₉N₄O₃S, 489; found, 489.

Compound 204

2-(5-(3-(ethylsulfonyl)phenyl)-7-fluoro-3-methyl-9H-pyrido[2,3-b]indol-8-yloxy)-N,N-dimethylethanamine

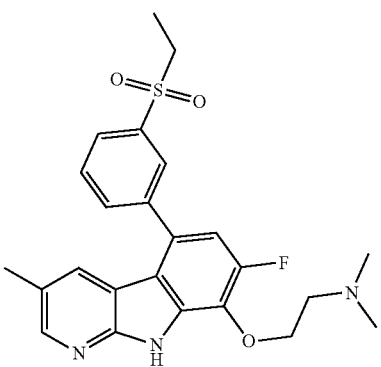

The title compound was synthesized by using an analogous synthetic sequence to that outlined in the preparation of Compound 200. ¹H NMR (400 MHz, MeOD) δ ppm 1.29 (t, J=7.45 Hz, 3H) 2.32 (s, 3H) 3.13 (s, 6H) 3.74 (t, J=4.8 Hz, 2H) 4.64 (t, J=4.80 Hz, 2H) 7.11 (d, J=12.63 Hz, 1H) 7.59 (s, 1H) 7.88 (t, J=7.71 Hz, 1H) 7.98 (dd, J=6.82, 2.02 Hz, 1H) 8.10

(dd, J=7.45, 1.64 Hz, 1H) 8.16 (t, J=1.64 Hz, 1H) 8.26 (s, 1H) [M+H] calc'd for $C_{24}H_{26}FN_3O_3S$, 456; found, 456.

Compound 205

3-(3-chloro-5-(3-(ethylsulfonyl)phenyl)-7-fluoro-9H-pyrido[2,3-b]indol-8-yloxy)-N,N-dimethylpropan-1-amine

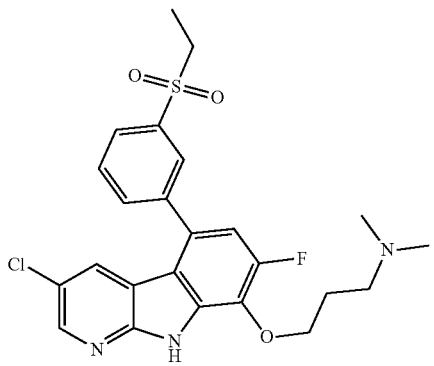

The title compound was synthesized by using an analogous synthetic sequence to that outlined in the preparation of Compound 200. $^1$H NMR (400 MHz, MeOD) δ ppm 1.31 (t, J=7.45 Hz, 3H) 2.34 (br. s., 2H) 3.00 (s, 6H) 3.54 (d, J=8.08 Hz, 2H) 4.46 (t, J=6.19 Hz, 2H) 7.09 (d, J=12.63 Hz, 1H) 7.57 (d, J=2.27 Hz, 1H) 7.89 (d, J=7.07 Hz, 1 H) 7.97 (d, J=9.35 Hz, 1H) 8.09-8.14 (m, 2H) 8.35 (s, 1H) [M+H] calc'd for $C_{24}H_{25}ClFN_3O_3S$, 490; found, 490.

Compound 206

3-(5-(3-(ethylsulfonyl)phenyl)-3-methyl-9H-pyrido[2,3-b]indol-8-yloxy)-N,N-dimethylpropan-1-amine

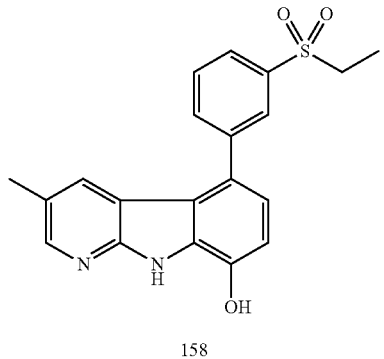

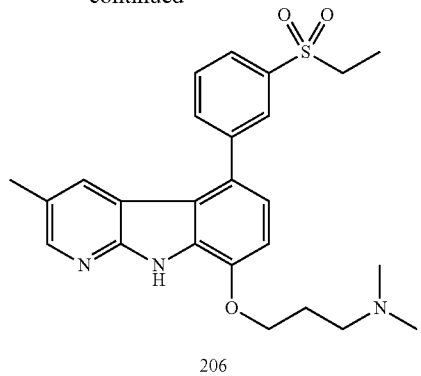

A 5 mL microwave vial was charged with Compound 158 (290 mg, 0.79 mmol), 3-(dimethylamino)propyl-4-methylbenzenesulfonate (224 mg, 0.87 mmol), potassium carbonate (218 mg, 1.58 mmol) and 2 mL of anhydrous DMF, under nitrogen atmosphere. The reaction mixture was heated at 200° C. for 30 min. in microwave with high absorption. The reaction was quenched with addition of water, and the solid precipitate out was collected by filtration and purified through preparative HPLC to provide title compound as a light yellow solid (143 mg, 40%). $^1$H NMR (400 MHz, DMSO-$d_6$) δ ppm 1.17 (t, J=7.33 Hz, 3H) 1.99 (qd, J=6.61, 6.44 Hz, 2H) 2.20 (s, 6H) 2.26 (s, 3H) 2.53-2.56 (m, 2H) 3.41 (q, J=7.33 Hz, 2H) 4.25 (t, J=6.19 Hz, 2H) 7.05-7.09 (m, 1H) 7.11-7.14 (m, 1H) 7.54 (d, J=1.52 Hz, 1H) 7.85 (t, J=7.83 Hz, 1H) 7.98 (t, J=6.95 Hz, 2H) 8.06-8.08 (m, 1H) 8.27 (d, J=1.77 Hz, 1H) 12.13 (s, 1H); [M+H] calc'd for $C_{25}H_{30}N_3O_3S$, 452.2; found, 452.4.

The hydrogen chloride salt of compound 206 was prepared by using an analogous procedure outlined in the preparation of the HCl salt of compound 88.

The bis-trifluoroacetic acid salt of compound 206 was prepared by using an analogous procedure outlined in the preparation of the TFA salt of compound 88.

Compound 207

2-(5-(3-(ethylsulfonyl)phenyl)-3-methyl-9H-pyrido[2,3-b]indol-8-yloxy)-N,N-dimethylethanamine

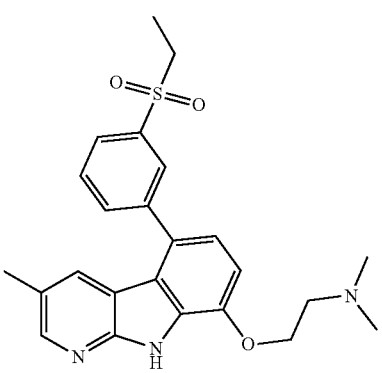

The title compound was synthesized from Compound 158 using an analogous procedure to that outlined in the preparation of Compound 206 using 2-bromo-N,N-dimethylethanamine. $^1$H NMR (400 MHz, MeOD) δ ppm 1.29 (t, J=7.33 Hz, 3H) 2.32 (s, 3H) 2.91 (t, J=5.31 Hz, 2H) 4.34 (t, J=5.43

Hz, 2H) 7.07-7.14 (m, 2H) 7.65 (d, J=2.02 Hz, 1H) 7.82 (t, J=7.83 Hz, 1H) 7.94-7.98 (m, 1H) 8.02 (dd, J=7.33, 1.52 Hz, 1H) 8.15 (t, J=1.64 Hz, 1H) 8.20 (d, J=2.02 Hz, 1H) [M+H] calc'd for $C_{24}H_{27}N_3O_3S$, 438; found, 438.

Compound 208

5-(3-(ethylsulfonyl)phenyl)-8-(2-methoxyethoxy)-3-methyl-9H-pyrido[2,3-b]indole

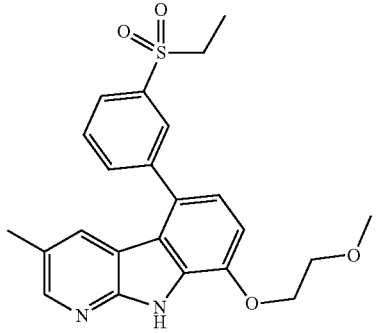

The title compound was synthesized from Compound 158 using an analogous procedure to that outlined in the preparation of Compound 206 using 2-bromoethylmethylether. $^1$H NMR (400 MHz, CDCl$_3$) δ 8.22 (s, 1H) 8.19 (s, 1H) 8.14 (m, 1H) 8.06 (m, 1H) 7.91 (m, 1H) 7.81 (m, 1H) 7.28 (d, J=8.32 Hz, 1H) 7.22 (d, J=8.32 Hz, 1H) 4.44 (m, 2H) 3.95 (m, 2H) 3.58 (s, 3H) 3.23 (q, J=7.32 Hz, 2H) 2.49 (s, 3H) 1.37 (t, J=7.32 Hz, 3H). [M+H] calc'd for $C_{23}H_{25}N_2O_4S$, 425; found, 425.

Compound 209

2-(5-(3-(ethylsulfonyl)phenyl)-3-methyl-9H-pyrido[2,3-b]indol-8-yloxy)acetonitrile

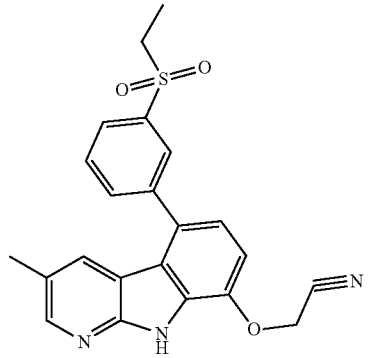

The title compound was synthesized from Compound 158 and 2-bromoacetonitrile using an analogous procedure to that outlined in the preparation of Compound 206. $^1$H NMR (400 MHz, CHLOROFORM-d) δ ppm 1.36 (t, J=7.33 Hz, 3H) 2.32 (s, 3H) 3.22 (q, J=7.33 Hz, 2H) 5.14 (s, 2H) 7.31-7.37 (m, 2H) 7.82 (t, J=7.71 Hz, 1H) 7.91 (d, J=7.83 Hz, 1H) 8.09 (d, J=7.83 Hz, 1H) 8.11-8.15 (m, 2H) 8.22 (s, 1H) 14.04 (br. s., 1H) [M+H] calc'd for $C_{22}H_{19}N_3O_3S$, 406; found, 406.

Compound 210

3-(5-(3-(ethylsulfonyl)phenyl)-3-methyl-9H-pyrido[2,3-b]indol-8-yloxy)propanenitrile

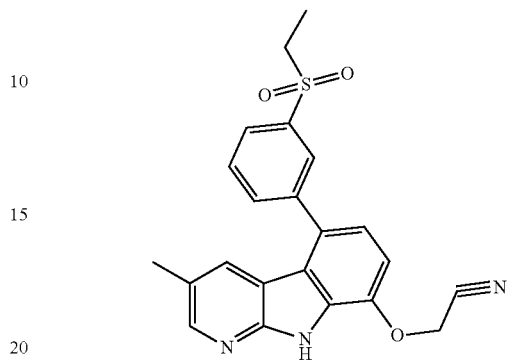

The title compound was synthesized from Compound 158 and 3-bromopropionitrile using an analogous procedure to that outlined in the preparation of Compound 206. $^1$H NMR (400 MHz, MeOD) δ ppm 1.28 (t, J=7.33 Hz, 3H) 2.30 (s, 3H) 3.10 (t, J=6.69 Hz, 2H) 5.12 (t, J=6.82 Hz, 2H) 7.00-7.05 (m, 2H) 7.53 (dd, J=2.02, 0.76 Hz, 1H) 7.81 (t, J=7.45 Hz, 1H) 7.92 (ddd, J=7.89, 1.45, 1.26 Hz, 1H) 8.02 (dt, J=7.83, 1.52 Hz, 1H) 8.10 (t, J=1.89 Hz, 1H) 8.26 (d, J=2.02 Hz, 1H) [M+H] calc'd for $C_{23}H_{21}N_3O_3S$, 421; found, 421.

Compound 211

(R)-8-(1-tert-butyldiphenylsilyloxy)propan-2-yloxy)-(5-(3-(ethylsulfonyl)phenyl)-3-methyl-9H-pyrido[2,3-b]indole

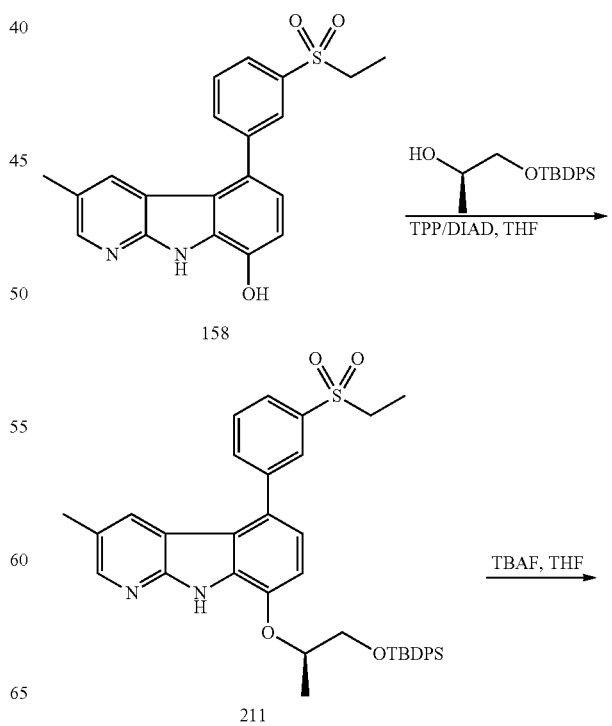

-continued

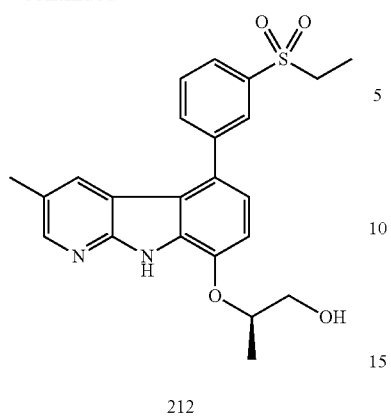

212

To a stirred solution of Compound 158 (75 mg, 0.204 mmol) in anhydrous THF (3.0 mL) were sequentially added (R)-(tert-butyldiphenylsilyloxy)propan-2-ol (77 mg, 0.245 mmol) and triphenyl phosphine (81 mg, 0.31 mmol). The reaction mixture was cooled to 0° C., and to it diisopropylazodicarboxylate (60 μL, 0.31 mmol) was added in drop wise manner. After the addition was over, stirring continued for another 0.5 h at 0° C. and then for 12 h at room temperature. Solvents were removed in vacuum and the residue was purified by silica gel column chromatography, provided the title compound (108 mg, 80%).

Compound 212

(R)-2-(5-(3-(ethylsulfonyl)phenyl)-3-methyl-9H-pyrido[2,3-b]indol-8-yloxy)propan-1-ol

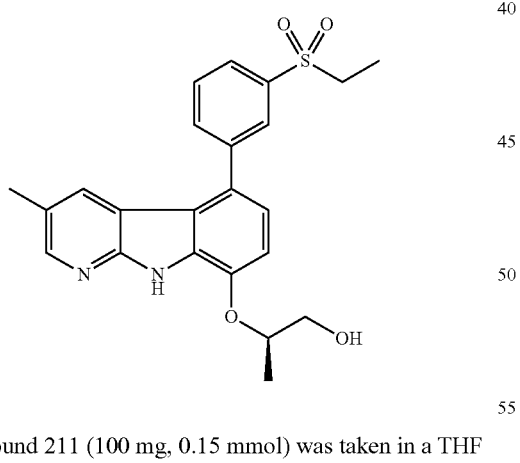

Compound 211 (100 mg, 0.15 mmol) was taken in a THF (3 mL) and stirred for 12 h at room temperature with TBAF (0.19 mL, 0.19 mmol, 1 M solution in THF). The reaction mixture was diluted with EtOAc and washed with aqueous NH₄Cl and brine. The organic extract was dried over Na₂SO₄, concentrated and purified by preparative HPLC to provide the title compound (50 mg, 73%). ¹H NMR (400 MHz, DMSO-d₆) δ ppm 1.17 (t, J=7.45 Hz, 3H) 1.36 (d, J=6.06 Hz, 3H) 2.26 (s, 3H) 3.40 (q, J=7.41 Hz, 2H) 3.63-3.72 (m, 2H) 4.63 (m, 1H) 4.90 (t, J=6.19 Hz, 1H) 7.07 (d, J=8.08 Hz, 1H) 7.15-7.19 (m, 1H) 7.56 (s, 1H) 7.85 (t, J=7.71 Hz, 1H) 7.97-7.99 (m, 2H) 8.07-8.10 (m, 1H) 8.27 (d, J=2.02 Hz, 1H) 11.82 (s, 1H); [M+H] calc'd for C₂₃H₂₅N₂O₄S, 425.2; found, 425.3.

Compound 213

(S)-2-(5-(3-(ethylsulfonyl)phenyl)-3-methyl-9H-pyrido[2,3-b]indol-8-yloxy)propan-1-ol

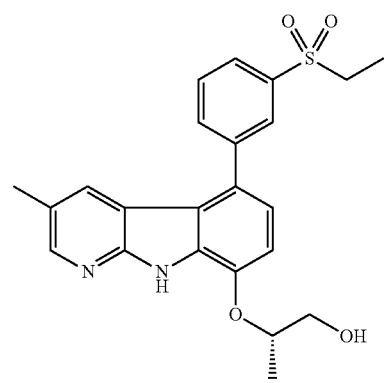

The title compound was synthesized from Compound 158 using an analogous procedure to that outlined in the preparation of Compound 212. ¹H NMR (400 MHz, DMSO-d₆) δ ppm 1.17 (t, J=7.45 Hz, 3H) 1.36 (d, J=6.06 Hz, 3H) 2.26 (s, 3H) 3.40 (q, J=7.41 Hz, 2H) 3.63-3.72 (m, 2H) 4.63 (m, 1H) 4.90 (t, J=6.19 Hz, 1H) 7.07 (d, J=8.08 Hz, 1H) 7.15-7.19 (m, 1H) 7.56 (s, 1H) 7.85 (t, J=7.71 Hz, 1H) 7.97-7.99 (m, 2H) 8.07-8.10 (m, 1H) 8.27 (d, J=2.02 Hz, 1H) 11.82 (s, 1H); [M+H] calc'd for C₂₃H₂₅N₂O₄S, 425.2; found, 425.3.

Compound 214

1-(5-(3-(ethylsulfonyl)phenyl)-3-methyl-9H-pyrido[2,3-b]indol-8-yloxy)propan-2-ol

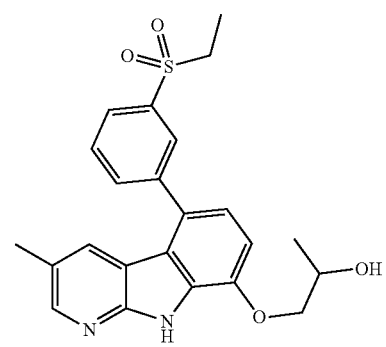

The title compound was synthesized from Compound 158 using an analogous procedure to that outlined in the preparation of Compound 212. ¹H NMR (400 MHz, Methanol-d₄) δ 8.28 (s, 1H) 8.19 (m, 1H) 8.06 (m, 1H) 8.00 (m, 1H) 7.92 (s, 1H) 7.87 (t, J=8.0 Hz, 1H) 7.26 (m, 2H) 4.31 (m, 2H) 4.10 (m, 1H) 3.30 (q, J=7.5 Hz, 2H) 2.40 (s, 3H) 1.40 (d, J=8 Hz, 3H) 1.31 (t, J=7.5 Hz, 3H). [M+H] calc'd for $C_{23}H_{25}N_2O_4S$, 425; found, 425.

Compound 215

(S)-4-(5-(3-(ethylsulfonyl)phenyl)-3-methyl-9H-pyrido[2,3-b]indol-8-yloxy)-2-methylpentan-2-ol

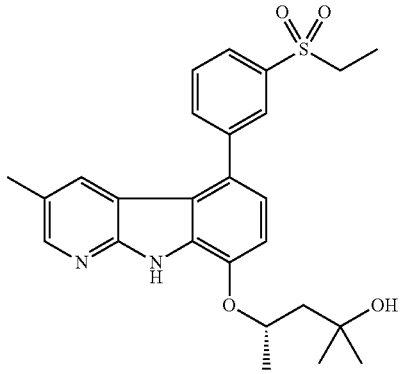

The title compound was synthesized from Compound 158 using an analogous procedure to that outlined in the preparation of Compound 212. $^1$H NMR (400 MHz, DMSO-$d_6$) δ ppm 1.16 (t, J=7.33 Hz, 3H) 1.17 (d, J=6.2 Hz, 3H) 1.43 (s, 3H) 1.46 (s, 3H) 1.93 (d, J=5.81 Hz, 2H) 2.26 (s, 3H) 3.41 (q, J=6.33 Hz, 2H) 4.05 (m, 1H) 7.07 (d, J=8.08 Hz, 1H) 7.23 (d, J=8.08 Hz, 1H) 7.53 (s, 1H) 7.86 (t, J=7.58 Hz, 1H) 8.00 (dd, J=7.71, 1.64 Hz, 2H) 8.09-8.11 (m, 1H) 8.28 (s, 1H) 11.95 (s, 1H); [M+H] calc'd for $C_{26}H_{31}N_2O_4S$, 467.2; found, 467.3.

Compound 216

2-(5-(3-(ethylsulfonyl)phenyl)-3-methyl-9H-pyrido[2,3-b]indol-8-yloxy)ethanol

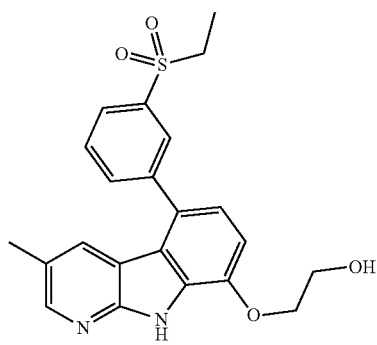

The title compound was synthesized from Compound 158 and 2-bromoethanol using an analogous procedure to that outlined in the preparation of Compound 206. $^1$H NMR (400 MHz, Methanol-$d_4$) δ 8.30 (s, 1H) 8.19 (m, 1H) 8.06 (m, 1H) 8.00 (m, 2H) 7.87 (t, J=8.0 Hz, 1H) 7.26 (m, 2H) 4.38 (t, J=4 Hz, 2H) 4.08 (t, J=4 Hz, 2H) 3.30 (q, J=7.5 Hz, 2H) 2.41 (s, 3H) 1.31 (t, J=7.5 Hz, 3H). [M+H] calc'd for $C_{22}H_{23}N_2O_4S$, 411; found, 411.

Compound 217

3-(5-(3-(ethylsulfonyl)phenyl)-3-methyl-9H-pyrido[2,3-b]indol-8-yloxy)propan-1-ol

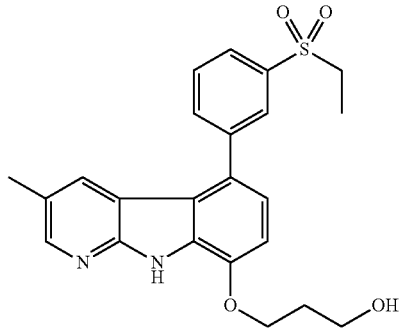

The title compound was synthesized from Compound 158 and 3-bromopropanol using an analogous procedure to that outlined in the preparation of Compound 206. $^1$H NMR (400 MHz, DMSO-$d_6$) δ ppm 1.18 (t, J=7.33 Hz, 3H) 2.01 (t, J=6.19 Hz, 2H) 2.27 (s, 3H) 3.41 (q, J=7.33 Hz, 2H) 3.72 (q, J=5.98 Hz, 2H) 4.30 (t, J=6.19 Hz, 2H) 4.57 (t, J=5.18 Hz, 1H) 7.06-7.17 (m, 2H) 7.55 (s, 1H) 7.85 (t, J=7.71 Hz, 1H) 8.00 (br. s., 1H) 7.98 (d, J=5.05 Hz, 2H) 8.08 (s, 1H) 8.28 (s, 1H) 11.99 (s, 1H); [M+H] calc'd for $C_{23}H_{25}N_2O_4S$ 425.15; found 425.3

Compound 218

3-(3-chloro-5-(3-(ethylsulfonyl)phenyl)-8-methoxy-9H-pyrido[2,3-b]indol-8-ol

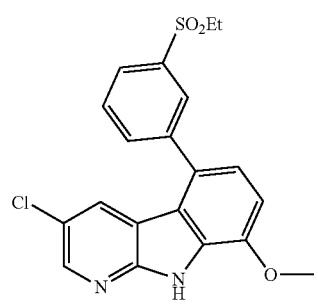

The title compound was synthesized by using an analogous synthetic sequence to that outlined in the preparation of Compound 200. $^1$H NMR (400 MHz, DMSO-$d_6$) δ ppm 1.18 (t, J=7.45 Hz, 3H) 3.42 (q, J=7.33 Hz, 2H) 4.05 (s, 3H) 7.15-7.19 (m, 1H) 7.21-7.25 (m, 1H) 7.62 (d, J=2.27 Hz, 1H) 7.88 (t, J=7.71 Hz, 1H) 7.98-8.03 (m, 2H) 8.06 (t, J=1.64 Hz, 1H)

8.44 (d, J=2.53 Hz, 1H) 12.47 (s, 1H). [M+H] calc'd for $C_{20}H_{18}ClN_2O_3S$ 401; found, 401.2.

Compound 219

(3-chloro-5-(3-(ethylsulfonyl)phenyl)-9H-pyrido[2,3-b]indol-8-ol

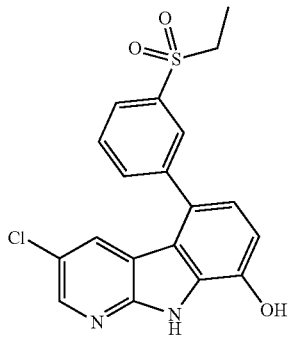

The title compound was prepared from Compound 218 by using an analogous procedure to that outlined in the preparation of Compound 158. $^1$H NMR (400 MHz, Methanol-$d_4$) δ 8.35 (s, 1H) 8.15 (m, 1H) 8.07 (m, 1H) 7.97 (m, 1H) 7.88 (t, J=8.0 Hz, 1 H) 7.66 (s, 1H) 7.23 (d, J=8.36 Hz, 1H) 7.16 (d, J=8.36 Hz, 1H) 4.44 (t, J=5.8 Hz, 2 H) 3.72 (t, J=8.0 Hz, 2H) 3.43 (q, J=7.32 Hz, 2H) 3.03 (s, 6H) 2.41 (m, 2H) 1.34 (t, J=7.32 Hz, 3H). [M+H] calc'd for $C_{24}H_{27}ClN_3O_3S$, 472; found, 472.

Compound 220

3-(3-chloro-5-(3-(ethylsulfonyl)phenyl)-9H-pyrido[2,3-b]indol-8-yloxy)-N,N-dimethylpropan-1-amine

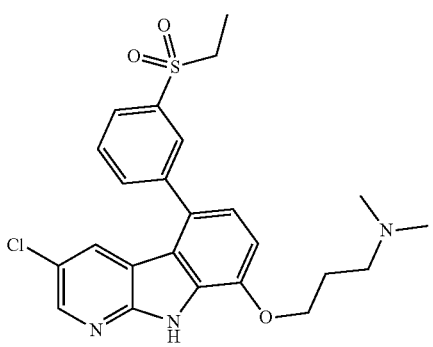

The title compound was prepared from Compound 219 by using an analogous procedure to that outlined in the preparation of Compound 206. Compound 220 was isolated as yellow solid. $^1$H NMR (400 MHz, Methanol-$d_4$) δ 8.35 (s, 1H) 8.15 (m, 1H) 8.07 (m, 1H) 7.97 (m, 1H) 7.88 (t, J=8.0 Hz, 1H) 7.66 (s, 1H) 7.23 (d, J=8.36 Hz, 1H) 7.16 (d, J=8.36 Hz, 1H) 4.44 (t, J=5.8 Hz, 2H) 3.72 (t, J=8.0 Hz, 2H) 3.43 (q, J=7.32 Hz, 2H) 3.03 (s, 6H) 2.41 (m, 2H) 1.34 (t, J=7.32 Hz, 3H). [M+H] calc'd for $C_{24}H_{27}ClN_3O_3S$, 472; found, 472.

The trifluoroacetic acid salt of compound 220 was prepared by using an analogous procedure outlined in the preparation of the TFA salt of compound 88.

Compound 221

2-(3-chloro-5-(3-(ethylsulfonyl)phenyl)-9H-pyrido[2,3-b]indol-8-yloxy)-N,N-diethylethanamine The title compound was prepared from Compound 219 by using an analogous procedure to that outlined in the preparation of Compound 206. $^1$H NMR (400 MHz, Methanol-$d_4$) δ 8.37 (s, 1H) 8.15 (m, 1H) 8.07 (m, 1H) 7.97 (m, 1H) 7.88 (t, J=8.0 Hz, 1H) 7.67 (s, 1H) 7.30 (d, J=8.08 Hz, 1H) 7.20 (d, J=8.08 Hz, 1H) 4.67 (t, J=4.0 Hz, 2 H) 3.80 (t, J=4.0 Hz, 2H) 3.51 (m, 4H) 3.41 (q, J=8.0 Hz, 2H) 1.45 (t, J=7.36 Hz, 6H) 1.33 (t, J=8.0 Hz, 3H). [M+H] calc'd for $C_{25}H_{29}ClN_3O_3S$, 486; found, 486.

Compound 222

2-(3-chloro-5-(3-(ethylsulfonyl)phenyl)-9H-pyrido[2,3-b]indol-8-yloxy)-N,N-dimethylethanamine The title compound was prepared from Compound 219 and 2-bromo-N,N'-dimethylethanamine using an analogous procedure to that outlined in the preparation of Compound 206. Compound 222 was isolated as light yellow solid. $^1$H NMR (400 MHz, Methanol-$d_4$) δ 8.40 (s, 1H) 8.14 (m, 1H) 8.10 (m, 1H) 8.00 (m, 1H) 7.89 (t, J=8.0 Hz, 1H) 7.69 (s, 1H) 7.28 (d, J=8.08 Hz, 1H) 7.20 (d, J=8.08 Hz, 1H) 4.68 (t, J=5.0 Hz, 2H) 3.80 (t, J=5.0 Hz, 2H) 3.43 (q, J=7.32 Hz, 2H) 3.13 (s, 6H) 1.33 (t, J=7.32 Hz, 3H). [M+H] calc'd for $C_{23}H_{25}ClN_3O_3S$, 458; found, 458.

The trifluoroacetic acid salt of compound 222 was prepared by using an analogous procedure outlined in the preparation of the TFA salt of compound 88.

Compound 223

3-chloro-5-(3-(ethylsulfonyl)phenyl)-8-(2-(pyrrolidin-1-yl)ethoxy)-9H-pyrido[2,3-b]indole

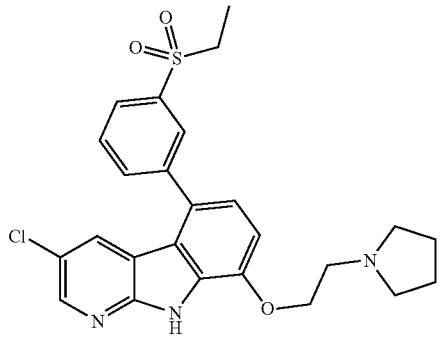

The title compound was prepared from Compound 219 by using an analogous procedure to that outlined in the preparation of Compound 206. $^1$H NMR (400 MHz, Methanol-$d_4$) δ 8.40 (s, 1H) 8.13 (m, 1H) 8.10 (m, 1H) 7.98 (m, 1H) 7.90 (t, J=8.0 Hz, 1H) 7.89 (s, 1H) 7.28 (d, J=8.32 Hz, 1H) 7.20 (d, J=8.32 Hz, 1H) 4.65 (t, J=5.0 Hz, 2H) 3.87 (t, J=5.0 Hz, 2H) 3.40 (q, J=7.32 Hz, 2H) 3.25 (br, 4H) 2.25 (br, 4H) 1.33 (t, J=7.32 Hz, 3H). [M+H] calc'd for $C_{25}H_{27}ClN_3O_3S$, 484; found, 484.

Compound 224

3-chloro-5-(3-(ethylsulfonyl)phenyl)-8-(2-(4-methylpiperazin-1-yl)ethoxy)-9H-pyrido[2,3-b]indole

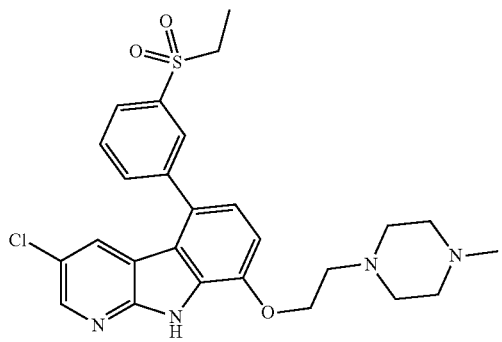

The title compound was prepared from Compound 219 by using an analogous procedure to that outlined in the preparation of Compound 206. $^1$H NMR (400 MHz, DMSO-$d_6$) δ 8.47 (s, 1H) 7.90 (m, 3H) 7.88 (t, J=8.0 Hz, 1H) 7.64 (s, 1H) 7.28 (d, J=8.08 Hz, 1H) 7.20 (d, J=8.08 Hz, 1H) 4.46 (t, J=5.0 Hz, 2H) 3.75-3.0 (m, br, 10H) 2.80 (s, 3H) 1.18 (t, J=7.6 Hz, 3H). [M+H] calc'd for $C_{26}H_{30}ClN_4O_3S$, 513; found, 513.

Compound 225

2-(3-chloro-5-(3-(ethylsulfonyl)phenyl)-9H-pyrido[2,3-b]indol-8-yloxy)ethanol

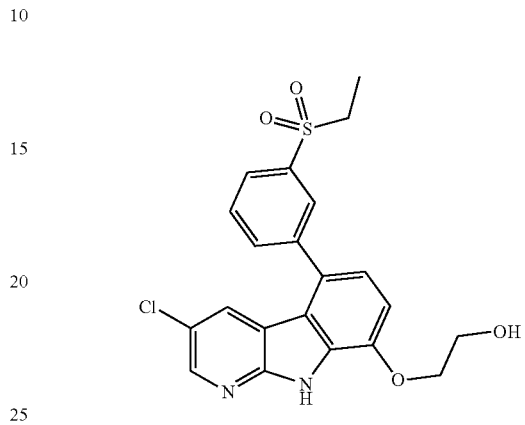

The title compound was prepared from Compound 219 by using an analogous procedure to that outlined in the preparation of Compound 216. $^1$H NMR (400 MHz, Methanol-$d_4$) δ 8.39 (s, 1H) 8.14 (m, 1H) 8.06 (m, 1H) 8.00 (m, 1H) 7.87 (t, J=8.0 Hz, 1H) 7.71 (d, J=4.0 Hz, 1H) 7.21 (d, J=8.0 Hz, 1H) 7.16 (d, J=8.0 Hz, 1H) 4.36 (t, J=4 Hz, 2H) 4.07 (t, J=4 Hz, 2H) 3.30 (q, J=7.5 Hz, 2H) 1.31 (t, J=7.5 Hz, 3H). [M+H] calc'd for $C_{21}H_{20}ClN_2O_4S$, 431; found, 431.

Compound 226

(S)-2-(5-(3-(ethylsulfonyl)phenyl)-3-methyl-9H-pyrido[2,3-b]indol-8-yloxy)ethyl 2-aminopropanoate

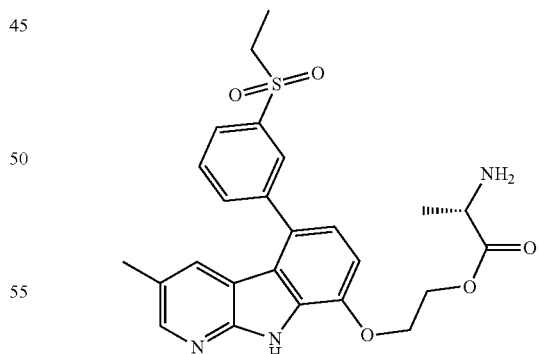

The title compound was prepared from Compound 216 by using an analogous procedure to that outlined in the preparation of Compound 65. $^1$H NMR (400 MHz, DMSO) δ ppm 1.18 (t, J=7.33 Hz, 3H) 1.40 (d, J=7.33 Hz, 3H) 2.27 (s, 3H) 3.42 (q, J=7.33 Hz, 2H) 4.20 (d, J=5.05 Hz, 1H) 4.53 (t, J=4.42 Hz, 2H) 4.58-4.69 (m, 2H) 7.12 (d, J=8.08 Hz, 1H) 7.23 (d, J=8.08 Hz, 1H) 7.55 (s, 1H) 7.87 (t, J=7.83 Hz, 1H)

8.00 (dd, J=12.63, 7.58 Hz, 2H) 8.08 (s, 1H) 8.29 (s, 1H) 8.33 (br. s., 2H) 11.95 (s, 1H) [M+H] calc'd for $C_{25}H_{27}N_3O_5S$, 482; found, 482.

Compound 227

(S)-3-(5-(3-(ethylsulfonyl)phenyl)-3-methyl-9H-pyrido[2,3-b]indol-8-yloxy)propyl 2-aminopropanoate

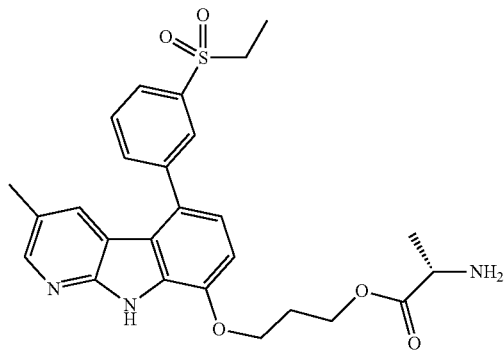

The title compound was prepared from Compound 217 by using an analogous procedure to that outlined in the preparation of Compound 65. $^1$H NMR (400 MHz, DMSO-d$_6$) δ ppm 1.17 (t, J=7.33 Hz, 3H) 1.39 (d, J=7.07 Hz, 3H) 2.20-2.24 (m, 2H) 2.26 (s, 3H) 4.14 (m, 1H) 4.32 (t, J=5.68 Hz, 2H) 4.54-4.58 (m., 2H) 7.08-7.11 (m, 1 H) 7.12-7.16 (m, 1H) 7.55 (s, 1H) 7.85 (t, J=7.83 Hz, 1H) 7.98 (dd, J=10.23, 8.46 Hz, 2H) 8.06 (s, 1H) 8.28 (br. s., 3H) 12.07 (s, 1H); [M+H] calc'd for $C_{26}H_{30}N_3O_5S$, 496.2; found, 496.4.

Compound 228

5-(3-(cyclopropylcarbamoyl)phenyl)-3,8-dimethyl-N-(1-methylpiperidin-4-yl)-9H-pyrido[2,3-b]indole-7-carboxamide

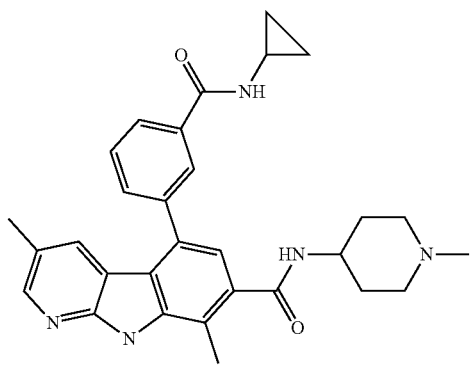

The title compound was synthesized from 5-chloro-3,8-dimethyl-N-(1-methylpiperidin-4-yl)-9H-pyrido[2,3-b]indole-7-carboxamide and 3-(cyclopropylcarbamoyl)phenylboronic acid using an analogous procedure to that described in the preparation of compound 88. $^1$H NMR (400 MHz, DMSO-d$_6$) δ ppm 0.77-0.82 (m, 4H) 1.53 (qd, J=11.66, 3.41 Hz, 2H) 1.79-1.82 (m, 3H) 1.95 (t, J=10.86 Hz, 2H) 2.15 (s, 3H) 2.27 (s, 3H) 2.59 (s, 3H) 2.74 (d, J=11.12 Hz, 2H) 3.75 (m, 1H) 6.98 (s, 1 H) 7.27 (d, J=7.58 Hz, 1H) 7.49 (t, J=7.96 Hz, 1H) 7.69 (d, J=2.02 Hz, 2H) 7.91 (s, 1H) 8.25-8.30 (m, 2H) 10.37 (s, 1H) 11.92 (br. s., 1H); [M+H] calc'd for $C_{30}H_{33}N_5O_2$, 496.3; found, 496.4.

Compound 229

(R)-8-((2,2-dimethyl-1,3-dioxolan-4-yl)methoxy-5-(3-ethylsulfonyl)phenyl)-3-methyl-9H-pyrido[2,3-b]indole

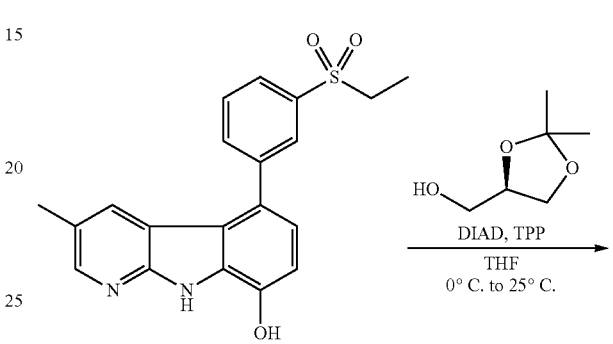

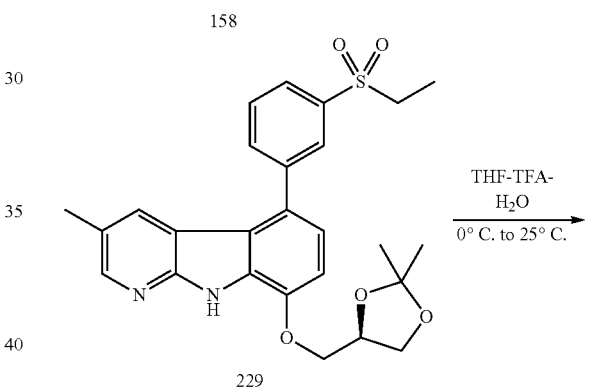

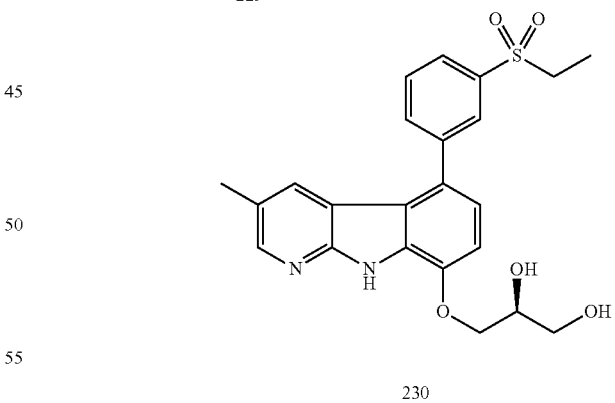

To a stirred solution of Compound 158 (160 mg, 0.44 mmol) in anhydrous THF (2.5 mL) were sequentially added (R)-(2,2-dimethyl-1,3-dioxolan-4-yl)methanol (82 μL, 0.66 mmol) and triphenyl phosphine (173 mg, 0.66 mmol). The reaction mixture was cooled to 0° C., and to it diisopropyl-azodicarboxylate (128 μL, 0.66 mmol) was added in drop wise manner. After the addition was over, stirring continued for another 0.5 h at 0° C. and then for 12 h at room temperature. Solvents were removed in vacuum and the residue was purified by silica gel column chromatography, providing the title compound (148 mg, 70%). [M+H] calc'd for C$_{26}$H$_{28}$N$_2$O$_5$S, 481.1; found, 481.3.

Compound 230

(S)-3-(5-(3-(ethylsulfonyl)phenyl)-3-methyl-9H-pyrido[2,3-b]indol-8-yloxy)propane-1,2-diol

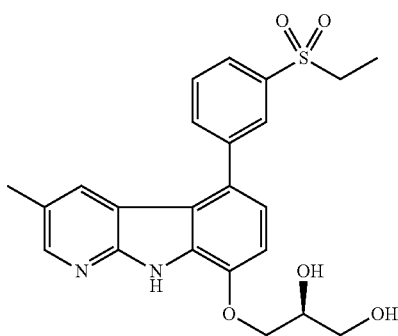

Compound 229 (120 mg, 0.25 mmol) was taken in a mixture of THF-TFA-H$_2$O (3:1:1, 5 mL) and stirred for 6 h at room temperature. The reaction mixture was diluted with methylene chloride and washed with aqueous NaHCO$_3$ and brine. The organic extract was dried over Na$_2$SO$_4$, concentrated and purified to afford the title compound. $^1$H NMR (400 MHz, DMSO-d$_6$) δ ppm 1.17 (t, J=7.33 Hz, 3H) 2.27 (s, 3H) 3.41 (q, J=7.41 Hz, 2 H) 3.60 (t, J=5.81 Hz, 2H) 3.96 (m, 1H) 4.11 (dd, J=9.60, 6.06 Hz, 1H) 4.27 (dd, J=9.60, 4.29 Hz, 1H) 4.73 (t, J=5.68 Hz, 1H) 4.99 (d, J=5.31 Hz, 1H) 7.07-7.15 (m, 2 H) 7.57 (d, J=1.77 Hz, 1H) 7.85 (t, J=7.71 Hz, 1H) 7.97 (t, J=1.64 Hz, 1H) 7.99 (m, 1 H) 8.09 (t, J=1.64 Hz, 1H) 8.28 (d, J=2.02 Hz, 1H) 11.93 (s, 1H); [M+H] calc'd for C$_{23}$H$_{25}$N$_2$O$_5$S, 441.1; found, 441.3.

Compound 231

(R)-3-(5-(3-(ethylsulfonyl)phenyl)-3-methyl-9H-pyrido[2,3-b]indol-8-yloxy)propane-1,2-diol

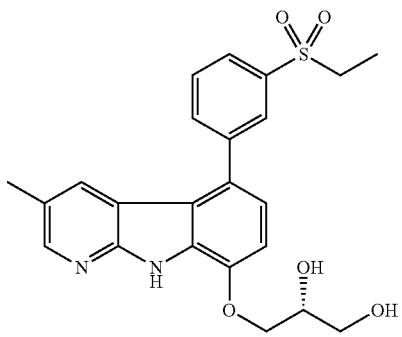

The title compound was prepared from Compound 158 using an analogous procedure to the procedure described for the preparation of Compound 230. $^1$H NMR (400 MHz, DMSO-d$_6$) δ ppm 1.17 (t, J=7.33 Hz, 3H) 2.27 (s, 3H) 3.41 (q, J=7.41 Hz, 2H) 3.60 (t, J=5.81 Hz, 2H) 3.96 (m, 1H) 4.11 (dd, J=9.60, 6.06 Hz, 1H) 4.27 (dd, J=9.60, 4.29 Hz, 1H) 4.73 (t, J=5.68 Hz, 1H) 4.99 (d, J=5.31 Hz, 1H) 7.07-7.15 (m, 2H) 7.57 (d, J=1.77 Hz, 1H) 7.85 (t, J=7.71 Hz, 1H) 7.97 (t, J=1.64 Hz, 1H) 7.99 (m, 1H) 8.09 (t, J=1.64 Hz, 1H) 8.28 (d, J=2.02 Hz, 1H) 11.93 (s, 1H); [M+H] calc'd for C$_{23}$H$_{25}$N$_2$O—$_5$S, 441.1; found, 441.4.

Compound 232

(R)-1-(dimethylamino)-3-(5-(3-(ethylsulfonyl)phenyl)-3-methyl-9H-pyrido[2,3-b]indol-8-yloxy)propan-2-ol

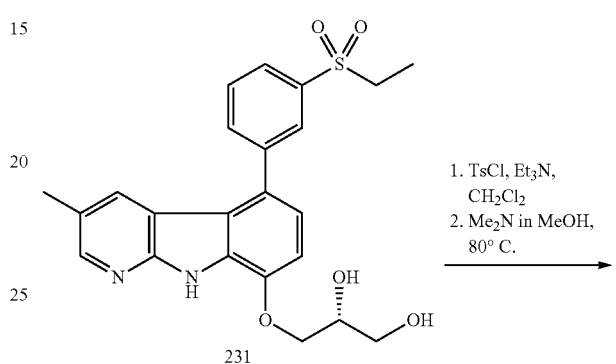

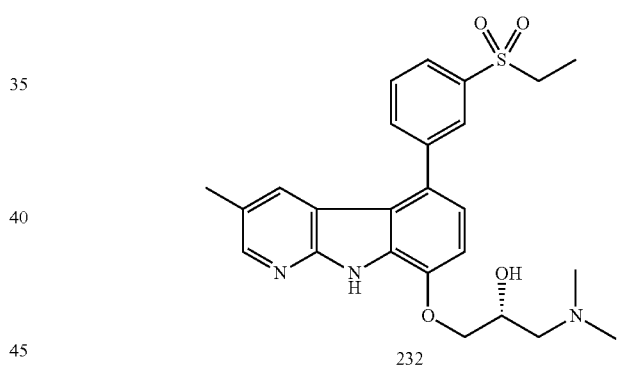

To a solution of Compound 231 (75 mg, 0.17 mmol) in a mixture of DMF and CH$_2$Cl$_2$ (5 mL, 2:3) were sequentially added triethyl amine (5 µL, 0.34 mmol) and p-toluenesulfonyl chloride (50 mg, 0.26 mmol) at 0° C. Slowly the reaction temperature was raised to room temperature and stirred for 12 h. The reaction was diluted with CH$_2$Cl$_2$ and the organic layer was successively washed with NH$_4$Cl and brine solution. Solvents were dried over Na$_2$SO$_4$ and removed under vacuum. The residual mass was directly used for next step.

The crude mass was taken in 1 mL of MeOH and treated with 0.5 mL of dimethyl amine in a sealed tube, at 80° C. for 6 h. Solvents were removed and directly subjected to preparative HPLC purification to give the title compound (22 mg, 27% for two steps). $^1$H NMR (400 MHz, DMSO-d$_6$) δ ppm 1.17 (t, J=7.45 Hz, 3H) 2.26 (s, 3H) 2.32 (s, 6H) 2.66-2.73 (m, 2H) 4.05-4.16 (m, 2H) 4.25 (dd, J=9.09, 3.28 Hz, 1H) 7.07-7.16 (m, 2H) 7.57 (s, 1H) 7.85 (t, J=7.71 Hz, 1H) 7.98 (dt, J=7.77, 1.80 Hz, 2H) 8.09 (s, 1H) 8.29 (d, J=1.77 Hz, 1H) 12.02 (s, 1H); [M+H] calc'd for C$_{25}$H$_{30}$N$_3$O$_4$S, 468.2; found, 468.3.

Compound 233

(R)-1-(5-(3-(ethylsulfonyl)phenyl)-3-methyl-9H-pyrido[2,3-b]indol-8-yloxy)propan-2-ol

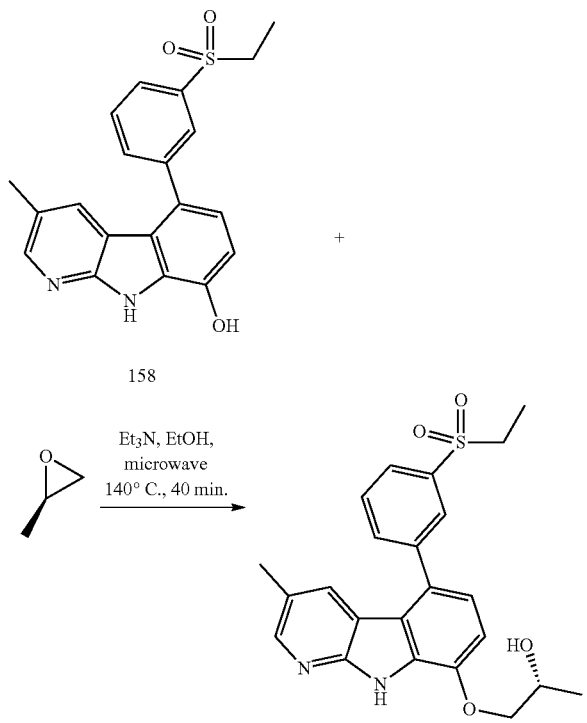

A 5 mL microwave vial was charged with Compound 158 (200 mg, 0.545 mmol), (R)-2-methyloxirane (191 μL, 2.72 mmol), triethyl amine (8 μL, 0.054 mmol) and 2 mL of EtOH. The reaction mixture was heated at 140° C. for 40 min. in microwave. Solvents were removed in vacuum and the residue was purified by preparative HPLC to yield the title compound (46 mg, 20%). $^1$H NMR (400 MHz, DMSO-$d_6$) δ ppm 1.17 (t, J=7.33 Hz, 3H) 1.25 (d, J=6.06 Hz, 3H) 2.27 (s, 3H) 3.41 (q, J=7.33 Hz, 2H) 3.94 (m, 1 H) 4.09-4.16 (m, 2H) 4.97 (d, J=4.04 Hz, 1H) 7.07-7.14 (m, 2H) 7.57 (s, 1H) 7.85 (t, J=7.71 Hz, 1H) 7.96-8.00 (m, 2H) 8.09 (s, 1H) 8.28 (d, J=1.52 Hz, 1H) 11.94 (s, 1H); [M+H] calc'd for $C_{23}H_{25}N_2O_4S$, 425.2; found, 425.3.

Compound 234

(S)-1-(5-(3-(ethylsulfonyl)phenyl)-3-methyl-9H-pyrido[2,3-b]indol-8-yloxy)propan-2-ol

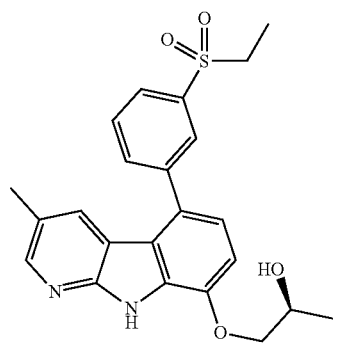

The title compound was prepared from Compound 158 using an analogous procedure as described for the preparation of Compound 233. $^1$H NMR (400 MHz, DMSO-$d_6$) δ ppm 1.17 (t, J=7.33 Hz, 3H) 1.25 (d, J=6.06 Hz, 3H) 2.27 (s, 3H) 3.41 (q, J=7.33 Hz, 2H) 3.94 (m, 1H) 4.09-4.16 (m, 2H) 4.97 (d, J=4.04 Hz, 1H) 7.07-7.14 (m, 2H) 7.57 (s, 1H) 7.85 (t, J=7.71 Hz, 1H) 7.96-8.00 (m, 2H) 8.09 (s, 1H) 8.28 (d, J=1.52 Hz, 1H) 11.94 (s, 1H); [M+H] calc'd for $C_{23}H_{25}N_2O_4S$, 425.2; found, 425.3.

Compound 235

3-2(-bromo-5-methoxyphenyl)-2-fluoro-5-methyl-pyridine

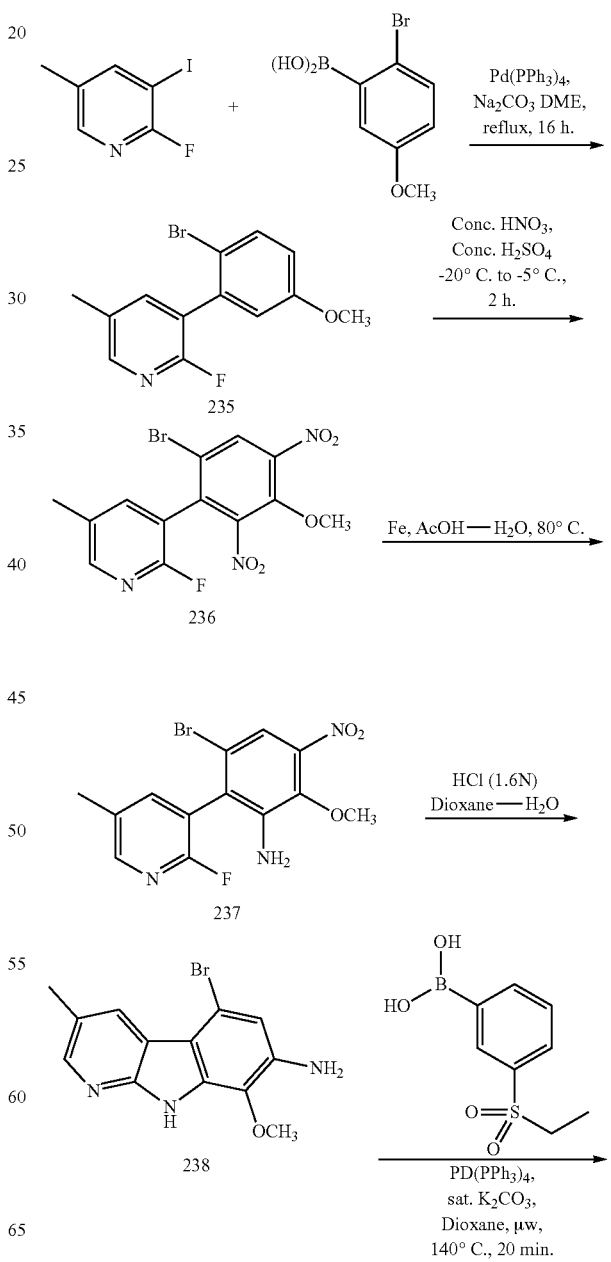

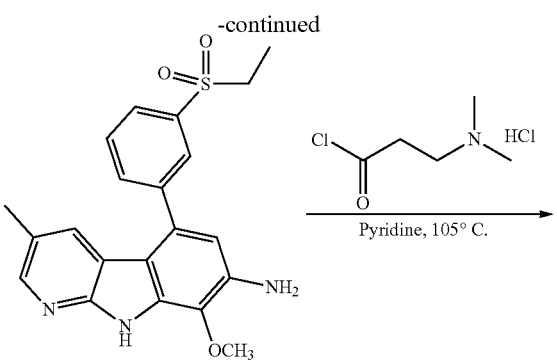

239

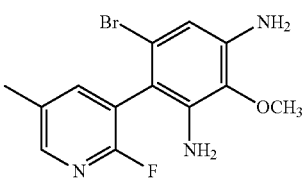

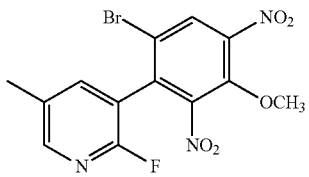

240

To a mixture of 2-fluoro-3-iodo-5-methylpyridine (4.65 g, 19.6 mmol) and Pd(PPh$_3$)$_4$ (2.26 g, 1.96 mmol) in DME (200 mL) were added a solution of 2-bromo-5-methoxyphenylboronic acid (4.99 g, 21.6 mmol) in EtOH (15 mL). To the above mixture was added an aqueous solution of Na$_2$CO$_3$ (3 M, 39.2 mL) and the mixture was heated under reflux for 16 h. The solution was filtered through a celite bed, concentrated and the remaining aqueous layer was extracted with ether, washed successively with water, 5% aqueous NaOH, 10% aqueous HCl, saturated aqueous NaHCO$_3$ and brine. Organic layer was dried (Na$_2$SO$_4$) and concentrated and purified by flash chromatography to yield the title compound (5.3 g, 91%). $^1$H NMR (400 MHz, DMSO-d$_6$) δ ppm 2.34 (s, 3H) 3.78 (s, 3H) 6.99 (dd, J=8.72, 3.16 Hz, 1H) 7.02-7.04 (m, 1H) 7.64 (d, J=8.84 Hz, 1H) 7.76 (dd, J=9.47, 1.89 Hz, 1H) 8.11 (s, 1H). [M+H] calc'd for C$_{13}$H$_{12}$BrFNO, 296.0; found 296.2.

Compound 236

3-(6-bromo-3-methoxy-2,4-dinitrophenyl)-2-fluoro-5-methylpyridine

Compound 235 (2.0 g, 6.75 mmol) was added to a mixture of conc. HNO$_3$ (90%) and conc. H$_2$SO$_4$ (95-98%) (20 mL, 2:3) at -20° C. Slowly the reaction was warmed to -5° C. and stirred for another 1.5 h. The crude mixture was poured into ice-water, solid precipitates out and collected by filtration, washed thoroughly with water and dried under vacuum to provide the title compound (2.08 g, 80%). $^1$H NMR (400 MHz, DMSO-d$_6$) δ ppm 2.34 (s, 3H) 3.97 (s, 3H) 7.87 (dd, J=9.22, 2.15 Hz, 1H) 8.27 (s, 1H) 8.78 (s, 1H). [M+H] calc'd for C$_{13}$H$_{10}$BrFN$_3$O$_5$, 385.97; found 386.2.

Compound 237

5-4-(2-fluoro-5-methylpyridine-3-yl)-methoxybenzene-1,3-diamine

To Compound 236 (1.02 g, 2.65 mmol) in AcOH—H$_2$O (8 mL, 3:1) at 80° C. was added iron powder (1.48 g, 26.5 mmol) and stirred for 2.0 h. Solvents were removed under vacuum and the residue was dissolved in CH$_2$Cl$_2$, and washed with aqueous NaHCO$_3$ and brine. The organic extracts were dried (Na$_2$SO$_4$) and concentrated and purified by flash chromatography to yield the title compound (830 mg, 96%). $^1$H NMR (400 MHz, DMSO-d$_6$) δ ppm 2.30 (s, 2H) 3.59 (s, 2H) 4.46 (s, 2H) 5.09 (s, 2H) 6.34 (s, 1H) 7.56 (dd, J=4.0, 12.0 Hz, 1H), 8.02 (s, 1H). [M+H] calc'd for C$_{13}$H$_{14}$BrFN$_3$O, 326.02; found 326.2.

Compound 238

5-bromo-8-methoxy-3-methyl-9H-pyrido[2,3-b]indol-7-amine

Compound 237 (5.0 g, 15.32 mmol) was taken into a mixture of dioxane-H$_2$O (100 mL, 1:4) and to it was added aqueous HCl (9.6 mL, 1.6 N in water). The reaction mixture was heated reflux for 6 h. Reaction was diluted with EtOAc and washed with aqueous NaHCO$_3$ and brine. The organic extracts were dried (Na$_2$SO$_4$) and concentrated and purified by flash chromatography to yield the title compound (4.2 g, 89%). $^1$H NMR (400 MHz, DMSO-d$_6$) δ ppm 2.41 (s, 3H) 3.77 (s, 3H) 5.36 (s, 2H) 6.81 (s, 1H) 8.12 (d, J=2.27 Hz, 1H)

8.33 (d, J=2.02 Hz, 1H) 11.65 (s, 1H); [M+H] calc'd for C$_{13}$H$_{13}$BrN$_3$O, 306.02; found, 306.2.

Compound 239

(5-(3-(ethylsulfonyl)phenyl)-8-methoxy-3-methyl-9H-pyrido[2,3-b]indol-7-amine

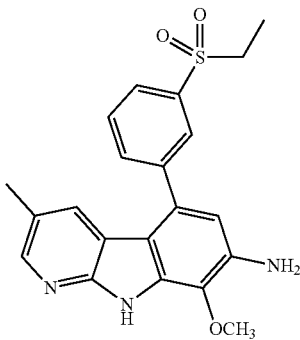

A 15 mL microwave vial was charged with Compound 238 (500 mg, 1.63 mmol), 3-(ethylsulfonyl)phenylboronic acid (419 mg, 1.96 mmol) and Pd(PPh$_3$)$_4$ (188 mg, 0.16 mmol). To the mixture was added dioxane (5 mL) and a saturated aqueous solution of K$_2$CO$_3$ (2.5 mL). The reaction mixture was heated at 140° C. for 20 min. in microwave. The reaction was diluted with EtOAc and washed with water and brine. The organic extracts were dried (Na$_2$SO$_4$) and concentrated and purified by flash chromatography to yield the title compound (528 mg, 82%). $^1$H NMR (400 MHz, DMSO-d$_6$) δ ppm 1.16 (t, J=7.33 Hz, 3H) 2.20 (s, 3H) 3.83 (s, 3H) 5.29 (s, 2H) 6.57 (s, 1H) 7.27 (d, J=2.24 Hz, 1 H) 7.83 (t, J=7.58 Hz, 1H) 7.94 (d, J=3.28 Hz, 1H) 7.98 (d, J=7.33 Hz, 1H) 8.02-8.05 (m, 2H) 11.59 (s., 1H); [M+H] calc'd for C$_{21}$H$_{21}$N$_3$O$_4$S, 396.2; found, 396.3.

Compound 240

3-(dimethylamino)-N-(5-(3-(ethylsulfonyl)phenyl)-8-methoxy-3-methyl-9H-pyrido[2,3-b]indol-7-yl)propanamide

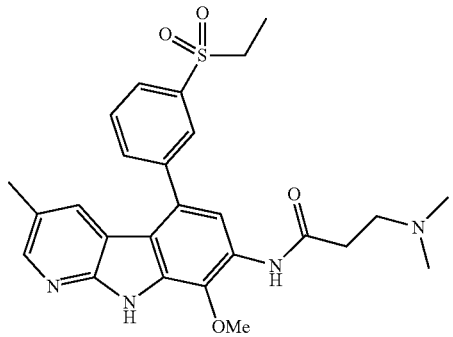

To a suspension of Compound 239 (150 mg, 0.38 mmol) in pyridine (2.0 mL) was added 3-(dimethylamino)propanoyl chloride (71 mg, 0.38 mmol) and the reaction mixture was heated at 105° C. for 5 h. and quenched with aqueous NH$_4$Cl solution. Organic matter was extracted with CH$_2$Cl$_2$ (with 10% EtOH) and washed with brine. The organic extracts were dried (Na$_2$SO$_4$) and concentrated and purified by preparative HPLC to yield the title compound (103 mg, 55%). $^1$H NMR (400 MHz, DMSO-d$_6$) δ ppm 1.16 (t, J=7.33 Hz, 3H) 2.24 (s, 3H) 2.33 (s, 6H) 2.56 (t, J=5.81 Hz, 2H) 2.62 (t, J=5.31 Hz, 2H) 3.41 (q, J=7.33 Hz, 2H) 3.93 (s, 3H) 7.41 (d, J=1.26 Hz, 1H) 7.87 (t, J=7.71 Hz, 1H) 7.93-7.97 (m, 1H) 8.03 (d, J=8.84 Hz, 1H) 8.06 (s, 2H) 8.22 (d, J=2.02 Hz, 1H) 10.99 (br. s., 1H) 12.07 (s, 1H); [M+H] calc'd for C$_{26}$H$_{31}$N$_4$O$_4$S, 495.2; found, 495.4.

Compound 241

N-(3-(7-amino-8-methoxy-3-methyl-9H-pyrido[2,3-b]indol-5-yl)phenyl)-cyclopropanecarboxamide

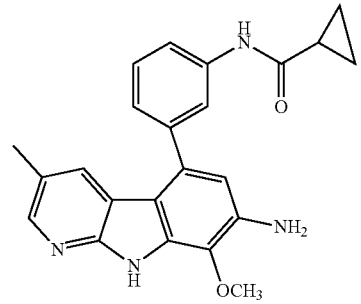

The title compound was prepared from Compound 238 by using an analogous procedure to that outlined in the preparation of Compound 239. $^1$H NMR (400 MHz, DMSO-d$_6$) δ ppm 0.77-0.81 (m, 4H) 1.79 (p, J=6.06 Hz, 1H) 2.20 (s, 3H) 3.82 (s, 3H) 5.21 (s, 2H) 6.48 (s, 1H) 7.18 (d, J=7.58 Hz, 1H) 7.45-7.41 (m, 2H) 7.63 (d, J=8.34 Hz, 1H) 7.83 (s, 1H) 8.00 (s, 1H) 10.31 (s, 1H) 11.47 (s, 1H); [M+H] calc'd for C$_{23}$H$_{22}$N$_4$O$_2$, 387.17; found, 387.13.

Compound 242

N-(5-(3-(ethylsulfonyl)phenyl)-8-methoxy-3-methyl-9H-pyrido[2,3-b]indol-7-yl)-cyclopropanecarboxamide

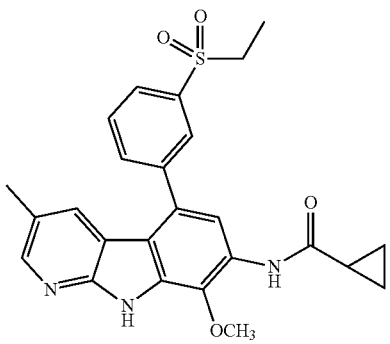

The title compound was prepared from Compound 239 by using an analogous procedure to that outlined in the preparation of Compound 240. $^1$H NMR (400 MHz, DMSO-d$_6$) δ ppm 0.82 (br. s., 4H) 1.16 (t, J=7.33 Hz, 3H) 2.17 (m., 1H) 2.25 (s, 3H) 3.95 (s, 3H) 7.44 (br. s., 1H) 7.78 (br. s., 1H) 7.87

(d, J=7.58 Hz, 1H) 7.96 (d, J=3.28 Hz, 1H) 8.01 (d, J=7.33 Hz, 1H) 8.07 (br. s., 1H) 8.23 (br. s., 1H) 9.88 (br. s., 1H) 12.07 (br. s., 1H); [M+H] calc'd for C$_{25}$H$_{26}$N$_3$O$_4$S, 464.2; found, 464.3.

Compound 243

1-acetyl-N-(5-(3-(ethylsulfonyl)phenyl)-8-methoxy-3-methyl-9H-pyrido[2,3-b]indol-7-yl)piperidine-4-carboxamide

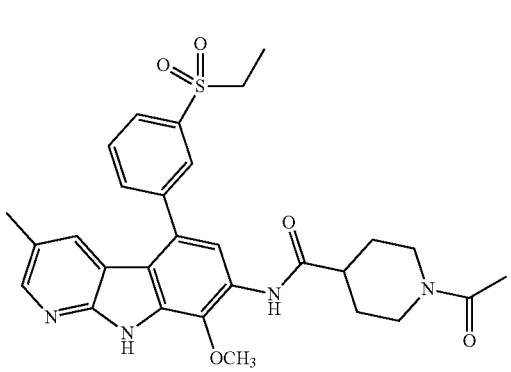

The title compound was prepared from Compound 239 by using an analogous procedure to that outlined in the preparation of Compound 240. $^1$H NMR (400 MHz, DMSO-d$_6$) δ ppm 1.16 (t, J=7.33 Hz, 3H) 1.45 (qd, J=12.25, 3.92 Hz, 1H) 1.60 (qd, J=12.08, 3.92 Hz, 1H) 1.86 (t, J=12.13 Hz, 1H) 1.85 (d, J=1.77 Hz, 1H) 2.01 (s, 3H) 2.25 (s, 3H) 2.57-2.65 (m, 1H) 2.87 (m, 1H) 3.08 (t, J=13.89 Hz, 1H) 3.41 (q, J=7.33 Hz, 2H) 3.88 (d, J=13.89 Hz, 1H) 3.93 (s, 3H) 4.42 (d, J=13.39 Hz, 1H) 7.44 (d, J=1.26 Hz, 1H) 7.70 (s, 1H) 7.87 (t, J=7.71 Hz, 1H) 7.96 (d, J=7.83 Hz, 1H) 8.02 (d, J=7.83 Hz, 1H) 8.06 (d, J=1.52 Hz, 1H) 8.24 (d, J=1.77 Hz, 1H) 9.62 (s, 1H) 12.09 (s, 1H); [M+H] calc'd for C$_{29}$H$_{33}$N$_4$O$_5$S, 549.2; found, 549.4.3.

Compound 244

3-(7-amino-8-methoxy-3-methyl-9H-pyrido[2,3-b]indol-5-yl)-N-cyclopropylbenzamide

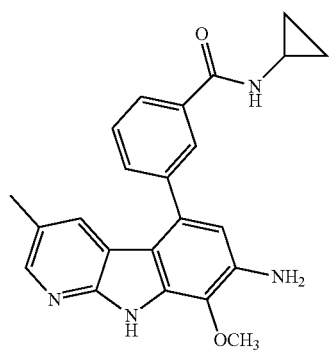

The title compound was prepared from Compound 238 by using an analogous procedure to that outlined in the preparation of Compound 239. $^1$H NMR (400 MHz, DMSO-d$_6$) δ ppm 0.77-0.80 (m, 4H) 1.79 (m, 1H) 2.20 (s, 3H) 3.82 (s, 3H) 5.21 (s, 2H) 6.48 (s, 1H) 7.18 (d, J=7.8 Hz, 1H), 7.41-7.45 (m, 2H) 7.62 (d, J=8.0 Hz, 1H) 7.83 (br. s, 1H) 8.00 (br. s, 1H) 10.31 (s, 1H) 11.47 (s, 1H); [M+H] calc'd for C$_{23}$H$_{22}$N$_4$O$_2$, 387.2; found, 387.4.

Compound 245

3-(7-(cyclopropanecarboxamido)-8-methoxy-3-methyl-9H-pyrido[2,3-b]indol-5-yl)-N-cyclopropylbenzamide

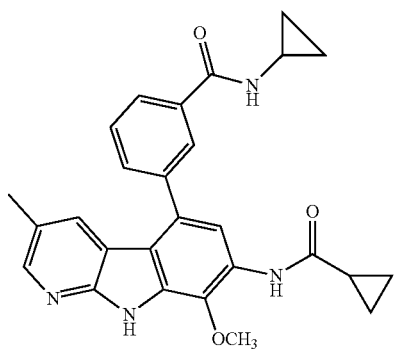

The title compound was prepared from Compound 244 by using an analogous procedure to that outlined in the preparation of Compound 240. $^1$H NMR (400 MHz, DMSO-d$_6$) δ ppm 0.53-0.57 (m, 2H) 0.68-0.71 (m, 2H) 0.81 (br. m, 4H) 2.17 (m, 1H) 2.23 (s, 3H) 2.87 (m, 1H) 3.94 (s, 3H) 7.40 (s, 1H) 7.63 (t, J=7.71 Hz, 1H) 7.72-7.71 (m, 2H) 7.94 (d, J=7.58 Hz, 1H) 8.01 (s, 1H) 8.21 (d, J=1.77 Hz, 1H) 8.54 (d, J=4.04 Hz, 1H) 9.84 (s, 1H) 12.00 (s, 1H); [M+H] calc'd for C$_{27}$H$_{27}$N$_4$O$_3$, 455.2; found, 455.4.

Compound 246

7-chloro-5-(3-(ethylsulfonyl)phenyl)-8-methoxy-3-methyl-9H-pyrido[2,3-b]indole

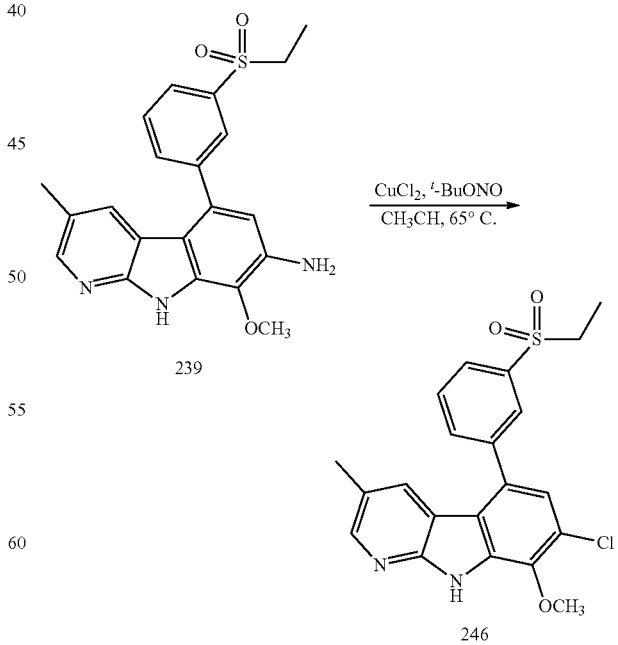

To a suspension of compound 239 (19.0 mg, 0.05 mmol) in CH$_3$CN (1 mL) was taken CuCl$_2$ (9.7 mg, 0.072 mmol) and $^t$-

BuONO (12.6 mL, 0.096 mmol). The reaction mixture was heated at 65° C. for 30 min. and quenched with aqueous NH₄Cl solution. Organic matter was extracted with EtOAc and washed with brine. The organic extracts were dried (Na₂SO₄) and concentrated and purified by preparative HPLC to yield the title compound (4.2 mg, 21%). ¹H NMR (400 MHz, Acetone) δ ppm 1.16 (t, J=7.33 Hz, 3H) 2.26 (s, 3H) 4.00 (s, 3H) 7.24 (s, 1H) 7.45 (s, 1H) 7.88 (t, J=7.71 Hz, 1H) 8.01 (dt, J=1.26, 8.02 Hz, 2H) 8.11 (s, 1H) 8.31 (s, 1H) 12.38 (s, 1H); [M+H] calc'd for $C_{21}H_{20}ClN_2O_3$, 415.1; found, 415.3.

Compound 247

7-chloro-5-(3-(ethylsulfonyl)phenyl)-3-methyl-9H-pyrido[2,3-b]indol-8-ol

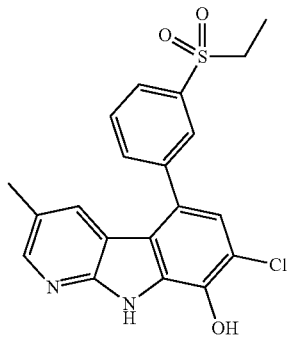

The title compound was prepared from Compound 246 by using an analogous procedure to that outlined in the preparation of Compound 158. ¹H NMR (400 MHz, DMSO-d₆) δ ppm 1.16 (t, J=7.33 Hz, 3H) 2.25 (s, 3H) 3.41 (q, J=7.58 Hz, 2H) 7.23 (s, 1 H) 7.46 (s, 1H) 7.87 (t, J=7.71 Hz, 1H) 8.03 (t, J=7.20 Hz, 2H) 8.11 (s, 1H) 8.31 (s, 1 H) 12.27 (br. s., 1H); [M+H] calc'd for $C_{20}H_{17}ClN_2O_3S$, 401.1; found, 401.3.

Compound 248

3-(7-chloro-5-(3-(ethylsulfonyl)phenyl)-3-methyl-9H-pyrido[2,3-b]indol-8-yloxy)propan-1-ol

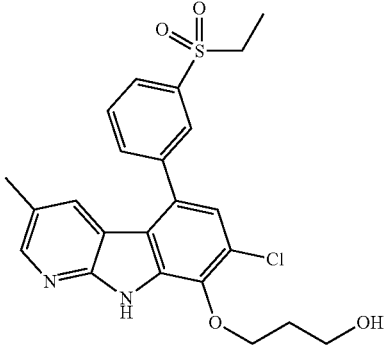

The title compound was synthesized from Compound 247 and 3-bromopropan-1-ol using an analogous procedure to that outlined in the preparation of Compound 206. ¹H NMR (400 MHz, DMSO-d₆) δ ppm 1.16 (t, J=7.33 Hz, 3H) 1.99- 2.06 (m, 2H) 2.25 (s, 3H) 3.41 (q, J=7.58 Hz, 2H) 3.71 (br. s., 2H) 4.26 (t, J=6.44 Hz, 2H) 4.81 (br. s., 1 H) 7.23 (s, 1H) 7.46 (s, 1H) 7.87 (t, J=7.71 Hz, 1H) 8.03 (t, J=7.20 Hz, 2H) 8.11 (s, 1 H) 8.31 (s, 1H) 12.27 (br. s., 1H); [M+H] calc'd for $C_{23}H_{24}ClN_2O_4S$, 459.1; found, 459.3.

Compound 249 tert-butyl 5-bromo-7-(tert-butoxycarbonylamino)-8-methoxy-3-methyl-9H-pyrido[2,3-b]indole-9-carboxylate

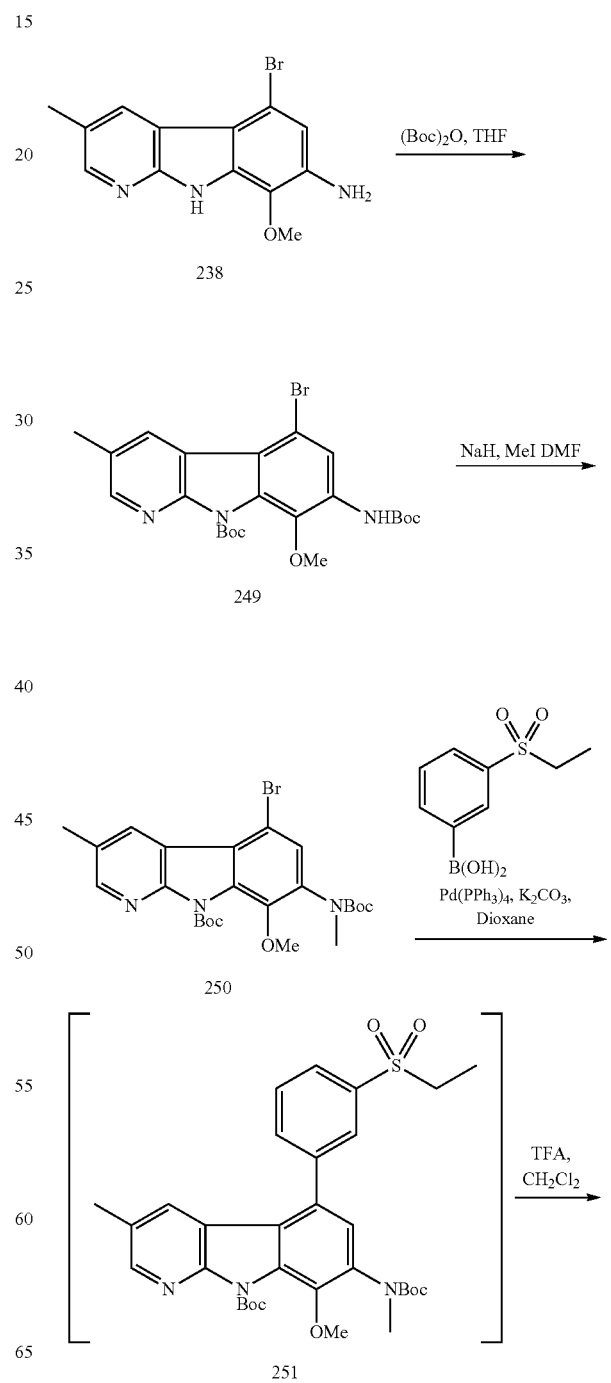

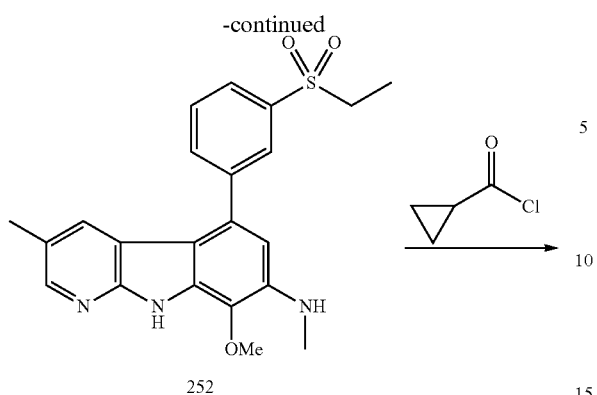

252

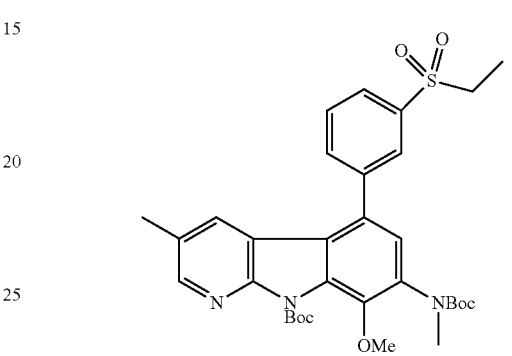

253

To a solution of Compound 238 (660 mg, 2.15 mmol) in a mixture of CH$_2$Cl$_2$-THF (4 mL, 1:1) was added (Boc)$_2$O (1.24 mL, 5.38 mmol) and the mixture was heated in a sealed tube for 24 h at a temperature of 50° C. Solvents were removed under vacuum and the crude residue was purified by flash chromatography to provide Compound 249 (762 mg, 70%). $^1$H NMR (400 MHz, DMSO-d$_6$) δ ppm 1.49 (s, 9H) 1.62 (s, 9H) 2.48 (s, 3H) 3.74 (s, 3H) 7.91 (s, 1H) 3.74 (s, 3H) 8.38 ((dd, J=1.5, 4.0 Hz, 1H), 8.62 ((dd, J=1.5, 4.0 Hz, 1H), 8.99 (s, 1H). [M+H] calc'd for C$_{23}$H$_{29}$BrN$_3$O$_5$, 506.12; found 506.3.

Compound 250 tert-butyl 5-bromo-7-(tert-butoxycarbonyl(methyl) amino)-8-methoxy-3-methyl-9H-pyrido[2,3-b]indole-9-carboxylate

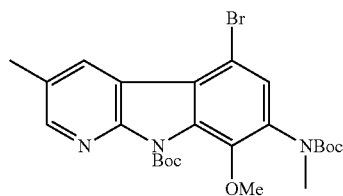

To a solution of Compound 249 (610 mg, 1.2 mmol) in dry DMF (3 mL) was added NaH (60 mg, 1.51 mmol) at 0° C. and the mixture was stirred for 20 min. To this ice cold reaction mixture was added MeI (0.72 mL, 1.44 mmol, 2 M solution) and stirred for another 30 min. at 0° C. Slowly the temperature was raised to room temperature and stirred for an additional hour. Reaction was quenched with water and extracted with ether, washed with brine, dried over Na$_2$SO$_4$ and finally purified flash chromatography to furnish Compound 250 (468 mg, 75%). $^1$H NMR (400 MHz, DMSO-d$_6$) δ ppm 1.35 (s, 9H) 1.63 (s, 9H) 3.20 (s, 3H) 3.77 (s, 3H) 7.52 (s, 1H) 8.44 (s, 1H) 8.68 (s, 1H). [M+H] calc'd for C$_{24}$H$_{31}$BrN$_3$O$_5$, 520.14; found 520.3.

Compound 251 tert-butyl 7-(tert-butoxycarbonyl(methyl)amino)-5-(3-(ethylsulfonyl)phenyl)-8-methoxy-3-methyl-9H-pyrido[2,3-b]indole-9-carboxylate

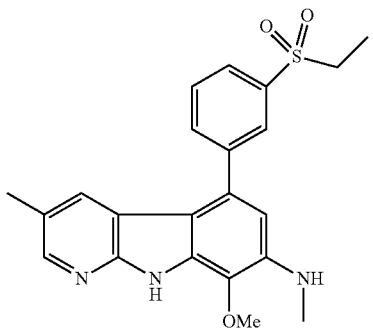

A 5 mL microwave vial was charged with Compound 250 (520 mg, 1.0 mmol), 3-(ethylsulfonyl)phenylboronic acid (321 mg, 1.5 mmol) and Pd(PPh$_3$)$_4$ (116 mg, 0.10 mmol). To the mixture was added dioxane (2 mL) and a saturated aqueous solution of K$_2$CO$_3$ (1 mL). The reaction mixture was heated at 140° C. for 20 min. in microwave. The reaction was diluted with EtOAc and washed with water and brine. The organic extracts were dried (Na$_2$SO$_4$) and concentrated and the crude Compound 251 was taken forward for Boc deprotection.

Compound 252

5-(3-(ethylsulfonyl)phenyl)-8-methoxy-N,3-dimethyl-9H-pyrido[2,3-b]indol-7-amine The crude residue from previous step (Compound 251) was dissolved in 3 mL CH$_2$Cl$_2$ and to it were sequentially added 0.2 mL of anisole and 1 mL of TFA. The mixture was stirred at room temperature for 2 h. Solvent was removed in vacuum and the residue was basified with saturated aqueous NaHCO$_3$ and extracted with EtOAc. The organic layer was washed with brine, dried over Na$_2$SO$_4$ and finally purified flash chromatography to furnish Compound 252 (287 mg, 70%, for 2 steps).

Compound 253

N-(5-(3-(ethylsulfonyl)phenyl)-8-methoxy-3-methyl-9H-pyrido[2,3-b]indol-7-yl)-N-methylcyclopropanecarboxamide

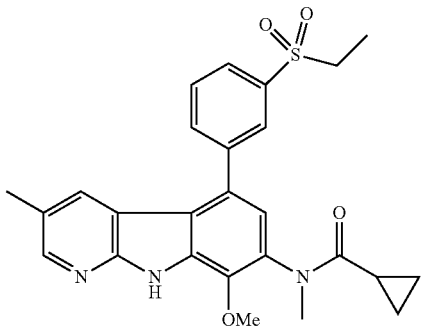

To a solution of Compound 252 (150 mg, 0.37 mmol) in dry THF (3 mL) was added cyclopropylcarbonyl chloride (34 µL, 0.37 mmol) at 0° C. Slowly the temperature was raised to room temperature and stirred for an additional hour. Reaction was quenched with aqueous NaHCO$_3$ solution and extracted with EtOAc, washed with brine, dried over Na$_2$SO$_4$ and finally purified preparative HPLC to provide Compound 253 (132 mg, 75%). $^1$H NMR (400 MHz, DMSO-d$_6$) δ ppm 0.63 (br. d, J=8.1 Hz, 2H) 0.80 (br. s., 2H) 1.18 (t, J=7.45 Hz, 3H) 1.48 (td, J=8.02, 3.92 Hz, 1H) 2.27 (s, 3H) 3.26 (s, 3H) 3.41 (q, J=7.45 Hz, 2H) 3.98 (s, 3H) 7.17 (s, 1H) 7.54 (s, 1H) 7.88 (t, J=7.71 Hz, 1H) 8.04 (d, J=8.08 Hz, 2H) 8.14 (s, 1H) 8.31 (d, J=1.26 Hz, 1H) 12.31 (s, 1H); [M+H] calc'd for C$_{26}$H$_{28}$N$_3$O$_4$S, 478.2; found, 478.3.

Compound 254

3-(dimethylamino)-N-(5-(3-(ethylsulfonyl)phenyl)-8-methoxy-3-methyl-9H-pyrido[2,3-b]indol-7-yl)-N-methylpropanamide

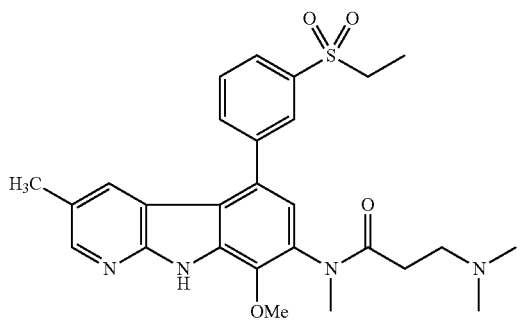

The title compound was prepared from Compound 252 by using an analogous procedure to that outlined in the preparation of Compound 240. $^1$H NMR (400 MHz, DMSO-d$_6$) δ ppm 1.17 (t, J=7.33 Hz, 3H) 2.02 (br. s., 6H) 2.19-2.33 (m, 7H) 3.26 (s, 3 H) 3.96 (s, 3H) 7.14 (s, 1H) 7.53 (s, 1H) 7.88 (t, J=7.71 Hz, 1H) 8.03 (d, J=8.08 Hz, 2 H) 8.12 (s, 1H) 8.32 (d, J=1.26 Hz, 1H) 12.31 (s, 1H); [M+H] calc'd for C$_{27}$H$_{33}$N$_4$O$_4$S, 509.2; found, 509.3.

Compound 255

4-(2-(3-chloro-5-(3-(ethylsulfonyl)phenyl)-9H-pyrido[2,3-b]indol-8-yloxy)ethyl)morpholine

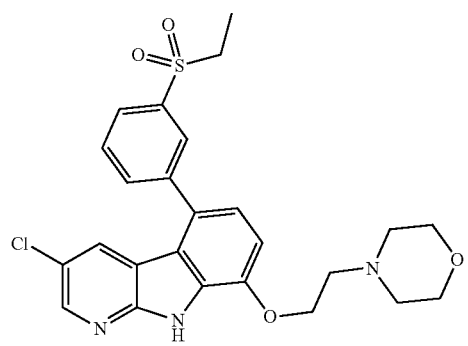

The title compound was prepared from Compound 219 by using an analogous procedure to that outlined in the preparation of Compound 206. $^1$H NMR (400 MHz, Methanol-d$_4$) δ 8.12 (s, 1H) 8.00 (m, 1H) 7.92 (m, 1H) 7.74 (t, J=7.84 Hz, 1H) 7.64 (s, 1H) 7.09 (m, 1H) 7.02 (m, 1H) 6.84 (s, 1H) 4.40 (t, J=5.0 Hz, 2H) 4.11 (br. m, 4H) 3.80 (br. m, 4H) 3.55 (t, J=5.0 Hz, 2H) 3.30 (q, J=7.32 Hz, 2H) 1.27 (t, J=7.32 Hz, 3 H). [M+H] calc'd for C$_{25}$H$_{27}$ClN$_3$O$_4$S, 500; found, 500.

Compound 256

3-(3-chloro-5-(3-(ethylsulfonyl)phenyl)-9H-pyrido[2,3-b]indol-8-yloxy)propanenitrile

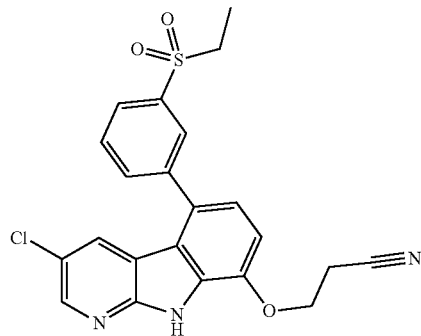

The title compound was prepared from Compound 219 by using an analogous procedure to that outlined in the preparation of Compound 206. $^1$H NMR (400 MHz, Methanol-d$_4$) δ 8.39 (d, J=2.24 Hz, 1H) 8.08 (m, 1H) 8.06 (m, 1H) 7.92 (m, 1H) 7.84 (t, J=7.56 Hz, 1H) 7.54 (d, J=2.24 Hz, 1H) 7.08 (d, J=8.08 Hz, 1H) 7.06 (d, J=8.08 Hz, 1 H) 5.13 (t, J=6.84 Hz, 2H) 3.30 (q, J=7.32 Hz, 2H) 3.13 (t, J=6.84 Hz, 2H) 1.27 (t, J=7.32 Hz, 3H). [M+H] calc'd for $C_{22}H_{19}ClN_3O_3S$, 440; found, 440.

Compound 257

3-chloro-5-(3-(ethylsulfonyl)phenyl)-8-(1-methylpi-peridin-4-yloxy)-9H-pyrido[2,3-b]indole

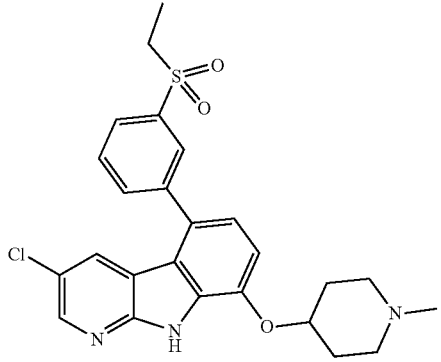

The title compound was prepared from Compound 219 by using an analogous procedure to that outlined in the preparation of Compound 206. $^1$H NMR (400 MHz, Methanol-d$_4$) δ 8.44 (br, 2H) 8.15 (s, 1H) 8.05 (m, 2H) 7.90 (t, J=7.84 Hz, 1H) 7.70 (s, 1H) 7.30 (s, 1H) 4.76 (br, 1H) 3.56 (m, br, 2H) 3.33 (m, 4H) 3.12 (s, 3H) 2.80 (m, 2H) 1.30 (m, 5H). [M+H] calc'd for $C_{25}H_{27}ClN_3O_3S$, 484; found, 484.

Compound 258

3-(5-(3-(ethylsulfonyl)phenyl)-3-(trifluoromethyl)-9H-pyrido[2,3-b]indol-8-yloxy)-N,N-dimethylpropan-1-amine

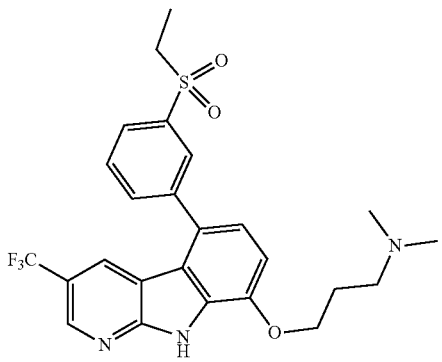

The title compound was synthesized by using an analogous synthetic sequence to that outlined in the preparation of Compound 200. $^1$H NMR (400 MHz, Methanol-d$_4$) δ 8.72 (s, 1H) 8.15 (s, 1H) 8.10 (m, 1H) 7.99 (m, 1H) 7.93 (s, 1H) 7.88 (t, J=7.6 Hz, 1 H) 7.28 (d, J=8.08 Hz, 1H) 7.23 (d, J=8.08 Hz, 1H) 4.44 (t, J=5.8 Hz, 2H) 3.72 (t, J=8.0 Hz, 2H) 3.43 (q, J=7.32 Hz, 2H) 3.03 (s, 6H) 2.41 (m, 2H) 1.34 (t, J=7.32 Hz, 3 H). [M+H] calc'd for $C_{25}H_{27}F_3N_3O_3S$, 506; found, 506.

Compound 259

(3-(8-methoxy-3-methyl-9H-pyrido[2,3-b]indol-5-yl)phenyl)(morpholino)methanone

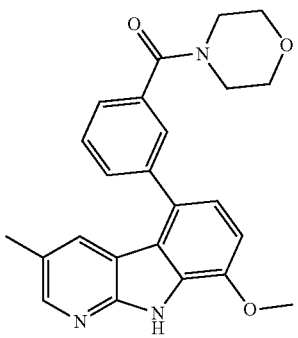

The title compound was synthesized from Compound 156 using an analogous procedure to that outlined in the preparation of Compound 157. $^1$H NMR (400 MHz, Methanol-d$_4$) δ 8.30 (s, 1H) 8.15 (s, 1H) 7.73 (m, 2H) 7.69 (m, 2H) 7.34 (d, J=8.32 Hz, 1H) 7.29 (d, J=8.32 Hz, 1H) 4.14 (s, 3H) 3.63-3.85 (m, 8H) 2.44 (s, 3H). [M+H] calc'd for $C_{24}H_{24}N_3O_3$, 402; found, 402.

Compound 260

N-methoxy-3-(8-methoxy-3-methyl-9H-pyrido[2,3-b]indol-5-yl)benzamide

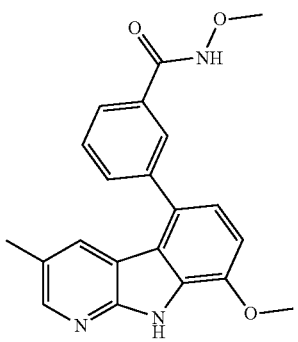

The title compound was synthesized from Compound 156 using an analogous procedure to that outlined in the preparation of Compound 157. $^1$H NMR (400 MHz, Methanol-d$_4$) δ 8.24 (s, 1H) 8.08 (m, 1H) 8.03 (m, 1H) 7.90 (m, 1H) 7.84 (m, 1H) 7.68 (t, J=8.08 Hz, 1H) 7.21 (d, J=8.08 Hz, 1H) 7.18 (d, J=8.08 Hz, 1H) 4.11 (s, 3H) 3.85 (s, 3H) 2.35 (s, 3H). [M+H] calc'd for $C_{21}H_{20}N_3O_3$, 362; found, 362.

Compound 261

5-(3-Ethanesulfonyl-phenyl)-8-(cyclopropyl-methoxy)-3-methyl-9H-dipyrido[2,3-b; 4',3'-d]pyrrole

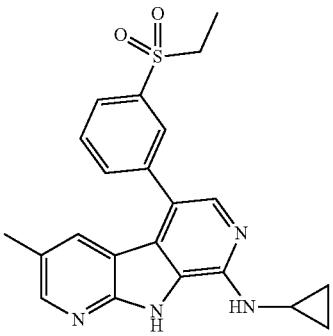

The title compound was prepared using cyclopropanamine in the procedure outlined for the preparation of compound 52. $^1$H NMR (400 MHz, Methanol-$d_4$) δ 8.35 (s, 1H) 8.20 (s, 1H) 8.02 (m, 2H) 7.83 (m, 3H) 3.43 (q, J=7.32 Hz, 2H) 3.0 (m, 1H) 2.37 (s, 3H) 1.31 (t, J=7.32 Hz, 3H) 0.93 (m, 2H) 0.67 (m, 2H). [M+H] calc'd for $C_{22}H_{23}N_4O_2S$, 407; found, 407.

Compound 262

N-(2-(diethylamino)ethyl)-5-(3-(ethylsulfonyl)phenyl)-3,8-dimethyl-9H-pyrido[2,3-b]indole-7-carboxamide

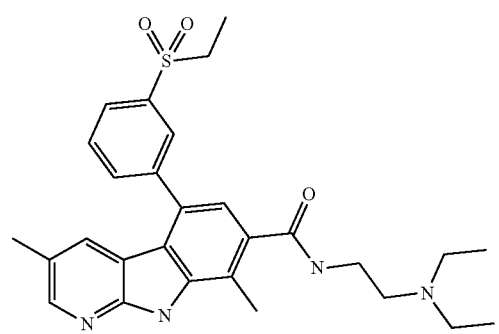

The title compound was synthesized using an analogous procedure to that described in the preparation of compound 88. ESI-MS: m/z calc'd for $C_{28}H_{34}N_4O_3S$ 506.2; found 507.4 [M+H]$^+$.

Compound 263

5-(3-(ethylsulfonyl)phenyl)-3,8-dimethyl-N-(3-morpholinopropyl)-9H-pyrido[2,3-b]indole-7-carboxamide

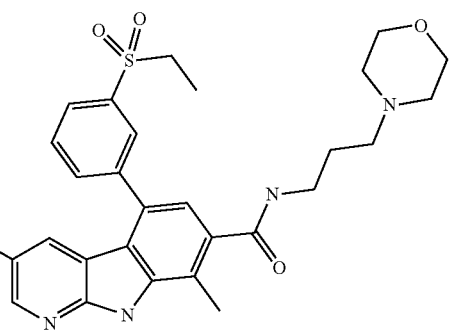

The title compound was synthesized using an analogous procedure to that described in the preparation of compound 88. ESI-MS: m/z calc'd for $C_{29}H_{34}N_4O_4S$ 534.6; found 535.7 [M+H]$^+$.

Compound 264

1-(3-(benzyloxy)propoxy)-4-chloro-2-iodobenzene

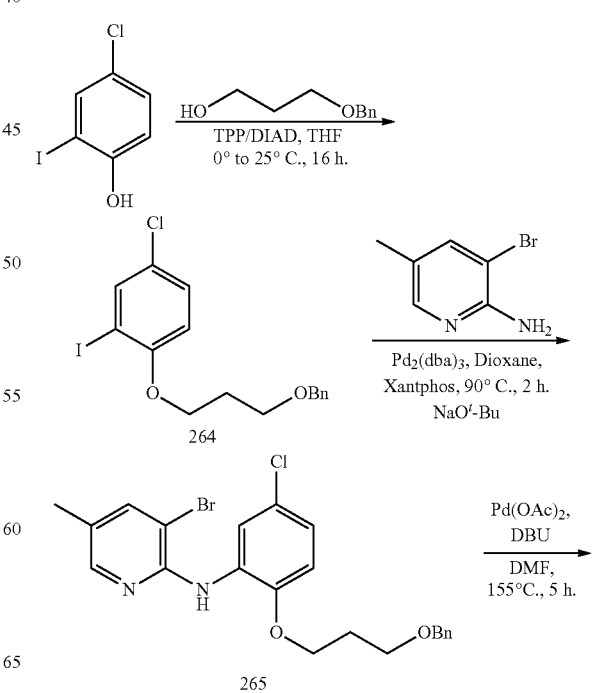

299

-continued

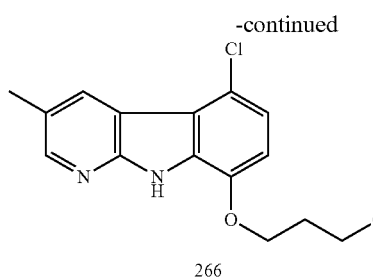
266

20% HCO₂H in MeOH,
10% Pd-C,
rt, 36 h.

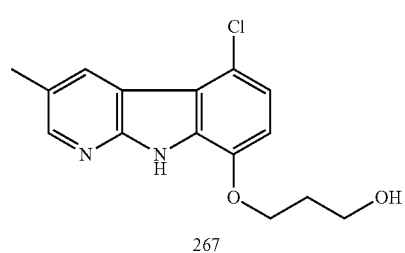
267

TPP, I₂
Imidazole
CH₂Cl₂,
rt, 12 h.

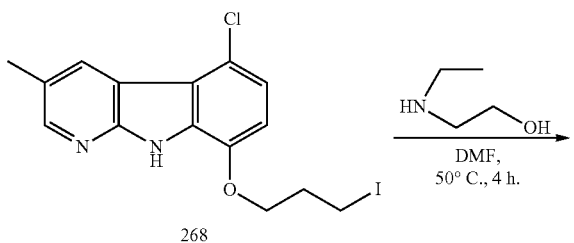
268

HN⟶OH
DMF,
50° C., 4 h.

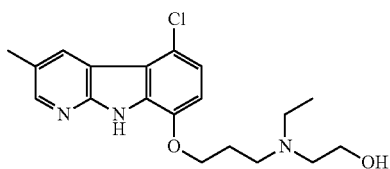
269

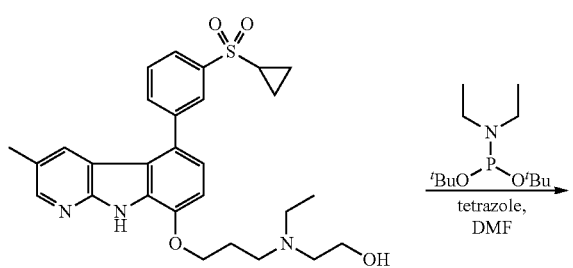
270

300

-continued

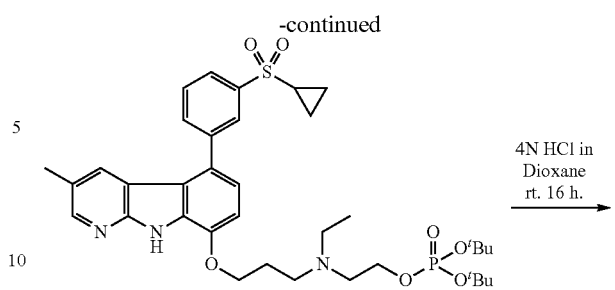
271

4N HCl in Dioxane
rt. 16 h.

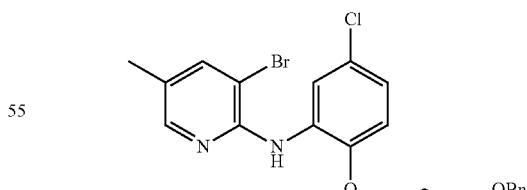
272

To a stirred solution of 4-chloro-2-iodophenol (20.0 g, 78.6 mmol) in anhydrous THF (300.0 mL) were sequentially added 3-(benzyloxy)propan-1-ol (18.75 mL, 117.9 mmol) and triphenyl phosphine (30.92 g, 117.9 mmol). The reaction mixture was cooled to 0° C., and to it diisopropylazodicarboxylate (22.8 mL, 117.9 mmol) was added in drop wise manner. After the addition was over, stirring continued for another 0.5 h at 0° C. and then for 12 h at room temperature. Solvents were removed in vacuum and the residue was purified by silica gel column chromatography, providing the title compound 264 (28.5 g, 90%). $^1$H NMR (400 MHz, CHLOROFORM-d) δ ppm 2.08 (p, J=5.2 Hz, 2H) 3.69 (t, J=5.68 Hz, 2H) 4.06 (t, J=6.06 Hz, 2H) 4.49 (s, 2H) 6.68 (d, J=8.84 Hz, 1H) 7.19-7.30 (m, 6H) 7.69 (d, J=2.53 Hz, 1H).

Compound 265

N-(2-(3-(benzyloxy)propoxy)-5-chlorophenyl)-3-bromo-5-methylpyridin-2-amine

In a oven dried 1.0 L round bottom flask were sequentially added compound 264 (31.0 g, 76.9 mmol), 3-bromo-5-methylpyridin-2-amine (15.84 g, 84.69 mmol), Pd₂(dba)₃ (3.52 g, 3.84 mmol), xantphos (6.67 g, 11.53 mmol) and Na$^t$BuO (11.09 g, 115.3 mmol) at room temperature. The solid materials were kept under vacuum for 5 min. and then refilled with nitrogen. This process was repeated thrice before adding dry, degassed dioxane (300 mL). The heterogeneous mixture was stirred at room temperature for 15 min. and then at 90° C. for 2 h. Finally upon completion of the reaction, it was diluted with ether and filtered through a small plug of silica gel with several washings. All the washings and filtrate were combined and concentrated in vacuum and the crude residue was further purified by flash chromatography to provide the title compound 265 (26.6, 75%). $^1$H NMR (400 MHz, DMSO-d$_6$) δ ppm 2.07 (p, J=6.13 Hz, 2H) 2.22 (s, 3H) 3.66 (t, J=6.32 Hz, 2H) 4.18 (t, J=6.06 Hz, 2H) 4.48 (s, 2H) 6.95 (dd, J=2.4, 8.59, Hz, 1H) 7.06 (d, J=8.59 Hz, 1H) 7.18-7.29 (m, 5H) 7.82 (s, 1H) 7.89 (d, J=2.02 Hz, 1H) 8.12 (s, 1H) 8.60 (d, J=2.53 Hz, 1H); [M+H] calc'd for C$_{22}$H$_{23}$BrClN$_2$O$_2$, 461.1; found, 461.2.

Compound 266

8-(3-(benzyloxy)propoxy)-5-chloro-3-methyl-9H-pyrido[2,3-b]indole

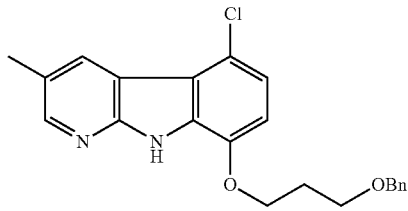

To a stirred solution of compound 265 (25.7 g, 55.65 mmol) in anhydrous and degassed DMF (200 mL), were added Pd(OAc)$_2$ (1.25 g, 5.56 mmol) and DBU (24.9 mL, 166.9 mmol), under nitrogen. After being stirred for 6 h. at 155° C. the reaction was cooled to ambient temperature and quenched by addition of water (250 mL). The solid precipitates out, filtered and washed thoroughly with water. The residue was triturated with ether and filtered, dried under vacuum to get the title compound 266 (12.72 g, 60%) and used directly for the next step. $^1$H NMR (400 MHz, DMSO-d$_6$) δ ppm 2.06 (p, J=6.25 Hz, 2H) 2.47 (s, 3H) 3.75 (t, J=6.32 Hz, 2H) 4.25 (t, J=6.19 Hz, 2H) 4.50 (s, 2H) 7.03 (d, J=8.34 Hz, 1H) 7.14 (d, J=8.34 Hz, 1H) 7.21-7.33 (m, 5H) 8.36 (d, J=2.02 Hz, 1H) 8.50 (d, J=1.26 Hz, 1H) 12.09 (s, 1H); [M+H] calc'd for C$_{22}$H$_{22}$ClN$_2$O$_2$, 381.1; found, 381.3.

Compound 267

3-(5-chloro-3-methyl-9H-pyrido[2,3-b]indol-8-yloxy)propan-1-ol

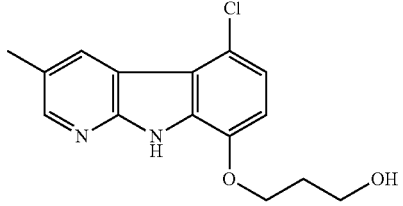

Compound 266 (6.5 g, 17.06 mmol) was taken in a solution of 25% formic acid in MeOH (400 mL) and treated with 10% Pd—C (1.5 g) under N$_2$-atmosphere. After being stirred for 24 h, the reaction mixture was filtered through a small plug of celite. The filter cake was washed several times with THF. The combined filtrate and washings were concentrated and dissolved in minimum volume of hot DMF and the solution was basified with 30% aqueous NH$_3$. Solid precipitated out and collected by filtration. The solid residue washed thoroughly with water, dried under vacuum to furnish the title compound 267 (3.47 g, 70%) which was used for next step without further purification. $^1$H NMR (400 MHz, DMSO-d$_6$) δ ppm 1.96 (p, J=6.13 Hz, 2H) 2.47 (s, 3H) 3.69 (q, J=5.81 Hz, 2 H) 4.23 (t, J=6.19 Hz, 2H) 4.55 (t, J=5.18 Hz, 1H) 7.03 (d, J=8.34 Hz, 1H) 7.14 (d, J=8.59 Hz, 1H) 8.35 (s, 1H) 8.49 (s, 1H) 12.09 (s, 1H); [M+H] calc'd for C$_{15}$H$_{16}$ClN$_2$O$_2$, 290.1; found, 291.3.

Compound 268

5-chloro-8-(3-iodopropoxy)-3-methyl-9H-pyrido[2,3-b]indole

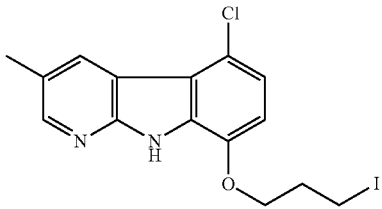

To a suspension of compound 267 (4.7 g, 16.16 mmol) in CH$_2$Cl$_2$ (150 mL) were sequentially added triphenyl phosphine (6.36 g, 24.2 mmol), imidazole (1.54 g, 22.62 mmol) and iodine (4.93 g, 19.39 mmol) at room temperature under N$_2$ atmosphere. After being stirred for 16 h, the reaction mixture was directly filtered and the solid obtained was washed twice with ether to provide the title compound 268 as yellow solid, which was directly used for next step without further purification.

Compound 269

2-(3-(5-chloro-3-methyl-9H-pyrido[2,3-b]indol-8-yloxy)propyl)-(ethyl)amino)ethanol

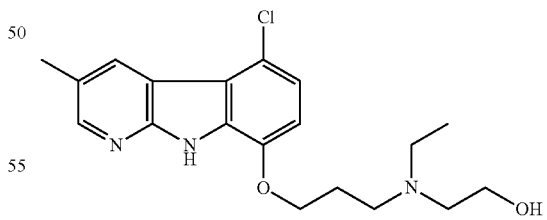

The crude product 268 (5.4 g, 16.72 mmol) obtained in previous step was taken in anhydrous DMF (50 mL) and treated with 2-(ethylamino)ethanol (4.89 mL, 50.16 mmol) under N$_2$ atmosphere. The reaction mixture was heated at 50° C. for 4 h., cooled to room temperature and water (100 mL) was added to it. Solid precipitate out, filtered and washed with water (3×50 mL). Residue was dried under vacuum and then subjected to silica gel column purification to provide the title compound 269 (2.81 g, 48% after 2 steps). $^1$H NMR (400

MHz, DMSO-d$_6$) δ ppm 0.94 (t, J=7.07 Hz, 3H) 1.90 (p, J=6.51 Hz, 2H) 2.47 (s, 3H) 2.48-2.53 (m, 4H) 2.68 (t, J=6.82 Hz, 2H) 3.44 (t, J=6.44 Hz, 2H) 4.19 (t, J=6.19 Hz, 2H) 4.32 (br. s., 1H) 7.01 (d, J=8.34 Hz, 1H) 7.11 (d, J=8.34 Hz, 1 H) 8.35 (d, J=2.02 Hz, 1H) 8.49 (d, J=1.52 Hz, 1H) 12.14 (br. s., 1H); [M+H] calc'd for C$_{19}$H$_{25}$ClN$_3$O$_2$, 362.2; found, 362.2.

Compound 270

2-((3-(5-(3-(cyclopropylsulfonyl)phenyl)-3-methyl-9H-pyrido[2,3-b]indol-8-yloxy)propyl)(ethyl)amino)ethanol

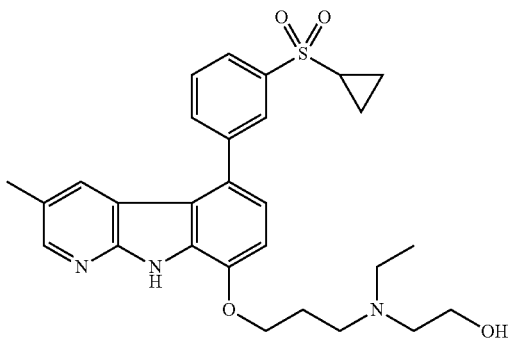

To a stirred solution of compound 269 (1.2 g, 3.32 mmol) and 2-(3-(cyclopropylsulfonyl)phenyl)-4,4,5,5-tetramethyl-1,3,2-dioxaborolane (2.55 g, 8.29 mmol) in anhydrous and degassed dioxane (50 mL), were added Pd(dba)$_2$ (286 mg, 0.5 mmol), PCy$_3$ (1.4 mL, 20% wt solution in toluene, 0.99 mmol) and Cs$_2$CO$_3$ (3.24 g, 9.96 mmol), under nitrogen. After being stirred for 6 h. under reflux (oil bath temperature 120° C.) the reaction was diluted with EtOAc and filtered through a small pad of celite. The residue was washed thoroughly with EtOAc and 10% MeOH in CH$_2$Cl$_2$. All the washings and filtrate were concentrated in vacuum and the crude residue was purified through preparative HPLC to furnish the title compound 270 (1.31 g, 78%). $^1$H NMR (400 MHz, DMSO-d$_6$) δ ppm 1.09 (td, J=6.69, 3.28 Hz, 2H) 1.15 (dd, J=4.80, 2.02 Hz, 2H) 1.29 (t, J=7.20 Hz, 3H) 2.24-2.28 (m, 2H) 2.28 (s, 3H) 2.98-3.05 (m, 1H) 3.23-3.32 (m, 4 H) 3.54-3.51 ((br. m, 2H) 3.80 (t, J=5.18 Hz, 2H) 4.33 (t, J=5.56 Hz, 2H) 7.10 (d, J=8.1 Hz, 1H) 7.16 (d, J=8.1 Hz, 1H) 7.58 (s, 1H) 7.85 (t, J=7.71 Hz, 1H) 7.96 (d, J=7.83 Hz, 1H) 8.01 (d, J=7.83 Hz, 1H) 8.09 (m, 1H) 8.30 (s, 1H) 9.28 (br. s., 1H) 12.03 (s, 1H); [M+H] calc'd for C$_{28}$H$_{34}$N$_3$O$_4$S, 508.2; found, 508.2.

Compound 271 di-tert-butyl-2-((3-(5-(3-(cyclopropylsulfonyl)phenyl)-3-methyl-9H-pyrido[2,3-b]indol-8-yloxy)propyl)(ethyl)amino)ethyl phosphate

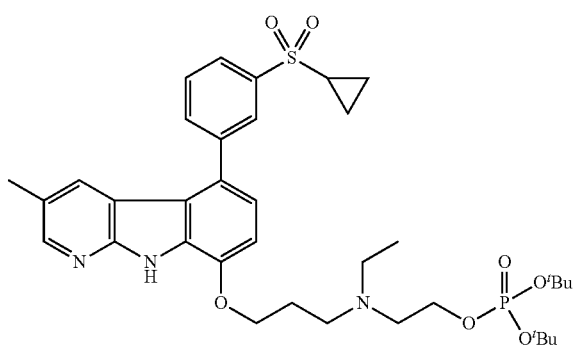

To a solution of compound 270 (1.53 g, 3.02 mmol) in dry DMF (15 mL) were sequentially added tetrazole (26.8 mL, 12.08 mmol, 0.4 M solution in CH$_3$CN) and di-tert-butyl-diethylphosphoramidite (1.81 mL, 6.05 mmol) at room temperature and stirred for 3 h. under N$_2$ atmosphere. The reaction mixture was then cooled to −60° C. and a solution of monoperoxyphthalic acid magnesium salt (896 mg, 1.81 mmol) in DMF (10 mL) was slowly added to it. The resultant mixture was stirred for 1.5 h at −60° C., after which a solution of sodium metabisulfite (5.74 g, 30.2 mmol) in water (20 mL) was added into it. The mixture was then slowly allowed to warm to ambient temperature. Solvents were removed under vacuum and the residue was purified by silicagel chromatography followed by preparative HPLC to provide the title compound 271 (1.1 g, 52%).

Compound 272

2-((3-(5-(3-(cyclopropylsulfonyl)phenyl)-3-methyl-9H-pyrido[2,3-b]indol-8-yloxy)propyl)(ethyl)amino)ethyl dihydrogen phosphate

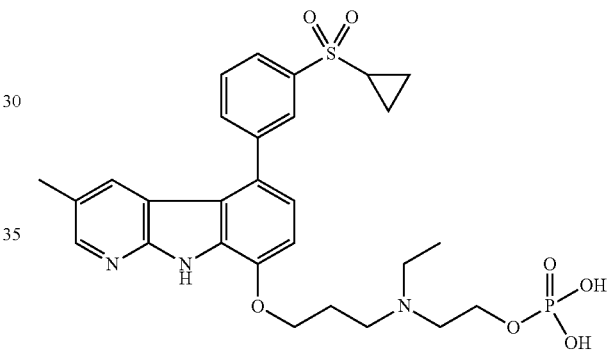

Compound 271 (462 mg, 0.66 mmol) was taken in 4N HCl in dioxane (10 mL) and stirred for 16 h. at room temperature. Solvents were removed in vacuum, and the title compound 272 was obtained as yellow dihydrochloride salt (427 mg, 98%). $^1$H NMR (400 MHz, DMSO-d$_6$) δ ppm 1.06-1.11 (m, 2H) 1.13-1.16 (m, 2H) 1.32 (t, J=7.20 Hz, 3H) 2.29 (s, 3H) 2.34-2.31 (m, 2H), 2.98-3.05 (m, 1H) 3.29 (q, J=7.07 Hz, 2H) 3.47 (t, J=4.67 Hz, 2H) 3.54 (br.t, J=7.2 Hz, 2H) 4.28-4.35 (m, 4H) 7.11-7.14 (m, 1H) 7.16-7.20 (m, 1H) 7.65 (d, J=1.26 Hz, 1H) 7.85 (t, J=7.71 Hz, 1H) 7.96 (dt, J=7.77, 1.29 Hz, 1H) 8.01 (dt, J=7.83, 1.39 Hz, 1H) 8.09 (t, J=1.77 Hz, 1H) 8.31 (d, J=1.77 Hz, 1H) 12.35 (br. s., 1H); [M+H] calc'd for C$_{28}$H$_{35}$N$_3$O$_7$PS, 588.2; found, 588.1.

The free base of Compound 272 was prepared as follows. To a solution of Compound 272 (730 mg, 1.105 mmol) in MeOH (15 mL) was added cyclohexeneoxide (2.23 mL, 22.1 mmol, 20 eq) and stirred for 48 h. White solid separated out. The reaction mixture was diluted with diethylether and filtered. The residue was washed thoroughly with diethylether and dried in high vacuum for 24 h to provide the free base (630 mg, 97%) as white solid.

The disodium salt of Compound 272 was prepared as follows. To a stirred suspension of the free base form of Compound 272 (116 mg, 0.197 mmol) in MeOH (4 mL) was added a solution of NaOMe (0.87 mL, 0.434 mmol, 0.5 M solution in MeOH) at 0° C. The resulting mixture was stirred for 1 h 0° C. and 1 h at room temperature, by which time reaction mixture turned homogenous and light yellow in color. Solvents were removed and the residue were dried in high vacuum for 24 h to provide the bis sodium salt of 272 (122 mg, 98%) as light yellow solid.

Compound 273

N-cyclopropyl-3-(8-(3-(ethyl(2-hydroxyethyl)amino)propoxy)-3-methyl-9H-pyrido[2,3-b]indol-5-yl)benzamide

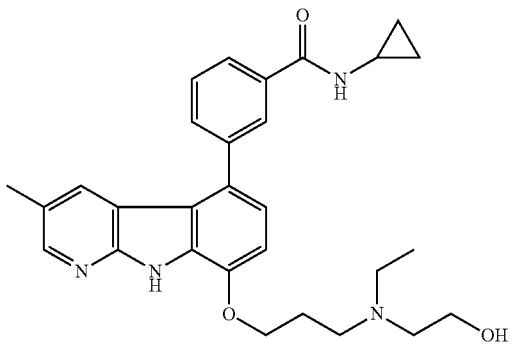

The title compound 273 (188 mg, 72%) was synthesized from compound 269 (195 mg, 0.54 mmol) and 3-(cyclopropylcarbamoyl)phenylboronic acid using an analogous procedure as outlined in the preparation of compound 270. $^1$H NMR (400 MHz, DMSO-$d_6$) δ ppm 0.53-0.59 (m, 2H) 0.68-0.71 (m, 2H) 1.29 (td, J=7.14, 2.91 Hz, 3H) 2.22-2.26 (m, 2H) 2.25 (s, 3H) 2.87 (dd, J=7.45, 3.66 Hz, 1H) 3.27 (br.d, J=2.78 Hz, 4 H) 3.48-3.67 (br.m, 4H) 4.31 (br. s., 2H) 7.05 (dd, J=7.96, 3.41 Hz, 1H) 7.12 (dd, J=3.28, 8.4 Hz, 1H) 7.53 (br. s., 1H) 7.62 (td, J=7.71, 3.28 Hz, 1H) 7.71 (m, 1H) 7.92 (br.d, J=8.34 Hz, 1H) 8.03 (br. s., 1H) 8.27 (br. s., 1H) 8.55 (br. s., 1H) 9.21 (br. s., 1H) 11.96 (br. s., 1H); [M+H] calc'd for $C_{29}H_{35}N_4O_3$, 487.3; found, 487.2.

Compound 274 di-tert-butyl-2-((3-(5-(3-(cyclopropylcarbamoyl)phenyl)-3-methyl-9H-pyrido[2,3-b]indol-8-yloxy)propyl)(ethyl)amino)ethyl phosphate

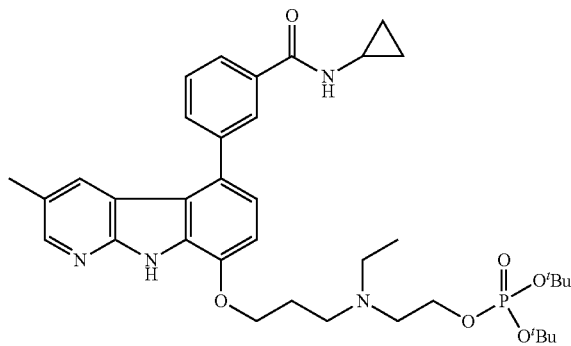

The title compound was prepared from compound 273 using an analogous procedure to that described in the preparation of compound 271.

Compound 275

2-(3-(5-(3-(cyclopropylcarbamoyl)phenyl)-3-methyl-9H-pyrido[2,3-b]indol-8-yloxy)propyl)(ethyl)amino)ethyl dihydrogen phosphate

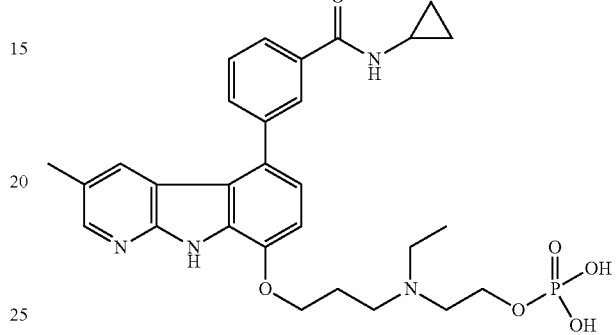

The title compound was prepared from compound 274 using an analogous procedure to that described in the preparation of compound 272. $^1$H NMR (400 MHz, DMSO-$d_6$) δ ppm 0.54-0.59 (m, 2H) 0.67-0.72 (m, 2H) 1.32 (t, J=7.20 Hz, 3H) 2.26 (s, 3H) 2.34 2.29 (m, 2H) 2.87 (td, J=7.33, 4.04 Hz, 1H) 3.29 (q, J=7.07 Hz, 2H) 3.48 (t, J=4.67 Hz, 2H) 3.57 (br. t., J=7.62 Hz, 2H) 4.25-4.34 (m, 4H) 7.07 (d, J=8.08 Hz, 1H) 7.15 (d, J=8.08 Hz, 1H) 7.58 (d, J=1.26 Hz, 1H) 7.62 (t, J=7.71 Hz, 1H) 7.73 (d, J=7.83 Hz, 1H) 7.93 (dd, J=7.58, 1.26 Hz, 1H) 8.04 (t, J=1.52 Hz, 1H) 8.28 (d, J=1.77 Hz, 1H) 8.56 (d, J=4.29 Hz, 1H) 12.22 (br. s., 1H); [M+H] calc'd for $C_{29}H_{36}N_4O_6P$, 567.2; found, 567.1.

Compound 276

2-(3-(4-chloro-6-methyl-9H-carbazol-1-yloxy)propyl)(ethyl)amino)-ethanol

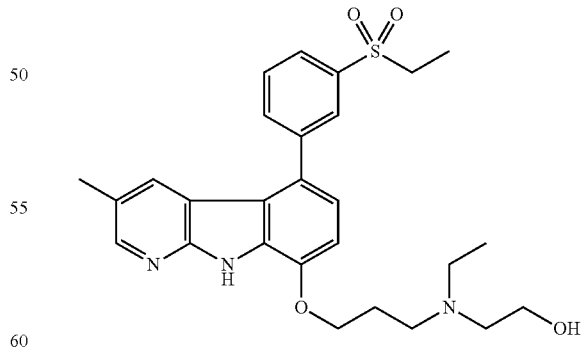

The title compound (1.15 g, 55%) was synthesized from compound 269 (1.53 g, 4.24 mmol) and 3-(ethylsulfonyl)phenylboronic acid using an analogous procedure as outlined in the preparation of compound 270. $^1$H NMR (400 MHz, DMSO-$d_6$) δ ppm 1.17 (t, J=7.33 Hz, 3H) 1.29 (t, J=7.20 Hz, 3H) 2.2-2.27 (m, 2H) 2.27 (s, 3H) 3.24-3.32 (m, 4H) 3.41 (q, J=7.33 Hz, 2H) 3.48-3.55 (m, 2H) 3.80 (t, J=5.05 Hz, 2H) 4.32 (t, J=5.68 Hz, 2H) 7.10 (d, J=8.4, Hz, 1H) 7.15 (d, J=8.4, Hz, 1H) 7.56 (d, J=1.52 Hz, 1H) 7.86 (t, J=7.71 Hz, 1H) 7.96-8.02 (m, 2H) 8.07 (t, J=1.64 Hz, 1H) 8.30 (d, J=1.77 Hz, 1H) 9.25 (br. s., 1H) 12.03 (s, 1H); [M+H] calc'd for $C_{27}H_{33}N_3O_4S$, 496.2; found, 496.4.

Compound 277 di-tert-butyl 2-(ethyl(3-(5-(3-(ethylsulfonyl)phenyl)-3-methyl-9H-pyrido[2,3-b]indol-8-yloxy)propyl)amino)ethyl phosphate

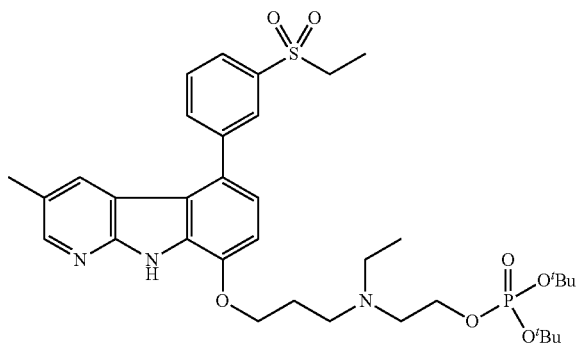

The title compound 277 was synthesized from compound 276 (124 mg, 0.25 mmol) using an analogous procedure as outlined for the preparation of compound 272. $^1$H NMR (400 MHz, DMSO-$d_6$) δ ppm 0.98 (t, J=7.07 Hz, 3H) 1.17 (t, J=7.33 Hz, 3H) 1.36 (s, 18H) 1.95 (m, 2H) 2.26 (s, 3H) 2.57 (q, J=7.33 Hz, 2H) 2.70 (t, J=6.44 Hz, 2H) 2.76 (t, J=6.82 Hz, 2H) 3.40 (q, J=7.33 Hz, 2H) 3.89 (q, J=7.33 Hz, 2H) 4.26 (t, J=6.06 Hz, 2H) 7.05 (d, J=8.4 Hz, 1H) 7.12 (d, J=8.4 Hz, 1H) 7.54 (s, 1H) 7.85 (t, J=7.71 Hz, 1H) 7.98 (dt, J=1.2, 7.6 Hz, 2H) 8.07 (t, J=1.64 Hz, 1H) 8.27 (d, J=2.02 Hz, 1H) 12.02 (s, 1H); [M+H] calc'd for $C_{35}H_{51}N_3O_7PS$, 688.3; found, 688.6.

Compound 278

2-(ethyl(3-(5-(3-(ethylsulfonyl)phenyl)-3-methyl-9H-pyrido[2,3-b]indol-8-yloxy)propyl)amino)ethyl dihydrogen phosphate

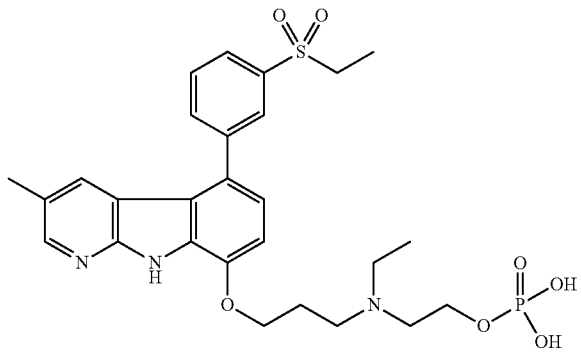

The dihydrochloride salt of the title compound 278 was synthesized from compound 277 using an analogous procedure as outlined for the preparation of compound 272. $^1$H NMR (400 MHz, DMSO-$d_6$) δ ppm 1.17 (t, J=7.33 Hz, 3H) 1.33 (t, J=7.20 Hz, 3 H) 2.29 (s, 3H) 2.28-2.36 (m, 2H) 3.29 (q, J=6.99 Hz, 2H) 3.41 (q, J=7.33 Hz, 2H) 3.48 (br. m, 2H) 3.57 (br. T, J=7.6 Hz, 2H) 4.29-4.36 (m, 4H) 7.14-7.23 (m, 2H) 7.70 (s, 1H) 7.86 (t, J=7.71 Hz, 1H) 7.99 (t, J=8.34 Hz, 2H) 8.09 (s, 1H) 8.33 (s, 1H) 10.86 (br. s., 1H) 12.59 (br. s., 1H); [M+H] calc'd for $C_{27}H_{35}N_3O_7PS$, 576.2; found, 576.1.

Compound 279

1-methyl-4-((4-nitrophenoxy)methyl)piperidine

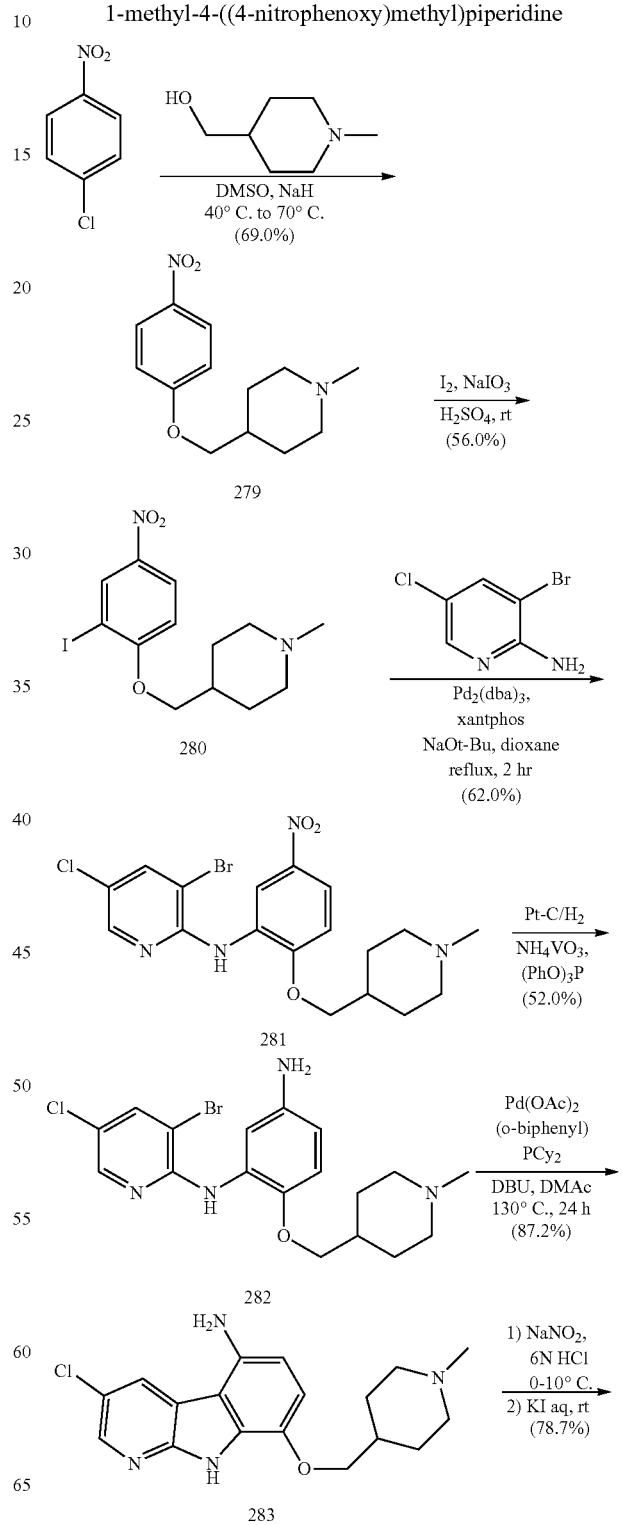

-continued

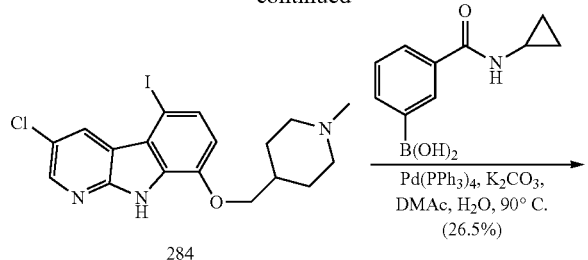

To a mixture of p-chloro nitrobenzene (6.0 g, 38 mmol) and 1-methyl-4-piperidinemethanol (4.91 g, 38 mmol) in anhydrous DMSO (60 mL) was added NaH (1.82 g, 45.6 mmol) in small portions at room temperature under N₂-atmosphere. After the addition was complete the reaction mixture was warmed at 40° C. and stirred for another 2 h. The reaction was quenched with water, and the product was extracted with EtOAc. The organic layer was washed with brine and dried over Na₂SO₄. The crude product was recrystallized from ether to yield 6.6 g (69%) of the title compound as an orange solid. ¹H NMR (400 MHz, CHLOROFORM-d) δ ppm 1.59-1.72 (m, 2H) 1.92 (d, J=11.37 Hz, 3 H) 2.19 (t, J=11.49 Hz, 2H) 2.44 (s, 3H) 3.09 (d, J=11.12 Hz, 2H) 3.93 (d, J=5.31 Hz, 2 H) 6.93 (d, J=9.2 Hz, 2H) 8.20 (d, J=9.6 Hz, 2H); [M+H] calc'd for $C_{13}H_{19}N_2O_3$, 251.2; found, 251.4.

Compound 280

4-((2-iodo-4-nitrophenoxy)methyl)-1-methylpiperidine

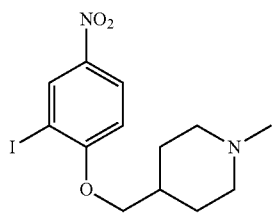

An oven-dried 200 mL round bottomed flask was charged with compound 279 (6.0 g, 23.9 mmol) and solid iodine (3.03 g, 11.9 mmol). To it was slowly added conc. H₂SO₄ (40 mL) followed by portion wise addition of NaIO₃ (2.36 g, 11.9 mmol), maintaining the reaction temperature below 30° C. After 4 h the reaction mixture was poured into cold water (160 mL). 10% aqueous Na₂SO₃ (160 mL) was added and the mixture stirred for 1 h. Solid separated out and was collected by filtration. The filtrate was basified using 50% aqueous NaOH solution, and extracted with ether. The ether layer was washed with brine, dried over Na₂SO₄. Solvent was removed under reduced pressure to get the second crop of iodinated product. The combined solid was purified by silica gel column chromatography to obtain 5.0 g (56%) of the title compound. ¹H NMR (400 MHz, CHLOROFORM-d) δ ppm 2.24 (br. m., 5H) 2.78-2.88 (m, 2H) 2.89 (d, J=4.80 Hz, 3H) 3.70 (d, J=11.87 Hz, 2H) 4.07 (d, J=3.54 Hz, 2H) 6.84 (d, J=9.09 Hz, 1H) 8.26 (dd, J=2.8, 8.8 Hz, 1H) 8.68 (d, J=2.78 Hz, 1H); [M+H] calc'd for $C_{13}H_{18}IN_2O_3$, 377.0; found, 377.2.

Compound 281

3-bromo-5-chloro-N-(2-((1-methylpiperidin-4-yl)methoxy)-5-nitrophenyl)pyridin-2-amine

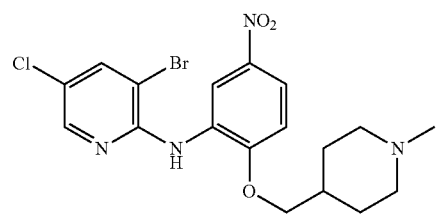

In an oven-dried 200 mL round bottom flask were sequentially added compound 280 (5.0 g, 13.3 mmol), 3-bromo-5-chloropyridin-2-amine (2.76 g, 13.3 mmol), Pd₂(dba)₃ (610 mg, 0.66 mmol), xantphos (1.15 g, 1.99 mmol) and Na'BuO (1.92 g, 19.93 mmol) at room temperature. The solid materials were kept under vacuum for 5 min. and then refilled with nitrogen. This process was repeated thrice before adding dry, degassed dioxane (60 mL). The heterogeneous mixture was stirred at room temperature for 15 min. and then at 100° C. for 1 h. After completion, the mixture was diluted with CH₂Cl₂ and filtered through a small plug of silica gel. The filtrate was concentrated in vacuo and the crude residue was purified by flash chromatography to provide 3.76 g (62%) of the title compound. ¹H NMR (400 MHz, DMSO-d₆) δ ppm 1.39 (dq, J=3.6, 12.0 Hz, 2H) 1.71-1.78 (m, 3H) 1.92 (t, J=11.37 Hz, 2H) 2.18 (s, 3H) 2.81 (br.d, J=10.86 Hz, 2H) 4.11 (d, J=6.06 Hz, 2H) 7.27 (d, J=9.09 Hz, 1H) 7.96 (dd, J=8.97, 2.91 Hz, 1H) 8.29 (d, J=2.0 Hz, 1H) 8.37 (d, J=2.0 Hz, 1H) 9.23 (d, J=3.03 Hz, 1H); [M+H] calc'd for $C_{18}H_{21}BrClN_4O_3$, 455.0; found, 455.2.

Compound 282

N1-(3-bromo-5-chloropyridin-2-yl)-6-((1-methylpiperidin-4-yl)methoxy)benzene-1,3-diamine

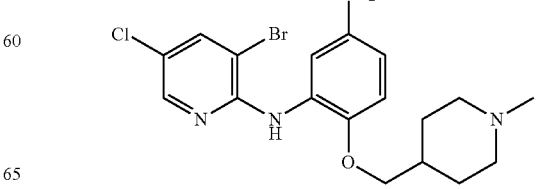

A mixture of compound 281, ammonium metavanadate (0.053 g, 0.45 mmol), phosphorous acid, triphenyl ester (0.1 mL, 0.4 mmol), and 5% Pt/C (0.35 g) was stirred overnight under hydrogen. After completion the reaction was filtered through celite and concentrated in vacuo. The residue was reconstituted in dichloromethane (5 mL), passed through a small plug of silica gel and the appropriate fractions dried in vacuo. The crude product was recrystallized from acetonitrile to yield 1.75 g (52.0%) of the title compound as a tan solid. $^1$H NMR (400 MHz, DMSO-$d_6$) δ ppm 1.25-1.44 (m, 2H) 1.66-1.83 (m, 3H) 1.93-2.12 (m, 2H) 2.24 (s, 3H) 2.87 (d, J=11.12 Hz, 2H) 3.80 (d, J=5.81 Hz, 2H) 4.70 (br. s., 2H) 6.20 (dd, J=8.59, 2.78 Hz, 1H) 6.75 (d, J=8.84 Hz, 1H) 7.66 (d, J=2.78 Hz, 1H) 7.91 (s, 1H) 8.18-8.20 (m, 1H) 8.20-8.21 (m, 1H). [M+H] calc'd for $C_{18}H_{22}BrClN_4O$, 427; found 427.2.

Compound 283

3-chloro-8-((1-methylpiperidin-4-yl)methoxy)-9H-pyrido[2,3-b]indol-5-amine

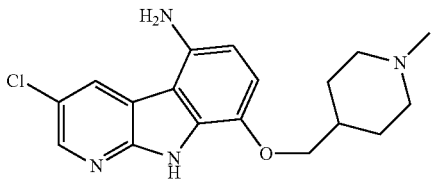

A mixture of Pd(OAc)$_2$ (6.3 mg, 5 mol %), 2-(Dicyclohexylphosphino)biphenyl (9.9 mg, 5 mol %), DBU (0.17 ml, 1.12 mmol), and degassed DMAc (1 ml) was stirred for 30 minutes at 80° C. Next, compound 282 (0.24 g, 0.56 mmol) was added and the mixture was stirred overnight at 130° C. After completion H$_2$O was added to the mixture affording a suspension. The resulting solids were filtered, rinsed with H$_2$O, and dried in vacuo to yield 0.17 g (87.2%) of the title compound as a dark brown solid. $^1$H NMR (400 MHz, DMSO-$d_6$) δ ppm 1.18-1.39 (m, 2H) 1.67-1.90 (m, 5H) 2.16 (s, 3H) 2.80 (d, J=10.36 Hz, 2H) 3.87 (d, J=6.32 Hz, 2H) 5.35 (s, 2H) 6.37 (d, J=8.34 Hz, 1H) 6.85 (d, J=8.59 Hz, 1H) 8.31 (d, J=2.53 Hz, 1H) 8.65 (d, J=2.27 Hz, 1H) 11.84 (br. s., 1H). [M+H] calc'd for $C_{18}H_{21}ClN_4O$, 345; found 345.3.

Compound 284

3-chloro-5-iodo-8-((1-methylpiperidin-4-yl)methoxy)-9H-pyrido[2,3-b]indole

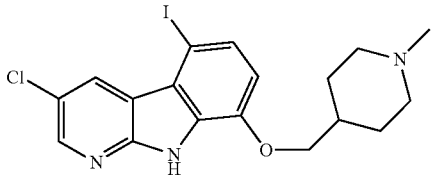

To a mixture of compound 283 (0.16 g, 0.47 mmol) and 6N HCl (3.3 ml) at 0° C. was added sodium nitrite (0.035 g, 0.5 mmol) as a solution in H$_2$O (3 ml) during 5 minutes. The mixture was allowed to warm to room temperature during 1 hour. Next, potassium iodide (0.24 g, 1.44 mmol) was added as a solution in H$_2$O during 5 minutes. After completion the reaction was diluted with methanol (1.0 ml) and 10% sodium sulfite (6.6 ml) followed by 5N NaOH (3.3 ml) affording a suspension. The resulting solids were filtered, rinsed with H$_2$O, and dried in vacuo to yield 0.17 g (78.7%) of the title compound as a dark brown solid. $^1$H NMR (400 MHz, DMSO-$d_6$) δ ppm 1.29-1.44 (m, 2H) 1.60-2.20 (m, 5H) 2.29 (br. s., 3H) 2.94 (m, 2H) 4.02 (d, J=6.57 Hz, 2H) 6.94 (d, J=8.84 Hz, 1H) 7.59 (d, J=8.34 Hz, 1H) 8.56 (br. s., 1H) 9.00 (br. s., 1H) 12.49 (br. s., 1H). [M+H] calc'd for $C_{18}H_{19}Cl_1N_3O$, 456; found 456.2.

Compound 285

3-(3-chloro-8-((1-methylpiperidin-4-yl)methoxy)-9H-pyrido[2,3-b]indol-5-yl)-N-cyclopropylbenzamide

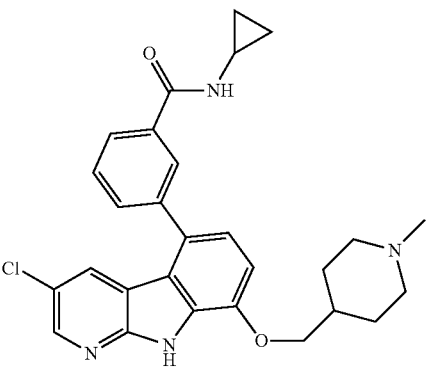

A mixture of compound 284 (0.17 g, 0.37 mmol), 3-(cyclopropylcarbamoyl)phenylboronic acid (152 mg, 0.74 mmol), Pd(PPh$_3$)$_4$ (21.5 mg, 5 mol %), potassium carbonate (0.1 g, 0.74 mmol), degassed DMAc (4 ml) and H$_2$O (1.5 ml) was stirred for 30 minutes at room temperature. Next, the mixture was heated at 90° C. for 1 hour. After completion, the reaction was filtered, rinsed with methanol, and concentrated in vacuo. The crude product was purified by Preparative HPLC to yield 0.048 g (26.5%) of the title compound as an off-white solid. $^1$H NMR (400 MHz, DMSO-$d_6$) δ ppm 0.57 (dd, J=3.79, 2.27 Hz, 2H) 0.69 (dd, J=6.95, 2.40 Hz, 2H) 1.34-1.48 (m, 2H) 1.82-1.97 (m, 5H) 2.19 (s, 3H) 2.85 (m, 3H) 4.08 (d, J=6.57 Hz, 2H) 7.08 (d, J=8.08 Hz, 1H) 7.17 (d, J=8.34 Hz, 1H) 7.59 (d, J=2.53 Hz, 1H) 7.64 (t, J=7.71 Hz, 1H) 7.74 (ddd, J=7.71, 1.39, 1.26 Hz, 1H) 7.94 (dt, J=7.83, 1.39 Hz, 1H) 8.03 (t, J=1.52 Hz, 1H) 8.43 (d, J=2.27 Hz, 1H) 8.54 (d, J=4.04 Hz, 1H) 12.38 (s, 1H). [M+H] calc'd for $C_{28}H_{29}Cl_1N_4O_2$ 489; found, 489.4.

Compound 286

3-chloro-5-(3-(cyclopropylsulfonyl)phenyl)-8-((1-methylpiperidin-4-yl)methoxy)-9H-pyrido[2,3-b]indole

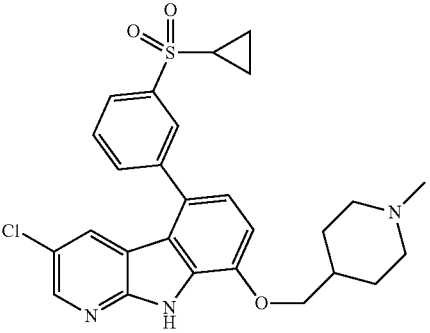

The title compound was prepared using an analogous procedure to that described in the preparation of compound 285. $^1$H NMR (400 MHz, DMSO-d$_6$) δ ppm 1.08-1.21 (m, 4H) 1.45-1.58 (m, 2H) 1.90-2.35 (m, 4H) 2.81 (d, J=4.80 Hz, 3H) 2.97-3.10 (m, 3H) 3.55 (m, 1H) 4.12 (d, J=7.07 Hz, 2H) 7.13-7.17 (m, 1H) 7.21-7.25 (m, 1H) 7.65 (d, J=2.27 Hz, 1H) 7.87 (t, J=7.71 Hz, 1H) 7.97 (ddd, J=7.71, 1.39, 1.26 Hz, 1H) 8.02-8.07 (m, 2H) 8.47 (d, J=2.53 Hz, 1H) 12.43 (s, 1H). [M+H] calc'd for C$_{27}$H$_{28}$ClN$_3$O$_3$S 510; found, 510.2.

Compound 287

5-(3-(ethylsulfonyl)phenyl)-3-fluoro-8-((1-methylpiperidin-4-yl)methoxy)-9H-pyrido[2,3-b]indole

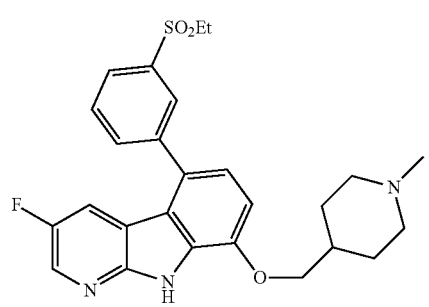

The title compound was prepared using an analogous procedure to that described in the preparation of compound 285. $^1$H NMR (400 MHz, DMSO-d$_6$) δ ppm 1.16 (t, J=7.33 Hz, 3H) 1.42-1.61 (m, 2H) 1.80-2.35 (m, 5H) 2.81 (d, J=4.55 Hz, 3H) 2.94-3.10 (m, 2H) 3.42 (q, J=7.33 Hz, 2H) 3.54 (d, J=11.62 Hz, 2H) 4.12 (d, J=7.07 Hz, 2H) 7.10-7.16 (m, 1H) 7.19-7.24 (m, 1H) 7.43 (dd, J=9.60, 2.78 Hz, 1H) 7.87 (t, J=7.71 Hz, 1H) 7.95-8.06 (m, 4H) 8.47 (dd, J=2.78, 1.52 Hz, 1H) 12.30 (s, 1H). [M+H] calc'd for C$_{26}$H$_{28}$FN$_3$O$_3$S 482; found, 482.4.

Compound 288

4-(3-(benzyloxy)propoxy)-3'-(ethylsulfonyl)-3-iodobiphenyl

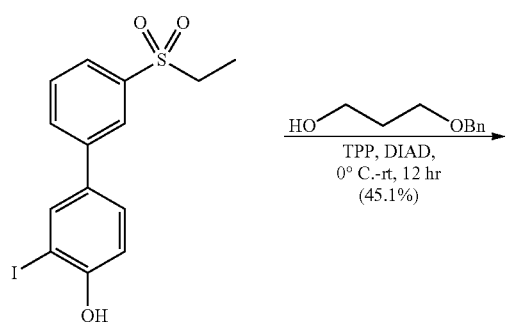

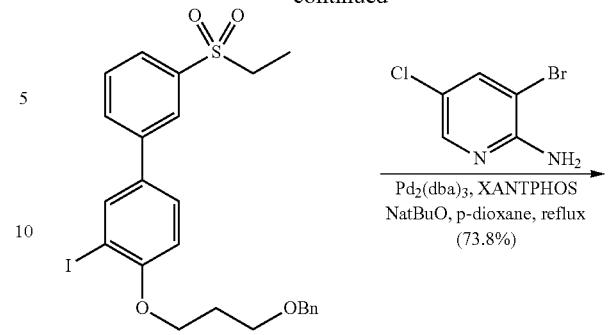

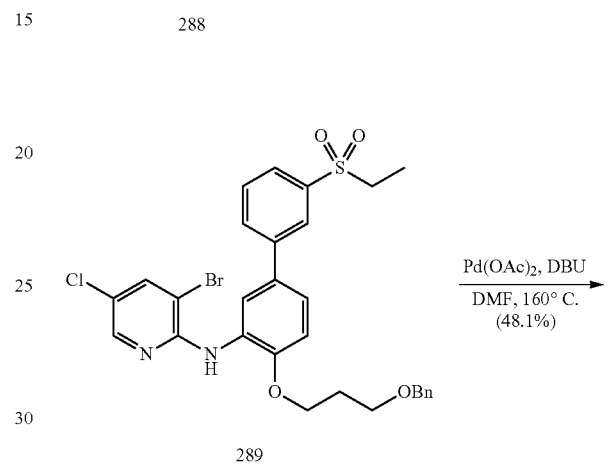

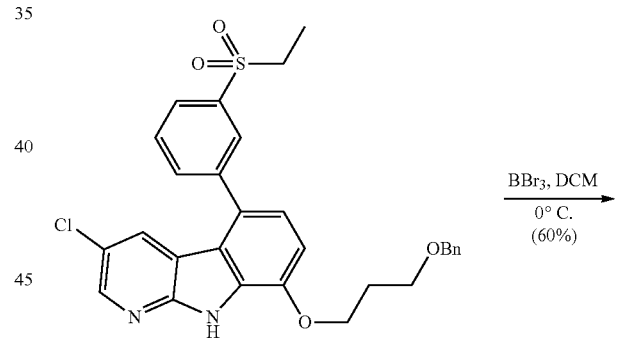

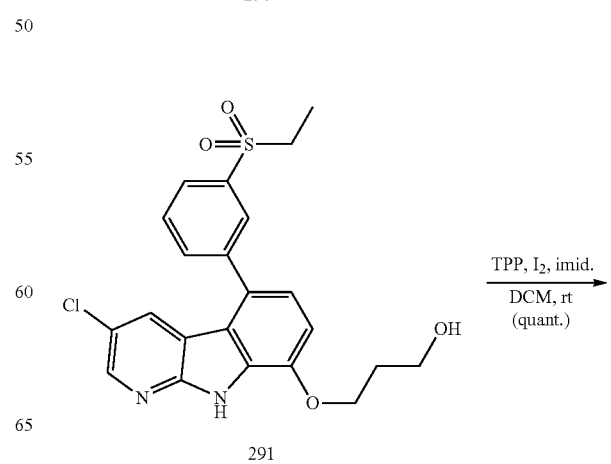

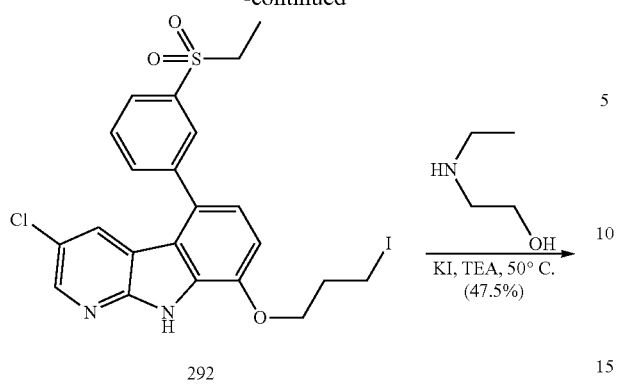

292

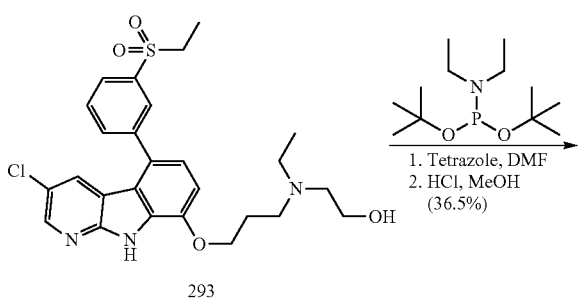

293

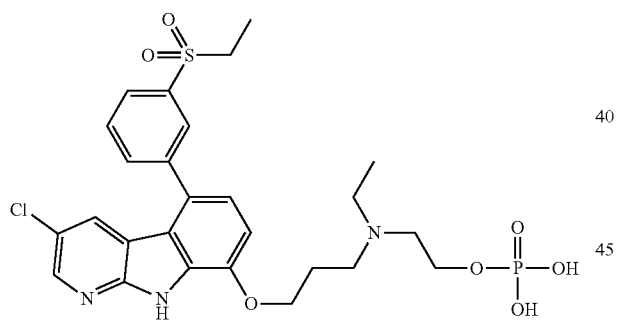

294

To a stirred solution of compound 197 (9.79 g, 25.2 mmol), 3-benzyloxy-1-propanol (5.03 g, 30.3 mmol) and triphenylphosphine (8.6 g, 33 mmol) in benzene (100 mL) was added DIAD (6.35 mL, 33 mmol) at 0° C. during 15 minutes. The reaction mixture was warmed to room temperature over a period of 1 h and further stirred for another 12 h. After completion, the mixture was concentrated in vacuo. The residue was dissolved in CH$_2$Cl$_2$ (10 mL) and purified on silica gel to yield 6.1 g (45.1%) of the title compound. $^1$H NMR (400 MHz, DMSO-d$_6$) δ ppm 1.13 (t, J=7.33 Hz, 3H) 2.01-2.09 (m, 2H) 3.39 (q, J=7.16 Hz, 2H) 3.69 (t, J=6.32 Hz, 2H) 4.19 (t, J=6.06 Hz, 2H) 4.51 (s, 2H) 7.17 (d, J=7.83 Hz, 1H) 7.13 (d, J=8.84 Hz, 1H) 7.23-7.33 (m, 5H) 7.69-7.85 (m, 2H) 8.07 (t, J=1.77 Hz, 1H) 8.01 (dt, J=7.83, 1.39 Hz, 1H). [M+Na] calc'd for C$_{24}$H$_{25}$IO$_4$SNa, 559; found 559.2.

Compound 289

N-(4-(3-(benzyloxy)propoxy)-3'-(ethylsulfonyl)biphenyl-3-yl)-3-bromo-5-chloropyridin-2-amine

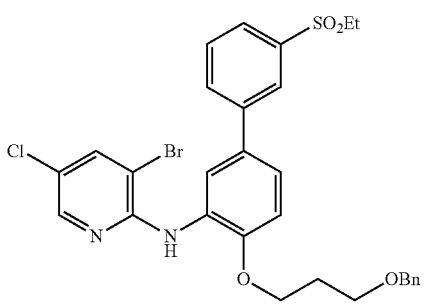

A mixture of Pd(OAc)$_2$ (0.124 g, 5 mol %), xantphos (0.318 g, 5 mol %), and degassed toluene (30 mL) was stirred at 80° C. for 30 minutes. This mixture was added to a reaction flask charged with 3-bromo-5-chloropyridin-2-amine (2.51 g, 12.1 mmol), compound 288 (5.90 g, 11 mmol), Cs$_2$CO$_3$ (7.17 g, 22 mmol), and degassed toluene (30 mL). The mixture was heated at reflux for 5 hours. After completion, the mixture was diluted with EtOAc, washed with H$_2$O (100 mL×1) and brine (100 mL×1). The organic layer was dried (MgSO$_4$), and concentrated in vacuo to yield 5.0 g (73.8%) of the title compound. $^1$H NMR (400 MHz, DMSO-d$_6$) δ ppm 1.15 (t, J=7.33 Hz, 3H) 2.01-2.10 (m, 2H) 3.38 (q, J=7.41 Hz, 2H) 3.62 (t, J=6.32 Hz, 2H) 4.24 (t, J=6.06 Hz, 2H) 4.47 (s, 2H) 7.20-7.33 (m, 5H) 7.42 (dd, J=8.59, 2.27 Hz, 1H) 7.75 (t, J=7.83 Hz, 1H) 7.85 (t, J=1.26 Hz, 1H) 7.83 (d, J=1.26 Hz, 1H) 7.97-8.02 (m, 2H) 8.05 (t, J=1.77 Hz, 1H) 8.22 (d, J=0.51 Hz, 1H) 8.23-8.25 (m, 1H) 8.62 (d, J=2.27 Hz, 1H). [M+H] calc'd for C$_{29}$H$_{28}$BrClN$_2$O$_4$S, 617; found 617.0.

Compound 290

8-(3-(benzyloxy)propoxy)-3-chloro-5-(3-(ethylsulfonyl)phenyl)-9H-pyrido[2,3-b]indole

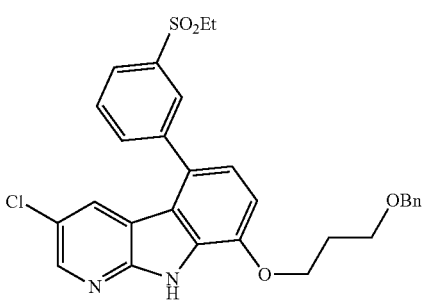

A mixture of compound 289 (4.99 g, 8.1 mmol), Pd(OAc)$_2$ (0.182 g, 10 mol %), DBU (3.63 mL, 24.3 mmol) and DMF (40 mL) was stirred overnight at 155° C. After completion the mixture was filtered through celite and diluted with CH$_2$Cl$_2$. The organic layer was washed with H$_2$O and brine. The organic layer was dried (MgSO$_4$) and concentrated in vacuo.

The residue was dissolved in CH$_2$Cl$_2$ (7 mL) and purified on silica gel to yield 2.1 g (48.1%) of the title compound. $^1$H NMR (400 MHz, DMSO-d$_6$) δ ppm 1.18 (t, J=7.33 Hz, 3H) 2.11-2.19 (m, 2H) 3.42 (q, J=7.41 Hz, 2H) 3.78 (t, J=6.32 Hz, 2H) 4.34 (t, J=6.06 Hz, 2H) 4.53 (s, 2H) 7.12-7.17 (m, 1H) 7.20-7.35 (m, 6H) 7.63 (d, J=2.27 Hz, 1H) 7.87 (t, J=7.71 Hz, 1H) 7.97-8.04 (m, 2H) 8.07 (t, J=1.64 Hz, 1H) 8.45 (d, J=2.27 Hz, 1H) 12.42 (s, 1H). [M+H] calc'd for C$_{29}$H$_{27}$ClN$_2$O$_4$S, 535; found 535.4.

Compound 291

3-(3-chloro-5-(3-(ethylsulfonyl)phenyl)-9H-pyrido[2,3-b]indol-8-yloxy)propan-1-ol

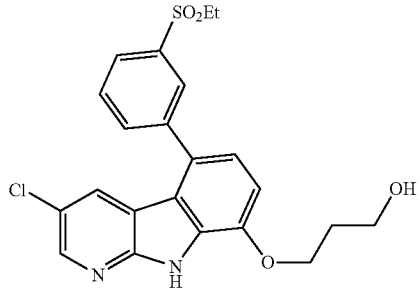

To a mixture of compound 290 (1.862 g, 3.48 mmol) and CH$_2$Cl$_2$ (35 mL) was added BBr$_3$ as a 1M solution in CH$_2$Cl$_2$ (3.48 mL, 3.48 mmol) at 0° C. After completion, the mixture was quenched with saturated NaHCO$_3$ (125 mL) and the aqueous layer was extracted with CH$_2$Cl$_2$ (25 mL×3). The organic extracts were combined, washed with brine, dried (MgSO$_4$), and concentrated in vacuo. The residue was dissolved in CH$_2$Cl$_2$ and purified on silica gel to yield 0.925 g (60%) of the title compound. $^1$H NMR (400 MHz, DMSO-d$_6$) δ ppm 1.18 (t, J=7.33 Hz, 3H) 1.98-2.05 (m, 2H) 3.42 (q, J=7.33 Hz, 2H) 3.72 (q, J=6.06 Hz, 2H) 4.32 (t, J=6.32 Hz, 2H) 4.58 (t, J=5.05 Hz, 1H) 7.13-7.17 (m, 1H) 7.20-7.24 (m, 1H) 7.63 (d, J=2.27 Hz, 1H) 7.87 (t, J=7.71 Hz, 1H) 8.00 (m, 2 H) 7.97-8.04 (m, 1H) 8.06 (t, J=1.64 Hz, 1H) 8.45 (d, J=2.27 Hz, 1H) 12.42 (s, 1H). [M+H] calc'd for C$_{22}$H$_{21}$ClN$_2$O$_4$S, 445; found 445.3.

In addition, the title compound was prepared from Compound 219 by using an analogous procedure to that outlined in the preparation of Compound 216. $^1$H NMR (400 MHz, Methanol-d$_4$) δ 8.45 (s, 1H) 8.06 (m, 1H) 8.01 (m, 2H) 7.87 (t, J=8.0 Hz, 1H) 7.63 (s, 1H) 7.23 (d, J=8.32 Hz, 1H) 7.16 (d, J=8.32 Hz, 1H) 4.34 (t, J=6.32 Hz, 2H) 3.72 (t, J=6.32 Hz, 2H) 3.43 (q, J=7.32 Hz, 2H) 2.02 (m, 2H) 1.18 (t, J=7.32 Hz, 3H). [M+H] calc'd for C$_{22}$H$_{22}$ClN$_2$O$_4$S, 445; found, 445.

Compound 292

3-chloro-5-(3-(ethylsulfonyl)phenyl)-8-(3-iodopropoxy)-9H-pyrido[2,3-b]indole

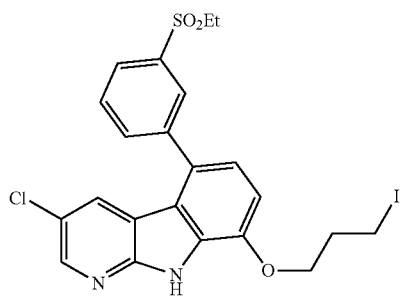

The title compound was synthesized using an analogous procedure to that described in the preparation of compound 268. $^1$H NMR (400 MHz, DMSO-d$_6$) δ ppm 1.18 (t, J=7.33 Hz, 3H) 2.29-2.37 (m, 2H) 3.42 (q, J=7.33 Hz, 2H) 3.70 (t, J=6.95 Hz, 2H) 4.27 (t, J=5.68 Hz, 2H) 7.15 (d, J=8.08 Hz, 1H) 7.21-7.25 (m, 1H) 7.64 (d, J=2.53 Hz, 1H) 7.88 (t, J=7.71 Hz, 1H) 7.98-8.03 (m, 2H) 8.07 (t, J=1.52 Hz, 1H) 8.46 (d, J=2.27 Hz, 1H) 12.47 (s, 1H). [M+H] calc'd for C$_{22}$H$_{20}$ClN$_2$O$_3$S, 555.0; found 555.3.

Compound 293

2-((3-(3-chloro-5-(3-(ethylsulfonyl)phenyl)-9H-pyrido[2,3-b]indol-8-yloxy)propyl)(ethyl)amino)ethanol

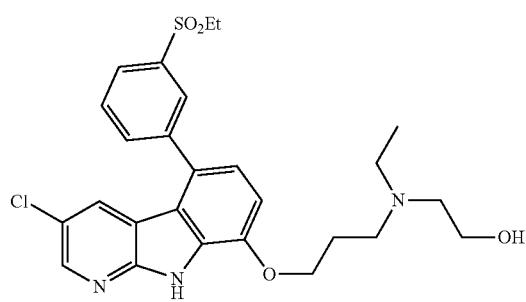

The title compound was synthesized using an analogous procedure to that described in the preparation of compound 269. $^1$H NMR (400 MHz, DMSO-d$_6$) δ ppm 0.94-1.08 (m, 2H) 1.18 (t, J=7.33 Hz, 3H) 1.95-2.05 (m, 2H) 2.55-2.68 (m, 3H) 2.70-2.88 (m, 2H) 3.42 (q, J=7.33 Hz, 3H) 3.50 (m, 2H) 4.29 (t, J=6.06 Hz, 2H) 7.13-7.17 (m, 1H) 7.19-7.24 (m, 1H) 7.63 (d, J=2.53 Hz, 1H) 7.87 (t, J=7.71 Hz, 1H) 7.98-8.03 (m, 2H) 8.06 (t, J=1.64 Hz, 1H) 8.45 (d, J=2.27 Hz, 1H) 12.43 (br. s., 1H). [M+H] calc'd for C$_{26}$H$_{30}$ClN$_3$O$_4$S, 516.0; found 516.3.

Compound 294

2-((3-(3-chloro-5-(3-(ethylsulfonyl)phenyl)-9H-pyrido[2,3-b]indol-8-yloxy)propyl)(ethyl)amino)ethyl dihydrogen phosphate

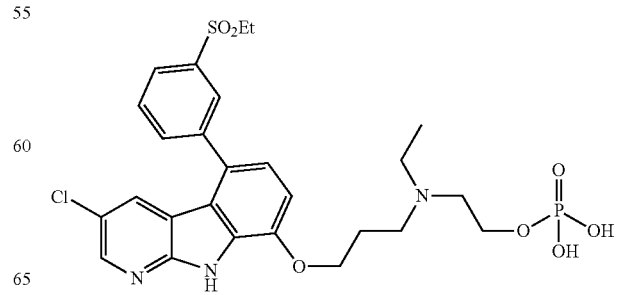

The title compound was synthesized using an analogous procedure to that described in the preparation of compound 272. ¹H NMR (400 MHz, DMSO-d₆) δ ppm 1.18 (t, J=7.33 Hz, 3H) 1.32 (t, J=7.20 Hz, 3H) 2.25-2.34 (m, 2H) 3.30 (q, J=7.33 Hz, 2 H) 3.42 (q, J=7.33 Hz, 2H) 3.46-3.50 (m, 2H) 3.50-3.57 (m, 2H) 4.25-4.30 (m, 2H) 4.35 (t, J=5.43 Hz, 2H) 7.15-7.19 (m, 1H) 7.21-7.25 (m, 1H) 7.64 (d, J=2.53 Hz, 1H) 7.88 (t, J=7.83 Hz, 1H) 7.98-8.04 (m, 2H) 8.06 (t, J=1.64 Hz, 1H) 8.47 (s, 1H) 12.50 (s, 1H). [M+H] calc'd for C₂₆H₃₁ClN₃O₇PS 596; found 596.3.

Compound 295

3-(8-(3-(dimethylamino)propoxy)-3-methyl-9H-pyrido[2,3-b]indol-5-yl)-N-ethylbenzenesulfonamide

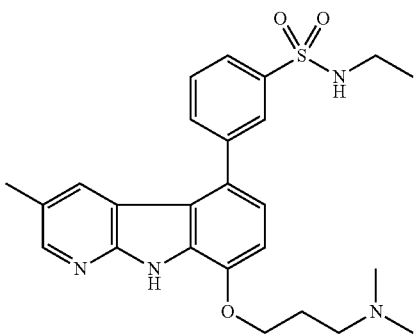

The title compound was synthesized from Compound 191 using an analogous procedure to that outlined in the preparation of Compound 177. ¹H NMR (400 MHz, DMSO-d₆) δ ppm 1.02 (t J=7.2 Hz, 3H) 2.21-2.24 (m, 2H) 2.26 (m, 5H) 2.47 (s, 3H) 3.32 (q, J=7.2 Hz, 2H) 3.47-3.52 (m, 2H) 4.29 (t, J=5.43 Hz, 2H) 7.05 (d, J=8.08 Hz, 1 H) 7.13 (d, J=8.08 Hz, 1H) 7.54 (s, 1H) 7.62 (t, J=7.71 Hz, 1H) 7.72 (d, J=7.58 Hz, 1 H) 7.93 (d, J=7.83 Hz, 1H) 8.03 (s, 1H) 8.28 (s, 1H) 8.55 (d, J=4.04 Hz, 1H) 9.60 (br. s., 1H) 11.93 (s, 1H); [M+H] calc'd for C₂₅H₃₀N₄O₃S, 467.2; found, 467.2.

Compound 296

3-(8-(3-(dimethylamino)propoxy)-3-methyl-9H-pyrido[2,3-b]indol-5-yl)-N,N-dimethylbenzenesulfonamide

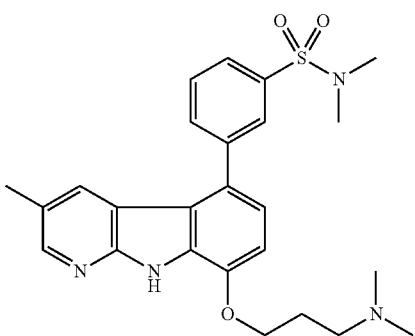

The title compound was synthesized from Compound 191 using an analogous procedure to that outlined in the preparation of Compound 177. ¹H NMR (400 MHz, DMSO-d₆) δ ppm 2.21-2.24 (m, 2H) 2.26 (s, 3H) 2.66 (s, 6H) 2.88 (s, 3H) 2.89 (s, 3 H) 3.47-3.52 (m, 2H) 4.29 (t, J=5.43 Hz, 2H) 7.05 (d, J=8.08 Hz, 1H) 7.13 (d, J=8.08 Hz, 1H) 7.54 (s, 1H) 7.62 (t, J=7.71 Hz, 1H) 7.72 (d, J=7.58 Hz, 1H) 7.93 (d, J=7.83 Hz, 1H) 8.03 (s, 1H) 8.28 (s, 1H) 8.55 (d, J=4.04 Hz, 1H) 9.60 (br. s., 1H) 11.93 (s, 1 H); [M+H] calc'd for C₂₅H₃₀N₄O₃S, 467.2; found, 467.2.

Compound 297

(S)-3-(3-chloro-5-(3-(ethylsulfonyl)phenyl)-9H-pyrido[2,3-b]indol-8-yloxy)propyl 2-aminopropanoate

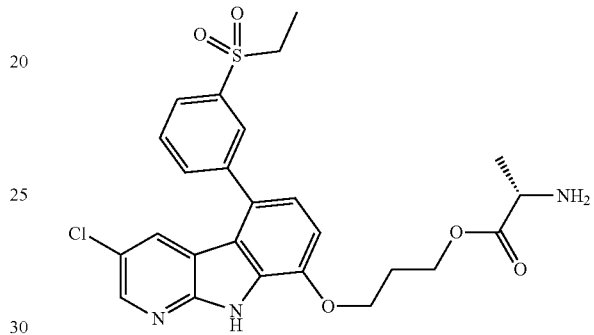

The title compound was prepared from Compound 291 by using an analogous procedure to that outlined in the preparation of Compound 65. ¹H NMR (400 MHz, Methanol-d₄) δ 8.36 (s, 1H) 8.12 (s, 1H) 8.08 (m, 1H) 7.97 (m, 1H) 7.88 (t, J=7.84 Hz, 1H) 7.69 (s, 1H) 7.21 (d, J=8.32 Hz, 1H) 7.16 (d, J=8.32 Hz, 1H) 4.65 (m, 2H) 4.42 (t, J=6.08 Hz, 2H) 4.14 (q, J=7.32 Hz, 1H) 3.36 (q, J=7.6 Hz, 2H) 2.39 (m, 2H) 1.55 (d, J=7.32 Hz, 3H) 1.33 (t, J=7.6 Hz, 3H). [M+H] calc'd for C₂₅H₂₇ClN₃O₅S, 516; found, 516.

Compound 298

2-((3-(3-chloro-5-(3-(cyclopropylsulfonyl)phenyl)-9H-pyrido[2,3-b]indol-8-yloxy)propyl)(ethyl)amino)ethanol

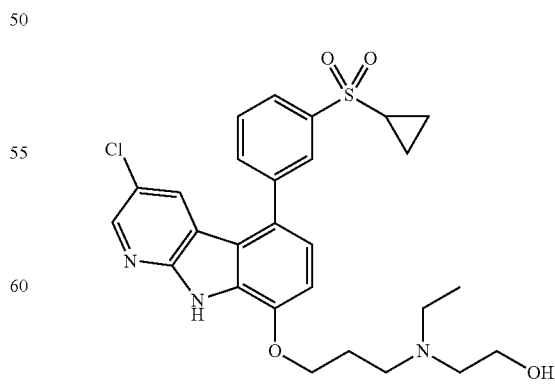

The title compound was synthesized using an analogous procedure to that described in the preparation of compound 269. ¹H NMR (400 MHz, DMSO-d₆) δ ppm 0.85 (br. s., 2H) 0.97-1.20 (m, 8H) 1.23 (s, 1H) 1.86-2.09 (m, 2H) 2.94-3.08 (m, 1 H) 3.47 (br. s., 2H) 4.30 (br. s., 2H) 7.10-7.18 (m, 1H) 7.18-7.26 (m, 1H) 7.64 (d, J=2.27 Hz, 1H) 7.87 (t, J=7.71 Hz, 1H) 7.93-8.00 (m, 1H) 8.06 (s, 1H) 8.03 (d, J=7.83 Hz, 1H) 8.46 (d, J=2.02 Hz, 1H). ESI-MS: m/z 528.3 (M+H)⁺.

Compound 299

2-((3-(3-chloro-5-(3-(cyclopropylsulfonyl)phenyl)-9H-pyrido[2,3-b]indol-8-yloxy)propyl)(ethyl)amino)ethyl dihydrogen phosphate

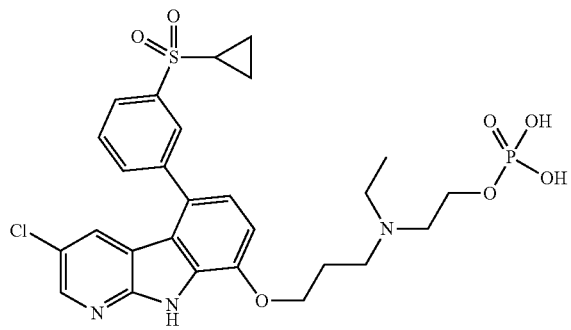

The title compound was synthesized using an analogous procedure to that described in the preparation of compound 272. [M+H] calc'd for C₂₇H₃₁ClN₃O₇PS 608.5, found 608.3.

Compound 300

1-(3-(5-(3-(cyclopropylsulfonyl)phenyl)-3-methyl-9H-pyrido[2,3-b]indol-8-yloxy)propyl)piperidin-4-ol

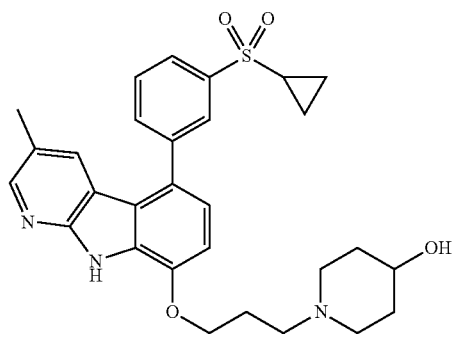

The title compound was synthesized following the same procedure as depicted in the synthesis of compound 270. ¹H NMR (400 MHz, DMSO-d₆) δ ppm 0.85 (br. s., 2 H) 0.97-1.20 (m, 8H) 1.23 (s, 1H) 1.86-2.09 (m, 2H) 2.94-3.08 (m, 1H) 3.47 (br. s., 2H) 4.30 (br. s., 2H) 7.10-7.18 (m, 1H) 7.18-7.26 (m, 1H) 7.64 (d, J=2.27 Hz, 1H) 7.87 (t, J=7.71 Hz, 1H) 7.93-8.00 (m, 1H) 8.06 (s, 1H) 8.03 (d, J=7.83 Hz, 1H) 8.46 (d, J=2.02 Hz, 1H). ESI-MS: m/z 520.1 (M+H)⁺.

Compound 301

8-(3-(1H-imidazol-1-yl)propoxy)-3-chloro-5-(3-(ethylsulfonyl)phenyl)-9H-pyrido[2,3-b]indole

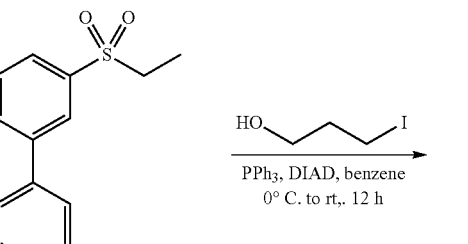

The title compound was isolated as a byproduct in the preparation of compound 293. ¹H NMR (400 MHz, DMSO-d₆) δ ppm 1.18 (t, J=7.45 Hz, 3H) 2.28-2.37 (m, 2H) 3.40 (q, J=7.58 Hz, 2H) 4.16 (t, J=5.68 Hz, 2H) 4.46 (t, J=6.95 Hz, 2H) 7.06-7.22 (m, 3H) 7.40 (br. s., 1H) 7.65 (d, J=2.27 Hz, 1H) 7.88 (t, J=7.71 Hz, 1H) 7.98-8.09 (m, 4 H) 8.48 (d, J=2.27 Hz, 1H) 12.50 (s, 1H). [M+H] calc'd for C₂₅H₂₃ClN₄O₃S, 495.0; found 495.3.

Compound 302

3'-(ethylsulfonyl)-3-iodo-4-(3-iodopropoxy)biphenyl

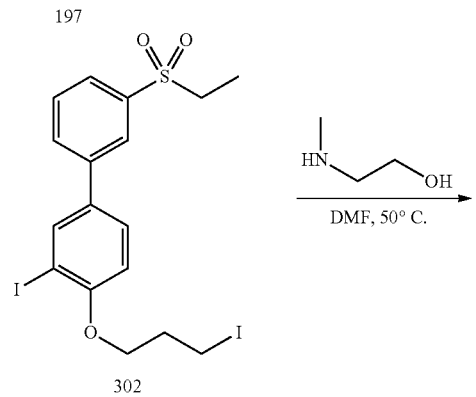

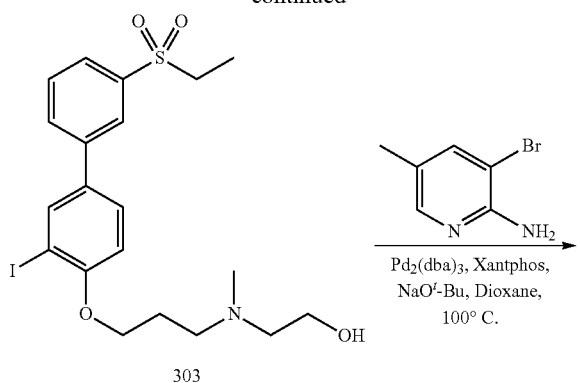

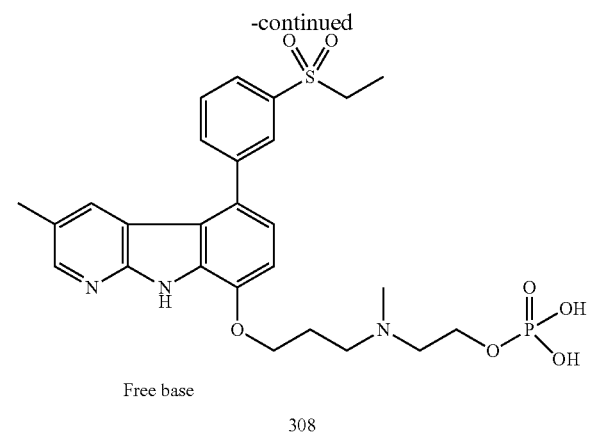

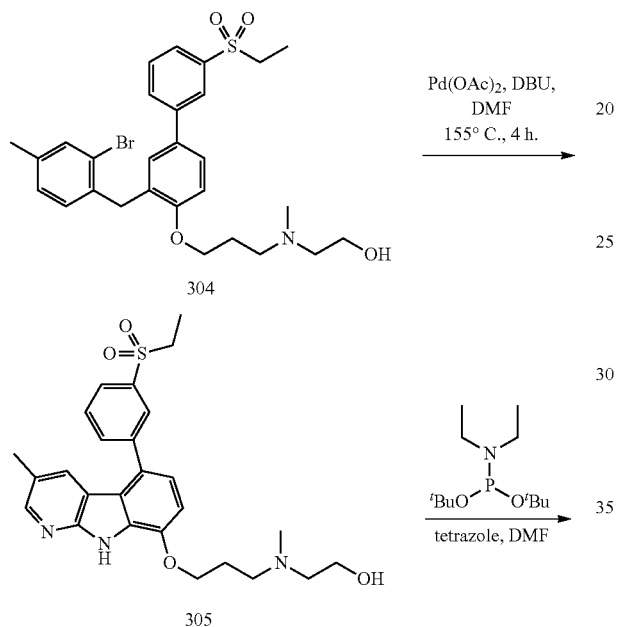

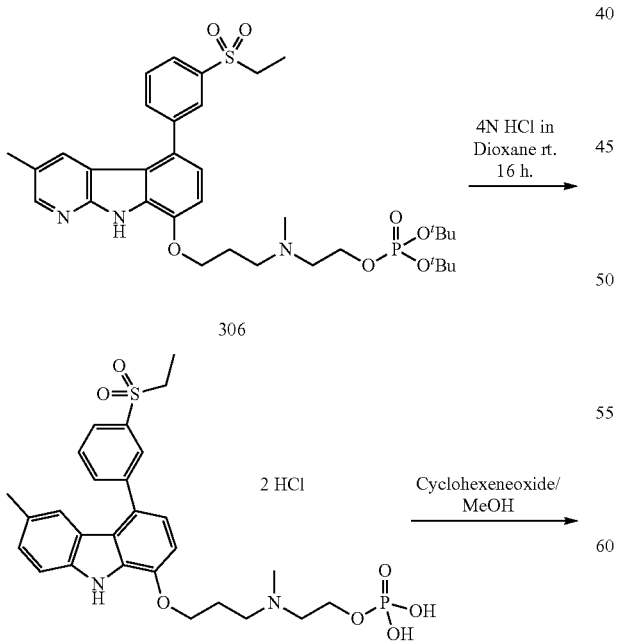

The title compound 302 was synthesized via Mitsunobu reaction using 1-iodopropanol and 197, following the method as described earlier for compound 198. $^1$H NMR (400 MHz, CHLOROFORM-d) δ ppm 1.32 (t, J=7.33 Hz, 3H) 2.35 (p, J=6.06 Hz, 2H) 3.17 (q, J=7.49 Hz, 2H) 3.51 (t, J=6.57 Hz, 2H) 4.16 (t, J=5.68 Hz, 2H) 6.92 (d, J=8.4 Hz, 1H) 7.56 (dd, J=2.4, 8.8 Hz, 1H) 7.63 (t, J=8.0 Hz, 1H) 7.80 (br. d, J=8.1 Hz, 1H) 7.86 (br. d, J=8.1 Hz, 1H) 8.03-8.05 (m, 2H).

Compound 303

2-(3-(3'-(ethylsulfonyl)-3-iodobiphenyl-4-yloxy)propyl)(methyl)amino)-ethanol

The title compound was synthesized following the same procedure as depicted in the synthesis of compound 269. $^1$H NMR (400 MHz, CHLOROFORM-d) δ ppm 1.32 (t, J=7.45 Hz, 3H) 2.06 (t, J=6.82 Hz, 2H) 2.33 (s, 3H) 2.60 (t, J=5.2 Hz, 2H) 2.73 (t, J=7.07 Hz, 2H) 3.17 (q, J=7.58 Hz, 2H) 3.62 (t, J=5.56 Hz, 2H) 4.14 (t, J=6.06 Hz, 2H) 6.89 (d, J=8.34 Hz, 1H) 7.55 (dd, J=8.59, 2.27 Hz, 1H) 7.63 (t, J=7.83 Hz, 1H) 7.81 (ddd, J=7.83, 1.89, 1.14 Hz, 1H) 7.85 (ddd, J=7.83, 1.77, 1.01 Hz, 1H) 8.04 (d, J=2.27 Hz, 1H) 8.05 (t, J=1.64 Hz, 1H). [M+H] calc'd for $C_{20}H_{27}INO_4S$, 504.06; found 504.1.

Compound 304

2-((3-(3-(3-bromo-5-methylpyridin-2-ylamino)-3'-(ethylsulfonyl)biphenyl-4-yloxy)propyl)(methyl)amino)ethanol

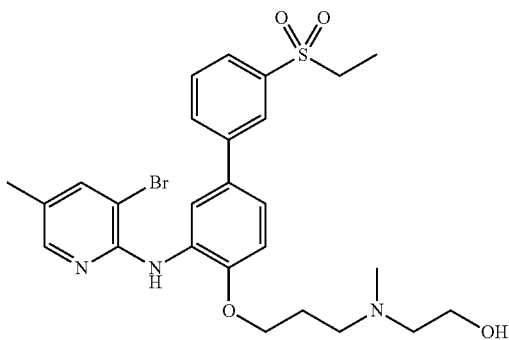

The title compound was synthesized following the same procedure as depicted in the synthesis of compound 265. $^1$H NMR (400 MHz, DMSO-d$_6$) δ ppm 1.15 (td, J=7.33, 1.52 Hz, 3H) 1.95 (t, J=6.57 Hz, 2H) 2.21 (s, 3H) 2.22 (s, 3H) 2.42 (t, J=6.19 Hz, 2H) 2.57 (t, J=6.95 Hz, 2H) 3.38 (dd, J=7.45, 1.39 Hz, 2H) 3.46 (q, J=6.6 Hz, 1H) 4.20 (t, J=5.68 Hz, 2H) 4.36 (br. s., 1H) 7.18 (d, J=8.59 Hz, 1H) 7.34 (d, J=8.59 Hz, 1H) 7.75 (t, J=7.07 Hz, 1H) 7.84 (dd, J=7.6, 1.01 Hz, 1H) 7.89 (d, J=11.37 Hz, 2H) 7.98 (dd, J=7.71, 1.14 Hz, 1H) 8.08 (s, 1H) 8.04 (d, J=1.26 Hz, 1H) 8.86 (d, J=1.77 Hz, 1H). [M+H] calc'd for C$_{26}$H$_{33}$BrN$_3$O$_4$S, 562.13; found 562.2.

Compound 305

2-(3-(5-(3-(ethylsulfonyl)phenyl)-3-methyl-9H-pyrido[2,3-b]indol-8-yloxy)propyl)(methyl)amino)ethanol

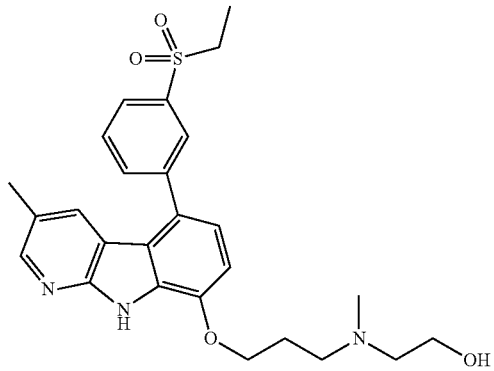

The title compound was synthesized following the same procedure as depicted in the synthesis of compound 266. $^1$H NMR (400 MHz, DMSO-d$_6$) δ ppm 1.17 (t, J=7.33 Hz, 3H) 2.27 (m, 5H) 2.89 (d, J=5.05 Hz, 3H) 3.15-3.20 (m, 2H) 3.41 (q, J=7.33 Hz, 2 H) 3.44-3.57 (m, 2H) 3.80 (t, J=5.31 Hz, 2H) 4.31 (t, J=6.1 Hz, 2H) 7.09-7.12 (m, 1 H) 7.14-7.17 (m, 1H) 7.56 (d, J=1.52 Hz, 1H) 7.86 (t, J=7.71 Hz, 1H) 7.99 (dd, J=12.38, 7.83 Hz, 1H) 7.99 (dd, J=9.47, 7.71 Hz, 1H) 8.07 (t, J=1.77 Hz, 1H) 8.30 (d, J=2.02 Hz, 1H) 9.35 (br. s., 1H) 11.99 (s, 1H). [M+H] calc'd for C$_{26}$H$_{32}$N$_3$O$_4$S, 482.2; found 482.2.

Compound 306 di-tert-butyl 2-((3-(5-(3-(ethylsulfonyl)phenyl)-3-methyl-9H-pyrido[2,3-b]indol-8-yloxy)propyl)(methyl)amino)ethyl phosphate

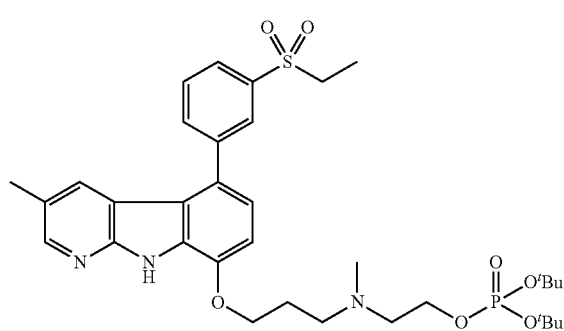

The title compound was synthesized following the same procedure as depicted in the synthesis of compound 271.

Compound 307

2-(3-(5-(3-(ethylsulfonyl)phenyl)-3-methyl-9H-pyrido[2,3-b]indol-8-yloxy)propyl)(methyl)amino)ethyl dihydrogen phosphate, dihydrochloride

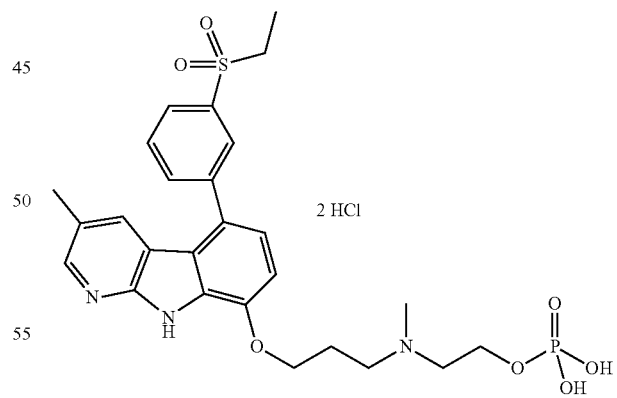

The title compound was synthesized following the same procedure as depicted in the synthesis of compound 272. $^1$H NMR (400 MHz, DMSO-d$_6$) δ ppm 1.17 (t, J=7.33 Hz, 3H) 2.28 (m, 5H) 2.91 (s, 3H) 3.41 (q, J=7.33 Hz, 2H) 3.48 (br. m., 2H) 3.56 (br. m., 2H) 4.27 (ddd, J=7.20, 5.18, 5.05 Hz, 2H) 4.32 (t, J=5.43 Hz, 2H) 7.10-7.13 (m, 1 H) 7.15-7.19 (m, 1H) 7.59 (d, J=1.77 Hz, 1H) 7.86 (t, J=7.83 Hz, 1H) 8.01 (t, J=1.52

Hz, 1H) 8.08 (t, J=1.77 Hz, 1H) 8.30 (d, J=1.77 Hz, 1H) 12.18 (br. s., 1H). [M+H] calc'd for $C_{26}H_{33}N_3O_7PSS$, 562.2; found 562.2.

Compound 308

2-((3-(5-(3-(ethylsulfonyl)phenyl)-3-methyl-9H-pyrido[2,3-b]indol-8-yloxy)propyl)(methyl)amino)ethyl dihydrogen phosphate Compound 307 (181 mg, 0.285 mmol) was dissolved in MeOH (3.5 mL) and treated with cyclohexeneoxide (0.57 mL, 5.7 mmol) at room temperature. The solution was stirred at ambient temperature for 48 h. during which time a white solid precipitated. The reaction mixture was diluted with ether (5 mL) and the solid was recovered by filtration, washed with ether and dried in vacuo to give the title compound as white solid (150 mg, 94%). $^1$H NMR (400 MHz, DMSO-$d_6$) δ ppm 1.17 (t, J=7.33 Hz, 3H) 2.20-2.29 (m, 2H) 2.26 (s, 3H) 2.78 (s, 3H) 3.25 (br. m., 2H) 3.34-3.44 (m, 4H) 4.03 (dd, J=13.26, 6.95 Hz, 2H) 4.31 (t, J=5.68 Hz, 2H) 7.07-7.16 (m, 2H) 7.55 (d, J=1.26 Hz, 1 H) 7.85 (t, J=7.71 Hz, 1H) 7.98 (ddd, J=7.14, 5.62, 1.64 Hz, 2H) 8.06-8.11 (m, 1H) 8.28 (d, J=2.02 Hz, 1H) 12.35 (br. s., 1H). [M+H] calc'd for $C_{26}H_{33}N_3O_7PS$, 562.2; found 562.2.

Compound 309

(S)-2-((4-chloro-2-iodophenoxy)methyl)oxirane

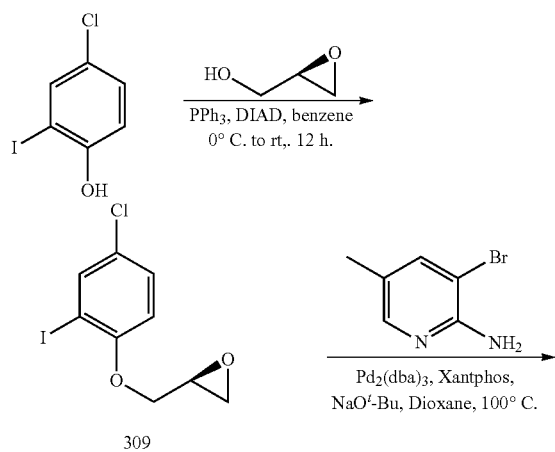

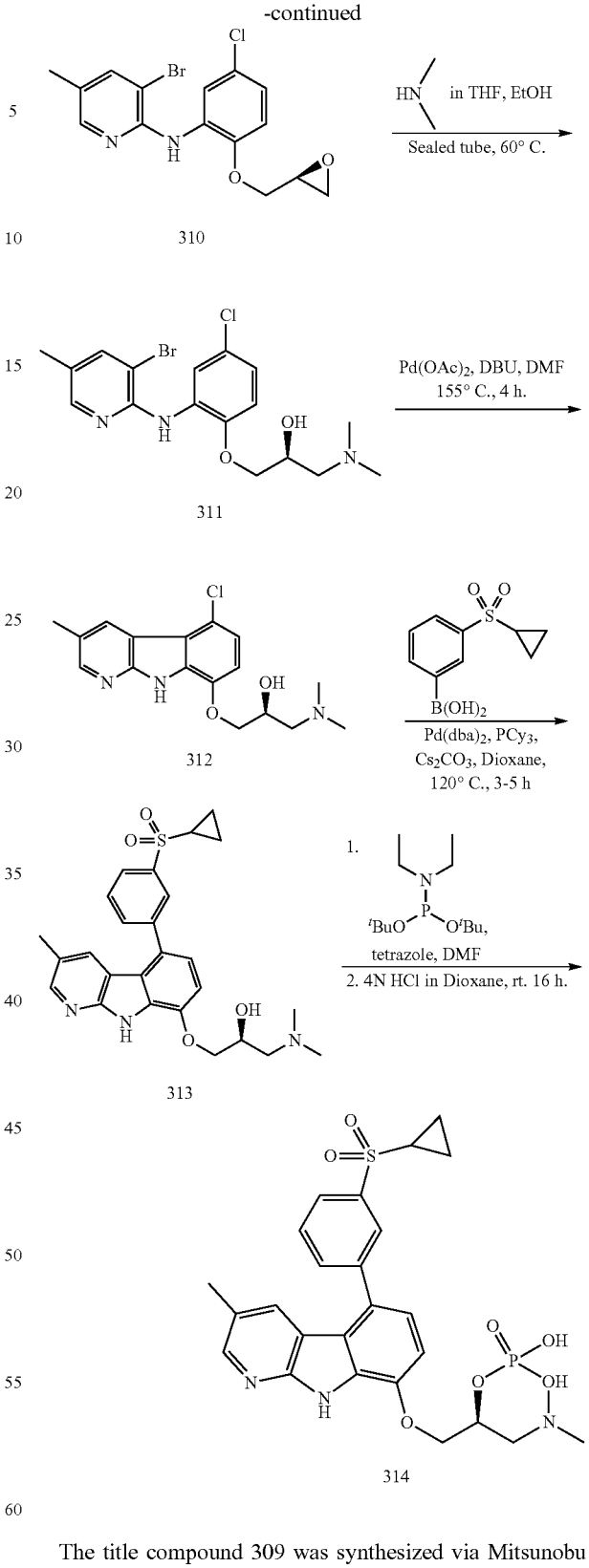

The title compound 309 was synthesized via Mitsunobu reaction using (R)-(+)-glycidol and 4-chloro-2-iodophenol, following the method as described earlier for compound 198. $^1$H NMR (400 MHz, CHLOROFORM-d) δ ppm 2.88 (dd, J=2.8, 5.2 Hz, 1H) 2.91 (dd, J=4.8, 5.2 Hz, 1H) 3.38-3.41 (m, 1H) 4.02 (dd, J=11.24, 5.18 Hz, 1H) 4.30 (dd, J=11.12, 2.78

Hz, 1H) 6.77 (d, J=8.84 Hz, 1H) 7.27 (dd, J=8.59, 2.53 Hz, 1H) 7.76 (d, J=2.53 Hz, 1H). [M+H] calc'd for $C_9H_9ClIO_2$, 310.9; found 310.9.

Compound 310

(S)-3-bromo-N-(5-chloro-2-(oxiran-2-ylmethoxy)phenyl)-5-methylpyridin-2-amine

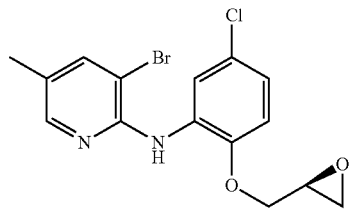

The title compound was synthesized following the same procedure as depicted in the synthesis of compound 265. $^1$H NMR (400 MHz, CHLOROFORM-d) δ ppm 2.26 (s, 3H) 2.85 (dd, J=4.93, 2.65 Hz, 1H) 2.95 (t, J=4.55 Hz, 1H) 3.43 (ddd, J=3.85, 3.03, 2.72 Hz, 1H) 4.06 (dd, J=10.86, 5.56 Hz, 1H) 4.35 (dd, J=10.99, 2.91 Hz, 1H) 6.79-6.83 (m, 1H) 6.87 (d, J=2.53 Hz, 1H) 7.63 (d, J=2.02 Hz, 1H) 7.83 (s, 1H) 8.07 (d, J=1.77 Hz, 1H) 8.73 (d, J=2.53 Hz, 1H). [M+H] calc'd for $C_{15}H_{15}BrClN_2O_2$, 368.99; found 369.2.

Compound 311

(S)-1-(2-(3-bromo-5-methylpyridin-2-ylamino)-4-chlorophenoxy)-3-(dimethylamino)propan-2-ol

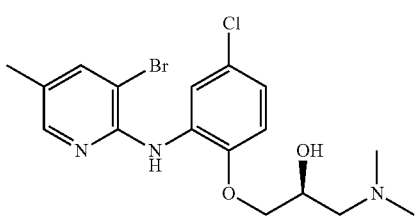

To a suspension of compound 310 (708 mg, 1.92 mmol) in EtOH (8 mL) was added dimethyl amine (2.87 mL, 5.75 mmol, 2 M solution in THF) and the resulting mixture was heated in a sealed tube at 60° C. for 4 h. After completion of the reaction the solvents were removed in vacuo and the crude mass was purified by flash chromatography to provide compound 311 (583 mg, 91%). $^1$H NMR (400 MHz, DMSO-d$_6$) δ ppm 2.18 (s, 6H) 2.22 (s, 3H) 2.38 (dd, J=12.1, 6.57 Hz, 1H) 2.47 (d, J=5.81 Hz, 1H) 3.94-4.03 (m, 2H) 4.08 (dd, J=3.54, 9.6 Hz, 1H) 4.94 (d, J=4.29 Hz, 1H) 6.95 (dd, J=8.34, 2.27 Hz, 1 H) 7.05 (d, J=8.59 Hz, 1H) 7.91 (d, J=2.02 Hz, 1H) 7.94 (s, 1H) 8.13 (d, J=2.02 Hz, 1 H) 8.57 (d, J=2.78 Hz, 1H). [M+H] calc'd for $C_{17}H_{22}BrClN_3O_2$, 414.1; found 414.2.

Compound 312

(S)-1-(5-chloro-3-methyl-9H-pyrido[2,3-b]indol-8-yloxy)-3-(dimethylamino)propan-2-ol

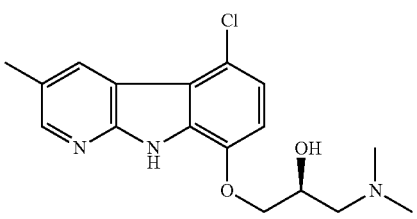

The title compound was synthesized following the same procedure as depicted in the synthesis of compound 266. $^1$H NMR (400 MHz, DMSO-d$_6$) δ ppm 2.22 (s, 6H) 2.39 (dd, J=12.25, 5.94 Hz, 1H) 2.48 (s, 3H) 2.55 (dd, J=12.4, 6.4 Hz, 1H) 3.96-4.08 (m, 2H) 4.15-4.22 (m, 1H) 4.88 (br. s., 1H) 7.03 (d, J=8.34 Hz, 1H) 7.14 (d, J=8.34 Hz, 1H) 8.36 (d, J=1.77 Hz, 1H) 8.50 (s, 1H) 12.12 (s, 1H). [M+H] calc'd for $C_{17}H_{21}ClN_3O_2$, 334.1; found 334.4.

Compound 313

(S)-1-(5-(3-(cyclopropylsulfonyl)phenyl)-3-methyl-9H-pyrido[2,3-b]indol-8-yloxy)-3-(dimethylamino)propan-2-ol

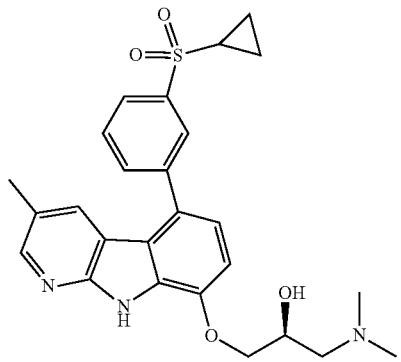

The title compound was synthesized following the same procedure as depicted in the synthesis of compound 270. $^1$H NMR (400 MHz, DMSO-d$_6$) δ ppm 1.06-1.1 (m, 2H) 1.13-1.18 (m, 2H) 2.24 (s, 6H) 2.28 (s, 3H) 2.45 (m, 1H) 2.56 (m, 1H) 3.02 (dd, J=12.88, 3.03 Hz, 1H) 4.02-4.12 (m, 2H) 4.25 (br. d, J=6.06 Hz, 1H) 4.93 (d, J=4.55 Hz, 1H) 7.06-7.10 (m, 1H) 7.11-7.16 (m, 1H) 7.59 (s, 1H) 7.84 (t, J=7.83 Hz, 1H)

7.94-8.01 (m, 2H) 8.09 (t, J=1.64 Hz, 1H) 8.29 (d, J=2.02 Hz, 1H) 12.02 (s, 1H). [M+H] calc'd for $C_{26}H_{30}N_3O_4S$, 480.2; found 480.1.

Compound 314

(S)-1-(5-(3-(cyclopropylsulfonyl)phenyl)-3-methyl-9H-pyrido[2,3-b]indol-8-yloxy)-3-(dimethylamino)propan-2-yl dihydrogen phosphate

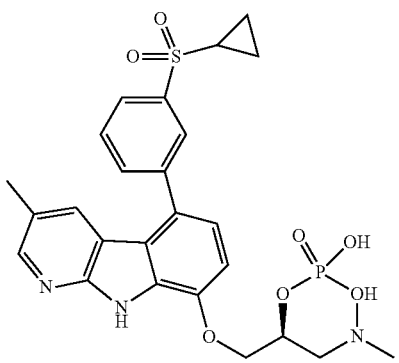

The title compound was obtained as a dihydrochloride salt following the same procedure as depicted in the synthesis of compound 272. $^1$H NMR (400 MHz, DMSO-$d_6$) δ ppm 6 ppm 1.06-1.19 (m, 4H) 2.28 (s, 3H) 2.97 (s, 6H) 3.00 (dd, J=8.84, 3.79 Hz, 1 H) 3.63 (d, J=13.64 Hz, 2H) 3.97 (dd, J=13.64, 9.60 Hz, 1H) 4.39 (dd, J=10.4, 3.2 Hz, 1 H) 4.53 (dd, J=10.4, 4.8 Hz, 1H) 4.96 (br. m, 1H) 7.09-7.19 (m, 2H) 7.58 (s, 1H) 7.85 (t, J=7.83 Hz, 1H) 7.96 (d, J=7.58 Hz, 1H) 8.02 (d, J=7.83 Hz, 1H) 8.08 (s, 1H) 8.31 (d, J=1.52 Hz, 1H) 12.01 (s, 1H). [M+H] calc'd for $C_{26}H_{31}N_3O_7PS$, 560.2; found 560.2.

Compound 315

(R)-1-(5-(3-(cyclopropylsulfonyl)phenyl)-3-methyl-9H-pyrido[2,3-b]indol-8-yloxy)-3-(dimethylamino)propan-2-yl dihydrogen phosphate

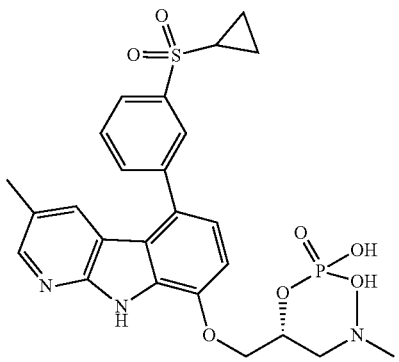

The title compound was obtained as a dihydrochloride salt following the same procedure as depicted in the synthesis of compound 272. $^1$H NMR (400 MHz, DMSO-$d_6$) δ ppm 1.06-1.19 (m, 4H) 2.28 (s, 3H) 2.97 (s, 6H) 3.00 (dd, J=8.84, 3.79 Hz, 1H) 3.63 (d, J=13.64 Hz, 2H) 3.97 (dd, J=13.64, 9.60 Hz, 1H) 4.39 (dd, J=10.4, 3.2 Hz, 1H) 4.53 (dd, J=10.4, 4.8 Hz, 1H) 4.96 (br. m, 1H) 7.09-7.19 (m, 2H) 7.58 (s, 1H) 7.85 (t, J=7.83 Hz, 1H) 7.96 (d, J=7.58 Hz, 1H) 8.02 (d, J=7.83 Hz, 1H) 8.08 (s, 1H) 8.31 (d, J=1.52 Hz, 1H) 12.01 (s, 1H). [M+H] calc'd for $C_{26}H_{31}N_3O_7PS$, 560.2; found 560.2.

Compound 316

3-chloro-N-(3-methyl-4-(4-methylpiperazin-1-yl)phenyl)-8-((1-methylpiperidin-4-yl)methoxy)-9H-pyrido[2,3-b]indol-5-amine

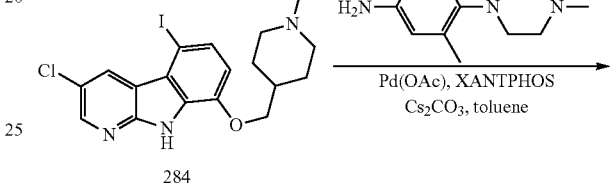

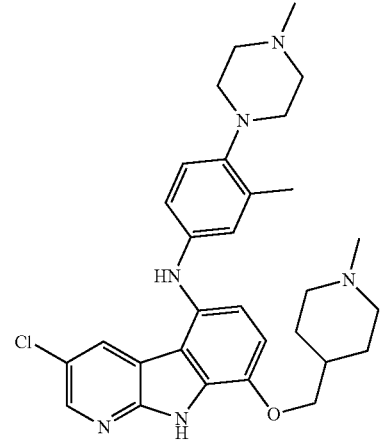

To a 15 mL screw cap vial was added 3-chloro-5-iodo-8-((1-methylpiperidin-4-yl)methoxy)-9H-pyrido[2,3-b]indole (77 mg, 0.168 mmol), 33-methyl-4-(4-methylpiperazin-1-yl)aniline (42 mg, 0.203 mmol), PALLADIUM(II) ACETATE (2.0 mg, 0.008 mmol), XANTPHOS (5.0 mg, 0.008 mmol) and CESIUM CARBONATE (110 mg, 0.338 mmol) in toluene (2 mL). The reaction was stirred at 115° C. for 3 h. The reaction was cooled to room temperature, filtered and purified by prep HPLC-MS to give the title compound. $^1$H NMR (400 MHz, DMSO-$d_6$) δ ppm 1.00 (d, J=6.32 Hz, 1H), 1.19 (d, J=6.06 Hz, 1H), 1.50 (br. s., 2H), 2.17 (s, 3H), 2.23 (d, J=1.77 Hz, 1H), 2.72-2.92 (m, 6H), 2.92-3.03 (m, 2H), 3.03-3.12 (m, 2H), 3.12-3.28 (m, 3H), 3.41-3.60 (m, 4H), 4.02 (d, 2H), 6.60-6.75 (m, 1H), 6.75-6.84 (m, 1H), 6.91 (s, 1H), 7.01-7.09

(m, 1H), 7.88 (br. s., 1H), 8.04 (d, J=2.02 Hz, 1H), 8.38 (d, J=2.27 Hz, 1H), 12.11 (s, 1H). ESI-MS: m/z 533.4 (M+H)+.

Compound 317

5-(3-(cyclopropylsulfonyl)phenyl)-8-((1-methylpiperidin-4-yl)methoxy)-9H-pyrido[2,3-b]indole

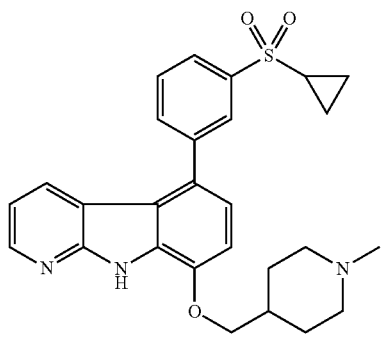

The title compound was isolated as a byproduct in the preparation of compound 286. ¹H NMR (400 MHz, DMSO-d₆) δ ppm 1.03-1.19 (m, 4H), 1.40 (dd, J=11.87, 3.03 Hz, 2H), 1.86-1.99 (m, 4H), 2.18 (s, 3H), 2.83 (d, J=11.87 Hz, 2H), 3.01 (dd, J=12.63, 2.78 Hz, 1H), 4.08 (d, J=6.57 Hz, 2H), 7.04 (dd, J=7.83, 4.80 Hz, 1H), 7.06-7.11 (m, 1 H), 7.12-7.17 (m, 1H), 7.71 (dd, J=7.96, 1.39 Hz, 1H), 7.84 (t, J=7.71 Hz, 1H), 7.98 (dd, J=13.26, 7.71 Hz, 2H), 8.02-8.07 (m, 1H), 8.42 (dd, J=4.67, 1.39 Hz, 1H), 12.20 (s, 1H). ESI-MS: m/z 510.3 (M+H)+.

Compound 318

2-((2-(5-(3-(cyclopropylsulfonyl)phenyl)-3-methyl-9H-pyrido[2,3-b]indol-8-yloxy)ethyl)(ethyl)amino)ethanol

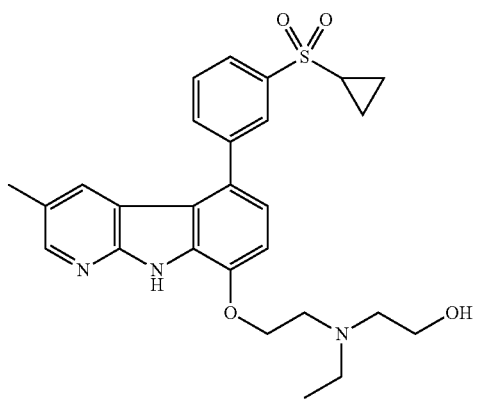

The title compound was synthesized following the same procedure as depicted in the synthesis of compound 270. ¹H NMR (400 MHz, DMSO-d₆) δ ppm 0.98-1.20 (m, 4H), 1.29 (t, J=7.20 Hz, 3H), 2.49 (s, 3H), 3.31-3.50 (m, 4H), 3.62-3.76 (m, 2H), 3.80 (t, J=5.05 Hz, 2H), 4.54 (d, J=4.04 Hz, 2H), 7.08-7.17 (m, 1H), 7.22 (t, J=4.04 Hz, 1H), 7.61 (d, J=7.58 Hz, 1H), 7.82-8.05 (m, 2H), 8.10 (d, J=8.84 Hz, 1H), 8.31 (d, J=2.02 Hz, 1H), 8.39 (d, J=2.27 Hz, 1H), 8.53 (d, J=1.52 Hz, 1H), 9.15 (br. s., 1H), 12.09 (s, 1H). ESI-MS: m/z 494.4 (M+H)+.

Compound 319

2-((2-(3-chloro-5-(3-(cyclopropylsulfonyl)phenyl)-9H-pyrido[2,3-b]indol-8-yloxy)ethyl)(methyl)amino)ethanol

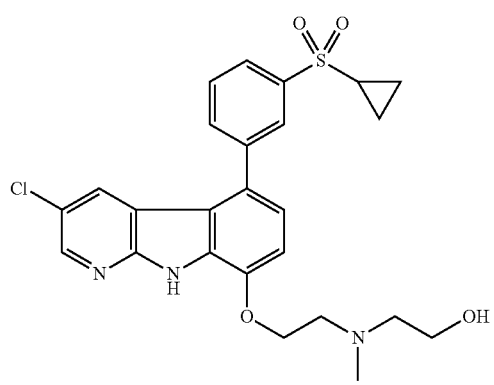

The title compound was synthesized using an analogous procedure to that described in the preparation of compound 293. ¹H NMR (400 MHz, DMSO-d₆) δ ppm ¹H NMR (400 MHz, DMSO-d₆) δ ppm 1.11 (m, 2H), 1.17 (d, J=2.59 Hz, 2H), 2.89-2.95 (m, 1H), 2.99-3.05 (m, 4H), 3.04 (s, 3H), 3.74-3.80 (m, 2H), 3.80-3.86 (m, 2 H), 7.17-7.25 (m, 1H), 7.28 (s, 1H), 7.69 (d, J=0.19 Hz, 1H), 7.82-7.92 (m, 1H), 7.96-8.01 (m, 1H), 8.04 (d, J=1.45 Hz, 1H), 8.07 (dt, J=1.23, 0.58 Hz, 1H), 8.50 (dd, J=2.40, 0.13 Hz, 1H), 12.35 (s, 1H). ESI-MS: m/z 500.2 (M+H)+.

Compound 320

2-((2-(5-(3-(cyclopropylsulfonyl)phenyl)-9H-pyrido[2,3-b]indol-8-yloxy)ethyl)(methyl)amino)ethanol

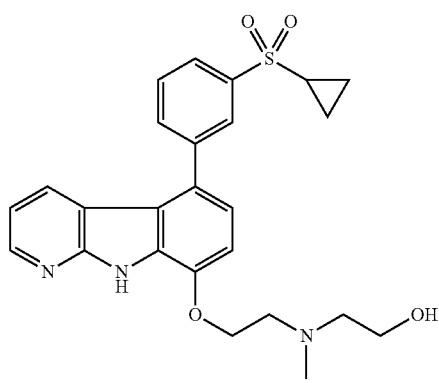

The title compound was isolated as a byproduct in the preparation of compound 319. ESI-MS: m/z 466.3 (M+H)+.

Compound 321

2-((2-(5-(3-(cyclopropylsulfonyl)phenyl)-3-methyl-9H-pyrido[2,3-b]indol-8-yloxy)ethyl)(methyl)amino)ethanol

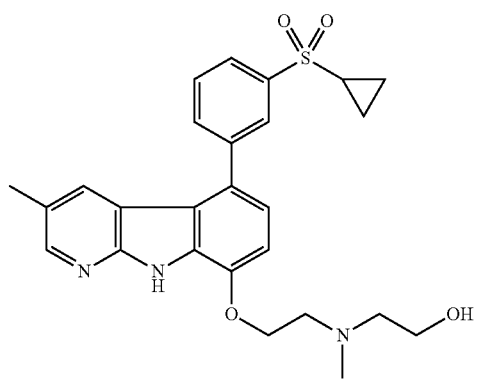

The title compound was synthesized following the same procedure as depicted in the synthesis of compound 270. ¹H NMR (400 MHz, DMSO-d₆) δ ppm 1.02-1.12 (m, 1H), 1.12-1.19 (m, 1H), 1.44-1.58 (m, 2H), 2.28 (s, 3H), 3.03 (s, 3H), 3.22-3.28 (m, 2H), 3.29-3.37 (m, 2H), 3.75-3.81 (m, 2H), 3.80-3.86 (m, 2H), 4.53-4.67 (m, 1H), 7.14 (d, J=8.08 Hz, 1H), 7.22 (d, J=8.34 Hz, 1H), 7.61 (s, 1H), 7.76 (d, J=8.59 Hz, 1H), 7.86 (t, J=7.71 Hz, 1H), 8.00-8.07 (m, 1H), 8.08 (t, J=1.77 Hz, 1H), 8.31 (d, J=1.52 Hz, 1H), 11.98 (s, 1H). ESI-MS: m/z 480.3 (M+H)+.

Compound 322

1-(2-(5-(3-(cyclopropylsulfonyl)phenyl)-3-methyl-9H-pyrido[2,3-b]indol-8-yloxy)ethyl)piperidin-4-ol

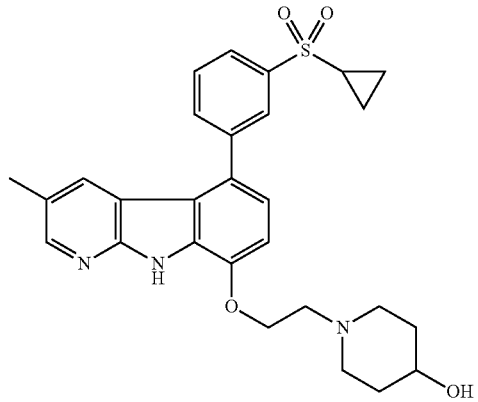

The title compound was synthesized following the same procedure as depicted in the synthesis of compound 270. ¹H NMR (400 MHz, DMSO-d₆) δ ppm 1.09 (dd, J=7.83, 2.27 Hz, 2H), 1.15 (ddd, J=4.99, 2.78, 2.59 Hz, 2H), 1.57-1.72 (m, 1H), 1.78-1.87 (m, 1H), 1.99-2.09 (m, 1H), 2.28 (s, 3H), 3.02 (dd, J=12.63, 3.03 Hz, 1H), 3.12-3.25 (m, 1H), 3.38 (d, J=12.88 Hz, 1H), 3.48-3.56 (m, 1H), 3.69 (dd, J=14.65, 4.29 Hz, 3H), 4.58 (d, J=4.80 Hz, 2H), 7.11-7.17 (m, 1H), 7.20-7.25 (m, 1H), 7.61 (s, 1H), 7.86 (t, J=7.71 Hz, 1H), 7.96 (d, J=1.26 Hz, 1H), 8.02 (d, J=7.83 Hz, 1H), 8.08 (s, 1H), 8.30-8.35 (m, 1H), 11.99 (d, J=9.09 Hz, 1H). ESI-MS: m/z 506.4 (M+H)+.

Compound 323

2-((2-(3-chloro-5-(3-(cyclopropylsulfonyl)phenyl)-9H-pyrido[2,3-b]indol-8-yloxy)ethyl)(ethyl)amino)ethanol

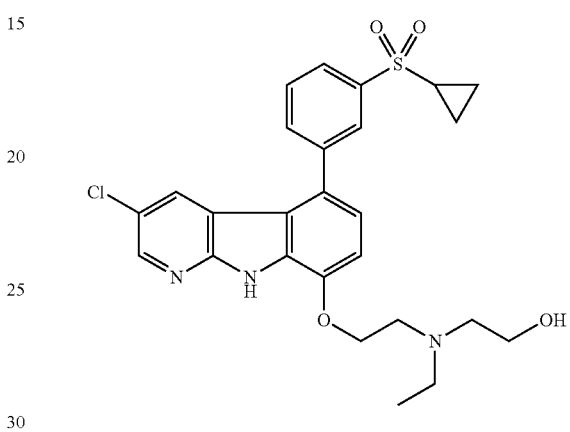

The title compound was synthesized using an analogous procedure to that described in the preparation of compound 293. ¹H NMR (400 MHz, DMSO-d₆) δ ppm 1.09 (ddd, J=15.92, 7.96, 2.15 Hz, 2H), 1.17 (d, J=5.05 Hz, 2H), 1.31 (t, J=7.20 Hz, 3H), 3.00 (ddd, J=12.69, 9.66, 4.93 Hz, 1H), 3.31 (br. s., 1H), 3.40-3.50 (m, 1H), 3.61-3.79 (m, 2H), 3.82 (t, J=5.05 Hz, 2H), 4.46 (t, J=4.80 Hz, 2H), 4.62 (d, J=4.29 Hz, 2H), 6.99 (d, J=8.84 Hz, 1H), 7.17-7.26 (m, 1H), 7.30 (d, J=8.08 Hz, 1H), 7.65-7.78 (m, 2H), 7.68-7.70 (m, 1H), 7.98 (d, J=7.58 Hz, 1H), 8.05 (d, J=9.09 Hz, 1H), 8.45 (d, J=2.53 Hz, 1H), 8.50 (d, J=2.27 Hz, 1H), 12.38 (s, 1H). ESI-MS: m/z 506.5 (M+H)+.

Compound 324

2-((2-(5-(3-(cyclopropylsulfonyl)phenyl)-9H-pyrido[2,3-b]indol-8-yloxy)ethyl)(ethyl)amino)ethanol

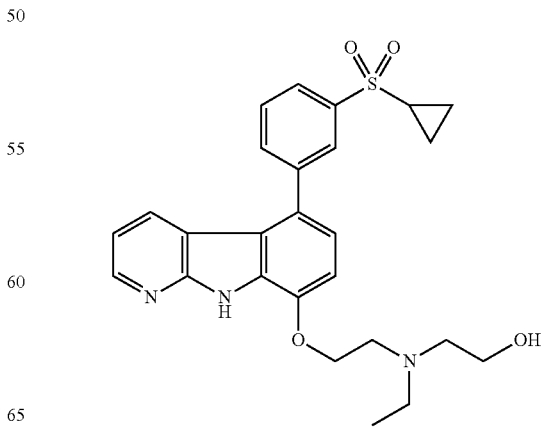

The title compound was isolated as a byproduct in the preparation of compound 323. ¹H NMR (400 MHz, DMSO-d₆) δ ppm 1.03-1.13 (m, 1H), 1.13-1.20 (m, 2H), 1.33 (t, 3H), 1.46-1.58 (m, 1H), 1.59-1.71 (m, 1H), 2.90-2.96 (m, 1H), 2.96-3.06 (m, 1H), 3.16-3.29 (m, 1H), 3.31-3.41 (m, 1H), 3.42-3.59 (m, 1H), 3.70-3.79 (m, 1H), 3.83 (s, 2H), 4.46-4.52 (m, 1H), 4.56-4.67 (m, 2H), 7.07-7.12 (m, 1H), 7.18 (d, J=0.13 Hz, 1H), 7.24 (d, 1H), 7.74 (s, 1H), 7.87 (d, J=0.44 Hz, 1H), 7.97 (br. s., 1H), 8.05 (dd, J=2.49, 0.35 Hz, 2H), 8.43-8.49 (m, 1H), 12.17 (s, 1H). ESI-MS: m/z 480.4 (M+H)⁺.

Compound 325

1-(2-(3-chloro-5-(3-(cyclopropylsulfonyl)phenyl)-9H-pyrido[2,3-b]indol-8-yloxy)ethyl)piperidin-4-ol

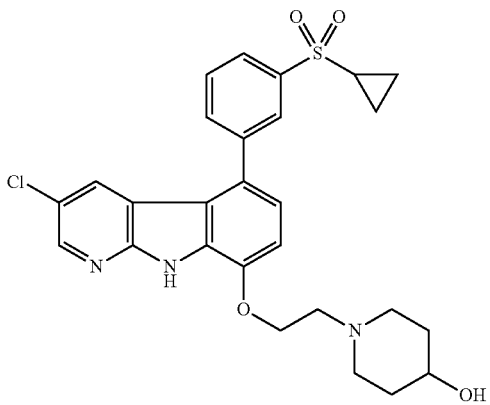

The title compound was synthesized using an analogous procedure to that described in the preparation of compound 293. ¹H NMR (400 MHz, DMSO-d₆) δ ppm 1.01-1.22 (m, 4H), 1.84 (m, 4H), 2.93-3.09 (m, 1H), 3.11-3.32 (m, 1H), 3.32-3.44 (m, 1H), 3.44-3.58 (m, 1H), 3.58-3.76 (m, 2H), 4.60 (d, J=4.55 Hz, 2H), 7.20 (d, J=8.08 Hz, 1H), 7.26-7.31 (m, 1H), 7.63-7.76 (m, 2H), 7.88 (t, J=7.96 Hz, 2H), 7.97 (d, J=7.83 Hz, 2H), 8.05 (d, J=1.26 Hz, 1H), 8.49 (t, J=2.15 Hz, 1H), 12.36 (d, J=10.86 Hz, 1H). ESI-MS: m/z 526.4 (M+H)⁺.

Compound 326

1-(2-(5-(3-(cyclopropylsulfonyl)phenyl)-9H-pyrido[2,3-b]indol-8-yloxy)ethyl)piperidin-4-ol

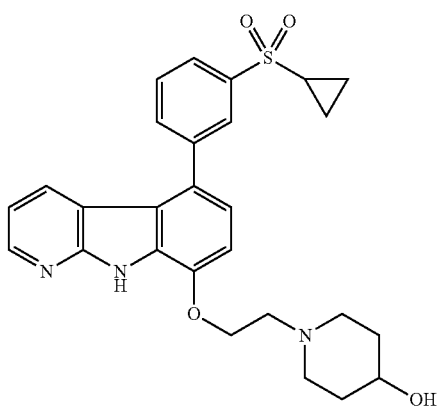

The title compound was isolated as a byproduct in the preparation of compound 325. ¹H NMR (400 MHz, DMSO-d₆) δ ppm 1.06-1.20 (m, 4H), 1.57-1.74 (m, 2H), 1.79-2.01 (m, 2H), 2.96-3.05 (m, 1H), 3.25 (t, J=6.95 Hz, 1H), 3.33 (t, J=6.69 Hz, 1H), 3.55 (d, J=9.35 Hz, 1H), 3.47 (t, J=5.68 Hz, 1H), 3.72 (br. s., 2H), 4.60 (d, J=3.79 Hz, 2H), 7.03-7.19 (m, 2H), 7.20-7.33 (m, 1H), 7.75 (d, J=7.07 Hz, 1H), 7.86 (t, J=7.71 Hz, 1H), 7.97 (d, J=7.58 Hz, 1H), 8.00-8.08 (m, 2H), 8.46 (d, J=4.80 Hz, 1H), 12.13 (d, J=9.35 Hz, 1H). ESI-MS: m/z 494.4 (M+H)⁺.

Compound 327

1-(2-(5-(3-(ethylsulfonyl)phenyl)-9H-pyrido[2,3-b]indol-8-yloxy)ethyl)piperidin-4-ol

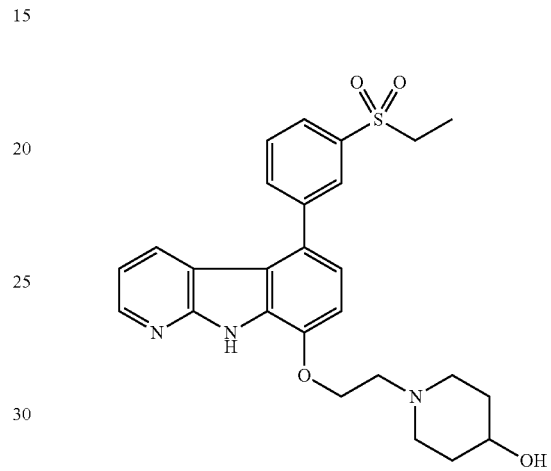

The title compound was isolated as a byproduct in the preparation of compound 329. ¹H NMR (400 MHz, DMSO-d₆) δ ppm 1.18 (t, J=7.33 Hz, 3H), 1.58-1.73 (m, 1H), 1.80-1.90 (m, 1H), 1.90-1.99 (m, 1H), 1.99-2.10 (m, 1H), 2.28 (s, 3H), 3.08-3.29 (m, 1H), 3.41 (q, J=7.16 Hz, 2H), 3.35-3.46 (m, 1H), 3.46-3.61 (m, 1H), 3.61-3.76 (m, 3H), 4.59 (d, J=4.55 Hz, 2H), 7.09-7.17 (m, 1H), 7.18-7.25 (m, 1H), 7.57 (s, 1H), 7.88 (d, J=7.58 Hz, 1H), 7.99 (dd, J=15.16, 7.83 Hz, 2H), 8.08 (s, 1H), 8.31 (s, 1H), 11.96 (d, J=8.34 Hz, 1H). ESI-MS: m/z 494.4 (M+H)⁺.

Compound 328

1-(2-(5-(3-(ethylsulfonyl)phenyl)-3-methyl-9H-pyrido[2,3-b]indol-8-yloxy)ethyl)piperidin-4-ol

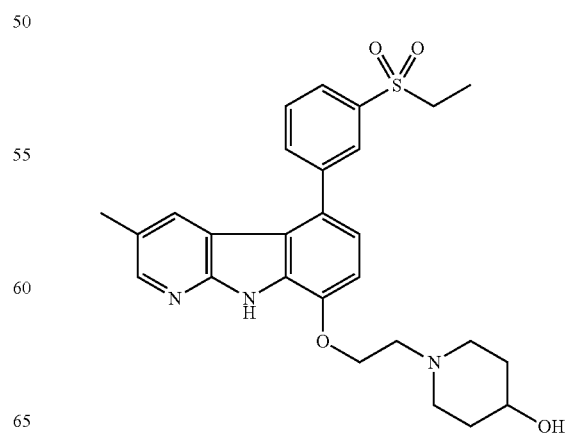

The title compound was synthesized following the same procedure as depicted in the synthesis of compound 270. ¹H NMR (400 MHz, DMSO-d₆) δ ppm ¹H NMR (400 MHz, DMSO-d₆) δ ppm 1.17 (t, J=7.33 Hz, 3H), 1.65 (t, J=9.73 Hz, 1H), 1.79-1.90 (m, 1H), 1.90-2.02 (m, 2H), 3.04-3.32 (m, 1H), 3.33-3.40 (m, 2H), 3.40 (q, J=7.83 Hz, 2 H), 3.46-3.56 (m, 1H), 3.61-3.76 (m, 2H), 4.37-4.45 (m, 1H), 4.60 (d, J=4.80 Hz, 2 H), 7.02-7.20 (m, 2H), 7.66-7.79 (m, 2H), 7.86 (t, J=7.83 Hz, 1H), 7.92-8.11 (m, 3 H), 8.45 (d, J=4.55 Hz, 1H), 12.10 (d, J=9.09 Hz, 1H). ESI-MS: m/z 480.4 (M+H)⁺.

Compound 329

1-(2-(3-chloro-5-(3-(ethylsulfonyl)phenyl)-9H-pyrido[2,3-b]indol-8-yloxy)ethyl)piperidin-4-ol

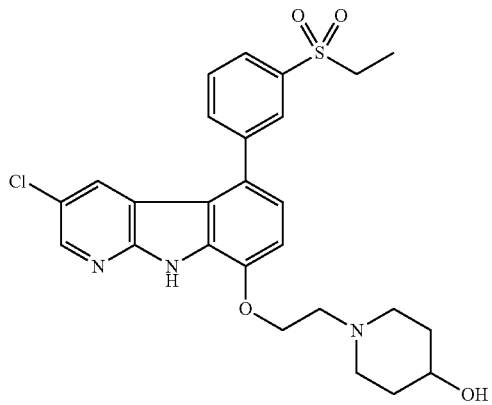

The title compound was synthesized following the same procedure as depicted in the synthesis of compound 293. ¹H NMR (400 MHz, DMSO-d₆) δ ppm 1.19 (t, J=7.45 Hz, 3H), 1.52-1.73 (m, 1H), 1.88-2.01 (m, 1H), 3.13-3.29 (m, 1H), 3.31-3.45 (m, 3 H), 3.51-3.57 (m, 3H), 3.60-3.78 (m, 2H), 4.42-4.49 (m, 1H), 4.61 (d, J=4.80 Hz, 2 H), 7.12-7.34 (m, 2H), 7.58-7.80 (m, 2H), 7.80-7.93 (m, 2H), 7.93-8.11 (m, 2H), 8.48 (t, J=1.77 Hz, 1H), 12.33 (d, J=10.61 Hz, 1H). ESI-MS: m/z 514.3 (M+H)⁺.

Compound 330

N-cyclopropyl-3-(8-(3-(dimethylamino)propoxy)-3-methyl-9H-pyrido[2,3-b]indol-5-yl)benzamide

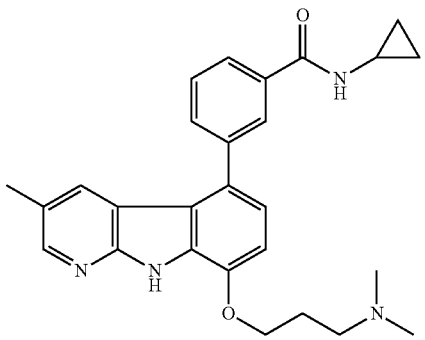

The title compound was synthesized from Compound 191 using an analogous procedure to that outlined in the preparation of Compound 177. ¹H NMR (400 MHz, DMSO-d₆) δ ppm 0.54-0.58 (m, 2H) 0.66-0.73 (m, 2H) 2.21-2.24 (m, 2H) 2.26 (s, 3 H) 2.85 (m, 1H) 2.88 (s, 3H) 2.89 (s, 3H) 3.47-3.52 (m, 2H) 4.29 (t, J=5.43 Hz, 2H) 7.05 (d, J=8.08 Hz, 1H) 7.13 (d, J=8.08 Hz, 1H) 7.54 (s, 1H) 7.62 (t, J=7.71 Hz, 1H) 7.72 (d, J=7.58 Hz, 1H) 7.93 (d, J=7.83 Hz, 1H) 8.03 (s, 1H) 8.28 (s, 1H) 8.55 (d, J=4.04 Hz, 1H) 9.60 (br. s., 1H) 11.93 (s, 1H); [M+H] calc'd for C₂₇H₃₁N₄O₂, 443.2; found, 443.3.

Compound 331

3-(8-(3-(dimethylamino)propoxy)-3-methyl-9H-pyrido[2,3-b]indol-5-yl)-N-methylbenzenesulfonamide

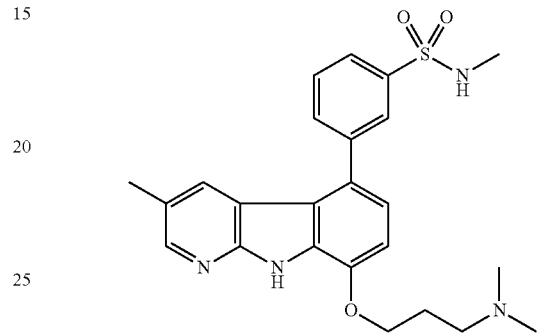

The title compound was synthesized from Compound 191 using an analogous procedure to that outlined in the preparation of Compound 177. ¹H NMR (400 MHz, DMSO-d₆) δ ppm 2.21-2.24 (m, 2H) 2.26 (s, 3H) 2.47 (s, 3H) 2.88 (s, 3H) 2.89 (s, 3 H) 3.47-3.52 (m, 2H) 4.29 (t, J=5.43 Hz, 2H) 7.05 (d, J=8.08 Hz, 1H) 7.13 (d, J=8.08 Hz, 1H) 7.54 (s, 1H) 7.62 (t, J=7.71 Hz, 1H) 7.72 (d, J=7.58 Hz, 1H) 7.93 (d, J=7.83 Hz, 1H) 8.03 (s, 1H) 8.28 (s, 1H) 8.55 (d, J=4.04 Hz, 1H) 9.60 (br. s., 1H) 11.93 (s, 1 H); [M+H] calc'd for C₂₄H₂₈N₄O₃S, 453.2; found, 453.4.

Compound 332

5-(3-(cyclopropylcarbamoyl)phenyl)-3,8-dimethyl-N-(1-methylpiperidin-4-yl)-9H-pyrido[2,3-b]indole-7-carboxamide

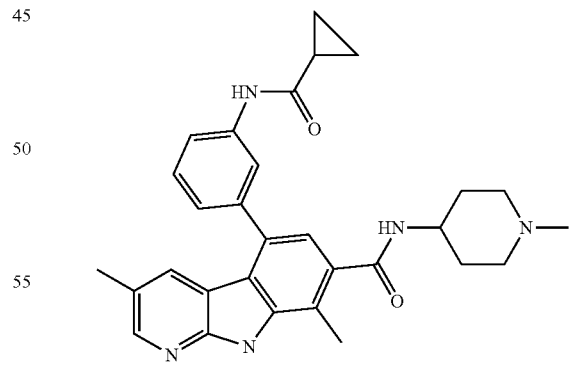

The title compound was synthesized from 5-chloro-3,8-dimethyl-N-(1-methylpiperidin-4-yl)-9H-pyrido[2,3-b]indole-7-carboxamide and 3-(cyclopropylcarbamoyl)phenylboronic acid using an analogous procedure to that described in the preparation of compound 88. ¹H NMR (400 MHz, DMSO-d₆) δ ppm 0.80 (d, J=5.81 Hz, 4H) 1.53 (qd, J=11.62, 3.03 Hz, 2H) 1.82 (br. s., 1H) 1.79 (d, J=5.56 Hz, 2 H) 1.95 (t, J=10.86 Hz, 2H) 2.15 (s, 3H) 2.27 (s, 3H) 2.59 (s, 3H) 2.74

(br. d, J=10.86 Hz, 2H) 3.75 (dt, J=7.33, 3.66 Hz, 1H) 6.98 (s, 1H) 7.27 (d, J=7.58 Hz, 1H) 7.49 (t, J=7.83 Hz, 1H) 7.69 (br. s., 2H) 7.91 (s, 1H) 8.24-8.31 (m, 2H) 10.37 (s, 1H) 11.92 (br. s., 1H) [M+H] calc'd for $C_{30}H_{34}N_5O_2$, 496.3; found, 496.4.

Compound 333

8-(2-(1H-imidazol-1-yl)ethoxy)-5-(3-(ethylsulfonyl) phenyl)-3-methyl-9H-pyrido[2,3-b]indole

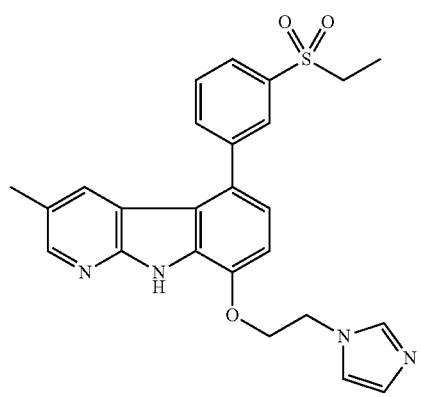

The title compound was synthesized from Compound 158 using an analogous procedure to that outlined in the preparation of Compound 206. $^1$H NMR (400 MHz, DMSO-$d_6$) δ ppm 1.15 (t, J=7.33 Hz, 3H), 2.27 (s, 3H), 3.40 (q, J=7.24 Hz, 2H), 4.53-4.63 (m, 2H), 4.68-4.79 (m, 2H), 7.06-7.16 (m, 1H), 7.25 (d, J=8.59 Hz, 1H), 7.69-7.75 (m, 1H), 7.75-7.82 (m, 2H), 7.82-7.91 (m, 1H), 7.92-8.08 (m, 1H), 8.17 (dd, J=13.39, 2.02 Hz, 2H), 8.50 (s, 1H), 9.16 (s, 1H), 12.03 (s, 1H). ESI-MS: m/z 461.2 (M+H)$^+$.

Compound 334

8-(2-(1H-imidazol-1-yl)ethoxy)-3-chloro-5-(3-(ethylsulfonyl)phenyl)-9H-pyrido[2,3-b]indole

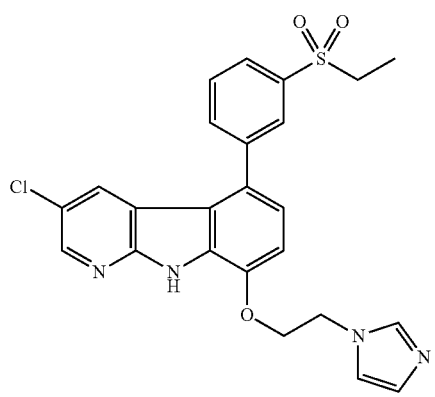

The title compound was synthesized from Compound 219 using an analogous procedure to that outlined in the preparation of Compound 206. $^1$H NMR (400 MHz, DMSO-$d_6$) δ ppm 1.14 (d, J=7.49 Hz, 3H), 3.37 (q, J=7.49 Hz, 2H), 4.49 (t, J=4.93 Hz, 2 H), 4.67 (t, J=4.80 Hz, 2H), 7.00 (d, J=8.84 Hz, 1H), 7.16 (d, J=8.59 Hz, 1H), 7.38 (dd, J=10.48, 1.89 Hz, 1H), 7.59-7.72 (m, 1H), 7.66 (dd, J=8.97, 2.65 Hz, 1H), 7.74 (quin, J=3.92 Hz, 1H), 7.80-7.90 (m, 1H), 8.02 (t, J=1.77 Hz, 1H), 8.12 (d, J=2.53 Hz, 1H), 8.30 (s, 1H), 8.41 (d, J=2.27 Hz, 1H), 9.15 (s, 1H). ESI-MS: m/z 481.2 (M+H)$^+$.

Compounds 335-353

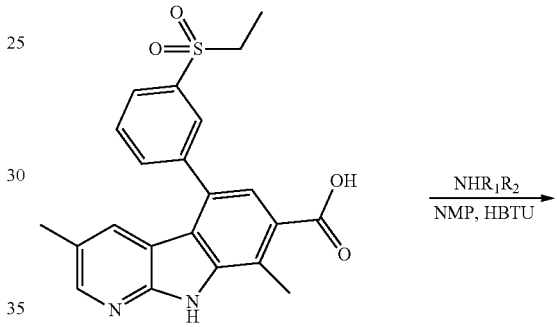

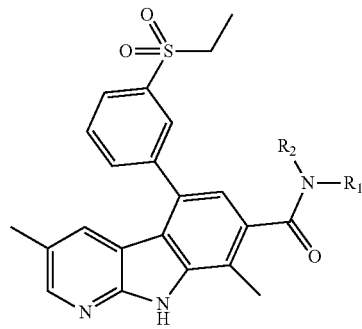

| Compound Name | | Structure |
|---|---|---|
| 335 | 5-(3-(ethylsulfonyl)phenyl)-N-((1r,4r)-4-hydroxycyclohexyl)-3,8-dimethyl-9H-pyrido[2,3-b]indole-7-carboxamide | 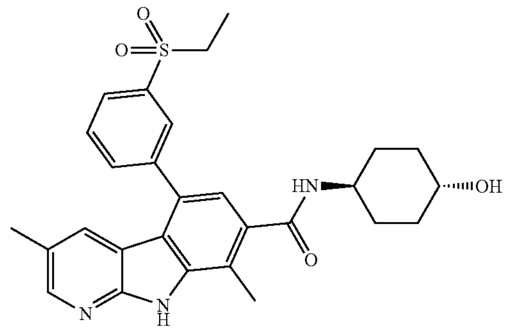 |
| 336 | 5-(3-(ethylsulfonyl)phenyl)-N-((1s,4s)-4-hydroxycyclohexyl)-3,8-dimethyl-9H-pyrido[2,3-b]indole-7-carboxamide | 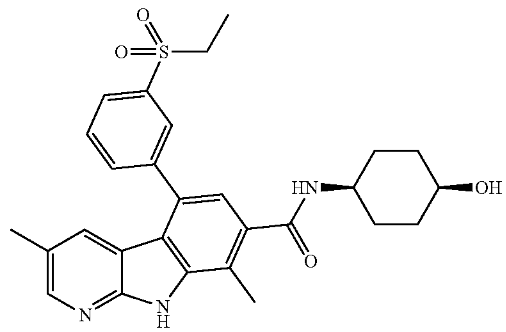 |
| 337 | 5-(3-(ethylsulfonyl)phenyl)-N-(4-(hydroxymethyl)cyclohexyl)-3,8-dimethyl-9H-pyrido[2,3-b]indole-7-carboxamide | 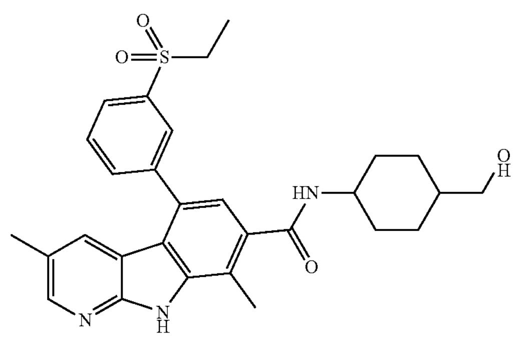 |
| 338 | 5-(3-(ethylsulfonyl)phenyl)-N-(4-(2-hydroxyethyl)cyclohexyl)-3,8-dimethyl-9H-pyrido[2,3-b]indole-7-carboxamide | 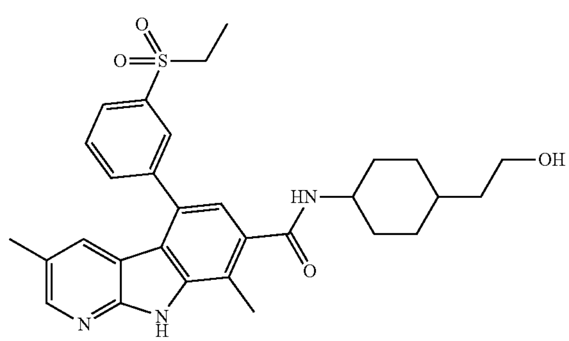 |

| Compound | Name | Structure |
|---|---|---|
| 339 | (5-(3-(ethylsulfonyl)phenyl)-3,8-dimethyl-9H-pyrido[2,3-b]indol-7-yl)(4-(hydroxymethyl)piperidin-1-yl)methanone | 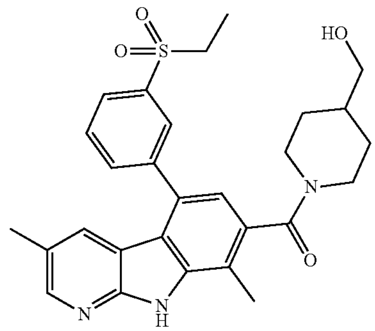 |
| 340 | (5-(3-(ethylsulfonyl)phenyl)-3,8-dimethyl-9H-pyrido[2,3-b]indol-7-yl)(4-(2-hydroxyethyl)piperidin-1-yl)methanone | 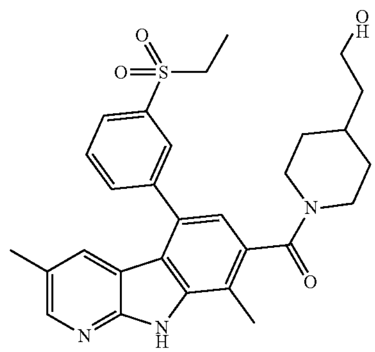 |
| 341 | (5-(3-(ethylsulfonyl)phenyl)-3,8-dimethyl-9H-pyrido[2,3-b]indol-7-yl)(4-hydroxypiperidin-1-yl)methanone | 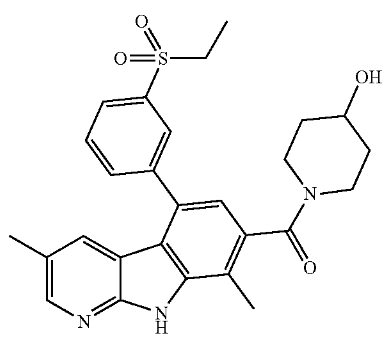 |
| 342 | (5-(3-(ethylsulfonyl)phenyl)-3,8-dimethyl-9H-pyrido[2,3-b]indol-7-yl)(2-(hydroxymethyl)pyrrolidin-1-yl)methanone | 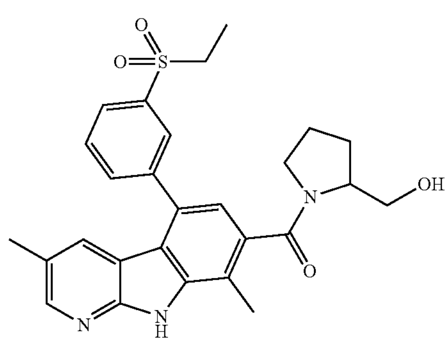 |

-continued

| Compound Name | | Structure |
|---|---|---|
| 343 | (5-(3-(ethylsulfonyl)phenyl)-3,8-dimethyl-9H-pyrido[2,3-b]indol-7-yl)(2-(hydroxymethyl)morpholino)methanone | 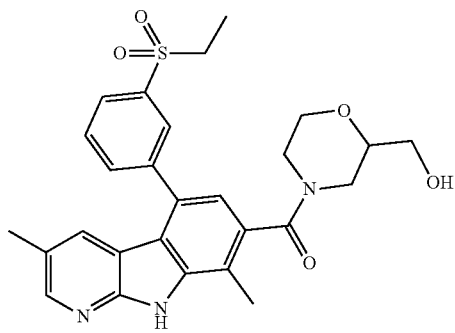 |
| 344 | 5-(3-(ethylsulfonyl)phenyl)-N-(3-hydroxypropyl)-3,8-dimethyl-9H-pyrido[2,3-b]indole-7-carboxamide | 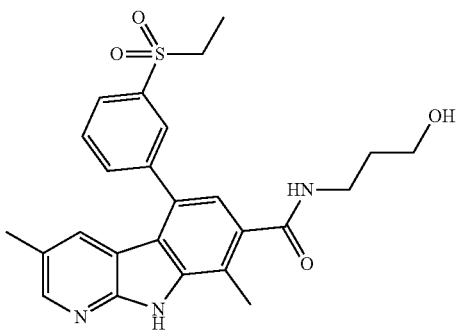 |
| 345 | (R)-5-(3-(ethylsulfonyl)phenyl)-N-(3-hydroxybutyl)-3,8-dimethyl-9H-pyrido[2,3-b]indole-7-carboxamide | 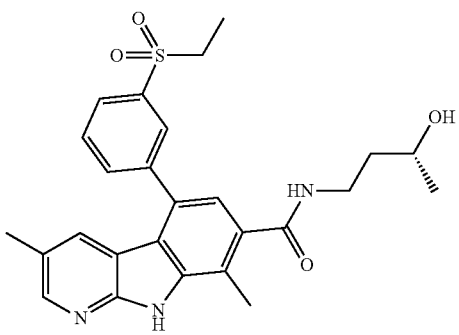 |
| 346 | (S)-5-(3-(ethylsulfonyl)phenyl)-N-(3-hydroxybutyl)-3,8-dimethyl-9H-pyrido[2,3-b]indole-7-carboxamide | 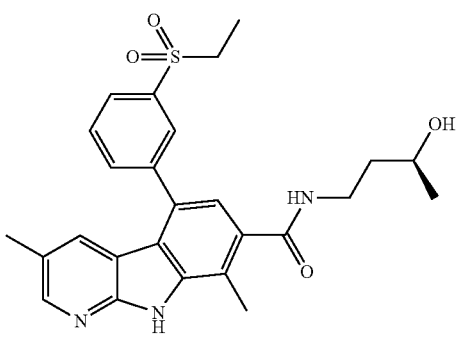 |

-continued

| Compound Name | | Structure |
|---|---|---|
| 347 | 5-(3-(ethylsulfonyl)phenyl)-N-(3-hydroxy-3-methylbutyl)-3,8-dimethyl-9H-pyrido[2,3-b]indole-7-carboxamide | 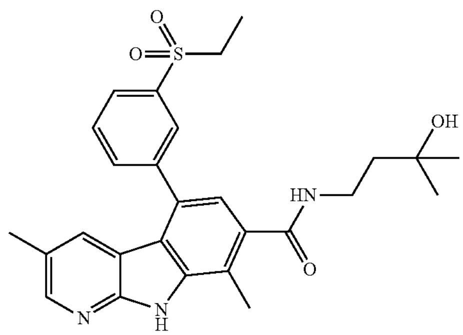 |
| 348 | (S)-N-(3-(dimethylamino)-2-hydroxypropyl)-5-(3-(ethylsulfonyl)phenyl)-3,8-dimethyl-9H-pyrido[2,3-b]indole-7-carboxamide | 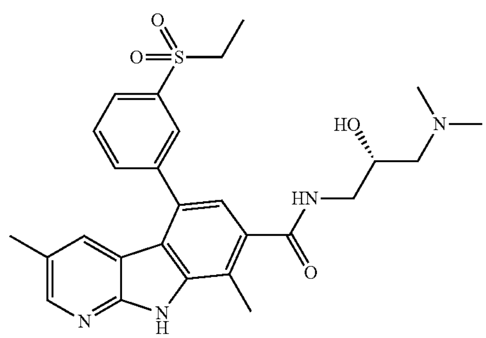 |
| 349 | (S)-N-(2-(dimethylamino)-3-hydroxypropyl)-5-(3-(ethylsulfonyl)phenyl)-3,8-dimethyl-9H-pyrido[2,3-b]indole-7-carboxamide | 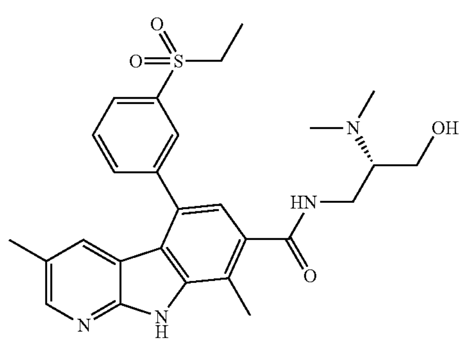 |
| 350 | N-(3-(ethyl(2-hydroxyethyl)amino)propyl)-5-(3-(ethylsulfonyl)phenyl)-3,8-dimethyl-9H-pyrido[2,3-b]indole-7-carboxamide | 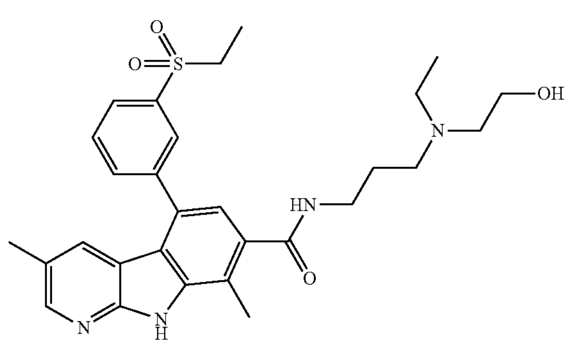 |

| Compound Name | Structure |
|---|---|
| 351 5-(3-(ethylsulfonyl)phenyl)-N-(3-((2-hydroxyethyl)(methyl)amino)propyl)-3,8-dimethyl-9H-pyrido[2,3-b]indole-7-carboxamide | 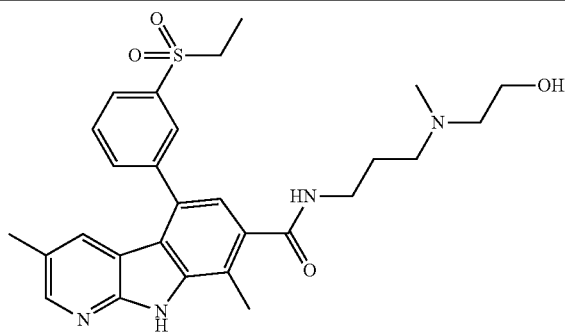 |
| 352 N-(2-(ethyl(2-hydroxyethyl)amino)ethyl)-5-(3-(ethylsulfonyl)phenyl)-3,8-dimethyl-9H-pyrido[2,3-b]indole-7-carboxamide | 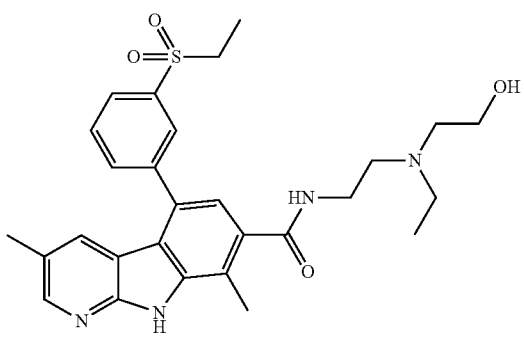 |
| 353 5-(3-(ethylsulfonyl)phenyl)-N-(2-((2-hydroxyethyl)(methyl)amino)ethyl)-3,8-dimethyl-9H-pyrido[2,3-b]indole-7-carboxamide | 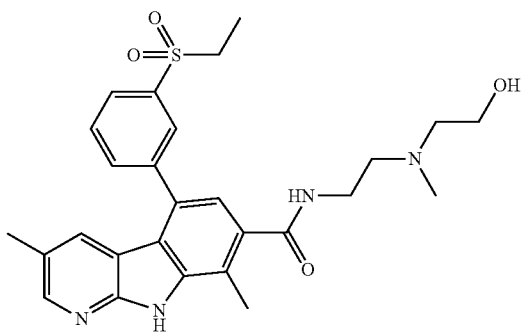 |

Compounds 335-353 can be prepared as follows. Crude 543-(ethylsulfonyl)phenyl)-3,8-dimethyl-9H-pyrido[2,3-b]indole-7-carboxylic acid (Compound 87; e.g., 124.3 g, 0.244 mol) is heated with NMP to give a thin slurry (e.g., 1.0 L of NMP heated to 70° C. for 39 min). The heat is removed and the mixture cooled (e.g., to 16° C. with the aid of a cold water bath). Appropriate amine (2.0 equiv) is added, followed by HBTU (92.6 g, 1.0 equiv) in portions over about 26 min. Over the next 2.5 h, additional HBTU (e.g., 4.7 and 4.65 g) can be added and the mixture stirred (e.g., overnight) until the reaction proceeds to completion (e.g., >99% conversion as indicated by HPLC analysis). The mixture is then be filtered (e.g., through a Celite impregnated pad, which is rinsed twice with NMP (27 and 39 g)). To the filtrate is added a solution of KOH (27.7 g, 1.7 equiv at 85% based on theoretical 5-(3-(ethylsulfonyl)phenyl)-3,8-dimethyl-9H-pyrido[2,3-b]indole-7-carboxylic acid) in water (250 mL) to give a solution with pH 11.7. After solids begin to form (e.g., about 15 min), water (500 mL) is added (e.g., over 30 min at 28-29° C.). After about 3 h at room temperature, the solids are removed by filtration, and the wet cake is rinsed with water (e.g., 1150 mL in several portions), and dried in a vacuum oven (45-55° C.) to give the desired product. HPLC analysis can be used to indicate purity (AUC at 215 nm).

Compounds according to the present invention can also be prepared as pharmaceutically acceptable salts. In addition, to the salts described above, salts of compounds of the present inventions can be formed using, for example, the following acids: benzoic acid, fumaric acid, HBr, HCl, hippuric acid, lactic acid, maleic acid, malic acid, MSA, phosphoric acid, p-TSA, succinic acid, sulfuric acid, tartaric acid, and the like. The salts of the above acids can be prepared by adding 0.5 to 2.0 equivalents of the appropriate acid in any of a variety of solvents (such as MeCN, EtOH, MeOH, DMA, THF, AcOH, and the like, or mixtures thereof) at a temperature of between about 10° C. and 75° C.

For example, the mono HCl salt of 5-(3-(ethylsulfonyl)phenyl)-3,8-dimethyl-N-(1-methylpiperidin-4-yl)-9H-pyrido[2,3-b]indole-7-carboxamide (Compound 113) was prepared as follows. To a solution of 5-(3-(ethylsulfonyl)phenyl)-3,8-dimethyl-N-(1-methylpiperidin-4-yl)-9H-pyrido[2,3-b]indole-7-carboxamide (2.105 g) in MeOH (20 mL) was added 4.38 mL of 1N aqueous HCl. The mixture was stirred for 15-30 min at 25° C. The solvent was removed to near dryness, and the resultant white solid filtered and dried to provide 2.23 g of the title compound. Mono HCl salts of the following compounds were also prepared using an analogous procedure:
5-(3-(ethylsulfonyl)phenyl)-3-methyl-8-((1-methylpiperidin-4-yl)methoxy)-9H-pyrido[2,3-b]indole (Compound 177 and 183);
3-chloro-5-(3-(ethylsulfonyl)phenyl)-8-((1-methylpiperidin-4-yl)methoxy)-9H-pyrido[2,3-b]indole (Compound 200);
3-(5-(3-(ethylsulfonyl)phenyl)-3-methyl-9H-pyrido[2,3-b]indol-8-yloxy)-N,N-dimethylpropan-1-amine (Compound 206);
3-(3-chloro-5-(3-(ethylsulfonyl)phenyl)-9H-pyrido[2,3-b]indol-8-yloxy)-N,N-dimethylpropan-1-amine (Compound 220); and
N-cyclopropyl-3-(3-methyl-8-((1-methylpiperidin-4-yl)methoxy)-9H-pyrido[2,3-b]indol-5-yl)benzamide (Compound 178).

In addition to the foregoing, the above reaction schemes and variations thereof can be used to prepare the following:

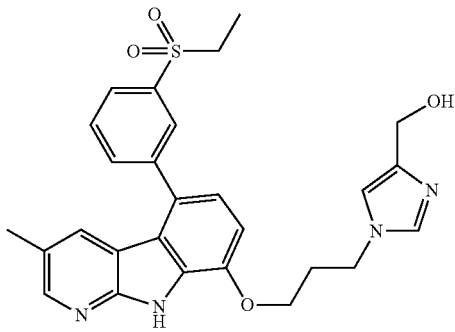

(1-(3-(5-(3-(ethylsulfonyl)phenyl)-3-methyl-9H-pyrido[2,3-b]indol-8-yloxy)propyl)-1H-imidazol-4-yl)methanol

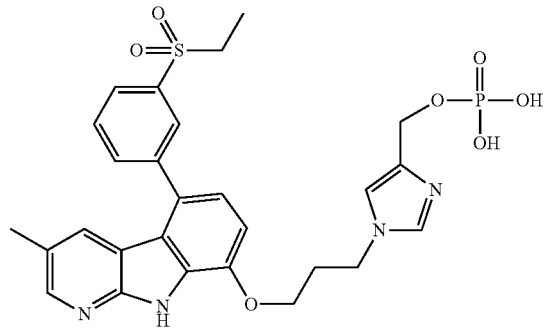

(1-(3-(5-(3-(ethylsulfonyl)phenyl)-3-methyl-9H-pyrido[2,3-b]indol-8-yloxy)propyl)-1H-imidazol-4-yl)methyl dihydrogen phosphate

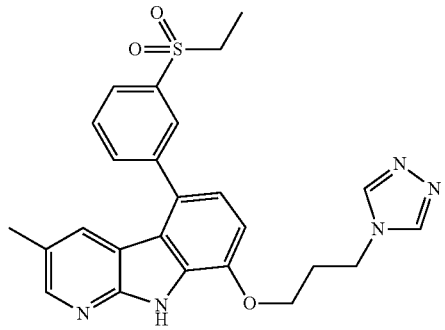

8-(3-(4H-1,2,4-triazol-4-yl)propoxy)-5-(3-(ethylsulfonyl)phenyl)-3-methyl-9H-pyrido[2,3-b]indole -continued
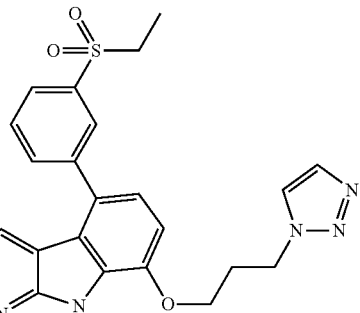
8-(3-(1H-1,2,3-triazol-1-yl)propoxy)-5-(3-(ethylsulfonyl)phenyl)-3-methyl-9H-pyrido[2,3-b]indole
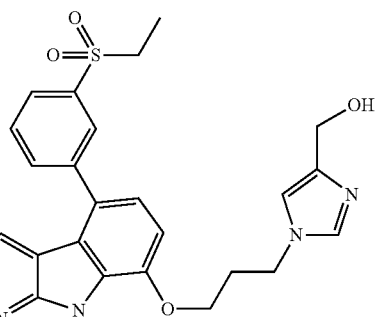
(1-(3-(3-chloro-5-(3-(ethylsulfonyl)phenyl)-9H-pyrido[2,3-b]indol-8-yloxy)propyl)-1H-imidazol-4-yl)methanol
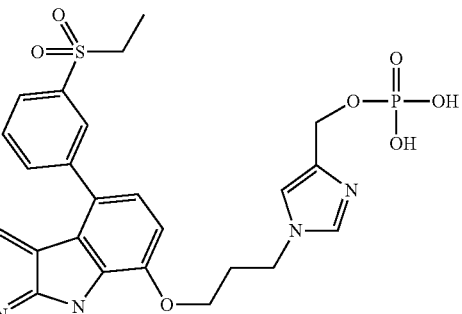
(1-(3-(3-chloro-5-(3-(ethylsulfonyl)phenyl)-9H-pyrido[2,3-b]indol-8-yloxy)propyl)-1H-imidazol-4-yl)methyl dihydrogen phosphate
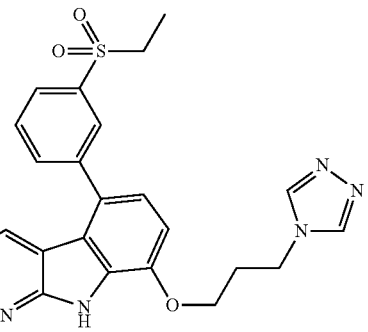
8-(3-(4H-1,2,4-triazol-4-yl)propoxy)-3-chloro-5-(3-(ethylsulfonyl)phenyl)-9H-pyrido[2,3-b]indole

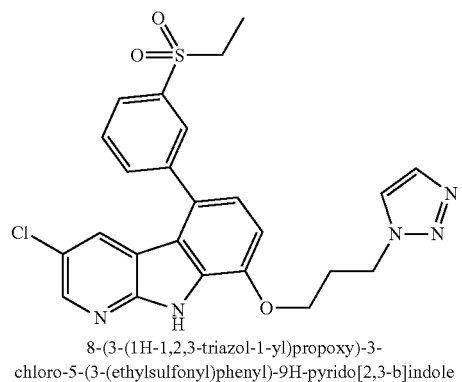
8-(3-(1H-1,2,3-triazol-1-yl)propoxy)-3-
chloro-5-(3-(ethylsulfonyl)phenyl)-9H-pyrido[2,3-b]indole
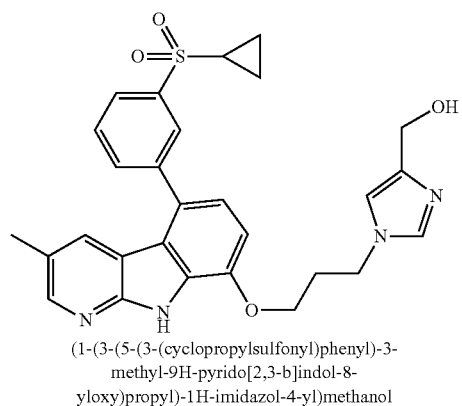
(1-(3-(5-(3-(cyclopropylsulfonyl)phenyl)-3-
methyl-9H-pyrido[2,3-b]indol-8-
yloxy)propyl)-1H-imidazol-4-yl)methanol
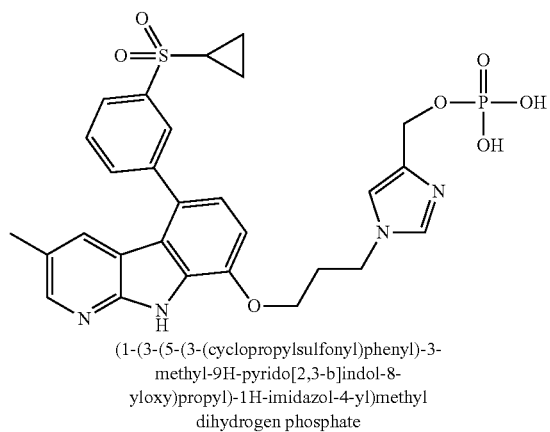
(1-(3-(5-(3-(cyclopropylsulfonyl)phenyl)-3-
methyl-9H-pyrido[2,3-b]indol-8-
yloxy)propyl)-1H-imidazol-4-yl)methyl
dihydrogen phosphate
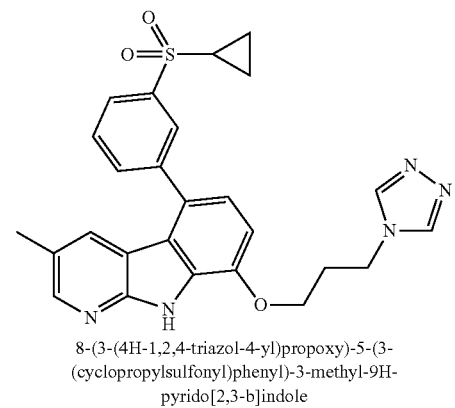
8-(3-(4H-1,2,4-triazol-4-yl)propoxy)-5-(3-
(cyclopropylsulfonyl)phenyl)-3-methyl-9H-
pyrido[2,3-b]indole

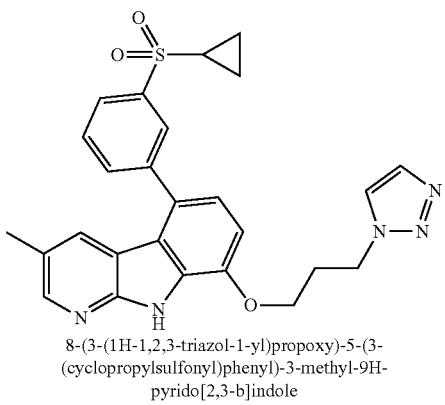
8-(3-(1H-1,2,3-triazol-1-yl)propoxy)-5-(3-(cyclopropylsulfonyl)phenyl)-3-methyl-9H-pyrido[2,3-b]indole
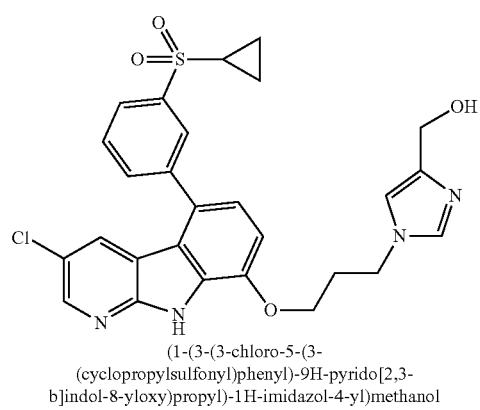
(1-(3-(3-chloro-5-(3-(cyclopropylsulfonyl)phenyl)-9H-pyrido[2,3-b]indol-8-yloxy)propyl)-1H-imidazol-4-yl)methanol
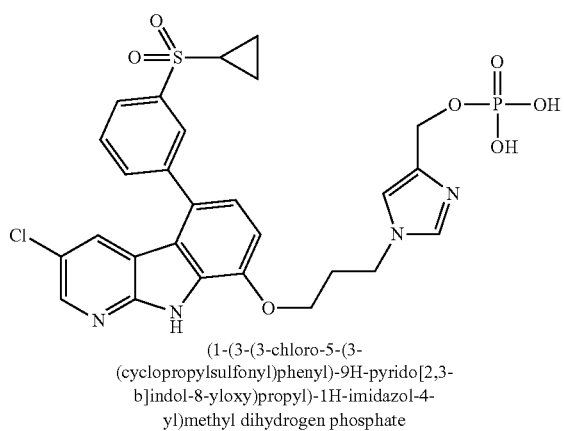
(1-(3-(3-chloro-5-(3-(cyclopropylsulfonyl)phenyl)-9H-pyrido[2,3-b]indol-8-yloxy)propyl)-1H-imidazol-4-yl)methyl dihydrogen phosphate
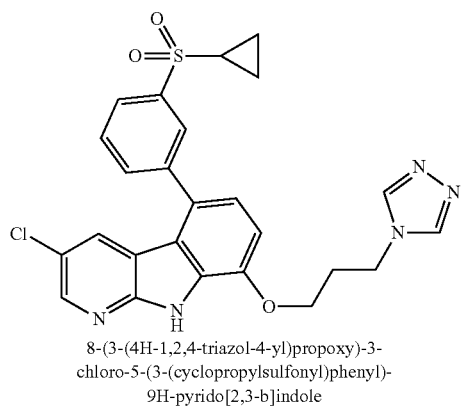
8-(3-(4H-1,2,4-triazol-4-yl)propoxy)-3-chloro-5-(3-(cyclopropylsulfonyl)phenyl)-9H-pyrido[2,3-b]indole

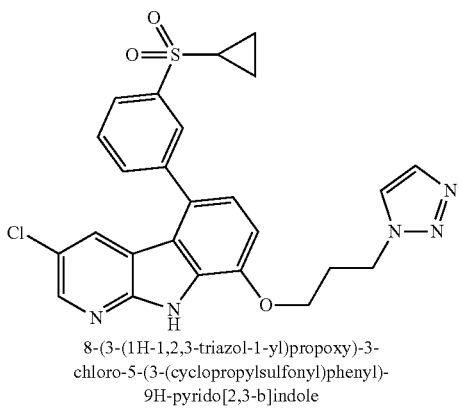

8-(3-(1H-1,2,3-triazol-1-yl)propoxy)-3-
chloro-5-(3-(cyclopropylsulfonyl)phenyl)-
9H-pyrido[2,3-b]indole

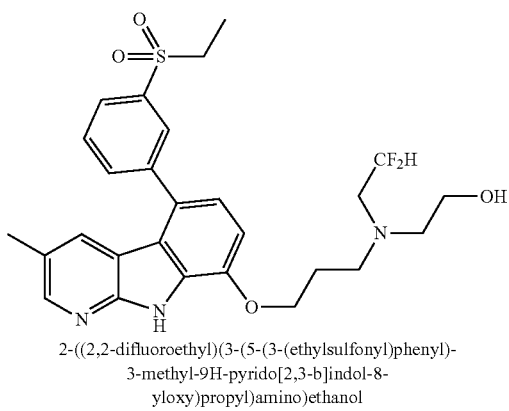

2-((2,2-difluoroethyl)(3-(5-(3-(ethylsulfonyl)phenyl)-
3-methyl-9H-pyrido[2,3-b]indol-8-
yloxy)propyl)amino)ethanol

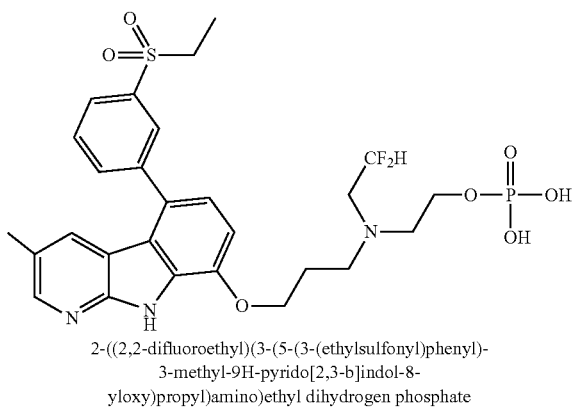

2-((2,2-difluoroethyl)(3-(5-(3-(ethylsulfonyl)phenyl)-
3-methyl-9H-pyrido[2,3-b]indol-8-
yloxy)propyl)amino)ethyl dihydrogen phosphate

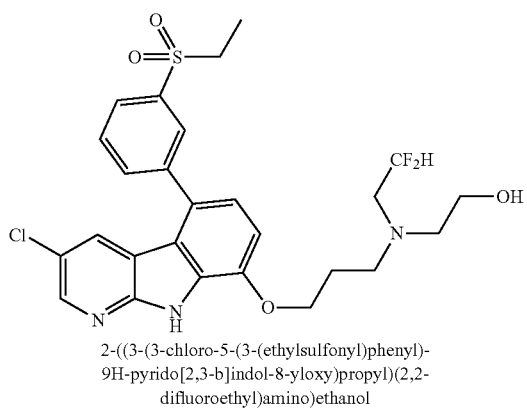

2-((3-(3-chloro-5-(3-(ethylsulfonyl)phenyl)-
9H-pyrido[2,3-b]indol-8-yloxy)propyl)(2,2-
difluoroethyl)amino)ethanol

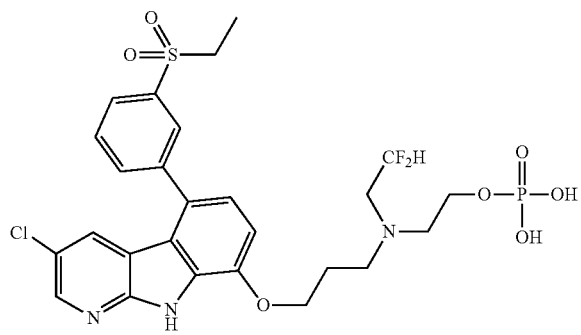

2-((3-(3-chloro-5-(3-(ethylsulfonyl)phenyl)-
9H-pyrido[2,3-b]indol-8-yloxy)propyl)(2,2-
difluoroethyl)amino)ethyl dihydrogen phosphate

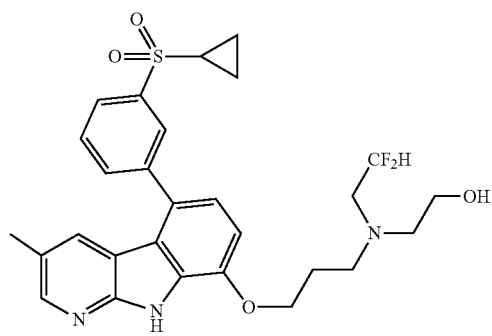

2-((3-(5-(3-(cyclopropylsulfonyl)phenyl)-3-
methyl-9H-pyrido[2,3-b]indol-8-
yloxy)propyl)(2,2-difluoroethyl)amino)ethanol

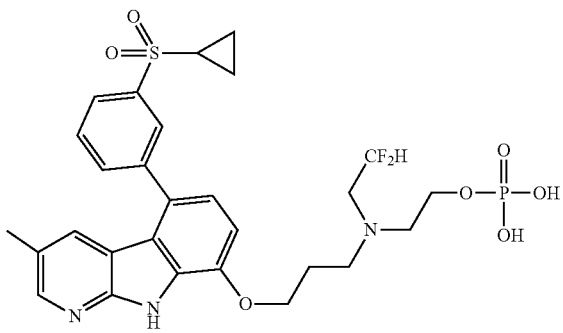

2-((3-(5-(3-(cyclopropylsulfonyl)phenyl)-3-
methyl-9H-pyrido[2,3-b]indol-8-
yloxy)propyl)(2,2-difluoroethyl)amino)ethyl dihydrogen phosphate

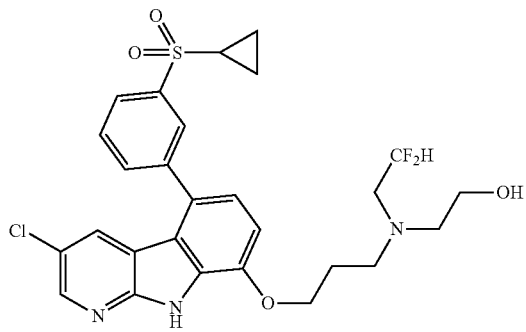

2-((3-(3-chloro-5-(3-
(cyclopropylsulfonyl)phenyl)-9H-pyrido[2,3-b]indol-
8-yloxy)propyl)(2,2-difluoroethyl)amino)ethanol -continued

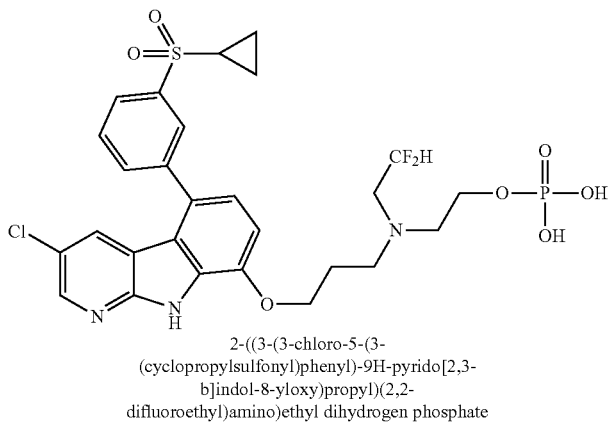

2-((3-(3-chloro-5-(3-(cyclopropylsulfonyl)phenyl)-9H-pyrido[2,3-b]indol-8-yloxy)propyl)(2,2-difluoroethyl)amino)ethyl dihydrogen phosphate

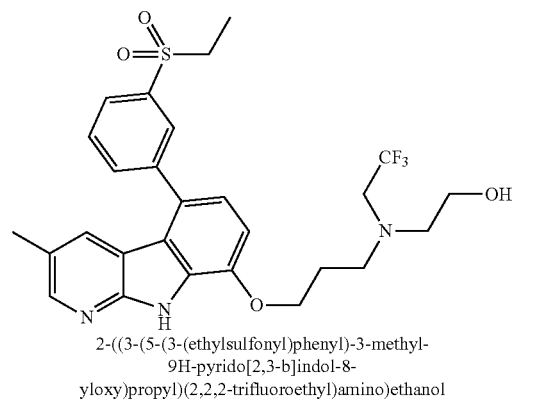

2-((3-(5-(3-(ethylsulfonyl)phenyl)-3-methyl-9H-pyrido[2,3-b]indol-8-yloxy)propyl)(2,2,2-trifluoroethyl)amino)ethanol

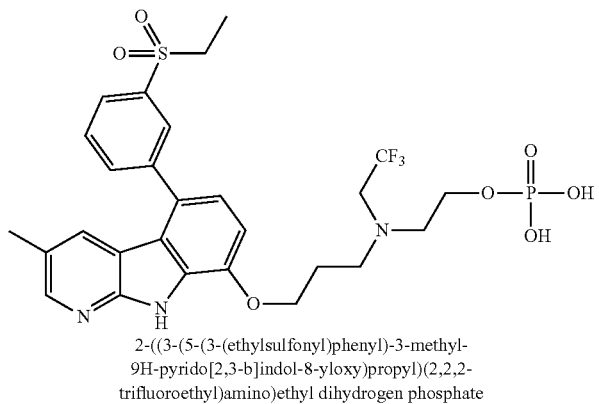

2-((3-(5-(3-(ethylsulfonyl)phenyl)-3-methyl-9H-pyrido[2,3-b]indol-8-yloxy)propyl)(2,2,2-trifluoroethyl)amino)ethyl dihydrogen phosphate

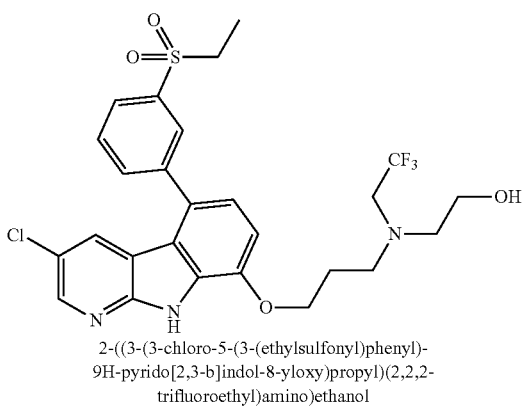

2-((3-(3-chloro-5-(3-(ethylsulfonyl)phenyl)-9H-pyrido[2,3-b]indol-8-yloxy)propyl)(2,2,2-trifluoroethyl)amino)ethanol

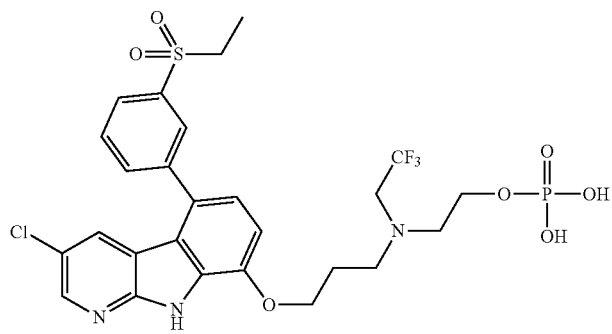

2-((3-(3-chloro-5-(3-(ethylsulfonyl)phenyl)-
9H-pyrido[2,3-b]indol-8-yloxy)propyl)(2,2,2-
trifluoroethyl)amino)ethyl dihydrogen phosphate

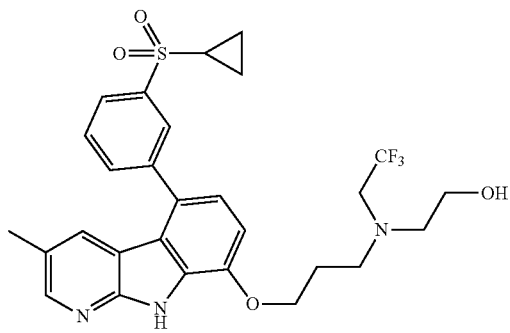

2-((3-(5-(3-(cyclopropylsulfonyl)phenyl)-3-
methyl-9H-pyrido[2,3-b]indol-8-yloxy)propyl)(2,2,2-
trifluoroethyl)amino)ethanol

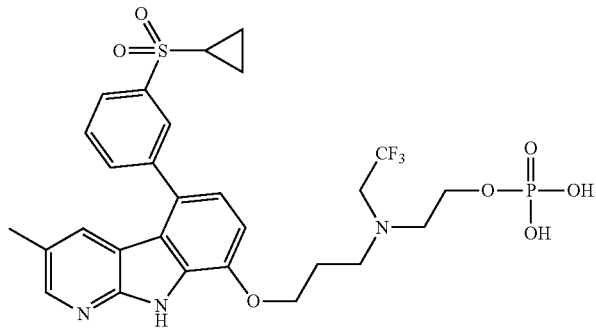

2-((3-(5-(3-(cyclopropylsulfonyl)phenyl)-3-
methyl-9H-pyrido[2,3-b]indol-8-yloxy)propyl)(2,2,2-
trifluoroethyl)amino)ethyl dihydrogen phosphate

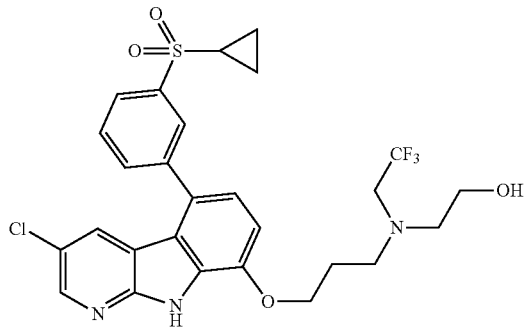

2-((3-(3-chloro-5-(3-
(cyclopropylsulfonyl)phenyl)-9H-pyrido[2,3-b]indol-
8-yloxy)propyl)(2,2,2-trifluoroethyl)amino)ethanol -continued

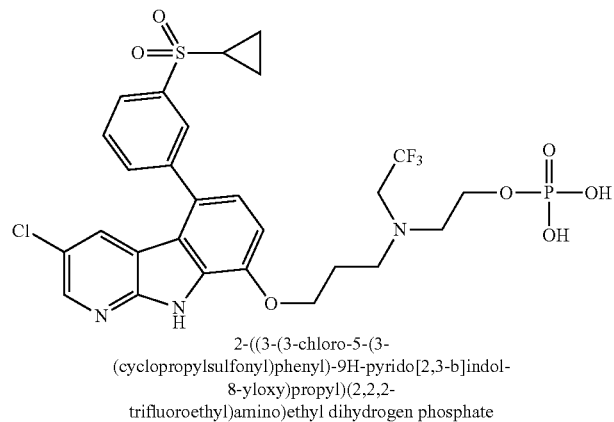

2-((3-(3-chloro-5-(3-(cyclopropylsulfonyl)phenyl)-9H-pyrido[2,3-b]indol-8-yloxy)propyl)(2,2,2-trifluoroethyl)amino)ethyl dihydrogen phosphate

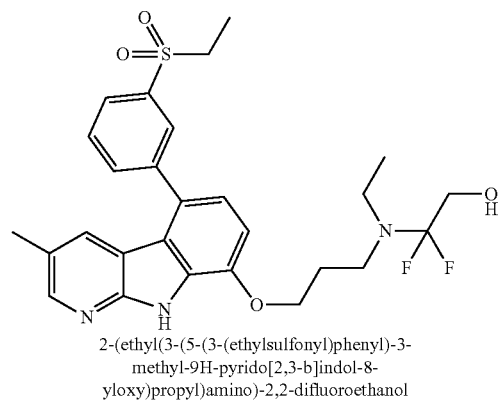

2-(ethyl(3-(5-(3-(ethylsulfonyl)phenyl)-3-methyl-9H-pyrido[2,3-b]indol-8-yloxy)propyl)amino)-2,2-difluoroethanol

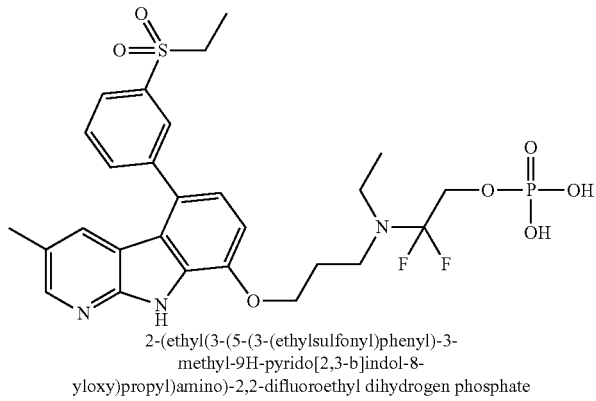

2-(ethyl(3-(5-(3-(ethylsulfonyl)phenyl)-3-methyl-9H-pyrido[2,3-b]indol-8-yloxy)propyl)amino)-2,2-difluoroethyl dihydrogen phosphate

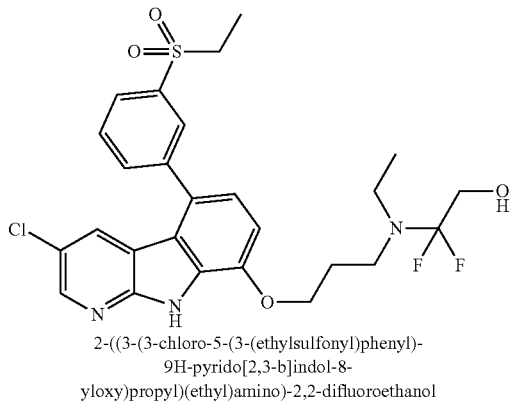

2-((3-(3-chloro-5-(3-(ethylsulfonyl)phenyl)-9H-pyrido[2,3-b]indol-8-yloxy)propyl)(ethyl)amino)-2,2-difluoroethanol

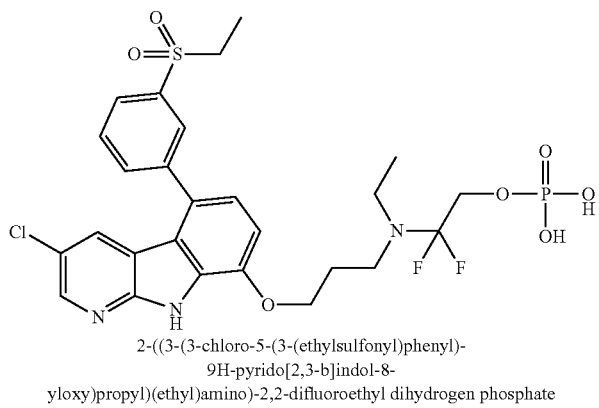

2-((3-(3-chloro-5-(3-(ethylsulfonyl)phenyl)-
9H-pyrido[2,3-b]indol-8-
yloxy)propyl)(ethyl)amino)-2,2-difluoroethyl dihydrogen phosphate

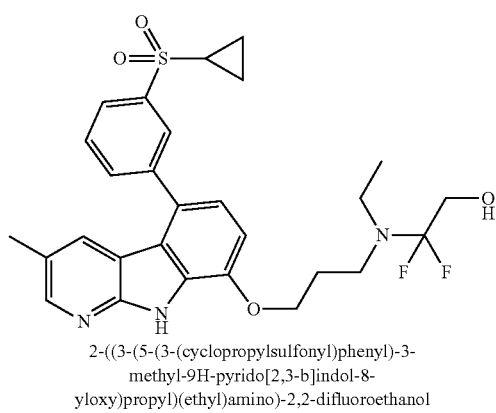

2-((3-(5-(3-(cyclopropylsulfonyl)phenyl)-3-
methyl-9H-pyrido[2,3-b]indol-8-
yloxy)propyl)(ethyl)amino)-2,2-difluoroethanol

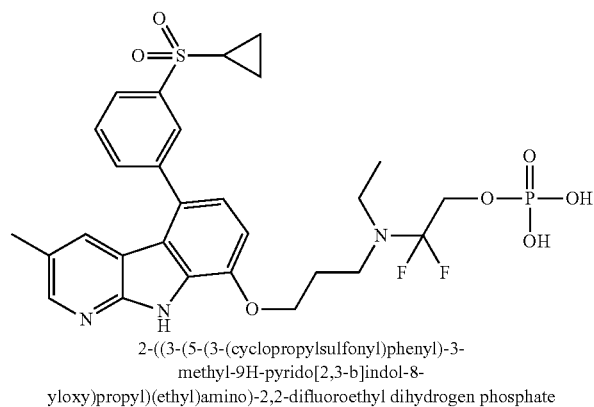

2-((3-(5-(3-(cyclopropylsulfonyl)phenyl)-3-
methyl-9H-pyrido[2,3-b]indol-8-
yloxy)propyl)(ethyl)amino)-2,2-difluoroethyl dihydrogen phosphate

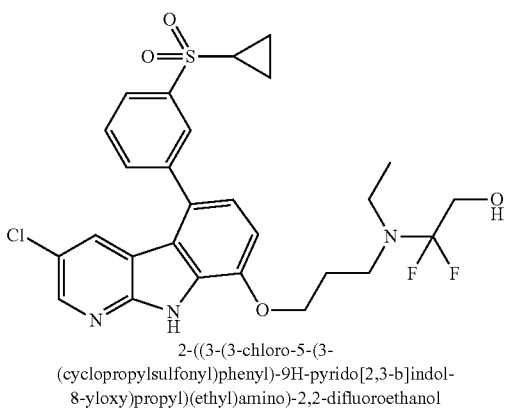

2-((3-(3-chloro-5-(3-
(cyclopropylsulfonyl)phenyl)-9H-pyrido[2,3-b]indol-
8-yloxy)propyl)(ethyl)amino)-2,2-difluoroethanol

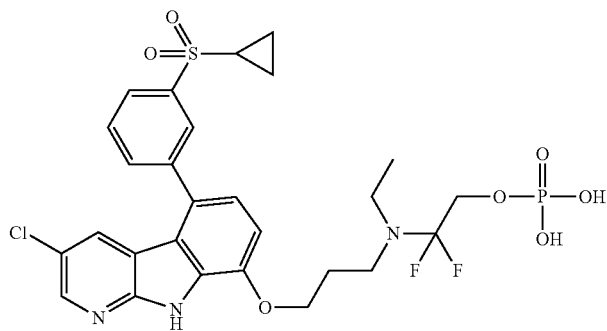

2-((3-(3-chloro-5-(3-(cyclopropylsulfonyl)phenyl)-9H-pyrido[2,3-b]indol-8-yloxy)propyl)(ethyl)amino)-2,2-difluoroethyl dihydrogen phosphate

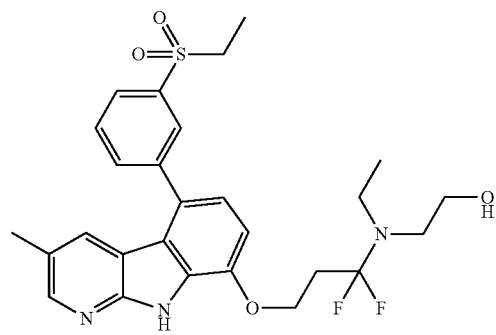

2-(ethyl(3-(5-(3-(ethylsulfonyl)phenyl)-3-methyl-9H-pyrido[2,3-b]indol-8-yloxy)-1,1-difluoropropyl)amino)ethanol

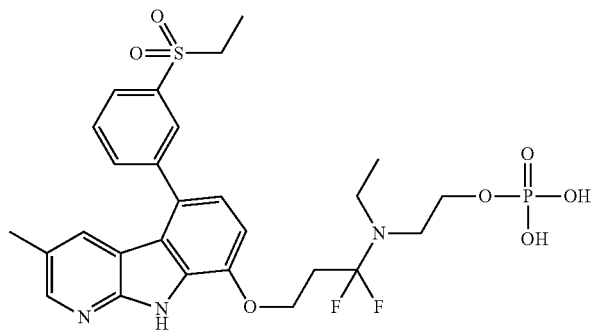

2-(ethyl(3-(5-(3-(ethylsulfonyl)phenyl)-3-methyl-9H-pyrido[2,3-b]indol-8-yloxy)-1,1-difluoropropyl)amino)ethyl dihydrogen phosphate

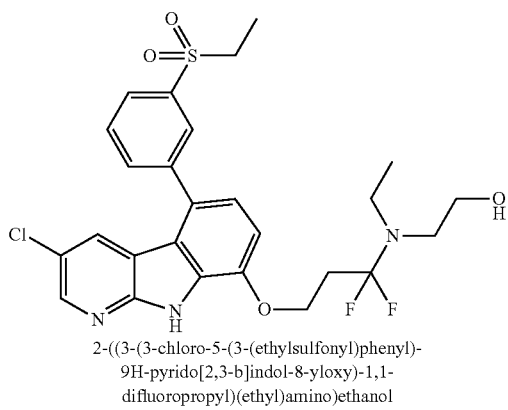

2-((3-(3-chloro-5-(3-(ethylsulfonyl)phenyl)-9H-pyrido[2,3-b]indol-8-yloxy)-1,1-difluoropropyl)(ethyl)amino)ethanol -continued

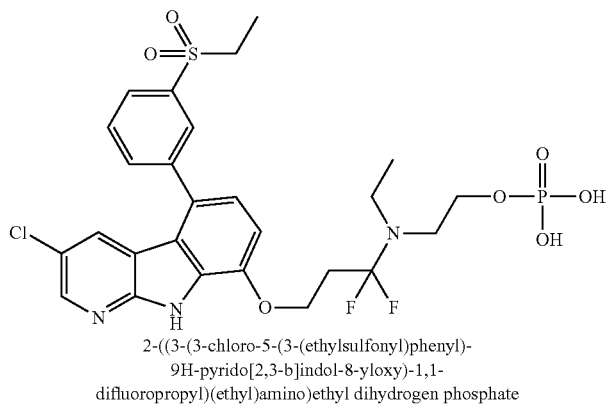

2-((3-(3-chloro-5-(3-(ethylsulfonyl)phenyl)-
9H-pyrido[2,3-b]indol-8-yloxy)-1,1-
difluoropropyl)(ethyl)amino)ethyl dihydrogen phosphate

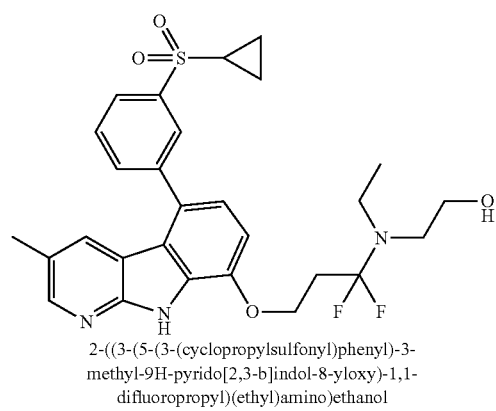

2-((3-(5-(3-(cyclopropylsulfonyl)phenyl)-3-
methyl-9H-pyrido[2,3-b]indol-8-yloxy)-1,1-
difluoropropyl)(ethyl)amino)ethanol

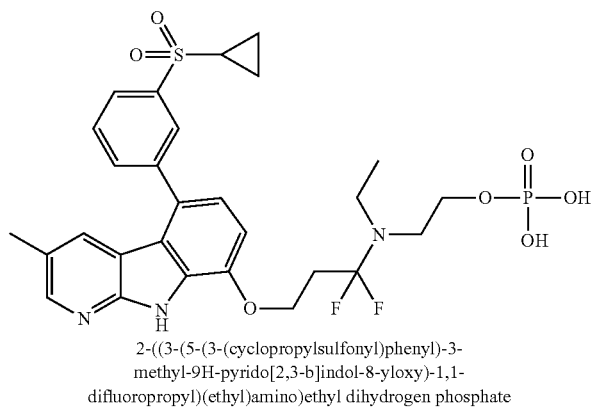

2-((3-(5-(3-(cyclopropylsulfonyl)phenyl)-3-
methyl-9H-pyrido[2,3-b]indol-8-yloxy)-1,1-
difluoropropyl)(ethyl)amino)ethyl dihydrogen phosphate

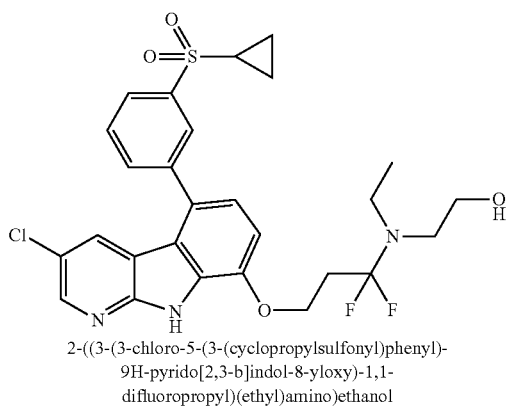

2-((3-(3-chloro-5-(3-(cyclopropylsulfonyl)phenyl)-
9H-pyrido[2,3-b]indol-8-yloxy)-1,1-
difluoropropyl)(ethyl)amino)ethanol

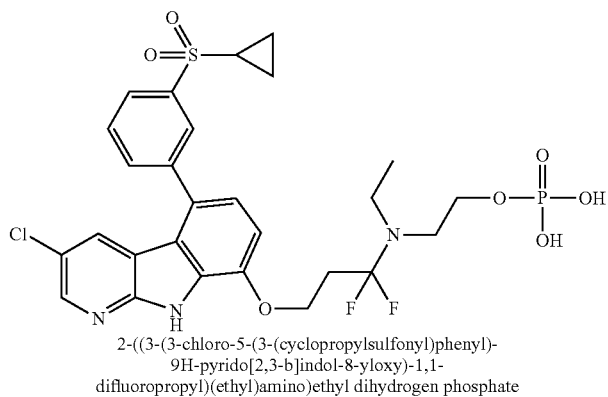

2-((3-(3-chloro-5-(3-(cyclopropylsulfonyl)phenyl)-
9H-pyrido[2,3-b]indol-8-yloxy)-1,1-
difluoropropyl)(ethyl)amino)ethyl dihydrogen phosphate

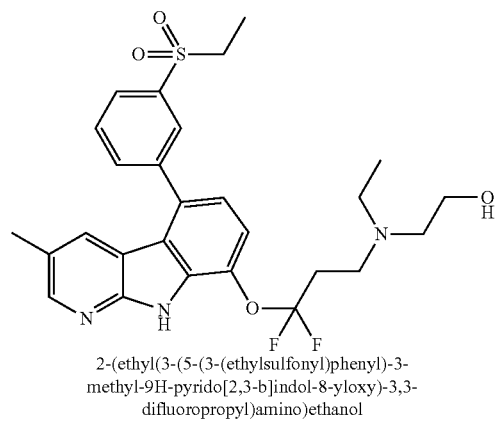

2-(ethyl(3-(5-(3-(ethylsulfonyl)phenyl)-3-
methyl-9H-pyrido[2,3-b]indol-8-yloxy)-3,3-
difluoropropyl)amino)ethanol

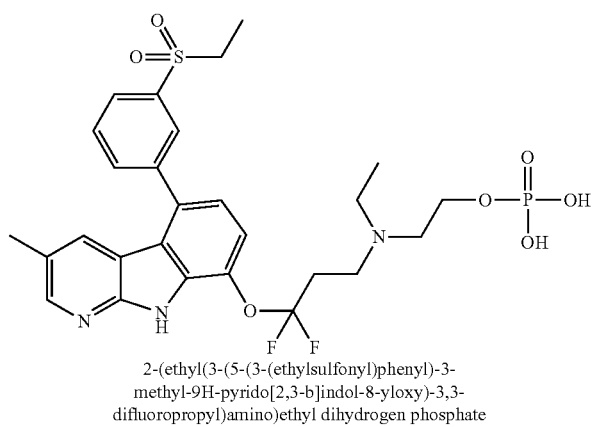

2-(ethyl(3-(5-(3-(ethylsulfonyl)phenyl)-3-
methyl-9H-pyrido[2,3-b]indol-8-yloxy)-3,3-
difluoropropyl)amino)ethyl dihydrogen phosphate

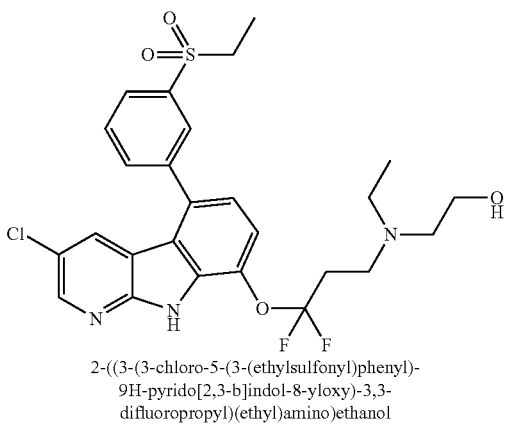

2-((3-(3-chloro-5-(3-(ethylsulfonyl)phenyl)-
9H-pyrido[2,3-b]indol-8-yloxy)-3,3-
difluoropropyl)(ethyl)amino)ethanol

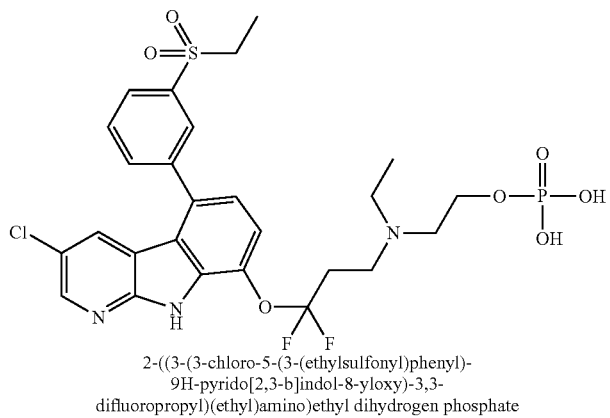

2-((3-(3-chloro-5-(3-(ethylsulfonyl)phenyl)-
9H-pyrido[2,3-b]indol-8-yloxy)-3,3-
difluoropropyl)(ethyl)amino)ethyl dihydrogen phosphate

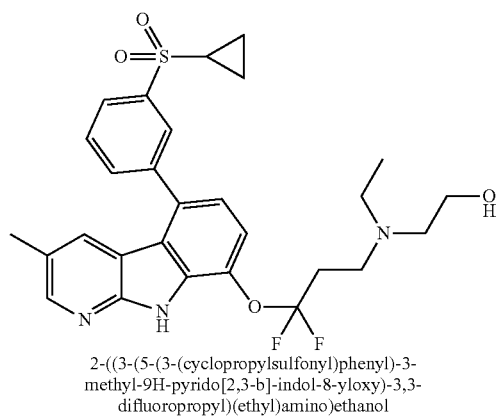

2-((3-(5-(3-(cyclopropylsulfonyl)phenyl)-3-
methyl-9H-pyrido[2,3-b]-indol-8-yloxy)-3,3-
difluoropropyl)(ethyl)amino)ethanol

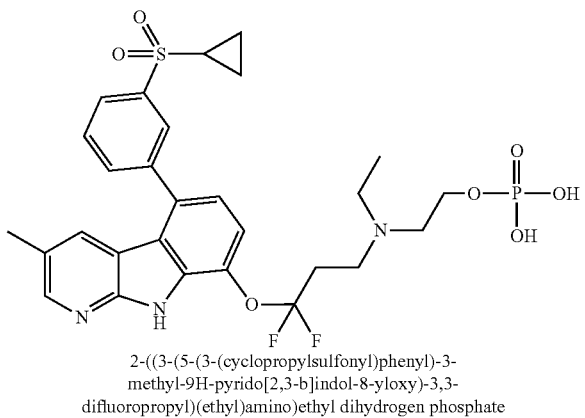

2-((3-(5-(3-(cyclopropylsulfonyl)phenyl)-3-
methyl-9H-pyrido[2,3-b]indol-8-yloxy)-3,3-
difluoropropyl)(ethyl)amino)ethyl dihydrogen phosphate

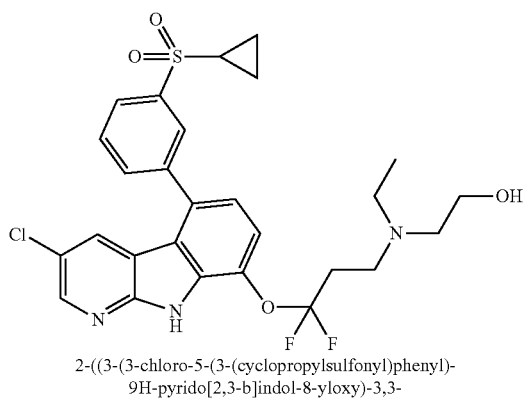

2-((3-(3-chloro-5-(3-(cyclopropylsulfonyl)phenyl)-
9H-pyrido[2,3-b]indol-8-yloxy)-3,3-

-continued difluoropropyl)(ethyl)amino)ethanol

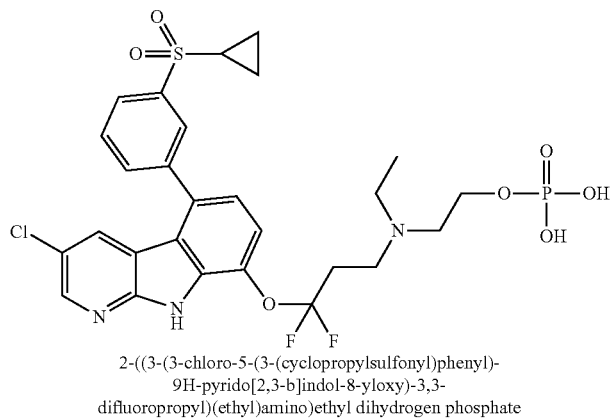

2-((3-(3-chloro-5-(3-(cyclopropylsulfonyl)phenyl)-
9H-pyrido[2,3-b]indol-8-yloxy)-3,3-
difluoropropyl)(ethyl)amino)ethyl dihydrogen phosphate

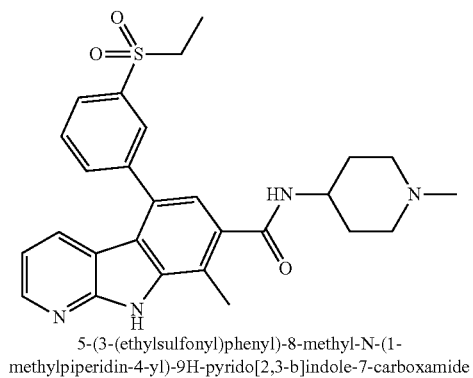

5-(3-(ethylsulfonyl)phenyl)-8-methyl-N-(1-
methylpiperidin-4-yl)-9H-pyrido[2,3-b]indole-7-carboxamide

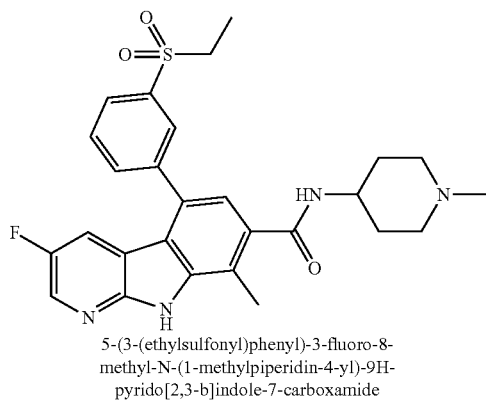

5-(3-(ethylsulfonyl)phenyl)-3-fluoro-8-
methyl-N-(1-methylpiperidin-4-yl)-9H-
pyrido[2,3-b]indole-7-carboxamide

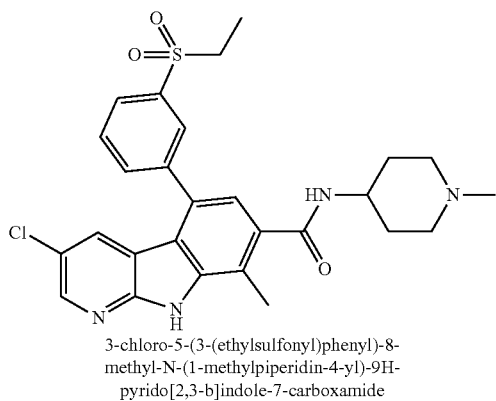

3-chloro-5-(3-(ethylsulfonyl)phenyl)-8-
methyl-N-(1-methylpiperidin-4-yl)-9H-
pyrido[2,3-b]indole-7-carboxamide

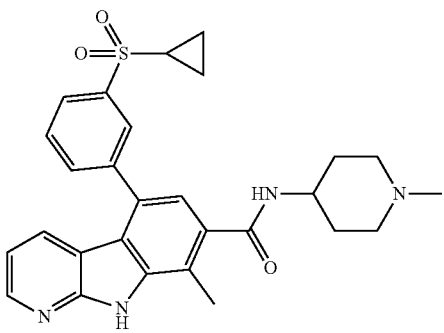

5-(3-(cyclopropylsulfonyl)phenyl)-8-methyl-
N-(1-methylpiperidin-4-yl)-9H-pyrido[2,3-
b]indole-7-carboxamide

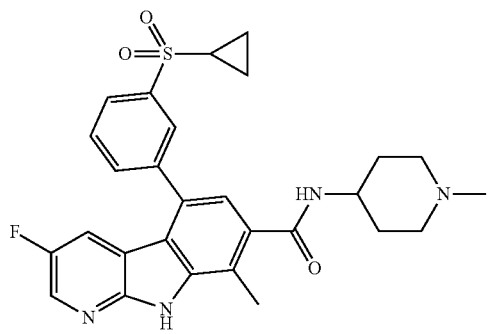

5-(3-(cyclopropylsulfonyl)phenyl)-3-fluoro-
8-methyl-N-(1-methylpiperidin-4-yl)-9H-
pyrido[2,3-b]indole-7-carboxamide

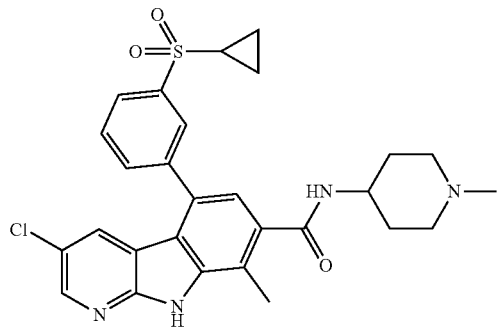

3-chloro-5-(3-(cyclopropylsulfonyl)phenyl)-
8-methyl-N-(1-methylpiperidin-4-yl)-9H-
pyrido[2,3-b]indole-7-carboxamide

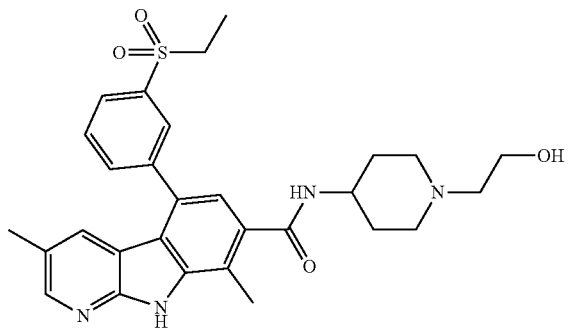

5-(3-(ethylsulfonyl)phenyl)-N-(1-(2-
hydroxyethyl)piperidin-4-yl)-3,8-dimethyl-
9H-pyrido[2,3-b]indole-7-carboxamide -continued

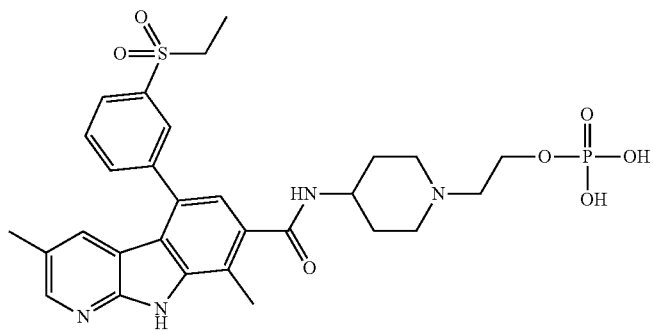

2-(4-(5-(3-(ethylsulfonyl)phenyl)-3,8-
dimethyl-9H-pyrido[2,3-b]indole-7-
carboxamido)piperidin-1-yl)ethyl dihydrogen phosphate

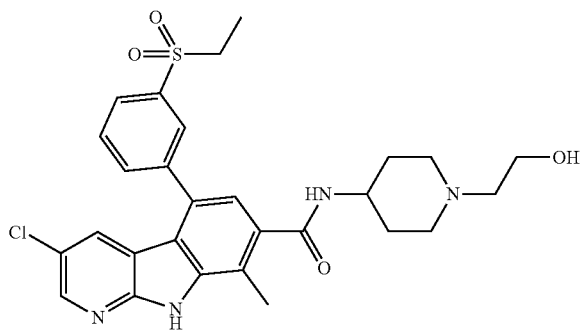

3-chloro-5-(3-(ethylsulfonyl)phenyl)-N-(1-
(2-hydroxyethyl)piperidin-4-yl)-8-methyl-
9H-pyrido[2,3-b]indole-7-carboxamide

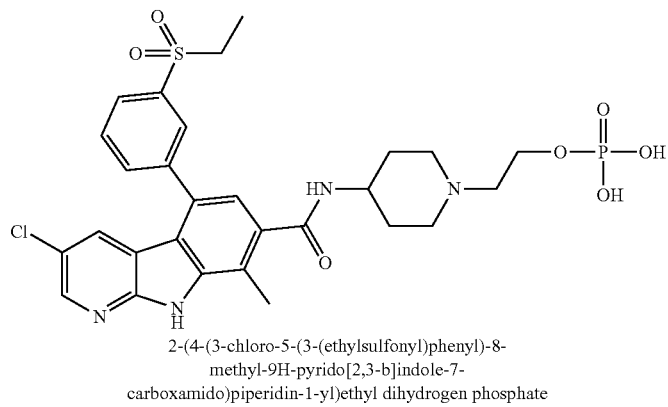

2-(4-(3-chloro-5-(3-(ethylsulfonyl)phenyl)-8-
methyl-9H-pyrido[2,3-b]indole-7-
carboxamido)piperidin-1-yl)ethyl dihydrogen phosphate

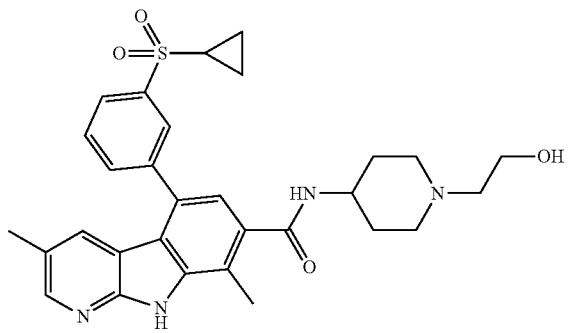

5-(3-(cyclopropylsulfonyl)phenyl)-N-(1-(2-
hydroxyethyl)piperidin-4-yl)-3,8-dimethyl-
9H-pyrido[2,3-b]indole-7-carboxamide

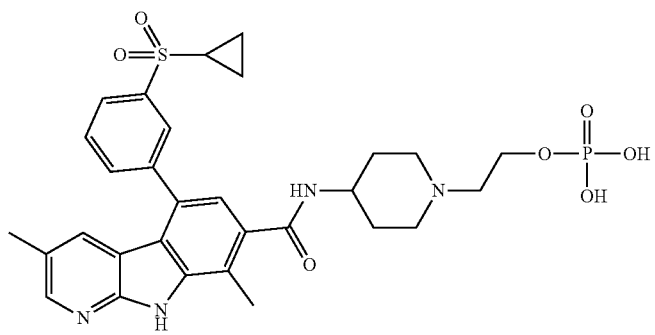

2-(4-(5-(3-(cyclopropylsulfonyl)phenyl)-3,8-
dimethyl-9H-pyrido[2,3-b]indole-7-
carboxamido)piperidin-1-yl)ethyl dihydrogen phosphate

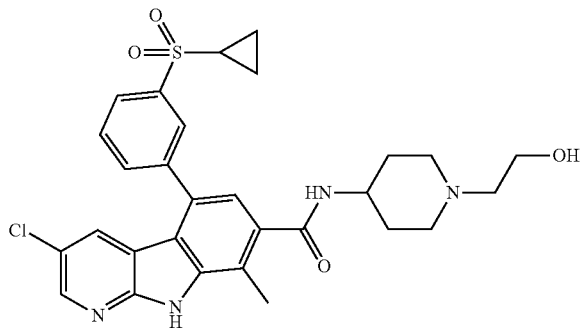

3-chloro-5-(3-(cyclopropylsulfonyl)phenyl)-
N-(1-(2-hydroxyethyl)piperidin-4-yl)-8-
methyl-9H-pyrido[2,3-b]indole-7-carboxamide

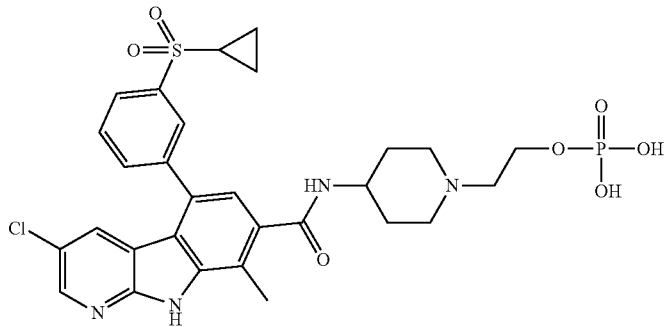

2-(4-(3-chloro-5-(3-(cyclopropylsulfonyl)phenyl)-8-
methyl-9H-pyrido[2,3-b]indole-7-
carboxamido)piperidin-1-yl)ethyl dihydrogen phosphate

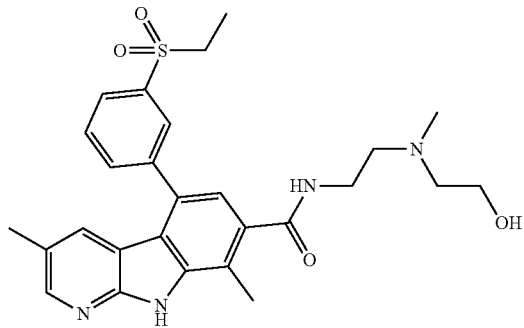

5-(3-(ethylsulfonyl)phenyl)-N-(2-((2-
hydroxyethyl)(methyl)amino)ethyl)-3,8-
dimethyl-9H-pyrido[2,3-b]indole-7-carboxamide

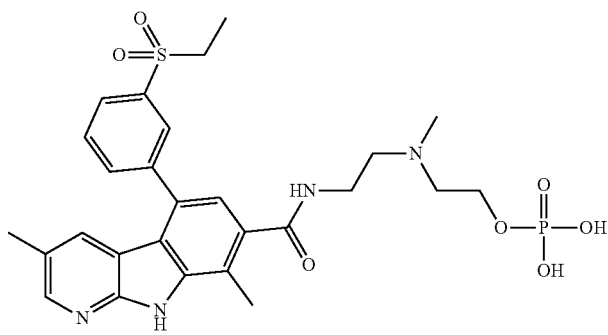

2-((2-(5-(3-(ethylsulfonyl)phenyl)-3,8-dimethyl-9H-pyrido[2,3-b]indole-7-carboxamido)ethyl)(methyl)amino)ethyl dihydrogen phosphate

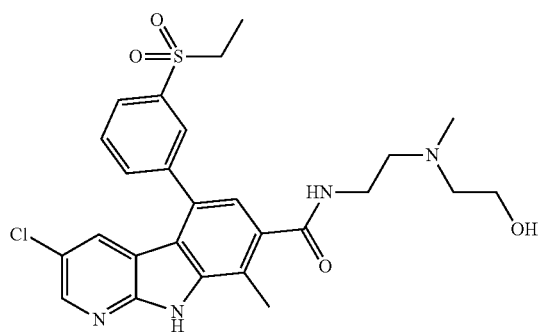

3-chloro-5-(3-(ethylsulfonyl)phenyl)-N-(2-((2-hydroxyethyl)(methyl)amino)ethyl)-8-methyl-9H-pyrido[2,3-b]indole-7-carboxamide

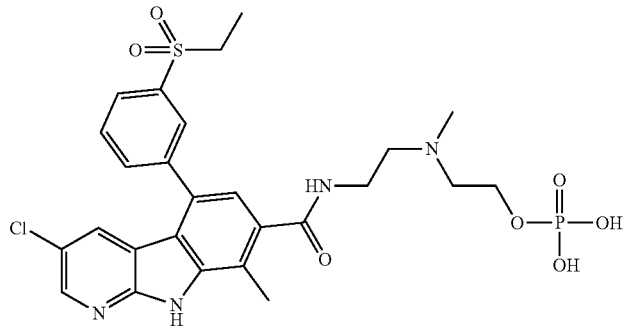

2-((2-(3-chloro-5-(3-(ethylsulfonyl)phenyl)-8-methyl-9H-pyrido[2,3-b]indole-7-carboxamido)ethyl)(methyl)amino)ethyl dihydrogen phosphate

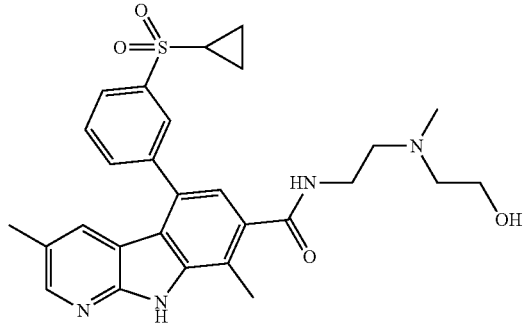

5-(3-(cyclopropylsulfonyl)phenyl)-N-(2-((2-hydroxyethyl)(methyl)amino)ethyl)-3,8-dimethyl-9H-pyrido[2,3-b]indole-7-carboxamide

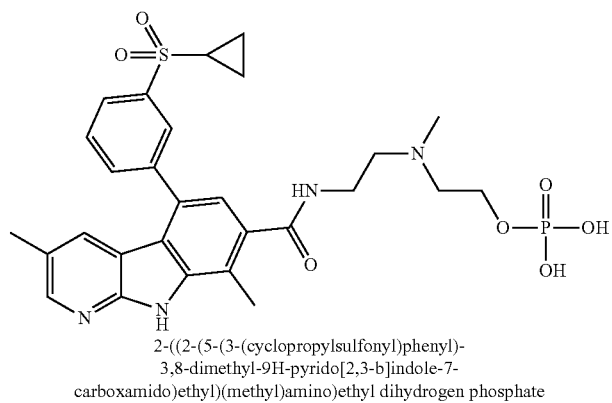

2-((2-(5-(3-(cyclopropylsulfonyl)phenyl)-
3,8-dimethyl-9H-pyrido[2,3-b]indole-7-
carboxamido)ethyl)(methyl)amino)ethyl dihydrogen phosphate

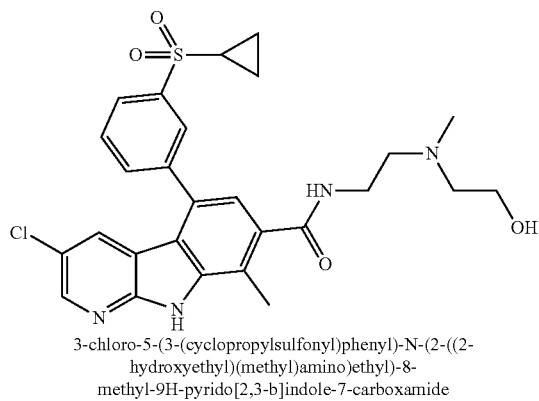

3-chloro-5-(3-(cyclopropylsulfonyl)phenyl)-N-(2-((2-
hydroxyethyl)(methyl)amino)ethyl)-8-
methyl-9H-pyrido[2,3-b]indole-7-carboxamide

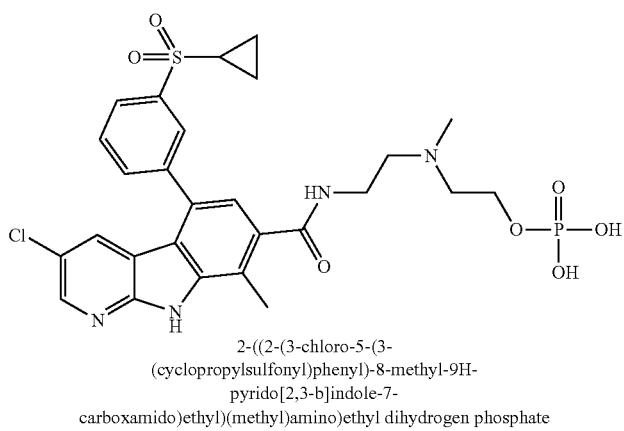

2-((2-(3-chloro-5-(3-
(cyclopropylsulfonyl)phenyl)-8-methyl-9H-
pyrido[2,3-b]indole-7-
carboxamido)ethyl)(methyl)amino)ethyl dihydrogen phosphate

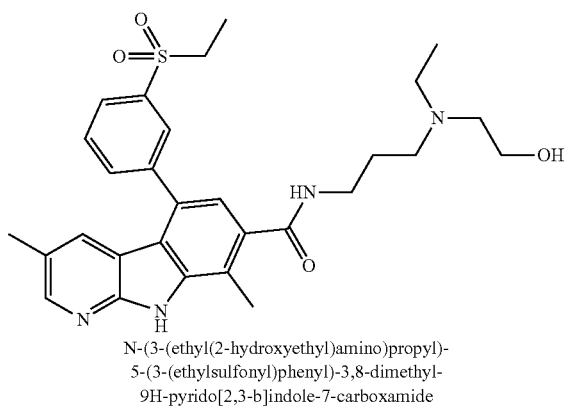

N-(3-(ethyl(2-hydroxyethyl)amino)propyl)-
5-(3-(ethylsulfonyl)phenyl)-3,8-dimethyl-
9H-pyrido[2,3-b]indole-7-carboxamide

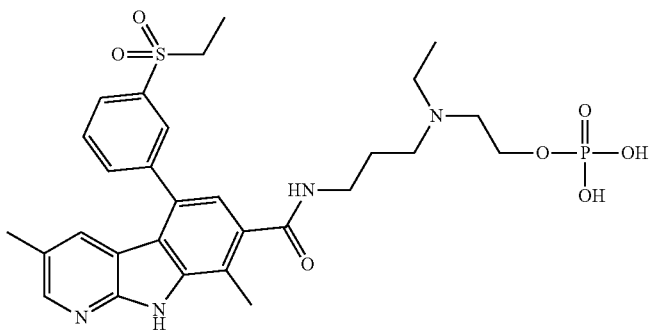

2-(ethyl(3-(5-(3-(ethylsulfonyl)phenyl)-3,8-dimethyl-9H-pyrido[2,3-b]indole-7-carboxamido)propyl)amino)ethyl dihydrogen phosphate

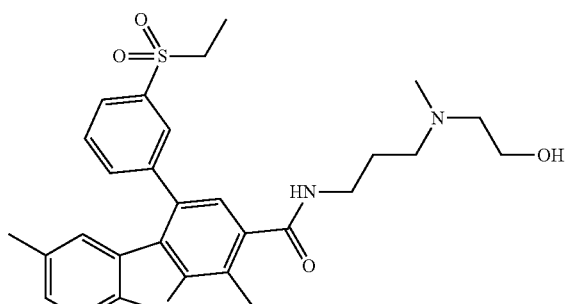

5-(3-(ethylsulfonyl)phenyl)-N-(3-((2-hydroxyethyl)(methyl)amino)propyl)-3,8-dimethyl-9H-pyrido[2,3-b]indole-7-carboxamide

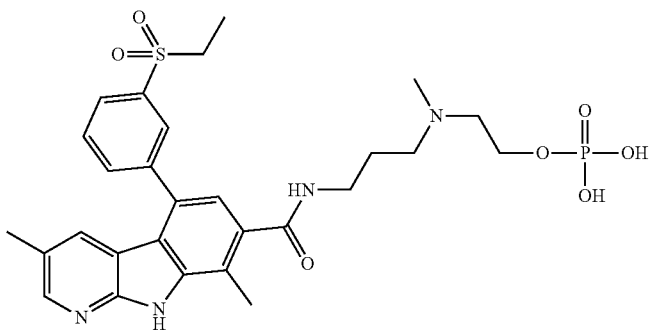

2-((3-(5-(3-(ethylsulfonyl)phenyl)-3,8-dimethyl-9H-pyrido[2,3-b]indole-7-carboxamido)propyl)(methyl)amino)ethyl dihydrogen phosphate Characterization of the Amorphous Form of Compound 88

The Amorphous Form of Compound 88 was characterized by XRPD and Ion Chromatograpgy.

1. X-Ray Powder Diffraction (XRPD)

X-ray powder diffraction (XRPD) analyses were performed using a Shimadzu XRD-6000 diffractometer. Real time data were collected using Cu-Kα radiation starting at approximately 3° 2θ at a scan rate of 2°/min with a step size of 0.04°. The tube voltage and amperage were set to 40 kV and 40 mA, respectively. The pattern is displayed from 2.5 to 45° 2θ. Samples were prepared for analysis by placing them on Si zero-return ultra-micro sample holders.

The resulting XRPD spectrum of the amorphous form of Compound 88 shows a diffuse halo with no discernable peaks, which confirms that the material is amorphous.

2. Ion Chromatography (IC)

Ion Chromatography (IC) was performed using a Dionex DX600 Ion Chromatograph using a Dionex IonPac AS 17, 250×4 mm column and a Dionex IonPac AS17, 50×4 mm guard column. The column temperature was 35±2° C. The detector was operated in a suppressed conductivity mode with a Dionex ASRS Ultra 4 mm suppressor and a suppressor current of 220 mA. Mobile phase A was purified water and mobile phase B was potassium hydroxide (KOH), which was delivered using an eluent generator. A flow rate of 1.5 mL/min and an injection volume of 10 µL were used. The following gradient conditions were used:

| Time (min) | Mobile Phase A | Concentration of KOH (mM) |
|---|---|---|
| 0.0 | 100% | 5 |
| 3.0 | 100% | 5 |
| 10.0 | 100% | 15 |

-continued

| Time (min) | Mobile Phase A | Concentration of KOH (mM) |
|---|---|---|
| 20.0 | 100% | 60 |
| 20.1 | 100% | 5 |
| 30.0 | 100% | 5 |

IC analysis of the amorphous form of Compound 88 showed 7.6 wt % Cl⁻ present, which is 1.0 wt % higher than expected for a mono-HCl salt.

Biological Testing

The activity of compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

A. Determination of Inhibition of AIK

The inhibitory properties of compounds relative to Aurora B/INCENP may be determined by the Direct Fluorescence Polarization detection method (FP) using a Greiner small volume black 384-well-plate format under the following reaction conditions: 50 mM Hepes pH 7.3, 10 mM MgCl$_2$, 10 mM NaCl, 1 mM DTT, 0.01% Brij35, 5FAM-GRTGRRNSI-NH2 (Provided by Anaspec), 5% DMSO, 10 uM ATP and 0.8 nM Aurora B/INCENP. Detection of the reaction product is performed by addition of Progressive IMAP binding reagent (Molecular Devices). Reaction product may be determined quantitatively by FP using an Analyst HT plate reader (Molecular Devices) with an excitation wavelength at 485 nm and emission at 530 nm and using a Fluorescein 505 dichroic mirror.

The assay reaction may be initiated as follows: 2 ul of (3×) 300 nM Fl-Peptide/30 uM ATP was added to each well of the plate, followed by the addition of 2 ul of (3×) inhibitor (2 fold serial dilutions for 11 data points for each inhibitor) containing 15% DMSO. Two microliters of (3×) 2.4 nM AuroraB/INCENP solution may be added to initiate the reaction (final enzyme concentration was 0.8 nM for Aurora B/INCENP). The reaction mixture may then be incubated at room temperature for 45 min, and quenched and developed by addition of 20 ul of 1 to 400 diluted Progressive IMAP binding reagent in 1× proprietary Progressive IMAP binding buffer A. Fluorescence polarization readings of the resulting reaction mixtures may be measured after a 60-minute incubation at room temperature.

IC$_{50}$ values may be calculated by non-linear curve fitting of the compound concentrations and fluorescent polarization values to the standard IC$_{50}$ equation. As a reference point for this assay, Staurosporine showed an IC$_{50}$ of <10 nM. IC$_{50}$ values for select compounds of the invention against AIK B are given in Table 1.

TABLE 1

IC$_{50}$ of Exemplified Compounds Against AIK B

| COMPOUND | IC$_{50}$ (nM) |
|---|---|
| 5 | ≧11 |
| 15 | ≦5 |

TABLE 1-continued

IC$_{50}$ of Exemplified Compounds Against AIK B

| COMPOUND | IC$_{50}$ (nM) |
|---|---|
| 18 | 6-10 |
| 40 | ≦5 |
| 41 | 6-10 |
| 51 | 6-10 |
| 52 | 6-10 |
| 54 | 6-10 |
| 55 | ≦5 |
| 62 | ≦5 |
| 72 | ≦5 |
| 88 | 6-10 |
| 90 | 6-10 |
| 95 | ≧11 |
| 100 | ≦5 |
| 101 | ≦5 |
| 105 | ≧11 |
| 112 | ≧11 |
| 113 | 6-10 |
| 114 | ≧11 |
| 117 | ≧11 |
| 120 | 6-10 |
| 128 | ≦5 |
| 140 | ≦5 |
| 142 | 6-10 |
| 153 | ≧11 |
| 154 | 6-10 |
| 157 | ≦5 |
| 158 | ≦5 |
| 163 | ≧11 |
| 170 | ≦5 |
| 171 | 6-10 |
| 173 | ≧11 |
| 177 | 6-10 |
| 178 | ≧11 |
| 179 | 6-10 |
| 182 | 6-10 |
| 185 | ≦5 |
| 194 | ≦5 |
| 195 | ≧11 |
| 200 | ≦5 |
| 201 | ≦5 |
| 206 | ≦5 |
| 217 | ≦5 |
| 220 | ≦5 |
| 231 | ≦5 |
| 232 | 6-10 |
| 270 | ≦5 |
| 271 | ≦5 |
| 272 | 6-10 |
| 285 | 6-10 |
| 286 | 6-10 |
| 295 | 6-10 |
| 299 | ≦5 |
| 308 | ≦5 |
| 313 | ≦5 |
| 314 | ≦5 |
| 315 | ≦5 |

B. Determination of Inhibition of c-KIT

The inhibitory properties of compounds relative to c-Kit may be determined by the Time-Resolved Fluorescence Resonance Energy Transfer (TR-FRET) method using a small volume black 384-well-plate (Greiner) format under the following reaction conditions: 50 mM Hepes pH 7.3, 10 mM MgCl$_2$, 10 mM NaCl, 1 mM DTT, 0.01% Brij35, 250 nM Biotin-EGPWLEEEEEAYGWMDF peptide (provided by SYNPEP), 5% DMSO, 100 uM ATP. Detection of the reaction product may be performed by addition of Streptavidin-APC (Prozyme) and Eu-Anti-phosphotyrosine antibody (Perkin Elmer). Reaction product may be determined quantitatively by TR-FRET reading using an Analyst HT plate reader (Molecular Devices) with an excitation wavelength at 330 nm and emission at 615 nm (Europium) compared to 330 nm excitation (Europium) and emission 665 nm (APC) and using an Europium 400 dichroic mirror.

The assay reaction may be initiated as follows: 4 ul of (2.5×) 625 nM Biotin-Peptide/250 uM ATP was added to each well of the plate, followed by the addition of 2 ul of (5×) inhibitor (2.5 fold serial dilutions for 11 data points for each inhibitor) containing 25% DMSO. 4 ul of (2.5×) c-Kit solution may be added to initiate the reaction (final enzyme concentration was 0.13 nM for c-Kit). The reaction mixture may then be incubated at room temperature for 30 min, and quenched and developed by addition of 10 ul of (2×) 3.2 nM Eu-Antibody and 25 nM Streptavidin-APC in 50 mM Hepes pH 7.3, mM EDTA, 0.1% Triton X-100 buffer. TR-FRET readings of the resulting reaction mixtures may be measured after a 60-minute incubation at room temperature on the Analyst HT.

$IC_{50}$ values may be calculated by non-linear curve fitting of the compound concentrations and ratio metric Eu:APC values to the standard $IC_{50}$ equation. As a reference point for this assay, Staurosporine showed an $IC_{50}$ of <5 nM.

The following abbreviations have been used:

| | |
|---|---|
| ATP | Adenosine Triphophatase |
| BSA | Bovine Serum Albumin |
| EDTA | Ethylenediaminetetraacetic acid |
| GSK3 | Glycogen synthase kinase 3 |
| MOPS | Morpholinepropanesulfonic acid |
| SPA | Scintillation Proximity Assay |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound selected from the group consisting of 2-((3-(3-chloro-5-(3-(ethylsulfonyl)phenyl)-9H-pyrido[2,3-b]indol-8-yloxy)propyl)(ethyl)amino)ethanol, 2-((3-(3-chloro-5-(3-(cyclopropylsulfonyl)phenyl)-9H-pyrido[2,3-b]indol-8-yloxy)propyl)(ethyl)amino)ethanol, 2-((2-(5-(3-(cyclopropylsulfonyl)phenyl)-3-methyl-9H-pyrido[2,3-b]indol-8-yloxy)ethyl)(ethyl)amino)ethanol, 2-((2-(3-chloro-5-(3-(cyclopropylsulfonyl)phenyl)-9H-pyrido[2,3-b]indol-8-yloxy)ethyl)(methyl)amino)ethanol, 2-((2-(5-(3-(cyclopropylsulfonyl)phenyl)-9H-pyrido[2,3-b]indol-8-yloxy)ethyl)(methyl)amino)ethanol, 2-((2-(3-chloro-5-(3-(cyclopropylsulfonyl)phenyl)-9H-pyrido[2,3-b]indol-8-yloxy)ethyl)(ethyl)amino)ethanol, and 2-((2-(5-(3-(cyclopropylsulfonyl)phenyl)-9H-pyrido[2,3-b]indol-8-yloxy)ethyl)(ethyl)amino)ethanol, or a pharmaceutically acceptable salt thereof.

2. The compound 2-((3-(5-(3-(cyclopropylsulfonyl)phenyl)-3-methyl-9H-pyrido[2,3-b]indol-8-yloxy)propyl)(ethyl)amino)ethanol or a pharmaceutically acceptable salt thereof.

3. The compound 2-((3-(5-(3-(ethylsulfonyl)phenyl)-3-methyl-9H-pyrido[2,3-b]indol-8-yloxy)propyl)(methyl)amino)ethanol or a pharmaceutically acceptable salt thereof.

* * * * *